US010882922B2

(12) United States Patent
Yang et al.

(10) Patent No.: US 10,882,922 B2
(45) Date of Patent: Jan. 5, 2021

(54) TRISPECIFIC AND/OR TRIVALENT BINDING PROTEINS

(71) Applicant: SANOFI, Paris (FR)

(72) Inventors: Zhi-Yong Yang, Bridgewater, NJ (US); Gary J. Nabel, Bridgewater, NJ (US); Lan Wu, Bridgewater, NJ (US); Edward Seung, Bridgewater, NJ (US); Ronnie Wei, Bridgewater, NJ (US); Jochen Beninga, Frankfurt am Main (DE); Ercole Rao, Frankfurt am Main (DE); Wulf Dirk Leuschner, Frankfurt am Main (DE); Christian Beil, Frankfurt am Main (DE); Christian Lange, Frankfurt am Main (DE); Carsten Corvey, Frankfurt am Main (DE)

(73) Assignee: SANOFI, Paris (FR)

( * ) Notice: Subject to any disclaimer, the term of this patent is extended or adjusted under 35 U.S.C. 154(b) by 70 days.

(21) Appl. No.: 15/487,243

(22) Filed: Apr. 13, 2017

(65) Prior Publication Data

US 2017/0320967 A1 Nov. 9, 2017

Related U.S. Application Data

(60) Provisional application No. 62/412,187, filed on Oct. 24, 2016, provisional application No. 62/331,191, filed on May 3, 2016, provisional application No. 62/322,036, filed on Apr. 13, 2016.

(30) Foreign Application Priority Data

Mar. 17, 2017 (EP) .................................... 17305298

(51) Int. Cl.

| | |
|---|---|
| ***A61K 39/00*** | (2006.01) |
| ***C07K 16/46*** | (2006.01) |
| ***C07K 16/24*** | (2006.01) |
| ***C07K 16/28*** | (2006.01) |
| ***C07K 16/32*** | (2006.01) |
| ***A61K 39/395*** | (2006.01) |
| ***A61K 45/06*** | (2006.01) |
| ***C07K 1/22*** | (2006.01) |

(52) U.S. Cl.

CPC ........ *C07K 16/468* (2013.01); *A61K 39/3955* (2013.01); *A61K 39/39558* (2013.01); *A61K 45/06* (2013.01); *C07K 1/22* (2013.01); *C07K 16/241* (2013.01); *C07K 16/244* (2013.01); *C07K 16/247* (2013.01); *C07K 16/2803* (2013.01); *C07K 16/2809* (2013.01); *C07K 16/2818* (2013.01); *C07K 16/2887* (2013.01); *C07K 16/2896* (2013.01); *C07K 16/32* (2013.01); *A61K 2039/505* (2013.01); *C07K 2317/31* (2013.01); *C07K 2317/35* (2013.01); *C07K 2317/52* (2013.01); *C07K 2317/526* (2013.01); *C07K 2317/56* (2013.01); *C07K 2317/565* (2013.01); *C07K 2317/64* (2013.01); *C07K 2317/73* (2013.01); *C07K 2317/75* (2013.01); *C07K 2317/76* (2013.01); *C07K 2317/92* (2013.01); *C07K 2317/94* (2013.01); *C07K 2319/00* (2013.01)

(58) Field of Classification Search

CPC .............................. C07K 16/468; A61K 39/00
USPC ...................................................... 424/136.1
See application file for complete search history.

(56) References Cited

U.S. PATENT DOCUMENTS

| | | | | |
|---|---|---|---|---|
| 9,181,349 | B2 | 11/2015 | Baurin et al. | |
| 9,221,917 | B2 | 12/2015 | Baurin et al. | |
| 2010/0226923 | A1 | 9/2010 | Rao | |
| 2012/0076782 | A1 | 3/2012 | Tesar et al. | |
| 2012/0201827 | A1* | 8/2012 | Elias | A61P 35/02 424/139.1 |
| 2012/0251541 | A1 | 10/2012 | Baurin et al. | |
| 2013/0345404 | A1 | 12/2013 | Baurin et al. | |
| 2014/0213772 | A1 | 7/2014 | Ghayur | |
| 2014/0322217 | A1 | 10/2014 | Moore et al. | |
| 2016/0200811 | A1 | 7/2016 | Baurin et al. | |
| 2018/0237511 | A1 | 8/2018 | Beil | |
| 2019/0054182 | A1 | 2/2019 | Yang et al. | |
| 2019/0106504 | A1 | 4/2019 | Wu et al. | |
| 2020/0054765 | A1 | 2/2020 | Yang | |

(Continued)

FOREIGN PATENT DOCUMENTS

| | | | |
|---|---|---|---|
| CN | 105837688 | A | 8/2016 |
| EP | 0308936 | A2 | 3/1989 |
| EP | 1378520 | A1 | 1/2004 |

(Continued)

OTHER PUBLICATIONS

Rudikoff et al (Proceedings of the National Academy of Sciences, 1982, 79:1979-1983).*

(Continued)

*Primary Examiner* — Sean E Aeder

(74) *Attorney, Agent, or Firm* — Morrison & Foerster LLP

(57) ABSTRACT

The disclosure provides trispecific and/or trivalent binding proteins comprising four polypeptide chains that form three antigen binding sites that specifically bind one or more target proteins, wherein a first pair of polypeptides forming the binding protein possess dual variable domains having a cross-over orientation and wherein a second pair of polypeptides forming the binding protein possess a single variable domain. The disclosure also provides methods for making trispecific and/or trivalent binding proteins and uses of such binding proteins.

47 Claims, 51 Drawing Sheets

Specification includes a Sequence Listing.

(56) References Cited

U.S. PATENT DOCUMENTS

2020/0140552 A1 5/2020 Wu

FOREIGN PATENT DOCUMENTS

| | | | |
|---|---|---|---|
| EP | 1736484 | A1 | 12/2006 |
| WO | WO-1996/027011 | A1 | 9/1996 |
| WO | WO-1999/051642 | A1 | 10/1999 |
| WO | WO-2005/000899 | A2 | 1/2005 |
| WO | WO2009149189 | A2 | 12/2009 |
| WO | WO2011038290 | A2 | 3/2011 |
| WO | WO2011154453 | A1 | 12/2011 |
| WO | WO-2012/092612 | A1 | 7/2012 |
| WO | WO-2012/135345 | A1 | 10/2012 |
| WO | WO2012154312 | A1 | 11/2012 |
| WO | WO2012158948 | A1 | 11/2012 |
| WO | WO2013070776 | A1 | 5/2013 |
| WO | WO2013086533 | A1 | 6/2013 |
| WO | WO2013163427 | A1 | 10/2013 |
| WO | WO2014116846 | A2 | 7/2014 |
| WO | WO2014144299 | A2 | 9/2014 |
| WO | WO-2015/063339 | A1 | 5/2015 |
| WO | WO2015149077 | A1 | 10/2015 |
| WO | WO2016033690 | A1 | 3/2016 |
| WO | WO-2016/116626 | A1 | 7/2016 |
| WO | WO2016196740 | A1 | 12/2016 |
| WO | WO2017053556 | A1 | 3/2017 |
| WO | WO-2017/074878 | A1 | 5/2017 |
| WO | WO2017106346 | A2 | 6/2017 |
| WO | WO2018120842 | A1 | 7/2018 |
| WO | WO2018151841 | A1 | 8/2018 |

OTHER PUBLICATIONS

Atwell, S. et al. (Jul. 4, 1997). "Stable Heterodimers from Remodeling the Domain Interface of a Homodimer Using a Phage Display Library," *J. Mol. Biol.* 270(1):26-35.
Chothia, C. et al. (Aug. 20, 1987). "Canonical Structures for the Hypervariable Regions of Immunoglobulins," *J. Mol. Biol.* 196(4):901-917.
Chothia, C. et al. (Dec. 21-28, 1989). "Conformations of Immunoglobulin Hypervariable Regions," *Nature* 342(6252): 877-883.
Hinton, P.R. et al. (Jan. 1, 2006). "An Engineered Human IgG1 Antibody With Longer Serum Half-Life," *J. Immunol.* 176(1):346-356.
Lefranc, M.P. et al. (Jan. 2003). "IMGT Unique Numbering for Immunoglobulin and T Cell Receptor Variable Domains and Ig Superfamily V-Like Domains," *Dev. Comp. Immunol.* 27(1):55-77.
MacCallum, R.M. et al. (Oct. 11, 1996). "Antibody-Antigen Interactions: Contact Analysis and Binding Site Topography," *J. Mol. Biol.* 262(5): 732-45.
Masui, S. et al. (Mar. 1, 2005). "An Efficient System to Establish Multiple Embryonic Stem Cell Lines Carrying an Inducible Expression Unit," *Nucleic Acids Res.* 33(4):e43, pp. 1-8.
McDermott, S.P. et al. (Jul. 15, 2010, e-published as Apr. 19, 2010). "Comparison of Human Cord Blood Engraftment Between Immunocompromised Mouse Strains," *Blood* 116(2):193-200.
Merchant, A.M. et al. (Jul. 1998). "An Efficient Route to Human Bispecific IgG," *Nature Biotechnol.* 16(7):677-681.
Niwa, H. et al. (Dec. 15, 1991). "Efficient Selection for High-Expression Transfectants with a Novel Eukaryotic Vector," *Gene* 108(2):193-199.
Padlan, E.A. et al. (Jan. 1995). "Identification of Specificity-Determining Residues in Antibodies," *FASEB J.* 9(1):133-139.
Ridgway, J.B. et al. (Jul. 1996). "'Knobs-Into-Holes' Engineering of Antibody CH3 Domains for Heavy Chain Heterodimerization," *Protein Eng.* 9(7):617-621.
Shields, R.L. et al. (Mar. 2, 2001). "High Resolution Mapping of the Binding Site on Human IgG1 for FcγRI, FcγRII, FcγRIII, and FcRn and Design of IgG1 Variants with Improved Binding to the FcγR," *J. Biol. Chem.* 276(9):6591-6604.
Shultz, L.D. et al. (Jul. 2014). "Human Cancer Growth and Therapy in NOD/SCID/IL2R$\gamma^{null}$ (NSG) Mice," *Cold Spring Harb. Protoc.* 2014(7):694-708.
Smith, E.J. et al. (Dec. 11, 2015). "A Novel, Native-Format Bispecific Antibody Triggering T-Cell Killing of B-Cells is Robustly Active in Mouse Tumor Models and Cynomolgus Monkeys," *Sci. Rep.* 5:17943, pp. 1-12.
Spiess, C. et al. (Sep. 13, 2013, e-published on Jul. 23, 2013). "Development of a Human IgG4 Bispecific Antibody for Dual Targeting of Interleukin-4 (IL-4) and Interleukin-13 (IL-13) Cytokines," *J. Biol. Chem.* 288:26583-26593.
Stebbings, R. et al. (Sep. 1, 2007). ""Cytokine Storm" In The Phase I Trial of Monoclonal Antibody TGN1412: Better Understanding the Causes to Improve Preclinical Testing of Immunotherapeutics," *J. Immunol.* 179(5):3325-3331.
Thompson, J.D. (Nov. 11, 1994). "CLUSTAL W: Improving the Sensitivity of Progressive Multiple Sequence Alignment Through Sequence Weighting, Position-Specific Gap Penalties and Weight Matrix Choice," *Nucleic Acids Res.* 22(22):4673-4680.
EBI Accession No. GSP: BAH64671 Sequence (Jan. 13, 2013). "Anti-HIV Human Antibody Variable Light Chain (VL), VRCO1," one page.
EBI Accession No. GSP: BAO38135 Sequence (Jul. 4, 2013). "Human Germline 10E8 Antibody Heavy Chain Revertant SEQ ID No. 149," one page.
International Preliminary Report on Patentability dated May 11, 2018 for PCT Application No. PCT/US2016/058540 filed on Oct. 24, 2016, eight pages.
international Preliminary Report on Patentability dated Oct. 25, 2018 for PCT Application No. PCT/US2017/027488, filed on Apr. 13, 2017, thirty two pages.
International Search Report and Written Opinion dated Jan. 2, 2018 for PCT Application No. PCT/US2017/027488, filed on Apr. 13, 2017, forty eight pages.
International Search Report and Written Opinion of the International Searching Authority dated Mar. 10, 2017 for PCT Application No. PCT/US2016/058540 filed on Oct. 24, 2016, fifteen pages.
Invitation to Pay Additional Fees and, Where Applicable, Protest Fee dated Oct. 16, 2017, for PCT Application No. PCT/US2017/027488, filed on Apr. 13, 2017, twenty eight pages.
Moore, G. et al. (Dec. 5, 2015). "1798 Tuning T Cell Affinity Improves Efficacy and Safety of Anti-CD38 × Anti-CD3 Bispecific Antibodies in Monkeys—a Potential Therapy for Multiple Myeloma," American Society of Hematology, Poster Abstract presented at 57th Annual Meeting & Exposition, Orlando, FL, three pages.
Sarzotti-Kelsoe, M. et al. (Jul. 2014; e-published on Dec. 1, 2013). "Optimization and validation of the TZM-bl assay for standardized assessments of neutralizing antibodies against HIV-1," J. Immunological Methods 409:131-146, thirty seven pages.
Song, Li-Ping et al. (Jun. 1, 2003). "A New Model of Trispecific Antibody with Cytotoxicity Against Tumor Cells," Acta Biochimica Etbiophysica Sinica 35(6):503-510.
Spiess, C. et al.(2015; e-pub. Jan. 27, 2015). "Alternative Molecular Formats and Therapeutic Applications for Bispecific Antibodies," Molecular Immunology 67(2):95-106.
Steinmetz, A. et al. (Mar. 16, 2016). "CODV-Ig, A Universal Bispecific Tetravalent and Multifunctional Immunoglobulin Format for Medical Applications," MABS 8(5):867-878, with Supplementary material, fifty nine pages.
U.S. Appl. No. 16/155,807, filed Oct. 9, 2018 by Wu et al. (Copy not submitted herewith pursuant to the waiver of 37 C.F.R. § 1.98(a)(2)(iii) issued by the Office on Sep. 21, 2004.).
Wang, X. (Apr. 1, 2004). "A New Recombinant Single Chain Trispecific Antibody Recruits T Lymphocytes to Kill CEA (Carcinoma Embryonic Antigen) Positive Tumor Cells In Vitro Efficiently," Journal of Biochemistry 135(4):555-565.
Willems, A. et al. (Nov. 1, 2005; e-pub. May 13, 2005). "CD3 CD28 Cross-Interacting Bispecific Antibodies Improve Tumor Cell Dependent T-Cell Activation," Cancer Immunology, Immunotherapy 54(11):1059-1071.
Alegre, M.L. et al. (Jun. 1, 1994). "A Non-Activating "Humanized" Anti-CD3 Monoclonal Antibody Retains Immunosuppressive Properties In Vivo," *Transplantation* 57(11):1537-1543.

(56) References Cited

OTHER PUBLICATIONS

Almeida, J. et al. (1999). "High-Sensitive Immunophenotyping and DNA Ploidy Studies for the Investigation of Minimal Residual Disease in Multiple Myeloma," *British J of Haematol*. 107:121-131.
Altschul, S.F. et al. (Sep. 1, 1997). "Gapped BLAST and PSI-BLAST: A New Generation of Protein Database Search Programs," *Nucleic Acids Res*. 25(17):3389-3402.
Brandsma, A.M. et al. (Oct. 1, 2017; e-pub. Aug. 16, 2017). "Single Nucleotide Polymorphisms of the High Affinity IgG Receptor FcγRI Reduce Immune Complex Binding and Downstream Effector Functions," *The Journal of Immunology* 199(7):2432-2439.
Chai, J.G. et al. (1997). "Immobilized Anti-CD3 mAb Induces Anergy in Murine Naive and Memory CD4+T Cells in vitro," *Int Immunol*. 9(7):935-944.
Chu, S.Y et al. (Dec. 4, 2014). "Immunotherapy with Long-Lived Anti-CD38 × Anti-CD3 Bispecific Antibodies Stimulates Potent T Cell-Mediated Killing of Human Myeloma Cell Lines and CD38+ Cells in Monkeys: A Potential Therapy for Multiple Myeloma," *Blood* 124(21): 4727, 6 pages.
Colombian Opposition mailed on Mar. 15, 2019 for CO Application No. NC2018/0012107 filed on Nov. 9, 2018, eighteen pages.
Deckert, J. et al. (2014; e-pub. Jul. 1, 2014). "SAR650984, a Novel Humanized CD38-Targeting Antibody, Demonstrates Potent Anti-Tumor Activity in Models of Multiple Myeloma and Other CD38+ Hematologic Malignancies," *Clin. Cancer Res* 20:4574-4583.
Digiammarino, E. et al. (Sep.-Oct. 2011, e-pub. Sep. 1, 2011). "Ligand Association Rates to the Inner-Variable-Domain of a Dual-Variable-Domain Immunoglobulin are Significantly Impacted by Linker Design," *MAbs*. 3(5):487-494.
Esensten, J.H. et al. (May 17, 2016). "CD28 Costimulation: From Mechanism to Therapy," *Immunity* 44:973-988.
Findlay, L. et al. (2010; e-pub. Nov. 4, 2009). "Improved In Vitro Methods to Predict the In Vivo Toxicity in Man of Therapeutic Monoclonal Antibodies Including TGN1412," *J ImmunolMethods* 352:1-12.
Fournier, P. et al. (Jan. 2010). "Tumor Antigen-Dependent and Tumor Antigen-Independent Activation of Antitumor Activity in T Cells by a Bispecific Antibody-Modified Tumor Vaccine," *Clinical & Developmental Immunology* 2010(1): Article IDS 423781, 12 pages.
Gratama, J,W. et al. (Sep. 1, 2001). "Tetramer-Based Quantification of Cytomegalovirus (CMV)—Specific CD81 T Lymphocytes in T-Cell—Depleted Stem Cell Grafts and After Transplantation May Identify Patients at Risk for Progressive CMV Infection," *Blood* 98(5):1358-1364.
Haas, C. et al. (Mar. 31, 2005; e-pub. Nov. 25, 2004). "T-cell Triggering by CD3- and CD28-Binding Molecules Linked to a Human Virus-Modified Tumor Cell Vaccine," *Vaccine* 23(19):2439-2453.
Hui, E. et al. (Mar. 31, 2017). "T Cell Costimulatory Receptor CD28 is a Primary Target for PD-1-Mediated Inhibition," *Science* 355(6332):1428-1433.
International Search Report and Written Opinion of the International Searching Authority dated May 17, 2019, for PCT Application No. PCT/US2018/055084, filed on Oct. 9, 2018, twenty-seven pages.
Invitation to Pay Additional Fees and, Where Applicable, Protest Fee dated Feb. 20, 2019, for PCT Application No. PCT/US2018/055084, filed on Oct. 9, 2018, twenty three pages.
Jakob, C.G. et al. (May 1, 2013, e-pub. Apr. 2, 2013). "Structure Reveals Function of the Dual Variable Domain Immunoglobulin (DVD-Ig™) Molecule," *MAbs*. 5(3):358-363.
Kalim, M. et al. (2017; e-pub. Aug. 2, 2017). "Intracellular Trafficking of New Anticancer Therapeutics: Antibody—Drug Conjugates," *Drug Des. Devel. Ther*. 11:2265-2276.
Kilpatrick, K.E. et al. (Aug. 1997). "Rapid Development of Affinity Matured Monoclonal Antibodies Using RIMMS," *Hybridoma* 16(4):381-389.
Li, T. et al. (Jun. 2, 2016). "Immuno-Targeting the Multifunctional CD38 Using Nanobody," *Scientific Reports* 6(1):27055, 11 pages.
Liu, Q. et al. (Sep. 2005). "Crystal Structure of Human CD38 Extracellular Domain," *Structure* 13(9):1331-1339.
Mateo, G. et al. (May 15, 2005). "Genetic Abnormalities and Patterns of Antigenic Expression in Multiple Myeloma," *Clin. Cancer Res*. 11(10):3661-3667.
McKeage, K. (Feb. 2016). "Daratumumab: First Global Approval," *Drugs*. 76(2):275-281.
Morphosys. (Nov. 25, 2010). "R&D Day 2010," 102 pages.
Nair, J.R. et al. (2011; e-pub. Jun. 29, 2011). "CD28 Expressed on Malignant Plasma Cells Induces a Prosurvival and Immunosuppressive Microenvironment," *J Immunol*. 187:1243-1253.
Parslow, A.C. et al. (2016). "Antibody—Drug Conjugates for Cancer Therapy," *Biomedicines* 4:14, pp. 1-17.
Penaranda, C.I. et al. (Aug. 15, 2011). "Anti-CD3 Therapy Promotes Tolerance by Selectively Depleting Pathogenic Cells While Preserving Regulatory T Cells," *J Immunol*. 187(4):2015-2022, 19 pages.
Peters, B. et al. (Mar. 2005; e-pub. Mar. 15, 2005). "The Immune Epitope Database and Analysis Resource: From Vision to Blueprint," *PLos Biol*. 3(3):e91, pp. 0379-0381.
Robillard, N. et al. (Jun. 1998). "CD28, a Marker Associated with Tumoral Expansion in Multiple Myeloma," *Clin Cancer Res*. 4:1521-1526.
Sharma, P. et al. (Apr. 3, 2015). "The Future of Immune Checkpoint Therapy," *Science* 348(6230):56-61.
Stevenson, G.T. (Nov.-Dec. 2006). "CD38 as a Therapeutic Target," *Mol. Med*. 12(11-12):345-346.
Suntharalingam, G. et al. (Sep. 7, 2006). "Cytokine Storm in a Phase 1 Trial of the Anti-CD28 Monoclonal Antibody TGN1412," *N Engl J Med* 355(10):1018-1028.
Tabares, P. et al. (Apr. 2014; e-pub. Feb. 1, 2014). "Human Regulatory T Cells are Selectively Activated by Low-Dose Application of the CD28 Superagonist TGN1412/TAB08," *Eur J Immunol*. 44:1225-1236.
Tiller, T. et al. (Oct. 2009, e-pub. Aug. 27, 2009). "Cloning and Expression of Murine Ig Genes From Single B Cells," *J. Immunol. Methods* 350(1-2):183-193.
Waibler, Z. et al. (Mar. 5, 2008). "Signaling Signatures and Functional Properties of Anti-Human CD28 Superagonistic Antibodies," *PLoS One* 3(3):e1708, pp. 1-13.
Wang, X. et al. (Jan. 2018; e-pub. Oct. 6, 2017). "IgG Fc Engineering to Modulate Antibody Effector Functions," *Protein & Cell* 9(1):63-73.
Wennerberg, A.E. et al. (Oct. 1993). "Hepatocyte Paraffin 1: A Monoclonal Antibody that Reacts with Hepatocytes and can be Used for Differential Diagnosis of Hepatic Tumors," *Am J Pathol*. 143(4):1050-1054.
Xu, L. et al. (Oct. 6, 2017; e-pub. Sep. 20, 2017). "Trispecific Broadly Neutralizing HIV Antibodies Mediate Potent SHIV Protection in Macaques," *Science* 358(6359):85-90, 17 pages.
Garfall, A.L. et al. (Nov. 21, 2019). "Three is a Charm for anAntibody to Fight Cancer," Nature 575:450-451.
Wu, L. et al. (Nov. 18, 2019). "Trispecific Antibodies Enhance the Therapeutic Efficacy of Tumor-Directed T Cell-Through T Cell Receptor Co-Stimulation," Nat Cancer 1:86-98.
U.S. Appl. No. 16/596,474, filed Oct. 8, 2019, for Wu et al. (Copy not submitted herewith pursuant to the waiver of 37 C.F.R. 1.98(a)(2)(iii) issued by the Office on Sep. 21, 2004).
Wu, L. et al. (Nov. 18, 2019). "Trispecific Antibodies Enhance the Therapeutic Efficacy of Tumor-Directed T Cells Through T Cell Receptor Co-Stimulation," Nat Cancer 1:86-98.
Chen, H.W. et al. (Apr. 1, 2006). "Ex Vivo Expansion of Dendritic-Cell-Activated Antigenspecific CD41\+ T Cells With Anti-CD3/CD28, Interleukin-? and Interleukin-15: Potential for Adoptive T Cell Immunotherapy," Clinical Immunology 119(1):21-31.
Hartman, W.R. et al. (May 17, 2010). "CD38 Expression, Function, and Gene Resequencing in a Human Lymphoblastoid Cell Line-Based Model System," Leukemia and Lymphoma 51(7):1315-1325, 20 pages.
International Search Report dated Dec. 17, 2019, for PCT Application No. PCT/US2019/055232, filed on Oct. 8, 2019, seven pages.
U.S. Appl. No. 16/596,474, filed Oct. 8, 2019, for Wu et al. (Copy not submitted herewith pursuant to the waiver of 37 C.F.R. 1.98(a)(2)(iii)

(56) References Cited

OTHER PUBLICATIONS issued by the Office on Sep. 21, 200(Copy not submitted herewith 3ursuant to the waiver of 37 C.F.R. 1.98(a)(2)(iii) issued by the Office on Sep. 21, 2004).
Written Opinion of the International Searching Authority dated Dec. 17, 2019, for PCT Application No. PCT/US2019/055232, filed on Oct. 8, 2019, six pages.

* cited by examiner

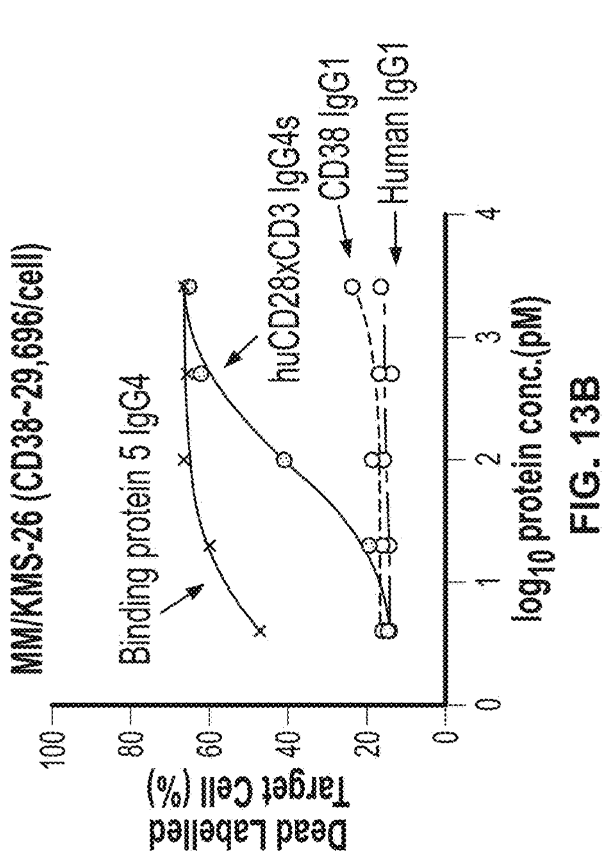
FIG. 13B
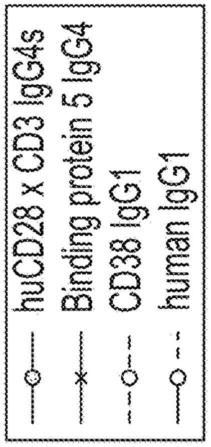
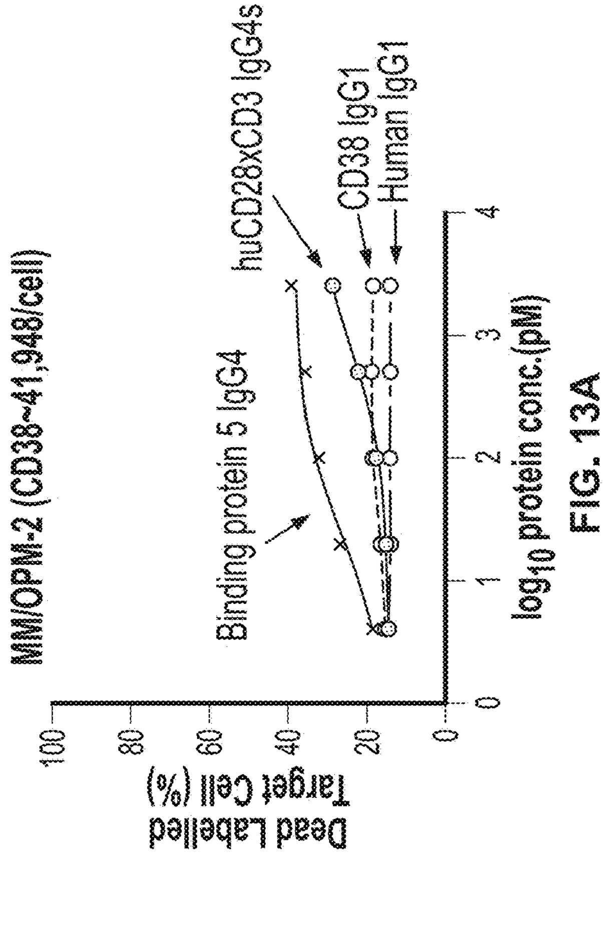
FIG. 13A
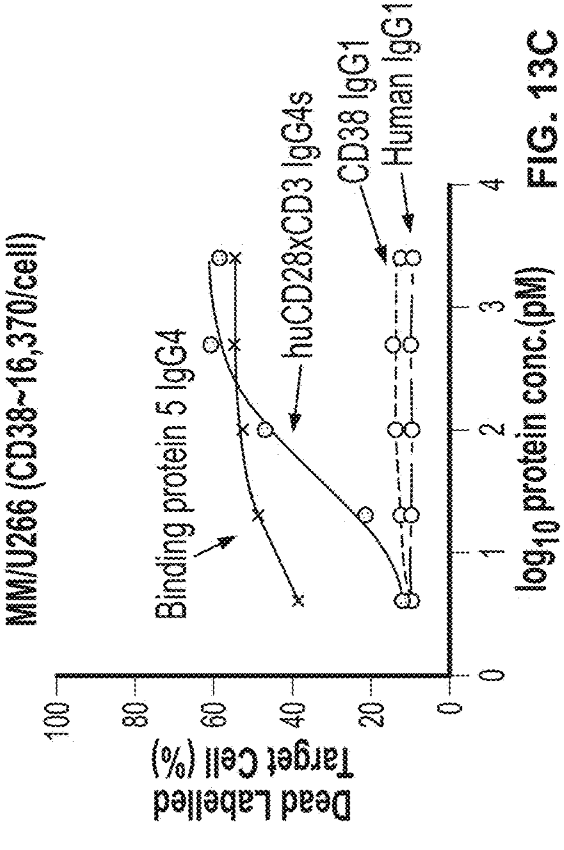
FIG. 13C

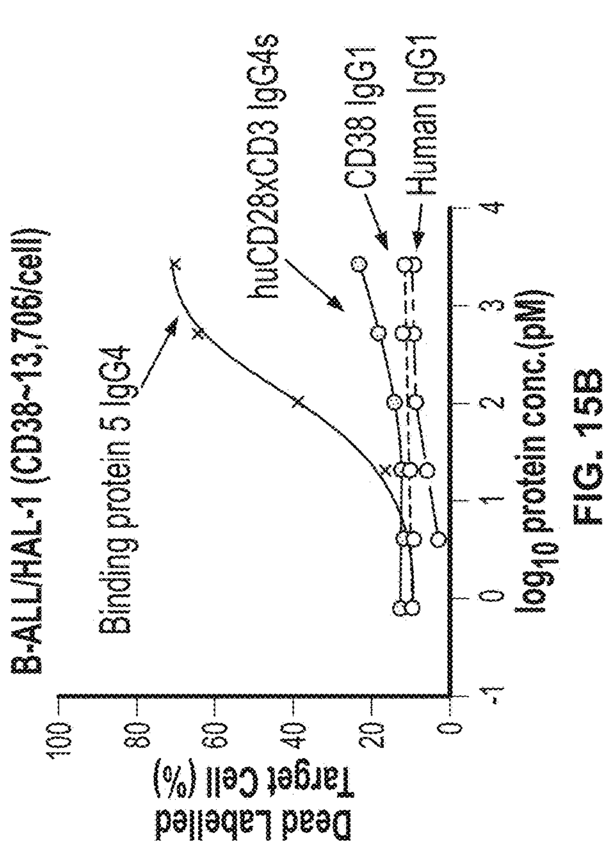
FIG. 15B
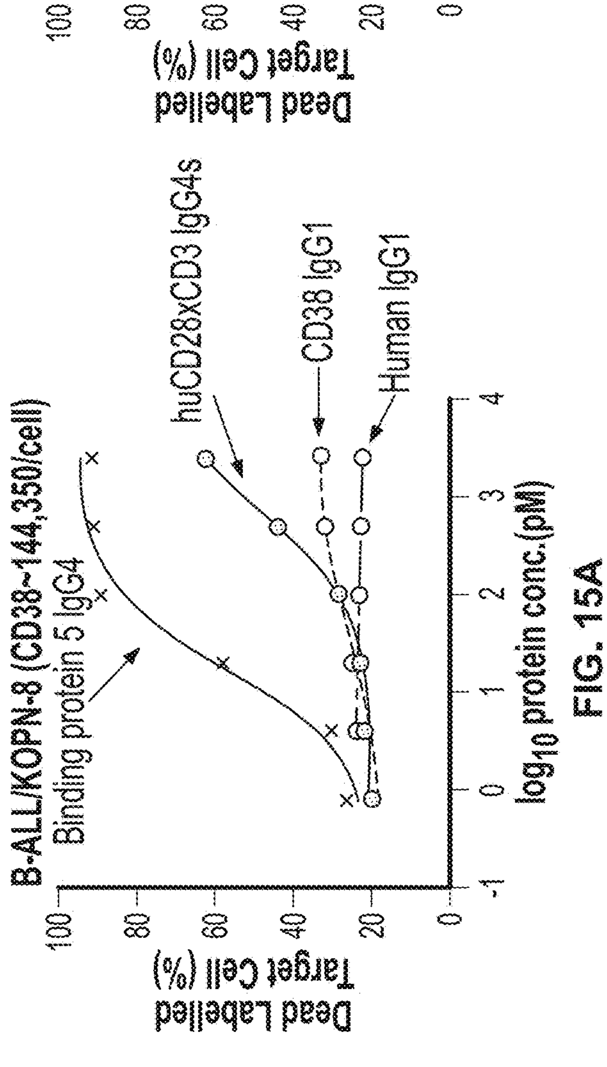
FIG. 15A
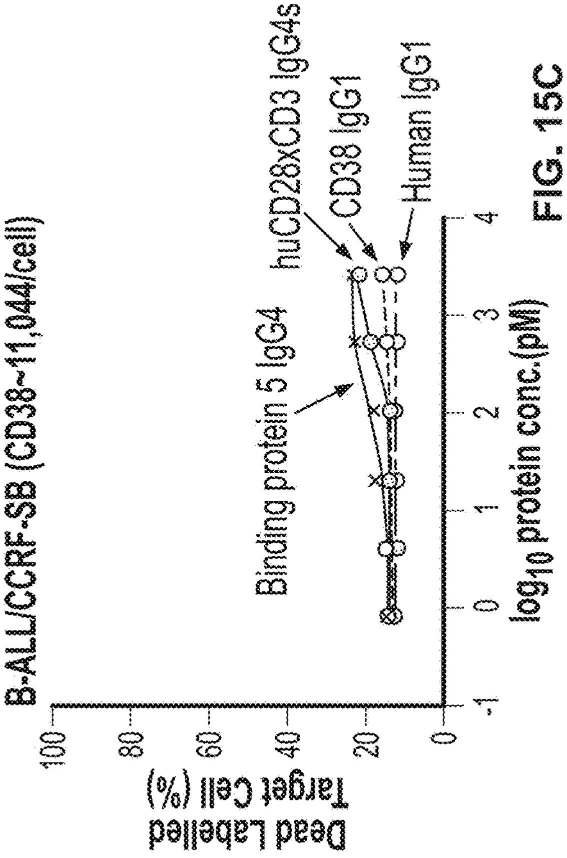
FIG. 15C 5 hr stimulation Anti-hCD8

Anti-hCD4

Binding Protein 9
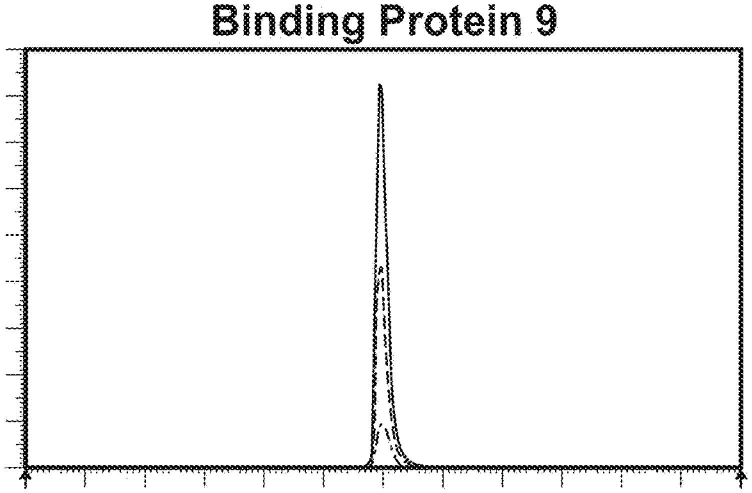
Binding Protein 10
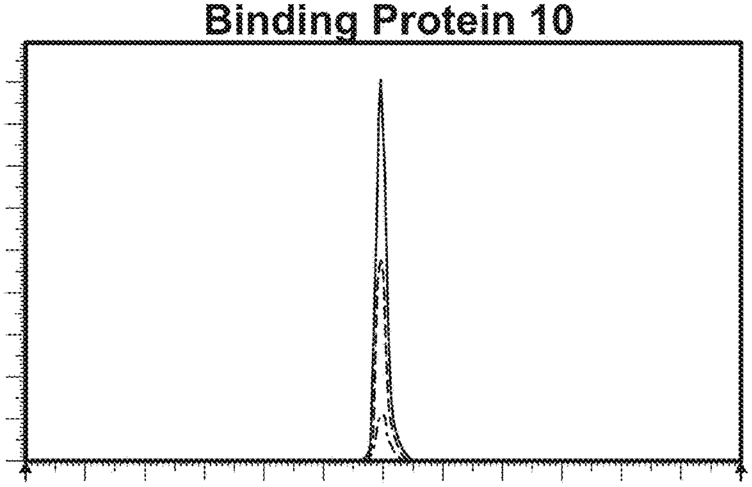
Binding Protein 11
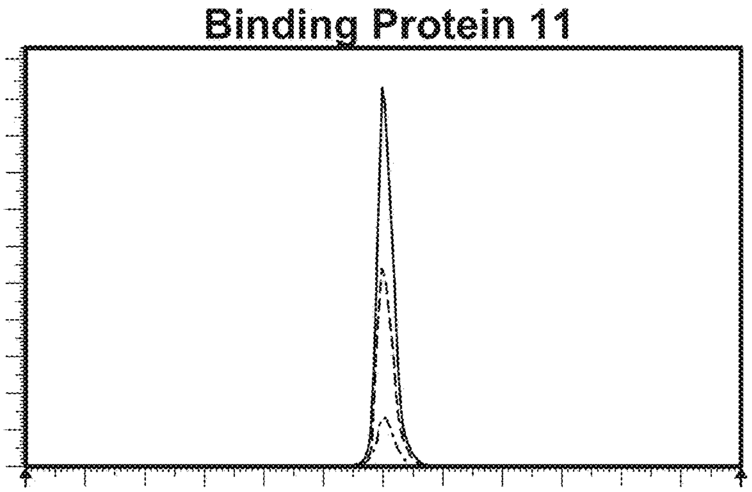
FIG. 27A Binding Protein 12
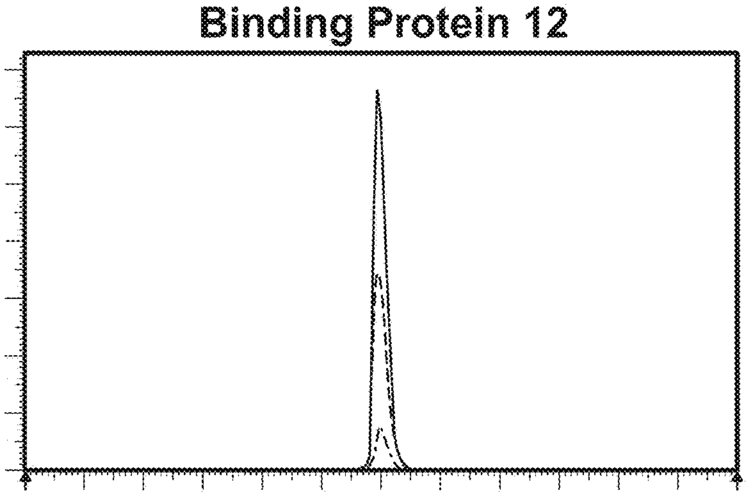
Binding Protein 13
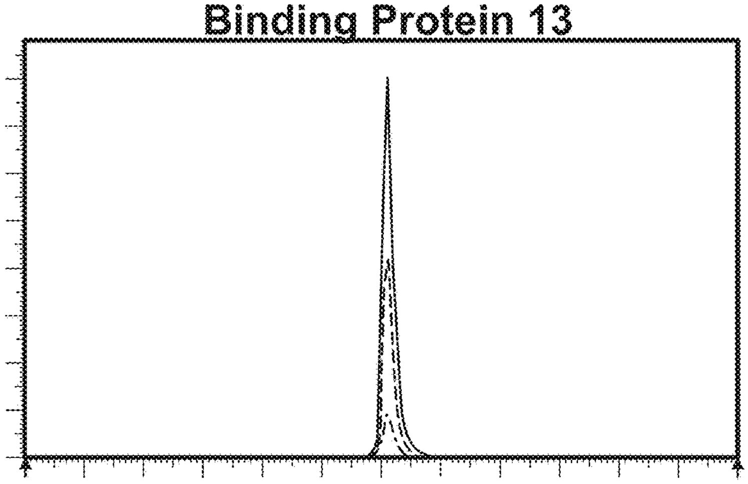
Binding Protein 14
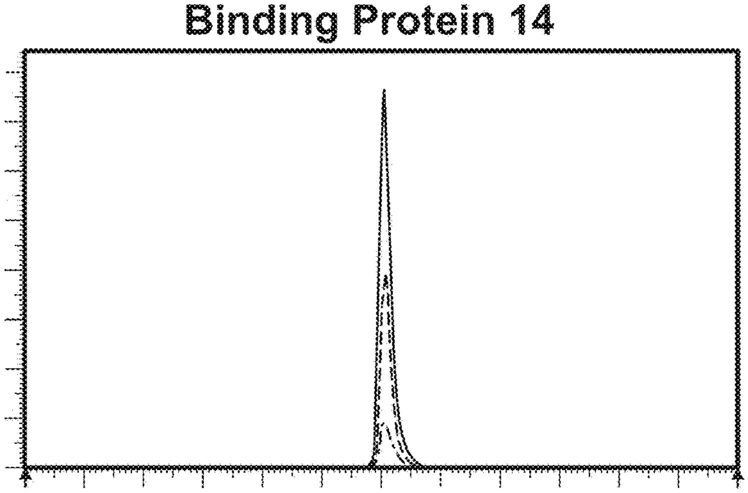
FIG. 27A (Cont.)

Binding Protein 15

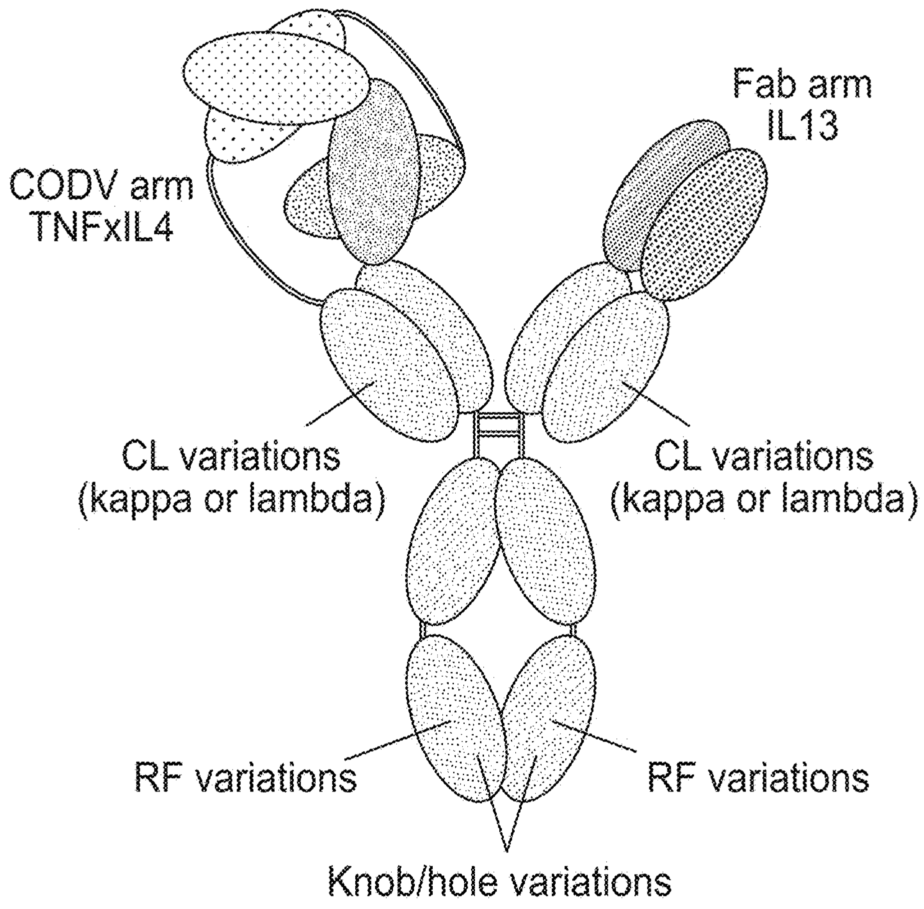

FIG. 28A

| CODV-arm | Fab-arm | CODV-arm | Fab-arm | RF mutation |
|---|---|---|---|---|
| Kappa | Kappa | Hole | Knob | no RF |
| Kappa | Kappa | Hole | Knob | Hole |
| Kappa | Kappa | Hole | Knob | Knob |
| Kappa | lambda | Knob | Hole | no RF |
| Kappa | lambda | Knob | Hole | Hole |
| Kappa | lambda | Knob | Hole | Knob |
| lambda | Kappa | Knob | Hole | no RF |
| lambda | Kappa | Knob | Hole | Hole |
| lambda | Kappa | Knob | Hole | Knob |
| Kappa | Kappa | Knob | Hole | no RF |
| Kappa | Kappa | Knob | Hole | Hole |
| Kappa | Kappa | Knob | Hole | Knob |
| Kappa | lambda | Hole | Knob | no RF |
| Kappa | lambda | Hole | Knob | Hole |
| Kappa | lambda | Hole | Knob | Knob |
| lambda | Kappa | Hole | Knob | no RF |
| lambda | Kappa | Hole | Knob | Hole |
| lambda | Kappa | Hole | Knob | Knob |

FIG. 28B

TRISPECIFIC AND/OR TRIVALENT BINDING PROTEINS

CROSS REFERENCES TO RELATED APPLICATIONS

This application claims the priority benefit of U.S. Provisional Application Ser. No. 62/322,036, filed Apr. 13, 2016; U.S. Provisional Application Ser. No. 62/331,191, filed May 3, 2016; U.S. Provisional Application Ser. No. 62/412,187, filed Oct. 24, 2016; and EP Application No. EP17305298.6, filed Mar. 17, 2017; which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 183952027100SEQLISTING.txt, date recorded: Apr. 12, 2017, size: 200 KB).

FIELD OF THE INVENTION

The disclosure relates to trispecific and/or trivalent binding proteins comprising four polypeptide chains that form three antigen binding sites that specifically bind one or more target proteins, wherein a first pair of polypeptides forming the binding protein possess dual variable domains having a cross-over orientation and wherein a second pair of polypeptides forming the binding protein possess a single variable domain. The disclosure also relates to methods for making trispecific and/or trivalent binding proteins and uses of such binding proteins.

BACKGROUND

Monoclonal antibody based biotherapeutics have become an important avenue for new drug development. Monoclonal antibody technology offers specific targeting, precise signaling delivery and/or payload to specific cell population, and provides long lasting biological effect through its Fc functions. Efforts in antibody engineering have allowed developing bispecific antibodies combining the specificities of two monoclonal antibodies for various biological applications, expanding the scope of antibody drug development. Newly discovered neutralizing antibodies with improved breadth and potency may provide more options for developing biotherapeutics to treat complexed diseases such as cancer, arthritis, and/or inflammatory disorders.

BRIEF SUMMARY

Provided herein are multispecific binding proteins (e.g., antibodies) that form three antigen binding sites. These binding proteins can specifically bind one, two, or three antigen targets or target proteins.

In one embodiment, the disclosure provides a binding protein comprising four polypeptide chains that form three antigen binding sites that specifically bind one or more antigen targets or target proteins, wherein a first polypeptide chain has a structure represented by the formula:

$$V_{L2}\text{-}L_1\text{-}V_{L1}\text{-}L_2\text{-}C_L \quad [I]$$

and a second polypeptide chain has a structure represented by the formula:

$$V_{H1}\text{-}L_3\text{-}V_{H2}\text{-}L_4\text{-}C_{H1} \quad [II]$$

and a third polypeptide chain has a structure represented by the formula:

$$V_{H3}\text{-}C_{H1} \quad [III]$$

and a fourth polypeptide chain has a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

and wherein the polypeptide of formula I and the polypeptide of formula II form a cross-over light chain-heavy chain pair.

In some embodiments, the second and/or third polypeptide chain further comprises an Fc region linked to $C_{H1}$, the Fc region comprising an immunoglobulin hinge region and $C_{H2}$ and $C_{H3}$ immunoglobulin heavy chain constant domains.

In another embodiment, the disclosure provides a binding protein comprising four polypeptide chains that form three antigen binding sites that specifically bind one or more target proteins, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}L_{H2}\text{-}L_4\text{-}C_{H1}\text{-hinge-}C_{H2}\text{-}C_{H3} \quad [II]$$

and a third polypeptide chain comprises a structure represented by the formula:

$$V_{H3}\text{-}C_{H1}\text{-hinge-}C_{H2}\text{-}C_{H3} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

and wherein the polypeptide of formula I and the polypeptide of formula II form a cross-over light chain-heavy chain pair.

In some embodiments, the binding protein is trispecific and capable of specifically binding three different antigen targets. In some embodiments, the binding protein is trivalent but bispecific and capable of specifically binding three antigen targets, two of them being identical. In some embodiments, the binding protein of the present disclosure is trivalent but monospecific and capable of specifically binding three antigen targets, all of them being identical. In some embodiments, the binding protein is capable of inhibiting the function of one or more target proteins. In some embodiments, the binding protein is trispecific and capable of specifically binding three different antigen targets.

In some embodiments, a binding protein of the present disclosure comprises one, two, or three antigen binding sites that specifically bind a target protein selected from A2AR, APRIL, ATPDase, BAFF, BAFFR, BCMA, BlyS, BTK, BTLA, B7DC, B7H1, B7H4 (also known as VTCN1), B7H5, B7H6, B7H7, B7RP1, B7-4, C3, C5, CCL2 (also known as MCP-1), CCL3 (also known as MIP-1a), CCL4 (also known as MIP-1b), CCL5 (also known as RANTES), CCL7 (also known as MCP-3), CCL8 (also known as mcp-2), CCL11 (also known as eotaxin), CCL15 (also known as MIP-1d), CCL17 (also known as TARC), CCL19 (also known as MIP-3b), CCL20 (also known as MIP-3a), CCL21 (also known as MIP-2), CCL24 (also known as MPIF-2/eotaxin-2), CCL25 (also known as TECK), CCL26 (also known as eotaxin-3), CCR3, CCR4, CD3, CD19, CD20, CD23 (also known as FCER2, a receptor for IgE), CD24, CD27, CD28, CD38, CD39, CD40, CD70, CD80 (also known as B7-1), CD86 (also known as B7-2), CD122, CD137 (also known as 41BB), CD137L, CD152 (also known as CTLA4), CD154 (also known as CD40L), CD160, CD272, CD273 (also known as PDL2), CD274 (also known as PDL1), CD275 (also known as B7H2), CD276 (also known as B7H3), CD278 (also known as ICOS), CD279 (also known as PD-1), CDH1 (also known as E-cadherin), chitinase, CLEC9, CLEC91, CRTH2, CSF-1 (also known as M-CSF), CSF-2 (also known as GM-CSF), CSF-3 (also known as GCSF), CX3CL1 (also known as SCYD1), CXCL12 (also known as SDF1), CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb (also known as a receptor for IL25), IL18, IL22, IL23, IL25, IL27, IL33, IL35, ITGB4 (also known as b4 integrin), ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2 (also known as a receptor for IL33), STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP (also known as a co-receptor for IL7Ra), TSLPR, TWEAK, VEGF, VISTA, Vstm3, WUCAM, and XCR1 (also known as GPR5/CCXCR1). In some embodiments, one or more of the above antigen targets are human antigen targets. In some embodiments, the binding protein of the present disclosure is trispecific and capable of specifically binding three different antigen targets selected from the above list. In some embodiments, the binding protein of the present disclosure is trivalent but bispecific and capable of specifically binding three antigen targets selected from the above list, two of them being identical. In some embodiments, the binding protein of the present disclosure is trivalent but monospecific and capable of specifically binding three antigen targets selected from the above list, all of them being identical. In some embodiments, the binding protein specifically binds three target proteins that correspond to two target proteins on T cells and to one tumor target protein. In some embodiments, one of said target proteins on T cells is CD3. In some embodiments, one of said target proteins on T cells is CD28. In some embodiments, said tumor target protein is CD38. In some embodiments, the binding protein specifically binds three target proteins that correspond to two target proteins on T cells and to one target protein selected from the group consisting of A2AR, APRIL, ATPDase, BAFF, BAFFR, BCMA, BlyS, BTK, BTLA, B7DC, B7H1, B7H4, B7H5, B7H6, B7H7, B7RP1, B7-4, C3, C5, CCL2, CCL3, CCL4, CCL5, CCL7, CCL8, CCL11, CCL15, CCL17, CCL19, CCL20, CCL21, CCL24, CCL25, CCL26, CCR3, CCR4, CD3, CD19, CD20, CD23, CD24, CD27, CD28, CD38, CD39, CD40, CD70, CD80, CD86, CD122, CD137, CD137L, CD152, CD154, CD160, CD272, CD273, CD274, CD275, CD276, CD278, CD279, CDH1, chitinase, CLEC9, CLEC91, CRTH2, CSF-1, CSF-2, CSF-3, CX3CL1, CXCL12, CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb, IL18, IL22, IL23, IL25, IL27, IL33, IL35, ITGB4, ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2, STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP, TSLPR, TWEAK, VEGF, VISTA, Vstm3, WUCAM, and XCR1.

In another embodiment, the disclosure provides a binding protein comprising four polypeptide chains that form three antigen binding sites, wherein a first polypeptide chain has a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}V_{H2}\text{-}L_4\text{-}C_{H1} \quad [II]$$

and a third polypeptide chain comprises a structure represented by the formula:

$$V_{H3}\text{-}C_{H1} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$L_1$, $L_2$, $L_3$ and $L_4$ are amino acid linkers;

wherein the polypeptide of formula I and the polypeptide of formula II form a cross-over light chain-heavy chain pair.

wherein:

(a) $V_{L1}$, $V_{L2}$ and $V_{L3}$ are each independently a variable domain derived from an amino acid sequence as set forth in any one of SEQ ID NOs: 2, 4, 10, 14, 18, 22, 115;

(b) $V_{L1}$, $V_{L2}$ and $V_{L3}$ each independently comprise light chain complementarity determining regions of a variable domain comprising an amino acid sequence as set forth in any one of SEQ ID NOs: 43-59, 123-125;

(c) $V_{L1}$, $V_{L2}$ and $V_{L3}$ each independently comprise a variable domain sequence as set forth in any one of SEQ ID NOs:151, 153, 155, 157, 159, 161, 163, 165, and 167;

(d) $V_{L1}$, $V_{L2}$ and $V_{L3}$ each independently comprise light chain complementarity determining regions comprising an amino acid sequence as set forth in any one of SEQ ID NOs: 43-59, 123-125, 138-140, and 149; or (e) $V_{L1}$, $V_{L2}$ and $V_{L3}$ each independently comprise light chain complementarity determining regions and/or a variable domain sequence shown in Tables 2-5; and wherein:

(a) $V_{H1}$, $V_{H2}$, and $V_{H3}$ are each independently a variable domain derived from an amino acid sequence as set forth in any one of SEQ ID NOs: 1, 3, 9, 13, 17, 21, 114;

(b) $V_{H1}$, $V_{H2}$ and $V_{H3}$ each independently comprise heavy chain complementarity determining regions of a variable domain comprising an amino acid sequence as set forth in any one of SEQ ID NOs: 25-42, 120-122;

(c) $V_{H1}$, $V_{H2}$, and $V_{H3}$ each independently comprise a variable domain sequence as set forth in any one of SEQ ID NOs:150, 152, 154, 156, 158, 160, 162, 164, and 166;

(d) $V_{H1}$, $V_{H2}$ and $V_{H3}$ each independently comprise heavy chain complementarity determining regions comprising an amino acid sequence as set forth in any one of SEQ ID NOs: 25-42, 120-122, and 126-128; or (e) $V_{H1}$, $V_{H2}$ and $V_{H3}$ each independently comprise heavy chain complementarity determining regions and/or a variable domain sequence shown in Tables 2-5.

In some embodiments, the second and/or third polypeptide chain further comprises an Fc region linked to $C_{H1}$, the Fc region comprising an immunoglobulin hinge region and $C_{H2}$ and $C_{H3}$ immunoglobulin heavy chain constant domains.

In another embodiment, the disclosure provides a binding protein comprising four polypeptide chains that form three antigen binding sites, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}L_{H2}\text{-}L_4\text{-}C_{H1}\text{-hinge-}C_{H2}\text{-}C_{H3} \quad [II]$$

and a third polypeptide chain comprises a structure represented by the formula:

$$V_{H3}\text{-}C_{H1}\text{-hinge-}C_{H2}\text{-}C_{H3} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair;

wherein:

(a) $V_{L1}$, $V_{L2}$ and $V_{L3}$ are each independently a variable domain derived from an amino acid sequence as set forth in any one of SEQ ID NOs: 2, 4, 10, 14, 18, 22, 115;

(b) $V_{L1}$, $V_{L2}$ and $V_{L3}$ each independently comprise light chain complementarity determining regions of a variable domain comprising an amino acid sequence as set forth in any one of SEQ ID NOs: 43-59, 123-125;

(c) $V_{L1}$, $V_{L2}$ and $V_{L3}$ each independently comprise a variable domain sequence as set forth in any one of SEQ ID NOs:151, 153, 155, 157, 159, 161, 163, 165, and 167;

(d) $V_{L1}$, $V_{L2}$ and $V_{L3}$ each independently comprise light chain complementarity determining regions comprising an amino acid sequence as set forth in any one of SEQ ID NOs: 43-59, 123-125, 138-140, and 149; or (e) $V_{L1}$, $V_{L2}$ and $V_{L3}$ each independently comprise light chain complementarity determining regions and/or a variable domain sequence shown in Tables 2-5;

wherein:

(a) $V_{H1}$, $V_{H2}$, and $V_{H3}$ are each independently a variable domain derived from an amino acid sequence as set forth in any one of SEQ ID NOs: 1, 3, 9, 13, 17, 21, 114;

(b) $V_{H1}$, $V_{H2}$ and $V_{H3}$ each independently comprise heavy chain complementarity determining regions of a variable domain comprising an amino acid sequence as set forth in any one of SEQ ID NOs: 25-42, 120-122;

(c) $V_{H1}$, $V_{H2}$, and $V_{H3}$ each independently comprise a variable domain sequence as set forth in any one of SEQ ID NOs:150, 152, 154, 156, 158, 160, 162, 164, and 166;

(d) $V_{H1}$, $V_{H2}$ and $V_{H3}$ each independently comprise heavy chain complementarity determining regions comprising an amino acid sequence as set forth in any one of SEQ ID NOs: 25-42, 120-122, and 126-128; or (e) $V_{H1}$, $V_{H2}$ and $V_{H3}$ each independently comprise heavy chain complementarity determining regions and/or a variable domain sequence shown in Tables 2-5.

In some embodiments, $V_{L1}$, $V_{L2}$ and $V_{L3}$ each independently comprise a variable domain sequence as set forth in any one of SEQ ID NOs:151, 153, 155, 157, 159, 161, 163, 165, and 167; and $V_{H1}$, $V_{H2}$, and $V_{H3}$ each independently comprise a variable domain sequence as set forth in any one of SEQ ID NOs:150, 152, 154, 156, 158, 160, 162, 164, and 166. In some embodiments, $V_{L1}$, $V_{L2}$ and $V_{L3}$ each independently comprise light chain complementarity determining regions comprising an amino acid sequence as set forth in any one of SEQ ID NOs: 43-59, 123-125, 138-140, and 149; and (d) $V_{H1}$, $V_{H2}$ and $V_{H3}$ each independently comprise heavy chain complementarity determining regions comprising an amino acid sequence as set forth in any one of SEQ ID NOs: 25-42, 120-122, and 126-128.

In some embodiments of any of the binding proteins described herein, (a) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and $V_{L3}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45; (b) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and $V_{L3}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45; (c) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:37, a CDR-H2 comprising the amino acid sequence of SEQ ID NO:38, and a CDR-H3 comprising the amino acid sequence of SEQ ID NO:39; and $V_{L3}$ comprises a CDR-L1 comprising the amino acid sequence of SEQ ID NO:55, a CDR-L2 comprising the amino acid sequence of SEQ ID NO:56, and a CDR-L3 comprising the amino acid sequence of SEQ ID NO:57; (d) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:37, a CDR-H2 comprising the amino acid sequence of SEQ ID NO:38, and a CDR-H3 comprising the amino acid sequence of SEQ ID NO:39; and $V_{L3}$ comprises a CDR-L1 comprising the amino acid sequence of SEQ ID NO:55, a CDR-L2 comprising the amino acid sequence of SEQ ID NO:56, and a CDR-L3 comprising the amino acid sequence of SEQ ID NO:57; (e) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:40, a CDR-H2 comprising the amino acid sequence of SEQ ID NO:41, and a CDR-H3 comprising the amino acid sequence of SEQ ID NO:42; and $V_{L3}$ comprises a CDR-L1 comprising the amino acid sequence of SEQ ID NO:58, a CDR-L2 comprising the amino acid sequence of SEQ ID NO:44, and a CDR-L3 comprising the amino acid sequence of SEQ ID NO:59; (f) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:40, a CDR-H2 comprising the amino acid sequence of SEQ ID NO:41, and a CDR-H3 comprising the amino acid sequence of SEQ ID NO:42; and $V_{L3}$ comprises a CDR-L1 comprising the amino acid sequence of SEQ ID NO:58, a CDR-L2 comprising the amino acid sequence of SEQ ID NO:44, and a CDR-L3 comprising the amino acid sequence of SEQ ID NO:59; (g) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:126, a CDR-H2 comprising the amino acid sequence of SEQ ID NO:127, and a CDR-H3 comprising the amino acid sequence of SEQ ID NO:128; and $V_{L3}$ comprises a CDR-L1 comprising the amino acid sequence of SEQ ID NO:138, a CDR-L2 comprising the amino acid sequence of SEQ ID NO:139, and a CDR-L3 comprising the amino acid sequence of SEQ ID NO:140; (h) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:126, a CDR-H2 comprising the amino acid sequence of SEQ ID NO:127, and a CDR-H3 comprising the amino acid sequence of SEQ ID NO:128; and $V_{L3}$ comprises a CDR-L1 comprising the amino acid sequence of SEQ ID NO:138, a CDR-L2 comprising the amino acid sequence of SEQ ID NO:139, and a CDR-L3 comprising the amino acid sequence of SEQ ID NO:140; (i) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:120, a CDR-H2 comprising the amino acid sequence of SEQ ID NO:121, and a CDR-H3 comprising the amino acid sequence of SEQ ID NO:122; and $V_{L3}$ comprises a CDR-L1 comprising the amino acid sequence of SEQ ID NO:123, a CDR-L2 comprising the amino acid sequence of SEQ ID NO:124, and a CDR-L3 comprising the amino acid sequence of SEQ ID NO:125; or (j) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:120, a CDR-H2 comprising the amino acid sequence of SEQ ID NO:121, and a CDR-H3 comprising the amino acid sequence of SEQ ID NO:122; and $V_{L3}$ comprises a CDR-L1 comprising the amino acid sequence of SEQ ID NO:123, a CDR-L2 comprising the amino acid sequence of SEQ ID NO:124, and a CDR-L3 comprising the amino acid sequence of SEQ ID NO:125. In some embodiments, (a) $V_{H1}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L1}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H2}$ comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; $V_{L2}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45; $V_{H3}$ comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and $V_{L3}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45.

In some embodiments, the binding protein comprises one antigen binding site that specifically binds a T-cell surface protein and another antigen binding site that specifically binds an antigen target, e.g., a tumor target protein. In some embodiments, the binding protein comprises an antigen binding site that specifically binds CD3, an antigen binding site that specifically binds CD28, and an antigen binding site that specifically binds a tumor target protein selected from the group consisting of CD19, CD20, CD38, Her2, and LAMP1. In some embodiments, $V_{H1}$ and $V_{L1}$ form a first antigen binding site that specifically binds human CD3, $V_{H2}$ and $V_{L2}$ form a second antigen binding site that specifically binds human CD28, and $V_{H3}$ and $V_{L3}$ form a third antigen binding site that specifically binds a human tumor target protein. In some embodiments, $V_{H1}$ and $V_{L1}$ form a first antigen binding site that specifically binds human CD28, $V_{H2}$ and $V_{L2}$ form a second antigen binding site that specifically binds human CD3, and $V_{H3}$ and $V_{L3}$ form a third binding site that specifically binds a human tumor target protein. In some embodiments, the antigen binding site specifically binds a human tumor target protein selected from the group consisting of CD19, CD20, CD38, Her2, and LAMP1. In some embodiments, the antigen binding site that specifically binds CD3 comprises: (a) a heavy chain variable domain comprising the amino acid sequence of SEQ ID NO: 152 and a light chain variable domain comprising the amino acid sequence of SEQ ID NO: 153; or (b) a heavy chain variable domain comprising the amino acid sequence of SEQ ID NO: 154 and a light chain variable domain comprising the amino acid sequence of SEQ ID NO: 155. In some embodiments, the antigen binding site that specifically binds CD3 comprises six CDRs, or a heavy chain and a light chain variable domain, shown in Tables 2-5. In some embodiments, the antigen binding site that specifically binds CD28 comprises: (a) a heavy chain variable domain comprising the amino acid sequence of SEQ ID NO: 160 and a light chain variable domain comprising the amino acid sequence of SEQ ID NO: 161; or (b) a heavy chain variable domain comprising the amino acid sequence of SEQ ID NO: 162 and a light chain variable domain comprising the amino acid sequence of SEQ ID NO: 163. In some embodiments, the antigen binding site that specifically binds CD28 comprises six CDRs, or a heavy chain and a light chain variable domain, shown in Tables 2-5. In some embodiments, the antigen binding site that specifically binds a tumor target protein comprises: (a) a heavy chain variable domain comprising the amino acid sequence of SEQ ID NO: 156 and a light chain variable domain comprising the amino acid sequence of SEQ ID NO: 157; (b) a heavy chain variable domain comprising the amino acid sequence of SEQ ID NO: 158 and a light chain variable domain comprising the amino acid sequence of SEQ ID NO: 159; (c) a heavy chain variable domain comprising the amino acid sequence of SEQ ID NO: 164 and a light chain variable domain comprising the amino acid sequence of SEQ ID NO: 165; (d) a heavy chain variable domain comprising the amino acid sequence of SEQ ID NO: 150 and a light chain variable domain comprising the amino acid sequence of SEQ ID NO: 151; or (e) a heavy chain variable domain comprising the amino acid sequence of SEQ ID NO: 166 and a light chain variable domain comprising the amino acid sequence of SEQ ID NO: 167. In some embodiments, the antigen binding site that specifically binds a tumor target protein comprises six CDRs, or a heavy chain and a light chain variable domain, shown in Tables 2-5. In some embodiments, the antigen binding site that specifically binds a tumor target protein comprises six CDRs, or a heavy chain and a light chain variable domain, of an anti-Her2, anti-CD19, anti-CD20, anti-CD38, or anti-LAMP1 binding domain shown in Tables 2-5.

In another embodiment, the disclosure provides a binding protein comprising four polypeptide chains that form three antigen binding sites, wherein a first polypeptide chain has a structure represented by the formula:

$$V_{L2}\text{-}L_1\text{-}V_{L1}\text{-}L_2\text{-}C_L \quad [I]$$

and a second polypeptide chain has a structure represented by the formula:

$$V_{H1}\text{-}L_3\text{-}V_{H2}\text{-}L_4\text{-}C_{H1} \quad [II]$$

and a third polypeptide chain has a structure represented by the formula:

$$V_{H3}\text{-}C_{H1} \quad [III]$$

and a fourth polypeptide chain has a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

wherein the polypeptide of formula I and the polypeptide of formula II form a cross-over light chain-heavy chain pair.

wherein:

(a) $V_{L1}$, $V_{L2}$ and $V_{L3}$ are each independently a variable domain derived from an amino acid sequence as set forth in any one of SEQ ID NOs: 61, 63, 69, 71, 74, 76, 82, 86, 88, 94; or (b) $V_{L1}$, $V_{L2}$ and $V_{L3}$ each independently comprise light chain complementarity determining regions of a variable domain of at least one amino acid sequence set forth in any one of SEQ ID NOs: 61, 63, 69, 71, 74, 76, 82, 86, 88, 94;

(c) $V_{L1}$, $V_{L2}$ and $V_{L3}$ each independently comprise a variable domain sequence as set forth in any one of SEQ ID NOs:169, 171, and 173;

(d) $V_{L1}$, $V_{L2}$ and $V_{L3}$ each independently comprise light chain complementarity determining regions comprising an amino acid sequence selected from the group consisting of SEQ ID NOs: 141-147, 178, and 179; or (e) $V_{L1}$, $V_{L2}$ and $V_{L3}$ each independently comprise light chain complementarity determining regions and/or a variable domain sequence shown in Tables 2-5; and wherein:

(a) $V_{H1}$, $V_{H2}$, and $V_{H3}$ are each independently a variable domain derived from an amino acid sequence as set forth in any one of SEQ ID NOs: 60, 62, 68, 73, 75, 81, 85, 87, 93; or (b) $V_{H1}$, $V_{H2}$, and $V_{H3}$ each independently comprise heavy chain complementarity determining regions of a variable domain of at least one amino acid sequence set forth in any one of in any one of SEQ ID NOs: 60, 62, 68, 73, 75, 81, 85, 87, 93;

(c) $V_{H1}$, $V_{H2}$, and $V_{H3}$ each independently comprise a variable domain sequence as set forth in any one of SEQ ID NOs:168, 170, and 172;

(d) $V_{H1}$, $V_{H2}$ and $V_{H3}$ each independently comprise heavy chain complementarity determining regions comprising an amino acid sequence selected from the group consisting of SEQ ID NOs: 129-137; or (e) $V_{H1}$, $V_{H2}$ and $V_{H3}$ each independently comprise heavy chain complementarity determining regions and/or a variable domain sequence shown in Tables 2-5.

In some embodiments, the second and/or third polypeptide chain further comprises an Fc region linked to $C_{H1}$, the Fc region comprising an immunoglobulin hinge region and $C_{H2}$ and $C_{H3}$ immunoglobulin heavy chain constant domains.

In another embodiment, the disclosure provides a binding protein comprising four polypeptide chains that form three antigen binding sites, wherein a first polypeptide chain comprises a structure represented by the formula:

$$V_{L2}\text{-}L_1\text{-}V_{L1}\text{-}L_2\text{-}C_L \qquad [I]$$

and a second polypeptide chain comprises a structure represented by the formula:

$$V_{H1}\text{-}L_3\text{-}L_{H2}\text{-}L_4\text{-}C_{H1}\text{-hinge-}C_{H2}\text{-}C_{H3} \qquad [II]$$

and a third polypeptide chain comprises a structure represented by the formula:

$$V_{H3}\text{-}C_{H1}\text{-hinge-}C_{H2}\text{-}C_{H3} \qquad [III]$$

and a fourth polypeptide chain comprises a structure represented by the formula:

$$V_{L3}\text{-}C_L \qquad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair;

wherein:

(a) $V_{L1}$, $V_{L2}$ and $V_{L3}$ are each independently a variable domain derived from an amino acid sequence as set forth in any one of SEQ ID NOs: 61, 63, 69, 71, 74, 76, 82, 86, 88, 94;

(b) $V_{L1}$, $V_{L2}$ and $V_{L3}$ each independently comprise light chain complementarity determining regions of a variable domain of at least one amino acid sequence set forth in any one of SEQ ID NOs: 61, 63, 69, 71, 74, 76, 82, 86, 88, 94;

(c) $V_{L1}$, $V_{L2}$ and $V_{L3}$ each independently comprise a variable domain sequence as set forth in any one of SEQ ID NOs:169, 171, and 173;

(d) $V_{L1}$, $V_{L2}$ and $V_{L3}$ each independently comprise light chain complementarity determining regions comprising an amino acid sequence selected from the group consisting of SEQ ID NOs: 141-147, 178, and 179; or (e) $V_{L1}$, $V_{L2}$ and $V_{L3}$ each independently comprise light chain complementarity determining regions and/or a variable domain sequence shown in Tables 2-5;

wherein:

(a) $V_{H1}$, $V_{H2}$, and $V_{H3}$ are each independently a variable domain derived from an amino acid sequence as set forth in any one of SEQ ID NOs: 60, 62, 68, 73, 75, 81, 85, 87, 93;

(b) $V_{H1}$, $V_{H2}$, and $V_{H3}$ each independently comprise heavy chain complementarity determining regions of a variable domain of at least one amino acid sequence set forth in any one of in any one of SEQ ID NOs: 60, 62, 68, 73, 75, 81, 85, 87, 93;

(c) $V_{H1}$, $V_{H2}$, and $V_{H3}$ each independently comprise a variable domain sequence as set forth in any one of SEQ ID NOs:168, 170, and 172;

(d) $V_{H1}$, $V_{H2}$ and $V_{H3}$ each independently comprise heavy chain complementarity determining regions comprising an amino acid sequence selected from the group consisting of SEQ ID NOs: 129-137;

(e) $V_{H1}$, $V_{H2}$ and $V_{H3}$ each independently comprise heavy chain complementarity determining regions and/or a variable domain sequence shown in Tables 2-5.

In some embodiments, $V_{L1}$, $V_{L2}$ and $V_{L3}$ each independently comprise a variable domain sequence as set forth in any one of SEQ ID NOs:169, 171, and 173; and $V_{H1}$, $V_{H2}$, and $V_{H3}$ each independently comprise a variable domain sequence as set forth in any one of SEQ ID NOs:168, 170, and 172. In some embodiments, $V_{L1}$, $V_{L2}$ and $V_{L3}$ each independently comprise light chain complementarity determining regions comprising an amino acid sequence selected from the group consisting of SEQ ID NOs: 141-147, 178, and 179; and $V_{H1}$, $V_{H2}$ and $V_{H3}$ each independently comprise heavy chain complementarity determining regions comprising an amino acid sequence selected from the group consisting of SEQ ID NOs: 129-137.

In some embodiments of any of the binding proteins described herein, (a) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; and $V_{L3}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; (b) $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; and $V_{L3}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; (c) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L2}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; (d) $V_{H1}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L1}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; (e) $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L2}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; (f) $V_{H1}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L1}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; (g)

$V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; (h) $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; (i) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; or (j) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144. In some embodiments, one or more of $V_{H1}$, $V_{L1}$, $V_{H2}$, $V_{L2}$, $V_{H3}$, and $V_{L3}$ comprises one, two, or three CDR sequences of an antibody shown in Tables 2-5.

In some embodiments, the binding protein comprises three antigen binding sites, where one, two, or three of the antigen binding site(s) specifically bind(s) a cytokine target protein selected from the group consisting of IL-4, IL-13 and TNFa. In some embodiments, (a) $V_{H1}$ and $V_{L1}$ form a first antigen binding site that specifically binds human TNFa, $V_{H2}$ and $V_{L2}$ form an antigen binding site that specifically binds human IL13, and $V_{H3}$ and $V_{L3}$ form an antigen binding site that specifically binds human IL4; (b) $V_{H1}$ and $V_{L1}$ form a first antigen binding site that specifically binds human TNFa, $V_{H2}$ and $V_{L2}$ form a second antigen binding site that specifically binds human IL4, and $V_{H3}$ and $V_{L3}$ form a third antigen binding site that specifically binds human IL13; (c) $V_{H1}$ and $V_{L1}$ form a first antigen binding site that specifically binds human IL4, $V_{H2}$ and $V_{L2}$ form a second antigen binding site that specifically binds human TNFa, and $V_{H3}$ and $V_{L3}$ form a third antigen binding site that specifically binds human IL13; (d) $V_{H1}$ and $V_{L1}$ form a first antigen binding site that specifically binds human IL4, $V_{H2}$ and $V_{L2}$ form a second antigen binding site that specifically binds human IL13, and $V_{H3}$ and $V_{L3}$ form a third antigen binding site that specifically binds human TNFa; (e) $V_{H1}$ and $V_{L1}$ form a first antigen binding site that specifically binds human IL13, $V_{H2}$ and $V_{L2}$ form a second antigen binding site that specifically binds human IL4, and $V_{H3}$ and $V_{L3}$ form a third antigen binding site that specifically binds human TNFa; or (f) $V_{H1}$ and $V_{L1}$ form a first antigen binding site that specifically binds human IL13, $V_{H2}$ and $V_{L2}$ form a second antigen binding site that specifically binds human TNFa, and $V_{H3}$ and $V_{L3}$ form a third antigen binding site that specifically binds human IL4. In some embodiments, the antigen binding site that specifically binds human TNFa comprises a heavy chain variable domain comprising the amino acid sequence of SEQ ID NO:168 and a light chain variable domain comprising the amino acid sequence of SEQ ID NO:169. In some embodiments, the antigen binding site that specifically binds human IL4 comprises a heavy chain variable domain comprising the amino acid sequence of SEQ ID NO:170 and a light chain variable domain comprising the amino acid sequence of SEQ ID NO:171. In some embodiments, the antigen binding site that specifically binds human IL13 comprises a heavy chain variable domain comprising the amino acid sequence of SEQ ID NO:172 and a light chain variable domain comprising the amino acid sequence of SEQ ID NO:173.

In some embodiments of any of the binding proteins described herein, the second and/or third polypeptide chain further comprises an Fc region linked to $C_{H1}$, the Fc region comprising an immunoglobulin hinge region and $C_{H2}$ and $C_{H3}$ immunoglobulin heavy chain constant domains. In some embodiments, at least one of $L_1$, $L_2$, $L_3$ or $L_4$ is independently 0 amino acids in length. In some embodiments, $L_1$, $L_2$, $L_3$ $_{or}$ $L_4$ are each independently at least one amino acid in length. In some embodiments, the binding protein is trispecific and capable of specifically binding three different antigen targets. In some embodiments, the binding protein is trispecific and capable of specifically binding three different antigen targets. In some embodiments, the binding protein is capable of inhibiting the function of one or more target proteins.

In some embodiments of any of the binding proteins described herein, at least one of $L_1$, $L_2$, $L_3$ or $L_4$ is independently 0 amino acids in length. In some embodiments, $L_1$, $L_2$, $L_3$ or $L_4$ are each independently at least one amino acid in length. In some embodiments, one, two, three, or all four of $L_1$, $L_2$, $L_3$ and $L_4$ are between 0 and 15 amino acids in length. In some embodiments, at least two of $L_1$, $L_2$, $L_3$ and $L_4$ are between 1 and 15 amino acids in length. In some embodiments, (a) $L_1$, $L_2$, $L_3$ and $L_4$ each independently are zero amino acids in length or comprise a sequence selected from the group consisting of GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148); or (b) $L_1$, $L_2$, $L_3$ and $L_4$ each independently comprise a sequence selected from the group consisting of GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148). In some embodiments, $L_1$ comprises the sequence GQPKAAP (SEQ ID NO: 175), $L_2$ comprises the sequence TKGPS (SEQ ID NO:106), $L_3$ comprises the sequence S, and $L_4$ comprises the sequence RT; $L_1$ comprises the sequence GGGGSGGGGS (SEQ ID NO:104), $L_2$ comprises the sequence GGGGSGGGGS (SEQ ID NO:104), $L_3$ is 0 amino acids in length, and $L_4$ is 0 amino acids in length; $L_1$ comprises the sequence GGSGSSGSGG (SEQ ID NO:148), $L_2$ comprises the sequence GGSGSSGSGG (SEQ ID NO:148), $L_3$ is 0 amino acids in length, and $L_4$ is 0 amino acids in length; or $L_1$ comprises the sequence GGGGSGGGGSGGGGS (SEQ ID NO:105), $L_2$ is 0 amino acids in length, $L_3$ comprises the sequence GGGGSGGGGSGGGGS (SEQ ID NO:105), and $L_4$ is 0 amino acids in length.

In some embodiments of any of the binding proteins described herein, the second polypeptide chain further comprises a first Fc region linked to $C_{H1}$, the first Fc region comprising an immunoglobulin hinge region and $C_{H2}$ and $C_{H3}$ immunoglobulin heavy chain constant domains, wherein the first Fc region comprises amino acid substitutions at positions corresponding to positions 354 and 366 of human IgG1 or IgG4 according to EU Index, wherein the amino acid substitutions are S354C and T366W; and wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains, wherein the second Fc region comprises amino acid substitutions at positions corresponding to positions 349, 366, 368, and 407 of human IgG1 or IgG4 according to EU Index, wherein the amino acid substitutions are Y349C, T366S, L368A, and Y407V. In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains, wherein the first Fc region comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains, wherein the second Fc region comprises amino acid substitutions at positions corresponding to positions 354 and 366 of human IgG1 or IgG4 according to EU Index, wherein the amino acid substitutions are S354C and T366W. In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains, and wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and/or second Fc regions comprise amino acid substitutions at positions corresponding to positions 428 and 434 of human IgG1 or IgG4 according to EU Index, wherein the amino acid substitutions are M428L and N434S. In some embodiments, the $C_{H3}$ domain of the second polypeptide chain comprises amino acid substitutions at positions corresponding to positions 354 and 366 of human IgG1 or IgG4 according to EU Index, wherein the amino acid substitutions are S354C and T366W; and wherein the $C_{H3}$ domain of the third polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V. In some embodiments, the $C_{H3}$ domain of the second polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the $C_{H3}$ domain of the third polypeptide chain comprises amino acid substitutions at positions corresponding to positions 354 and 366 of human IgG1 or IgG4 according to EU Index, wherein the amino acid substitutions are S354C and T366W. In some embodiments, the $C_{H3}$ domains of the second and the third polypeptide chains both comprise amino acid substitutions at positions corresponding to positions 428 and 434 of human IgG1 or IgG4 according to EU Index, wherein the amino acid substitutions are M428L and N434S. In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; and wherein only one of the first and the second Fc regions comprises amino acid substitutions at positions corresponding to positions 435 and 436 of human IgG1 or IgG4 according to EU Index, wherein the amino acid substitutions are H435R and Y436F. In some embodiments, the $C_{H3}$ domains of the second and the third polypeptide chains are human IgG1 $C_{H3}$ domains, and wherein only one of the $C_{H3}$ domains comprises amino acid substitutions at positions corresponding to positions 435 and 436 of human IgG1 or IgG4 according to EU Index, wherein the amino acid substitutions are H435R and Y436F. In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and/or second Fc regions are human IgG4 Fc regions; and wherein the first and the second Fc regions each comprise amino acid substitutions at positions corresponding to positions 228 and 409 of human IgG4 according to EU Index, wherein the amino acid substitutions are S228P and R409K. In some embodiments, the $C_{H3}$ domains of the second and the third polypeptide chains are human IgG4 $C_{H3}$ domains, and wherein the $C_{H3}$ domains each comprise amino acid substitutions at positions corresponding to positions 228 and 409 of human IgG4 according to EU Index, wherein the amino acid substitutions are S228P and R409K. In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and/or second Fc regions are human IgG4 Fc regions; and wherein the first and the second Fc regions each comprise amino acid substitutions at positions corresponding to positions 234 and 235 of human IgG4 according to EU Index, wherein the amino acid substitutions are F234A and L235A. In some embodiments, the $C_{H3}$ domains of the second and the third polypeptide chains are human IgG4 $C_{H3}$ domains, and wherein the $C_{H3}$ domains each comprise amino acid substitutions at positions corresponding to positions 234 and 235 of human IgG4 according to EU Index, wherein the amino acid substitutions are F234A and L235A. In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and/or second Fc regions are human IgG1 Fc regions; and wherein the first and the second Fc regions each comprise amino acid substitutions at positions corresponding to positions 234 and 235 of human IgG1 according to EU Index, wherein the amino acid substitutions are L234A and L235A. In some embodiments, the $C_{H3}$ domains of the second and the third polypeptide chains are human IgG1 $C_{H3}$ domains, and wherein the $C_{H3}$ domains each comprise amino acid substitutions at positions corresponding to positions 234 and 235 of human IgG1 according to EU Index, wherein the amino acid substitutions are L234A and L235A. In some embodiments, the first and/or second Fc regions are human IgG1 Fc regions. In some embodiments, the first and/or second Fc regions are human IgG4 Fc regions.

In some embodiments of any of the binding proteins described herein, the $C_L$ domain of the first polypeptide chain is a human kappa $C_L$ domain, and the $C_L$ domain of the fourth polypeptide chain is a human lambda $C_L$ domain; or the $C_L$ domain of the first polypeptide chain is a human lambda $C_L$ domain, and the $C_L$ domain of the fourth polypeptide chain is a human kappa $C_L$ domain. In some embodiments, the first polypeptide chain comprises a lambda $C_L$ domain; wherein the $C_{H3}$ domain of the second polypeptide chain comprises amino acid substitutions at positions corresponding to positions 354 and 366 of human IgG1 or IgG4 according to EU Index, wherein the amino acid substitutions are S354C and T366W; wherein the $C_{H3}$ domain of the third polypeptide chain comprises amino acid substitutions at positions corresponding to positions 349, 366, 368, 407, 435, and 436 of human IgG1 or IgG4 according to EU Index, wherein the amino acid substitutions are Y349C, T366S, L368A, Y407V, H435R, and Y436F; and wherein the fourth polypeptide chain comprises a kappa $C_L$ domain. In some embodiments, the first polypeptide chain comprises a lambda $C_L$ domain; wherein the $C_{H3}$ domain of the third polypeptide chain comprises amino acid substitutions at positions corresponding to positions 354 and 366 of human IgG1 or IgG4 according to EU Index, wherein the amino acid substitutions are S354C and T366W; wherein the $C_{H3}$ domain of the second polypeptide chain comprises amino acid substitutions at positions corresponding to positions 349, 366, 368, 407, 435, and 436 of human IgG1 or IgG4 according to EU Index, wherein the amino acid substitutions are Y349C, T366S, L368A, Y407V, H435R, and Y436F; and wherein the fourth polypeptide chain comprises a kappa $C_L$ domain. In some embodiments, the first polypeptide chain comprises a lambda $C_L$ domain; wherein the $C_{H3}$ domain of the second polypeptide chain comprises amino acid substitutions at positions corresponding to positions 354, 366, 435, and 436 of human IgG1 or IgG4 according to EU Index, wherein the amino acid substitutions are S354C, T366W, H435R, and Y436F; wherein the $C_{H3}$ domain of the third polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the fourth polypeptide chain comprises a kappa $C_L$ domain. In some embodiments, the first polypeptide chain comprises a kappa $C_L$ domain; wherein the $C_{H3}$ domain of the second polypeptide chain comprises amino acid substitutions at positions corresponding to positions 354 and 366 of human IgG1 or IgG4 according to EU Index, wherein the amino acid substitutions are S354C and T366W; wherein the $C_{H3}$ domain of the third polypeptide chain comprises amino acid substitutions at positions corresponding to positions 349, 366, 368, 407, 435, and 436 of human IgG1 or IgG4 according to EU Index, wherein the amino acid substitutions are Y349C, T366S, L368A, Y407V, H435R, and Y436F; and wherein the fourth polypeptide chain comprises a lambda $C_L$ domain. In some embodiments, second and/or third polypeptide chain comprise a human IgG1 or IgG4 Fc region.

In another embodiment, the disclosure provides a binding protein comprising a first polypeptide chain, a second polypeptide chain, a third polypeptide chain and a fourth polypeptide chain wherein:

(a) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 1 or an amino acid sequence that is at least 95% identical to the amino acid sequence of SEQ ID NO: 1; and the fourth polypeptide chain comprises the amino acid sequence of SEQ ID NO: 2 or an amino acid sequence that is at least 95% identical to the amino acid sequence of SEQ ID NO: 2;

(b) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 1 or an amino acid sequence that is at least 95% identical to the amino acid sequence of SEQ ID NO: 1; and the fourth polypeptide chain comprises the amino acid sequence of SEQ ID NO: 2 or an amino acid sequence that is at least 95% identical to the amino acid sequence of SEQ ID NO: 2;

(c) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 13 or an amino acid sequence that is at least 95% identical to the amino acid sequence of SEQ ID NO: 13; and the fourth polypeptide chain comprises the amino acid sequence of SEQ ID NO: 14 or an amino acid sequence that is at least 95% identical to the amino acid sequence of SEQ ID NO: 14;

(d) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 13 or an amino acid sequence that is at least 95% identical to the amino acid sequence of SEQ ID NO: 13; and the fourth polypeptide chain comprises the amino acid sequence of SEQ ID NO: 14 or an amino acid sequence that is at least 95% identical to the amino acid sequence of SEQ ID NO: 14;

(e) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 17 or an amino acid sequence that is at least 95% identical to the amino acid sequence of SEQ ID NO: 17; and the fourth polypeptide chain comprises the amino acid sequence of SEQ ID NO: 18 or an amino acid sequence that is at least 95% identical to the amino acid sequence of SEQ ID NO: 18

(f) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 17 or an amino acid sequence that is at least 95% identical to the amino acid sequence of SEQ ID NO: 17; and the fourth polypeptide chain comprises the amino acid sequence of SEQ ID NO: 18 or an amino acid sequence that is at least 95% identical to the amino acid sequence of SEQ ID NO: 18;

(g) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 21 or an amino acid sequence that is at least 95% identical to the amino acid sequence of SEQ ID NO: 21; and the fourth polypeptide chain comprises the amino acid sequence of SEQ ID NO: 22 or an amino acid sequence that is at least 95% identical to the amino acid sequence of SEQ ID NO: 22;

(h) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 21 or an amino acid sequence that is at least 95% identical to the amino acid sequence of SEQ ID NO: 21; and the fourth polypeptide chain comprises the amino acid sequence of SEQ ID NO: 22 or an amino acid sequence that is at least 95% identical to the amino acid sequence of SEQ ID NO: 22;

(i) the first polypeptide chain comprises the amino acid sequence of SEQ ID NO: 63 or an amino acid sequence that is at least 95% identical to the amino acid sequence of SEQ ID NO: 63; the second polypeptide chain comprises the amino acid sequence of SEQ ID NO: 62 or an amino acid sequence that is at least 95% identical to the amino acid sequence of SEQ ID NO: 62; the third polypeptide chain comprises the amino acid sequence of SEQ ID NO: 60 or an amino acid sequence that is at least 95% identical to the amino acid sequence of SEQ ID NO: 60; and the fourth polypeptide chain comprises the amino acid sequence of SEQ ID NO: 61 or an amino acid sequence that is at least 95% identical to the amino acid sequence of SEQ ID NO: 61;

(j) the first polypeptide chain comprises the amino acid sequence of SEQ ID NO: 69 or an amino acid sequence that is at least 95% identical to the amino acid sequence of SEQ ID NO: 69; the second polypeptide chain comprises the amino acid sequence of SEQ ID NO: 68 or an amino acid sequence that is at least 95% identical to the amino acid sequence of SEQ ID NO: 68; the third polypeptide chain comprises the amino acid sequence of SEQ ID NO: 60 or an amino acid sequence that is at least 95% identical to the amino acid sequence of SEQ ID NO: 60; and the fourth polypeptide chain comprises the amino acid sequence of SEQ ID NO: 61 or an amino acid sequence that is at least 95% identical to the amino acid sequence of SEQ ID NO: 61;

(k) the first polypeptide chain comprises the amino acid sequence of SEQ ID NO: 69 or an amino acid sequence that is at least 95% identical to the amino acid sequence of SEQ ID NO: 69; the second polypeptide chain comprises the amino acid sequence of SEQ ID NO: 68 or an amino acid sequence that is at least 95% identical to the amino acid sequence of SEQ ID NO: 68; the third polypeptide chain comprises the amino acid sequence of SEQ ID NO: 60 or an amino acid sequence that is at least 95% identical to the amino acid sequence of SEQ ID NO: 60; and the fourth polypeptide chain comprises the amino acid sequence of SEQ ID NO: 71 or an amino acid sequence that is at least 95% identical to the amino acid sequence of SEQ ID NO: 71;

(l) the first polypeptide chain comprises the amino acid sequence of SEQ ID NO: 76 or an amino acid sequence that is at least 95% identical to the amino acid sequence of SEQ ID NO: 76; the second polypeptide chain comprises the amino acid sequence of SEQ ID NO: 75 or an amino acid sequence that is at least 95% identical to the amino acid sequence of SEQ ID NO: 75; the third polypeptide chain comprises the amino acid sequence of SEQ ID NO: 73 or an amino acid sequence that is at least 95% identical to the amino acid sequence of SEQ ID NO: 73; and the fourth polypeptide chain comprises the amino acid sequence of SEQ ID NO: 74 or an amino acid sequence that is at least 95% identical to the amino acid sequence of SEQ ID NO: 74;

(m) the first polypeptide chain comprises the amino acid sequence of SEQ ID NO: 82 or an amino acid sequence that is at least 95% identical to the amino acid sequence of SEQ ID NO: 82; the second polypeptide chain comprises the amino acid sequence of SEQ ID NO: 81 or an amino acid sequence that is at least 95% identical to the amino acid sequence of SEQ ID NO:81; the third polypeptide chain comprises the amino acid sequence of SEQ ID NO: 73 or an amino acid sequence that is at least 95% identical to the amino acid sequence of SEQ ID NO: 73; and the fourth polypeptide chain comprises the amino acid sequence of SEQ ID NO: 74 or an amino acid sequence that is at least 95% identical to the amino acid sequence of SEQ ID NO: 74;

(n) the first polypeptide chain comprises the amino acid sequence of SEQ ID NO: 88 or an amino acid sequence that is at least 95% identical to the amino acid sequence of SEQ ID NO:88; the second polypeptide chain comprises the amino acid sequence of SEQ ID NO: 87 or an amino acid sequence that is at least 95% identical to the amino acid sequence of SEQ ID NO: 87; the third polypeptide chain comprises the amino acid sequence of SEQ ID NO: 85 or an amino acid sequence that is at least 95% identical to the amino acid sequence of SEQ ID NO: 85; and the fourth polypeptide chain comprises the amino acid sequence of SEQ ID NO: 86 or an amino acid sequence that is at least 95% identical to the amino acid sequence of SEQ ID NO: 86;

(o) the first polypeptide chain comprises the amino acid sequence of SEQ ID NO: 94 or an amino acid sequence that is at least 95% identical to the amino acid sequence of SEQ ID NO: 94; the second polypeptide chain comprises the amino acid sequence of SEQ ID NO: 93 or an amino acid sequence that is at least 95% identical to the amino acid sequence of SEQ ID NO: 93; the third polypeptide chain comprises the amino acid sequence of SEQ ID NO: 85 or an amino acid sequence that is at least 95% identical to the amino acid sequence of SEQ ID NO: 85; and the fourth polypeptide chain comprises the amino acid sequence of SEQ ID NO: 86 or an amino acid sequence that is at least 95% identical to the amino acid sequence of SEQ ID NO: 86;

(p) the first polypeptide chain comprises the amino acid sequence of SEQ ID NO: 69 or an amino acid sequence that is at least 95% identical to the amino acid sequence of SEQ ID NO: 69; the second polypeptide chain comprises the amino acid sequence of SEQ ID NO: 68 or an amino acid sequence that is at least 95% identical to the amino acid sequence of SEQ ID NO: 68; the third polypeptide chain comprises the amino acid sequence of SEQ ID NO: 73 or an amino acid sequence that is at least 95% identical to the amino acid sequence of SEQ ID NO: 73; and the fourth polypeptide chain comprises the amino acid sequence of SEQ ID NO: 74 or an amino acid sequence that is at least 95% identical to the amino acid sequence of SEQ ID NO: 74;

(q) the first polypeptide chain comprises the amino acid sequence of SEQ ID NO: 69 or an amino acid sequence that is at least 95% identical to the amino acid sequence of SEQ ID NO: 69; the second polypeptide chain comprises the amino acid sequence of SEQ ID NO: 68 or an amino acid sequence that is at least 95% identical to the amino acid sequence of SEQ ID NO: 68; the third polypeptide chain comprises the amino acid sequence of SEQ ID NO: 85 or an amino acid sequence that is at least 95% identical to the amino acid sequence of SEQ ID NO: 85; and the fourth polypeptide chain comprises the amino acid sequence of SEQ ID NO: 86 or an amino acid sequence that is at least 95% identical to the amino acid sequence of SEQ ID NO: 86;

(r) the first polypeptide chain comprises the amino acid sequence of SEQ ID NO: 63 or an amino acid sequence that is at least 95% identical to the amino acid sequence of SEQ ID NO: 63; the second polypeptide chain comprises the amino acid sequence of SEQ ID NO: 62 or an amino acid sequence that is at least 95% identical to the amino acid sequence of SEQ ID NO: 62; the third polypeptide chain comprises the amino acid sequence of SEQ ID NO: 73 or an amino acid sequence that is at least 95% identical to the amino acid sequence of SEQ ID NO: 73; and the fourth polypeptide chain comprises the amino acid sequence of SEQ ID NO: 74 or an amino acid sequence that is at least 95% identical to the amino acid sequence of SEQ ID NO: 74;

(s) the first polypeptide chain comprises the amino acid sequence of SEQ ID NO: 63 or an amino acid sequence that is at least 95% identical to the amino acid sequence of SEQ ID NO: 63; the second polypeptide chain comprises the amino acid sequence of SEQ ID NO: 62 or an amino acid sequence that is at least 95% identical to the amino acid sequence of SEQ ID NO: 62; the third polypeptide chain comprises the amino acid sequence of SEQ ID NO: 85 or an amino acid sequence that is at least 95% identical to the amino acid sequence of SEQ ID NO: 85; and the fourth polypeptide chain comprises the amino acid sequence of SEQ ID NO: 86 or an amino acid sequence that is at least 95% identical to the amino acid sequence of SEQ ID NO: 86;

(t) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 114 or an amino acid sequence that is at least 95% identical to the amino acid sequence of SEQ ID NO: 114; and the fourth polypeptide chain comprises the amino acid sequence of SEQ ID NO: 115 or an amino acid sequence that is at least 95% identical to the amino acid sequence of SEQ ID NO: 115; or (u) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 114 or an amino acid sequence that is at least 95% identical to the amino acid sequence of SEQ ID NO: 114; and the fourth polypeptide chain comprises the amino acid sequence of SEQ ID NO: 115 or an amino acid sequence that is at least 95% identical to the amino acid sequence of SEQ ID NO: 115.

In another embodiment, the disclosure provides an isolated nucleic acid molecule comprising a nucleotide sequence encoding the binding protein or polypeptide thereof according to any of the above embodiments. In another embodiment, the disclosure provides an expression vector comprising the nucleic acid molecule according to one of the above embodiments. In another embodiment, the disclosure provides an isolated host cell comprising the nucleic acid molecule according to any of the above embodiments. In another embodiment, the disclosure provides an isolated host cell comprising the expression vector according to any of the above embodiments. In some embodiments, the isolated host cell is a mammalian cell or an insect cell. In one embodiment, the disclosure provides a vector system comprising one or more vectors encoding a first, second, third, and fourth polypeptide chain of a binding protein according to any of the above embodiments. In some embodiments, the vector system comprises a first vector encoding the first polypeptide chain of the binding protein, a second vector encoding the second polypeptide chain of the binding protein, a third vector encoding the third polypeptide chain of the binding protein, and a fourth vector encoding the fourth polypeptide chain of the binding protein. In some embodiments, the vector system comprises a first vector encoding the first and second polypeptide chains of the binding protein, and a second vector encoding the third and fourth polypeptide chains of the binding protein. In some embodiments, the one or more vectors are expression vectors. In one embodiment, the disclosure provides an isolated host cell comprising the vector system according to any of the above embodiments. In one embodiment, the disclosure provides a method of producing a binding protein, the method comprising: a) culturing a host cell according to any of the above embodiments under conditions such that the host cell expresses the binding protein; and b) isolating the binding protein from the host cell. In one embodiment, the disclosure provides a pharmaceutical composition comprising the binding protein according to any of the above embodiments and a pharmaceutically acceptable carrier.

In another embodiment, the disclosure provides a method of preventing and/or treating cancer in a patient comprising administering to the patient a therapeutically effective amount of at least one binding protein or pharmaceutical composition according to any of the above embodiments. In another embodiment, the disclosure provides a binding protein or pharmaceutical composition according to any of the above embodiments for use in preventing and/or treating cancer in a patient. In another embodiment, the disclosure provides a binding protein according to any of the above embodiments for the manufacture of a medicament for preventing and/or treating cancer in a patient. In some embodiments, the binding protein comprises one antigen binding site that specifically binds a T-cell surface protein and another antigen binding site that specifically binds a tumor target protein. In some embodiments, the binding protein comprises an antigen binding site that specifically binds CD3, an antigen binding site that specifically binds CD28, and an antigen binding site that specifically binds a tumor target protein selected from the group consisting of CD19, CD20, CD38, Her2, and LAMP1. In some embodiments, the at least one binding protein is co-administered with a chemotherapeutic agent. In some embodiments, the patient is a human. In some embodiments, the binding protein is capable of inhibiting the function of one or more target proteins selected from the group consisting of A2AR, APRIL, ATPDase, BAFF, BAFFR, BCMA, BlyS, BTK, BTLA, B7DC, B7H1, B7H4, B7H5, B7H6, B7H7, B7RP1, B7-4, C3, C5, CCL2, CCL3, CCL4, CCL5, CCL7, CCL8, CCL11, CCL15, CCL17, CCL19, CCL20, CCL21, CCL24, CCL25, CCL26, CCR3, CCR4, CD3, CD19, CD20, CD23, CD24, CD27, CD28, CD38, CD39, CD40, CD70, CD80, CD86, CD122, CD137, CD137L, CD152, CD154, CD160, CD272, CD273, CD274, CD275, CD276, CD278, CD279, CDH1, chitinase, CLEC9, CLEC91, CRTH2, CSF-1, CSF-2, CSF-3, CX3CL1, CXCL12, CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb, IL18, IL22, IL23, IL25, IL27, IL33, IL35, ITGB4, ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2, STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP, TSLPR, TWEAK, VEGF, VISTA, Vstm3, WUCAM, and XCR1.

In another embodiment, the disclosure provides a method of preventing and/or treating an inflammatory disease or disorder in a patient comprising administering to the patient a therapeutically effective amount of at least one binding protein or pharmaceutical composition according to any of the above embodiments. In another embodiment, the disclosure provides a binding protein or pharmaceutical composition according to any of the above embodiments for use in preventing and/or treating an inflammatory disease or disorder in a patient. In another embodiment, the disclosure provides a binding protein according to any of the above embodiments for the manufacture of a medicament for preventing and/or treating an inflammatory disease or disorder in a patient. In some embodiments, the binding protein comprises three antigen binding sites that each specifically bind a cytokine target protein selected from the group consisting of IL-4, IL-13 and TNFa. In some embodiments, two of the three binding sites specifically bind a cytokine target protein selected from the group consisting of IL-4, IL-13 and TNFa. In some embodiments, the at least one binding protein is co-administered with an anti-inflammatory agent. In some embodiments, the patient is a human. In some embodiments, the binding protein is capable of inhibiting the function of one or more target proteins selected from the group consisting of A2AR, APRIL, ATPDase, BAFF, BAFFR, BCMA, BlyS, BTK, BTLA, B7DC, B7H1, B7H4, B7H5, B7H6, B7H7, B7RP1, B7-4, C3, C5, CCL2, CCL3, CCL4, CCL5, CCL7, CCL8, CCL11, CCL15, CCL17, CCL19, CCL20, CCL21, CCL24, CCL25, CCL26, CCR3, CCR4, CD3, CD19, CD20, CD23, CD24, CD27, CD28, CD38, CD39, CD40, CD70, CD80, CD86, CD122, CD137, CD137L, CD152, CD154, CD160, CD272, CD273, CD274, CD275, CD276, CD278, CD279, CDH1, chitinase, CLEC9, CLEC91, CRTH2, CSF-1, CSF-2, CSF-3, CX3CL1, CXCL12, CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb, IL18, IL22, IL23, IL25, IL27, IL33, IL35, ITGB4, ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2, STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP, TSLPR, TWEAK, VEGF, VISTA, Vstm3, WUCAM, and XCR1.

In another embodiment, the disclosure provides a method of purifying a binding protein produced by a host cell, comprising:

(a) producing in a host cell a binding protein comprising four polypeptide chains that form three antigen binding sites that specifically bind one or more antigen targets or target proteins, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}L_{H2}\text{-}L_4\text{-}C_{H1}\text{-hinge-}C_{H2}\text{-}C_{H3} \quad [II]$$

and a third polypeptide chain comprises a structure represented by the formula:

$$V_{H3}\text{-}C_{H1} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair; wherein only one of the $C_{H3}$ domain of the second polypeptide chain and the $C_{H3}$ domain of the third polypeptide chain comprises amino acid substitutions at positions corresponding to positions 435 and 436 of human IgG1 or IgG4 according to EU Index, wherein the amino acid substitutions are H435R and Y436F;

(b) contacting the binding protein produced in (a) with Protein A; and (c) eluting the binding protein from Protein A under conditions suitable for isolating the binding protein away from binding proteins comprising either 0 or 2 $C_{H3}$ domains comprising the amino acid substitutions are H435R and Y436F.

In some embodiments, the $C_L$ domain of the first polypeptide chain is a human kappa $C_L$ domain, and the $C_L$ domain of the fourth polypeptide chain is a human lambda $C_L$ domain; or the $C_L$ domain of the first polypeptide chain is a human lambda $C_L$ domain, and the $C_L$ domain of the fourth polypeptide chain is a human kappa $C_L$ domain, and the method further comprises: (d) contacting the binding protein eluted in (c) with a kappa light chain affinity medium; and (e) eluting the binding protein from the kappa light chain affinity medium under conditions suitable for isolating the binding protein away from binding proteins comprising only lambda $C_L$ domains. In some embodiments, the method further comprises, after (e), (f) contacting the binding protein eluted in (e) with a lambda light chain affinity medium; and (g) eluting the binding protein from the lambda light chain affinity medium under conditions suitable for isolating the binding protein away from binding proteins comprising only kappa $C_L$ domains. In some embodiments, the $C_L$ domain of the first polypeptide chain is a human kappa $C_L$ domain, and the $C_L$ domain of the fourth polypeptide chain is a human lambda $C_L$ domain; or the $C_L$ domain of the first polypeptide chain is a human lambda $C_L$ domain, and the $C_L$ domain of the fourth polypeptide chain is a human kappa $C_L$ domain, and the method further comprises: (d) contacting the binding protein eluted in (c) with a lambda light chain affinity medium; and (e) eluting the binding protein from the lambda light chain affinity medium under conditions suitable for isolating the binding protein away from binding proteins comprising only kappa $C_L$ domains. In some embodiments, the method further comprises, after (e), (f) contacting the binding protein eluted in (e) with a kappa light chain affinity medium; and (g) eluting the binding protein from the kappa light chain affinity medium under conditions suitable for isolating the binding protein away from binding proteins comprising only lambda $C_L$ domains. In some embodiments, the first polypeptide chain comprises a lambda $C_L$ domain; wherein the $C_{H3}$ domain of the second polypeptide chain comprises amino acid substitutions at positions corresponding to positions 354 and 366 of human IgG1 according to EU Index, wherein the amino acid substitutions are S354C and T366W; wherein the $C_{H3}$ domain of the third polypeptide chain comprises amino acid substitutions at positions corresponding to positions 349, 366, 368, 407, 435, and 436 of human IgG1 according to EU Index, wherein the amino acid substitutions are Y349C, T366S, L368A, Y407V, H435R, and Y436F; and wherein the fourth polypeptide chain comprises a kappa $C_L$ domain. In some embodiments, the binding protein is detected in one or more of (c) and (e) using hydrophobic interaction chromatography (HIC). In some embodiments, the $C_{H3}$ domains and/or Fc regions of the second and the third polypeptide chains are human IgG1 or IgG4 $C_{H3}$ domains and/or Fc regions.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIG. 1A shows a trispecific binding protein comprising a "knobs-into-holes" mutation, where the knob is on the second pair of polypeptides with a single variable domain. FIG. 1B shows a trispecific binding protein comprising a "knobs-into-holes" mutation, where the knob is on the first pair of polypeptides having the cross-over orientation. FIG. 1C shows the orientation of variable domains on the polypeptide chains, and the knob/hole orientation for the binding proteins shown in Tables 1-3. "Heavy chain A" (e.g., a third polypeptide chain of the present disclosure) indicates the variable domain of heavy chain A. "Light chain A" (e.g., a fourth polypeptide chain of the present disclosure) indicates the variable domain of light chain A. "Heavy chain B" (e.g., a second polypeptide chain of the present disclosure) indicates variable domain 1 and variable domain 2 of heavy chain B. "Light chain B" (e.g., a first polypeptide chain of the present disclosure) indicates variable domain 1 and variable domain 2 of light chain B.

FIG. 3A shows the results of trispecific antibody-mediated specific killing of ZR-75-1 cells. FIG. 3B shows the results of trispecific antibody-mediated specific killing of AU565 cells. FIG. 3C shows the results of FACS analysis determining the cell surface expression of the indicated markers on ZR-75-1 and AU565 cells.

FIG. 4 shows the results of antibody-mediated specific killing of ZR-75-1 cells using human peripheral blood mononuclear cells (PBMCs) from donor KP45926 at E:T=10. FIG. 5 shows the results of antibody-mediated specific killing of AU565 cells using human PBMCs from donor KP45944 at E:T=10. FIGS. 4 & 5 confirm similar cell killing results as shown in FIGS. 3A-3C using PBMCs from a different donor.

FIG. 6A shows the activation ($CD69^+$) of human $CD4^+$ T cells from three donors. FIG. 6B shows the activation ($CD69^+$) of human $CD8^+$ T cells from three donors. $CD28_{sup}$: anti-CD28 superagonist antibody. $CD3_{mid}$: anti-CD3 antibody.

FIG. 9A shows the results of antibody-mediated specific killing of OCI-LY19 cells. FIG. 9N shows the results of antibody-mediated specific killing of OCI-Ly3 cells using PBMCs from donor KP48775 at E:T=10.

FIG. 11A shows the results of antibody-mediated specific killing of MOLP-8 cells using human PBMC as effector cells at E:T=10. FIG. 11B shows the results of antibody-mediated specific killing of RPMI-8226 cells using human PBMC as effector cells at E:T=10. FIG. 11C shows the results of antibody-mediated specific killing of KMS-12-BM cells using human PBMC as effector cells at E:T=10. FIG. 11D shows the results of FACS analysis determining the cell surface expression of the indicated markers on MOLP-8, RPMI-8226, and KMS-12-BM cells.

FIG. 12A shows the results of antibody-mediated specific killing of NCI-H929 cells. FIG. 12B shows the results of antibody-mediated specific killing of MM.1S cells. FIG. 12C shows the results of antibody-mediated specific killing of MM.1R cells. FIG. 12D shows the results of FACS analysis determining the cell surface expression of the indicated markers on NCI-H929, MM.1S, and MM.1R cells.

FIGS. 13A-13D show the results of antibody-mediated specific killing of $CD38^+$ human multiple myeloma cancer cells using an anti-CD38×CD28×CD3 IgG4 trispecific antibody (Binding protein 5), an anti-CD28×CD3 IgG4 bispecific antibody (huCD28×CD3), an anti-CD38 IgG1 antibody, or a control antibody (human-IgG1), using human PBMC as effector cells at E:T=10. FIG. 13A shows the results of antibody-mediated specific killing of OPM-2 cells. FIG. 13B shows the results of antibody-mediated specific killing of KMS-26 cells. FIG. 13C shows the results of antibody-mediated specific killing of U266 cells. FIG. 13D shows the results of FACS analysis determining the cell surface expression of the indicated markers on OPM-2, KMS-26, and U226 cells.

FIG. 14A shows the results of antibody-mediated specific killing of SUDHL-8 cells. FIG. 14B shows the results of antibody-mediated specific killing of OCI-LY19 cells. FIG. 14C shows the results of FACS analysis determining the cell surface expression of the indicated markers on SUDHL-8 and OCI-LY19 cells.

FIGS. 15A-15D show the results of antibody-mediated specific killing of $CD38^+$ ALL cancer cells using an anti-CD38×CD28×CD3 IgG4 trispecific antibody (Binding protein 5), an anti-CD28×CD3 IgG4 bispecific antibody (huCD28×CD3), an anti-CD38 IgG1 antibody, or a control antibody (human-IgG1), using human PBMC as effector cells at E:T=10. FIG. 15A shows the results of antibody-mediated specific killing of KOPN-8 cells. FIG. 15B shows the results of antibody-mediated specific killing of HAL-1 cells. FIG. 15C shows the results of antibody-mediated specific killing of CCRF-SB cells. FIG. 15D shows the results of FACS analysis determining the cell surface expression of the indicated markers on KOPN-8, HAL-1, and CCRF-SB cells.

FIG. 18A shows the results of circulating $CD4^+$ T cells percentage in each animal, 6 hours post administering the anti-Her2×CD28×CD3 trispecific antibody. FIG. 18B shows the results of circulating $CD8^+$ T cells percentage in each animal, 6 hours post administering the anti-Her2×CD28×CD3 trispecific antibody. FIG. 18C shows the results of the activation ($CD69^+$) of circulating $CD4^+$ T cells 6 hours post dosing. FIG. 18D shows the results of the activation ($CD69^+$) of circulating $CD8^+$ T cells 6 hours post dosing. FIG. 18E shows the inflammatory cytokine release observed 6 hours post administering the anti-Her2×CD28×CD3 trispecific antibody at each dosing.

FIG. 19A shows the change in body weight of mice treated with the indicated concentrations of the anti-Her2×CD28×CD3 trispecific binding protein or PBS control. FIG. 19B shows the change in tumor volume in mice treated with the indicated concentrations of the anti-Her2×CD28×CD3 trispecific binding protein or PBS control.

FIG. 20A shows the effect of administering the indicated concentrations of the anti-Her2×CD28×CD3 trispecific binding protein, the indicated concentrations of Herceptin, or vehicle control, on the body weight of the mice. FIG. 20B shows the dose-dependent anti-tumor activity of the anti-Her2×CD28×CD3 trispecific binding protein, Herceptin or indicated controls, as in individual mice. FIG. 20C shows the average tumor volume in the mice after administration of the indicated concentrations of the anti-Her2×CD28×CD3 trispecific binding protein or PBS control. FIG. 20D shows the average tumor volume in the mice after administration of the indicated concentrations of Herceptin or PBS control. FIG. 20E shows bar graphs of the average tumor volume at day 34 in the mice after administration of the indicated concentrations of the anti-Her2×CD28×CD3 trispecific binding protein, the indicated concentrations of Herceptin, or PBS control. FIG. 20F shows the average tumor weight at day 34 in the mice after administration of the indicated concentrations of the anti-Her2×CD28×CD3 trispecific binding protein, the indicated concentrations of Herceptin, or PBS control. FIG. 20G shows the human CD45+, CD3+, CD4+, CD8+ cells in the blood of the mice at the end of the study. FIG. 20H shows the human CD45+, CD3+, CD4+, CD8+ cells in the spleens of the mice at the end of the study.

FIG. 21A shows T cell activation ($CD69^+$) (line graph) and proliferation (bar graph) of circulating $CD4^+$ T cells after administration of the anti-CD38×CD28×CD3 trispecific antibody. FIG. 21B shows T cell activation ($CD69^+$) (line graph) and proliferation (bar graph) of circulating $CD8^+$ T cells after administration of the anti-CD38×CD28×CD3 trispecific antibody. FIG. 21C shows IL6 release in animals receiving the anti-CD38×CD28×CD3 trispecific antibody 6 hours post each dosing by individual animal. FIG. 21D shows IL10 release in animals receiving the anti-CD38×CD28×CD3 trispecific antibody 6 hours post each dosing by individual animal. FIG. 21E shows TNFα release in animals receiving the anti-CD38×CD28×CD3 trispecific antibody. FIG. 21F shows IFNγ release in animals receiving the anti-CD38×CD28×CD3 trispecific antibody 6 hours post each dosing by individual animal.

FIG. 22A shows the in vivo tumor growth curve in groups of the indicated concentrations of the anti-CD38×CD28×CD3 trispecific binding protein or controls. FIG. 22B shows tumor infiltrating human $CD8^+$ T cells in mice administered the anti-CD38×CD28×CD3 trispecific binding protein or the indicated controls. FIG. 22C shows tumor infiltrating human $CD4^+$ T cells in mice administered the anti-CD38×CD28×CD3 trispecific binding protein or the indicated controls.

FIG. 23A shows the change in body weight of mice treated with the indicated concentrations of the anti-CD38×CD28×CD3 trispecific binding protein or PBS control. FIG. 23B shows the change in tumor volume in mice treated with the indicated concentrations of the anti-CD38×CD28×CD3 trispecific binding protein or PBS control. FIG. 23C shows the tumor volumes in each group at Day 19. The tumor volumes in all treated groups showed marked reduction, which are statistically different form the PBS control group. FIG. 23D shows the serum concentration of inflammatory cytokines IFN-g, TNF, and IL-2 in mice four hours after the first dose of the indicated concentrations of the anti-CD38×CD28×CD3 trispecific binding protein or PBS control.

FIG. 24 shows the in vivo activation of $CD4^+$ T cells. FIG. 25 shows the in vivo activation of $CD8^+$ T cells.

FIG. 26A shows the serum levels of IL-2. FIG. 26B shows the serum levels of TNF. FIG. 26C shows the serum levels of IFN-γ.

FIG. 27A shows the purification of Binding Proteins 9-15 by size exclusion chromatography. FIG. 27B shows the purification of Binding Proteins 16-19 by size exclusion chromatography.

FIG. 28A depicts the trispecific binding protein used in experiments for optimizing a purification scheme and configuration of optional binding protein features (e.g., kappa/lambda light chains, knob/hole mutations, and H435R/Y436F mutations).

FIG. 28B shows each of the configurations tested.

FIG. 30A) and SDS-PAGE (FIG. 30B).

DETAILED DESCRIPTION

Figure 1A:
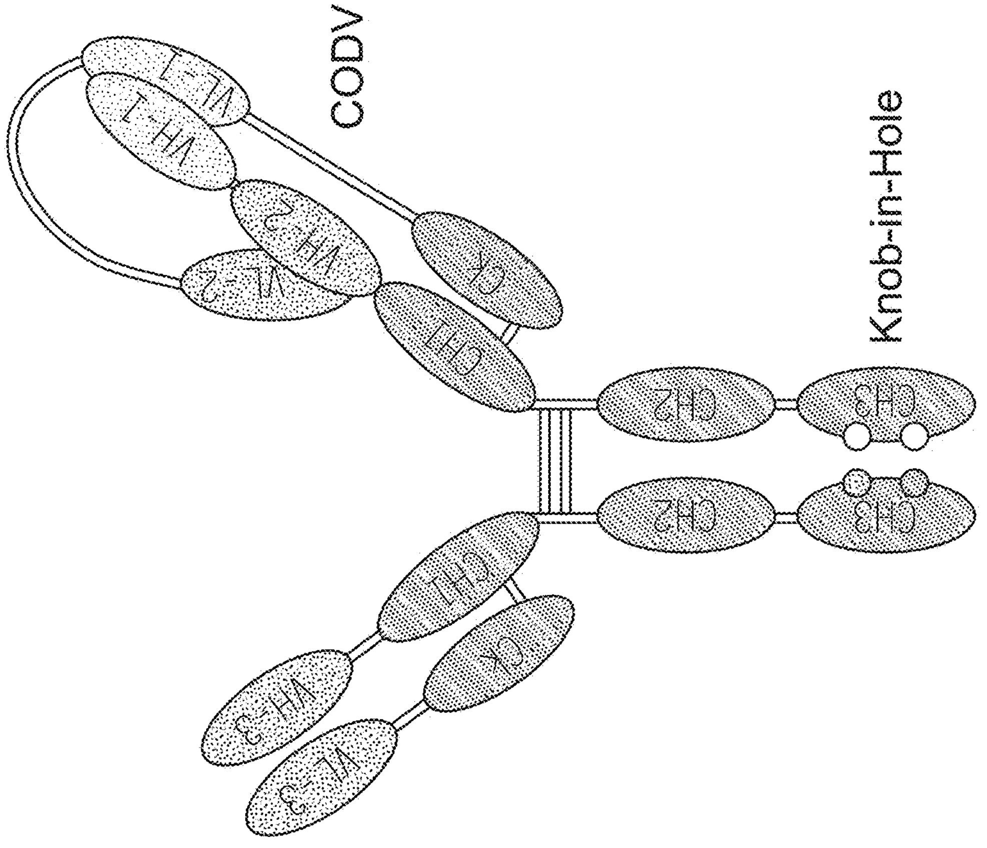
FIGS. 1A-1C show schematic representations of trispecific binding proteins comprising four polypeptide chains that form three antigen binding sites that specifically binds three target proteins, wherein a first pair of polypeptides possess dual variable domains having a cross-over orientation (VH1-VH2 and VL2-VL1) forming two antigen binding sites, and wherein a second pair of polypeptides possess a single variable domain (VH3 and VL3) forming a single antigen binding site.

The disclosure provides trispecific and/or trivalent binding proteins comprising four polypeptide chains that form three antigen binding sites that specifically bind to one or more target proteins, wherein a first pair of polypeptides forming the binding protein possess dual variable domains having a cross-over orientation and wherein a second pair of polypeptides forming the binding protein possess a single variable domain.

General Definitions

As utilized in accordance with the present disclosure, the following terms, unless otherwise indicated, shall be understood to have the following meanings. Unless otherwise required by context, singular terms shall include pluralities and plural terms shall include the singular.

The term "polynucleotide" as used herein refers to single-stranded or double-stranded nucleic acid polymers of at least 10 nucleotides in length. In certain embodiments, the nucleotides comprising the polynucleotide can be ribonucleotides or deoxyribonucleotides or a modified form of either type of nucleotide. Such modifications include base modifications such as bromuridine, ribose modifications such as arabinoside and 2',3'-dideoxyribose, and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single-stranded and double-stranded forms of DNA.

An "isolated polynucleotide" is a polynucleotide of genomic, cDNA, or synthetic origin or some combination thereof, which: (1) is not associated with all or a portion of a polynucleotide in which the isolated polynucleotide is found in nature, (2) is linked to a polynucleotide to which it is not linked in nature, or (3) does not occur in nature as part of a larger sequence.

An "isolated polypeptide" is one that: (1) is free of at least some other polypeptides with which it would normally be found, (2) is essentially free of other polypeptides from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a polypeptide with which the "isolated polypeptide" is associated in nature, (6) is operably associated (by covalent or noncovalent interaction) with a polypeptide with which it is not associated in nature, or (7) does not occur in nature. Such an isolated polypeptide can be encoded by genomic DNA, cDNA, mRNA or other RNA, of synthetic origin, or any combination thereof. Preferably, the isolated polypeptide is substantially free from polypeptides or other contaminants that are found in its natural environment that would interfere with its use (therapeutic, diagnostic, prophylactic, research or otherwise).

Naturally occurring antibodies typically comprise a tetramer. Each such tetramer is typically composed of two identical pairs of polypeptide chains, each pair having one full-length "light" chain (typically having a molecular weight of about 25 kDa) and one full-length "heavy" chain (typically having a molecular weight of about 50-70 kDa). The terms "heavy chain" and "light chain" as used herein refer to any immunoglobulin polypeptide having sufficient variable domain sequence to confer specificity for a target antigen. The amino-terminal portion of each light and heavy chain typically includes a variable domain of about 100 to 110 or more amino acids that typically is responsible for antigen recognition. The carboxy-terminal portion of each chain typically defines a constant domain responsible for effector function. Thus, in a naturally occurring antibody, a full-length heavy chain immunoglobulin polypeptide includes a variable domain ($V_H$) and three constant domains ($C_{H1}$, $C_{H2}$, and $C_{H3}$), wherein the $V_H$ domain is at the amino-terminus of the polypeptide and the $C_{H3}$ domain is at the carboxyl-terminus, and a full-length light chain immunoglobulin polypeptide includes a variable domain ($V_L$) and a constant domain ($C_L$), wherein the $V_L$ domain is at the amino-terminus of the polypeptide and the $C_L$ domain is at the carboxyl-terminus.

Human light chains are typically classified as kappa and lambda light chains, and human heavy chains are typically classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses including, but not limited to, IgM1 and IgM2. IgA is similarly subdivided into subclasses including, but not limited to, IgA1 and IgA2. Within full-length light and heavy chains, the variable and constant domains typically are joined by a "J" region of about 12 or more amino acids, with the heavy chain also including a "D" region of about 10 more amino acids. See, e.g., FUNDAMENTAL IMMUNOLOGY (Paul, W., ed., Raven Press, 2nd ed., 1989), which is incorporated by reference in its entirety for all purposes. The variable regions of each light/heavy chain pair typically form an antigen binding site. The variable domains of naturally occurring antibodies typically exhibit the same general structure of relatively conserved framework regions (FR) joined by three hypervariable regions, also called complementarity determining regions or CDRs. The CDRs from the two chains of each pair typically are aligned by the framework regions, which may enable binding to a specific epitope. From the amino-terminus to the carboxyl-terminus, both light and heavy chain variable domains typically comprise the domains FR1, CDR1, FR2, CDR2, FR3, CDR3, and FR4.

The term "CDR set" refers to a group of three CDRs that occur in a single variable region capable of binding the antigen. The exact boundaries of these CDRs have been defined differently according to different systems. The system described by Kabat (Kabat et al., SEQUENCES OF PROTEINS OF IMMUNOLOGICAL INTEREST (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia and Lesk, 1987, *J. Mol. Biol.* 196: 901-17; Chothia et al., 1989, *Nature* 342: 877-83) found that certain sub-portions within Kabat CDRs adopt nearly identical peptide backbone conformations, despite having great diversity at the level of amino acid sequence. These sub-portions were designated as L1, L2, and L3 or H1, H2, and H3 where the "L" and the "H" designates the light chain and the heavy chain regions, respectively. These regions may be referred to as Chothia CDRs, which have boundaries that overlap with Kabat CDRs. Other boundaries defining CDRs overlapping with the Kabat CDRs have been described by Padlan, 1995, *FASEB J.* 9: 133-39; MacCallum, 1996, *J. Mol. Biol.* 262(5): 732-45; and Lefranc, 2003, *Dev. Comp. Immunol.* 27: 55-77. Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs. Identification of predicted CDRs using the amino acid sequence is well known in the field, such as in Martin, A. C. "Protein sequence and structure analysis of antibody variable domains," *In Antibody Engineering*, Vol. 2. Kontermann R., Dübel S., eds. Springer-Verlag, Berlin, p. 33-51 (2010). The amino acid sequence of the heavy and/or light chain variable domain may be also inspected to identify the sequences of the CDRs by other conventional methods, e.g., by comparison to known amino acid sequences of other heavy and light chain variable regions to determine the regions of sequence hypervariability. The numbered sequences may be aligned by eye, or by employing an alignment program such as one of the CLUSTAL suite of programs, as described in Thompson, 1994, *Nucleic Acids Res.* 22: 4673-80. Molecular models are conventionally used to correctly delineate framework and CDR regions and thus correct the sequence-based assignments.

The term "Fc" as used herein refers to a molecule comprising the sequence of a non-antigen-binding fragment resulting from digestion of an antibody or produced by other means, whether in monomeric or multimeric form, and can contain the hinge region. The original immunoglobulin source of the native Fc is preferably of human origin and can be any of the immunoglobulins, although IgG1 and IgG2 are preferred. Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgGA2). One example of a Fc is a disulfide-bonded dimer resulting from papain digestion of an IgG. The term "native Fc" as used herein is generic to the monomeric, dimeric, and multimeric forms.

A F(ab) fragment typically includes one light chain and the $V_H$ and $C_{H1}$ domains of one heavy chain, wherein the $V_H$-$C_{H1}$ heavy chain portion of the F(ab) fragment cannot form a disulfide bond with another heavy chain polypeptide. As used herein, a F(ab) fragment can also include one light chain containing two variable domains separated by an amino acid linker and one heavy chain containing two variable domains separated by an amino acid linker and a $C_{H1}$ domain.

A F(ab') fragment typically includes one light chain and a portion of one heavy chain that contains more of the constant region (between the $C_{H1}$ and $C_{H2}$ domains), such that an interchain disulfide bond can be formed between two heavy chains to form a F(ab')$_2$ molecule.

The term "binding protein" as used herein refers to a non-naturally occurring (or recombinant or engineered) molecule that specifically binds to at least one target antigen, and which comprises four polypeptide chains that form at least three antigen binding sites, wherein a first polypeptide chain has a structure represented by the formula:

$$V_{L2}\text{-}L_1\text{-}V_{L1}\text{-}L_2\text{-}C_L \qquad [I]$$

and a second polypeptide chain has a structure represented by the formula:

$$V_{H1}\text{-}L_3\text{-}V_{H2}\text{-}L_4\text{-}C_{H1} \qquad [II]$$

and a third polypeptide chain has a structure represented by the formula:

$$V_{H3}\text{-}C_{H1} \qquad [III]$$

and a fourth polypeptide chain has a structure represented by the formula:

$$V_{L3}\text{-}C_L \qquad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

and wherein the polypeptide of formula I and the polypeptide of formula II form a cross-over light chain-heavy chain pair.

A "recombinant" molecule is one that has been prepared, expressed, created, or isolated by recombinant means.

One embodiment of the disclosure provides binding proteins having biological and immunological specificity to between one and three target antigens. Another embodiment of the disclosure provides nucleic acid molecules comprising nucleotide sequences encoding polypeptide chains that form such binding proteins. Another embodiment of the disclosure provides expression vectors comprising nucleic acid molecules comprising nucleotide sequences encoding polypeptide chains that form such binding proteins. Yet another embodiment of the disclosure provides host cells that express such binding proteins (i.e., comprising nucleic acid molecules or vectors encoding polypeptide chains that form such binding proteins).

The term "swapability" as used herein refers to the interchangeability of variable domains within the binding protein format and with retention of folding and ultimate binding affinity. "Full swapability" refers to the ability to swap the order of both $V_{H1}$ and $V_{H2}$ domains, and therefore the order of $V_{L1}$ and $V_{L2}$ domains, in the polypeptide chain of formula I or the polypeptide chain of formula II (i.e., to reverse the order) while maintaining full functionality of the binding protein as evidenced by the retention of binding affinity. Furthermore, it should be noted that the designations $V_H$ and $V_L$ refer only to the domain's location on a particular protein chain in the final format. For example, $V_{H1}$ and $V_{H2}$ could be derived from $V_{L1}$ and $V_{L2}$ domains in parent antibodies and placed into the $V_{H1}$ and $V_{H2}$ positions in the binding protein. Likewise, $V_{L1}$ and $V_{L2}$ could be derived from $V_{H1}$ and $V_{H2}$ domains in parent antibodies and placed in the $V_{H1}$ and $V_{H2}$ positions in the binding protein. Thus, the $V_H$ and $V_L$ designations refer to the present location and not the original location in a parent antibody. $V_H$ and $V_L$ domains are therefore "swappable."

The term "antigen" or "target antigen" or "antigen target" as used herein refers to a molecule or a portion of a molecule that is capable of being bound by a binding protein, and additionally is capable of being used in an animal to produce antibodies capable of binding to an epitope of that antigen.

A target antigen may have one or more epitopes. With respect to each target antigen recognized by a binding protein, the binding protein is capable of competing with an intact antibody that recognizes the target antigen.

The term "Her2" refers to human epidermal growth factor receptor 2 which is a member of the epidermal growth factor receptor family.

"CD3" is cluster of differentiation factor 3 polypeptide and is a T-cell surface protein that is typically part of the T cell receptor (TCR) complex.

"CD28" is cluster of differentiation 28 polypeptide and is a T-cell surface protein that provides co-stimulatory signals for T-cell activation and survival.

"CD19" is cluster of differentiation 19 polypeptide and is located on B-cells.

"CD20" is cluster of differentiation 20 polypeptide and is an activated-glycosylated phosphoprotein expressed on the surface of B-cells.

"CD38" is cluster of differentiation 38 polypeptide and is a glycoprotein found on the surface of many immune cells.

"LAMP1" is lysosomal-associated membrane protein 1.

"IL-4" is interleukin 4 and is a cytokine that induces differentiation of naïve helper T cells.

"IL-13" is interleukin 13 and is a cytokine secreted by many cell types such as T-cells.

"TNFa" is tumor necrosis factor alpha and is a cytokine involved in systematic inflammation.

The term "T-cell engager" refers to binding proteins directed to a host's immune system, more specifically the T cells' cytotoxic activity as well as directed to a tumor target protein.

The term "monospecific binding protein" refers to a binding protein that specifically binds to one antigen target.

The term "monovalent binding protein" refers to a binding protein that has one antigen binding site.

The term "bispecific binding protein" refers to a binding protein that specifically binds to two different antigen targets.

The term "bivalent binding protein" refers to a binding protein that has two binding sites.

The term "trispecific binding protein" refers to a binding protein that specifically binds to three different antigen targets.

The term "trivalent binding protein" refers to a binding protein that has three binding sites. In particular embodiments the trivalent binding protein can bind to one antigen target. In other embodiments, the trivalent binding protein can bind to two antigen targets. In other embodiments, the trivalent binding protein can bind to three antigen targets.

An "isolated" binding protein is one that has been identified and separated and/or recovered from a component of its natural environment. Contaminant components of its natural environment are materials that would interfere with diagnostic or therapeutic uses for the binding protein, and may include enzymes, hormones, and other proteinaceous or non-proteinaceous solutes. In some embodiments, the binding protein will be purified: (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated binding proteins include the binding protein in situ within recombinant cells since at least one component of the binding protein's natural environment will not be present.

The terms "substantially pure" or "substantially purified" as used herein refer to a compound or species that is the predominant species present (i.e., on a molar basis it is more abundant than any other individual species in the composition). In some embodiments, a substantially purified fraction is a composition wherein the species comprises at least about 50% (on a molar basis) of all macromolecular species present. In other embodiments, a substantially pure composition will comprise more than about 80%, 85%, 90%, 95%, or 99% of all macromolar species present in the composition. In still other embodiments, the species is purified to essential homogeneity (contaminant species cannot be detected in the composition by conventional detection methods) wherein the composition consists essentially of a single macromolecular species.

A "neutralizing" binding protein as used herein refers to a molecule that is able to block or substantially reduce an effector function of a target antigen to which it binds. As used herein, "substantially reduce" means at least about 60%, preferably at least about 70%, more preferably at least about 75%, even more preferably at least about 80%, still more preferably at least about 85%, most preferably at least about 90% reduction of an effector function of the target antigen.

The term "epitope" includes any determinant, preferably a polypeptide determinant, capable of specifically binding to an immunoglobulin or T-cell receptor. In certain embodiments, epitope determinants include chemically active surface groupings of molecules such as amino acids, sugar side chains, phosphoryl groups, or sulfonyl groups, and, in certain embodiments, may have specific three-dimensional structural characteristics and/or specific charge characteristics. An epitope is a region of an antigen that is bound by an antibody or binding protein. In certain embodiments, a binding protein is said to specifically bind an antigen when it preferentially recognizes its target antigen in a complex mixture of proteins and/or macromolecules. In some embodiments, a binding protein is said to specifically bind an antigen when the equilibrium dissociation constant is $\leq 10^{-8}$ M, more preferably when the equilibrium dissociation constant is $\leq 10^{-9}$ M, and most preferably when the dissociation constant is $\leq 10^{-10}$ M.

The dissociation constant ($K_D$) of a binding protein can be determined, for example, by surface plasmon resonance. Generally, surface plasmon resonance analysis measures real-time binding interactions between ligand (a target antigen on a biosensor matrix) and analyte (a binding protein in solution) by surface plasmon resonance (SPR) using the BIAcore system (Pharmacia Biosensor; Piscataway, N.J.). Surface plasmon analysis can also be performed by immobilizing the analyte (binding protein on a biosensor matrix) and presenting the ligand (target antigen). The term "$K_D$," as used herein refers to the dissociation constant of the interaction between a particular binding protein and a target antigen.

The term "specifically binds" as used herein refers to the ability of a binding protein or an antigen-binding fragment thereof to bind to an antigen containing an epitope with an Kd of at least about $1\times10^{-6}$ M, $1\times10^{-7}$ M, $1\times10^{-8}$ M, $1\times10^{-9}$ M, $1\times10^{-10}$ M, $1\times10^{-11}$ M, $1\times10^{-12}$ M, or more, and/or to bind to an epitope with an affinity that is at least two-fold greater than its affinity for a nonspecific antigen.

The term "linker" as used herein refers to one or more amino acid residues inserted between immunoglobulin domains to provide sufficient mobility for the domains of the light and heavy chains to fold into cross over dual variable region immunoglobulins. A linker is inserted at the transition between variable domains or between variable and constant domains, respectively, at the sequence level. The transition between domains can be identified because the approximate size of the immunoglobulin domains are well understood. The precise location of a domain transition can be determined by locating peptide stretches that do not form secondary structural elements such as beta-sheets or alpha-helices as demonstrated by experimental data or as can be assumed by techniques of modeling or secondary structure prediction. The linkers described herein are referred to as $L_1$, which is located on the light chain between the C-terminus of the $V_{L2}$ and the N-terminus of the $V_{L1}$ domain; and $L_2$, which is located on the light chain between the C-terminus of the $V_{L1}$ and the N-terminus of the $C_L$ domain. The heavy chain linkers are known as $L_3$, which is located between the C-terminus of the $V_{H1}$ and the N-terminus of the $V_{Hz}$ domain; and $L_4$, which is located between the C-terminus of the $V_{H2}$ and the N-terminus of the $C_{H1}$ domain.

The term "vector" as used herein refers to any molecule (e.g., nucleic acid, plasmid, or virus) that is used to transfer coding information to a host cell. The term "vector" includes a nucleic acid molecule that is capable of transporting another nucleic acid to which it has been linked. One type of vector is a "plasmid," which refers to a circular double-stranded DNA molecule into which additional DNA segments may be inserted. Another type of vector is a viral vector, wherein additional DNA segments may be inserted into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with the host genome. In addition, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. The terms "plasmid" and "vector" may be used interchangeably herein, as a plasmid is the most commonly used form of vector. However, the disclosure is intended to include other forms of expression vectors, such as viral vectors (e.g., replication defective retroviruses, adenoviruses, and adeno-associated viruses), which serve equivalent functions.

The phrase "recombinant host cell" (or "host cell") as used herein refers to a cell into which a recombinant expression vector has been introduced. A recombinant host cell or host cell is intended to refer not only to the particular subject cell, but also to the progeny of such a cell. Because certain modifications may occur in succeeding generations due to either mutation or environmental influences, such progeny may not, in fact, be identical to the parent cell, but such cells are still included within the scope of the term "host cell" as used herein. A wide variety of host cell expression systems can be used to express the binding proteins, including bacterial, yeast, baculoviral, and mammalian expression systems (as well as phage display expression systems). An example of a suitable bacterial expression vector is pUC19. To express a binding protein recombinantly, a host cell is transformed or transfected with one or more recombinant expression vectors carrying DNA fragments encoding the polypeptide chains of the binding protein such that the polypeptide chains are expressed in the host cell and, preferably, secreted into the medium in which the host cells are cultured, from which medium the binding protein can be recovered.

The term "transformation" as used herein refers to a change in a cell's genetic characteristics, and a cell has been transformed when it has been modified to contain a new DNA. For example, a cell is transformed where it is genetically modified from its native state. Following transformation, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "transfection" as used herein refers to the uptake of foreign or exogenous DNA by a cell, and a cell has been "transfected" when the exogenous DNA has been introduced inside the cell membrane. A number of transfection techniques are well known in the art. Such techniques can be used to introduce one or more exogenous DNA molecules into suitable host cells.

The term "naturally occurring" as used herein and applied to an object refers to the fact that the object can be found in nature and has not been manipulated by man. For example, a polynucleotide or polypeptide that is present in an organism (including viruses) that can be isolated from a source in nature and that has not been intentionally modified by man is naturally-occurring. Similarly, "non-naturally occurring" as used herein refers to an object that is not found in nature or that has been structurally modified or synthesized by man.

As used herein, the twenty conventional amino acids and their abbreviations follow conventional usage. Stereoisomers (e.g., D-amino acids) of the twenty conventional amino acids; unnatural amino acids and analogs such as α-, α-disubstituted amino acids, N-alkyl amino acids, lactic acid, and other unconventional amino acids may also be suitable components for the polypeptide chains of the binding proteins. Examples of unconventional amino acids include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxyl-terminal direction, in accordance with standard usage and convention.

Naturally occurring residues may be divided into classes based on common side chain properties:

(1) hydrophobic: Met, Ala, Val, Leu, Ile, Phe, Trp, Tyr, Pro;

(2) polar hydrophilic: Arg, Asn, Asp, Gln, Glu, His, Lys, Ser, Thr;

(3) aliphatic: Ala, Gly, Ile, Leu, Val, Pro;

(4) aliphatic hydrophobic: Ala, Ile, Leu, Val, Pro;

(5) neutral hydrophilic: Cys, Ser, Thr, Asn, Gln;

(6) acidic: Asp, Glu;

(7) basic: His, Lys, Arg;

(8) residues that influence chain orientation: Gly, Pro;

(9) aromatic: His, Trp, Tyr, Phe; and

(10) aromatic hydrophobic: Phe, Trp, Tyr.

Conservative amino acid substitutions may involve exchange of a member of one of these classes with another member of the same class. Non-conservative substitutions may involve the exchange of a member of one of these classes for a member from another class.

A skilled artisan will be able to determine suitable variants of the polypeptide chains of the binding proteins using well-known techniques. For example, one skilled in the art may identify suitable areas of a polypeptide chain that may be changed without destroying activity by targeting regions not believed to be important for activity. Alternatively, one skilled in the art can identify residues and portions of the molecules that are conserved among similar polypeptides. In addition, even areas that may be important for biological activity or for structure may be subject to conservative amino acid substitutions without destroying the biological activity or without adversely affecting the polypeptide structure.

The term "patient" as used herein includes human and animal subjects.

The terms "treatment" or "treat" as used herein refer to both therapeutic treatment and prophylactic or preventative measures. Those in need of treatment include those having a disorder as well as those prone to have the disorder or those in which the disorder is to be prevented. In particular embodiments, binding proteins can be used to treat humans with cancer, or humans susceptible to cancer, or ameliorate cancer in a human subject. The binding proteins can also be used to prevent cancer in a human patient. In particular embodiments, the cancer is multiple myeloma, acute lymphoblastic leukemia, chronic lymphocytic leukemia, acute myeloid leukemia, lymphoma, breast cancer such as Her2+ breast cancer, germinal center B-cell lympohoma or B-cell acute lymphoblastic leukemia, In other embodiments, the binding proteins can be used to treat humans with inflammatory disorders, or humans susceptible to inflammatory disorders, or ameliorate inflammatory disorders in a human subject.

The terms "pharmaceutical composition" or "therapeutic composition" as used herein refer to a compound or composition capable of inducing a desired therapeutic effect when properly administered to a patient.

The term "pharmaceutically acceptable carrier" or "physiologically acceptable carrier" as used herein refers to one or more formulation materials suitable for accomplishing or enhancing the delivery of a binding protein.

The terms "effective amount" and "therapeutically effective amount" when used in reference to a pharmaceutical composition comprising one or more binding proteins refer to an amount or dosage sufficient to produce a desired therapeutic result. More specifically, a therapeutically effective amount is an amount of a binding protein sufficient to inhibit, for some period of time, one or more of the clinically defined pathological processes associated with the condition being treated. The effective amount may vary depending on the specific binding protein that is being used, and also depends on a variety of factors and conditions related to the patient being treated and the severity of the disorder. For example, if the binding protein is to be administered in vivo, factors such as the age, weight, and health of the patient as well as dose response curves and toxicity data obtained in preclinical animal work would be among those factors considered. The determination of an effective amount or therapeutically effective amount of a given pharmaceutical composition is well within the ability of those skilled in the art.

One embodiment of the disclosure provides a pharmaceutical composition comprising a pharmaceutically acceptable carrier and a therapeutically effective amount of a binding protein.

Trispecific and/or Trivalent Binding Proteins

In one embodiment, the binding protein of the disclosure is a trispecific and/or trivalent binding protein comprising four polypeptide chains that form three antigen binding sites that specifically bind one or more (e.g., three) different antigen targets or target proteins, wherein a first polypeptide chain comprises a structure represented by the formula:

$$V_{L2}\text{-}L_1\text{-}V_{L1}\text{-}L_2\text{-}C_L \qquad [I]$$

and a second polypeptide chain has a structure represented by the formula:

$$V_{H1}\text{-}L_3\text{-}V_{H2}\text{-}L_4\text{-}C_{H1} \qquad [II]$$

and a third polypeptide chain has a structure represented by the formula:

$$V_{H3}\text{-}C_{H1} \qquad [III]$$

and a fourth polypeptide chain has a structure represented by the formula:

$$V_{L3}\text{-}C_L \qquad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

and wherein the polypeptide of formula I and the polypeptide of formula II form a cross-over light chain-heavy chain pair.

In one embodiment, the binding protein of the disclosure is a trispecific and/or trivalent binding protein comprising four polypeptide chains that form three antigen binding sites that specifically bind one or more (e.g., three) antigen targets or target proteins, wherein a first polypeptide chain comprises a structure represented by the formula:

$$V_{L2}\text{-}L_1\text{-}V_{L1}\text{-}L_2\text{-}C_L \qquad [I]$$

and a second polypeptide chain has a structure represented by the formula:

$$V_{H1}\text{-}L_3\text{-}V_{H2}\text{-}L_4\text{-}C_{H1} \qquad [II]$$

and a third polypeptide chain has a structure represented by the formula:

$$V_{H3}\text{-}C_{H1} \qquad [III]$$

and a fourth polypeptide chain has a structure represented by the formula:

$$V_{L3}\text{-}C_L \qquad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

and wherein the polypeptide of formula I and the polypeptide of formula II form a cross-over light chain-heavy chain pair.

In one embodiment, the binding protein of the disclosure is a trispecific and/or trivalent binding protein comprising four polypeptide chains that form three antigen binding sites that specifically bind one or more (e.g., three) different antigen targets or target proteins, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}L_{H2}\text{-}L_4\text{-}C_{H1}\text{-hinge-}C_{H2}\text{-}C_{H3} \quad [II]$$

and a third polypeptide chain comprises a structure represented by the formula:

$$V_{H3}\text{-}C_{H1}\text{-hinge-}C_{H2}\text{-}C_{H3} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

and wherein the polypeptide of formula I and the polypeptide of formula II form a cross-over light chain-heavy chain pair.

In one embodiment, the binding protein of the disclosure is a trispecific and/or trivalent binding protein comprising four polypeptide chains that form three antigen binding sites that specifically bind one or more (e.g., three) antigen targets or target proteins, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}L_{H2}\text{-}L_4\text{-}C_{H1}\text{-hinge-}C_{H2}\text{-}C_{H3} \quad [II]$$

and a third polypeptide chain comprises a structure represented by the formula:

$$V_{H3}\text{-}C_{H1}\text{-hinge-}C_{H2}\text{-}C_{H3} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

and wherein the polypeptide of formula I and the polypeptide of formula II form a cross-over light chain-heavy chain pair.

In some embodiments, the first polypeptide chain and the second polypeptide chain have a cross-over orientation that forms two district antigen binding sites. In some embodiments, the VH1 and VL1 form a binding pair and form the first antigen binding site. In some embodiments, the VH2 and VL2 form a binding pair and form the second antigen binding site. In some embodiments, the third polypeptide and the fourth polypeptide form a third antigen binding site. In some embodiments, the VH3 and VL3 form a binding pair and form the third antigen binding site.

In one embodiment, the binding protein of the disclosure is a trispecific and/or trivalent binding protein comprising four polypeptide chains that form three antigen binding sites that specifically bind one or more (e.g., three) antigen targets or target proteins, wherein a first polypeptide chain comprises a structure represented by the formula:

$$V_{D1}\text{-}L_1\text{-}V_{D2}\text{-}L_2\text{-}C_L \quad [I]$$

and a second polypeptide chain comprises a structure represented by the formula:

$$V_{D3}\text{-}L_3\text{-}L_{D4}\text{-}L_4\text{-}C_{H1}\text{-hinge-}C_{H2}\text{-}C_{H3} \quad [II]$$

and a third polypeptide chain comprises a structure represented by the formula:

$$V_{H3}\text{-}C_{H1}\text{-hinge-}C_{H2}\text{-}C_{H3} \quad [III]$$

and a fourth polypeptide chain comprises a structure represented by the formula:

$$V_{L3}\text{-}C_L \quad [IV]$$

wherein:

$V_{D1}$ is a variable domain of heavy or light chain of a first immunoglobulin;

$V_{D2}$ is a variable domain of heavy or light chain of a second immunoglobulin;

$V_{D3}$ is a variable domain of heavy or light chain of a third immunoglobulin;

$V_{D4}$ is a variable domain of heavy or light chain of a fourth immunoglobulin;

$V_{H3}$ is an immunoglobulin heavy chain variable domain;

$V_{L3}$ is an immunoglobulin light chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

and wherein the polypeptide of formula I and the polypeptide of formula II form a cross-over light chain-heavy chain pair.

In some embodiments, the binding protein of the disclosure comprises three antigen binding sites that specifically bind one, two, or three antigen targets or target proteins. In some embodiments, the binding protein binds three antigen targets. In some embodiments, the binding protein binds three different antigen targets. In some embodiments, two of the antigen binding sites bind the same antigen target. In those embodiments, the binding protein comprises the same binding domains twice, or different binding domains, and/or specifically binds different antigens or epitopes on the same antigen target. In some embodiments, three of the antigen binding sites bind the same antigen target. In those embodiments, the binding protein comprises the same binding domains three times, or different binding domains, and/or specifically binds different antigens or epitopes on the same antigen target.

In some embodiments, $V_{L1}$, $V_{L2}$ and $V_{L3}$ are each independently a variable domain derived from an amino acid sequence as set forth in any one of SEQ ID NOs: 2, 4, 10, 14, 18, 22 or 115; and $V_{H1}$, $V_{H2}$ and $V_{H3}$, are each independently a variable domain derived from an amino acid sequence as set forth in any one of SEQ ID NOs: 1, 3, 9, 13, 17, 21 or 114. In other embodiments, $V_{L1}$, $V_{L2}$ and $V_{L3}$ are each independently a variable domain derived from an amino acid sequence as set forth in any one of SEQ ID NOs: 61, 63, 69, 71, 74, 76, 82, 86, 88 or 94; and $V_{H1}$, $V_{H2}$ and $V_{H3}$, are each independently a variable domain derived from an amino acid sequence as set forth in any one of SEQ ID NOs: 60, 62, 68, 73, 75, 81, 85, 87 or 93. In other embodiments, $V_{L1}$, $V_{L2}$ and $V_{L3}$ each independently comprise light chain complementarity determining regions of a variable domain comprising an amino acid sequence as set forth in any one of SEQ ID NOs: 43-59, 123-125; and $V_{H1}$, $V_{H2}$ and $V_{H3}$ each independently comprise heavy chain complementarity determining regions of a variable domain comprising an amino acid sequence as set forth in any one of SEQ ID NOs: 25-42, 120-122. In other embodiments, $V_{L1}$, $V_{L2}$ and $V_{L3}$ each independently comprise light chain complementarity determining regions of a variable domain comprising an amino acid sequence as set forth in any one of SEQ ID NOs: 61, 63, 69, 71, 74, 76, 82, 86, 88 or 94; and $V_{H1}$, $V_{H2}$ and $V_{H3}$ each independently comprise heavy chain complementarity determining regions of a variable domain comprising an amino acid sequence as set forth in any one of SEQ ID NOs: 60, 62, 68, 73, 75, 81, 85, 87 or 93. In some embodiments, $V_{H1}$, $V_{H2}$ and $V_{H3}$ each independently comprise heavy chain complementarity determining regions and/or a variable domain sequence shown in Tables 2-5.

In some embodiments, $V_{L1}$, $V_{L2}$ and $V_{L3}$ each independently comprise a variable domain sequence as set forth in any one of SEQ ID NOs:169, 171, and 173; and/or $V_{H1}$, $V_{H2}$, and $V_{H3}$ each independently comprise a variable domain sequence as set forth in any one of SEQ ID NOs: 168, 170, and 172. In some embodiments, $V_{L1}$, $V_{L2}$ and $V_{L3}$ each independently comprise light chain complementarity determining regions comprising an amino acid sequence selected from the group consisting of SEQ ID NOs: 141-147, 178, and 179; and/or $V_{H1}$, $V_{H2}$ and $V_{H3}$ each independently comprise heavy chain complementarity determining regions comprising an amino acid sequence selected from the group consisting of SEQ ID NOs: 129-137. In some embodiments, $V_{L1}$, $V_{L2}$ and $V_{L3}$ each independently comprise a variable domain sequence as set forth in any one of SEQ ID NOs:151, 153, 155, 157, 159, 161, 163, 165, and 167; and/or $V_{H1}$, $V_{H2}$, and $V_{H3}$ each independently comprise a variable domain sequence as set forth in any one of SEQ ID NOs:150, 152, 154, 156, 158, 160, 162, 164, and 166. In some embodiments, $V_{L1}$, $V_{L2}$ and $V_{L3}$ each independently comprise light chain complementarity determining regions comprising an amino acid sequence as set forth in any one of SEQ ID NOs: 43-59, 123-125, 138-140, and 149; and/or $V_{H1}$, $V_{H2}$ and $V_{H3}$ each independently comprise heavy chain complementarity determining regions of a variable domain comprising an amino acid sequence as set forth in any one of SEQ ID NOs: 25-42, 120-122, and 126-128. In some embodiments, $V_{L1}$, $V_{L2}$ and $V_{L3}$ each independently comprise light chain complementarity determining regions and/or a variable domain sequence shown in Tables 2-5.

In particular embodiments, the order of the $V_{H1}$ and $V_{H2}$ domains, and therefore the order of $V_{L1}$ and $V_{L2}$ domains, in the polypeptide chain of formula I or the polypeptide chain of formula II (i.e., to reverse the order) are swapped.

In some embodiments, the first polypeptide chain comprises the amino acid sequence of SEQ ID NO: 4 or an amino acid sequence that is at least 95% identical to the amino acid sequence of SEQ ID NO: 4 optionally comprising CDRs that are 100% identical to the CDRs of the polypeptide chain of SEQ ID NO: 4; the second polypeptide chain comprises the amino acid sequence of SEQ ID NO: 3 or an amino acid sequence that is at least 95% identical to the amino acid sequence of SEQ ID NO: 3 optionally comprising CDRs that are 100% identical to the CDRs of the polypeptide chain of SEQ ID NO: 3; the third polypeptide chain comprises the amino acid sequence of SEQ ID NO: 1 or an amino acid sequence that is at least 95% identical to the amino acid sequence of SEQ ID NO: 1 optionally comprising CDRs that are 100% identical to the CDRs of the polypeptide chain of SEQ ID NO: 1; and the fourth polypeptide chain comprises the amino acid sequence of SEQ ID NO: 2 or an amino acid sequence that is at least 95% identical to the amino acid sequence of SEQ ID NO: 2 optionally comprising CDRs that are 100% identical to the CDRs of the polypeptide chain of SEQ ID NO: 2.

In some embodiments, the first polypeptide chain comprises the amino acid sequence of SEQ ID NO: 10 or an amino acid sequence that is at least 95% identical to the amino acid sequence of SEQ ID NO: 10 optionally comprising CDRs that are 100% identical to the CDRs of the polypeptide chain of SEQ ID NO: 10; the second polypeptide chain comprises the amino acid sequence of SEQ ID NO: 9 or an amino acid sequence that is at least 95% identical to the amino acid sequence of SEQ ID NO: 9 optionally comprising CDRs that are 100% identical to the CDRs of the polypeptide chain of SEQ ID NO: 9; the third polypeptide chain comprises the amino acid sequence of SEQ ID NO: 1 or an amino acid sequence that is at least 95% identical to the amino acid sequence of SEQ ID NO: 1 optionally comprising CDRs that are 100% identical to the CDRs of the polypeptide chain of SEQ ID NO: 1; and the fourth polypeptide chain comprises the amino acid sequence of SEQ ID NO: 2 or an amino acid sequence that is at least 95% identical to the amino acid sequence of SEQ ID NO: 2 optionally comprising CDRs that are 100% identical to the CDRs of the polypeptide chain of SEQ ID NO: 2.

In some embodiments, the first polypeptide chain comprises the amino acid sequence of SEQ ID NO: 4 or an amino acid sequence that is at least 95% identical to the amino acid sequence of SEQ ID NO: 4 optionally comprising CDRs that are 100% identical to the CDRs of the polypeptide chain of SEQ ID NO: 4; the second polypeptide chain comprises the amino acid sequence of SEQ ID NO: 3 or an amino acid sequence that is at least 95% identical to the amino acid sequence of SEQ ID NO: 3 optionally comprising CDRs that are 100% identical to the CDRs of the polypeptide chain of SEQ ID NO: 3; the third polypeptide chain comprises the amino acid sequence of SEQ ID NO: 13 or an amino acid sequence that is at least 95% identical to the amino acid sequence of SEQ ID NO: 13 optionally comprising CDRs that are 100% identical to the CDRs of the polypeptide chain of SEQ ID NO: 13; and the fourth polypeptide chain comprises the amino acid sequence of SEQ ID NO: 14 or an amino acid sequence that is at least 95% identical to the amino acid sequence of SEQ ID NO: 14 optionally comprising CDRs that are 100% identical to the CDRs of the polypeptide chain of SEQ ID NO: 14.

In some embodiments, the first polypeptide chain comprises the amino acid sequence of SEQ ID NO: 10 or an amino acid sequence that is at least 95% identical to the amino acid sequence of SEQ ID NO: 10 optionally comprising CDRs that are 100% identical to the CDRs of the polypeptide chain of SEQ ID NO: 10; the second polypeptide chain comprises the amino acid sequence of SEQ ID NO: 9 or an amino acid sequence that is at least 95% identical to the amino acid sequence of SEQ ID NO: 9 optionally comprising CDRs that are 100% identical to the CDRs of the polypeptide chain of SEQ ID NO: 9; the third polypeptide chain comprises the amino acid sequence of SEQ ID NO: 13 or an amino acid sequence that is at least 95% identical to the amino acid sequence of SEQ ID NO: 13 optionally comprising CDRs that are 100% identical to the CDRs of the polypeptide chain of SEQ ID NO: 13; and the fourth polypeptide chain comprises the amino acid sequence of SEQ ID NO: 14 or an amino acid sequence that is at least 95% identical to the amino acid sequence of SEQ ID NO: 14 optionally comprising CDRs that are 100% identical to the CDRs of the polypeptide chain of SEQ ID NO: 14.

In some embodiments, the first polypeptide chain comprises the amino acid sequence of SEQ ID NO: 4 or an amino acid sequence that is at least 95% identical to the amino acid sequence of SEQ ID NO: 4 optionally comprising CDRs that are 100% identical to the CDRs of the polypeptide chain of SEQ ID NO: 4; the second polypeptide chain comprises the amino acid sequence of SEQ ID NO: 3 or an amino acid sequence that is at least 95% identical to the amino acid sequence of SEQ ID NO: 3 optionally comprising CDRs that are 100% identical to the CDRs of the polypeptide chain of SEQ ID NO: 3; the third polypeptide chain comprises the amino acid sequence of SEQ ID NO: 17 or an amino acid sequence that is at least 95% identical to the amino acid sequence of SEQ ID NO: 17 optionally comprising CDRs that are 100% identical to the CDRs of the polypeptide chain of SEQ ID NO: 17; and the fourth polypeptide chain comprises the amino acid sequence of SEQ ID NO: 18 or an amino acid sequence that is at least 95% identical to the amino acid sequence of SEQ ID NO: 18 optionally comprising CDRs that are 100% identical to the CDRs of the polypeptide chain of SEQ ID NO: 18.

In some embodiments, the first polypeptide chain comprises the amino acid sequence of SEQ ID NO: 10 or an amino acid sequence that is at least 95% identical to the amino acid sequence of SEQ ID NO: 10 optionally comprising CDRs that are 100% identical to the CDRs of the polypeptide chain of SEQ ID NO: 10; the second polypeptide chain comprises the amino acid sequence of SEQ ID NO: 9 or an amino acid sequence that is at least 95% identical to the amino acid sequence of SEQ ID NO: 9 optionally comprising CDRs that are 100% identical to the CDRs of the polypeptide chain of SEQ ID NO: 9; the third polypeptide chain comprises the amino acid sequence of SEQ ID NO: 17 or an amino acid sequence that is at least 95% identical to the amino acid sequence of SEQ ID NO: 17 optionally comprising CDRs that are 100% identical to the CDRs of the polypeptide chain of SEQ ID NO: 17; and the fourth polypeptide chain comprises the amino acid sequence of SEQ ID NO: 18 or an amino acid sequence that is at least 95% identical to the amino acid sequence of SEQ ID NO: 18 optionally comprising CDRs that are 100% identical to the CDRs of the polypeptide chain of SEQ ID NO: 18.

In some embodiments, the first polypeptide chain comprises the amino acid sequence of SEQ ID NO: 4 or an amino acid sequence that is at least 95% identical to the amino acid sequence of SEQ ID NO: 4 optionally comprising CDRs that are 100% identical to the CDRs of the polypeptide chain of SEQ ID NO: 4; the second polypeptide chain comprises the amino acid sequence of SEQ ID NO: 3 or an amino acid sequence that is at least 95% identical to the amino acid sequence of SEQ ID NO: 3 optionally comprising CDRs that are 100% identical to the CDRs of the polypeptide chain of SEQ ID NO: 3; the third polypeptide chain comprises the amino acid sequence of SEQ ID NO: 21 or an amino acid sequence that is at least 95% identical to the amino acid sequence of SEQ ID NO: 21 optionally comprising CDRs that are 100% identical to the CDRs of the polypeptide chain of SEQ ID NO: 21; and the fourth polypeptide chain comprises the amino acid sequence of SEQ ID NO: 22 or an amino acid sequence that is at least 95% identical to the amino acid sequence of SEQ ID NO: 22 optionally comprising CDRs that are 100% identical to the CDRs of the polypeptide chain of SEQ ID NO: 22.

In some embodiments, the first polypeptide chain comprises the amino acid sequence of SEQ ID NO: 10 or an amino acid sequence that is at least 95% identical to the amino acid sequence of SEQ ID NO: 10 optionally comprising CDRs that are 100% identical to the CDRs of the polypeptide chain of SEQ ID NO: 10; the second polypeptide chain comprises the amino acid sequence of SEQ ID NO: 9 or an amino acid sequence that is at least 95% identical to the amino acid sequence of SEQ ID NO: 9 optionally comprising CDRs that are 100% identical to the CDRs of the polypeptide chain of SEQ ID NO: 9; the third polypeptide chain comprises the amino acid sequence of SEQ ID NO: 21 or an amino acid sequence that is at least 95% identical to the amino acid sequence of SEQ ID NO: 21 optionally comprising CDRs that are 100% identical to the CDRs of the polypeptide chain of SEQ ID NO: 21; and the fourth polypeptide chain comprises the amino acid sequence of SEQ ID NO: 22 or an amino acid sequence that is at least 95% identical to the amino acid sequence of SEQ ID NO: 22 optionally comprising CDRs that are 100% identical to the CDRs of the polypeptide chain of SEQ ID NO: 22.

In some embodiments, the first polypeptide chain comprises the amino acid sequence of SEQ ID NO: 63 or an amino acid sequence that is at least 95% identical to the amino acid sequence of SEQ ID NO: 63 optionally comprising CDRs that are 100% identical to the CDRs of the polypeptide chain of SEQ ID NO: 63; the second polypeptide chain comprises the amino acid sequence of SEQ ID NO: 62 or an amino acid sequence that is at least 95% identical to the amino acid sequence of SEQ ID NO: 62 optionally comprising CDRs that are 100% identical to the CDRs of the polypeptide chain of SEQ ID NO: 62; the third polypeptide chain comprises the amino acid sequence of SEQ ID NO: 60 or an amino acid sequence that is at least 95% identical to the amino acid sequence of SEQ ID NO: 60 optionally comprising CDRs that are 100% identical to the CDRs of the polypeptide chain of SEQ ID NO: 60; and the fourth polypeptide chain comprises the amino acid sequence of SEQ ID NO: 61 or an amino acid sequence that is at least 95% identical to the amino acid sequence of SEQ ID NO: 61 optionally comprising CDRs that are 100% identical to the CDRs of the polypeptide chain of SEQ ID NO: 61.

In some embodiments, the first polypeptide chain comprises the amino acid sequence of SEQ ID NO: 69 or an amino acid sequence that is at least 95% identical to the amino acid sequence of SEQ ID NO: 69 optionally comprising CDRs that are 100% identical to the CDRs of the polypeptide chain of SEQ ID NO: 69; the second polypeptide chain comprises the amino acid sequence of SEQ ID NO: 68 or an amino acid sequence that is at least 95% identical to the amino acid sequence of SEQ ID NO: 68 optionally comprising CDRs that are 100% identical to the CDRs of the polypeptide chain of SEQ ID NO: 68; the third polypeptide chain comprises the amino acid sequence of SEQ ID NO: 60 or an amino acid sequence that is at least 95% identical to the amino acid sequence of SEQ ID NO: 60 optionally comprising CDRs that are 100% identical to the CDRs of the polypeptide chain of SEQ ID NO: 60; and the fourth polypeptide chain comprises the amino acid sequence of SEQ ID NO: 61 or an amino acid sequence that is at least 95% identical to the amino acid sequence of SEQ ID NO: 61 optionally comprising CDRs that are 100% identical to the CDRs of the polypeptide chain of SEQ ID NO: 61.

In some embodiments, the first polypeptide chain comprises the amino acid sequence of SEQ ID NO: 69 or an amino acid sequence that is at least 95% identical to the amino acid sequence of SEQ ID NO: 69 optionally comprising CDRs that are 100% identical to the CDRs of the polypeptide chain of SEQ ID NO: 69; the second polypeptide chain comprises the amino acid sequence of SEQ ID NO: 68 or an amino acid sequence that is at least 95% identical to the amino acid sequence of SEQ ID NO: 68 optionally comprising CDRs that are 100% identical to the CDRs of the polypeptide chain of SEQ ID NO: 68; the third polypeptide chain comprises the amino acid sequence of SEQ ID NO: 60 or an amino acid sequence that is at least 95% identical to the amino acid sequence of SEQ ID NO: 60 optionally comprising CDRs that are 100% identical to the CDRs of the polypeptide chain of SEQ ID NO: 60; and the fourth polypeptide chain comprises the amino acid sequence of SEQ ID NO: 71 or an amino acid sequence that is at least 95% identical to the amino acid sequence of SEQ ID NO: 71 optionally comprising CDRs that are 100% identical to the CDRs of the polypeptide chain of SEQ ID NO: 71.

In some embodiments, the first polypeptide chain comprises the amino acid sequence of SEQ ID NO: 76 or an amino acid sequence that is at least 95% identical to the amino acid sequence of SEQ ID NO: 76 optionally comprising CDRs that are 100% identical to the CDRs of the polypeptide chain of SEQ ID NO: 76; the second polypeptide chain comprises the amino acid sequence of SEQ ID NO: 75 or an amino acid sequence that is at least 95% identical to the amino acid sequence of SEQ ID NO: 75 optionally comprising CDRs that are 100% identical to the CDRs of the polypeptide chain of SEQ ID NO: 75; the third polypeptide chain comprises the amino acid sequence of SEQ ID NO: 73 or an amino acid sequence that is at least 95% identical to the amino acid sequence of SEQ ID NO: 73 optionally comprising CDRs that are 100% identical to the CDRs of the polypeptide chain of SEQ ID NO: 73; and the fourth polypeptide chain comprises the amino acid sequence of SEQ ID NO: 74 or an amino acid sequence that is at least 95% identical to the amino acid sequence of SEQ ID NO: 74 optionally comprising CDRs that are 100% identical to the CDRs of the polypeptide chain of SEQ ID NO: 74.

In some embodiments, the first polypeptide chain comprises the amino acid sequence of SEQ ID NO: 82 or an amino acid sequence that is at least 95% identical to the amino acid sequence of SEQ ID NO: 82 optionally comprising CDRs that are 100% identical to the CDRs of the polypeptide chain of SEQ ID NO: 82; the second polypeptide chain comprises the amino acid sequence of SEQ ID NO: 81 or an amino acid sequence that is at least 95% identical to the amino acid sequence of SEQ ID NO:81 optionally comprising CDRs that are 100% identical to the CDRs of the polypeptide chain of SEQ ID NO: 81; the third polypeptide chain comprises the amino acid sequence of SEQ ID NO: 73 or an amino acid sequence that is at least 95% identical to the amino acid sequence of SEQ ID NO: 73 optionally comprising CDRs that are 100% identical to the CDRs of the polypeptide chain of SEQ ID NO: 73; and the fourth polypeptide chain comprises the amino acid sequence of SEQ ID NO: 74 or an amino acid sequence that is at least 95% identical to the amino acid sequence of SEQ ID NO: 74 optionally comprising CDRs that are 100% identical to the CDRs of the polypeptide chain of SEQ ID NO: 74.

In some embodiments, the first polypeptide chain comprises the amino acid sequence of SEQ ID NO: 88 or an amino acid sequence that is at least 95% identical to the amino acid sequence of SEQ ID NO: 88 optionally comprising CDRs that are 100% identical to the CDRs of the polypeptide chain of SEQ ID NO: 88; the second polypeptide chain comprises the amino acid sequence of SEQ ID NO: 87 or an amino acid sequence that is at least 95% identical to the amino acid sequence of SEQ ID NO: 87 optionally comprising CDRs that are 100% identical to the CDRs of the polypeptide chain of SEQ ID NO: 87; the third polypeptide chain comprises the amino acid sequence of SEQ ID NO: 85 or an amino acid sequence that is at least 95% identical to the amino acid sequence of SEQ ID NO: 85 optionally comprising CDRs that are 100% identical to the CDRs of the polypeptide chain of SEQ ID NO: 85; and the fourth polypeptide chain comprises the amino acid sequence of SEQ ID NO: 86 or an amino acid sequence that is at least 95% identical to the amino acid sequence of SEQ ID NO: 86 optionally comprising CDRs that are 100% identical to the CDRs of the polypeptide chain of SEQ ID NO: 86.

In some embodiments, the first polypeptide chain comprises the amino acid sequence of SEQ ID NO: 94 or an amino acid sequence that is at least 95% identical to the amino acid sequence of SEQ ID NO: 94 optionally comprising CDRs that are 100% identical to the CDRs of the polypeptide chain of SEQ ID NO: 94; the second polypeptide chain comprises the amino acid sequence of SEQ ID NO: 93 or an amino acid sequence that is at least 95% identical to the amino acid sequence of SEQ ID NO: 93 optionally comprising CDRs that are 100% identical to the CDRs of the polypeptide chain of SEQ ID NO: 93; the third polypeptide chain comprises the amino acid sequence of SEQ ID NO: 85 or an amino acid sequence that is at least 95% identical to the amino acid sequence of SEQ ID NO: 85 optionally comprising CDRs that are 100% identical to the CDRs of the polypeptide chain of SEQ ID NO: 85; and the fourth polypeptide chain comprises the amino acid sequence of SEQ ID NO: 86 or an amino acid sequence that is at least 95% identical to the amino acid sequence of SEQ ID NO: 86 optionally comprising CDRs that are 100% identical to the CDRs of the polypeptide chain of SEQ ID NO: 86.

In some embodiments, the first polypeptide chain comprises the amino acid sequence of SEQ ID NO: 69 or an amino acid sequence that is at least 95% identical to the amino acid sequence of SEQ ID NO: 69 optionally comprising CDRs that are 100% identical to the CDRs of the polypeptide chain of SEQ ID NO: 69; the second polypeptide chain comprises the amino acid sequence of SEQ ID NO: 68 or an amino acid sequence that is at least 95% identical to the amino acid sequence of SEQ ID NO: 68 optionally comprising CDRs that are 100% identical to the CDRs of the polypeptide chain of SEQ ID NO: 68; the third polypeptide chain comprises the amino acid sequence of SEQ ID NO: 73 or an amino acid sequence that is at least 95% identical to the amino acid sequence of SEQ ID NO: 73 optionally comprising CDRs that are 100% identical to the CDRs of the polypeptide chain of SEQ ID NO: 73; and the fourth polypeptide chain comprises the amino acid sequence of SEQ ID NO: 74 or an amino acid sequence that is at least 95% identical to the amino acid sequence of SEQ ID NO: 74 optionally comprising CDRs that are 100% identical to the CDRs of the polypeptide chain of SEQ ID NO: 74.

In some embodiments, the first polypeptide chain comprises the amino acid sequence of SEQ ID NO: 69 or an amino acid sequence that is at least 95% identical to the amino acid sequence of SEQ ID NO: 69 optionally comprising CDRs that are 100% identical to the CDRs of the polypeptide chain of SEQ ID NO: 69; the second polypeptide chain comprises the amino acid sequence of SEQ ID NO: 68 or an amino acid sequence that is at least 95% identical to the amino acid sequence of SEQ ID NO: 68 optionally comprising CDRs that are 100% identical to the CDRs of the polypeptide chain of SEQ ID NO: 68; the third polypeptide chain comprises the amino acid sequence of SEQ ID NO: 85 or an amino acid sequence that is at least 95% identical to the amino acid sequence of SEQ ID NO: 85 optionally comprising CDRs that are 100% identical to the CDRs of the polypeptide chain of SEQ ID NO: 85; and the fourth polypeptide chain comprises the amino acid sequence of SEQ ID NO: 86 or an amino acid sequence that is at least 95% identical to the amino acid sequence of SEQ ID NO: 86 optionally comprising CDRs that are 100% identical to the CDRs of the polypeptide chain of SEQ ID NO: 86.

In some embodiments, the first polypeptide chain comprises the amino acid sequence of SEQ ID NO: 63 or an amino acid sequence that is at least 95% identical to the amino acid sequence of SEQ ID NO: 63 optionally comprising CDRs that are 100% identical to the CDRs of the polypeptide chain of SEQ ID NO: 63; the second polypeptide chain comprises the amino acid sequence of SEQ ID NO: 62 or an amino acid sequence that is at least 95% identical to the amino acid sequence of SEQ ID NO: 62 optionally comprising CDRs that are 100% identical to the CDRs of the polypeptide chain of SEQ ID NO: 62; the third polypeptide chain comprises the amino acid sequence of SEQ ID NO: 73 or an amino acid sequence that is at least 95% identical to the amino acid sequence of SEQ ID NO: 73 optionally comprising CDRs that are 100% identical to the CDRs of the polypeptide chain of SEQ ID NO: 73; and the fourth polypeptide chain comprises the amino acid sequence of SEQ ID NO: 74 or an amino acid sequence that is at least 95% identical to the amino acid sequence of SEQ ID NO: 74 optionally comprising CDRs that are 100% identical to the CDRs of the polypeptide chain of SEQ ID NO: 74.

In some embodiments, the first polypeptide chain comprises the amino acid sequence of SEQ ID NO: 63 or an amino acid sequence that is at least 95% identical to the amino acid sequence of SEQ ID NO: 63 optionally comprising CDRs that are 100% identical to the CDRs of the polypeptide chain of SEQ ID NO: 63; the second polypeptide chain comprises the amino acid sequence of SEQ ID NO: 62 or an amino acid sequence that is at least 95% identical to the amino acid sequence of SEQ ID NO: 62 optionally comprising CDRs that are 100% identical to the CDRs of the polypeptide chain of SEQ ID NO: 62; the third polypeptide chain comprises the amino acid sequence of SEQ ID NO: 85 or an amino acid sequence that is at least 95% identical to the amino acid sequence of SEQ ID NO: 85 optionally comprising CDRs that are 100% identical to the CDRs of the polypeptide chain of SEQ ID NO: 85; and the fourth polypeptide chain comprises the amino acid sequence of SEQ ID NO: 86 or an amino acid sequence that is at least 95% identical to the amino acid sequence of SEQ ID NO: 86 optionally comprising CDRs that are 100% identical to the CDRs of the polypeptide chain of SEQ ID NO: 86.

In some embodiments, the first polypeptide chain comprises the amino acid sequence of SEQ ID NO: 4 or an amino acid sequence that is at least 95% identical to the amino acid sequence of SEQ ID NO: 4 optionally comprising CDRs that are 100% identical to the CDRs of the polypeptide chain of SEQ ID NO: 4; the second polypeptide chain comprises the amino acid sequence of SEQ ID NO: 3 or an amino acid sequence that is at least 95% identical to the amino acid sequence of SEQ ID NO: 3 optionally comprising CDRs that are 100% identical to the CDRs of the polypeptide chain of SEQ ID NO: 3; the third polypeptide chain comprises the amino acid sequence of SEQ ID NO: 114 or an amino acid sequence that is at least 95% identical to the amino acid sequence of SEQ ID NO: 114 optionally comprising CDRs that are 100% identical to the CDRs of the polypeptide chain of SEQ ID NO: 114; and the fourth polypeptide chain comprises the amino acid sequence of SEQ ID NO: 115 or an amino acid sequence that is at least 95% identical to the amino acid sequence of SEQ ID NO: 115 optionally comprising CDRs that are 100% identical to the CDRs of the polypeptide chain of SEQ ID NO: 115.

In some embodiments, the first polypeptide chain comprises the amino acid sequence of SEQ ID NO: 10 or an amino acid sequence that is at least 95% identical to the amino acid sequence of SEQ ID NO: 10 optionally comprising CDRs that are 100% identical to the CDRs of the polypeptide chain of SEQ ID NO: 10; the second polypeptide chain comprises the amino acid sequence of SEQ ID NO: 9 or an amino acid sequence that is at least 95% identical to the amino acid sequence of SEQ ID NO: 9 optionally comprising CDRs that are 100% identical to the CDRs of the polypeptide chain of SEQ ID NO: 9; the third polypeptide chain comprises the amino acid sequence of SEQ ID NO: 114 or an amino acid sequence that is at least 95% identical to the amino acid sequence of SEQ ID NO:

114 optionally comprising CDRs that are 100% identical to the CDRs of the polypeptide chain of SEQ ID NO: 114; and the fourth polypeptide chain comprises the amino acid sequence of SEQ ID NO: 115 or an amino acid sequence that is at least 95% identical to the amino acid sequence of SEQ ID NO: 115 optionally comprising CDRs that are 100% identical to the CDRs of the polypeptide chain of SEQ ID NO: 115.

In other embodiments, the binding protein of the disclosure is a trispecific and/or trivalent binding protein comprising four polypeptide chains that form three antigen binding sites that specifically bind one or more (e.g., three) different target proteins, wherein a first polypeptide chain has a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}L_{H2}\text{-}L_4\text{-}C_{H1}\text{-hinge-}C_{H2}\text{-}C_{H3}\text{(hole)} \quad [II]$$

and a third polypeptide chain comprises a structure represented by the formula:

$$V_{H3}\text{-}C_{H1}\text{-hinge-}C_{H2}\text{-}C_{H3}\text{(knob)} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

and wherein the polypeptide of formula I and the polypeptide of formula II form a cross-over light chain-heavy chain pair.

In other embodiments, the binding protein of the disclosure is a trispecific and/or trivalent binding protein comprising four polypeptide chains that form three antigen binding sites that specifically bind one or more (e.g., three) target proteins, wherein a first polypeptide chain has a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}L_{H2}\text{-}L_4\text{-}C_{H1}\text{-hinge-}C_{H2}\text{-}C_{H3}\text{(hole)} \quad [II]$$

and a third polypeptide chain comprises a structure represented by the formula:

$$V_{H3}\text{-}C_{H1}\text{-hinge-}C_{H2}\text{-}C_{H3}\text{(knob)} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

and wherein the polypeptide of formula I and the polypeptide of formula II form a cross-over light chain-heavy chain pair.

In some embodiments, the first polypeptide chain and the second polypeptide chain have a cross-over orientation that forms two distinct antigen binding sites. In some embodiments, the VH1 and VL1 form a binding pair and form the first antigen binding site. In some embodiments, the VH2 and VL2 form a binding pair and form the second antigen binding site. In some embodiments, the third polypeptide and the fourth polypeptide form a third antigen binding site. In some embodiments, the VH3 and VL3 form a binding pair and form the third antigen binding site. In some embodiments, the second polypeptide chain and the third polypeptide chain comprise one or more modifications. In some embodiments, the second polypeptide chain and the third polypeptide chain of a binding protein are different, e.g., having different $C_{H1}$, $C_{H2}$, and/or $C_{H3}$ domain(s) (such as those including a modification described herein). In some embodiments, the first polypeptide chain and the fourth polypeptide chain comprise one or more modifications. In some embodiments, the first polypeptide chain and the fourth polypeptide chain of a binding protein are different, e.g., having different $C_L$ domains (such as those including a modification described herein, and/or lambda vs. kapp $C_L$ domains).

In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:150, optionally comprising CDRs that are 100% identical to the CDRs of the polypeptide chain of SEQ ID NO: 150, and/or a light chain variable domain comprising an amino acid sequence that is at least 95%, at least 96%, at least 97%, at least 98%, at least 99%, or 100% identical to SEQ ID NO:151, optionally comprising CDRs that are 100% identical to the CDRs of the polypeptide chain of SEQ ID NO: 151. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:152, optionally comprising CDRs that are 100% identical to the CDRs of the polypeptide chain of SEQ ID NO: 152, and/or a light chain variable domain comprising an amino acid sequence that is at least 95%, at least 96%, at least 97%, at least 98%, at least 99%, or 100% identical to SEQ ID NO:153, optionally comprising CDRs that are 100% identical to the CDRs of the polypeptide chain of SEQ ID NO: 153. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:154, optionally comprising CDRs that are 100% identical to the CDRs of the polypeptide chain of SEQ ID NO: 154, and/or a light chain variable domain comprising an amino acid sequence that is at least 95%, at least 96%, at least 97%, at least 98%, at least 99%, or 100% identical to SEQ ID NO:155, optionally comprising CDRs that are 100% identical to the CDRs of the polypeptide chain of SEQ ID NO: 155. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:156, optionally comprising CDRs that are 100% identical to the CDRs of the polypeptide chain of SEQ ID NO: 156, and/or a light chain variable domain comprising an amino acid sequence that is at least 95%, at least 96%, at least 97%, at least 98%, at least 99%, or 100% identical to SEQ ID NO:157, optionally comprising CDRs that are 100% identical to the CDRs of the polypeptide chain of SEQ ID NO: 157. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:158, optionally comprising CDRs that are 100% identical to the CDRs of the polypeptide chain of SEQ ID NO: 158, and/or a light chain variable domain comprising an amino acid sequence that is at least 95%, at least 96%, at least 97%, at least 98%, at least 99%, or 100% identical to SEQ ID NO:159, optionally comprising CDRs that are 100% identical to the CDRs of the polypeptide chain of SEQ ID NO: 159. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:160, optionally comprising CDRs that are 100% identical to the CDRs of the polypeptide chain of SEQ ID NO: 160, and/or a light chain variable domain comprising an amino acid sequence that is at least 95%, at least 96%, at least 97%, at least 98%, at least 99%, or 100% identical to SEQ ID NO:161, optionally comprising CDRs that are 100% identical to the CDRs of the polypeptide chain of SEQ ID NO: 161. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:162, optionally comprising CDRs that are 100% identical to the CDRs of the polypeptide chain of SEQ ID NO: 162, and/or a light chain variable domain comprising an amino acid sequence that is at least 95%, at least 96%, at least 97%, at least 98%, at least 99%, or 100% identical to SEQ ID NO:163, optionally comprising CDRs that are 100% identical to the CDRs of the polypeptide chain of SEQ ID NO: 163. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:164, optionally comprising CDRs that are 100% identical to the CDRs of the polypeptide chain of SEQ ID NO: 164, and/or a light chain variable domain comprising an amino acid sequence that is at least 95%, at least 96%, at least 97%, at least 98%, at least 99%, or 100% identical to SEQ ID NO:165, optionally comprising CDRs that are 100% identical to the CDRs of the polypeptide chain of SEQ ID NO: 165. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:166, optionally comprising CDRs that are 100% identical to the CDRs of the polypeptide chain of SEQ ID NO: 166, and/or a light chain variable domain comprising an amino acid sequence that is at least 95%, at least 96%, at least 97%, at least 98%, at least 99%, or 100% identical to SEQ ID NO:167, optionally comprising CDRs that are 100% identical to the CDRs of the polypeptide chain of SEQ ID NO: 167. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:168, optionally comprising CDRs that are 100% identical to the CDRs of the polypeptide chain of SEQ ID NO: 168, and/or a light chain variable domain comprising an amino acid sequence that is at least 95%, at least 96%, at least 97%, at least 98%, at least 99%, or 100% identical to SEQ ID NO:169, optionally comprising CDRs that are 100% identical to the CDRs of the polypeptide chain of SEQ ID NO: 169. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:170, optionally comprising CDRs that are 100% identical to the CDRs of the polypeptide chain of SEQ ID NO: 170, and/or a light chain variable domain comprising an amino acid sequence that is at least 95%, at least 96%, at least 97%, at least 98%, at least 99%, or 100% identical to SEQ ID NO:171, optionally comprising CDRs that are 100% identical to the CDRs of the polypeptide chain of SEQ ID NO: 171. In some embodiments, a binding protein of the present disclosure comprises an antigen binding site comprising a heavy chain variable domain comprising an amino acid sequence that is at least 95%, at least 96%, at least 97%, at least 98%, at least 99%, or 100% identical to SEQ ID NO:172, optionally comprising CDRs that are 100% identical to the CDRs of the polypeptide chain of SEQ ID NO: 172, and/or a light chain variable domain comprising an amino acid sequence that is at least 95%, at least 96%, at least 97%, at least 98%, at least 99%, or 100% identical to SEQ ID NO:173, optionally comprising CDRs that are 100% identical to the CDRs of the polypeptide chain of SEQ ID NO: 173.

In some embodiments, a binding protein of the present disclosure binds to one, two, or three antigen targets with an equilibrium dissociation constant ($K_D$) that is less than or equal to 1 μM, 500 nM, 100 nM, 50 nM, 10 nM, 5 nM, or 1 nM. Exemplary assays for determining $K_D$ are known in the art. For example, in some embodiments, $K_D$ is determined by measuring binding kinetics at between 0° C. and 37° C. e.g., at 0° C., 4° C., 25° C., or 37° C.) using the techniques described in Example 1 (e.g., SPR or ELISA).

In some embodiments, a binding protein of the present disclosure activates CD4 and/or CD8 T cells in vitro and/or induces antibody-mediated in vitro cell killing of a cell expressing one or more antigen targets of one or more binding domains of the binding protein. Exemplary in vitro cell killing and T cell activation assays are known in the art.

For example, in some embodiments, in vitro cell killing and/or T cell activation is assayed using the techniques described in Example 1.

In some embodiments, a binding protein of the present disclosure specifically binds to, and/or blocks signaling mediated by, one or more cytokines. Exemplary cytokine release assays are known in the art. For example, in some embodiments, cytokine release is assayed using the techniques described in Example 1.

In some embodiments, a binding protein of the present disclosure comprises a first antigen binding site that specifically binds a target protein on T cells, a second antigen binding site that specifically binds a target protein on T cells, and a third antigen binding site that specifically binds an antigen target or target protein. In some embodiments, a binding protein of the present disclosure comprises a first antigen binding site that specifically binds a target protein on T cells, a second antigen binding site that specifically binds a target protein on T cells, and a third antigen binding site that specifically binds a tumor target protein. In some embodiments, a binding protein of the present disclosure comprises a first antigen binding site that specifically binds a target protein on T cells, a second antigen binding site that specifically binds a target protein on T cells, and a third antigen binding site that specifically binds a human tumor target protein. In some embodiments, the first and second antigen binding sites specifically bind a tumor target protein for instance selected from CD3 and CD28, respectively. In some embodiments, the first and second antigen binding sites specifically bind a tumor target protein for instance selected from CD28 and CD3, respectively. In some embodiments, the third antigen binding site specifically binds CD19, CD20, CD38, Her2, or LAMP1. Further examples of such targets and target proteins are provided infra.

In some embodiments, a binding protein of the present disclosure comprises a first antigen binding site that specifically binds CD3, a second antigen binding site that specifically binds CD28, and a third antigen binding site that specifically binds an antigen target or target protein. In some embodiments, a binding protein of the present disclosure comprises a first antigen binding site that specifically binds CD28, a second antigen binding site that specifically binds CD3, and a third antigen binding site that specifically binds an antigen target or target protein. Further examples of such antigen targets or target proteins are provided infra. In some embodiments, a binding protein of the present disclosure comprises a first antigen binding site that specifically binds CD3, a second antigen binding site that specifically binds CD28, and a third antigen binding site that specifically binds a tumor target protein. In some embodiments, a binding protein of the present disclosure comprises a first antigen binding site that specifically binds human CD3, a second antigen binding site that specifically binds human CD28, and a third antigen binding site that specifically binds a human tumor target protein. In some embodiments, a binding protein of the present disclosure comprises a first antigen binding site that specifically binds CD28, a second antigen binding site that specifically binds CD3, and a third antigen binding site that specifically binds a tumor target protein. In some embodiments, a binding protein of the present disclosure comprises a first antigen binding site that specifically binds human CD28, a second antigen binding site that specifically binds human CD3, and a third antigen binding site that specifically binds a human tumor target protein. In some embodiments, the third antigen binding site specifically binds CD19, CD20, CD38, Her2, or LAMP1. Further examples of such tumor antigen targets or tumor target proteins are provided infra.

In some embodiments, the antigen binding site that specifically binds CD3 comprises a heavy chain variable domain comprising the amino acid sequence of SEQ ID NO: 152 and a light chain variable domain comprising the amino acid sequence of SEQ ID NO: 153; or a heavy chain variable domain comprising the amino acid sequence of SEQ ID NO: 154 and a light chain variable domain comprising the amino acid sequence of SEQ ID NO: 155. Additional VH, VL, and/or CDR sequences of antibodies that specifically bind CD3 suitable for use in any of the binding proteins described herein may be found in International Publication No. WO2016/116626, which is incorporated by reference herein in its entirety. In some embodiments, the antigen binding site that specifically binds CD3 comprises six CDRs, or a heavy chain and a light chain variable domain, shown in Tables 2-5. In some embodiments, the antigen binding site that specifically binds CD3 comprises (i) three heavy chain CDRs of SEQ ID Nos. 34, 35 and 36, respectively, and three light chain CDRs of SEQ ID Nos. 52, 53 and 54, respectively; or (ii) three heavy chain CDRs of SEQ ID Nos. 34, 35 and 36, respectively, and three light chain CDRs of SEQ ID Nos. 149, 53 and 54, respectively. In some embodiments, the antigen binding site that specifically binds CD3 is part of a polypeptide chain comprising the amino acid sequence of SEQ ID NO:3 or an amino acid sequence that is at least 95% identical to the amino acid sequence of SEQ ID NO:3 optionally comprising CDRs that are 100% identical to the CDRs of the polypeptide chain of SEQ ID NO:3. In some embodiments, the antigen binding site that specifically binds CD3 is part of a polypeptide chain comprising the amino acid sequence of SEQ ID NO:4 or an amino acid sequence that is at least 95% identical to the amino acid sequence of SEQ ID NO:4 optionally comprising CDRs that are 100% identical to the CDRs of the polypeptide chain of SEQ ID NO:4.

In some embodiments, the antigen binding site that specifically binds CD28 comprises a heavy chain variable domain comprising the amino acid sequence of SEQ ID NO: 160 and a light chain variable domain comprising the amino acid sequence of SEQ ID NO: 161; or a heavy chain variable domain comprising the amino acid sequence of SEQ ID NO: 162 and a light chain variable domain comprising the amino acid sequence of SEQ ID NO: 163. In some embodiments, the antigen binding site that specifically binds CD28 comprises six CDRs, or a heavy chain and a light chain variable domain, shown in Tables 2-5. In some embodiments, the antigen binding site that specifically binds CD28 comprises (i) three heavy chain CDRs of SEQ ID Nos. 28, 29 and 30, respectively, and three light chain CDRs of SEQ ID Nos. 46, 47 and 48, respectively; or (ii) three heavy chain CDRs of SEQ ID Nos. 31, 32 and 33, respectively, and three light chain CDRs of SEQ ID Nos. 49, 50 and 51, respectively. In some embodiments, the antigen binding site that specifically binds CD28 is part of a polypeptide chain comprising the amino acid sequence of SEQ ID NO:3 or an amino acid sequence that is at least 95% identical to the amino acid sequence of SEQ ID NO:3 optionally comprising CDRs that are 100% identical to the CDRs of the polypeptide chain of SEQ ID NO:3. In some embodiments, the antigen binding site that specifically binds CD28 is part of a polypeptide chain comprising the amino acid sequence of SEQ ID NO:4 or an amino acid sequence that is at least 95% identical to the amino acid sequence of SEQ ID NO:4 optionally comprising CDRs that are 100% identical to the CDRs of the polypeptide chain of SEQ ID NO:4.

In some embodiments, a binding protein of the present disclosure comprises a first antigen binding site that specifically binds CD3, a second antigen binding site that specifically binds CD28, and a third antigen binding site that specifically binds CD38, or a first antigen binding site that specifically binds CD28, a second antigen binding site that specifically binds CD3, and a third antigen binding site that specifically binds CD38, wherein:

- the antigen binding site specifically binding CD3 comprises (i) three heavy chain CDRs of SEQ ID Nos. 34, 35 and 36, respectively, and three light chain CDRs of SEQ ID Nos. 52, 53 and 54, respectively; or (ii) three heavy chain CDRs of SEQ ID Nos. 34, 35 and 36, respectively, and three light chain CDRs of SEQ ID Nos. 149, 53 and 54, respectively; and
- the antigen binding site specifically binding CD28 comprises (i) three heavy chain CDRs of SEQ ID Nos. 28, 29 and 30, respectively, and three light chain CDRs of SEQ ID Nos. 46, 47 and 48, respectively; or (ii) three heavy chain CDRs of SEQ ID Nos. 31, 32 and 33, respectively, and three light chain CDRs of SEQ ID Nos. 49, 50 and 51, respectively; and
- the antigen binding site specifically binding CD38 comprises (i) three heavy chain CDRs of SEQ ID Nos. 40, 41 and 42, respectively, and three light chain CDRs of SEQ ID Nos. 58, 44 and 59, respectively.

In some embodiments, the antigen binding site that specifically binds a tumor target protein comprises a heavy chain variable domain comprising the amino acid sequence of SEQ ID NO: 156 and a light chain variable domain comprising the amino acid sequence of SEQ ID NO: 157; a heavy chain variable domain comprising the amino acid sequence of SEQ ID NO: 158 and a light chain variable domain comprising the amino acid sequence of SEQ ID NO: 159; a heavy chain variable domain comprising the amino acid sequence of SEQ ID NO: 164 and a light chain variable domain comprising the amino acid sequence of SEQ ID NO: 165; a heavy chain variable domain comprising the amino acid sequence of SEQ ID NO: 150 and a light chain variable domain comprising the amino acid sequence of SEQ ID NO: 151; or a heavy chain variable domain comprising the amino acid sequence of SEQ ID NO: 166 and a light chain variable domain comprising the amino acid sequence of SEQ ID NO: 167. In some embodiments, the antigen binding site that specifically binds a tumor target protein comprises six CDRs, or a heavy chain and a light chain variable domain, shown in Tables 2-5. In some embodiments, the antigen binding site that specifically binds a tumor target protein comprises six CDRs of an anti-Her2, anti-CD19, anti-CD20, anti-CD38, or anti-LAMP1 binding domain shown in Tables 2-5.

In some embodiments, a binding protein of the present disclosure comprises four polypeptide chains that form three antigen binding sites, wherein a first polypeptide chain comprises a structure represented by the formula:

$$V_{L2}\text{-}L_1\text{-}V_{L1}\text{-}L_2\text{-}C_L \qquad [I]$$

and a second polypeptide chain comprises a structure represented by the formula:

$$V_{H1}\text{-}L_3\text{-}L_{H2}\text{-}L_4\text{-}C_{H1}\text{-hinge-}C_{H2}\text{-}C_{H3} \qquad [II]$$

and a third polypeptide chain comprises a structure represented by the formula:

$$V_{H3}\text{-}C_{H1}\text{-hinge-}C_{H2}\text{-}C_{H3} \qquad [III]$$

and a fourth polypeptide chain comprises a structure represented by the formula:

$$V_{L3}\text{-}C_L \qquad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair;

wherein:

$V_{L1}$, $V_{L2}$ and $V_{L3}$ each independently comprise a variable domain sequence as set forth in any one of SEQ ID NOs: 169, 171, and 173; and wherein:

$V_{H1}$, $V_{H2}$, and $V_{H3}$ each independently comprise a variable domain sequence as set forth in any one of SEQ ID NOs:168, 170, and 172.

In some embodiments, a binding protein of the present disclosure comprises four polypeptide chains that form three antigen binding sites, wherein a first polypeptide chain comprises a structure represented by the formula:

$$V_{L2}\text{-}L_1\text{-}V_{L1}\text{-}L_2\text{-}C_L \qquad [I]$$

and a second polypeptide chain comprises a structure represented by the formula:

$$V_{H1}\text{-}L_3\text{-}L_{H2}\text{-}L_4\text{-}C_{H1}\text{-hinge-}C_{H2}\text{-}C_{H3} \qquad [II]$$

and a third polypeptide chain comprises a structure represented by the formula:

$$V_{H3}\text{-}C_{H1}\text{-hinge-}C_{H2}\text{-}C_{H3} \qquad [III]$$

and a fourth polypeptide chain comprises a structure represented by the formula:

$$V_{L3}\text{-}C_L \qquad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair;

wherein:

$V_{L1}$, $V_{L2}$ and $V_{L3}$ each independently comprise light chain complementarity determining regions comprising an amino acid sequence selected from the group consisting of SEQ ID NOs: 141-147, 178, and 179; and wherein:

$V_{H1}$, $V_{H2}$ and $V_{H3}$ each independently comprise heavy chain complementarity determining regions comprising an amino acid sequence selected from the group consisting of SEQ ID NOs: 129-137.

In some embodiments, a binding protein of the present disclosure comprises four polypeptide chains that form three antigen binding sites, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}L_{H2}\text{-}L_4\text{-}C_{H1}\text{-hinge-}C_{H2}\text{-}C_{H3} \quad [II]$$

and a third polypeptide chain comprises a structure represented by the formula:

$$V_{H3}\text{-}C_{H1}\text{-hinge-}C_{H2}\text{-}C_{H3} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair;

wherein:

$V_{L1}$, $V_{L2}$ and $V_{L3}$ each independently comprise a variable domain sequence as set forth in any one of SEQ ID NOs: 151, 153, 155, 157, 159, 161, 163, 165, and 167; and wherein:

$V_{H1}$, $V_{H2}$, and $V_{H3}$ each independently comprise a variable domain sequence as set forth in any one of SEQ ID NOs:150, 152, 154, 156, 158, 160, 162, 164, and 166.

In some embodiments, a binding protein of the present disclosure comprises four polypeptide chains that form three antigen binding sites, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}L_{H2}\text{-}L_4\text{-}C_{H1}\text{-hinge-}C_{H2}\text{-}C_{H3} \quad [II]$$

and a third polypeptide chain comprises a structure represented by the formula:

$$V_{H3}\text{-}C_{H1}\text{-hinge-}C_{H2}\text{-}C_{H3} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair;

wherein:

$V_{L1}$, $V_{L2}$ and $V_{L3}$ each independently comprise light chain complementarity determining regions comprising an amino acid sequence as set forth in any one of SEQ ID NOs: 43-59, 123-125, 138-140, and 149; and wherein:

$V_{H1}$, $V_{H2}$ and $V_{H3}$ each independently comprise heavy chain complementarity determining regions comprising an amino acid sequence as set forth in any one of SEQ ID NOs: 25-42, 120-122, and 126-128.

In some embodiments, a binding protein of the present disclosure comprises an antigen binding site that specifically binds CD3, an antigen binding site that specifically binds CD28, and an antigen binding site that specifically binds an antigen target other than CD3 or CD28. In some embodiments, a binding protein of the present disclosure comprises an antigen binding site that specifically binds human CD3, an antigen binding site that specifically binds human CD28, and an antigen binding site that specifically binds a human antigen target other than CD3 or CD28. In some embodiments, a binding protein of the present disclosure comprises (a) an antigen binding site that specifically binds CD3, wherein the antigen binding site that specifically binds CD3 comprises (i) a heavy chain variable domain comprising the amino acid sequence of SEQ ID NO: 152 and a light chain variable domain comprising the amino acid sequence of SEQ ID NO: 153, (ii) a heavy chain variable domain comprising the amino acid sequence of SEQ ID NO: 154 and a light chain variable domain comprising the amino acid sequence of SEQ ID NO: 155, (iii) a heavy chain variable domain comprising a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36, and a light chain variable domain comprising a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54, or (iv) a heavy chain variable domain comprising a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36, and a light chain variable domain comprising a CDR-L1 comprising the amino acid sequence of SEQ ID NO:149, a CDR-L2 comprising the amino acid sequence of SEQ ID NO:53, and a CDR-L3 comprising the amino acid sequence of SEQ ID NO:54; (b) an antigen binding site that specifically binds CD28, wherein the antigen binding site that specifically binds CD28 comprises (i) a heavy chain variable domain comprising the amino acid sequence of SEQ ID NO: 160 and a light chain variable domain comprising the amino acid sequence of SEQ ID NO: 161, (ii) a heavy chain variable domain comprising the amino acid sequence of SEQ ID NO: 162 and a light chain variable domain comprising the amino acid sequence of SEQ ID NO: 163, (iii) a heavy chain variable domain comprising a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30, and a light chain variable domain comprising a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48, or (iv) a heavy chain variable domain comprising a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33, and a light chain variable domain comprising a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; and (c) an antigen binding site that specifically binds an antigen target other than CD3 or CD28. In some embodiments, a binding protein of the present disclosure comprises a first polypeptide chain comprising the amino acid sequence of SEQ ID NO:4 or 10, a second polypeptide chain comprising the amino acid sequence of SEQ ID NO:3 or 9, and a third and a fourth polypeptide chain, wherein the third and fourth polypeptide chains form an antigen binding domain that specifically binds an antigen target other than CD3 or CD28. In some embodiments, the antigen binding site that specifically binds an antigen target other than CD3 or CD28 binds an antigen target selected from A2AR, APRIL, ATPDase, BAFF, BAFFR, BCMA, BlyS, BTK, BTLA, B7DC, B7H1, B7H4 (also known as VTCN1), B7H5, B7H6, B7H7, B7RP1, B7-4, C3, C5, CCL2 (also known as MCP-1), CCL3 (also known as MIP-1a), CCL4 (also known as MIP-1b), CCL5 (also known as RANTES), CCL7 (also known as MCP-3), CCL8 (also known as mcp-2), CCL11 (also known as eotaxin), CCL15 (also known as CCL17 (also known as TARC), CCL19 (also known as MIP-3b), CCL20 (also known as MIP-3a), CCL21 (also known as MIP-2), CCL24 (also known as MPIF-2/eotaxin-2), CCL25 (also known as TECK), CCL26 (also known as eotaxin-3), CCR3, CCR4, CD19, CD20, CD23 (also known as FCER2, a receptor for IgE), CD24, CD27, CD38, CD39, CD40, CD70, CD80 (also known as B7-1), CD86 (also known as B7-2), CD122, CD137 (also known as 41BB), CD137L, CD152 (also known as CTLA4), CD154 (also known as CD40L), CD160, CD272, CD273 (also known as PDL2), CD274 (also known as PDL1), CD275 (also known as B7H2), CD276 (also known as B7H3), CD278 (also known as ICOS), CD279 (also known as PD-1), CDH1 (also known as E-cadherin), chitinase, CLEC9, CLEC91, CRTH2, CSF-1 (also known as M-CSF), CSF-2 (also known as GM-CSF), CSF-3 (also known as GCSF), CX3CL1 (also known as SCYD1), CXCL12 (also known as SDF1), CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb (also known as a receptor for IL25), IL18, IL22, IL23, IL25, IL27, IL33, IL35, ITGB4 (also known as b4 integrin), ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2 (also known as a receptor for IL33), STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP (also known as a co-receptor for IL7Ra), TSLPR, TWEAK, VEGF, VISTA, Vstm3, WUCAM, and XCR1 (also known as GPR5/CCXCR1).

In some embodiments, $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and $V_{L3}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45.

In some embodiments, $V_{H1}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L1}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H2}$ comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; $V_{L2}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45; $V_{H3}$ comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and $V_{L3}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45.

In some embodiments, $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and $V_{L3}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45.

In some embodiments, $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:37, a CDR-H2 comprising the amino acid sequence of SEQ ID NO:38, and a CDR-H3 comprising the amino acid sequence of SEQ ID NO:39; and $V_{L3}$ comprises a CDR-L1 comprising the amino acid sequence of SEQ ID NO:55, a CDR-L2 comprising the amino acid sequence of SEQ ID NO:56, and a CDR-L3 comprising the amino acid sequence of SEQ ID NO:57.

In some embodiments, $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:37, a CDR-H2 comprising the amino acid sequence of SEQ ID NO:38, and a CDR-H3 comprising the amino acid sequence of SEQ ID NO:39; and $V_{L3}$ comprises a CDR-L1 comprising the amino acid sequence of SEQ ID NO:55, a CDR-L2 comprising the amino acid sequence of SEQ ID NO:56, and a CDR-L3 comprising the amino acid sequence of SEQ ID NO:57.

In some embodiments, $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:40, a CDR-H2 comprising the amino acid sequence of SEQ ID NO:41, and a CDR-H3 comprising the amino acid sequence of SEQ ID NO:42; and $V_{L3}$ comprises a CDR-L1 comprising the amino acid sequence of SEQ ID NO:58, a CDR-L2 comprising the amino acid sequence of SEQ ID NO:44, and a CDR-L3 comprising the amino acid sequence of SEQ ID NO:59.

In some embodiments, $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:40, a CDR-H2 comprising the amino acid sequence of SEQ ID NO:41, and a CDR-H3 comprising the amino acid sequence of SEQ ID NO:42; and $V_{L3}$ comprises a CDR-L1 comprising the amino acid sequence of SEQ ID NO:58, a CDR-L2 comprising the amino acid sequence of SEQ ID NO:44, and a CDR-L3 comprising the amino acid sequence of SEQ ID NO:59.

In some embodiments, $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:126, a CDR-H2 comprising the amino acid sequence of SEQ ID NO:127, and a CDR-H3 comprising the amino acid sequence of SEQ ID NO:128; and $V_{L3}$ comprises a CDR-L1 comprising the amino acid sequence of SEQ ID NO:138, a CDR-L2 comprising the amino acid sequence of SEQ ID NO:139, and a CDR-L3 comprising the amino acid sequence of SEQ ID NO:140.

In some embodiments, $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:126, a CDR-H2 comprising the amino acid sequence of SEQ ID NO:127, and a CDR-H3 comprising the amino acid sequence of SEQ ID NO:128; and $V_{L3}$ comprises a CDR-L1 comprising the amino acid sequence of SEQ ID NO:138, a CDR-L2 comprising the amino acid sequence of SEQ ID NO:139, and a CDR-L3 comprising the amino acid sequence of SEQ ID NO:140.

In some embodiments, $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; and $V_{L3}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142.

In some embodiments, $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; and $V_{L3}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142.

In some embodiments, $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; and $V_{L3}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142.

In some embodiments, $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L2}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147.

In some embodiments, $V_{H1}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L1}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147.

In some embodiments, $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L2}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144.

In some embodiments, $V_{H1}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L1}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144.

In some embodiments, $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147.

In some embodiments, $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144.

In some embodiments, $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147.

In some embodiments, $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144.

In some embodiments, $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:120, a CDR-H2 comprising the amino acid sequence of SEQ ID NO:121, and a CDR-H3 comprising the amino acid sequence of SEQ ID NO:122; and $V_{L3}$ comprises a CDR-L1 comprising the amino acid sequence of SEQ ID NO:123, a CDR-L2 comprising the amino acid sequence of SEQ ID NO:124, and a CDR-L3 comprising the amino acid sequence of SEQ ID NO:125.

In some embodiments, $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:120, a CDR-H2 comprising the amino acid sequence of SEQ ID NO:121, and a CDR-H3 comprising the amino acid sequence of SEQ ID NO:122; and $V_{L3}$ comprises a CDR-L1 comprising the amino acid sequence of SEQ ID NO:123, a CDR-L2 comprising the amino acid sequence of SEQ ID NO:124, and a CDR-L3 comprising the amino acid sequence of SEQ ID NO:125.

Antigen Targets

In some embodiments, a binding protein of the present disclosure binds one or more (e.g., one, two, or three) of the following antigen targets or target proteins: A2AR, APRIL, ATPDase, BAFF, BAFFR, BCMA, BlyS, BTK, BTLA, B7DC, B7H1, B7H4 (also known as VTCN1), B7H5, B7H6, B7H7, B7RP1, B7-4, C3, C5, CCL2 (also known as MCP-1), CCL3 (also known as MIP-1a), CCL4 (also known as MIP-1b), CCL5 (also known as RANTES), CCL7 (also known as MCP-3), CCL8 (also known as mcp-2), CCL11 (also known as eotaxin), CCL15 (also known as MIP-1d), CCL17 (also known as TARC), CCL19 (also known as MIP-3b), CCL20 (also known as MIP-3a), CCL21 (also known as MIP-2), CCL24 (also known as MPIF-2/eotaxin-2), CCL25 (also known as TECK), CCL26 (also known as eotaxin-3), CCR3, CCR4, CD3, CD19, CD20, CD23 (also known as FCER2, a receptor for IgE), CD24, CD27, CD28, CD38, CD39, CD40, CD70, CD80 (also known as B7-1), CD86 (also known as B7-2), CD122, CD137 (also known as 41BB), CD137L, CD152 (also known as CTLA4), CD154 (also known as CD40L), CD160, CD272, CD273 (also known as PDL2), CD274 (also known as PDL1), CD275 (also known as B7H2), CD276 (also known as B7H3), CD278 (also known as ICOS), CD279 (also known as PD-1), CDH1 (also known as E-cadherin), chitinase, CLEC9, CLEC91, CRTH2, CSF-1 (also known as M-CSF), CSF-2 (also known as GM-CSF), CSF-3 (also known as GCSF), CX3CL1 (also known as SCYD1), CXCL12 (also known as SDF1), CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb (also known as a receptor for IL25), IL18, IL22, IL23, IL25, IL27, IL33, IL35, ITGB4 (also known as b4 integrin), ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2 (also known as a receptor for IL33), STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP (also known as a co-receptor for IL7Ra), TSLPR, TWEAK, VEGF, VISTA, Vstm3, WUCAM, and XCR1 (also known as GPR5/CCXCR1). In some embodiments, one or more of the above antigen targets are human antigen targets.

In one embodiment, the binding proteins specifically bind to one or more tumor antigen targets (e.g., target proteins). In other embodiments, the binding proteins specifically bind to one or more tumor target protein and one or more target protein on a T-cell including a T cell receptor complex. These T-cell engager binding proteins are capable of recruiting T cells transiently to target cells and, at the same time, activating the cytolytic activity of the T cells. Examples of target proteins on T cells include but are not limited to CD3 and CD28, among others. Further examples of such antigen targets or target proteins are provided supra. In some embodiments, the trispecific binding proteins may be generated by combining the antigen binding domains of two or more monospecific antibodies (parent antibodies) into one antibody. In some embodiments, a binding protein of the present disclosure binds one or more (e.g., one, two, or three) of the following antigen targets: CD3, CD19, CD20, CD28, CD38, Her2, LAMP1, IL-4, IL-13 and TNFa.

In some embodiments of the disclosure, the trivalent binding protein is capable of binding three antigen targets. In some embodiments of the disclosure, the trivalent binding protein is capable of binding three different antigen targets. In one embodiment, the binding protein is trispecific and one light chain-heavy chain pair is capable of binding two different antigen targets or epitopes and one light chain-heavy chain pair is capable of binding one antigen target or epitope. In another embodiment, the binding protein is capable of binding three tumor antigen targets. In another embodiment, the binding protein is capable of binding three different tumor antigen targets. In other embodiments, the binding protein is capable of inhibiting the function of one or more of the antigen targets.

In some embodiments, a binding protein of the present disclosure binds one or more tumor target proteins. In some embodiments, the binding protein is capable of specifically binding three epitopes on a single tumor target protein. In some embodiments, the binding protein is capable of specifically binding three different epitopes on a single tumor target protein. In some embodiments, the binding protein is capable of binding two different epitopes on a first tumor target protein, and one epitope on a second tumor target protein. In some embodiments, the first and second tumor target proteins are different. In some embodiments, the binding protein is capable of specifically binding three different tumor target proteins.

In some embodiments, a binding protein of the present disclosure binds one or more cytokine target proteins. In some embodiments, the binding protein is capable of specifically binding three epitopes on a single cytokine target protein. In some embodiments, the binding protein is capable of specifically binding three different epitopes on a single cytokine target protein. In some embodiments, the binding protein is capable of binding two different epitopes on a first cytokine target protein, and one epitope on a second cytokine target protein. In some embodiments, the first and second cytokine target proteins are different. In some embodiments, the binding protein is capable of specifically binding three different cytokine target proteins. In some embodiments, the one or more cytokine target proteins are one or more of IL-4, IL-13 and/or TNFa. Further examples of cytokine target proteins are provided infra.

In some embodiments, a binding protein of the present disclosure binds one or more tumor target proteins and one or more T cell target proteins. In some embodiments, the binding protein is capable of specifically binding one tumor target protein and two different epitopes on a single T cell target protein. In some embodiments, the binding protein is capable of specifically binding one tumor target protein and two different T cell target proteins (e.g., CD28 and CD3). In some embodiments, the binding protein is capable of specifically binding one T cell target protein and two different epitopes on a single tumor target protein. In some embodiments, the binding protein is capable of specifically binding one T cell target protein and two different tumor target proteins. In some embodiments, the first and second polypeptide chains of the binding protein form two antigen binding sites that specifically target two T cell target proteins, and the third and fourth polypeptide chains of the binding protein form an antigen binding site that specifically binds a tumor target protein. In some embodiments, the first and second polypeptide chains of the binding protein form two antigen binding sites that specifically target two tumor target proteins, and the third and fourth polypeptide chains of the binding protein form an antigen binding site that specifically binds a T cell target protein. In some embodiments, the one or more tumor target proteins are one or more of CD3, CD19, CD20, CD28, CD38, Her2, LAMP1, IL-4, IL-13 and/or TNFa. In some embodiments, the one or more T cell target proteins are one or more of CD3 and CD28. Further examples of tumor target proteins and T cell target proteins are provided supra.

In some embodiments, a binding protein of the present disclosure binds, independently of each other, same or different, one, two or three antigen targets or target proteins, selected from cytokine target proteins, tumor target antigens or tumor target proteins, T cell target proteins, immune checkpoint inhibitors, immune checkpoint modulators, immune checkpoint costimulatory molecules, and/or target molecules on the surface of an immune cell. In some embodiments, a binding protein of the present disclosure is trivalent but bispecific and capable of specifically binding twice to the same antigen targets or target proteins. In some embodiments, a binding protein of the present disclosure is capable of specifically binding two different epitopes on a single cytokine target proteins, tumor target antigens or tumor target proteins, T cell target proteins, immune checkpoint inhibitors, immune checkpoint modulators, immune checkpoint costimulatory molecules, and/or target molecules on the surface of an immune cell. Further examples of such antigen targets or target proteins are provided supra.

The binding proteins of the disclosure may be prepared using domains or sequences obtained or derived from any human or non-human antibody, including, for example, human, murine, or humanized antibodies.

Linkers

In some embodiments, the linkers $L_1$, $L_2$, $L_3$ and $L_4$ range from no amino acids (length=0) to about 100 amino acids long, or less than 100, 50, 40, 30, 20, or 15 amino acids or less. The linkers can also be 10, 9, 8, 7, 6, 5, 4, 3, 2, or 1 amino acids long. $L_1$, $L_2$, $L_3$ and $L_4$ in one binding protein may all have the same amino acid sequence or may all have different amino acid sequences.

Examples of suitable linkers include a single glycine (Gly) residue; a diglycine peptide (Gly-Gly); a tripeptide (Gly-Gly-Gly); a peptide with four glycine residues (Gly-Gly-Gly-Gly; SEQ ID NO: 98); a peptide with five glycine residues (Gly-Gly-Gly-Gly-Gly; SEQ ID NO: 99); a peptide with six glycine residues (Gly-Gly-Gly-Gly-Gly-Gly; SEQ ID NO: 100); a peptide with seven glycine residues (Gly-Gly-Gly-Gly-Gly-Gly-Gly; SEQ ID NO: 101); a peptide with eight glycine residues (Gly-Gly-Gly-Gly-Gly-Gly-Gly-Gly; SEQ ID NO: 102). Other combinations of amino acid residues may be used such as the peptide Gly-Gly-Gly-Gly-Ser (SEQ ID NO: 103), the peptide Gly-Gly-Gly-Gly-Ser-Gly-Gly-Gly-Gly-Ser (SEQ ID NO: 104), the peptide Gly-Gly-Gly-Gly-Ser-Gly-Gly-Gly-Gly-Ser-Gly-Gly-Gly-Gly-Ser (SEQ ID NO: 105), and the peptide Gly-Gly-Ser-Gly-Ser-Ser-Gly-Ser-Gly-Gly (SEQ ID NO:148). Other suitable linkers include a single Ser, and Val residue; the dipeptide Arg-Thr, Gln-Pro, Ser-Ser, Thr-Lys, and Ser-Leu; Thr-Lys-Gly-Pro-Ser (SEQ ID NO: 106), Thr-Val-Ala-Ala-Pro (SEQ ID NO: 107), Gln-Pro-Lys-Ala-Ala (SEQ ID NO: 108), Gln-Arg-Ile-Glu-Gly (SEQ ID NO: 109); Ala-Ser-Thr-Lys-Gly-Pro-Ser (SEQ ID NO: 110), Arg-Thr-Val-Ala-Ala-Pro-Ser (SEQ ID NO:111), Gly-Gln-Pro-Lys-Ala-Ala-Pro (SEQ ID NO:112), and His-Ile-Asp-Ser-Pro-Asn-Lys (SEQ ID NO:113). The examples listed above are not intended to limit the scope of the disclosure in any way, and linkers comprising randomly selected amino acids selected from the group consisting of valine, leucine, isoleucine, serine, threonine, lysine, arginine, histidine, aspartate, glutamate, asparagine, glutamine, glycine, and proline have been shown to be suitable in the binding proteins. For additional descriptions of linker sequences, see, e.g., WO2012135345.

The identity and sequence of amino acid residues in the linker may vary depending on the type of secondary structural element necessary to achieve in the linker. For example, glycine, serine, and alanine are best for linkers having maximum flexibility. Some combination of glycine, proline, threonine, and serine are useful if a more rigid and extended linker is necessary. Any amino acid residue may be considered as a linker in combination with other amino acid residues to construct larger peptide linkers as necessary depending on the desired properties.

In some embodiments, the length of $L_1$ is at least twice the length of $L_3$. In some embodiments, the length of $L_2$ is at least twice the length of $L_4$. In some embodiments, the length of $L_1$ is at least twice the length of $L_3$, and the length of $L_2$ is at least twice the length of $L_4$. In some embodiments, $L_1$ is 3 to 12 amino acid residues in length, $L_2$ is 3 to 14 amino acid residues in length, $L_3$ is 1 to 8 amino acid residues in length, and $L_4$ is 1 to 3 amino acid residues in length. In some embodiments, $L_1$ is 5 to 10 amino acid residues in length, $L_2$ is 5 to 8 amino acid residues in length, $L_3$ is 1 to 5 amino acid residues in length, and $L_4$ is 1 to 2 amino acid residues in length. In some embodiments, $L_1$ is 7 amino acid residues in length, $L_2$ is 5 amino acid residues in length, $L_3$ is 1 amino acid residue in length, and $L_4$ is 2 amino acid residues in length. In some embodiments, $L_1$ is 10 amino acid residues in length, $L_2$ is 10 amino acid residues in length, $L_3$ is 0 amino acid residue in length, and $L_4$ is 0 amino acid residues in length. In some embodiments, $L_1$, $L_2$, $L_3$, and $L_4$ each have an independently selected length from 0 to 15 amino acids (e.g., 0, 1, 2, 3, 4, 5, 6, 7, 8, 9, 10, 11, 12, 13, 14, or 15 amino acids), wherein at least two of the linkers have a length of 1 to 15 amino acids (e.g., 1, 2, 3, 4, 5, 6, 7, 8, 9, 10, 11, 12, 13, 14, or 15 amino acids). In some embodiments, $L_1$, $L_2$, $L_3$, and $L_4$ are each 0 amino acids in length.

In some embodiments, $L_1$, $L_2$, $L_3$, and/or $L_4$ comprise the sequence Asp-Lys-Thr-His-Thr (SEQ ID NO: 525). In some embodiments, $L_1$ comprises the sequence Asp-Lys-Thr-His-Thr (SEQ ID NO: 525). In some embodiments, $L_3$ comprises the sequence Asp-Lys-Thr-His-Thr (SEQ ID NO: 525).

In some embodiments, $L_1$, $L_2$, $L_3$, and/or $L_4$ comprise a sequence derived from a naturally occurring sequence at the junction between an antibody variable domain and an antibody constant domain (e.g., as described in WO2012/135345). For example, in some embodiments, the linker comprises a sequence found at the transition between an endogenous $V_H$ and $C_{H1}$ domain, or between an endogenous $V_L$ and $C_L$ domain (e.g., kappa or lambda). In some embodiments, the linker comprises a sequence found at the transition between an endogenous human $V_H$ and $C_{H1}$ domain, or between an endogenous human $V_L$ and $C_L$ domain (e.g., human kappa or lambda).

In some embodiments, $L_1$, $L_2$, $L_3$, and/or $L_4$ comprise the sequence Gly-Gln-Pro-Lys-Ala-Ala-Pro (SEQ ID NO: 175). In some embodiments, $L_1$ comprises the sequence Gly-Gln-Pro-Lys-Ala-Ala-Pro (SEQ ID NO: 175). In some embodiments, $L_1$ comprises the sequence Gly-Gln-Pro-Lys-Ala-Ala-Pro (SEQ ID NO: 175), $L_2$ comprises the sequence Thr-Lys-Gly-Pro-Ser-Arg (SEQ ID NO: 176), $L_3$ comprises the sequence Ser, and $L_4$ comprises the sequence Arg-Thr. In some embodiments, $L_3$ comprises the sequence Gly-Gln-Pro-Lys-Ala-Ala-Pro (SEQ ID NO: 175). In some embodiments, $L_1$ comprises the sequence Ser, $L_2$ comprises the sequence Arg-Thr, $L_3$ comprises the sequence Gly-Gln-Pro-Lys-Ala-Ala-Pro (SEQ ID NO: 175) and $L_4$ comprises the sequence Thr-Lys-Gly-Pro-Ser-Arg (SEQ ID NO: 176).

In some embodiments, $L_1$, $L_2$, $L_3$ and $L_4$ each independently comprise a sequence selected from $(GGGGS)_n$ (wherein n is an integer between 0 and 5; SEQ ID NO:174), GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148). In some embodiments, $L_1$ comprises the sequence GQPKAAP (SEQ ID NO: 175), $L_2$ comprises the sequence TKGPS (SEQ ID NO:106), $L_3$ comprises the sequence S, and $L_4$ comprises the sequence RT. In some embodiments, $L_1$ comprises the sequence GGGGSGGGGS (SEQ ID NO:104), $L_2$ comprises the sequence GGGGSGGGGS (SEQ ID NO:104), $L_3$ is 0 amino acids in length, and $L_4$ is 0 amino acids in length. In some embodiments, $L_1$ comprises the sequence GGSGSSGSGG (SEQ ID NO:148), $L_2$ comprises the sequence GGSGSSGSGG (SEQ ID NO:148), $L_3$ is 0 amino acids in length, and $L_4$ is 0 amino acids in length. In some embodiments, $L_1$ comprises the sequence GGGGSGGGGSGGGGS (SEQ ID NO:105), $L_2$ is 0 amino acids in length, $L_3$ comprises the sequence GGGGSGGGGSGGGGS (SEQ ID NO:105), and $L_4$ is 0 amino acids in length. In some embodiments, $L_1$ and $L_2$ are zero amino acids in length, and $L_3$ and $L_4$ each comprise an independently selected sequence selected from $(GGGGS)_n$ (wherein n is an integer between 0 and 5; SEQ ID NO:174), GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148). In some embodiments, $L_3$ and $L_4$ are zero amino acids in length, and $L_1$ and $L_2$ each comprise an independently selected sequence selected from $(GGGGS)_n$ (wherein n is an integer between 0 and 5; SEQ ID NO:174), GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148).

Fc Regions and Constant Domains

In some embodiments, a binding protein of the present disclosure comprises a second polypeptide chain further comprising an Fc region linked to CH1, the Fc region comprising an immunoglobulin hinge region and CH2 and CH3 immunoglobulin heavy chain constant domains. In some embodiments, a binding protein of the present disclosure comprises a third polypeptide chain further comprising an Fc region linked to CH1, the Fc region comprising an immunoglobulin hinge region and CH2 and CH3 immunoglobulin heavy chain constant domains. In some embodiments, a binding protein of the present disclosure comprises a second polypeptide chain further comprising an Fc region linked to CH1, the Fc region comprising an immunoglobulin hinge region and CH2 and CH3 immunoglobulin heavy chain constant domains, and a third polypeptide chain further comprising an Fc region linked to CH1, the Fc region comprising an immunoglobulin hinge region and CH2 and CH3 immunoglobulin heavy chain constant domains.

In some embodiments, a binding protein of the present disclosure includes one or two Fc variants. The term "Fc variant" as used herein refers to a molecule or sequence that is modified from a native Fc but still comprises a binding site for the salvage receptor, FcRn (neonatal Fc receptor). Exemplary Fc variants, and their interaction with the salvage receptor, are known in the art. Thus, the term "Fc variant" can comprise a molecule or sequence that is humanized from a non-human native Fc. Furthermore, a native Fc comprises regions that can be removed because they provide structural features or biological activity that are not required for the antibody-like binding proteins of the invention. Thus, the term "Fc variant" comprises a molecule or sequence that lacks one or more native Fc sites or residues, or in which one or more Fc sites or residues has be modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

To improve the yields of the binding proteins, the $C_{H3}$ domains can be altered by the "knob-into-holes" technology which is described in detail with several examples in, for example, International Publication No. WO 96/027011, Ridgway et al., 1996, *Protein Eng.* 9: 617-21; and Merchant et al., 1998, *Nat. Biotechnol.* 16: 677-81. Specifically, the interaction surfaces of the two $C_{H3}$ domains are altered to increase the heterodimerisation of both heavy chains containing these two $C_{H3}$ domains. Each of the two $C_{H3}$ domains (of the two heavy chains) can be the "knob," while the other is the "hole." The introduction of a disulfide bridge further stabilizes the heterodimers (Merchant et al., 1998; Atwell et al., 1997, *J. Mol. Biol.* 270: 26-35) and increases the yield. In particular embodiments, the knob is on the second pair of polypeptides with a single variable domain. In other embodiments, the knob is on the first pair of polypeptides having the cross-over orientation. In yet other embodiments, the $C_{H3}$ domains do not include a knob in hole.

In some embodiments, a binding protein of the present disclosure comprises a "knob" mutation on the second polypeptide chain and a "hole" mutation on the third polypeptide chain. In some embodiments, a binding protein of the present disclosure comprises a "knob" mutation on the third polypeptide chain and a "hole" mutation on the second polypeptide chain. In some embodiments, the "knob" mutation comprises substitution(s) at positions corresponding to positions 354 and/or 366 of human IgG1 or IgG4 according to EU Index. In some embodiments, the amino acid substitutions are S354C, T366W, T366Y, S354C and T366W, or S354C and T366Y. In some embodiments, the "knob" mutation comprises substitutions at positions corresponding to positions 354 and 366 of human IgG1 or IgG4 according to EU Index. In some embodiments, the amino acid substitutions are S354C and T366W. In some embodiments, the "hole" mutation comprises substitution(s) at positions corresponding to positions 407 and, optionally, 349, 366, and/or 368 and of human IgG1 or IgG4 according to EU Index. In some embodiments, the amino acid substitutions are Y407V or Y407T and optionally Y349C, T366S, and/or L368A. In some embodiments, the "hole" mutation comprises substitutions at positions corresponding to positions 349, 366, 368, and 407 of human IgG1 or IgG4 according to EU Index. In some embodiments, the amino acid substitutions are Y349C, T366S, L368A, and Y407V.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitution(s) at positions corresponding to positions 366 and optionally 354 of human IgG1 or IgG4 according to EU Index, wherein the amino acid substitutions are T366W or T366Y and optionally S354C; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitution(s) at positions corresponding to positions 407 and optionally 349, 366, and/or 368 and of human IgG1 or IgG4 according to EU Index, wherein the amino acid substitutions are Y407V or Y407T and optionally Y349C, T366S, and/or L368A.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitution(s) at positions corresponding to positions 407 and optionally 349, 366, and/or 368 and of human IgG1 or IgG4 according to EU Index, wherein the amino acid substitutions are Y407V or Y407T and optionally Y349C, T366S, and/or L368A; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitution(s) at positions corresponding to positions 366 and optionally 354 of human IgG1 or IgG4 according to EU Index, wherein the amino acid substitutions are T366W or T366Y and optionally S354C.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitution at position corresponding to position 366 of human IgG1 or IgG4 according to EU Index, wherein the amino acid substitution is T366W; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitution(s) at positions corresponding to positions 366, 368, and/or 407 and of human IgG1 or IgG4 according to EU Index, wherein the amino acid substitutions are T366S, L368A, and/or Y407V.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitution(s) at positions corresponding to positions 366, 368, and/or 407 and of human IgG1 or IgG4 according to EU Index, wherein the amino acid substitutions are T366S, L368A, and/or Y407V; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitution at position corresponding to position 366 of human IgG1 or IgG4 according to EU Index, wherein the amino acid substitution is T366W.

In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitutions at positions corresponding to positions 354 and 366 of human IgG1 or IgG4 according to EU Index, wherein the amino acid substitutions are S354C and T366W; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitutions at positions corresponding to positions 349, 366, 368, and 407 of human IgG1 or IgG4 according to EU Index, wherein the amino acid substitutions are Y349C, T366S, L368A, and Y407V. In some embodiments, the second polypeptide chain further comprises a first Fc region linked to CH1, the first Fc region comprising an immunoglobulin hinge region and CH2 and CH3 immunoglobulin heavy chain constant domains, wherein the first Fc region comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the third polypeptide chain further comprises a second Fc region linked to CH1, the second Fc region comprising an immunoglobulin hinge region and CH2 and CH3 immunoglobulin heavy chain constant domains, wherein the second Fc region comprises amino acid substitutions at positions corresponding to positions 354 and 366 of human IgG1 or IgG4 according to EU Index, wherein the amino acid substitutions are S354C and T366W. In some embodiments, the first and/or second Fc regions are human IgG1 Fc regions. In some embodiments, the first and/or second Fc regions are human IgG4 Fc regions.

In some embodiments, a binding protein of the present disclosure comprises one or more mutations to improve serum half-life (See e.g., Hinton, P. R. et al. (2006) J. Immunol. 176(1):346-56). In some embodiments, the mutation comprises substitutions at positions corresponding to positions 428 and 434 of human IgG1 or IgG4 according to EU Index, wherein the amino acid substitutions are M428L and N434S. In some embodiments, the binding protein comprises a second polypeptide chain further comprising a first Fc region linked to CH1, the first Fc region comprising an immunoglobulin hinge region and CH2 and CH3 immunoglobulin heavy chain constant domains, and a third polypeptide chain further comprising a second Fc region linked to CH1, the second Fc region comprising an immunoglobulin hinge region and CH2 and CH3 immunoglobulin heavy chain constant domains, wherein the first and/or second Fc regions comprise amino acid substitutions at positions corresponding to positions 428 and 434 of human IgG1 or IgG4 according to EU Index, wherein the amino acid substitutions are M428L and N434S. In some embodiments, a binding protein of the present disclosure comprises knob and hole mutations and one or more mutations to improve serum half-life. In some embodiments, the first and/or second Fc regions are human IgG1 Fc regions. In some embodiments, the first and/or second Fc regions are human IgG4 Fc regions.

In some embodiments, a binding protein of the present disclosure comprises one or more mutations to improve stability, e.g., of the hinge region and/or dimer interface of IgG4 (See e.g., Spiess, C. et al. (2013) *J. Biol. Chem.* 288:26583-26593). In some embodiments, the mutation comprises substitutions at positions corresponding to positions 228 and 409 of human IgG4 according to EU Index, wherein the amino acid substitutions are S228P and R409K. In some embodiments, the binding protein comprises a second polypeptide chain further comprising a first Fc region linked to $C_{H1}$, the first Fc region comprising an immunoglobulin hinge region and $C_{H2}$ and $C_{H3}$ immunoglobulin heavy chain constant domains, and a third polypeptide chain further comprising a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG4 Fc regions; and wherein the first and the second Fc regions each comprise amino acid substitutions at positions corresponding to positions 228 and 409 of human IgG4 according to EU Index, wherein the amino acid substitutions are S228P and R409K. In some embodiments, a binding protein of the present disclosure comprises knob and hole mutations and one or more mutations to improve stability. In some embodiments, the first and/or second Fc regions are human IgG4 Fc regions.

In some embodiments, a binding protein of the present disclosure comprises one or more mutations to improve purification, e.g., by modulating the affinity for a purification reagent. For example, it is known that heterodimeric binding proteins can be selectively purified away from their homodimeric forms if one of the two Fc regions of the heterodimeric form contains mutation(s) that reduce or eliminate binding to Protein A, because the heterodimeric form will have an intermediate affinity for Protein A-based purification than either homodimeric form and can be selectively eluted from Protein A, e.g., by use of a different pH (See e.g., Smith, E. J. et al. (2015) *Sci. Rep.* 5:17943). In some embodiments, the mutation comprises substitutions at positions corresponding to positions 435 and 436 of human IgG1 or IgG4 according to EU Index, wherein the amino acid substitutions are H435R and Y436F. In some embodiments, the binding protein comprises a second polypeptide chain further comprising a first Fc region linked to $C_{H1}$, the first Fc region comprising an immunoglobulin hinge region and $C_{H2}$ and $C_{H3}$ immunoglobulin heavy chain constant domains, and a third polypeptide chain further comprising a second Fc region linked to $C_{H1}$, the second Fc region comprising an immunoglobulin hinge region and $C_{H2}$ and $C_{H3}$ immunoglobulin heavy chain constant domains; and wherein only one of the first and the second Fc regions comprises amino acid substitutions at positions corresponding to positions 435 and 436 of human IgG1 or IgG4 according to EU Index, wherein the amino acid substitutions are H435R and Y436F. In some embodiments, a binding protein of the present disclosure comprises knob and hole mutations and one or more mutations to improve purification. In some embodiments, the first and/or second Fc regions are human IgG1 Fc regions. In some embodiments, the first and/or second Fc regions are human IgG4 Fc regions.

In some embodiments, a binding protein of the present disclosure comprises one or more mutations to reduce effector function, e.g., Fc receptor-mediated antibody-dependent cellular phagocytosis (ADCP), complement-dependent cytotoxicity (CDC), and/or antibody-dependent cellular cytotoxicity (ADCC). In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG1 Fc regions; and wherein the first and the second Fc regions each comprise amino acid substitutions at positions corresponding to positions 234 and 235 of human IgG1 according to EU Index, wherein the amino acid substitutions are L234A and L235A. In some embodiments, the Fc regions of the second and the third polypeptide chains are human IgG1 Fc regions, and wherein the Fc regions each comprise amino acid substitutions at positions corresponding to positions 234 and 235 of human IgG1 according to EU Index, wherein the amino acid substitutions are L234A and L235A. In some embodiments, the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG1 Fc regions; and wherein the first and the second Fc regions each comprise amino acid substitutions at positions corresponding to positions 234, 235, 329 of human IgG1 according to EU Index, wherein the amino acid substitutions are L234A, L235A, and P329A. In some embodiments, the Fc regions of the second and the third polypeptide chains are human IgG1 Fc regions, and wherein the Fc regions each comprise amino acid substitutions at positions corresponding to positions 234, 235, and 329 of human IgG1 according to EU Index, wherein the amino acid substitutions are L234A, L235A, and P329A. In some embodiments, the mutation comprises substitutions at positions corresponding to positions 234 and 235 of human IgG4 according to EU Index, wherein the amino acid substitutions are F234A and L235A. In some embodiments, the binding protein comprises a second polypeptide chain further comprising a first Fc region linked to $C_{H1}$, the first Fc region comprising an immunoglobulin hinge region and $C_{H2}$ and $C_{H3}$ immunoglobulin heavy chain constant domains, and a third polypeptide chain further comprising a second Fc region linked to $C_{H1}$, the second Fc region comprising an immunoglobulin hinge region and $C_{H2}$ and $C_{H3}$ immunoglobulin heavy chain constant domains; and wherein the first and the second Fc regions each comprise amino acid substitutions at positions corresponding to positions 234 and 235 of human IgG4 according to EU Index, wherein the amino acid substitutions are F234A and L235A. In some embodiments, a binding protein of the present disclosure comprises knob and hole mutations and one or more mutations to reduce effector function. In some embodiments, the first and/or second Fc regions are human IgG1 Fc regions. In some embodiments, the first and/or second Fc regions are human IgG4 Fc regions. For further description of Fc mutations at position 329, see, e.g., Shields, R. L. et al. (2001) *J. Biol. Chem.* 276:6591-6604 and WO1999051642.

In some embodiments, the types of mutations described supra can be combined in any order or combination. For example, a binding protein of the present disclosure can comprise two or more of the "knob" and "hole" mutations, the one or more mutations to improve serum half-life, the one or more mutations to improve IgG4 stability, the one or more mutations to improve purification, and/or the one or more mutations to reduce effector function described supra.

In certain embodiments, a binding protein of the present disclosure comprises: a first polypeptide chain that comprises a lambda $C_L$ domain; a $C_{H3}$ domain of a second polypeptide chain that comprises amino acid substitutions at positions corresponding to positions 354 and 366 of human IgG1 according to EU Index, wherein the amino acid substitutions are S354C and T366W; a $C_{H3}$ domain of a third polypeptide chain that comprises amino acid substitutions at positions corresponding to positions 349, 366, 368, 407, 435, and 436 of human IgG1 according to EU Index, wherein the amino acid substitutions are Y349C, T366S, L368A, Y407V, H435R, and Y436F; and a fourth polypeptide chain that comprises a kappa $C_L$ domain. In some embodiments, the first polypeptide chain comprises a lambda $C_L$ domain; wherein the $C_{H3}$ domain of the third polypeptide chain comprises amino acid substitutions at positions corresponding to positions 354 and 366 of human IgG1 according to EU Index, wherein the amino acid substitutions are S354C and T366W; wherein the $C_{H3}$ domain of the second polypeptide chain comprises amino acid substitutions at positions corresponding to positions 349, 366, 368, 407, 435, and 436 of human IgG1 according to EU Index, wherein the amino acid substitutions are Y349C, T366S, L368A, Y407V, H435R, and Y436F; and wherein the fourth polypeptide chain comprises a kappa $C_L$ domain. In some embodiments, the first polypeptide chain comprises a lambda $C_L$ domain; wherein the $C_{H3}$ domain of the second polypeptide chain comprises amino acid substitutions at positions corresponding to positions 354, 366, 435, and 436 of human IgG1 according to EU Index, wherein the amino acid substitutions are S354C, T366W, H435R, and Y436F; wherein the $C_{H3}$ domain of the third polypeptide chain comprises amino acid substitutions at positions corresponding to positions 349, 366, 368, and 407 of human IgG1 according to EU Index, wherein the amino acid substitutions are Y349C, T366S, L368A, and Y407V; and wherein the fourth polypeptide chain comprises a kappa $C_L$ domain. In some embodiments, the first polypeptide chain comprises a kappa $C_L$ domain; wherein the $C_{H3}$ domain of the second polypeptide chain comprises amino acid substitutions at positions corresponding to positions 354 and 366 of human IgG1 according to EU Index, wherein the amino acid substitutions are S354C and T366W; wherein the $C_{H3}$ domain of the third polypeptide chain comprises amino acid substitutions at positions corresponding to positions 349, 366, 368, 407, 435, and 436 of human IgG1 according to EU Index, wherein the amino acid substitutions are Y349C, T366S, L368A, Y407V, H435R, and Y436F; and wherein the fourth polypeptide chain comprises a lambda $C_L$ domain.

In some embodiments, a binding protein of the present disclosure is purified by protein A affinity chromatography, kappa light chain affinity chromatography (e.g., using a KappaSelect resin according to manufacturer's instructions; GE Healthcare), and optionally lambda light chain affinity chromatography (e.g., using a LambdaFabSelect resin according to manufacturer's instructions; GE Healthcare). In some embodiments, a binding protein of the present disclosure is purified by Protein A affinity chromatography, lambda light chain affinity chromatography (e.g., using a LambdaFabSelect resin according to manufacturer's instructions; GE Healthcare), and optionally kappa light chain affinity chromatography (e.g., using a KappaSelect resin according to manufacturer's instructions; GE Healthcare). In some embodiments, the binding protein comprises two Fc regions, each comprising a $C_{H3}$ domain, and only one of the $C_{H3}$ domains comprises amino acid substitutions at positions corresponding to positions 435 and 436 of human IgG1 or IgG4 according to EU Index, wherein the amino acid substitutions are H435R and Y436F. In some embodiments, a binding protein of the present disclosure is purified by protein A affinity chromatography, then kappa light chain affinity chromatography (e.g., using a KappaSelect resin according to manufacturer's instructions; GE Healthcare), then optionally lambda light chain affinity chromatography (e.g., using a LambdaFabSelect resin according to manufacturer's instructions; GE Healthcare) in sequence. In some embodiments, a binding protein of the present disclosure is purified by Protein A affinity chromatography, then lambda light chain affinity chromatography (e.g., using a LambdaFabSelect resin according to manufacturer's instructions; GE Healthcare), then optionally kappa light chain affinity chromatography (e.g., using a KappaSelect resin according to manufacturer's instructions; GE Healthcare) in sequence. For example, in some embodiments, the binding protein is contacted with Protein A, eluted from Protein A under conditions suitable for isolating the binding protein away from binding proteins comprising either 0 or 2 $C_{H3}$ domains comprising the amino acid substitutions are H435R and Y436F, contacted with a kappa light chain affinity medium (e.g., as used in the KappaSelect resin; GE Healthcare), and eluted from the kappa light chain affinity medium under conditions suitable for isolating the binding protein away from binding proteins comprising only lambda $C_L$ domains (e.g., according to manufacturer's instructions). Conditions suitable for the Protein A elution are known in the art, including without limitation a stepwise elution gradient from pH4.5-2.8. In some embodiments, Protein A or a Protein A variant useful for protein purification is employed. In some embodiments, the Protein A is attached to a substrate or resin, e.g., as part of a chromatography medium. In some embodiments, after elution from the kappa light chain affinity medium, the binding protein is contacted with a lambda light chain affinity medium (e.g., as used in the LambdaFabSelect resin; GE Healthcare), and eluted from the lambda light chain affinity medium under conditions suitable for isolating the binding protein away from binding proteins comprising only kappa $C_L$ domains (e.g., according to manufacturer's instructions). In some embodiments, a binding protein of the present disclosure is detected using HIC chromatography. In some embodiments, the binding protein comprises: a first polypeptide chain that comprises a lambda $C_L$ domain; a $C_{H3}$ domain of a second polypeptide chain that comprises amino acid substitutions at positions corresponding to positions 354 and 366 of human IgG1 or IgG4 according to EU Index, wherein the amino acid substitutions are S354C and T366W; a $C_{H3}$ domain of a third polypeptide chain that comprises amino acid substitutions at positions corresponding to positions 349, 366, 368, 407, 435, and 436 of human IgG1 or IgG4 according to EU Index, wherein the amino acid substitutions are Y349C, T366S, L368A, Y407V, H435R, and Y436F; and a fourth polypeptide chain that comprises a kappa $C_L$ domain. In some embodiments, the binding protein is produced by a host cell. In some embodiments, the binding protein is purified from a cell culture medium or host cell extract. In some embodiments, the binding proteins are secreted by a host cell or produced and extracted from a host cell (e.g., before being contacted with Protein A). In some embodiments, the binding protein is in a cell culture medium or host cell extract when contacted with Protein A. In some embodiments, the binding protein is purified away from other binding proteins, polypeptides, and/or other cellular components.

In some embodiments, CH1, CH2, CH3 and CL of the trispecific binding proteins described herein may comprise any of CH1, CH2, CH3 and CL sequences of binding proteins 1-53.

Nucleic Acids

Standard recombinant DNA methodologies are used to construct the polynucleotides that encode the polypeptides which form the binding proteins, incorporate these polynucleotides into recombinant expression vectors, and introduce such vectors into host cells. See e.g., Sambrook et al., 2001, Molecular Cloning: A Laboratory Manual (Cold Spring Harbor Laboratory Press, 3rd ed.). Enzymatic reactions and purification techniques may be performed according to manufacturer's specifications, as commonly accomplished in the art, or as described herein. Unless specific definitions are provided, the nomenclature utilized in connection with, and the laboratory procedures and techniques of, analytical chemistry, synthetic organic chemistry, and medicinal and pharmaceutical chemistry described herein are those well-known and commonly used in the art. Similarly, conventional techniques may be used for chemical syntheses, chemical analyses, pharmaceutical preparation, formulation, delivery, and treatment of patients.

Other aspects of the present disclosure relate to isolated nucleic acid molecules comprising a nucleotide sequence encoding any of the binding proteins described herein. In some embodiments, the isolated nucleic acid is operably linked to a heterologous promoter to direct transcription of the binding protein-coding nucleic acid sequence. A promoter may refer to nucleic acid control sequences which direct transcription of a nucleic acid. A first nucleic acid sequence is operably linked to a second nucleic acid sequence when the first nucleic acid sequence is placed in a functional relationship with the second nucleic acid sequence. For instance, a promoter is operably linked to a coding sequence of a binding protein if the promoter affects the transcription or expression of the coding sequence. Examples of promoters may include, but are not limited to, promoters obtained from the genomes of viruses (such as polyoma virus, fowlpox virus, adenovirus (such as Adenovirus 2), bovine papilloma virus, avian sarcoma virus, cytomegalovirus, a retrovirus, hepatitis-B virus, Simian Virus 40 (SV40), and the like), from heterologous eukaryotic promoters (such as the actin promoter, an immunoglobulin promoter, from heat-shock promoters, and the like), the CAG-promoter (Niwa et al., Gene 108(2):193-9, 1991), the phosphoglycerate kinase (PGK)-promoter, a tetracycline-inducible promoter (Masui et al., Nucleic Acids Res. 33:e43, 2005), the lac system, the trp system, the tac system, the trc system, major operator and promoter regions of phage lambda, the promoter for 3-phosphoglycerate kinase, the promoters of yeast acid phosphatase, and the promoter of the yeast alpha-mating factors. Polynucleotides encoding binding proteins of the present disclosure may be under the control of a constitutive promoter, an inducible promoter, or any other suitable promoter described herein or other suitable promoter that will be readily recognized by one skilled in the art.

In some embodiments, the isolated nucleic acid is incorporated into a vector. In some embodiments, the vector is an expression vector. Expression vectors may include one or more regulatory sequences operatively linked to the polynucleotide to be expressed. The term "regulatory sequence" includes promoters, enhancers and other expression control elements (e.g., polyadenylation signals). Examples of suitable enhancers may include, but are not limited to, enhancer sequences from mammalian genes (such as globin, elastase, albumin, α-fetoprotein, insulin and the like), and enhancer sequences from a eukaryotic cell virus (such as SV40 enhancer on the late side of the replication origin (bp 100-270), the cytomegalovirus early promoter enhancer, the polyoma enhancer on the late side of the replication origin, adenovirus enhancers, and the like). Examples of suitable vectors may include, for example, plasmids, cosmids, episomes, transposons, and viral vectors (e.g., adenoviral, vaccinia viral, Sindbis-viral, measles, herpes viral, lentiviral, retroviral, adeno-associated viral vectors, etc.). Expression vectors can be used to transfect host cells, such as, for example, bacterial cells, yeast cells, insect cells, and mammalian cells. Biologically functional viral and plasmid DNA vectors capable of expression and replication in a host are known in the art, and can be used to transfect any cell of interest.

Other aspects of the present disclosure relate to a vector system comprising one or more vectors encoding a first, second, third, and fourth polypeptide chain of any of the binding proteins described herein. In some embodiments, the vector system comprises a first vector encoding the first polypeptide chain of the binding protein, a second vector encoding the second polypeptide chain of the binding protein, a third vector encoding the third polypeptide chain of the binding protein, and a fourth vector encoding the fourth polypeptide chain of the binding protein. In some embodiments, the vector system comprises a first vector encoding the first and second polypeptide chains of the binding protein, and a second vector encoding the third and fourth polypeptide chains of the binding protein. In some embodiments, the vector system comprises a first vector encoding the first and third polypeptide chains of the binding protein, and a second vector encoding the second and fourth polypeptide chains of the binding protein. In some embodiments, the vector system comprises a first vector encoding the first and fourth polypeptide chains of the binding protein, and a second vector encoding the second and third polypeptide chains of the binding protein. In some embodiments, the vector system comprises a first vector encoding the first, second, third, and fourth polypeptide chains of the binding protein. The one or more vectors of the vector system may be any of the vectors described herein. In some embodiments, the one or more vectors are expression vectors.

Isolated Host Cells

Other aspects of the present disclosure relate to an isolated host cell comprising one or more isolated polynucleotides, vectors, and/or vector systems described herein. In some embodiments, the host cell is a bacterial cell (e.g., an *E. coli* cell). In some embodiments, the host cell is a yeast cell (e.g., an *S. cerevisiae* cell). In some embodiments, the host cell is an insect cell. Examples of insect host cells may include, for example, *Drosophila* cells (e.g., S2 cells), *Trichoplusia ni* cells (e.g., High Five™ cells), and *Spodoptera frugiperda* cells (e.g., Sf21 or Sf9 cells). In some embodiments, the host cell is a mammalian cell. Examples of mammalian host cells may include, for example, human embryonic kidney cells (e.g., 293 or 293 cells subcloned for growth in suspension culture), Expi293™ cells, CHO cells, baby hamster kidney cells (e.g., BHK, ATCC CCL 10), mouse sertoli cells (e.g., TM4 cells), monkey kidney cells (e.g., CV1 ATCC CCL 70), African green monkey kidney cells (e.g., VERO-76, ATCC CRL-1587), human cervical carcinoma cells (e.g., HELA, ATCC CCL 2), canine kidney cells (e.g., MDCK, ATCC CCL 34), buffalo rat liver cells (e.g., BRL 3A, ATCC CRL 1442), human lung cells (e.g., W138, ATCC CCL 75), human liver cells (e.g., Hep G2, HB 8065), mouse mammary tumor cells (e.g., MMT 060562, ATCC CCL51), TRI cells, MRC 5 cells, FS4 cells, a human hepatoma line (e.g., Hep G2), and myeloma cells (e.g., NSO and Sp2/0 cells).

Other aspects of the present disclosure relate to a method of producing any of the binding proteins described herein. In some embodiments, the method includes a) culturing a host cell (e.g., any of the host cells described herein) comprising an isolated nucleic acid, vector, and/or vector system (e.g., any of the isolated nucleic acids, vectors, and/or vector systems described herein) under conditions such that the host cell expresses the binding protein; and b) isolating the binding protein from the host cell. Methods of culturing host cells under conditions to express a protein are well known to one of ordinary skill in the art. Methods of isolating proteins from cultured host cells are well known to one of ordinary skill in the art, including, for example, by affinity chromatography (e.g., two step affinity chromatography comprising protein A affinity chromatography followed by size exclusion chromatography).

Uses for Binding Proteins

The binding proteins can be employed in any known assay method, such as competitive binding assays, direct and indirect sandwich assays, and immunoprecipitation assays for the detection and quantitation of one or more target antigens. The binding proteins will bind the one or more target antigens with an affinity that is appropriate for the assay method being employed.

For diagnostic applications, in certain embodiments, binding proteins can be labeled with a detectable moiety. The detectable moiety can be any one that is capable of producing, either directly or indirectly, a detectable signal. For example, the detectable moiety can be a radioisotope, such as $^{3}H$ $^{14}C$, $^{32}P$, $^{35}S$ $^{125}I$, $^{99}Tc$, $^{111}In$, or $^{67}Ga$; a fluorescent or chemiluminescent compound, such as fluorescein isothiocyanate, rhodamine, or luciferin; or an enzyme, such as alkaline phosphatase, β-galactosidase, or horseradish peroxidase.

The binding proteins are also useful for in vivo imaging. A binding protein labeled with a detectable moiety can be administered to an animal, preferably into the bloodstream, and the presence and location of the labeled antibody in the host assayed. The binding protein can be labeled with any moiety that is detectable in an animal, whether by nuclear magnetic resonance, radiology, or other detection means known in the art.

The binding proteins can also be used for cell activation, tumor targeting, neutralization of cytokine activities, neutralization of viral infection, combination of multiple signaling events, to treat cancer, arthritis, and/or inflammatory disorders. For example, in some embodiments, a binding protein specifically binds one, two, or three antigen targets selected from A2AR, APRIL, ATPDase, BAFF, BAFFR, BCMA, BlyS, BTK, BTLA, B7DC, B7H1, B7H4 (also known as VTCN1), B7H5, B7H6, B7H7, B7RP1, B7-4, C3, C5, CCL2 (also known as MCP-1), CCL3 (also known as MIP-1a), CCL4 (also known as MIP-1b), CCL5 (also known as RANTES), CCL7 (also known as MCP-3), CCL8 (also known as mcp-2), CCL11 (also known as eotaxin), CCL15 (also known as MIP-1d), CCL17 (also known as TARC), CCL19 (also known as MIP-3b), CCL20 (also known as MIP-3a), CCL21 (also known as MIP-2), CCL24 (also known as MPIF-2/eotaxin-2), CCL25 (also known as TECK), CCL26 (also known as eotaxin-3), CCR3, CCR4, CD3, CD19, CD20, CD23 (also known as FCER2, a receptor for IgE), CD24, CD27, CD28, CD38, CD39, CD40, CD70, CD80 (also known as B7-1), CD86 (also known as B7-2), CD122, CD137 (also known as 41BB), CD137L, CD152 (also known as CTLA4), CD154 (also known as CD40L), CD160, CD272, CD273 (also known as PDL2), CD274 (also known as PDL1), CD275 (also known as B7H2), CD276 (also known as B7H3), CD278 (also known as ICOS), CD279 (also known as PD-1), CDH1 (also known as E-cadherin), chitinase, CLEC9, CLEC91, CRTH2, CSF-1 (also known as M-CSF), CSF-2 (also known as GM-CSF), CSF-3 (also known as GCSF), CX3CL1 (also known as SCYD1), CXCL12 (also known as SDF1), CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb (also known as a receptor for IL25), IL18, IL22, IL23, IL25, IL27, IL33, IL35, ITGB4 (also known as b4 integrin), ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2 (also known as a receptor for IL33), STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP (also known as a co-receptor for IL7Ra), TSLPR, TWEAK, VEGF, VISTA, Vstm3, WUCAM, and XCR1 (also known as GPR5/CCXCR1). In some embodiments, one or more of the above antigen targets are human antigen targets.

In some embodiments, a binding protein of the present disclosure is adminstered to a patient in need thereof for the treatment or prevention of cancer. For example, in some embodiments, the binding protein comprises one antigen binding site that specifically binds a T-cell surface protein and another antigen binding site that specifically binds a tumor target protein (e.g., two antigen binding sites that specifically bind T-cell surface proteins and one antigen binding site that specifically binds a tumor target protein, or two antigen binding sites that specifically bind tumor target proteins and one antigen binding site that specifically binds a T-cell surface protein). In certain embodiments, the binding protein comprises an antigen binding site that specifically binds CD3, an antigen binding site that specifically binds CD28, and an antigen binding site that specifically binds a tumor target protein selected from CD19, CD20, CD38, Her2, and LAMP1. In some embodiments, the binding protein is co-administered with a chemotherapeutic agent. In some embodiments, the patient is a human.

In some embodiments, a binding protein of the present disclosure is adminstered to a patient in need thereof for the treatment or prevention of an inflammatory disease or disorder. In some embodiments, the binding protein comprises three antigen binding sites that each specifically bind a cytokine target protein selected from IL-4, IL-13 and TNFa. In some embodiments, the binding protein is co-administered with an anti-inflammatory agent. In some embodiments, the patient is a human.

The disclosure also relates to a kit comprising a binding protein and other reagents useful for detecting target antigen levels in biological samples. Such reagents can include a detectable label, blocking serum, positive and negative control samples, and detection reagents. In some embodiments, the kit comprises a composition comprising any binding protein, polynucleotide, vector, vector system, and/or host cell described herein. In some embodiments, the kit comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing a condition and may have a sterile access port (for example the container may be an intravenous solution bag or a vial having a stopper pierceable by a hypodermic injection needle). In some embodiments, the label or package insert indicates that the composition is used for preventing, diagnosing, and/or treating the condition of choice. Alternatively, or additionally, the article of manufacture or kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Binding Protein Therapeutic Compositions and Administration Thereof

Therapeutic or pharmaceutical compositions comprising binding proteins are within the scope of the disclosure. Such therapeutic or pharmaceutical compositions can comprise a therapeutically effective amount of a binding protein, or binding protein-drug conjugate, in admixture with a pharmaceutically or physiologically acceptable formulation agent selected for suitability with the mode of administration.

Acceptable formulation materials preferably are nontoxic to recipients at the dosages and concentrations employed.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., REMINGTON'S PHARMACEUTICAL SCIENCES (18th Ed., A. R. Gennaro, ed., Mack Publishing Company 1990), and subsequent editions of the same, incorporated herein by reference for any purpose).

The optimal pharmaceutical composition will be determined by a skilled artisan depending upon, for example, the intended route of administration, delivery format, and desired dosage. Such compositions can influence the physical state, stability, rate of in vivo release, and rate of in vivo clearance of the binding protein.

The primary vehicle or carrier in a pharmaceutical composition can be either aqueous or non-aqueous in nature. For example, a suitable vehicle or carrier for injection can be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which can further include sorbitol or a suitable substitute. In one embodiment of the disclosure, binding protein compositions can be prepared for storage by mixing the selected composition having the desired degree of purity with optional formulation agents in the form of a lyophilized cake or an aqueous solution. Further, the binding protein can be formulated as a lyophilizate using appropriate excipients such as sucrose.

The pharmaceutical compositions of the disclosure can be selected for parenteral delivery or subcutaneous. Alternatively, the compositions can be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use can be in the form of a pyrogen-free, parenterally acceptable, aqueous solution comprising the desired binding protein in a pharmaceutically acceptable vehicle. A particularly suitable vehicle for parenteral injection is sterile distilled water in which a binding protein is formulated as a sterile, isotonic solution, properly preserved. Yet another preparation can involve the formulation of the desired molecule with an agent, such as injectable micro spheres, bio-erodible particles, polymeric compounds (such as polylactic acid or polyglycolic acid), beads, or liposomes, that provides for the controlled or sustained release of the product which can then be delivered via a depot injection. Hyaluronic acid can also be used, and this can have the effect of promoting sustained duration in the circulation. Other suitable means for the introduction of the desired molecule include implantable drug delivery devices.

In one embodiment, a pharmaceutical composition can be formulated for inhalation. For example, a binding protein can be formulated as a dry powder for inhalation. Binding protein inhalation solutions can also be formulated with a propellant for aerosol delivery. In yet another embodiment, solutions can be nebulized.

It is also contemplated that certain formulations can be administered orally. In one embodiment of the disclosure, binding proteins that are administered in this fashion can be formulated with or without those carriers customarily used in the compounding of solid dosage forms such as tablets and capsules. For example, a capsule can be designed to release the active portion of the formulation at the point in the gastrointestinal tract when bioavailability is maximized and pre-systemic degradation is minimized. Additional agents can be included to facilitate absorption of the binding protein. Diluents, flavorings, low melting point waxes, vegetable oils, lubricants, suspending agents, tablet disintegrating agents, and binders can also be employed.

Another pharmaceutical composition can involve an effective quantity of binding proteins in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions of the disclosure will be evident to those skilled in the art, including formulations involving binding proteins in sustained- or controlled-delivery formulations. Techniques for formulating a variety of other sustained- or controlled-delivery means, such as liposome carriers, bio-erodible microparticles or porous beads and depot injections, are also known to those skilled in the art. Additional examples of sustained-release preparations include semipermeable polymer matrices in the form of shaped articles, e.g. films, or microcapsules. Sustained release matrices can include polyesters, hydrogels, polylactides, copolymers of L-glutamic acid and gamma ethyl-L-glutamate, poly(2-hydroxyethyl-methacrylate), ethylene vinyl acetate, or poly-D(−)-3-hydroxybutyric acid. Sustained-release compositions can also include liposomes, which can be prepared by any of several methods known in the art.

Pharmaceutical compositions to be used for in vivo administration typically must be sterile. This can be accomplished by filtration through sterile filtration membranes.

Where the composition is lyophilized, sterilization using this method can be conducted either prior to, or following, lyophilization and reconstitution. The composition for parenteral administration can be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it can be stored in sterile vials as a solution, suspension, gel, emulsion, solid, or as a dehydrated or lyophilized powder. Such formulations can be stored either in a ready-to-use form or in a form (e.g., lyophilized) requiring reconstitution prior to administration.

The disclosure also encompasses kits for producing a single-dose administration unit. The kits can each contain both a first container having a dried protein and a second container having an aqueous formulation. Also included within the scope of this disclosure are kits containing single and multi-chambered pre-filled syringes (e.g., liquid syringes and lyosyringes).

The effective amount of a binding protein pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the binding protein is being used, the route of administration, and the size (body weight, body surface, or organ size) and condition (the age and general health) of the patient. Accordingly, the clinician can titer the dosage and modify the route of administration to obtain the optimal therapeutic effect.

Dosing frequency will depend upon the pharmacokinetic parameters of the binding protein in the formulation being used. Typically, a clinician will administer the composition until a dosage is reached that achieves the desired effect. The composition can therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages can be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions can be administered by bolus injection or continuously by infusion, or by implantation device.

The composition can also be administered locally via implantation of a membrane, sponge, or other appropriate material onto which the desired molecule has been absorbed or encapsulated. Where an implantation device is used, the device can be implanted into any suitable tissue or organ, and delivery of the desired molecule can be via diffusion, timed-release bolus, or continuous administration.

In some embodiments, the present disclosure relates to a method of preventing and/or treating a proliferative disease or disorder (e.g., cancer). In some embodiments, the method comprises administering to a patient a therapeutically effective amount of at least one of the binding proteins described herein. In some embodiments, the patient is a human. In some embodiments, the at least one binding protein is administered in combination with one or more anti-cancer therapies (e.g., any anti-cancer therapy known in the art). In some embodiments, the at least one binding protein is administered before the one or more anti-cancer therapies. In some embodiments, the at least one binding protein is administered concurrently with the one or more anti-cancer therapies. In some embodiments, the at least one binding protein is administered after the one or more anti-retroviral therapies.

In some embodiments, the present disclosure relates to a method of preventing and/or treating an inflammatory disease or disorder (e.g., cancer). In some embodiments, the method comprises administering to a patient a therapeutically effective amount of at least one of the binding proteins described herein. In some embodiments, the patient is a human. In some embodiments, the at least one binding protein is administered in combination with one or more anti-inflammatory therapies (e.g., any anti-inflammatory therapy known in the art). In some embodiments, the at least one binding protein is administered before the one or more anti-inflammatory therapies. In some embodiments, the at least one binding protein is administered concurrently with the one or more anti-inflammatory therapies. In some embodiments, the at least one binding protein is administered after the one or more anti-inflammatory therapies.

Without limiting the present disclosure, a number of embodiments of the present disclosure are described below for purpose of illustration.

Item 1: A binding protein comprising four polypeptide chains that form three antigen binding sites that specifically bind one or more target proteins, wherein a first polypeptide chain comprises a structure represented by the formula:

$$V_{L2}\text{-}L_1\text{-}V_{L1}\text{-}L_2\text{-}C_L \quad [I]$$

and a second polypeptide chain has a structure represented by the formula:

$$V_{H1}\text{-}L_3\text{-}V_{H2}\text{-}L_4\text{-}C_{H1} \quad [II]$$

and a third polypeptide chain has a structure represented by the formula:

$$V_{H3}\text{-}C_{H1} \quad [III]$$

and a fourth polypeptide chain has a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

and wherein the polypeptide of formula I and the polypeptide of formula II form a cross-over light chain-heavy chain pair.

Item 2: A binding protein comprising four polypeptide chains that form three antigen binding sites that specifically bind one or more target proteins, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}L_{H2}\text{-}L_4\text{-}C_{H1}\text{-hinge-}C_{H2}\text{-}C_{H3} \quad [II]$$

and a third polypeptide chain comprises a structure represented by the formula:

$$V_{H3}\text{-}C_{H1}\text{-hinge-}C_{H2}\text{-}C_{H3} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

and wherein the polypeptide of formula I and the polypeptide of formula II form a cross-over light chain-heavy chain pair.

Item 3: The binding protein of item 1, wherein the second and/or the third polypeptide chain further comprises an Fc region linked to $C_{H1}$, the Fc region comprising an immunoglobulin hinge region and $C_{H2}$ and $C_{H3}$ immunoglobulin heavy chain constant domains.

Item 4: The binding protein of any one of items 1-3, wherein at least one of $L_1$, $L_2$, $L_3$ or $L_4$ is independently 0 amino acids in length.

Item 5: The binding protein of any one of items 1-3, wherein $L_1$, $L_2$, $L_3$ or $L_4$ are each independently at least one amino acid in length.

Item 6: The binding protein of any one of items 1-3 and 5, wherein (a) $L_1$, $L_2$, $L_3$ and $L_4$ each independently are zero amino acids in length or comprise a sequence selected from the group consisting of GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148); or (b) $L_1$, $L_2$, $L_3$ and $L_4$ each independently comprise a sequence selected from the group consisting of GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148).

Item 7: The binding protein of any one of items 1-5, wherein (a) $L_1$ comprises the sequence GQPKAAP (SEQ ID NO: 175), $L_2$ comprises the sequence TKGPS (SEQ ID NO:106), $L_3$ comprises the sequence S, and $L_4$ comprises the sequence RT;

(b) $L_1$ comprises the sequence GGGGSGGGGS (SEQ ID NO:104), $L_2$ comprises the sequence GGGGSGGGGS (SEQ ID NO:104), $L_3$ is 0 amino acids in length, and $L_4$ is 0 amino acids in length;

(c) $L_1$ comprises the sequence GGSGSSGSGG (SEQ ID NO:148), $L_2$ comprises the sequence GGSGSSGSGG (SEQ ID NO:148), $L_3$ is 0 amino acids in length, and $L_4$ is 0 amino acids in length; or (d) $L_1$ comprises the sequence GGGGSGGGGSGGGGS (SEQ ID NO:105), $L_2$ is 0 amino acids in length, $L_3$ comprises the sequence GGGGSGGGGSGGGGS (SEQ ID NO:105), and $L_4$ is 0 amino acids in length.

Item 8: The binding protein of any one of items 1-7, wherein the binding protein is trispecific and capable of specifically binding three different antigen targets.

Item 9: The binding protein of any one of items 1-8, wherein the binding protein specifically binds three target proteins that correspond to two target proteins on T cells and to one tumor target protein.

Item 10: The binding protein of item 9, wherein one of said target proteins on T cells is CD3.

Item 11: The binding protein of item 9 or item 10, wherein one of said target proteins on T cells is CD28.

Item 12: The binding protein of any one of items 9-11, wherein said tumor target protein is CD38.

Item 13: The binding protein of any one of items 1-8, wherein the binding protein specifically binds three target proteins that correspond to two target proteins on T cells and to one target protein selected from the group consisting of A2AR, APRIL, ATPDase, BAFF, BAFFR, BCMA, BlyS, BTK, BTLA, B7DC, B7H1, B7H4, B7H5, B7H6, B7H7, B7RP1, B7-4, C3, C5, CCL2, CCL3, CCL4, CCL5, CCL7, CCL8, CCL11, CCL15, CCL17, CCL19, CCL20, CCL21, CCL24, CCL25, CCL26, CCR3, CCR4, CD3, CD19, CD20, CD23, CD24, CD27, CD28, CD38, CD39, CD40, CD70, CD80, CD86, CD122, CD137, CD137L, CD152, CD154, CD160, CD272, CD273, CD274, CD275, CD276, CD278, CD279, CDH1, chitinase, CLEC9, CLEC91, CRTH2, CSF-1, CSF-2, CSF-3, CX3CL1, CXCL12, CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb, IL18, IL22, IL23, IL25, IL27, IL33, IL35, ITGB4, ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2, STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP, TSLPR, TWEAK, VEGF, VISTA, Vstm3, WUCAM, and XCR1.

Item 14: The binding protein of any one of items 1-13, wherein the binding protein is capable of inhibiting the function of one or more target proteins.

Item 15: The binding protein of item 14, wherein the one or more target proteins are selected from the group consisting of A2AR, APRIL, ATPDase, BAFF, BAFFR, BCMA, BlyS, BTK, BTLA, B7DC, B7H1, B7H4, B7H5, B7H6, B7H7, B7RP1, B7-4, C3, C5, CCL2, CCL3, CCL4, CCL5, CCL7, CCL8, CCL11, CCL15, CCL17, CCL19, CCL20, CCL21, CCL24, CCL25, CCL26, CCR3, CCR4, CD3, CD19, CD20, CD23, CD24, CD27, CD28, CD38, CD39, CD40, CD70, CD80, CD86, CD122, CD137, CD137L, CD152, CD154, CD160, CD272, CD273, CD274, CD275, CD276, CD278, CD279, CDH1, chitinase, CLEC9, CLEC91, CRTH2, CSF-1, CSF-2, CSF-3, CX3CL1, CXCL12, CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb, IL18, IL22, IL23, IL25, IL27, IL33, IL35, ITGB4, ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2, STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP, TSLPR, TWEAK, VEGF, VISTA, Vstm3, WUCAM, and XCR1.

Item 16: A binding protein comprising four polypeptide chains that form three antigen binding sites, wherein a first polypeptide chain comprises a structure represented by the formula:

$$V_{L2}\text{-}L_1\text{-}V_{L1}\text{-}L_2\text{-}C_L \quad [I]$$

and a second polypeptide chain has a structure represented by the formula:

$$V_{H1}\text{-}L_3\text{-}V_{H2}\text{-}L_4\text{-}C_{H1} \quad [II]$$

and a third polypeptide chain has a structure represented by the formula:

$$V_{H3}\text{-}C_{H1} \quad [III]$$

and a fourth polypeptide chain has a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

wherein the polypeptide of formula I and the polypeptide of formula II form a cross-over light chain-heavy chain pair.

wherein:

(a) $V_{L1}$, $V_{L2}$ and $V_{L3}$ each independently comprise a variable domain sequence as set forth in any one of SEQ ID NOs:151, 153, 155, 157, 159, 161, 163, 165, and 167; or (b) $V_{L1}$, $V_{L2}$ and $V_{L3}$ each independently comprise light chain complementarity determining regions comprising an amino acid sequence as set forth in any one of SEQ ID NOs: 43-59, 123-125, 138-140, and 149; and wherein:

(a) $V_{H1}$, $V_{H2}$, and $V_{H3}$ each independently comprise a variable domain sequence as set forth in any one of SEQ ID NOs:150, 152, 154, 156, 158, 160, 162, 164, and 166; or (b) $V_{H1}$, $V_{H2}$ and $V_{H3}$ each independently comprise heavy chain complementarity determining regions comprising an amino acid sequence as set forth in any one of SEQ ID NOs: 25-42, 120-122, and 126-128.

Item 17: A binding protein comprising four polypeptide chains that form three antigen binding sites, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}L_{H2}\text{-}L_4\text{-}C_{H1}\text{-hinge-}C_{H2}\text{-}C_{H3} \quad [II]$$

and a third polypeptide chain comprises a structure represented by the formula:

$$V_{H3}\text{-}C_{H1}\text{-hinge-}C_{H2}\text{-}C_{H3} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair;

wherein:

(a) $V_{L1}$, $V_{L2}$ and $V_{L3}$ each independently comprise a variable domain sequence as set forth in any one of SEQ ID NOs:151, 153, 155, 157, 159, 161, 163, 165, and 167; or (b) $V_{L1}$, $V_{L2}$ and $V_{L3}$ each independently comprise light chain complementarity determining regions comprising an amino acid sequence as set forth in any one of SEQ ID NOs: 43-59, 123-125, 138-140, and 149; and wherein:

(a) $V_{H1}$, $V_{H2}$, and $V_{H3}$ each independently comprise a variable domain sequence as set forth in any one of SEQ ID NOs:150, 152, 154, 156, 158, 160, 162, 164, and 166; or (b) $V_{H1}$, $V_{H2}$ and $V_{H3}$ each independently comprise heavy chain complementarity determining regions comprising an amino acid sequence as set forth in any one of SEQ ID NOs: 25-42, 120-122, and 126-128.

Item 18: The binding protein of item 16, wherein the second and/or the third polypeptide chain further comprises an Fc region linked to $C_{H1}$, the Fc region comprising an immunoglobulin hinge region and $C_{H2}$ and $C_{H3}$ immunoglobulin heavy chain constant domains.

Item 19: The binding protein of any one of items 16-18, wherein at least one of $L_1$, $L_2$, $L_3$ or $L_4$, is independently 0 amino acids in length.

Item 20: The binding protein of any one of items 16-18, wherein $L_1$, $L_2$, $L_3$ or $L_4$ are each independently at least one amino acid in length.

Item 21: The binding protein of any one of items 16-18 and 20, wherein (a) $L_1$, $L_2$, $L_3$ and $L_4$ each independently are zero amino acids in length or comprise a sequence selected from the group consisting of GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148); or (b) $L_1$, $L_2$, $L_3$ and $L_4$ each independently comprise a sequence selected from the group consisting of GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148).

Item 22: The binding protein of any one of items 16-20, wherein:

(a) $L_1$ comprises the sequence GQPKAAP (SEQ ID NO: 175), $L_2$ comprises the sequence TKGPS (SEQ ID NO:106), $L_3$ comprises the sequence S, and $L_4$ comprises the sequence RT;

(b) $L_1$ comprises the sequence GGGGSGGGGS (SEQ ID NO:104), $L_2$ comprises the sequence GGGGSGGGGS (SEQ ID NO:104), $L_3$ is 0 amino acids in length, and $L_4$ is 0 amino acids in length;

(c) $L_1$ comprises the sequence GGSGSSGSGG (SEQ ID NO:148), $L_2$ comprises the sequence GGSGSSGSGG (SEQ ID NO:148), $L_3$ is 0 amino acids in length, and $L_4$ is 0 amino acids in length; or (d) $L_1$ comprises the sequence GGGGSGGGGSGGGGS (SEQ ID NO:105), $L_2$ is 0 amino acids in length, $L_3$ comprises the sequence GGGGSGGGGSGGGGS (SEQ ID NO:105), and $L_4$ is 0 amino acids in length.

Item 23: The binding protein of any one of items 16-22, wherein:

(a) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and $V_{L3}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45;

(b) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and $V_{L3}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45;

(c) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:37, a CDR-H2 comprising the amino acid sequence of SEQ ID NO:38, and a CDR-H3 comprising the amino acid sequence of SEQ ID NO:39; and $V_{L3}$ comprises a CDR-L1 comprising the amino acid sequence of SEQ ID NO:55, a CDR-L2 comprising the amino acid sequence of SEQ ID NO:56, and a CDR-L3 comprising the amino acid sequence of SEQ ID NO:57;

(d) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:37, a CDR-H2 comprising the amino acid sequence of SEQ ID NO:38, and a CDR-H3 comprising the amino acid sequence of SEQ ID NO:39; and $V_{L3}$ comprises a CDR-L1 comprising the amino acid sequence of SEQ ID NO:55, a CDR-L2 comprising the amino acid sequence of SEQ ID NO:56, and a CDR-L3 comprising the amino acid sequence of SEQ ID NO:57;

(e) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO:179, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:40, a CDR-H2 comprising the amino acid sequence of SEQ ID NO:41, and a CDR-H3 comprising the amino acid sequence of SEQ ID NO:42; and $V_{L3}$ comprises a CDR-L1 comprising the amino acid sequence of SEQ ID NO:58, a CDR-L2 comprising the amino acid sequence of SEQ ID NO:44, and a CDR-L3 comprising the amino acid sequence of SEQ ID NO:59;

(f) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:40, a CDR-H2 comprising the amino acid sequence of SEQ ID NO:41, and a CDR-H3 comprising the amino acid sequence of SEQ ID NO:42; and $V_{L3}$ comprises a CDR-L1 comprising the amino acid sequence of SEQ ID NO:58, a CDR-L2 comprising the amino acid sequence of SEQ ID NO:44, and a CDR-L3 comprising the amino acid sequence of SEQ ID NO:59;

(g) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:126, a CDR-H2 comprising the amino acid sequence of SEQ ID NO:127, and a CDR-H3 comprising the amino acid sequence of SEQ ID NO:128; and $V_{L3}$ comprises a CDR-L1 comprising the amino acid sequence of SEQ ID NO:138, a CDR-L2 comprising the amino acid sequence of SEQ ID NO:139, and a CDR-L3 comprising the amino acid sequence of SEQ ID NO:140;

(h) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:126, a CDR-H2 comprising the amino acid sequence of SEQ ID NO:127, and a CDR-H3 comprising the amino acid sequence of SEQ ID NO:128; and $V_{L3}$ comprises a CDR-L1 comprising the amino acid sequence of SEQ ID NO:138, a CDR-L2 comprising the amino acid sequence of SEQ ID NO:139, and a CDR-L3 comprising the amino acid sequence of SEQ ID NO:140;

(i) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:120, a CDR-H2 comprising the amino acid sequence of SEQ ID NO:121, and a CDR-H3 comprising the amino acid sequence of SEQ ID NO:122; and $V_{L3}$ comprises a CDR-L1 comprising the amino acid sequence of SEQ ID NO:123, a CDR-L2 comprising the amino acid sequence of SEQ ID NO:124, and a CDR-L3 comprising the amino acid sequence of SEQ ID NO:125; or (j) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:120, a CDR-H2 comprising the amino acid sequence of SEQ ID NO:121, and a CDR-H3 comprising the amino acid sequence of SEQ ID NO:122; and $V_{L3}$ comprises a CDR-L1 comprising the amino acid sequence of SEQ ID NO:123, a CDR-L2 comprising the amino acid sequence of SEQ ID NO:124, and a CDR-L3 comprising the amino acid sequence of SEQ ID NO:125.

Item 24: A binding protein comprising four polypeptide chains that form three antigen binding sites, wherein a first polypeptide chain comprises a structure represented by the formula:

$$V_{L2}\text{-}L_1\text{-}V_{L1}\text{-}L_2\text{-}C_L \quad [I]$$

and a second polypeptide chain has a structure represented by the formula:

$$V_{H1}\text{-}L_3\text{-}V_{H2}\text{-}L_4\text{-}C_{H1} \quad [II]$$

and a third polypeptide chain has a structure represented by the formula:

$$V_{H3}\text{-}C_{H1} \quad [III]$$

and a fourth polypeptide chain has a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain; and $L_1$, $L_2$, $L_3$ and $L_4$ are amino acid linkers;

wherein the polypeptide of formula I and the polypeptide of formula II form a cross-over light chain-heavy chain pair.

wherein:

(a) $V_{L1}$, $V_{L2}$ and $V_{L3}$ each independently comprise a variable domain sequence as set forth in any one of SEQ ID NOs:169, 171, and 173; or (b) $V_{L1}$, $V_{L2}$ and $V_{L3}$ each independently comprise light chain complementarity determining regions comprising an amino acid sequence selected from the group consisting of SEQ ID NOs: 141-147, 178, and 179;

wherein:

(a) $V_{H1}$, $V_{H2}$, and $V_{H3}$ each independently comprise a variable domain sequence as set forth in any one of SEQ ID NOs:168, 170, and 172; or (b) $V_{H1}$, $V_{H2}$ and $V_{H3}$ each independently comprise heavy chain complementarity determining regions comprising an amino acid sequence selected from the group consisting of SEQ ID NOs: 129-137.

Item 25: A binding protein comprising four polypeptide chains that form three antigen binding sites, wherein a first polypeptide chain comprises a structure represented by the formula:

$$V_{L2}\text{-}L_1\text{-}V_{L1}\text{-}L_2\text{-}C_L \quad [I]$$

and a second polypeptide chain comprises a structure represented by the formula:

$$V_{H1}\text{-}L_3\text{-}L_{H2}\text{-}L_4\text{-}C_{H1}\text{-hinge-}C_{H2}\text{-}C_{H3} \quad [II]$$

and a third polypeptide chain comprises a structure represented by the formula:

$$V_{H3}\text{-}C_{H1}\text{-hinge-}C_{H2}\text{-}C_{H3} \quad [III]$$

and a fourth polypeptide chain comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are amino acid linkers;

wherein the polypeptide of formula I and the polypeptide of formula II form a cross-over light chain-heavy chain pair;

wherein:

(a) $V_{L1}$, $V_{L2}$ and $V_{L3}$ each independently comprise a variable domain sequence as set forth in any one of SEQ ID NOs:169, 171, and 173; or (b) $V_{L1}$, $V_{L2}$ and $V_{L3}$ each independently comprise light chain complementarity determining regions comprising an amino acid sequence selected from the group consisting of SEQ ID NOs: 141-147, 178, and 179;

wherein:

(a) $V_{H1}$, $V_{H2}$, and $V_{H3}$ each independently comprise a variable domain sequence as set forth in any one of SEQ ID NOs:168, 170, and 172; or (b) $V_{H1}$, $V_{H2}$ and $V_{H3}$ each independently comprise heavy chain complementarity determining regions comprising an amino acid sequence selected from the group consisting of SEQ ID NOs: 129-137.

Item 26: The binding protein of item 24, wherein the second and/or the third polypeptide chain further comprises an Fc region linked to $C_{H1}$, the Fc region comprising an immunoglobulin hinge region and $C_{H2}$ and $C_{H3}$ immunoglobulin heavy chain constant domains.

Item 27: The binding protein of any one of items 24-26, wherein at least one of $L_1$, $L_2$, $L_3$ and $L_4$, is independently 0 amino acids in length.

Item 28: The binding protein of any one of items 24-26, wherein $L_1$, $L_2$, $L_3$ and $L_4$ are each independently at least one amino acid in length.

Item 29: The binding protein of any one of items 24-26 and 28, wherein (a) $L_1$, $L_2$, $L_3$ and $L_4$ each independently are zero amino acids in length or comprise a sequence selected from the group consisting of GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148); or (b) $L_1$, $L_2$, $L_3$ and $L_4$ each independently comprise a sequence selected from the group consisting of GGGGSGGGGS (SEQ ID NO:104), GGGGSGGGGSGGGGS (SEQ ID NO:105), S, RT, TKGPS (SEQ ID NO:106), GQPKAAP (SEQ ID NO: 175), and GGSGSSGSGG (SEQ ID NO:148).

Item 30: The binding protein of any one of items 24-28, wherein:

(a) $L_1$ comprises the sequence GQPKAAP (SEQ ID NO: 175), $L_2$ comprises the sequence TKGPS (SEQ ID NO:106), $L_3$ comprises the sequence S, and $L_4$ comprises the sequence RT;

(b) $L_1$ comprises the sequence GGGGSGGGGS (SEQ ID NO:104), $L_2$ comprises the sequence GGGGSGGGGS (SEQ ID NO:104), $L_3$ is 0 amino acids in length, and $L_4$ is 0 amino acids in length;

(c) $L_1$ comprises the sequence GGSGSSGSGG (SEQ ID NO:148), $L_2$ comprises the sequence GGSGSSGSGG (SEQ ID NO:148), $L_3$ is 0 amino acids in length, and $L_4$ is 0 amino acids in length; or (d) $L_1$ comprises the sequence GGGGSGGGGSGGGGS (SEQ ID NO:105), $L_2$ is 0 amino acids in length, $L_3$ comprises the sequence GGGGSGGGGSGGGGS (SEQ ID NO:105), and $L_4$ is 0 amino acids in length.

Item 31: The binding protein of any one of items 24-30, wherein:

(a) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; and $V_{L3}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142;

(b) $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:47, and a CDR-L3 comprising the amino acid sequence of SEQ ID NO:144; $V_{H3}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; and $V_{L3}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142;

(c) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L2}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147;

(d) $V_{H1}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L1}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147;

(e) $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L2}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144;

(f) $V_{H1}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L1}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144;

(g) $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147;

(h) $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144;

(i) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; or (j) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144.

Item 32: The binding protein of any one of items 1, 3-16, 18-24, and 26-31, wherein the second polypeptide chain further comprises a first Fc region linked to $C_{H1}$, the first Fc region comprising an immunoglobulin hinge region and $C_{H2}$ and $C_{H3}$ immunoglobulin heavy chain constant domains, wherein the first Fc region comprises amino acid substitutions at positions corresponding to positions 354 and 366 of human IgG1 or IgG4 according to EU Index, wherein the amino acid substitutions are S354C and T366W; and wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains, wherein the second Fc region comprises amino acid substitutions at positions corresponding to positions 349, 366, 368, and 407 of human IgG1 or IgG4 according to EU Index, wherein the amino acid substitutions are Y349C, T366S, L368A, and Y407V.

Item 33: The binding protein of any one of items 1, 3-16, 18-24, and 26-31, wherein the second polypeptide chain further comprises a first Fc region linked to $C_{H1}$, the first Fc region comprising an immunoglobulin hinge region and $C_{H2}$ and $C_{H3}$ immunoglobulin heavy chain constant domains, wherein the first Fc region comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains, wherein the second Fc region comprises amino acid substitutions at positions corresponding to positions 354 and 366 of human IgG1 or IgG4 according to EU Index, wherein the amino acid substitutions are S354C and T366W.

Item 34: The binding protein of any one of items 1, 3-16, 18-24, and 26-33, wherein the second polypeptide chain further comprises a first Fc region linked to $C_{H1}$, the first Fc region comprising an immunoglobulin hinge region and $C_{H2}$ and $C_{H3}$ immunoglobulin heavy chain constant domains, and wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions comprise amino acid substitutions at positions corresponding to positions 428 and 434 of human IgG1 or IgG4 according to EU Index, wherein the amino acid substitutions are M428L and N434S.

Item 35: The binding protein of any one of items 2, 4-15, 17, 19-23, 25, and 27-31, wherein the $C_{H3}$ domain of the second polypeptide chain comprises amino acid substitutions at positions corresponding to positions 354 and 366 of human IgG1 or IgG4 according to EU Index, wherein the amino acid substitutions are S354C and T366W; and wherein the $C_{H3}$ domain of the third polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V.

Item 36: The binding protein of any one of items 2, 4-15, 17, 19-23, 25, and 27-31, wherein the $C_{H3}$ domain of the second polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the $C_{H3}$ domain of the third polypeptide chain comprises amino acid substitutions at positions corresponding to positions 354 and 366 of human IgG1 or IgG4 according to EU Index, wherein the amino acid substitutions are S354C and T366W.

Item 37: The binding protein of any one of items 2, 4-15, 17, 19-23, 25, 27-31, 35, and 36, wherein the $C_{H3}$ domains of the second and the third polypeptide chains both comprise amino acid substitutions at positions corresponding to positions 428 and 434 of human IgG1 or IgG4 according to EU Index, wherein the amino acid substitutions are M428L and N434S Item 38: The binding protein of any one of items 1, 3-16, 18-24, and 26-34, wherein the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG1 or IgG4 Fc regions; and wherein only one of the first and the second Fc regions comprises amino acid substitutions at positions corresponding to positions 435 and 436 of human IgG1 or IgG4 according to EU Index, wherein the amino acid substitutions are H435R and Y436F.

Item 39: The binding protein of any one of items 2, 4-15, 17, 19-23, 25, 27-31, and 35-37, wherein the $C_{H3}$ domains of the second and the third polypeptide chains are human IgG1 or IgG4 $C_{H3}$ domains, and wherein only one of the $C_{H3}$ domains comprises amino acid substitutions at positions corresponding to positions 435 and 436 of human IgG1 or IgG4 according to EU Index, wherein the amino acid substitutions are H435R and Y436F.

Item 40: The binding protein of any one of items 1, 3-16, 18-24, 26-34, and 38, wherein the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG4 Fc regions; and wherein the first and the second Fc regions each comprise amino acid substitutions at positions corresponding to positions 228 and 409 of human IgG4 according to EU Index, wherein the amino acid substitutions are S228P and R409K.

Item 41: The binding protein of any one of items 2, 4-15, 17, 19-23, 25, 27-31, 35-37, and 39, wherein the $C_{H3}$ domains of the second and the third polypeptide chains are human IgG4 $C_{H3}$ domains, and wherein the $C_{H3}$ domains each comprise amino acid substitutions at positions corresponding to positions 228 and 409 of human IgG4 according to EU Index, wherein the amino acid substitutions are S228P and R409K.

Item 42: The binding protein of any one of items 1, 3-16, 18-24, 26-34, 38, and 40, wherein the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG4 Fc regions; and wherein the first and the second Fc regions each comprise amino acid substitutions at positions corresponding to positions 234 and 235 of human IgG4 according to EU Index, wherein the amino acid substitutions are F234A and L235A.

Item 43: The binding protein of any one of items 2, 4-15, 17, 19-23, 25, 27-31, 35-37, 39, and 41, wherein the $C_{H3}$ domains of the second and the third polypeptide chains are human IgG4 $C_{H3}$ domains, and wherein the $C_{H3}$ domains each comprise amino acid substitutions at positions corresponding to positions 234 and 235 of human IgG4 according to EU Index, wherein the amino acid substitutions are F234A and L235A.

Item 44: The binding protein of any one of items 1, 3-16, 18-24, 26-34, 38, and 40, wherein the second polypeptide chain further comprises a first Fc region linked to $C_{H1}$, the first Fc region comprising an immunoglobulin hinge region and $C_{H2}$ and $C_{H3}$ immunoglobulin heavy chain constant domains; wherein the third polypeptide chain further comprises a second Fc region linked to $C_{H1}$, the second Fc region comprising an immunoglobulin hinge region and $C_{H2}$ and $C_{H3}$ immunoglobulin heavy chain constant domains; wherein the first and second Fc regions are human IgG1 Fc regions; and wherein the first and the second Fc regions each comprise amino acid substitutions at positions corresponding to positions 234 and 235 of human IgG4 according to EU Index, wherein the amino acid substitutions are L234A and L235A.

Item 45: The binding protein of any one of items 2, 4-15, 17, 19-23, 25, 27-31, 35-37, 39, and 41, wherein the $C_{H3}$ domains of the second and the third polypeptide chains are human IgG1 $C_{H3}$ domains, and wherein the $C_{H3}$ domains each comprise amino acid substitutions at positions corresponding to positions 234 and 235 of human IgG4 according to EU Index, wherein the amino acid substitutions are L234A and L235A.

Item 46: The binding protein of any one of items 2, 4-15, 17, 19-23, 25, 27-31, 35-37, 39, 41, 43, and 45, wherein VH1 and VL1 form a first antigen binding site that specifically binds human CD3, wherein VH2 and VL2 form a second antigen binding site that specifically binds human CD28, and wherein VH3 and VL3 form a third antigen binding site that specifically binds a human tumor target protein.

Item 47: The binding protein of any one of items 2, 4-15, 17, 19-23, 25, 27-31, 35-37, 39, 41, 43, and 45, wherein VH1 and VL1 form a first antigen binding site that specifically binds human CD28, wherein VH2 and VL2 form a second antigen binding site that specifically binds human CD3, and wherein VH3 and VL3 form a third antigen binding site that specifically binds a human tumor target protein.

Item 48: The binding protein of item 46 or item 47, wherein the third antigen binding site specifically binds a human tumor target protein selected from the group consisting of CD19, CD20, CD38, Her2, and LAMP1.

Item 49: The binding protein of any one of items 46-48, wherein the antigen binding site that specifically binds CD3 comprises:

(a) a heavy chain variable domain comprising the amino acid sequence of SEQ ID NO: 152 and a light chain variable domain comprising the amino acid sequence of SEQ ID NO: 153; or (b) a heavy chain variable domain comprising the amino acid sequence of SEQ ID NO: 154 and a light chain variable domain comprising the amino acid sequence of SEQ ID NO: 155.

Item 50: The binding protein of any one of items 46-49, wherein the antigen binding site that specifically binds CD28 comprises:

(a) a heavy chain variable domain comprising the amino acid sequence of SEQ ID NO: 160 and a light chain variable domain comprising the amino acid sequence of SEQ ID NO: 161; or (b) a heavy chain variable domain comprising the amino acid sequence of SEQ ID NO: 162 and a light chain variable domain comprising the amino acid sequence of SEQ ID NO: 163.

Item 51: The binding protein of any one of items 46-50, wherein the antigen binding site that specifically binds a tumor target protein comprises:

(a) a heavy chain variable domain comprising the amino acid sequence of SEQ ID NO: 156 and a light chain variable domain comprising the amino acid sequence of SEQ ID NO: 157;

(b) a heavy chain variable domain comprising the amino acid sequence of SEQ ID NO: 158 and a light chain variable domain comprising the amino acid sequence of SEQ ID NO: 159;

(c) a heavy chain variable domain comprising the amino acid sequence of SEQ ID NO: 164 and a light chain variable domain comprising the amino acid sequence of SEQ ID NO: 165;

(d) a heavy chain variable domain comprising the amino acid sequence of SEQ ID NO: 150 and a light chain variable domain comprising the amino acid sequence of SEQ ID NO: 151; or (e) a heavy chain variable domain comprising the amino acid sequence of SEQ ID NO: 166 and a light chain variable domain comprising the amino acid sequence of SEQ ID NO: 167.

Item 52: The binding protein of any one of items 2, 17, 35-37, 39, 41, 43, and 45, wherein:

(a) VH1 and VL1 form a first antigen binding site that specifically binds human TNFa, VH2 and VL2 form a second antigen binding site that specifically binds human IL13, and VH3 and VL3 form a third antigen binding site that specifically binds human IL4;

(b) VH1 and VL1 form a first antigen binding site that specifically binds human TNFa, VH2 and VL2 form a second antigen binding site that specifically binds human IL4, and VH3 and VL3 form a third antigen binding site that specifically binds human IL13;

(c) VH1 and VL1 form a first antigen binding site that specifically binds human IL4, VH2 and VL2 form a second antigen binding site that specifically binds human TNFa, and VH3 and VL3 form a third antigen binding site that specifically binds human IL13;

(d) VH1 and VL1 form a first antigen binding site that specifically binds human IL4, VH2 and VL2 form a second antigen binding site that specifically binds human IL13, and VH3 and VL3 form a third antigen binding site that specifically binds human TNFa;

(e) VH1 and VL1 form a first antigen binding site that specifically binds human IL13, VH2 and VL2 form a second antigen binding site that specifically binds human IL4, and VH3 and VL3 form a third antigen binding site that specifically binds human TNFa; or (f) VH1 and VL1 form a first antigen binding site that specifically binds human IL13, VH2 and VL2 form a second antigen binding site that specifically binds human TNFa, and VH3 and VL3 form a third antigen binding site that specifically binds human IL4.

Item 53: The binding protein of item 52, wherein the antigen binding site that specifically binds human TNFa comprises a heavy chain variable domain comprising the amino acid sequence of SEQ ID NO:168 and a light chain variable domain comprising the amino acid sequence of SEQ ID NO:169.

Item 54: The binding protein of item 52 or item 53, wherein the antigen binding site that specifically binds human IL4 comprises a heavy chain variable domain comprising the amino acid sequence of SEQ ID NO:170 and a light chain variable domain comprising the amino acid sequence of SEQ ID NO:171.

Item 55: The binding protein of any one of items 52-54, wherein the antigen binding site that specifically binds human IL13 comprises a heavy chain variable domain comprising the amino acid sequence of SEQ ID NO:172 and a light chain variable domain comprising the amino acid sequence of SEQ ID NO:173.

Item 56: The binding protein of any one of items 1-55, wherein:

(a) the $C_L$ domain of the first polypeptide chain is a human kappa $C_L$ domain, and the $C_L$ domain of the fourth polypeptide chain is a human lambda $C_L$ domain; or (b) the $C_L$ domain of the first polypeptide chain is a human lambda $C_L$ domain, and the $C_L$ domain of the fourth polypeptide chain is a human kappa $C_L$ domain.

Item 57: The binding protein of any one of items 2, 17, 25, 35-37, 39, 41, and 43-55, wherein the first polypeptide chain comprises a lambda $C_L$ domain; wherein the C domain of the second polypeptide chain comprises amino acid substitutions at positions corresponding to positions 354 and 366 of human IgG1 according to EU Index, wherein the amino acid substitutions are S354C and T366W; wherein the $C_{H3}$ domain of the third polypeptide chain comprises amino acid substitutions at positions corresponding to positions 349, 366, 368, 407, 435, and 436 of human IgG1 according to EU Index, wherein the amino acid substitutions are Y349C, T366S, L368A, Y407V, H435R, and Y436F; and wherein the fourth polypeptide chain comprises a kappa $C_L$ domain.

Item 58: A binding protein comprising a first polypeptide chain, a second polypeptide chain, a third polypeptide chain and a fourth polypeptide chain wherein:

(a) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 1 or an amino acid sequence that is at least 95% identical to the amino acid sequence of SEQ ID NO: 1; and the fourth polypeptide chain comprises the amino acid sequence of SEQ ID NO: 2 or an amino acid sequence that is at least 95% identical to the amino acid sequence of SEQ ID NO: 2;

(b) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 1 or an amino acid sequence that is at least 95% identical to the amino acid sequence of SEQ ID NO: 1; and the fourth polypeptide chain comprises the amino acid sequence of SEQ ID NO: 2 or an amino acid sequence that is at least 95% identical to the amino acid sequence of SEQ ID NO: 2;

(c) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 13 or an amino acid sequence that is at least 95% identical to the amino acid sequence of SEQ ID NO: 13; and the fourth polypeptide chain comprises the amino acid sequence of SEQ ID NO: 14 or an amino acid sequence that is at least 95% identical to the amino acid sequence of SEQ ID NO: 14;

(d) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 13 or an amino acid sequence that is at least 95% identical to the amino acid sequence of SEQ ID NO: 13; and the fourth polypeptide chain comprises the amino acid sequence of SEQ ID NO: 14 or an amino acid sequence that is at least 95% identical to the amino acid sequence of SEQ ID NO: 14;

(e) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 17 or an amino acid sequence that is at least 95% identical to the amino acid sequence of SEQ ID NO: 17; and the fourth polypeptide chain comprises the amino acid sequence of SEQ ID NO: 18 or an amino acid sequence that is at least 95% identical to the amino acid sequence of SEQ ID NO: 18;

(f) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 17 or an amino acid sequence that is at least 95% identical to the amino acid sequence of SEQ ID NO: 17; and the fourth polypeptide chain comprises the amino acid sequence of SEQ ID NO: 18 or an amino acid sequence that is at least 95% identical to the amino acid sequence of SEQ ID NO: 18;

(g) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 21 or an amino acid sequence that is at least 95% identical to the amino acid sequence of SEQ ID NO: 21; and the fourth polypeptide chain comprises the amino acid sequence of SEQ ID NO: 22 or an amino acid sequence that is at least 95% identical to the amino acid sequence of SEQ ID NO: 22;

(h) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 21 or an amino acid sequence that is at least 95% identical to the amino acid sequence of SEQ ID NO: 21; and the fourth polypeptide chain comprises the amino acid sequence of SEQ ID NO: 22 or an amino acid sequence that is at least 95% identical to the amino acid sequence of SEQ ID NO: 22;

(i) the first polypeptide chain comprises the amino acid sequence of SEQ ID NO: 63 or an amino acid sequence that is at least 95% identical to the amino acid sequence of SEQ ID NO: 63; the second polypeptide chain comprises the amino acid sequence of SEQ ID NO: 62 or an amino acid sequence that is at least 95% identical to the amino acid sequence of SEQ ID NO: 62; the third polypeptide chain comprises the amino acid sequence of SEQ ID NO: 60 or an amino acid sequence that is at least 95% identical to the amino acid sequence of SEQ ID NO: 60; and the fourth polypeptide chain comprises the amino acid sequence of SEQ ID NO: 61 or an amino acid sequence that is at least 95% identical to the amino acid sequence of SEQ ID NO: 61;

(j) the first polypeptide chain comprises the amino acid sequence of SEQ ID NO: 69 or an amino acid sequence that is at least 95% identical to the amino acid sequence of SEQ ID NO: 69; the second polypeptide chain comprises the amino acid sequence of SEQ ID NO: 68 or an amino acid sequence that is at least 95% identical to the amino acid sequence of SEQ ID NO: 68; the third polypeptide chain comprises the amino acid sequence of SEQ ID NO: 60 or an amino acid sequence that is at least 95% identical to the amino acid sequence of SEQ ID NO: 60; and the fourth polypeptide chain comprises the amino acid sequence of SEQ ID NO: 61 or an amino acid sequence that is at least 95% identical to the amino acid sequence of SEQ ID NO: 61;

(k) the first polypeptide chain comprises the amino acid sequence of SEQ ID NO: 69 or an amino acid sequence that is at least 95% identical to the amino acid sequence of SEQ ID NO: 69; the second polypeptide chain comprises the amino acid sequence of SEQ ID NO: 68 or an amino acid sequence that is at least 95% identical to the amino acid sequence of SEQ ID NO: 68; the third polypeptide chain comprises the amino acid sequence of SEQ ID NO: 60 or an amino acid sequence that is at least 95% identical to the amino acid sequence of SEQ ID NO: 60; and the fourth polypeptide chain comprises the amino acid sequence of SEQ ID NO: 71 or an amino acid sequence that is at least 95% identical to the amino acid sequence of SEQ ID NO: 71;

(l) the first polypeptide chain comprises the amino acid sequence of SEQ ID NO: 76 or an amino acid sequence that is at least 95% identical to the amino acid sequence of SEQ ID NO: 76; the second polypeptide chain comprises the amino acid sequence of SEQ ID NO: 75 or an amino acid sequence that is at least 95% identical to the amino acid sequence of SEQ ID NO: 75; the third polypeptide chain comprises the amino acid sequence of SEQ ID NO: 73 or an amino acid sequence that is at least 95% identical to the amino acid sequence of SEQ ID NO: 73; and the fourth polypeptide chain comprises the amino acid sequence of SEQ ID NO: 74 or an amino acid sequence that is at least 95% identical to the amino acid sequence of SEQ ID NO: 74;

(m) the first polypeptide chain comprises the amino acid sequence of SEQ ID NO: 82 or an amino acid sequence that is at least 95% identical to the amino acid sequence of SEQ ID NO: 82; the second polypeptide chain comprises the amino acid sequence of SEQ ID NO: 81 or an amino acid sequence that is at least 95% identical to the amino acid sequence of SEQ ID NO:81; the third polypeptide chain comprises the amino acid sequence of SEQ ID NO: 73 or an amino acid sequence that is at least 95% identical to the amino acid sequence of SEQ ID NO: 73; and the fourth polypeptide chain comprises the amino acid sequence of SEQ ID NO: 74 or an amino acid sequence that is at least 95% identical to the amino acid sequence of SEQ ID NO: 74;

(n) the first polypeptide chain comprises the amino acid sequence of SEQ ID NO: 88 or an amino acid sequence that is at least 95% identical to the amino acid sequence of SEQ ID NO:88; the second polypeptide chain comprises the amino acid sequence of SEQ ID NO: 87 or an amino acid sequence that is at least 95% identical to the amino acid sequence of SEQ ID NO: 87; the third polypeptide chain comprises the amino acid sequence of SEQ ID NO: 85 or an amino acid sequence that is at least 95% identical to the amino acid sequence of SEQ ID NO: 85; and the fourth polypeptide chain comprises the amino acid sequence of SEQ ID NO: 86 or an amino acid sequence that is at least 95% identical to the amino acid sequence of SEQ ID NO: 86;

(o) the first polypeptide chain comprises the amino acid sequence of SEQ ID NO: 94 or an amino acid sequence that is at least 95% identical to the amino acid sequence of SEQ ID NO: 94; the second polypeptide chain comprises the amino acid sequence of SEQ ID NO: 93 or an amino acid sequence that is at least 95% identical to the amino acid sequence of SEQ ID NO: 93; the third polypeptide chain comprises the amino acid sequence of SEQ ID NO: 85 or an amino acid sequence that is at least 95% identical to the amino acid sequence of SEQ ID NO: 85; and the fourth polypeptide chain comprises the amino acid sequence of SEQ ID NO: 86 or an amino acid sequence that is at least 95% identical to the amino acid sequence of SEQ ID NO: 86;

(p) the first polypeptide chain comprises the amino acid sequence of SEQ ID NO: 69 or an amino acid sequence that is at least 95% identical to the amino acid sequence of SEQ ID NO: 69; the second polypeptide chain comprises the amino acid sequence of SEQ ID NO: 68 or an amino acid sequence that is at least 95% identical to the amino acid sequence of SEQ ID NO: 68; the third polypeptide chain comprises the amino acid sequence of SEQ ID NO: 73 or an amino acid sequence that is at least 95% identical to the amino acid sequence of SEQ ID NO: 73; and the fourth polypeptide chain comprises the amino acid sequence of SEQ ID NO: 74 or an amino acid sequence that is at least 95% identical to the amino acid sequence of SEQ ID NO: 74;

(q) the first polypeptide chain comprises the amino acid sequence of SEQ ID NO: 69 or an amino acid sequence that is at least 95% identical to the amino acid sequence of SEQ ID NO: 69; the second polypeptide chain comprises the amino acid sequence of SEQ ID NO: 68 or an amino acid sequence that is at least 95% identical to the amino acid sequence of SEQ ID NO: 68; the third polypeptide chain comprises the amino acid sequence of SEQ ID NO: 85 or an amino acid sequence that is at least 95% identical to the amino acid sequence of SEQ ID NO: 85; and the fourth polypeptide chain comprises the amino acid sequence of SEQ ID NO: 86 or an amino acid sequence that is at least 95% identical to the amino acid sequence of SEQ ID NO: 86;

(r) the first polypeptide chain comprises the amino acid sequence of SEQ ID NO: 63 or an amino acid sequence that is at least 95% identical to the amino acid sequence of SEQ ID NO: 63; the second polypeptide chain comprises the amino acid sequence of SEQ ID NO: 62 or an amino acid sequence that is at least 95% identical to the amino acid sequence of SEQ ID NO: 62; the third polypeptide chain comprises the amino acid sequence of SEQ ID NO: 73 or an amino acid sequence that is at least 95% identical to the amino acid sequence of SEQ ID NO: 73; and the fourth polypeptide chain comprises the amino acid sequence of SEQ ID NO: 74 or an amino acid sequence that is at least 95% identical to the amino acid sequence of SEQ ID NO: 74;

(s) the first polypeptide chain comprises the amino acid sequence of SEQ ID NO: 63 or an amino acid sequence that is at least 95% identical to the amino acid sequence of SEQ ID NO: 63; the second polypeptide chain comprises the amino acid sequence of SEQ ID NO: 62 or an amino acid sequence that is at least 95% identical to the amino acid sequence of SEQ ID NO: 62; the third polypeptide chain comprises the amino acid sequence of SEQ ID NO: 85 or an amino acid sequence that is at least 95% identical to the amino acid sequence of SEQ ID NO: 85; and the fourth polypeptide chain comprises the amino acid sequence of SEQ ID NO: 86 or an amino acid sequence that is at least 95% identical to the amino acid sequence of SEQ ID NO: 86;

(t) the first polypeptide chain comprises the amino acid sequence of SEQ ID NO: 4 or an amino acid sequence that is at least 95% identical to the amino acid sequence of SEQ ID NO: 4; the second polypeptide chain comprises the amino acid sequence of SEQ ID NO: 3 or an amino acid sequence that is at least 95% identical to the amino acid sequence of SEQ ID NO: 3; the third polypeptide chain comprises the amino acid sequence of SEQ ID NO: 114 or an amino acid sequence that is at least 95% identical to the amino acid sequence of SEQ ID NO: 114; and the fourth polypeptide chain comprises the amino acid sequence of SEQ ID NO: 115 or an amino acid sequence that is at least 95% identical to the amino acid sequence of SEQ ID NO: 115; or (u) the first polypeptide chain comprises the amino acid sequence of SEQ ID NO: 10 or an amino acid sequence that is at least 95% identical to the amino acid sequence of SEQ ID NO: 10; the second polypeptide chain comprises the amino acid sequence of SEQ ID NO: 9 or an amino acid sequence that is at least 95% identical to the amino acid sequence of SEQ ID NO: 9; the third polypeptide chain comprises the amino acid sequence of SEQ ID NO: 114 or an amino acid sequence that is at least 95% identical to the amino acid sequence of SEQ ID NO: 114; and the fourth polypeptide chain comprises the amino acid sequence of SEQ ID NO: 115 or an amino acid sequence that is at least 95% identical to the amino acid sequence of SEQ ID NO: 115.

Item 59: An isolated nucleic acid molecule comprising a nucleotide sequence encoding the binding protein of any one of items 1-58.

Item 60: An expression vector comprising the nucleic acid molecule of item 59.

Item 61: An isolated host cell comprising the nucleic acid molecule of item 59.

Item 62: An isolated host cell comprising the expression vector of item 60.

Item 63: The isolated host cell of item 61 or item 62, wherein the host cell is a mammalian cell or an insect cell.

Item 64: A pharmaceutical composition comprising the binding protein of any one of items 1-58 and a pharmaceutically acceptable carrier.

Item 65: A method of preventing and/or treating cancer in a patient comprising administering to the patient a therapeutically effective amount of at least one binding protein of any one of items 1-23 and 32-58 or the pharmaceutical composition of item 64.

Item 66: The method of item 65, wherein the binding protein comprises one antigen binding site that specifically binds a T-cell surface protein and another antigen binding site that specifically binds a tumor target protein.

Item 67: The method of item 66, wherein the binding protein comprises a first antigen binding site that specifically binds CD3, a second antigen binding site that specifically binds CD28, and a third antigen binding site that specifically binds a tumor target protein selected from the group consisting of CD19, CD20, CD38, Her2, and LAMP1.

Item 68: The method of any one of items 65-67, wherein the at least one binding protein is co-administered with a chemotherapeutic agent.

Item 69: A method of preventing and/or treating an inflammatory disease or disorder in a patient comprising administering to the patient a therapeutically effective amount of at least one binding protein of any one of items 1-15, 24-45, and 52-58 or the pharmaceutical composition of item 64.

Item 70: The method of item 69, wherein the binding protein comprises three antigen binding sites that each specifically bind a cytokine target protein selected from the group consisting of IL-4, IL-13 and TNFa.

Item 71: The method of item 69 or item 70, wherein the at least one binding protein is co-administered with an anti-inflammatory agent.

Item 72: The method of any one of items 65-71, wherein the patient is a human.

Item 73: The method of item 65 or item 69, wherein the binding protein is capable of inhibiting the function of one or more target proteins selected from the group consisting of A2AR, APRIL, ATPDase, BAFF, BAFFR, BCMA, BlyS, BTK, BTLA, B7DC, B7H1, B7H4, B7H5, B7H6, B7H7, B7RP1, B7-4, C3, C5, CCL2, CCL3, CCL4, CCL5, CCL7, CCL8, CCL11, CCL15, CCL17, CCL19, CCL20, CCL21, CCL24, CCL25, CCL26, CCR3, CCR4, CD3, CD19, CD20, CD23, CD24, CD27, CD28, CD38, CD39, CD40, CD70, CD80, CD86, CD122, CD137, CD137L, CD152, CD154, CD160, CD272, CD273, CD274, CD275, CD276, CD278, CD279, CDH1, chitinase, CLEC9, CLEC91, CRTH2, CSF-1, CSF-2, CSF-3, CX3CL1, CXCL12, CXCL13, CXCR3, DNGR-1, ectonucleoside triphosphate diphosphohydrolase 1, EGFR, ENTPD1, FCER1A, FCER1, FLAP, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb, IL18, IL22, IL23, IL25, IL27, IL33, IL35, ITGB4, ITK, KIR, LAG3, LAMP1, leptin, LPFS2, MHC class II, NCR3LG1, NKG2D, NTPDase-1, OX40, OX40L, PD-1H, platelet receptor, S152, SISP1, SLC, SPG64, ST2, Syk kinase, TACI, TDO, T14, TIGIT, TIM3, TLR, TLR2, TLR4, TLR5, TLR9, TNFa, TNFRSF7, Tp55, TREM1, TSLP, TSLPR, TWEAK, VEGF, VISTA, Vstm3, WUCAM, and XCR1.

Item 74: The binding protein of any one of items 1-23 and 32-58 or the composition of item 64 for use in preventing and/or treating cancer in a patient.

Item 75: The binding protein for use or the composition for use of item 74, wherein the binding protein comprises one antigen binding site that specifically binds a T-cell surface protein and another antigen binding site that specifically binds a tumor target protein.

Item 76: The binding protein for use or the composition for use of item 75, wherein the binding protein comprises a first antigen binding site that specifically binds CD3, a second antigen binding site that specifically binds CD28, and a third antigen binding site that specifically binds a tumor target protein selected from the group consisting of CD19, CD20, CD38, Her2, and LAMP1.

Item 77: The binding protein for use or the composition for use of any one of items 74-76, wherein the binding protein is co-administered with a chemotherapeutic agent.

Item 78: The binding protein of any one of items 1-15, 24-45, and 52-58 or the pharmaceutical composition of item 64 for use in preventing and/or treating an inflammatory disease or disorder in a patient.

Item 79: The binding protein for use or the composition for use of item 78, wherein the binding protein comprises three antigen binding sites that each specifically bind a cytokine target protein selected from the group consisting of IL-4, IL-13 and TNFa.

Item 80: The binding protein for use or the composition for use of item 78 or item 79, wherein the binding protein is co-administered with an anti-inflammatory agent.

Item 81: The binding protein for use or the composition for use of any one of items 74-80, wherein the patient is a human.

Item 82: The binding protein for use or the composition for use of item 74 or item 78, wherein the binding protein is capable of inhibiting the function of one or more target proteins selected from the group consisting of A2AR, APRIL, ATPDase, BAFF, BAFFR, BCMA, BlyS, BTK, BTLA, B7DC, B7H1, B7H4, B7H5, B7H6, B7H7, B7RP1, B7-4, C3, C5, CCL2, CCL3, CCL4, CCL5, CCL7, CCL8, CCL11, CCL15, CCL17, CCL19, CCL20, CCL21, CCL24, CCL25, CCL26, CCR3, CCR4, CD3, CD19, CD20, CD23, CD24, CD27, CD28, CD38, CD39, CD40, CD70, CD80, CD86, CD122, CD137, CD137L, CD152, CD154, CD160, CD272, CD273, CD274, CD275, CD276, CD278, CD279, CDH1, chitinase, CLEC9, CLEC91, CRTH2, CSF-1, CSF-2, CSF-3, CX3CL1, CXCL12, CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb, IL18, IL22, IL23, IL25, IL27, IL33, IL35, ITGB4, ITK, KIR, LAG3, LAMP1, leptin, LPFS2, MHC class II, NCR3LG1, NKG2D, NTPDase-1, OX40, OX40L, PD-1H, platelet receptor, PROM1, S152, SISP1, SLC, SPG64, ST2, STEAP2, Syk kinase, TACI, TDO, T14, TIGIT, TIM3, TLR, TLR2, TLR4, TLR5, TLR9, TMEF1, TNFa, TNFRSF7, Tp55, TREM1, TSLP, TSLPR, TWEAK, VEGF, VISTA, Vstm3, WUCAM, and XCR1.

Item 83: A method of purifying a binding protein produced by a host cell, comprising:

(a) producing the binding protein of any one of items 2, 17, 25, 35-37, 41, 43, 45, and 46-55 in a host cell, wherein only one of the $C_{H3}$ domain of the second polypeptide chain and the $C_{H3}$ domain of the third polypeptide chain comprises amino acid substitutions at positions corresponding to positions 435 and 436 of human IgG1 or IgG4 according to EU Index, wherein the amino acid substitutions are H435R and Y436F;

(b) contacting the binding protein produced in (a) with Protein A; and (c) eluting the binding protein from Protein A under conditions suitable for isolating the binding protein away from binding proteins comprising either 0 or 2 $C_{H3}$ domains comprising the amino acid substitutions are H435R and Y436F, thereby purifying the binding protein.

Item 84: The method of item 83, wherein the $C_L$ domain of the first polypeptide chain is a human kappa $C_L$ domain, and the $C_L$ domain of the fourth polypeptide chain is a human lambda $C_L$ domain; or the $C_L$ domain of the first polypeptide chain is a human lambda $C_L$ domain, and the $C_L$ domain of the fourth polypeptide chain is a human kappa $C_L$ domain, and the method further comprises:

(d) contacting the binding protein eluted in (c) with a kappa light chain affinity medium; and (e) eluting the binding protein from the kappa light chain affinity medium under conditions suitable for isolating the binding protein away from binding proteins comprising only lambda $C_L$ domains.

Item 85: The method of item 84, further comprising, after (e):

(f) contacting the binding protein eluted in (e) with a lambda light chain affinity medium; and (g) eluting the binding protein from the lambda light chain affinity medium under conditions suitable for isolating the binding protein away from binding proteins comprising only kappa $C_L$ domains.

Item 86: The method of item 83, wherein the $C_L$ domain of the first polypeptide chain is a human kappa $C_L$ domain, and the $C_L$ domain of the fourth polypeptide chain is a human lambda $C_L$ domain; or the $C_L$ domain of the first polypeptide chain is a human lambda $C_L$ domain, and the $C_L$ domain of the fourth polypeptide chain is a human kappa $C_L$ domain, and the method further comprises:

(d) contacting the binding protein eluted in (c) with a lambda light chain affinity medium; and (e) eluting the binding protein from the lambda light chain affinity medium under conditions suitable for isolating the binding protein away from binding proteins comprising only kappa $C_L$ domains.

Item 87: The method of item 86, further comprising, after (e):

(f) contacting the binding protein eluted in (e) with a kappa light chain affinity medium; and (g) eluting the binding protein from the kappa light chain affinity medium under conditions suitable for isolating the binding protein away from binding proteins comprising only lambda $C_L$ domains.

Item 88: The method of any one of items 83-87, wherein the first polypeptide chain comprises a lambda $C_L$ domain; wherein the $C_{H3}$ domain of the second polypeptide chain comprises amino acid substitutions at positions corresponding to positions 354 and 366 of human IgG1 according to EU Index, wherein the amino acid substitutions are S354C and T366W; wherein the $C_{H3}$ domain of the third polypeptide chain comprises amino acid substitutions at positions corresponding to positions 349, 366, 368, 407, 435, and 436 of human IgG1 according to EU Index, wherein the amino acid substitutions are Y349C, T366S, L368A, Y407V, H435R, and Y436F; and wherein the fourth polypeptide chain comprises a kappa $C_L$ domain.

Item 89: The method of any one of items 83-88, wherein the binding protein is detected in one or more of (c) and (e) using hydrophobic interaction chromatography (HIC).

Item 90: The method of any one of items 83-89, wherein the $C_{H3}$ domains of the second and the third polypeptide chains are human IgG1 or IgG4 $C_{H3}$ domains.

EXAMPLES

The Examples that follow are illustrative of specific embodiments of the disclosure, and various uses thereof. They are set forth for explanatory purposes only, and should not be construed as limiting the scope of the invention in any way.

Example 1: Materials and Methods

The following materials and methods were used for the experiments described in Examples 2-5.

Trispecific Antibody Design

Figure 1B:
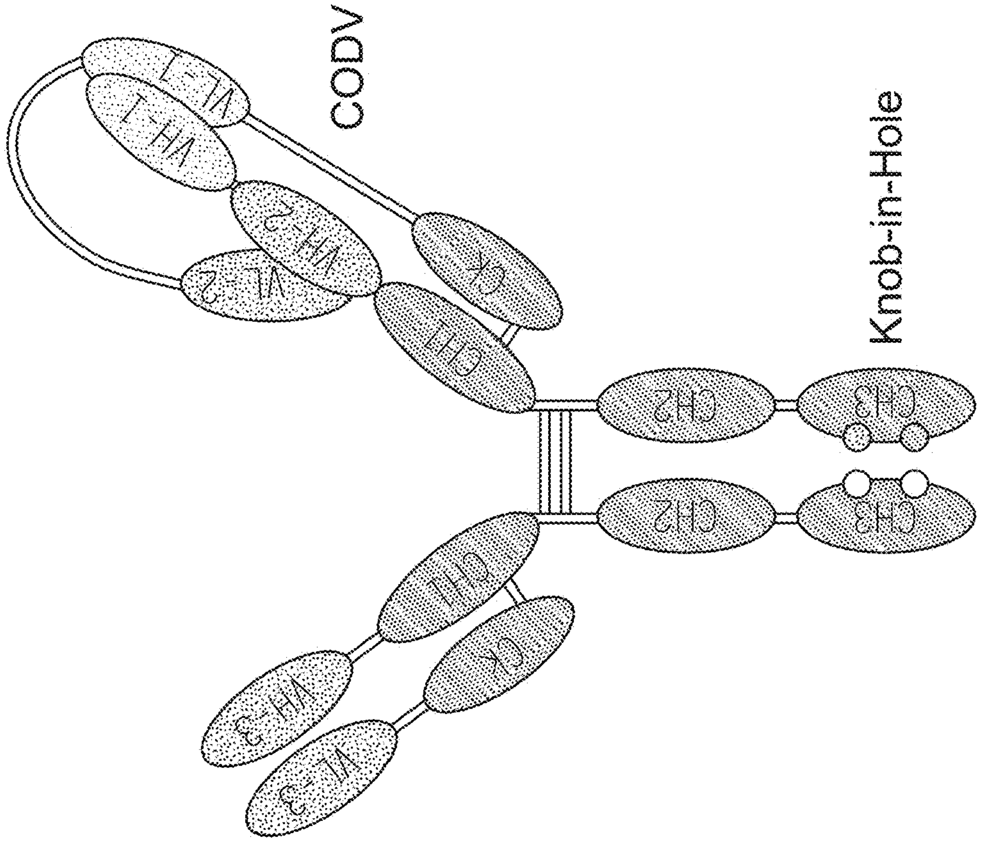
Figure 1C:
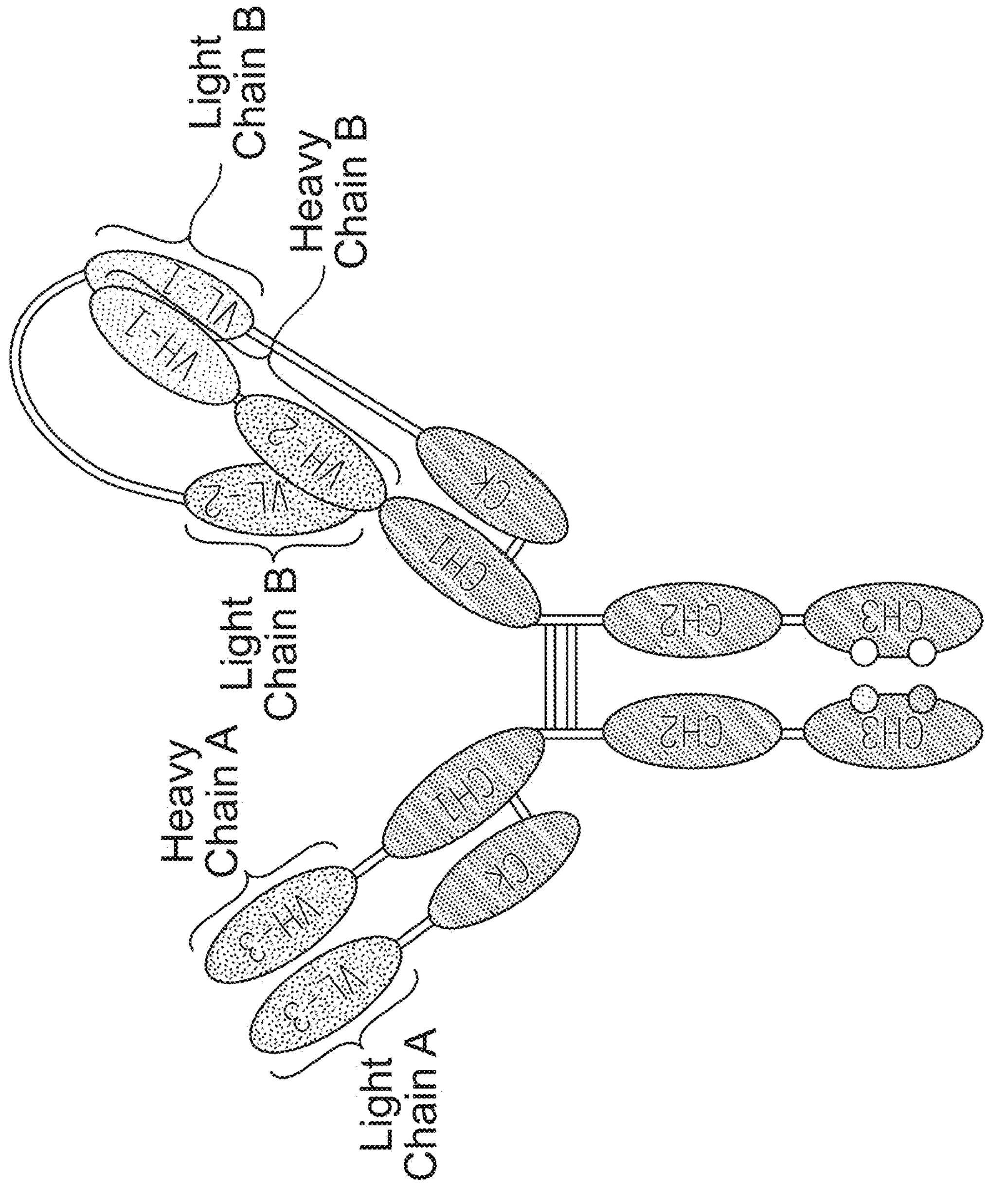

A schematic illustration of the general trispecific antibody design is illustrated in FIGS. 1A-1C. Individual trispecific antibodies were designed based on 5 parameters: 1) Selection of antibody binding sites; 2) Consideration of the position of each binding site; 3) Choice of linkers for the bispecific binding arm (i.e., heavy chain/light chain B in FIG. 1C); 4). "Knob" and "Hole" mutation integration into respective halves of the antibody; 5) Choice of Fc isotype (IgG1 or IgG4). After assembly of the amino acid sequences for each trispecific molecule, four genes for each trispecific Ab were synthesized using human preferred codons (CambrY Applied Biosciences, Cambridge, Mass., USA), and cloned into a eukaryotic expression vector.

Production and Purification of Trispecific Antibodies

Trispecific antibodies were produced by transient transfection of 4 expression plasmids into Expi293 cells using ExpiFectamine™ 293 Transfection Kit (Thermo Fisher Scientific) according to manufacturer's protocol. Briefly, 25% (w/w) of each plasmid was diluted into Opti-MEM, mixed with pre-diluted ExpiFectamine reagent for 20-30 minutes at room temperature (RT), and added into Expi293 cells ($2.5\times 10^6$ cells/ml). An optimization of transfection to determine the best ratio of plasmids was often used in order to produce the trispecific antibody with good yield and purity.

4-5 days post transfection, the supernatant from transfected cells was collected and filtered through 0.45 μm filter unit (Nalgene). The trispecific antibody in the supernatant was purified using a 3-step procedure. First, protein A affinity purification was used, and the bound Ab was eluted using "IgG Elution Buffer" (Thermo Fisher Scientific). Second, product was dialyzed against PBS (pH7.4) overnight with 2 changes of PBS buffer. Any precipitate was cleared by filtration through 0.45 μm filter unit (Nalgene) before next step. Third, size-exclusion chromatography (SEC) purification (Hiload 16/600 Superdex 200 pg, or Hiload 26/600 Superdex 200 pg, GE Healthcare) was used to remove aggregates and different species in the prep. The fractions were analyzed on reduced and non-reduced SDS-PAGE to identify the fractions that contained the monomeric trispecific antibody before combining them. The purified antibody can be aliquoted and stored at −80° C. long term.

ELISA Assays

The binding properties of the purified antibodies were analyzed either using ELISA or SPR methods. For ELISA, corresponding antigens for each binding site in the trispecific antibody were used to coat a 96-well Immuno Plate (Nunc 439454, Thermo Fisher Scientific) overnight at 4° C. using 2 μg/ml each antigen in PBS (pH7.4). The coated plate was blocked using 5% skim milk+2% BSA in PBS for one hour at RT, followed by washing with PBS+0.25% Tween 20 three times (Aqua Max 400, Molecular Devices). Serial dilution of antibodies (trispecific and control Abs) were prepared and added onto the ELISA plates (100 μl/well in duplicate), incubated at RT for one hour, followed by washing 5 times with PBS+0.25% Tween 20.

After washing, the HRP conjugated secondary anti-human Fab (1:5000, Cat. No. 109-035-097, Jackson ImmunoResearch Inc) was added to each well and incubated at RT for 30 minutes. After washing 5 times with PBS+0.25% Tween 20, 100 μl of TMB Microwell Peroxidase Substrate (KPL, Gaithersburg, Md., USA) was added to each well. The reaction was terminated by adding 50 μl 1M $H_2SO_4$, and $OD_{450}$ was measured using SpectraMax M5 (Molecular Devices) and analyzed using SoftMax Pro6.3 software (Molecular Devices). The final data was transferred to GraphPad Prism software (GraphPad Software, CA, USA), and plotted as shown. EC50 was calculated using the same software.

SPR Assays

Two pairs of heavy and light chains were selected for full kinetic analysis. Kinetic characterization of purified antibodies was performed using surface plasmon resonance (SPR) technology on a BIACORE 3000 (GE Healthcare). A capture assay using a tag specific antibody capture and orientation of the investigated antibodies was used. For capture of Fc containing protein constructs the human antibody capture kit (GE Healthcare) was used, for capture of His tag containing protein constructs the His capture kit (GE Healthcare) was used. The capture antibody was immobilized via primary amine groups (11000 RU) on a research grade CMS chip (GE Life Sciences) using standard procedures. The analyzed antibody was captured at a flow rate of 10 μL/min with an adjusted RU value that would result in maximal analyte binding signal of typically 30 RU.

For an exemplary assay, recombinant human IL13 (catalog #IL012) and human IL4 (catalog #IL004) were purchased from Millipore, recombinant human TNFa (catalog #H8916) was purchased from Sigma Aldrich. Binding kinetics were measured against recombinant human IL4 and IL13 over a concentration range between 0.1 to 3 nM for IL4 and 0.8 to 25 nM for IL13. For human TNFα a concentration range from 3 to 100 nM was used. As assay buffer HBS EP (10 mM HEPES, pH 7.4, 150 mM NaCl, 3 mM EDTA, and 0.005% Surfactant P20) was used at a flow rate of 30 μl/min. Chip surfaces were regenerated with the regeneration solution of the respective capture kit. Kinetic parameters were analyzed and calculated in the BIAevaluation program package v4.1 using a flow cell without captured antibody as reference and the 1:1 Langmuir binding model with mass transfer. To study simultaneous binding of antigens the trispecific antibodies were captured by an anti-human antibody capture surface. Antigens were used in single concentrations with IL4 at 3 nM, IL13 at 25 nM and TNFα at 100 nM. To show simultaneous binding of all three antigens, a mixture of IL4, IL13 and TNFα was injected. In separate analysis cycles, IL13 was injected alone, followed by either IL4 or TNFα, and followed by a co-inject of either IL4/

TNFα or a co-inject of TNFα/IL4. The final response measured in each cycle was compared to show similarity of consecutive binding of either two or three antigens and simultaneous binding of a mixture of all three antigens.

In Vitro T Cell Activation and Proliferation Assays

Human PBMCs were purified from buffy coat purchased from Blood Research Component (Brookline, Mass., USA) using Ficoll-Paque Plus method. Briefly, fresh buffy coat was first diluted at 1:3 ratio in PBS (pH7.4), and mixed with Ficoll-Paque Plus solution (Ficoll) thoroughly before use by inverting the bottle several times. 15 mL density gradient medium was added to each Leucosep® tube and spin for 30 s at 1000×g, RT. The medium is now located below the porous barrier. 30-40 mL diluted buffy coat then was carefully poured into each Leucosep tube, and centrifuged at 800×g for 15 minutes at room temperature, with the brake off and Max accel at 5. Plasma layer was removed, and the rest of the supernatant, which contains the enriched PBMCs, was transferred into a new tube (Leucosep tube was not held in the inverted position for longer than 2 seconds). Enriched PBMCs were washed with 45 ml PBS, and spun down at 250×g for 10 minutes at room temperature. Wash was repeated, and multiple tubes were combined into one tube. Cells were resuspended in 20 mL PBS and counted using a Bio-Rad TC20.

To set up the in vitro T cell activation assay, purified human PBMCs were resuspended in culture medium (RPMI1640 with 10% FBS and supplemented with glutamine/Streptomycin)(Thermo Fisher Scientific) ($10^6$ cells/ml). Indicated concentrations of different trispecific and control antibodies were added to each well, or used to coat the plate before use as described in Stebbings, R. et al. (2007) *J. Immunol.* 179:3325-3331, and incubated for 16-24 hours in a tissue culture incubator. The cells were spin down, and the supernatant was either collected for measuring cytokine release, or discarded. The cells were stained with florescent labeled antibodies for T cell markers (CD3, CD4, CD8, etc.) and activation markers (CD69, CD62L, etc.), and analyzed by running the samples on an Fortessa flow cytometer (Beckton Dickinson, San Jose, Calif.), followed by analysis using the Flowjo software (FlowJo v10) and plotted as shown.

To set up the in vitro T cell proliferation assay, purified human PBMCs were resuspended in culture medium (RPMI1640 with 10% FBS and supplemented with glutamine/Streptomycin)(Thermo Fisher Scientific) ($10^6$ cells/ml). Indicated concentrations of different trispecific and control antibodies were added to each well and incubated for 1-7 days in a tissue culture incubator. The cells were spun down, and the supernatant was either collected for measuring cytokine release, or discarded. The cells were stained with florescent labeled antibodies for T cell markers (CD3, CD4, CD8, etc.) and activation markers (CD69, CD62L, etc.), and analyzed by running the samples on an Fortessa flow cytometer (Beckton Dickinson, San Jose, Calif.), followed by analysis using the Flowjo software (FlowJo v10) and plotted as shown.

In Vitro Cell Killing Assay

Purified human PBMCs were using for in vitro killing assays against various cancer cells using different trispecific antibodies. Briefly, the killing assay was set up in 96-well V-bottom plate. For each plate, 40 ml PBMCs from each donor were plated at 2×10^6 cells/ml, and 30 ml of PKH26 (Sigma #MINI26) labeled target cells at 2.5×10^5 cells/ml (4 μL of dye to stain up to 1×10^7 cells) were prepared. First 20 μL/well test proteins at various concentrations or PMA were added into each well, followed by adding 80 μL/well labeled target cells into each well (2×10^4 cells/well). 100 μL of PBMC were then added to each well, reaching E:T=10:1 well (2×10^5 cells/well), and incubated for 24 hours at 37° C. 5% CO2 incubator. The cells were spin down, and the supernatant was either collected for measuring cytokine release, or discarded. The cells were stained with Vivid LIVE/DEAD™ Fixable Violet Dead Cell Staining buffer (Life Technology #L34955) (staining buffer was prepared by adding 60 μL Vivid reagent into 60 ml PBS). Cells were resuspended into 100 μL staining buffer by incubation for 15 min at RT in the dark. After washing the cells with 1×PBS, the cells were resuspended in 200 μL PBS with 0.5% Paraformaldehyde, and PKH26+Vivid+ cancer cells were collected by Fortessa flow cytometer (Beckton Dickinson, San Jose, Calif.), followed by analysis using the Flowjo software. The percentage of killing is calculated as "specific killing-spontaneous killing/total cells and plotted as shown.

Cytokine Release Assay

For measuring inflammatory cytokine concentrations in the in vitro activation assays, in vitro killing assays, in vivo activation assays in CD34+ umbilical cord cell humanized NSG mice, and the toxicity study, cell culture supernatant was collected, and serum samples were diluted according to manufacturer's protocol using Milliplex Human High Sensitivity T cell 13-plex Kit (EMD Millipore). These were subsequently analyzed by EMD Millipore MAGPIX® System, and MILLIPLEX® Analyst 5.1 software.

In Vivo Mouse Models and Efficacy Studies

Human CD34+ hematopoietic stem cell-engrafted NSG mice (hu-CD34) were used as an in vivo mouse model. These mice develop multi-lineage human immune cells, and are a validated platform for immuno-oncology efficacy studies (see, e.g., Shultz, L. D. et al. (2014) *Cold Spring Harb. Protoc.* 2014:694-708). Hu-$CD34^+$ NSG mice are produced by injecting $CD34^+$ hematopoietic stem cells, showing effective multi-lineage engraftment of human immune cell populations including T cells, B cells and some other populations (McDermott, S. P. et al. (2010) *Blood* 116:193-200). Multi-lineage hematopoiesis occurs within 12 weeks. Engraftment is stable for over one year without graft-versus-host disease.

For the efficacy study using hu-CD34 NSG mice, mice were purchased from The Jackson Laboratory (Maine, USA), and human cell populations were validated before use. In general, $5\times10^6$ tumor cells mixed in Matrigel (BD Biosciences) (50% v/v) were used for inoculating tumor in each mouse. Once tumor size reached the range of 100-150 $mm^3$, mice were selected and randomized into each group for study. Antibodies were given intravenously at given doses 3 times weekly. Body weight was monitored 1-3 times weekly. Tumor size was measured by caliper tumor measurements 1-3 times/week. All mice were terminated when the tumor size reached 1,500 $mm^3$, or 24 hours after the last dose. Terminal blood samples (0.3 mL) were collected into serum separator tubes, mixed by gently inverting five times, and placed into a tube rack. Terminal tumors were also collected and weighed before being put into fixative for immunohistochemistry analysis.

Human PBMC humanized (hu-PBMC) NSG mice were used as another in vivo mouse model. These mice are produced by injecting purified human PBMC from health donors, which have the fastest engraftment rate using adult peripheral blood mononuclear cells and enable short-term studies requiring a strong effector and memory T cell and NK cell function, and are suitable for short term efficacy study (3-4 weeks) due to graft-versus-host disease.

For the efficacy study using hu-PBMC NSG mice, 8-10 week old NSG mice (Cat. No: 005557, NOD.Cg-Prkdcscid Il2rgtm1Wjl/SzJ) were purchased from The Jackson Laboratory (Maine, USA). Each mouse was innoculated with $5\times10^6$ tumor cells mixed in Matrigel (BD Biosciences) (50% v/v). Once tumor size reached the range of 50-100 $mm^3$, $10\times10^6$ human PBMCs from a healthy donor were reconstituted to each mouse. Human cell reconstitution was validated the next day. Once tumor size reached the range of 100-150 $mm^3$, mice were selected and randomized into each group for study. Antibodies were given intravenously at given doses 3 times weekly. Body weight was monitored 1-3 times weekly. Tumor size was measured by caliper tumor measurements 1-3 times/week. All mice were terminated when the tumor size reached 1,500 $mm^3$ or 24 hours after the last dose. Terminal blood samples (0.3 mL) were collected into serum separator tubes, mixed by gently inverting five times, and placed into a tube rack. Terminal tumors were also collected and weighed before being put into fixative for immunohistochemistry analysis.

NHP Tolerability and Pharmacokinetic Study

All NHP studies were carried out by Covance (Princeton, N.J., USA) according to Covance ICUCA protocol. Drug- and protein-naïve or protein-naïve male Cynomolgus Monkeys were used in all studies. Based on study design, monkeys were selected and grouped for each trispecific antibody. Antibody was given by intravenous infusion for 1 hour via saphenous vein. Increasing doses were given on consecutive days for low doses (<10 μg/kg), but with a 1-2 day interval for higher doses (>10 μg/kg) for observation purposes. Blood samples were collected at 0 hour (Day 1 only), 0.5 hour (mid-infusion), 1, and 6 hours from start of infusion for all animals after each dose, as specified. Additional unscheduled blood samples were collected at the discretion of the study director, pathologist, and/or clinical veterinarian. All animals were returned to colony on Day 60. PBMC and serum from the blood samples were prepared using standard methods, and preserved for future analysis.

Luciferase Reporter Assay

GloResponse™ IL2-luc2P Jurkat Cells, Thaw and Use (Promega part #CS187002) and GloResponse™ NFAT-Luc2 Jurkat Cells (Promega Cat #CS176401) were purchased from Promega (WI, USA), and prepared for use according to manufacturer's protocol.

Briefly, the cells were thawed for 2 min in a 37° C. water bath and gently transferred to a 15 mL conical centrifuge tube containing 10 mL pre-warmed R10 media. Tube was centrifuged at 300 g for 5 min at RT. Supernatant was removed, and the cells were resuspended in 20 mL pre-warmed R10 media and transferred to a 75 cm2 culture flask, followed by incubation in 37° C. tissue culture incubator until cells were growing and stable (~3-4 days). The cells were split twice a week to 0.1e6 cells/mL. Cells were maintained in R10+ Hygromycin B media for selection. Cells were used for assays ~7 days after thawing.

For antibody stimulation, trispecific or control antibodies were prepared at various concentrations and serially diluted in PBS. 25 μL of antibodies were dispensed per well. For plate-bound Abs, Maxisorp plate was used and incubated at 4° C. overnight. For soluble Abs, a U-bottom plate was used. Reporter cells were resuspended to 0.3-0.5 e6/mL, and 175 μL cells were added to each well, and incubated in 37° C. $CO_2$ incubator for 6 hours. The plate was then taken out of the incubator and allowed to equilibrate to ambient temperature (10-15 min). Then 50 μl of Bio-Glo™ Reagent (Promega Cat #G7941) (ambient temperature) was added to the each well of the assay plate. After incubation for 5 minutes, luminescence activity was measured using MicroBeta2 LumiJET microplate counter (Perkin Elmer; is read time). Data were plotted using GraphPad Prism software.

Conformational Stability

Thermostability measurements (e.g., melting points, $T_m$) were determined using differential scanning fluorimetry (DSF). Samples were diluted in D-PBS buffer (Invitrogen) to a final concentration of 0.2 μg/μl including a 4× concentrated solution of SYPRO-Orange dye (Invitrogen, 5000× stock in DMSO) in D-PBS in white semi-skirt 96-well plates (BIORAD). All measurements were done in duplicate using a MyiQ2 real time PCR instrument (BIORAD). Negative first derivative curves (−d(RFU)/dT) of the melting curves were generated in the iQ5 Software v2.1 (BIORAD). Data were then exported into Microsoft Excel for Tm determination and graphical display of the data.

IC50 Measurements

Detection of Antibody Activity Against IL-4 and IL-13 with a Reporter Cell Line

Activities of bispecific antibodies or derivatives against cytokines IL4 and IL13 were determined in commercially available HEK-Blue IL-4/IL-13 reporter cells (InvivoGen). HEK-Blue IL-4/IL-13 cells are designed to monitor the activation of the STAT6 pathway by IL-4 or IL13. Stimulation of the cells with either cytokine results in production of the reporter gene secreted embryonic alkaline phosphatase (SEAP) which can be measured in the culture supernatant with the QUANTI-Blue assay. To test antibody activities against IL4 or IL13, the cytokines were pre-incubated for 1 hour with different concentrations of the antibodies and added to 50.000 HEK-Blue IL-4/IL-13 cells. Cytokine-mediated induction of SEAP was measured after 24 hours incubation in the cell culture supernant with the QUANTI-Blue assay (InvivoGen). Each experiment was performed with n=3 datapoints for each antibody concentration. The half-maximal inhibitory concentration (IC50) for each antibody was calculated via the internal application Biostat-Speed V2.0 (Sanofi).

Detection of Antibody Activity Against TNFα with a Reporter Cell Line

Activities of bispecific antibodies or derivatives against TNFa were determined by using commercially available HEK-Blue TNF-a reporter cells (InvivoGen). HEK-Blue TNF-a cells are designed to detect bioactive TNFa by monitoring the activation of the NFkB pathway via the expression of the reporter gene secreted embryonic alkaline phosphatase (SEAP) which can be measured in the culture supernatant with an QUANTI Blue Assay (InvivoGen). To determine antibody activities against TNFa the cytokines were pre-incubated for 1 hour with different concentrations of the antibodies and added to 50,000 HEK Blue TNF-a cells. Cytokine mediated induction of SEAP was measured after 24 hours in the culture supernatant with the QUANTI-Blue assay (InvivoGen). Each experiment was performed with n=3 datapoints for each antibody concentration. The half maximal inhibitory concentration for each antibody was calculated.

Example 2: Overview of the Trispecific Binding Proteins

A novel strategy was developed for the generation of trispecific binding proteins. The trispecific proteins comprised four polypeptides that formed three target binding sites (FIGS. 1A-C). Each target binding site comprised the $V_H$ and $V_L$ domain from an antibody that targeted a distinct human antigen target (See e.g., Table 1). The trispecific binding proteins contained a first pair of polypeptides that possessed dual variable domains having a cross-over orientation forming two distinct antigen binding sites (called the CODV Ig format), and a second pair of polypeptides, each with a single variable domain that formed a third antigen binding site (FIGS. 1A and 1B).

TABLE 1

Heavy and light chain SEQ ID NOs for binding proteins 1-21, and the target antigens to which the binding proteins are directed.

| Binding Protein # | SEQ ID NOS | Directed to: |
|---|---|---|
| 1 | 1, 2, 3, 4 | Her2 × (CD28 × CD3) |
| 2 | 1, 2, 9, 10 | Her2 × (CD28 × CD3) |
| 3 | 13, 14, 3, 4 | CD19 × (CD28 × CD3) |
| 4 | 13, 14, 9, 10 | CD19 × (CD28 × CD3) |
| 5 | 17, 18, 3, 4 | CD38 × (CD28 × CD3) |
| 6 | 17, 18, 9, 10 | CD38 × (CD28 × CD3) |
| 7 | 21, 22, 3, 4 | LAMP1 × (CD28 × CD3) |
| 8 | 21, 22, 9, 10 | LAMP1 × (CD28 × CD3) |
| 9 | 60, 61, 62, 63 | TNFa × (IL4 × IL13) |
| 10 | 60, 61, 68, 69 | TNFa × (IL13 × IL4) |
| 11 | 60, 71, 68, 69 | TNFa × (IL13 × IL4) |
| 12 | 73, 74, 75, 76 | IL13 × (IL4 × TNFa) |
| 13 | 73, 74, 81, 82 | IL13 × (TNFa × IL4) |
| 14 | 85, 86, 87, 88 | IL4 × (IL13 × TNFa) |
| 15 | 85, 86, 93, 94 | IL4 × (TNFa × IL13) |
| 16 | 73, 74, 68, 69 | IL13 × (IL13 × IL4) |
| 17 | 85, 86, 68, 69 | IL4 × (IL13 × IL4) |
| 18 | 73, 74, 62, 63 | IL13 × (IL4 × IL13) |
| 19 | 85, 86, 62, 63 | IL4 × (IL4 × IL13) |
| 20 | 114, 115, 3, 4 | CD20 × (CD28 × CD3) |
| 21 | 114, 115, 9, 10 | CD20 × (CD28 × CD3) |

The first pair of polypeptides (that possessed the dual variable domains) comprised a first polypeptide having the structure $V_{L1}$-Linker-$V_{L2}$-Linker-Immunoglobulin light chain constant domain, and a second polypeptide having the structure $V_{H1}$-Linker-$V_{H2}$-Linker-Immunoglobulin $C_{H1}$ heavy chain constant domain, resulting in a pair of polypeptides which had a cross over orientation that formed two distinct antigen binding sites: and $V_{H2}$-$V_{L2}$ (FIG. 1C, see light and heavy chains B). Table A provides a summary of the design of the bispecific arm (i.e., the arm comprising heavy and light chains B) of IgG1 and IgG4 variants of representative trispecific binding proteins, including indicating the various combinations of the linkers used in the bispecific arm of the trispecific binding proteins. The second pair of polypeptides (that each possessed a single variable domain) comprised a first polypeptide having the structure $V_{H3}$-Immunoglobulin $C_{H1}$ heavy chain constant domain, and a second polypeptide having the structure $V_{L3}$-Immunoglobulin light chain constant domain, resulting in a pair of polypeptides that formed a third antigen binding site: $V_{H3}$-$V_{L3}$ (FIG. 1C, see light and heavy chains A). Furthermore, the trispecific binding proteins were constructed such that either of the $C_{H3}$ domains could include a knob or a hole modification to facilitate antibody heterodimerization (FIG. 1).

TABLE A summary of the design of the bispecific arm of the trispecific binding proteins as an IgG1 (Hole) or IgG4 (Hole)

| | | CD28 × CD3 | | | CD3 × CD28 | | | CD28 × CD3 | | | CD3 × CD28 | | |
|---|---|---|---|---|---|---|---|---|---|---|---|---|---|
| | | HC -1 | HC -2 | HC -3 | HC -1 | HC -2 | HC -3 | HC -1 | HC -2 | HC -3 | HC -1 | HC -2 | HC -3 |
| CD28 | LC-1 | X | | | | | | | | | | | |
| × | LC-2 | | X | | | | | | | | | | |
| CD3 | LC-3 | | | X | | | | | | | | | |
| CD3 | LC-1 | | | | X | | | | | | | | |
| × | LC-2 | | | | | X | | | | | | | |
| CD28 | LC-3 | | | | | | X | | | | | | |
| CD28 | LC-1 | | | | | | | X | | | | | |
| × | LC-2 | | | | | | | | X | | | | |
| CD3 | LC-3 | | | | | | | | | X | | | |
| CD3 | LC-1 | | | | | | | | | | X | | |
| × | LC-2 | | | | | | | | | | | X | |
| CD28 | LC-3 | | | | | | | | | | | | X |

Linkers: [L3, L4]/[L1, L2]-[S, RT]/[GQPKAAP (SEQ ID NO: 175), TKGPS (SEQ ID NO: 106)]; [,]/[GGGGSGGGGS (SEQ ID NO: 104), GGGGSGGGGS (SEQ ID NO: 104)]; or [GGGGSGGGGSGGGGS (SEQ ID NO: 105),]/[GGGGSGGGGSGGGGS (SEQ ID NO: 105),]

Example 3: In Vitro Binding Activity and Antibody-Mediated Specific Killing of T Cell Engagers This example describes in vitro assays for characterizing the activities of the T cell engagers.

Using the approach described in Example 2 above for trispecific binding protein design, four trispecific binding proteins (Binding Proteins 1, 3, 5, and 6) were generated. These trispecific binding proteins were created by grafting onto a trispecific binding protein framework the $V_H$ and $V_L$ domains isolated from antibodies targeting distinct human proteins: CD3, CD19, CD28, CD38, or Her2. Binding Protein 1 was constructed such that the first pair of polypeptides (which formed two antigen binding sites) targeted CD28 and CD3, and the second pair of polypeptides (which formed the single antigen binding site) targeted Her2 (Binding Protein 1=Her2×(CD28×CD3)). Binding Protein 3 was constructed such that the first pair of polypeptides (which formed two antigen binding sites) targeted CD28 and CD3, and the second pair of polypeptides (which formed the single antigen binding site) targeted CD19 (Binding Protein 3=CD19×(CD28×CD3)). Binding Protein 5 was constructed such that the first pair of polypeptides (which formed two antigen binding sites) targeted CD28 and CD3, and the second pair of polypeptides (which formed the single antigen binding site) targeted CD38 (Binding Protein 5=CD38×(CD28×CD3)). Binding Protein 6 was constructed such that the first pair of polypeptides (which formed two antigen binding sites) targeted CD28 and CD3, and the second pair of polypeptides (which formed the single antigen binding site) targeted CD38 (Binding Protein 6=CD38×(CD28×CD3)).

In Vitro Assays Using Trispecific Binding Proteins Comprising Anti-Her2

Figure 2:
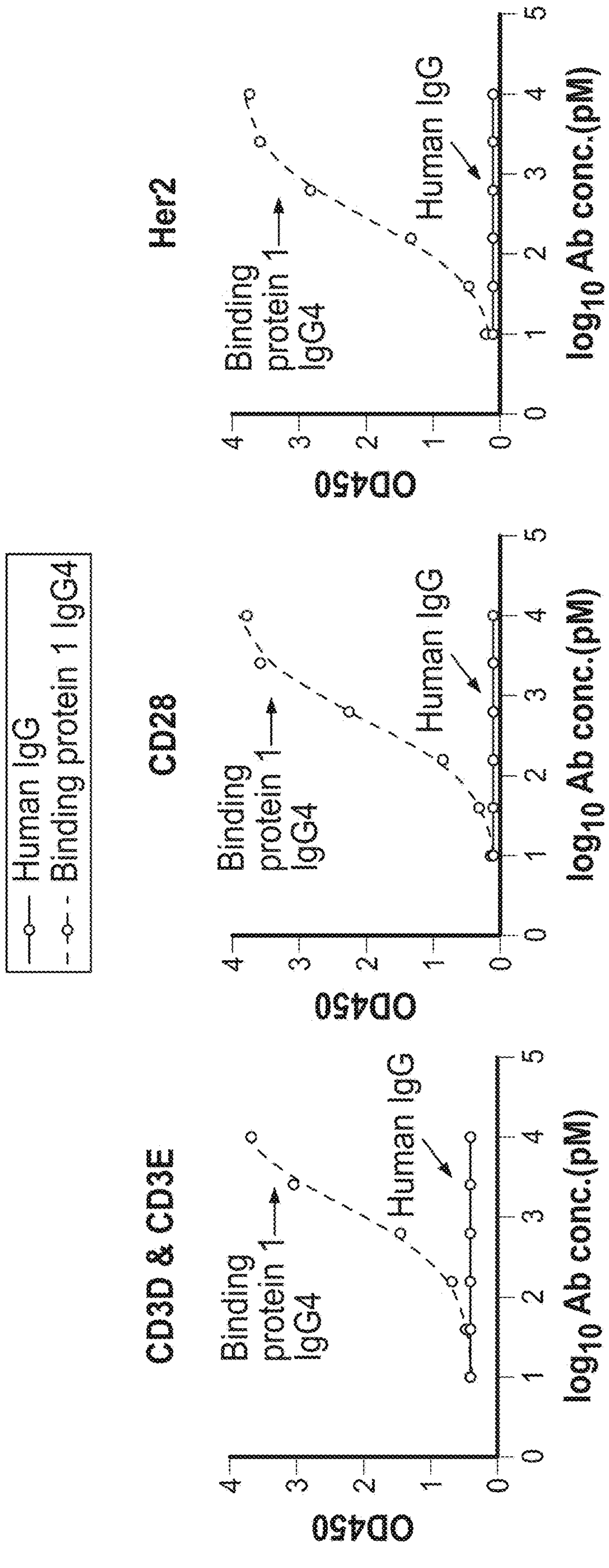
FIG. 2 shows the results of an ELISA assay determining the binding of an anti-Her2×CD28×CD3 IgG4 trispecific antibody (Binding Protein 1), or isotype control antibody, to human CD3, CD28 and Her2. The bound antibodies were detected using a horseradish peroxidase (HRP)-conjugated anti-Fab secondary antibody.

To test the ability of the trispecific binding proteins to target and bind three different human antigens, the specificity of Binding Protein 1 for its targets was first examined by ELISA assay. Binding Protein 1 was capable of binding all three of its target proteins—CD3, CD28, and Her2 (FIG. 2)—indicating that each binding domain in the trispecific format retained its function.

ZR-75-1, AU565 ($Her2^+$), ARH-77 ($CD19^+$), MOLP-8, RPMI-8226, KMS-12_BM, NCI-H929, MM.1.S, MM.1., R OPM-2, KMS-26, and U266 cells ($CD38^+$) were labeled with the membrane dye PKH-26 (Sigma) and used as target cells in a cytotoxicity assay. These labeled cell lines were co-cultured at an E:T ratio of 10:1 with enriched human Pan T cells in the presence of increasing concentrations of a trispecific antibody, bispecific antibody, or control proteins for 24 hours. The extent of cell lysis in the target cells was determined by staining with a live/dead cell marker (Life Technologies) and measuring the number of dead cells in the labeled target cell population by running the samples on a Fortessa flow cytometer (Beckton Dickinson, San Jose, Calif.) followed by analysis using the Flowjo software (FlowJo v10).

Her2+, CD19+, CD38+ tumor cell lines were stained with fluorescently conjugated antibodies against human CD3, CD28, CD19, CD38, LAMP1, and/or Her2 (Biolegend). Staining with respective isotype-matched control antibodies was also included. The cells were then acquired on the Fortessa (Beckton Dickinson, San Jose, Calif.) instrument. Flow analysis was performed on FlowJo v10. The mediated killing results of various binding proteins are shown in FIGS. 3A-5, 9A, 9B, & 11A-16.

Figure 3B:
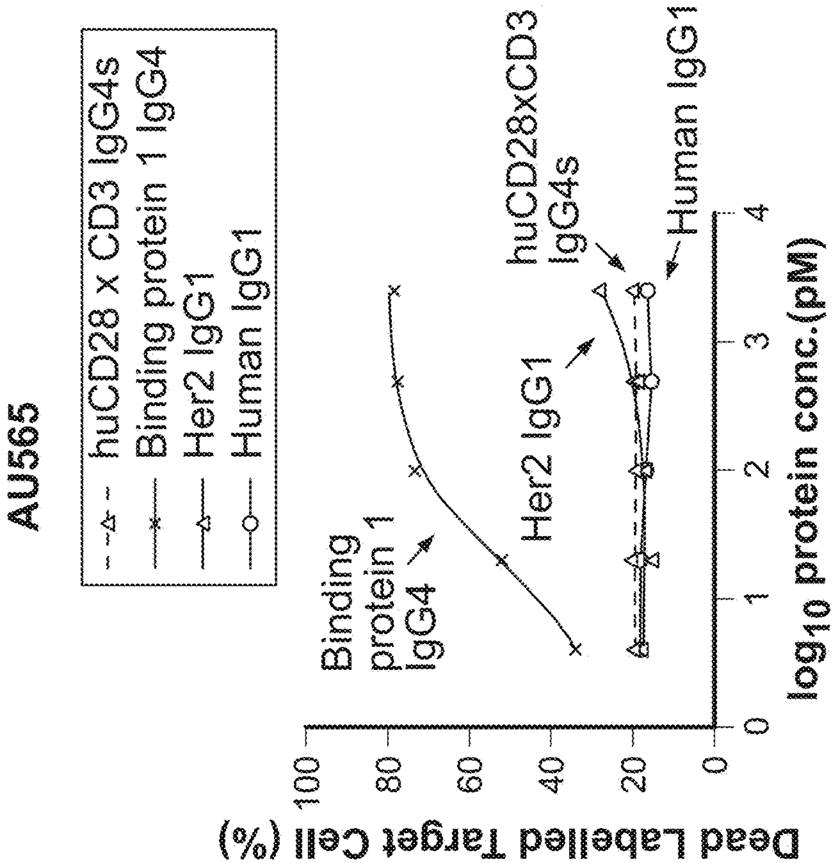
FIGS. 3A-3C show the results of antibody-mediated specific killing of $Her2^+$ breast cancer cells using an anti-Her2×CD28×CD3 IgG4 trispecific antibody (referred to herein as "Binding protein 1"), an anti-CD28×CD3 IgG4 bispecific antibody (huCD28×CD3), an anti-Her2 IgG1 antibody, or a control antibody (human-IgG1), using human PBMC at the E:T=10.
Figure 3A:
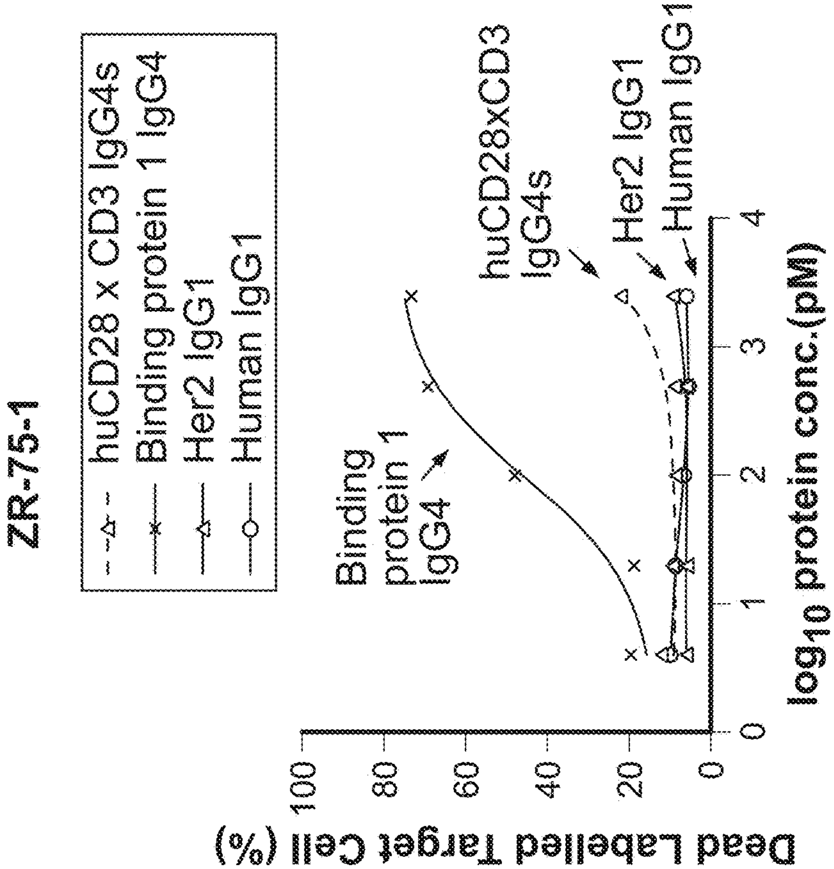
Figure 3C:
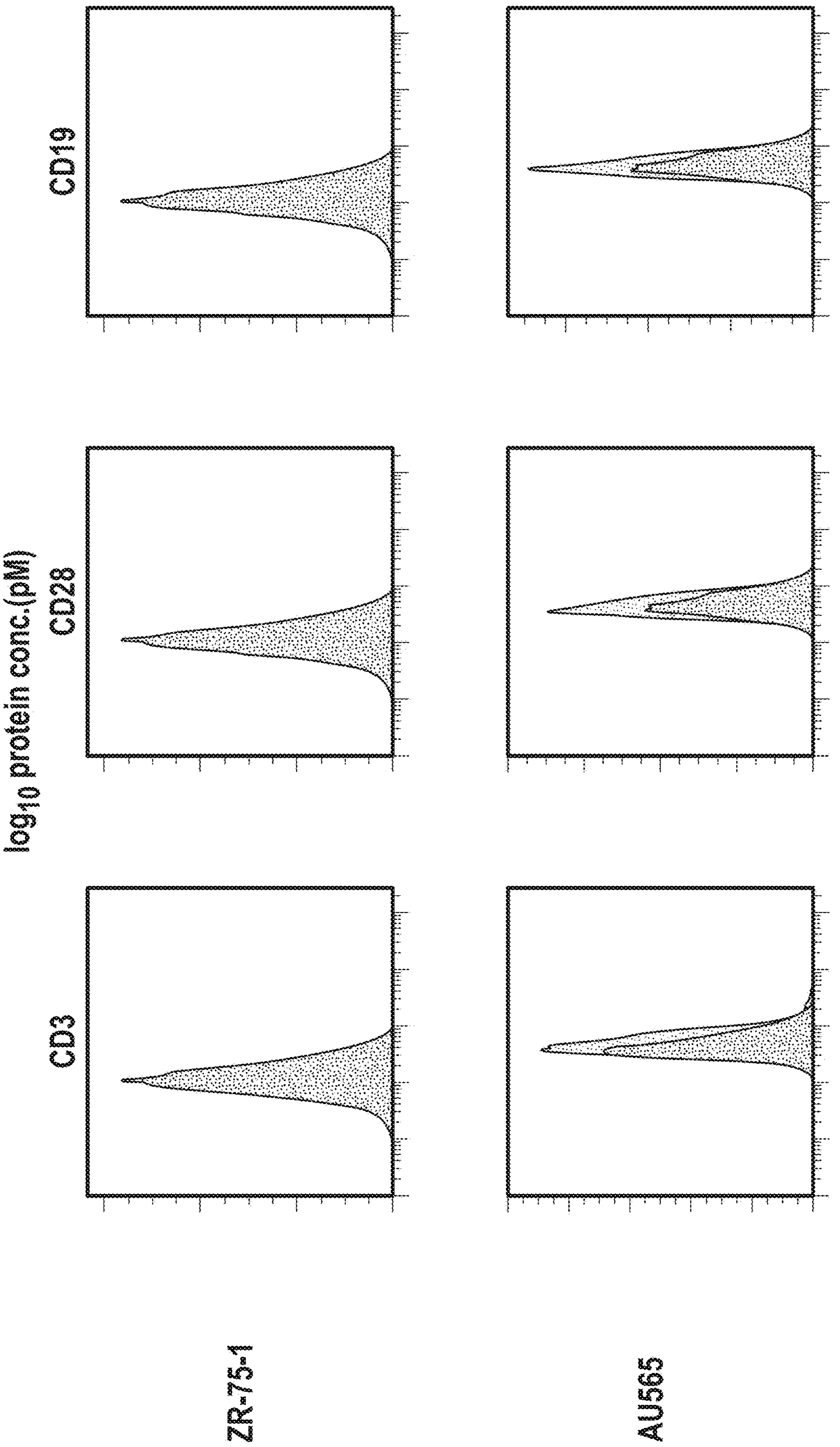
Figure 3C:
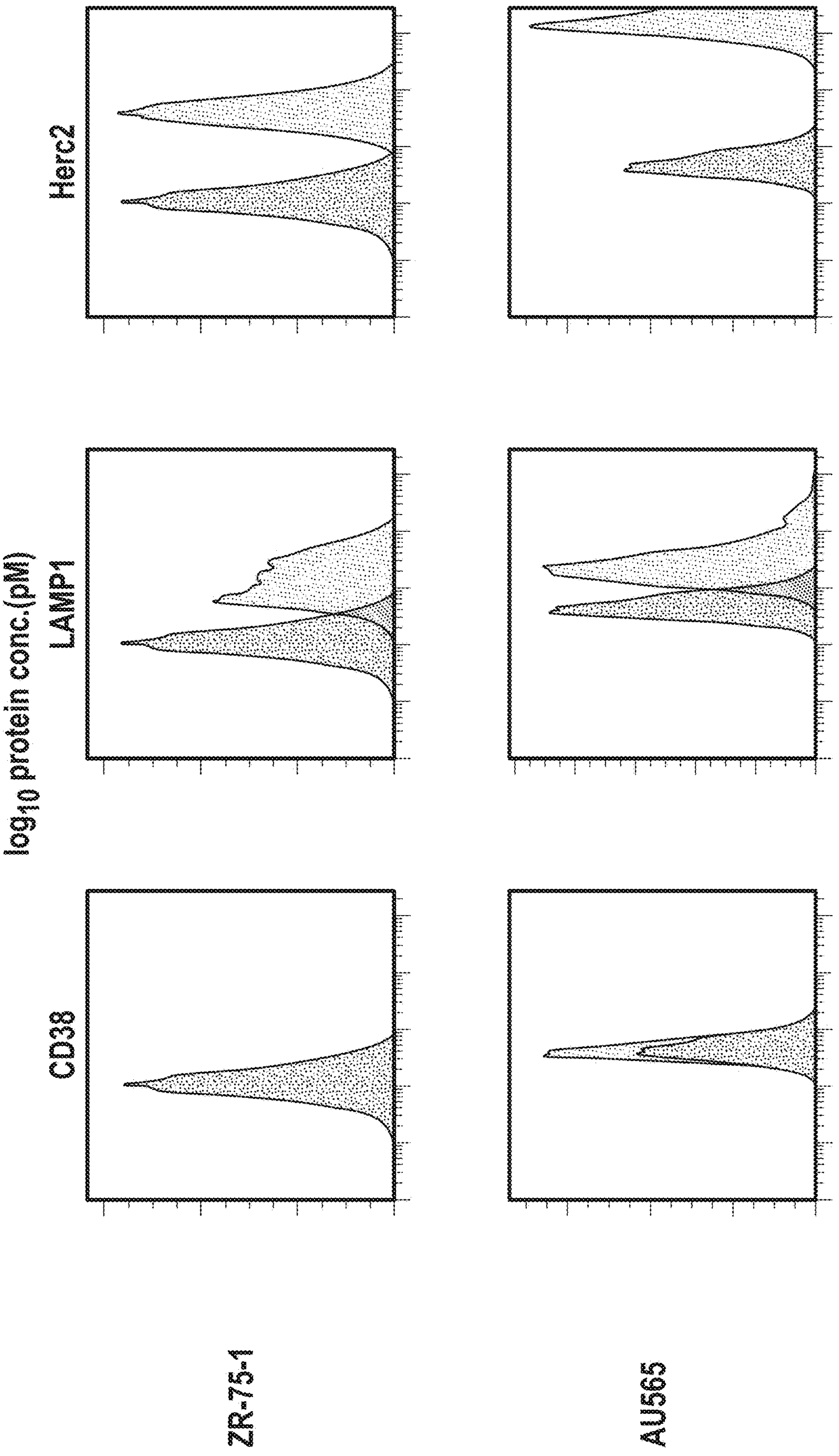
Figure 4:
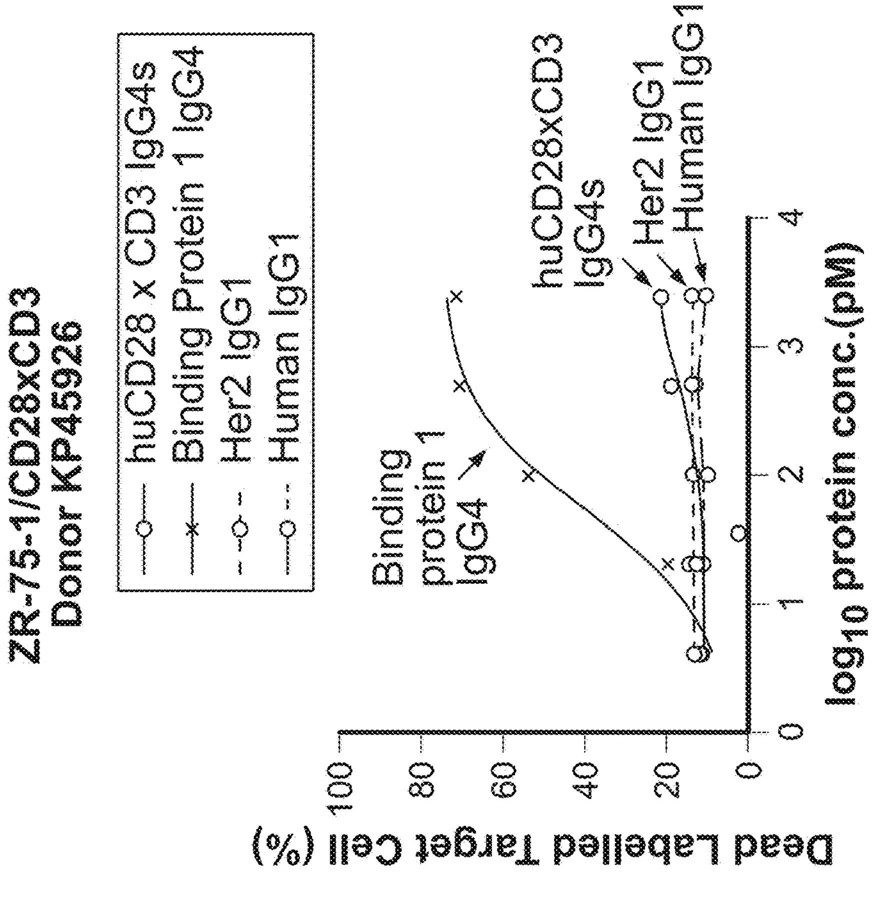
FIGS. 4 & 5 show the results of antibody-mediated specific killing of $Her2^+$ breast cancer cells using an anti-Her2×CD28×CD3 IgG4 trispecific antibody (Binding protein 1), an anti-CD28×CD3 IgG4 bispecific antibody (huCD28×CD3), an anti-Her2 IgG1 antibody, or a control antibody (human-IgG1).
Figure 5:
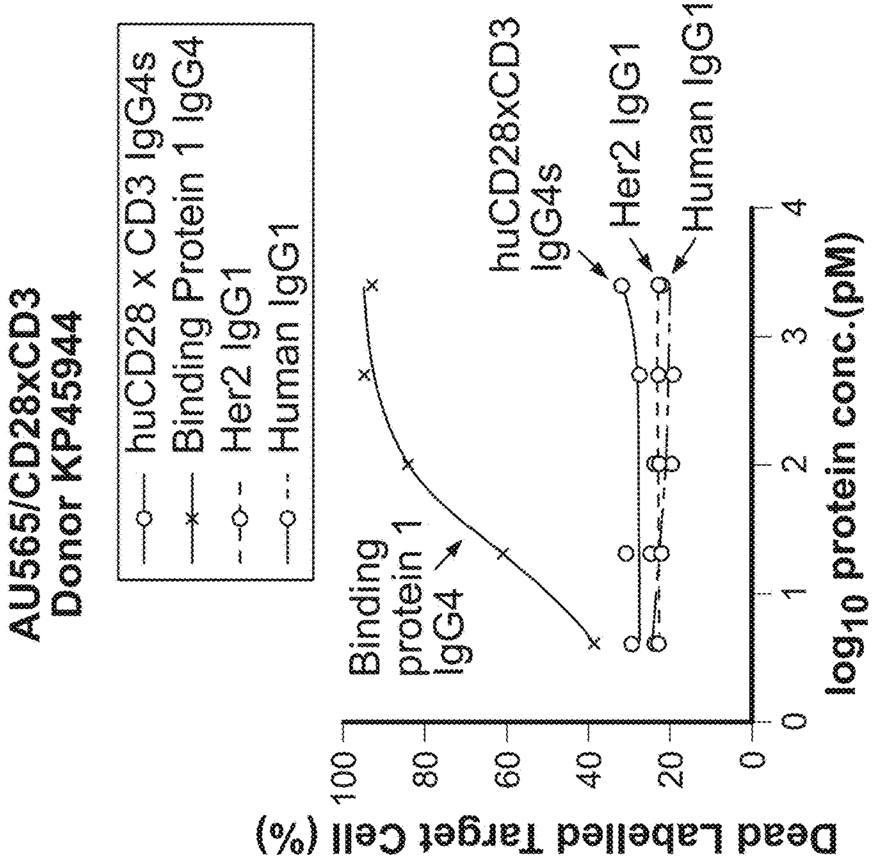

The ability of Binding Protein 1 to induce antibody-mediated cell killing of tumor cells expressing HER2 proteins on their surface was tested. Not only was Binding Protein 1 capable of binding to all three of its target proteins, but it was also able to induce antibody-mediated cell killing of $Her2^+$ cell lines (FIGS. 3A-4). Binding Protein 1 exhibited potent antibody-mediated cell killing activities, while anti-CD3/CD28 bispecific Ab and anti-Her2 antibodies showed minimal killing activities. (FIGS. 3A, 3B, 4, & 5), demonstrating the effectiveness of using the trispecific Ab to engage tumor cells with T cells through a tumor antigen (HER2) and T cell markers (CD3 and CD28). Anti-CD3/CD28 is not only important for T cell recruitment, but it also provides more effective T cell activation and survival signaling, potentially improving the efficacy.

Figure 6A:
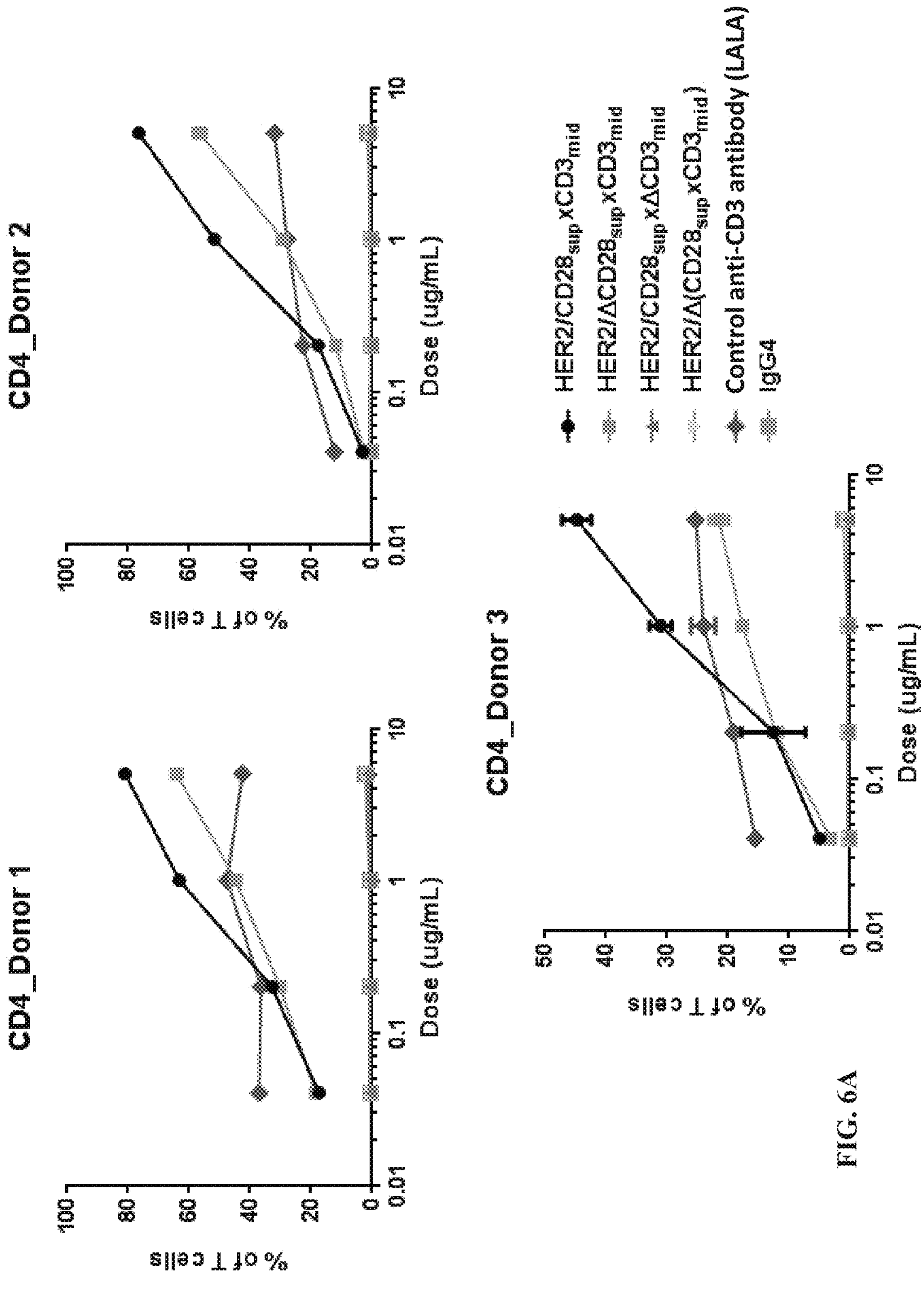
FIGS. 6A & 6B show the activation ($CD69^+$) and proliferation of human T cells treated with anti-Her2×CD28×CD3 IgG4 trispecific binding protein (HER2/$CD28_{sup}$×$CD3_{mid}$; referred to herein as "Binding Protein 1"), anti-Her2×CD28×CD3 IgG4 trispecific binding protein lacking the anti-CD28 binding domain (HER2/Δ$CD28_{sup}$×$CD3_{mid}$), anti-Her2×CD28×CD3 IgG4 trispecific binding protein lacking the anti-CD3 binding domain (HER2/$CD28_{sup}$×Δ$CD3_{mid}$), anti-Her2×CD28×CD3 IgG4 trispecific binding protein lacking both anti-CD28 and anti-CD3 binding domains (HER2/Δ($CD28_{sup}$×Δ$CD3_{mid}$)), control anti-CD3 monoclonal antibody, or control IgG4 antibody.
Figure 6B:
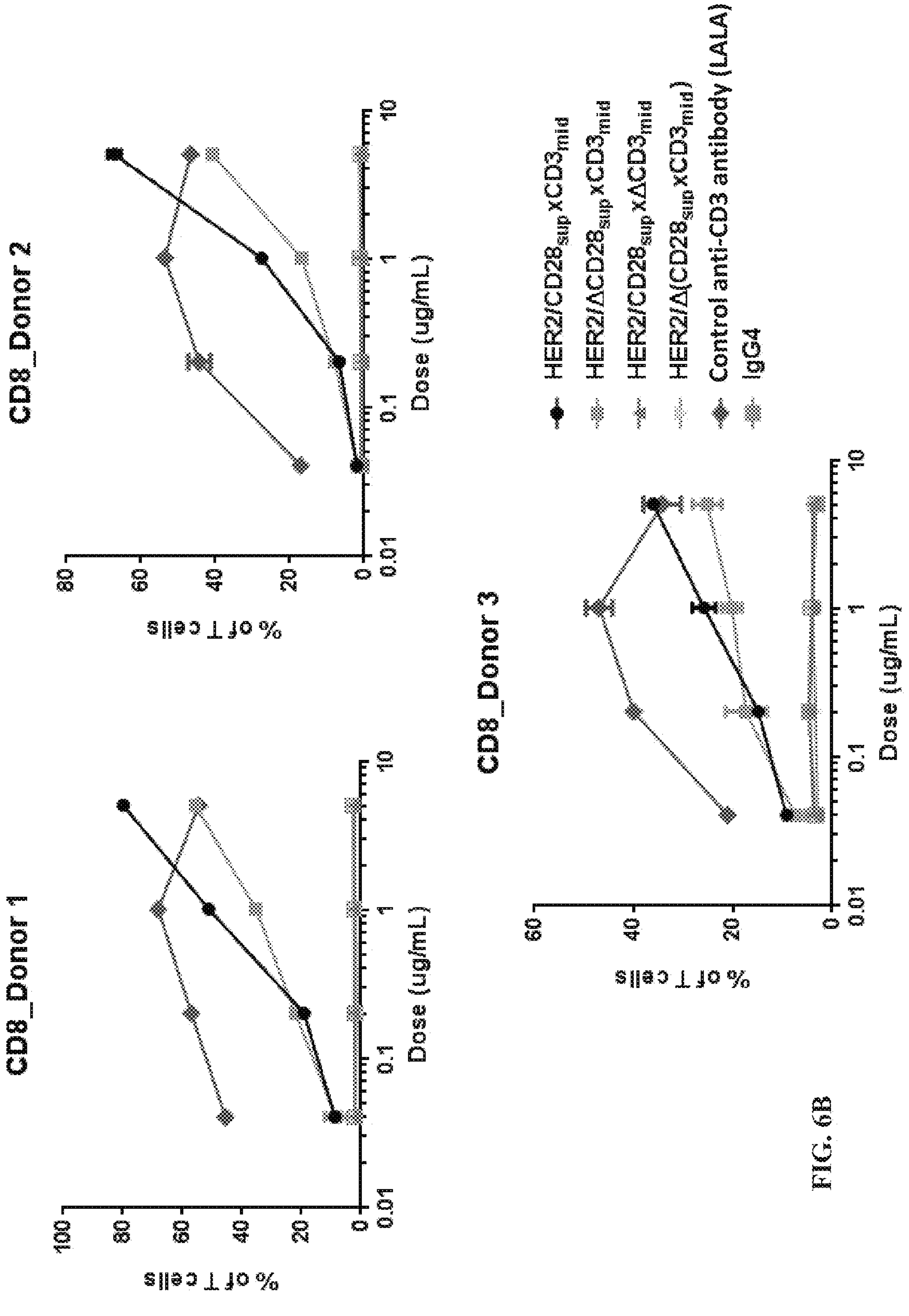
Figure 7B:
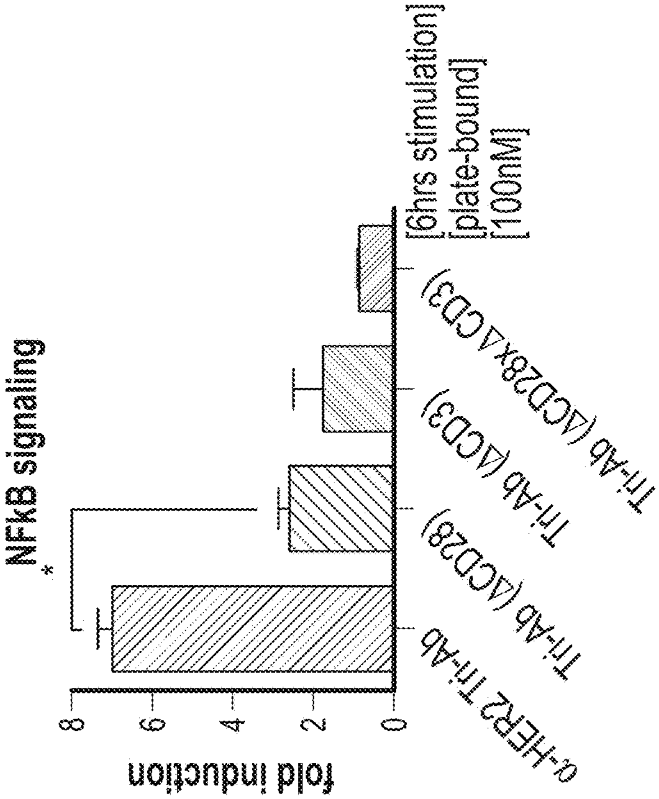
FIGS. 7A-C show IL-2, NFκB, and nuclear factor of activated T-cells (NFAT) pathway activation via anti-CD3 and anti-CD28 signaling, as measured by luciferase assay using human Jurkat T cells with an IL-2 promoter-luciferase construct (FIG. 7A), an NFκB promoter-luciferase construct (FIG. 7B), or an NFAT promoter-luciferase construct (FIG. 7C). Antibodies tested were those described above in reference to FIGS. 6A-6D.
Figure 7C:
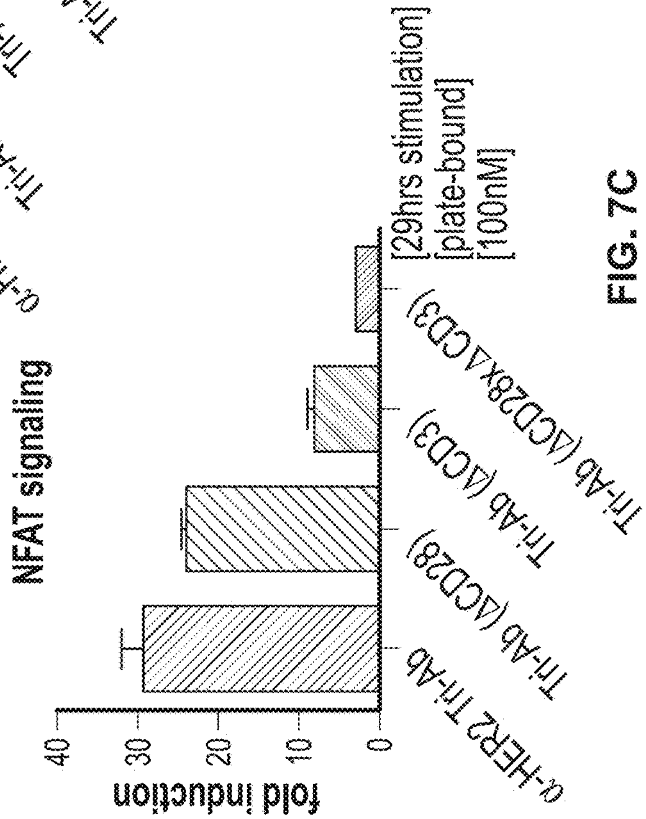
Figure 7A:
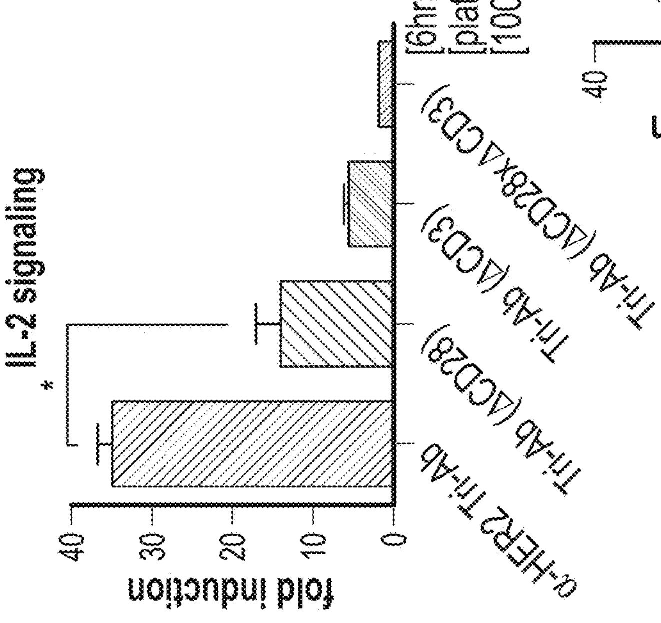

Additionally, studies were carried out on in vitro T cell activation and proliferation, as well as cytokine production, using the anti-Her2×CD28×CD3 trispecific antibody (Binding Protein 1). Binding protein 1 and control variants having one or two binding domains inactivated by site-directed mutagenesis (ΔCD28: anti-CD28 inactivated; ΔCD3: anti-CD3 inactivated; Δ(CD3×CD28): both anti-CD3 and anti-CD28 inactivated) were used in human PBMC in vitro activation assay as described in Example 1. The results showed that Binding protein 1 activated both human primary CD4 T cells and CD8 T cells effectively in vitro. Inactivation of anti-CD28 reduced the activation potency, indicating the importance of anti-CD28 co-signaling pathway. Inactivation of anti-CD3 binding site rendered Binding protein 1 to minimal activity, suggesting that the anti-CD3 provided the primary T cell activation signaling (FIGS. 6A & 6B). Similar results were obtained using IL2 and NFAT reporter human T cell lines (Jurkat-IL2 and Jurkat-NFAT) (FIGS. 7A-7C).

In Vitro Assays Using Trispecific Binding Proteins Comprising Anti-CD19

Figure 8:
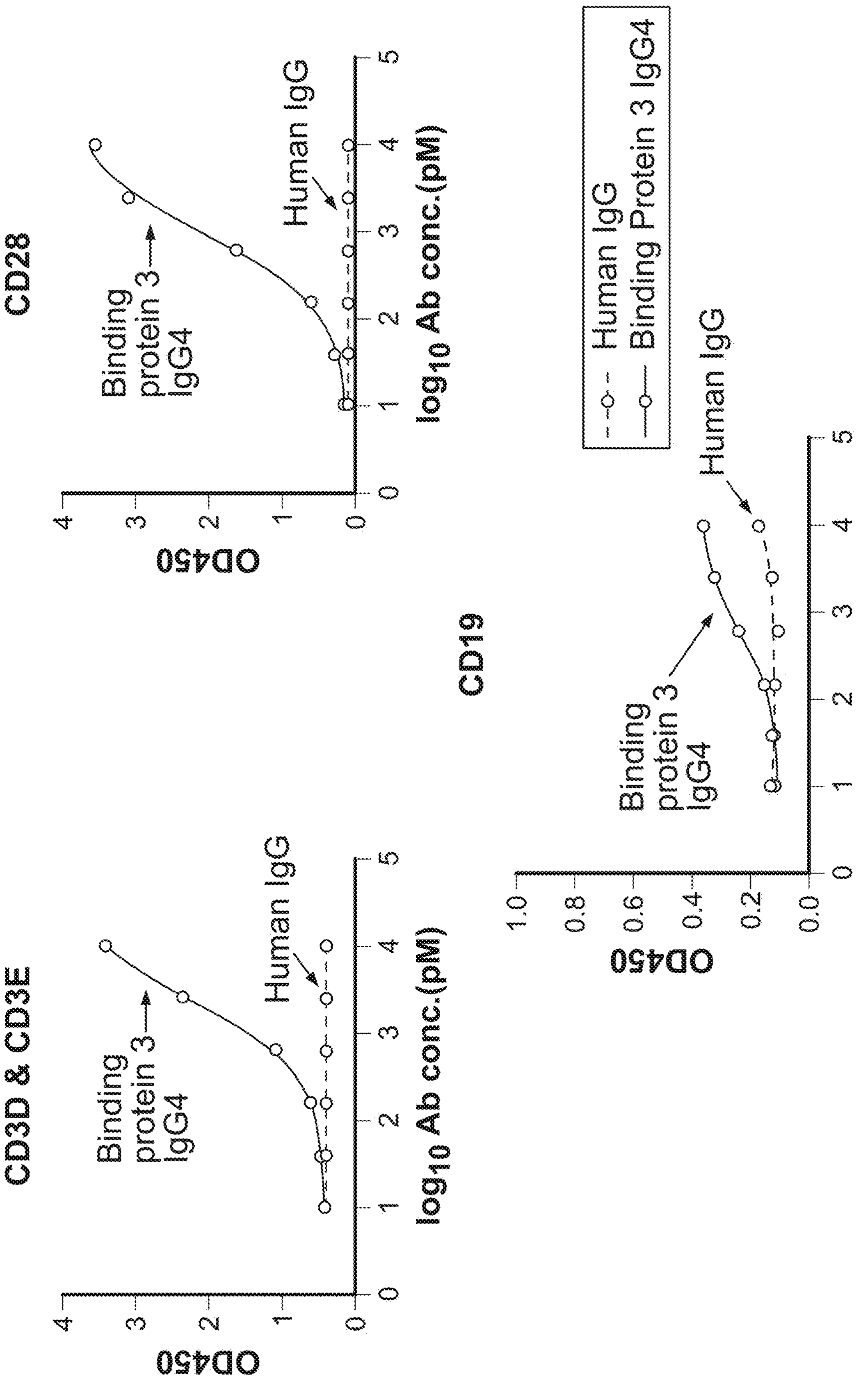
FIG. 8 shows the results of an ELISA assay determining binding of an anti-CD19×CD28×CD3 IgG4 trispecific antibody (referred to herein as "Binding Protein 3"), or isotype control antibody, to CD3, CD28, and CD19. The bound antibodies were detected using a horseradish peroxidase (HRP)-conjugated anti-Fab secondary antibody.

The anti-CD19×CD28×CD3 trispecific binding protein was capable of binding its target antigens (FIG. 8), indicating that each binding domain in the trispecific format retained its function.

Figure 9A:
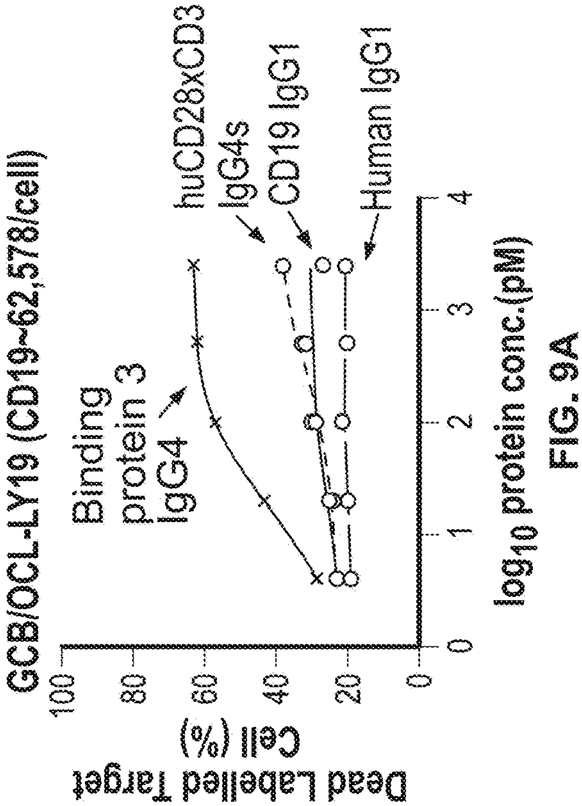
FIGS. 9A-9N show the results of antibody-mediated specific killing of $CD19^+$ human GCB lymphoma cells using an anti-CD19×CD28×CD3 IgG4 trispecific antibody (referred to herein as "Binding Protein 3"), or the indicated controls, using human PBMC as effector cells at E:T=10.
Figure 9B:
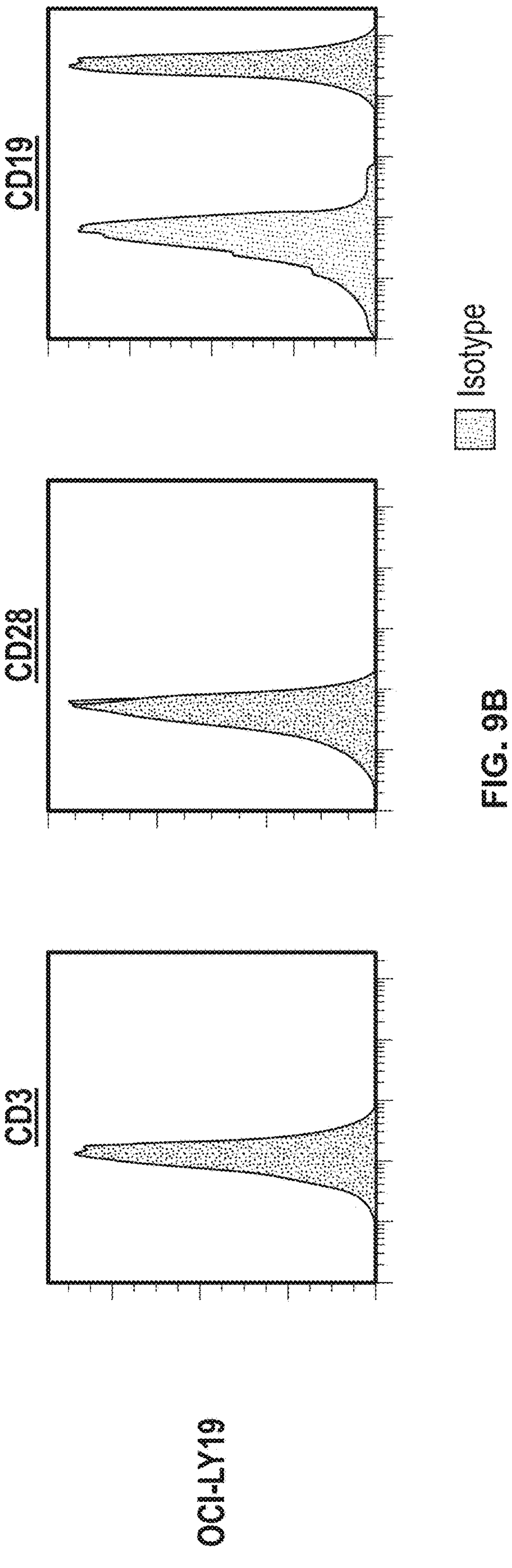
FIG. 9B shows the results of FACS analysis determining the cell surface expression of the indicated markers on OCI-LY19 cells.
Figure 9C:
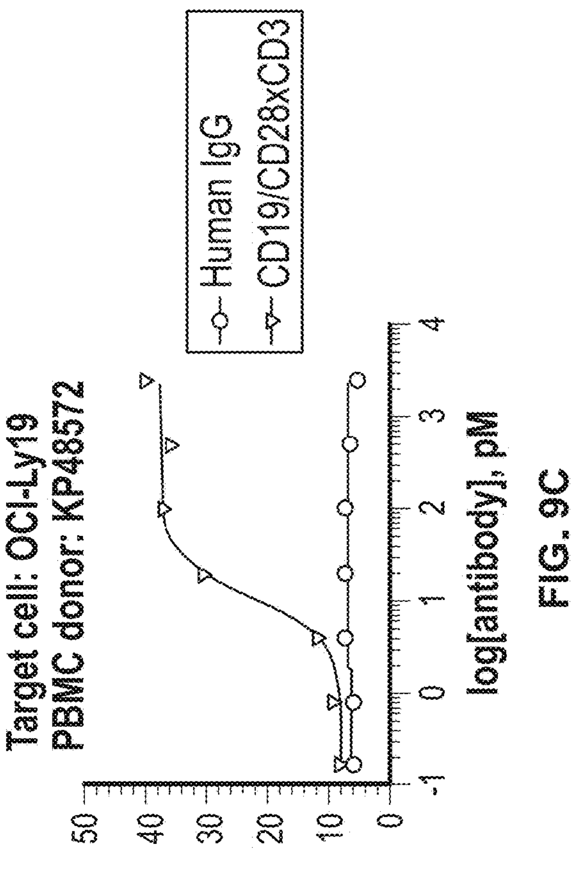
FIG. 9C shows the results of antibody-mediated specific killing of OCI-LY19 cells using PBMCs from donor KP48572 at E:T=10.
Figure 9D:
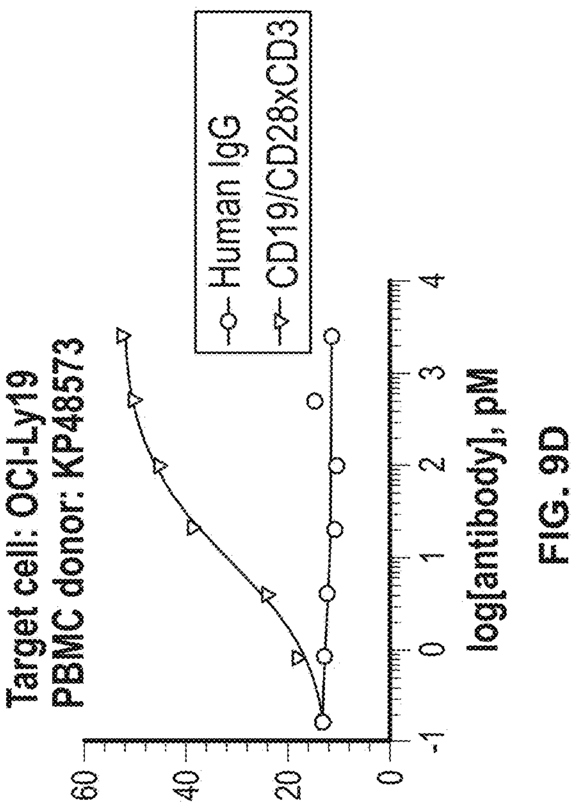
FIG. 9D shows the results of antibody-mediated specific killing of OCI-LY19 cells using PBMCs from donor KP48573 at E:T=10.
Figure 9E:
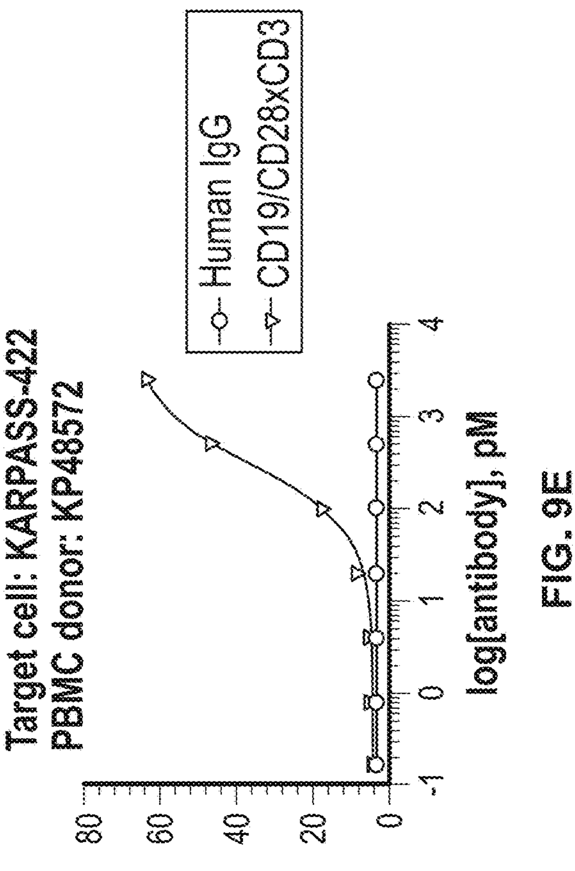
FIG. 9E shows the results of antibody-mediated specific killing of human lymphoma KARPASS-422 cells using PBMCs from donor KP48572 at E:T=10.
Figure 9F:
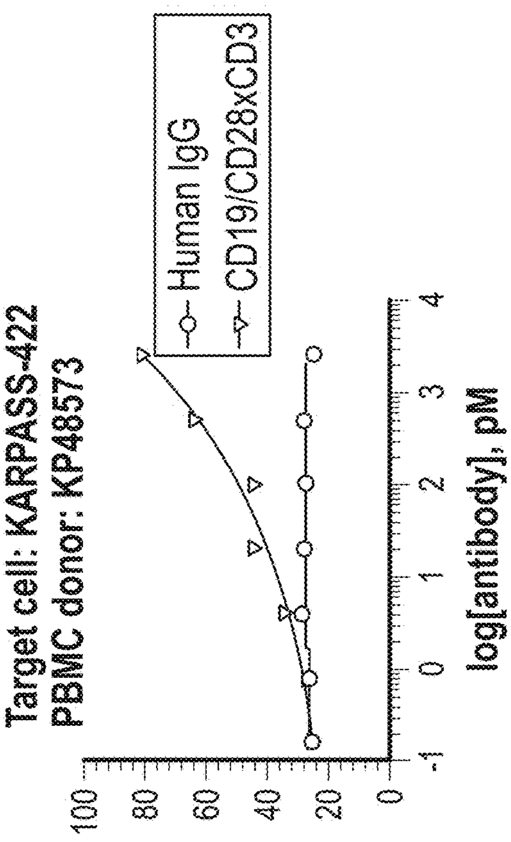
FIG. 9F shows the results of antibody-mediated specific killing of KARPASS-422 cells using PBMCs from donor KP48573 at E:T=10.
Figure 9G:
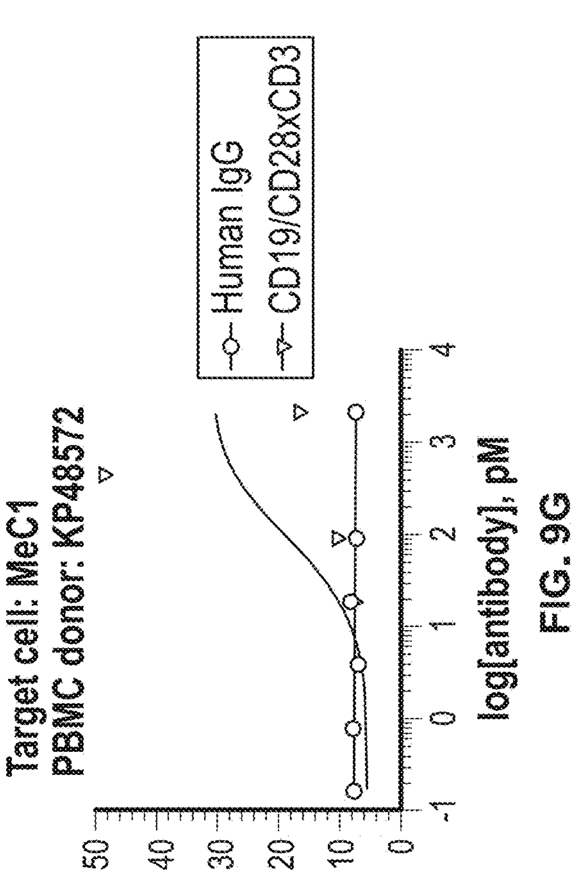
FIG. 9G shows the results of antibody-mediated specific killing of human chronic B cell leukemia MeCl cells using PBMCs from donor KP48572 at E:T=10.
Figure 9H:
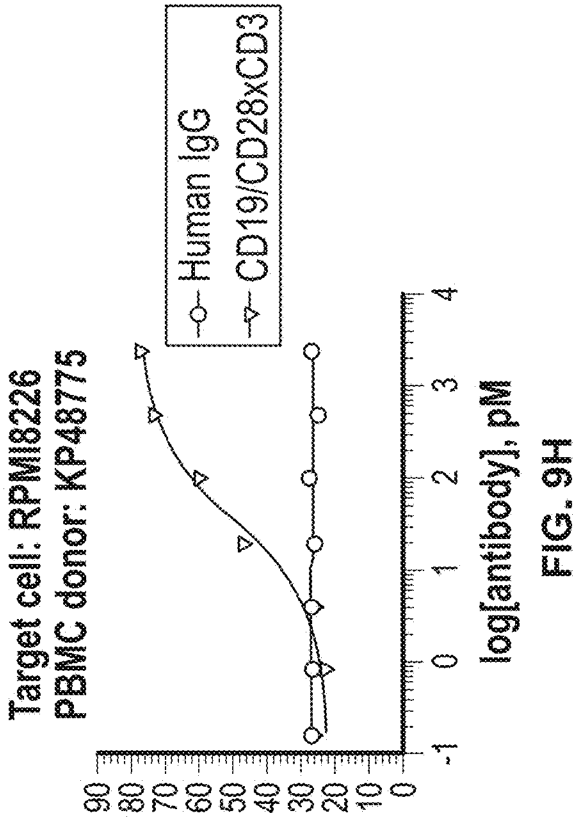
FIG. 9H shows the results of antibody-mediated specific killing of human multiple myeloma RPMI8226 cells using PBMCs from donor KP48775 at E:T=10.
Figure 9I:
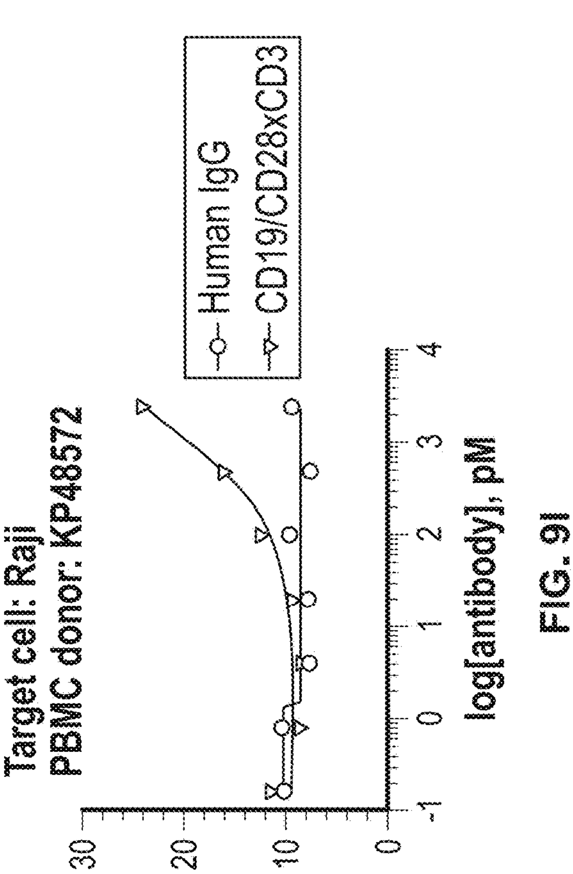
FIG. 9I shows the results of antibody-mediated specific killing of human Burkitt's lymphoma Raji cells using PBMCs from donor KP48572 at E:T=10.
Figure 9J:
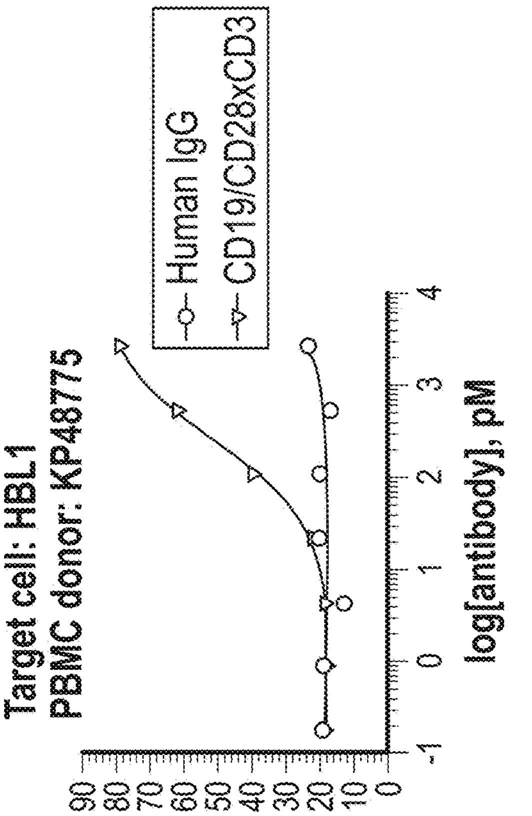
FIG. 9J shows the results of antibody-mediated specific killing of Human diffuse large B-cell lymphoma HBL1 cells using PBMCs from donor KP48775 at E:T=10.
Figure 9K:
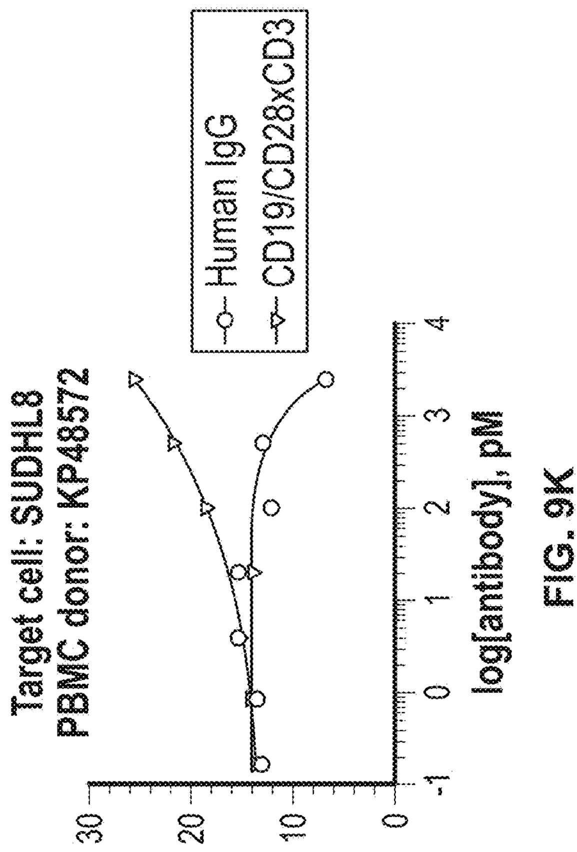
FIG. 9K shows the results of antibody-mediated specific killing of Large cell lymphoma SUDHL8 cells using PBMCs from donor KP48572 at E:T=10.
Figure 9L:
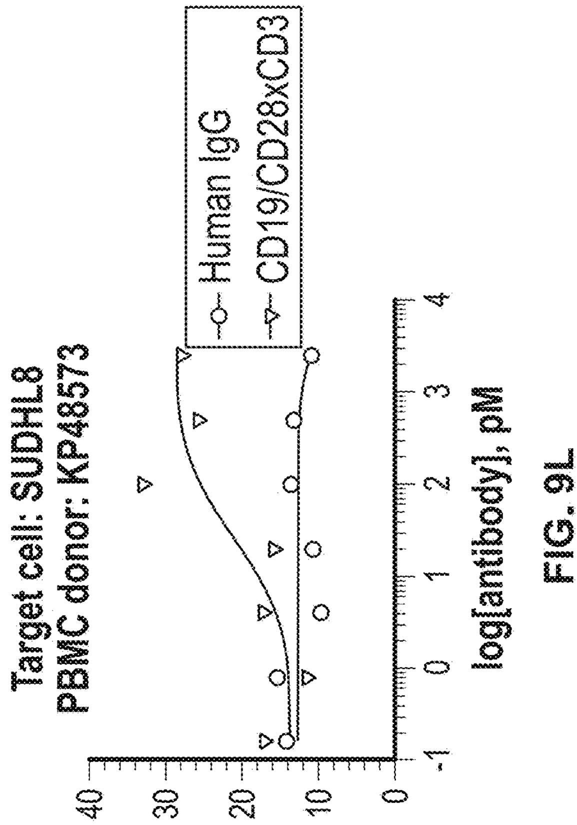
FIG. 9L shows the results of antibody-mediated specific killing of SUDHL8 cells using PBMCs from donor KP48573 at E:T=10.
Figure 9M:
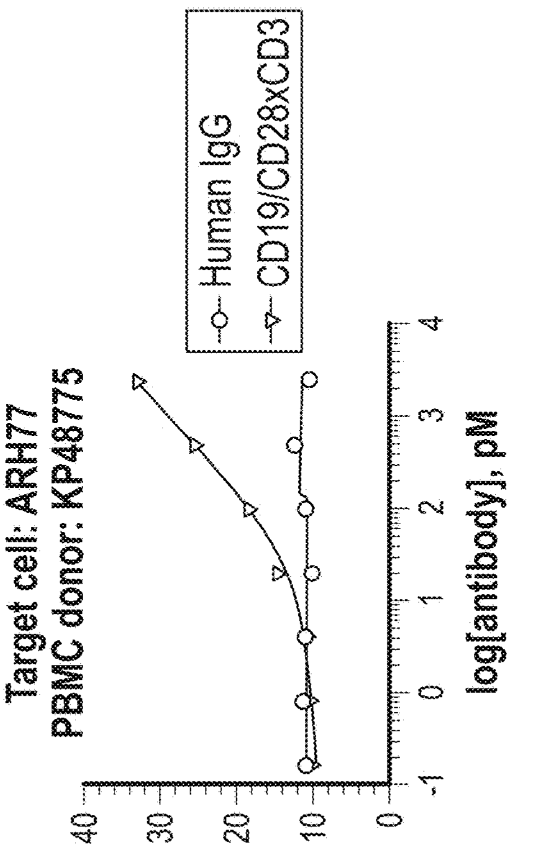
FIG. 9M shows the results of antibody-mediated specific killing of human B cell lymphoma ARH77 cells using PBMCs from donor KP48775 at E:T=10.
Figure 9N:
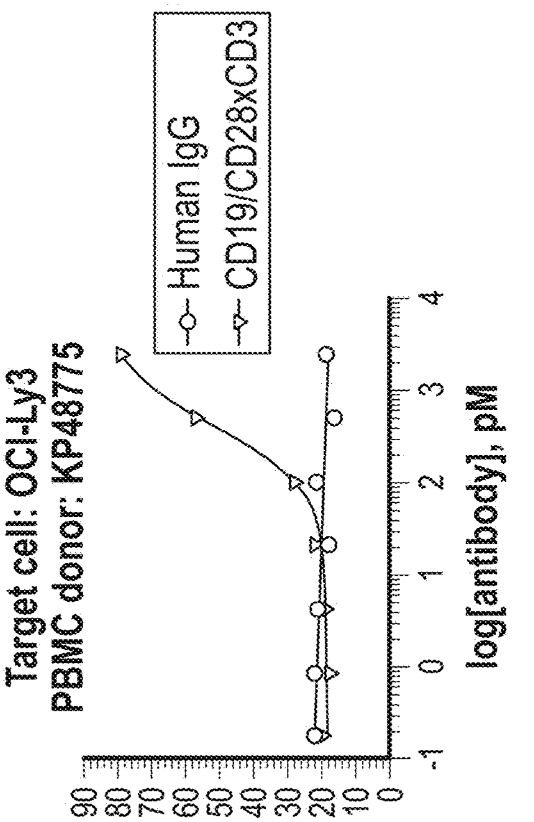

The anti-CD19×CD28×CD3 trispecific binding protein was also capable of inducing antibody-mediated cell killing of CD19+ cells (FIGS. 9A-9N). Similarly, anti-CD19×CD28×CD3 trispecific binding protein exhibited potent killing activity against human lymphoma cells, while both the anti-CD3/CD28, anti-CD19, and isotype control antibodies showed minimal killing activities, demonstrating the effectiveness of using the trispecific Ab to engage tumor cells with T cells through a tumor antigen (CD19) and T cell markers (CD3 and CD28).

In Vitro Assays Using Trispecific Binding Proteins Comprising Anti-CD38

Figure 10:
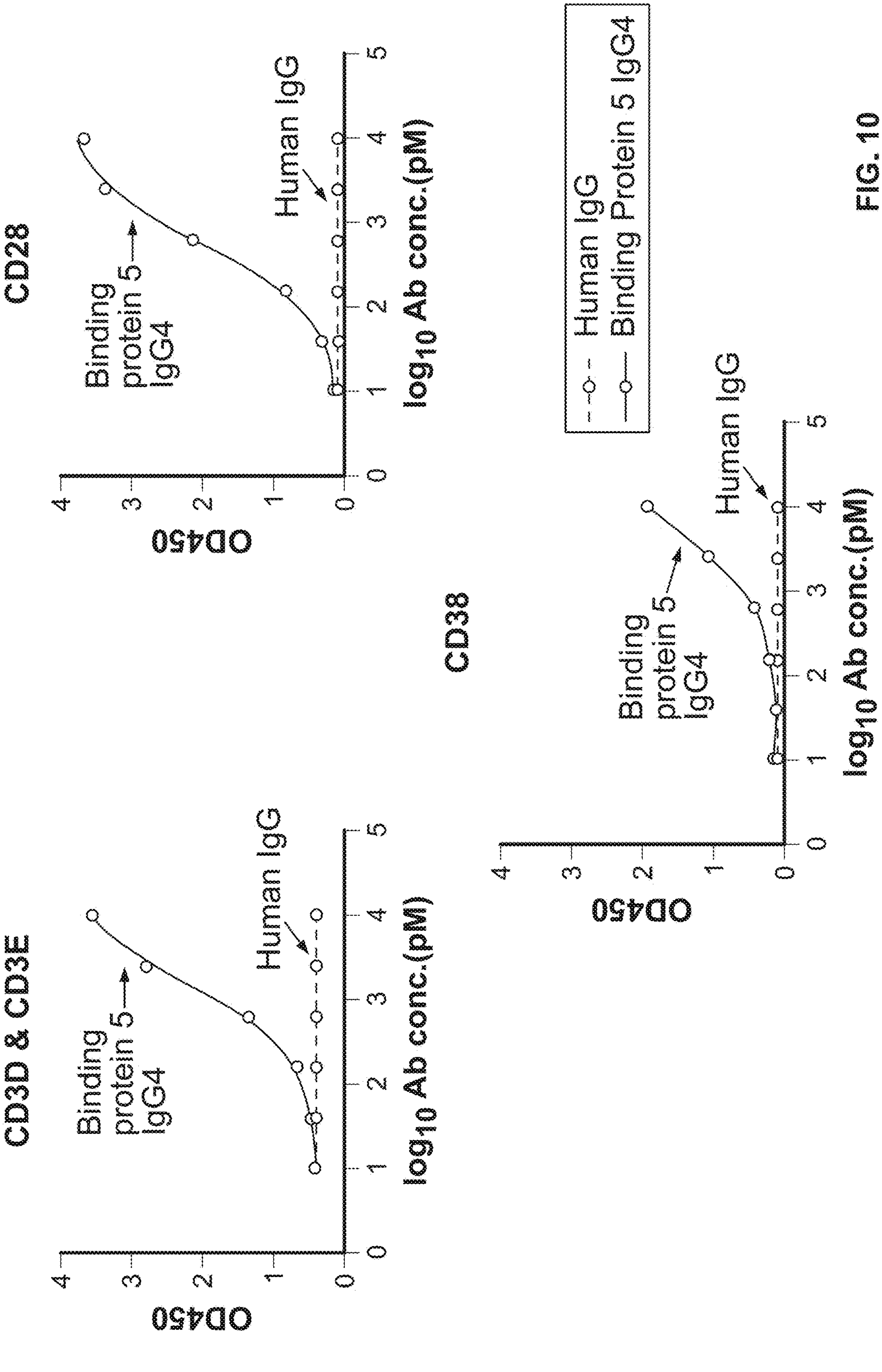
FIG. 10 shows the results of an ELISA assay determining binding of an anti-CD38×CD28×CD3 IgG4 trispecific antibody (Binding Protein 5), or isotype control antibody, to CD3, CD28 and CD38. The bound antibodies were detected using a horseradish peroxidase (HRP)-conjugated anti-Fab secondary antibody.

As observed with Binding Proteins 1 and 3, Binding Protein 5 was able to bind all three of its target proteins (CD3, CD28, and CD38), as assessed by ELISA assay (FIG. 10), indicating that each binding domain in the trispecific format retained its function.

Figures 11A, 11B, 11C:
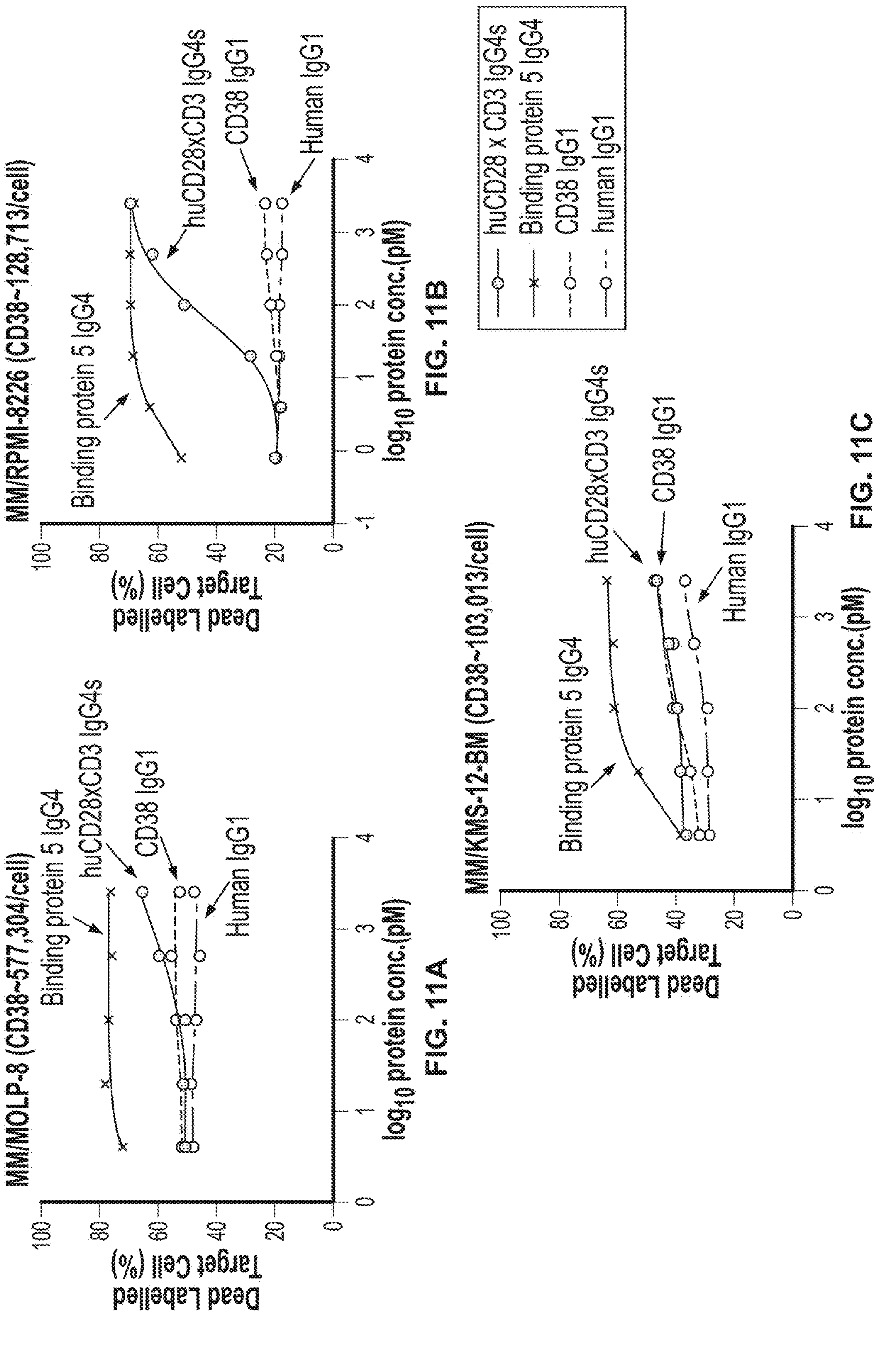
FIGS. 11A-11D show the results of antibody-mediated specific killing of $CD38^+$ human multiple myeloma cancer cells using an anti-CD38×CD28×CD3 IgG4 trispecific antibody (Binding protein 5), an anti-CD28×CD3 IgG4 bispecific antibody (huCD28×CD3), an anti-CD38 IgG1 antibody, or a control antibody (human-IgG1).
Figure 11D:
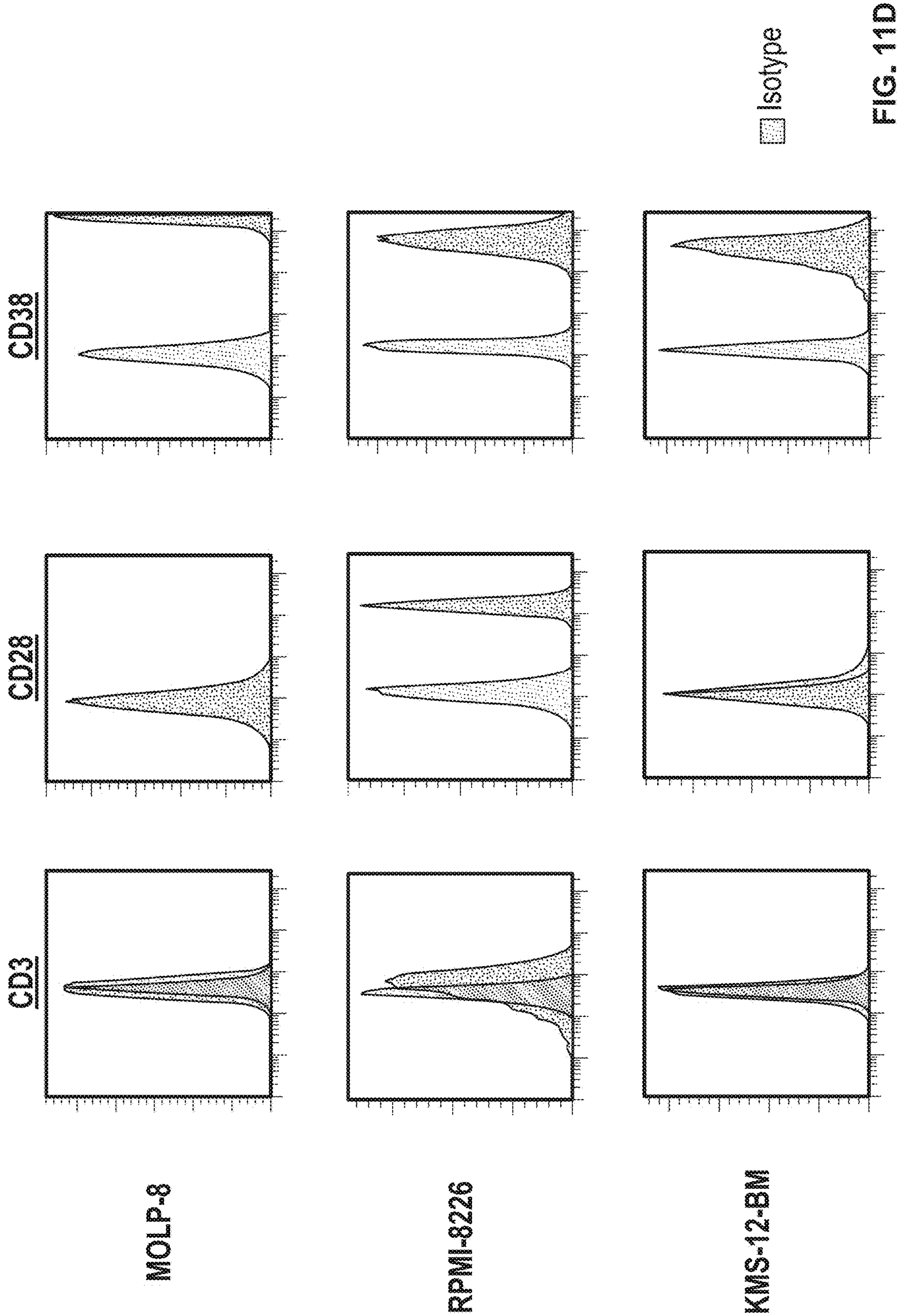
Figures 12A, 12B, 12C:
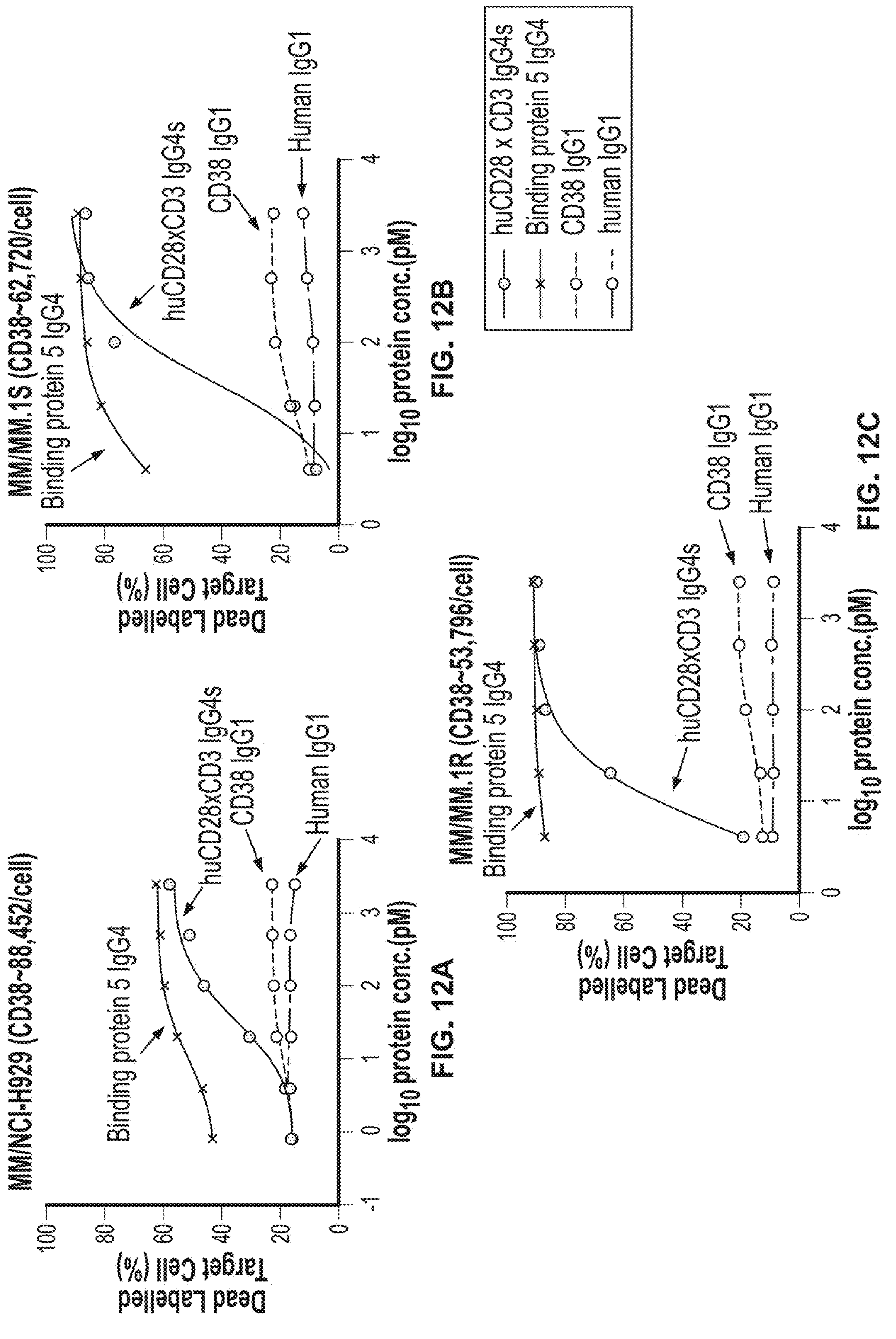
FIGS. 12A-12D show the results of antibody-mediated specific killing of $CD38^+$ human multiple myeloma cancer cells using an anti-CD38×CD28×CD3 IgG4 trispecific antibody (Binding protein 5), an anti-CD28×CD3 IgG4 bispecific antibody (huCD28×CD3), an anti-CD38 IgG1 antibody, or a control antibody (human-IgG1), using human PBMC as effector cells at E:T=10.
Figure 12D:
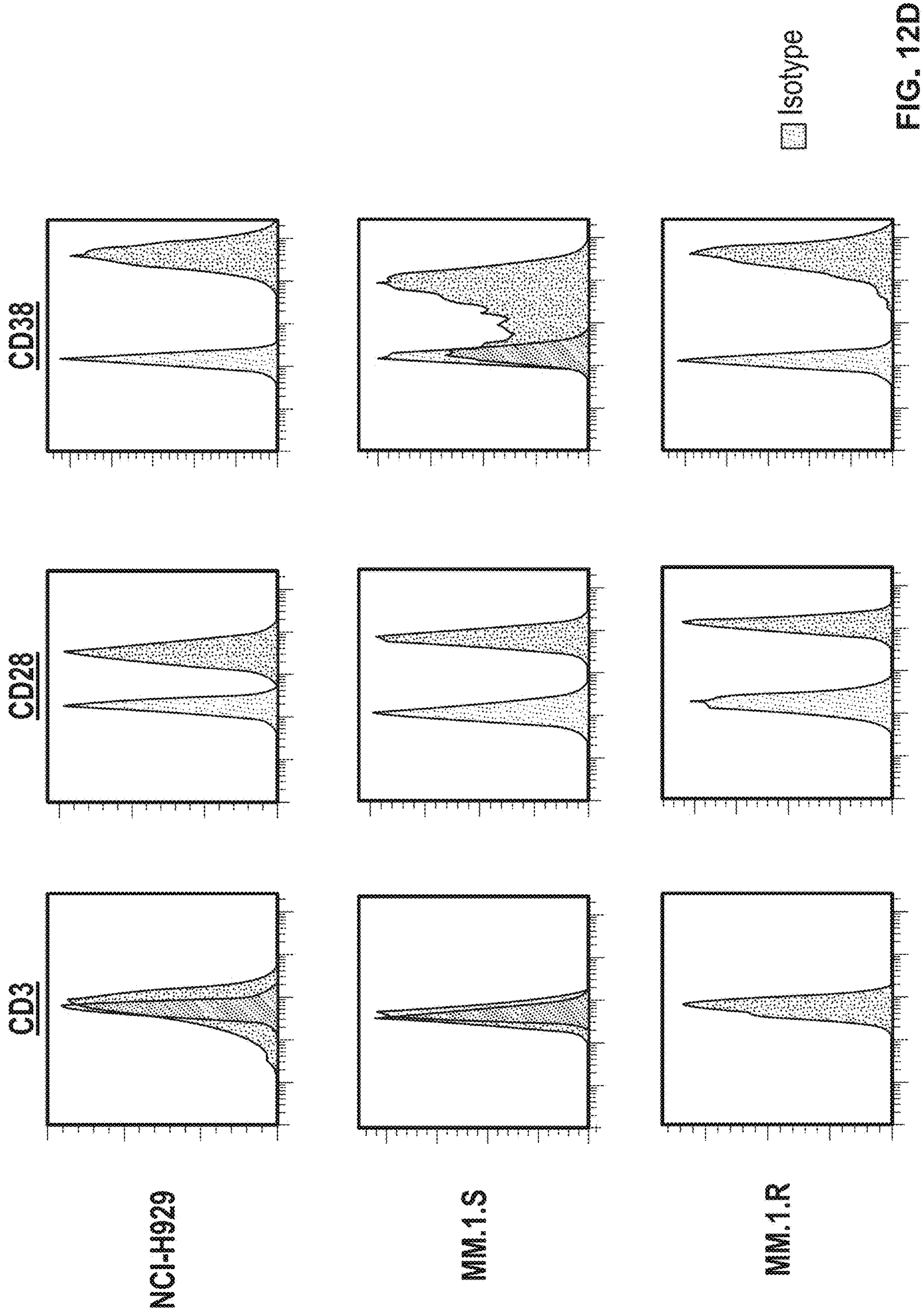
Figure 13D:
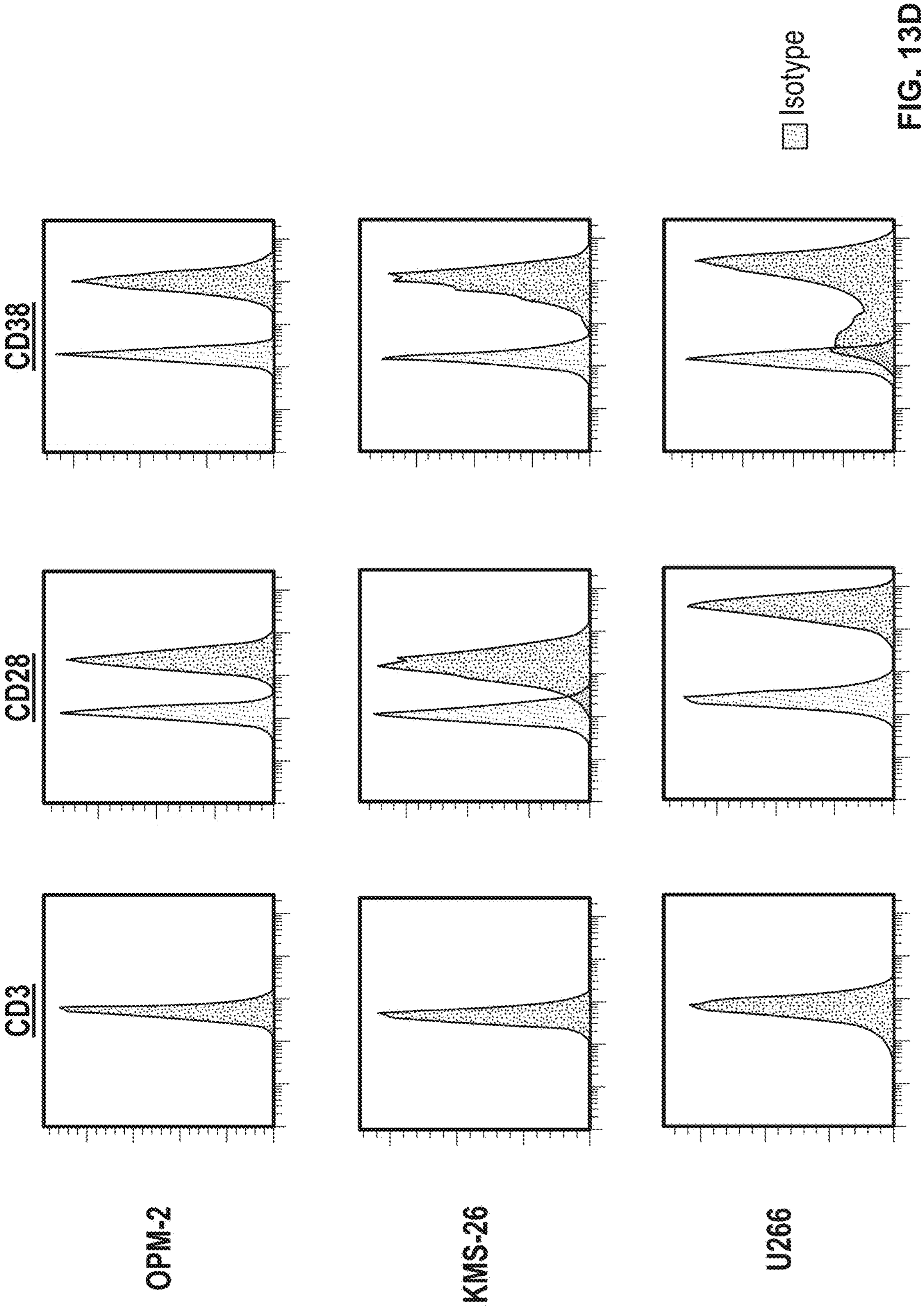
Figure 14B:
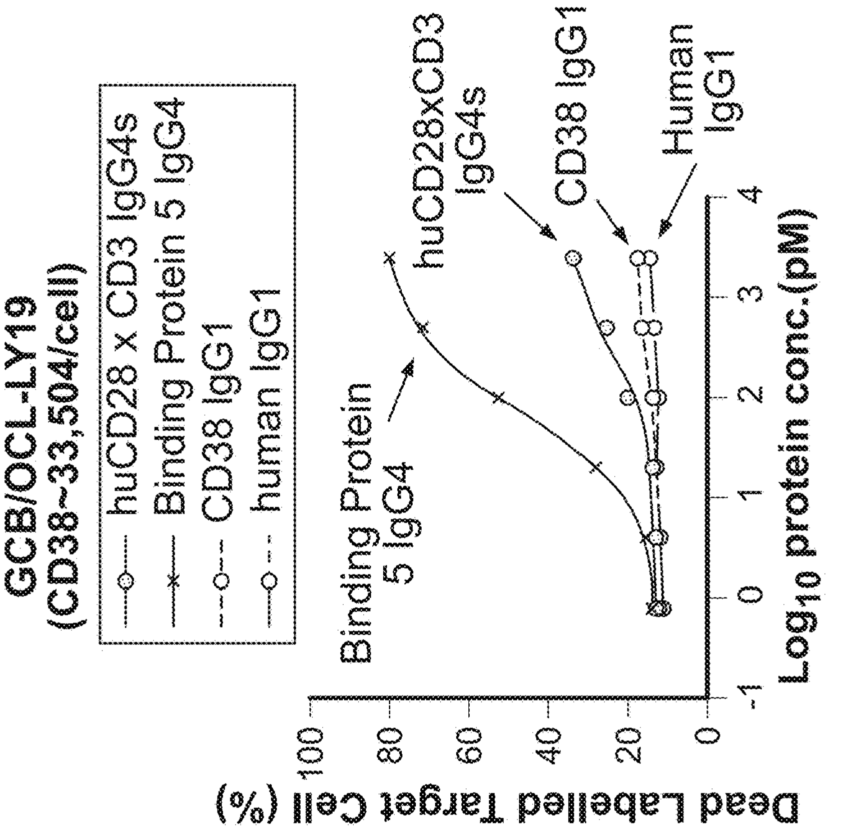
FIGS. 14A-14C show the results of antibody-mediated specific killing of $CD38^+$ human lymphoma cancer cells using an anti-CD38×CD28×CD3 IgG4 trispecific antibody (Binding protein 5), an anti-CD28×CD3 IgG4 bispecific antibody (huCD28×CD3), an anti-CD38 IgG1 antibody, or a control antibody (human-IgG1), using human PBMC as effector cells at E:T=10.
Figure 14A:
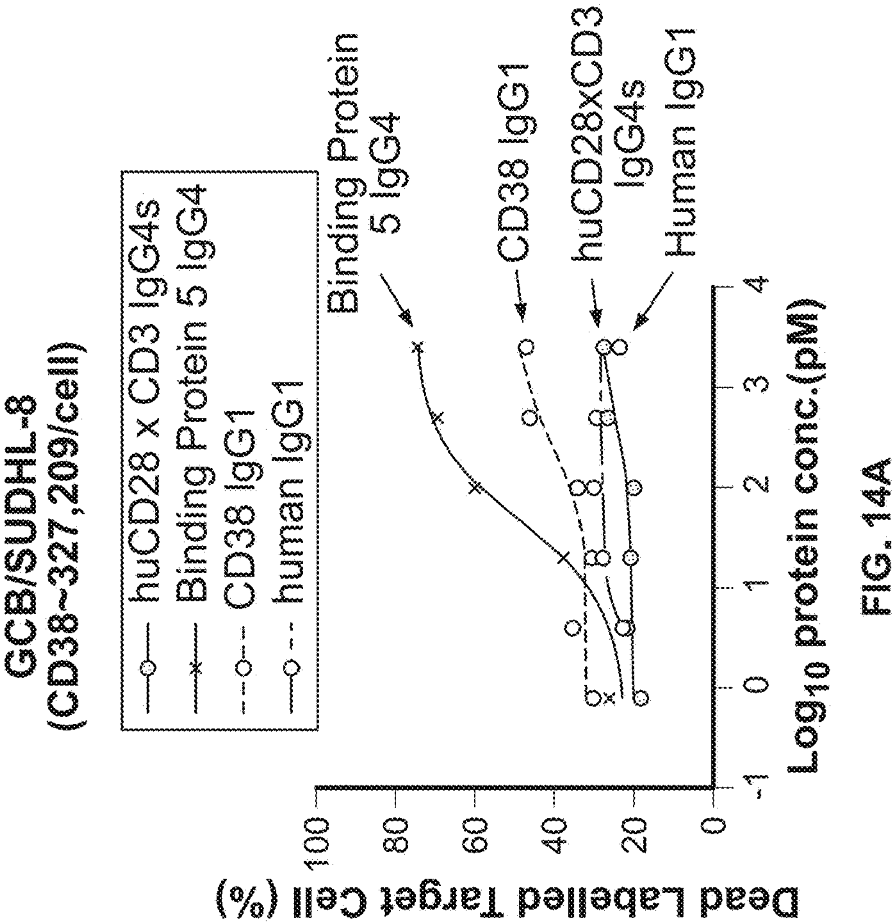
Figure 14C:
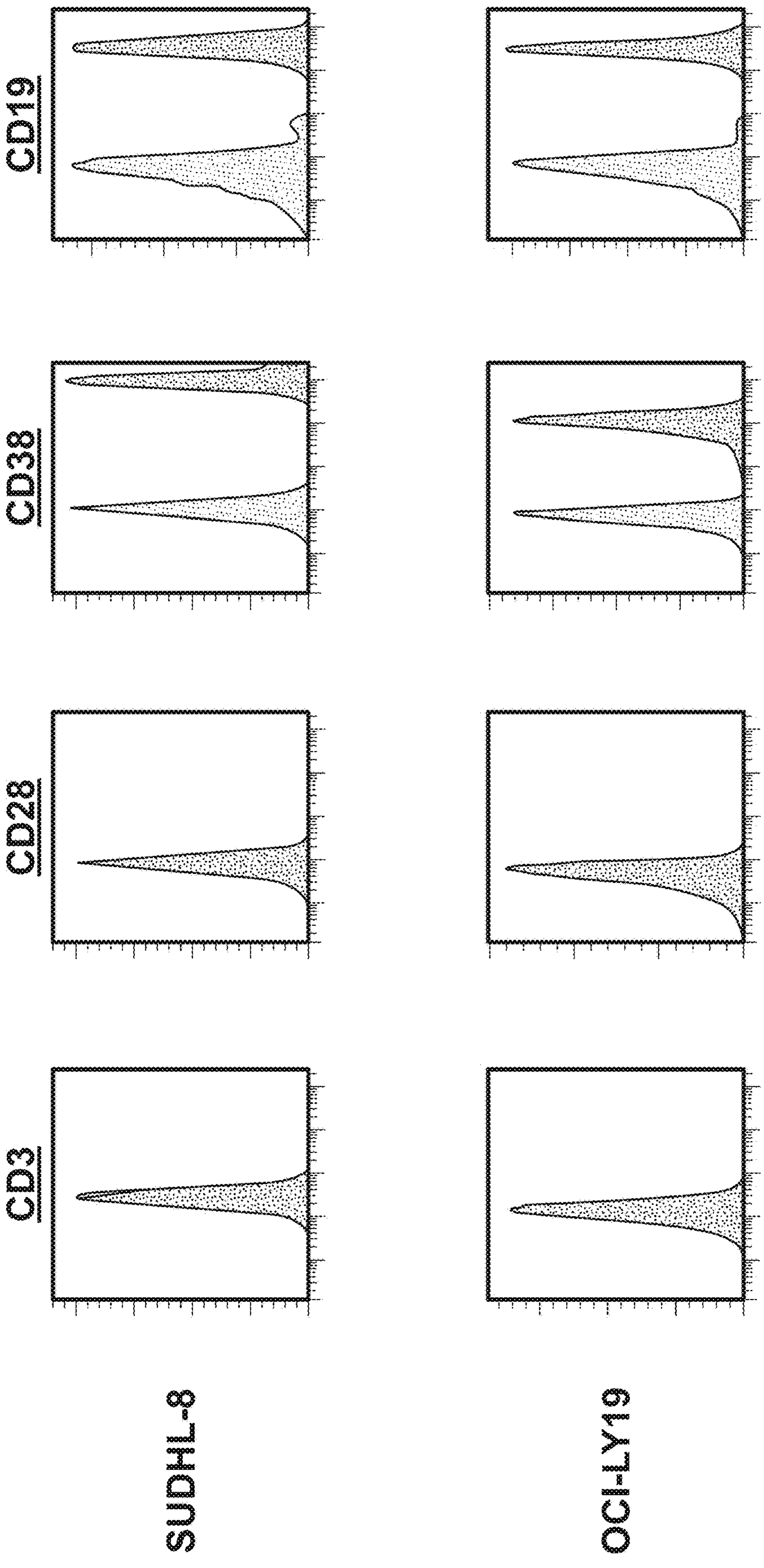
Figure 15D:
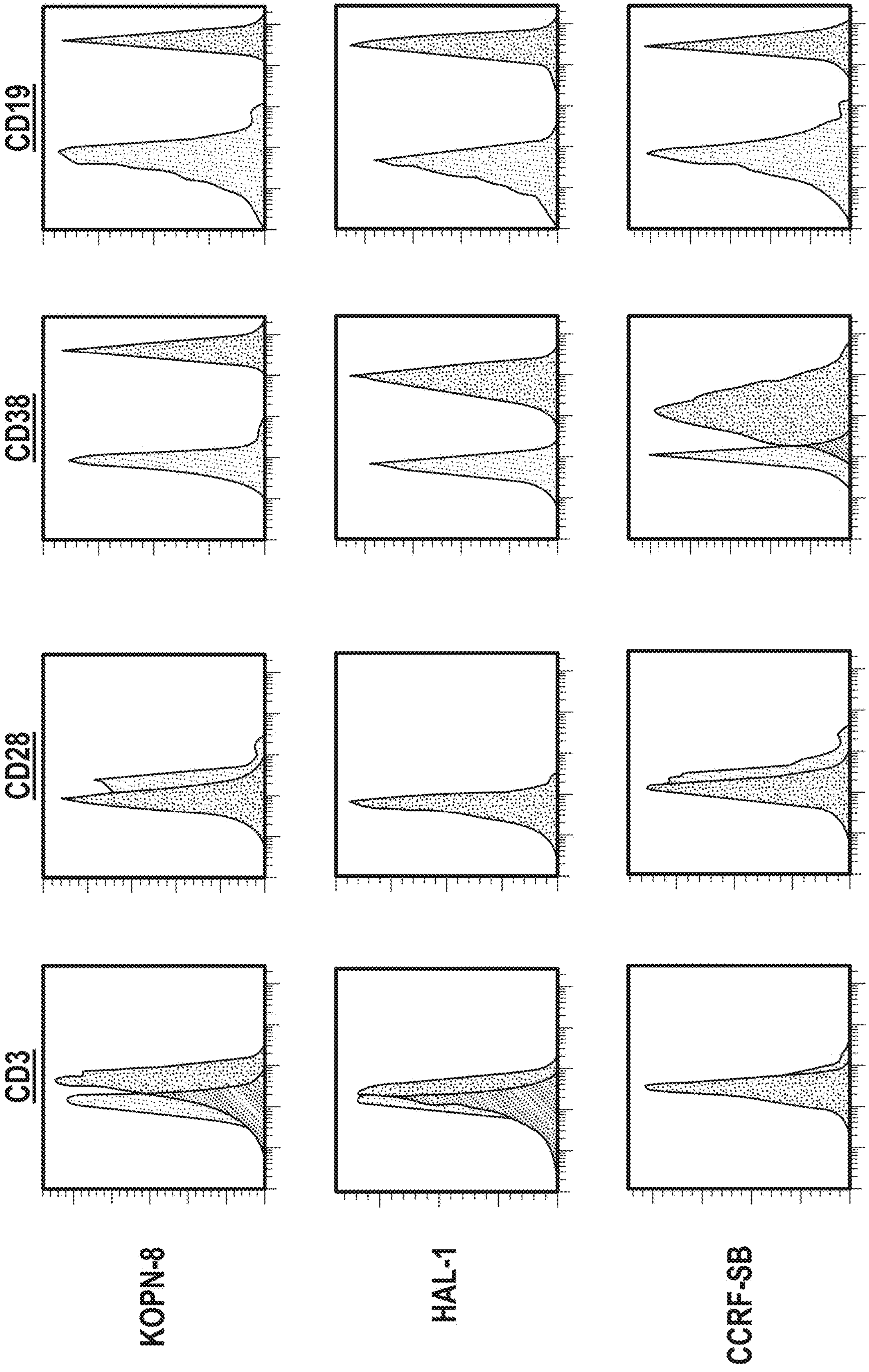

Binding Protein 5 was also found to induce antibody-mediated cell killing of cells (FIGS. 11A-15D) against 9 human multiple myeloma cells with various levels of CD38 and CD28 expression (see FIGS. 11D, 12D, & 13D). Similarly, trispecific Binding protein 5 exhibited potent killing activity against human multiple myeloma cells, while both the anti-CD38 and isotype control antibodies showed minimal killing activities, demonstrating the effectiveness of using the trispecific Ab to engage tumor cells with T cells through tumor antigens (CD38 and CD28) and T cell markers (CD3 and CD28). Bispecific anti-CD3/CD28 control antibody also showed marginal killing activity against CD28+MM cells see FIGS. 11B, 12A-C, & 13A-C).

These results demonstrate that the trispecific antibody platform described herein provides the possibility of integrating binding sites for two tumor markers, or two binding sites for T cell markers, allowing flexibility for scientific designs and various applications. Binding Protein 5 was also effective against 5 CD38+ human lymphoma cell lines (FIGS. 14C & 15D), showing potent killing activities (FIGS. 14A-B & 15A-C).

Figure 16:
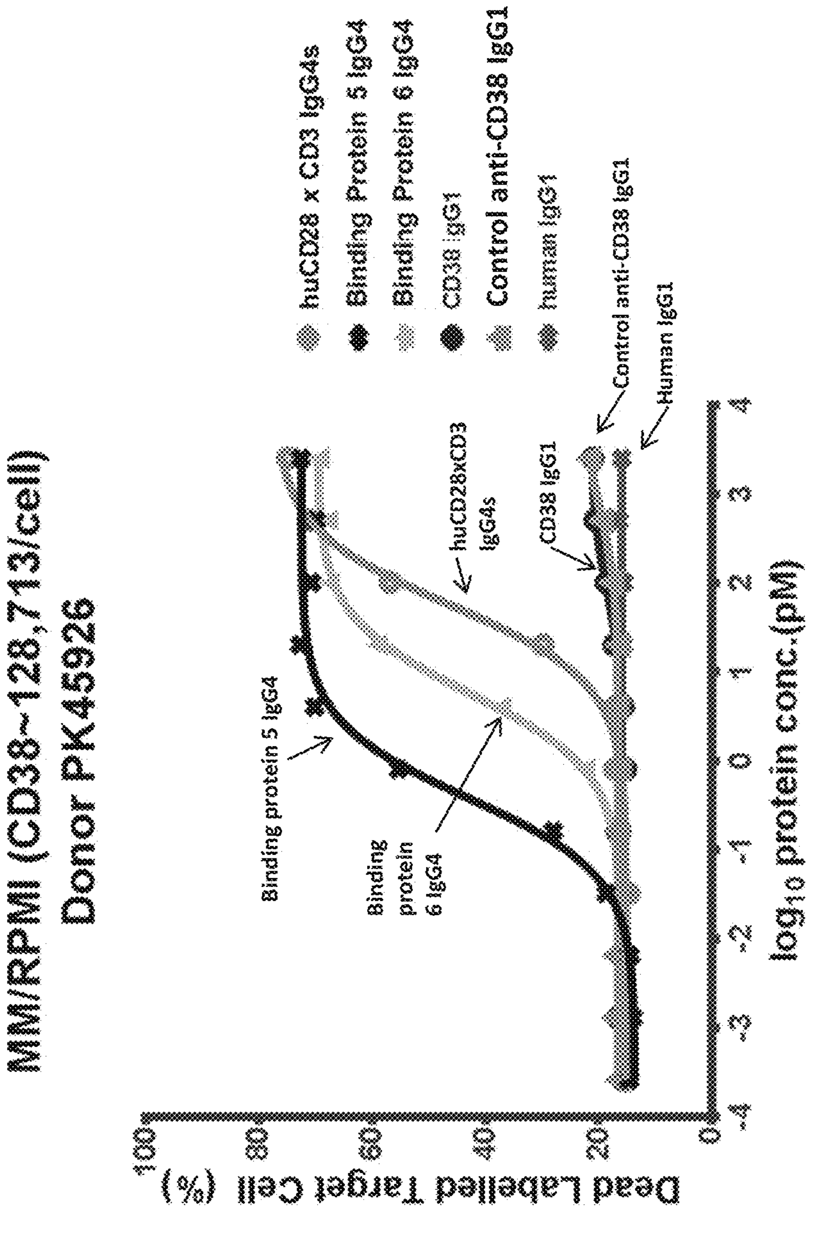
FIG. 16 shows the results of antibody-mediated specific killing of $CD38^+$ myeloma cancer cells using anti-CD38×CD28×CD3 IgG4 trispecific antibodies (referred to herein as "Binding protein 5" and "Binding Protein 6," depending on the specific anti-CD28 binding domain used), an anti-CD28×CD3 IgG4 bispecific antibody (huCD28×CD3), an anti-CD38 IgG1 antibody, a control anti-CD38 IgG1 antibody, or a control antibody (human-IgG1), using PBMCs from donor PK45926 at E:T=10.

The antibody-mediated cell killing against multiple myeloma cell line RPMI8226 using Binding Proteins 5 and 6 were tested, and their $EC_{50}$s were calculated and compared to that of a CODV format bispecific antibody targeting CD28 and CD3 (FIG. 16 and Table B). Binding proteins 5 and 6 differ only in anti-CD28 binding domain; Binding protein 5 contains an anti-CD28 superagonist, while Binding protein 6 contains a conventional anti-CD28. Binding protein 5 showed more potent killing activity.

TABLE B

| EC$_{50}$ values calculated for bispecific and trispecific binding proteins | |
|---|---|
| | EC$_{50}$ (pM) |
| huCD28 × CD3 IgG4 | 56.16 |
| Binding Protein 5 IgG4 | 0.3787 |
| Binding Protein 6 IgG4 | 5.709 |

Figure 17A:
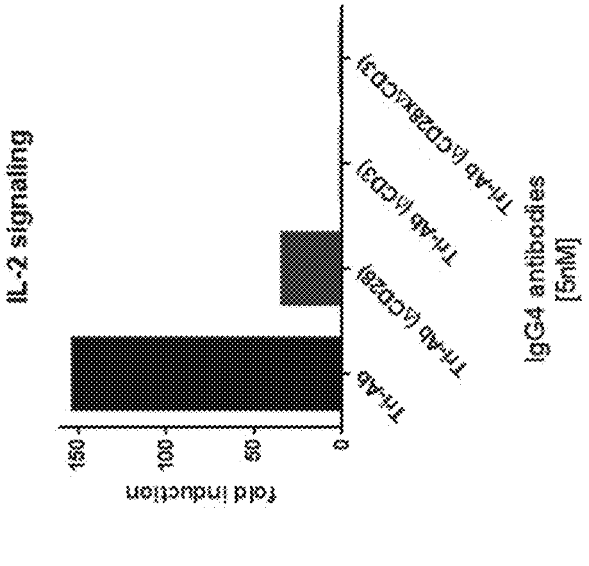
FIGS. 17A & 17B show IL-2, NFκB, and nuclear factor of activated T-cells (NFAT) pathway activation via anti-CD3 and anti-CD28 signaling, as measured by luciferase assay using human Jurkat T cells with an IL-2 promoter-luciferase construct (FIG. 17A) or an NFAT promoter-luciferase construct (FIG. 17B). Antibodies tested were anti-CD38×CD28×CD3 IgG4 trispecific IgG4 antibody (Binding Protein 5, labeled as "Tri-Ab"), anti-CD38×CD28×CD3 IgG4 trispecific IgG4 antibody lacking the CD28 binding domain (labeled as "Tri-Ab (ΔCD28)), anti-CD38×CD28×CD3 IgG4 trispecific IgG4 antibody lacking the CD3 binding domain (labeled as "Tri-Ab (ΔCD3)), and anti-CD38×CD28×CD3 IgG4 trispecific IgG4 antibody lacking the CD3 and CD28 binding domains (labeled as "Tri-Ab (ΔCD28×ΔCD3)). Luciferase assays were performed in duplicate for each of the indicated Tri-Abs.
Figure 17B:
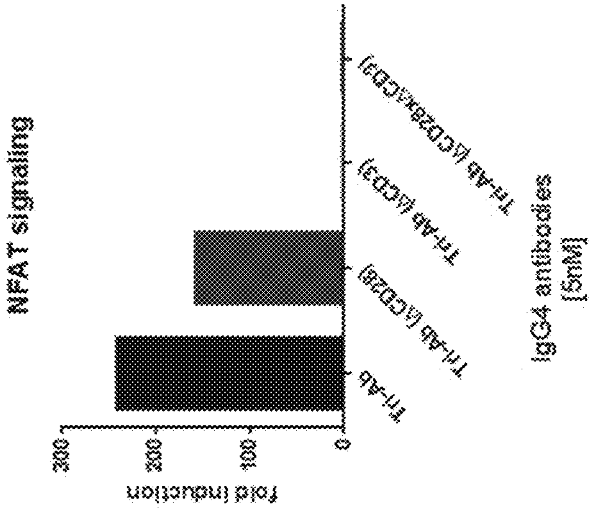

The activity of the anti-CD38×CD28×CD3 trispecific binding protein 5 and control variants having one or two binding domains inactivated by site-directed mutagenesis (ΔCD28: anti-CD28 inactivated; ΔCD3: anti-CD3 inactivated; Δ(CD3×CD28): both anti-CD3 and anti-CD28 inactivated) were tested using IL2 and NFAT reporter human T cell lines (Jurkat-IL2 and Jurkat-NFAT) in the in vitro activation assay as described in Example 1. The results showed that Binding protein 5 activated both human IL2 and NFAT promoters effectively in vitro (FIGS. 17A & 17B). Inactivation of anti-CD28 reduced the activation potency, which was more prominent for IL2 reporter, indicating the importance of anti-CD28 co-signaling pathway. Inactivation of anti-CD3 binding site rendered Binding protein 5 to minimal activity, suggesting that the anti-CD3 provided the primary T cell activation signaling.

Example 4: In Vivo Activity of the T Cell Engagers

This example describes experiments characterizing the properties and activities of the anti-Her2 or anti-CD38 containing T cell engagers in vivo.

In Vivo Assays Using Trispecific Binding Proteins Comprising Anti-Her2

Figure 18A:
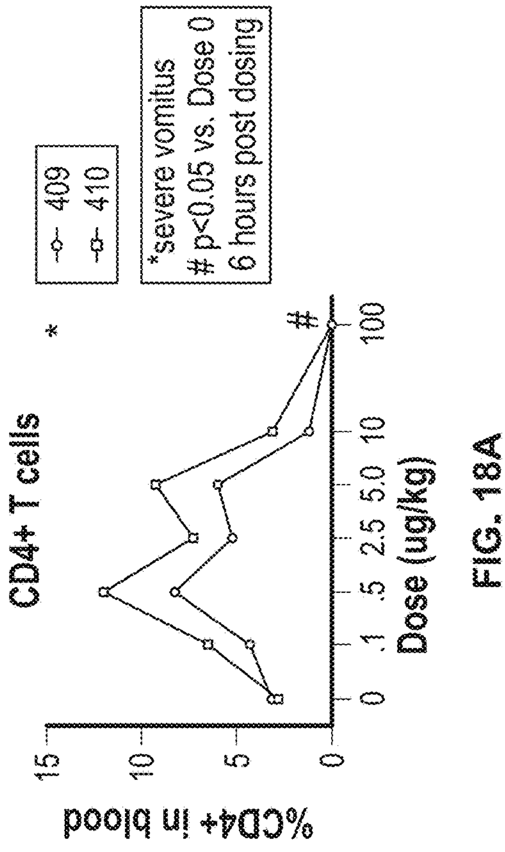
FIGS. 18A-18E show the results of a dose escalation toxicity study using the anti-Her2×CD28×CD3 IgG4 trispecific antibody (referred to herein as "Binding protein F") in non-human primates (dose escalating from 0.1, 0.5, 2.5, 5, 10, to 100 μg/kg; animals labeled as "409" and "410").
Figure 18B:
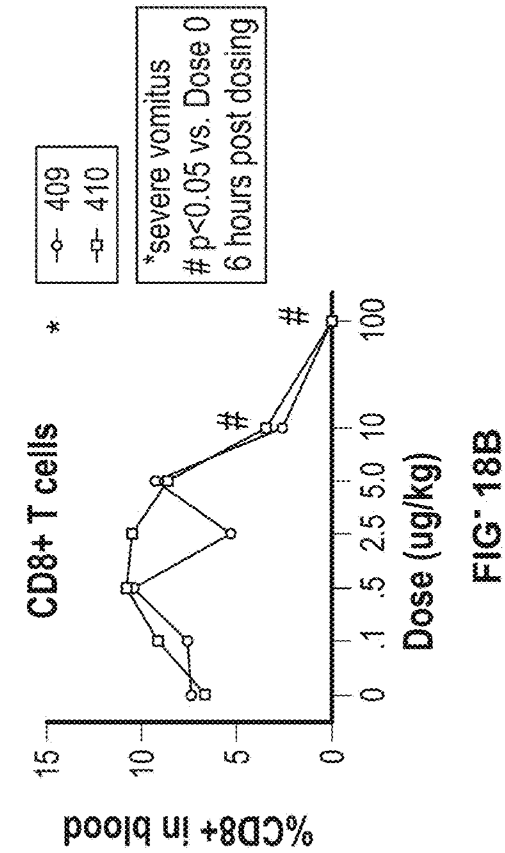
Figure 18C:
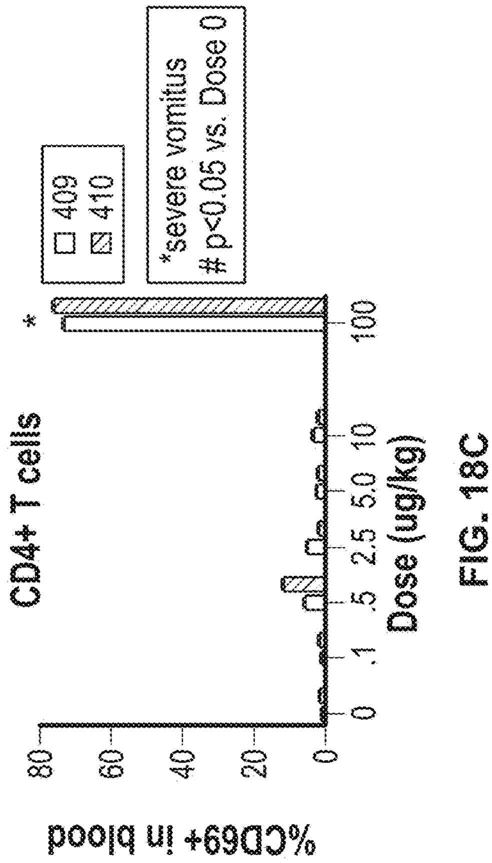
Figure 18D:
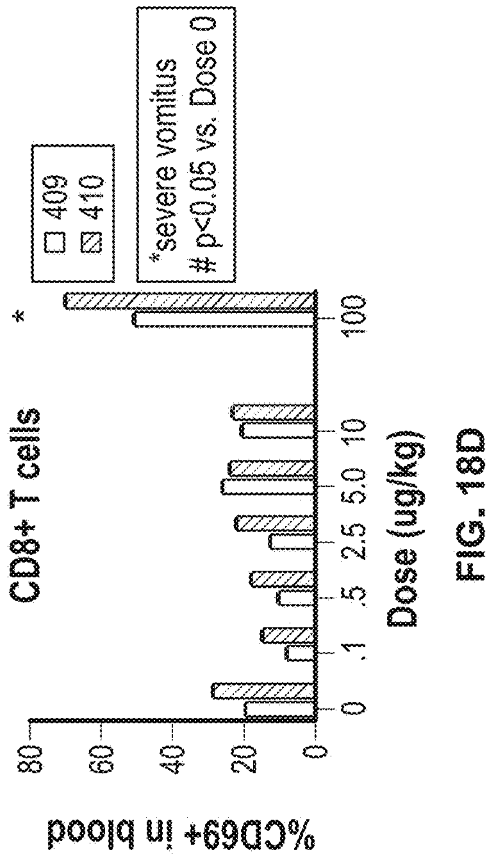
Figure 18E:
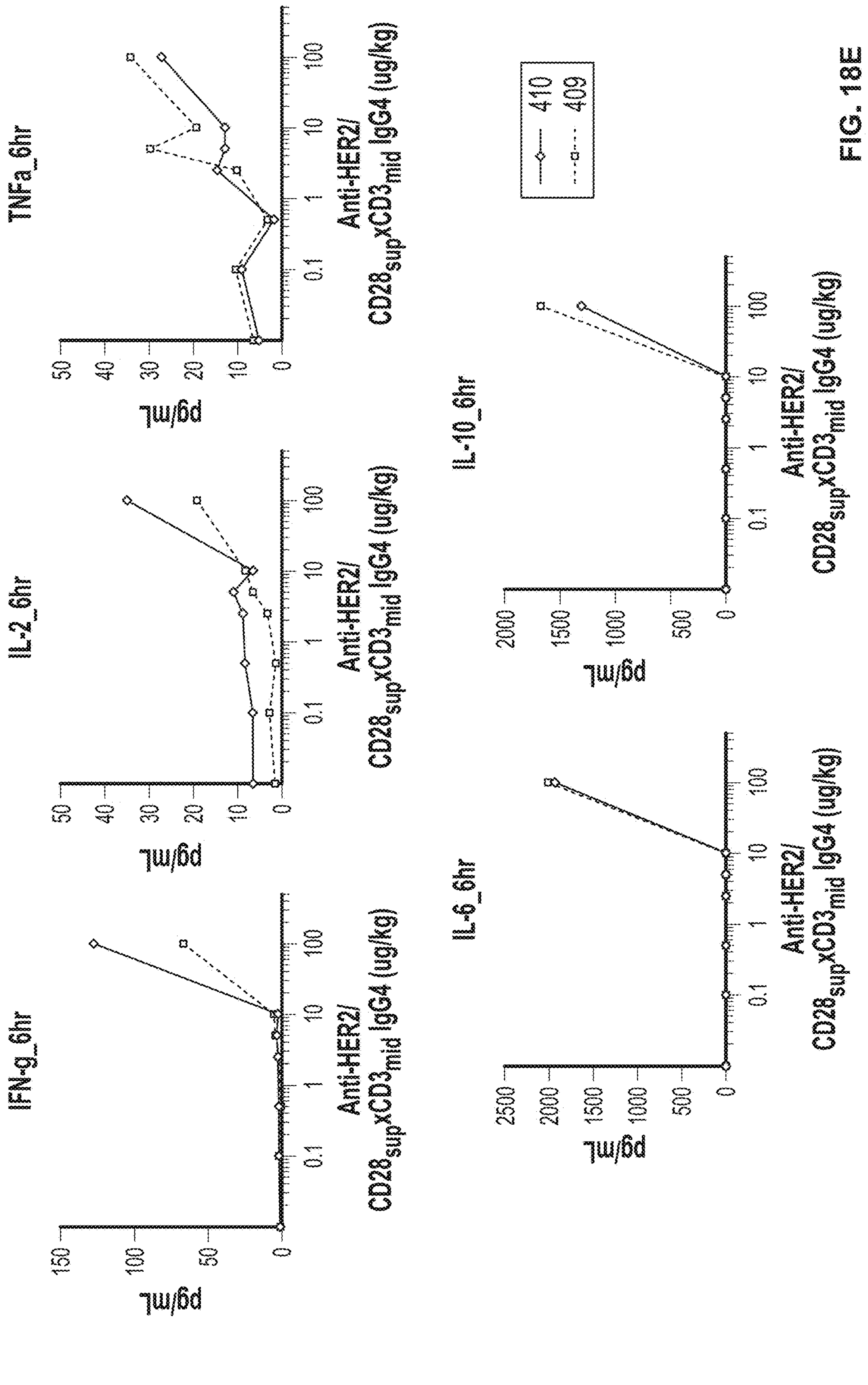

A dose escalation study using the Her2×CD28×CD3 trispecific antibody was carried out in non-human primates (FIGS. 18A-18E) as described in Example 1. All three binding domains in Binding protein 1 are cross-reactive with monkey CD3/CD28/HER2. A dose escalation toxicity study was devised to assess the potential toxicity profile of the molecular. Blood samples were collected for serum and PBMC isolations. Circulating T cell populations were investigated after each dosing (FIGS. 18A & 18B), along with T cell subpopulation activation (CD69+) (FIGS. 18C & 18D). Percentage of CD4 and CD8 T-cells in circulation were increased at low dose escalation, but eventually decreased at high dose escalation. Significant CD4 and CD8 T cell activation were only prominent at 100 μg/kg dose, suggesting rather a relative high tolerable dose. Serum level of several cytokines were also measured. Significant cytokine release was only observed at the highest dose (100 μg/kg; FIG. 18E).

Figure 19A:
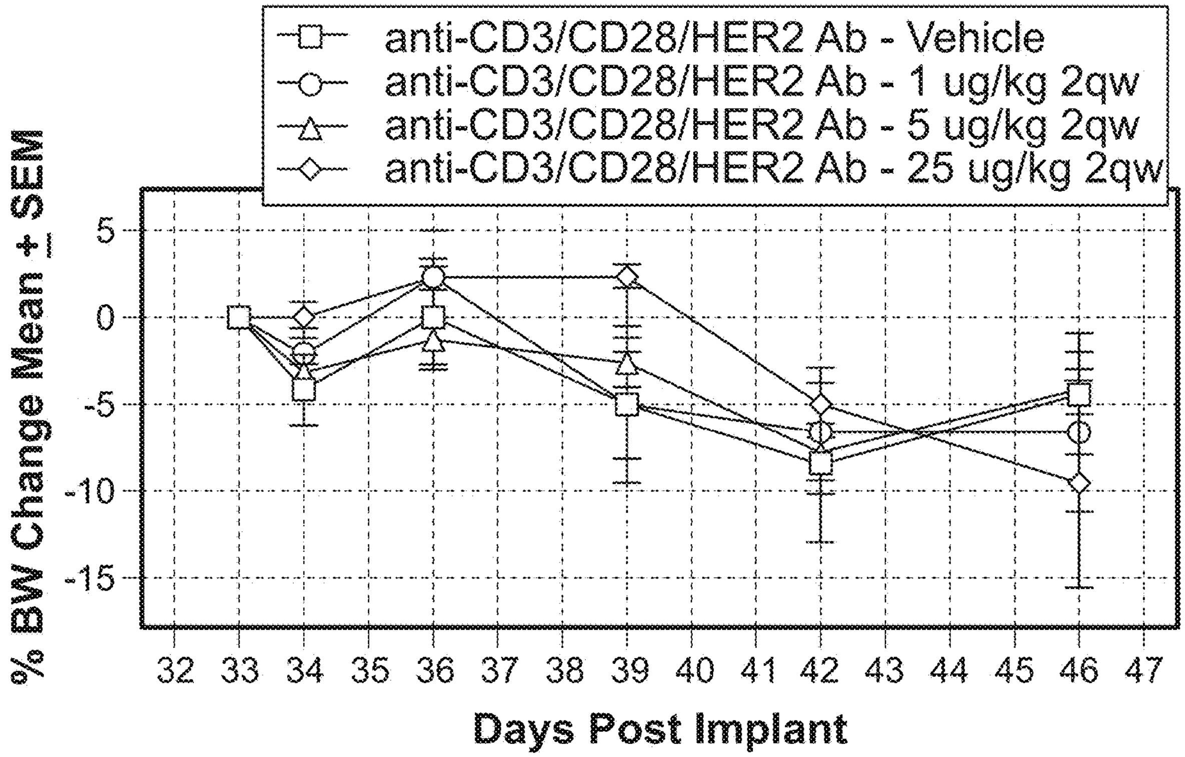
FIGS. 19A-B show the in vivo anti-tumor activity of the anti-Her2×CD28×CD3 IgG4 trispecific antibody (referred to herein as "Binding protein 1") in the $CD34^+$ umbilical cord blood cell humanized NSG mouse model implanted with BT474 cells.
Figure 19B:
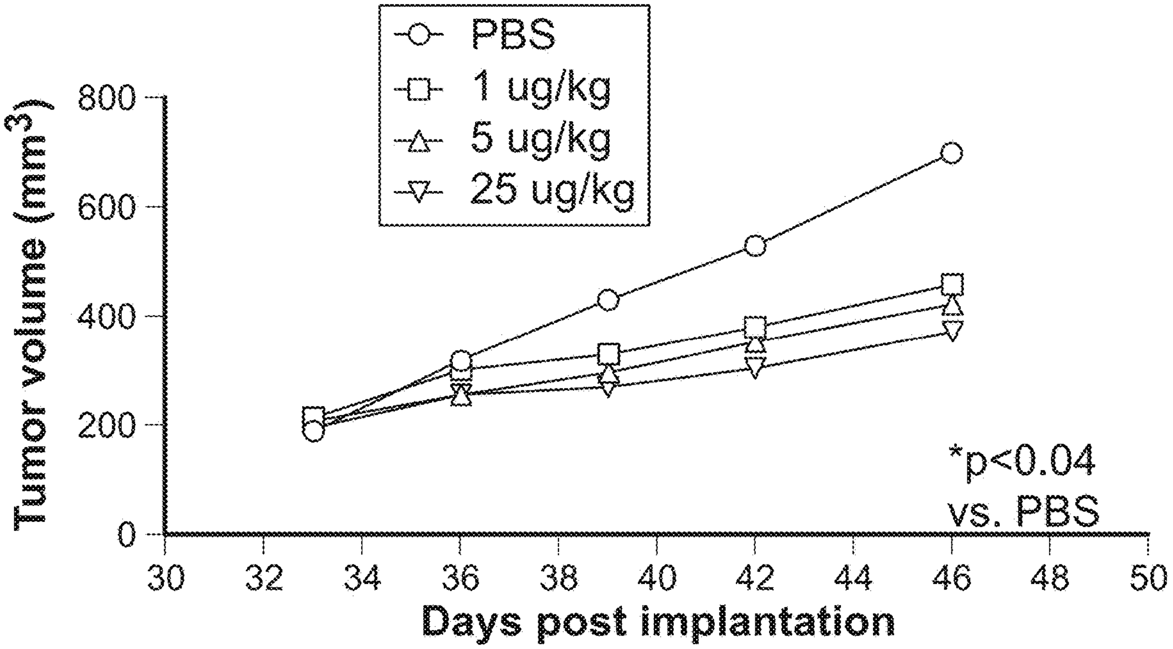
Figure 20A:
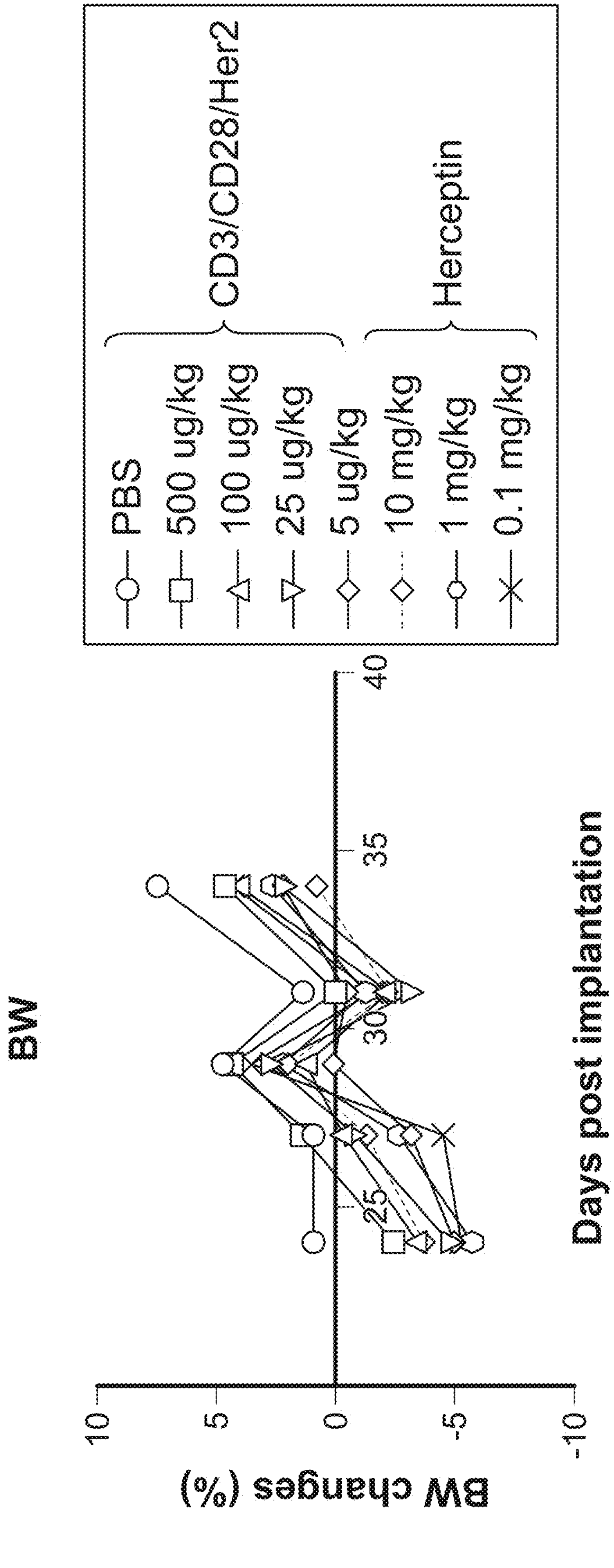
FIGS. 20A-20H show the in vivo anti-tumor activity of the anti-Her2×CD28×CD3 IgG4 trispecific antibody (referred to herein as "Binding protein 1") in the human PBMCs humanized NSG mouse model implanted with BT474 cells.
Figure 20B:
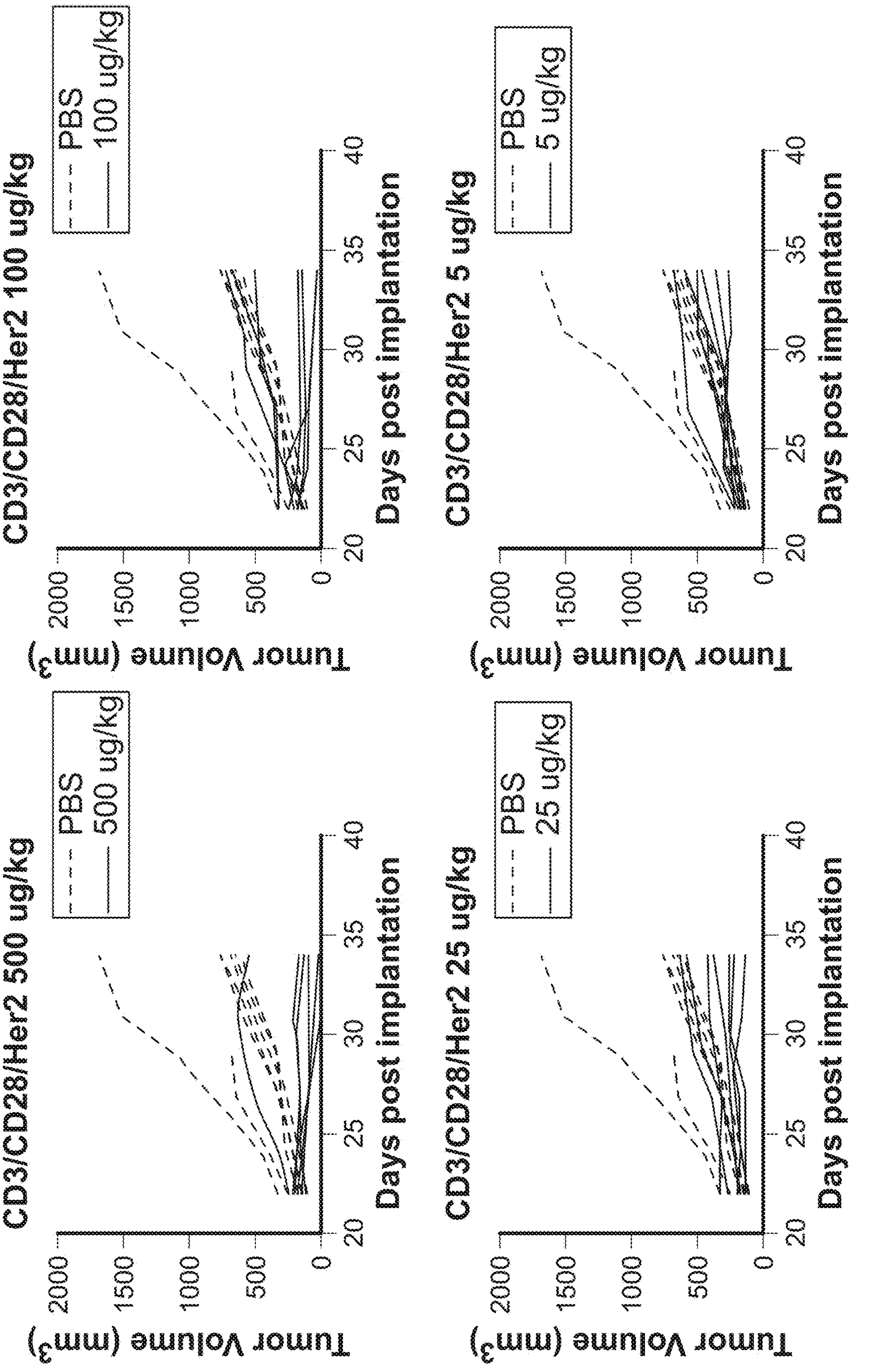
Figure 20B:
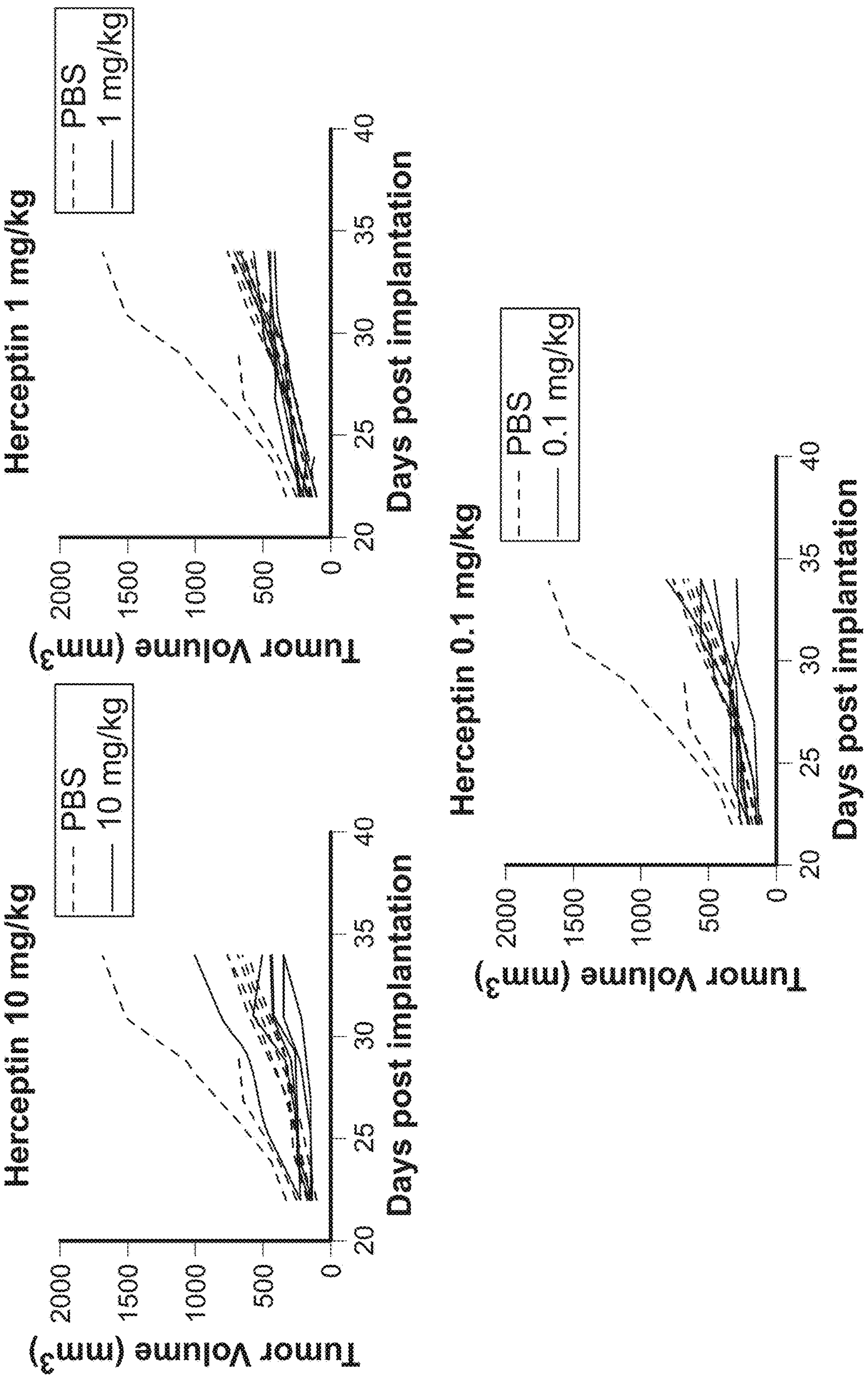
Figure 20C:
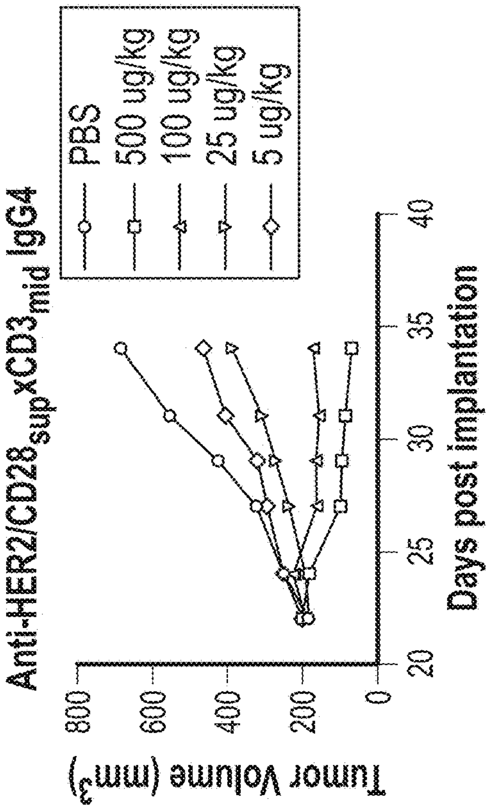
Figure 20D:
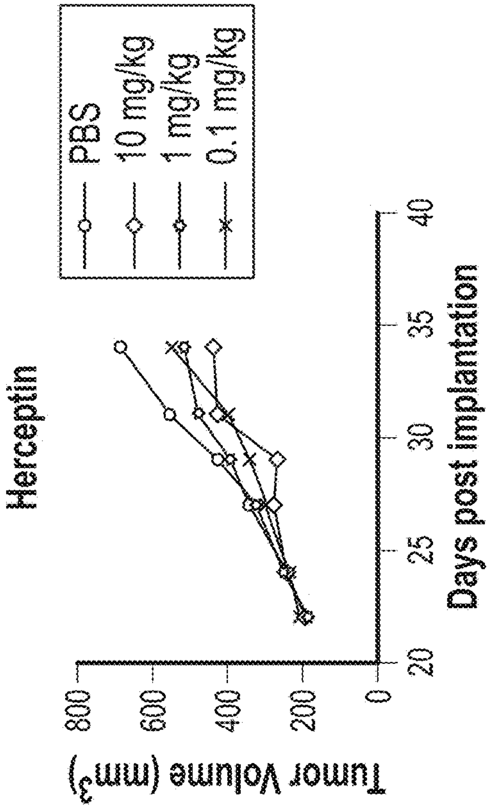
Figure 20E:
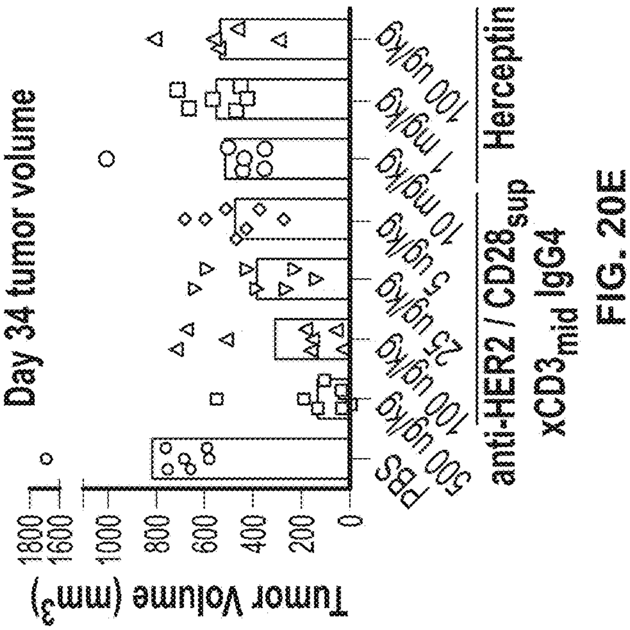
Figure 20F:
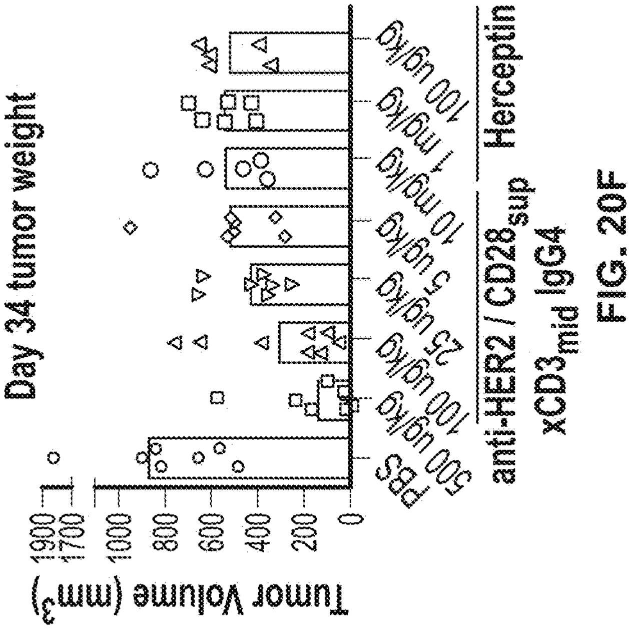
Figure 20G:
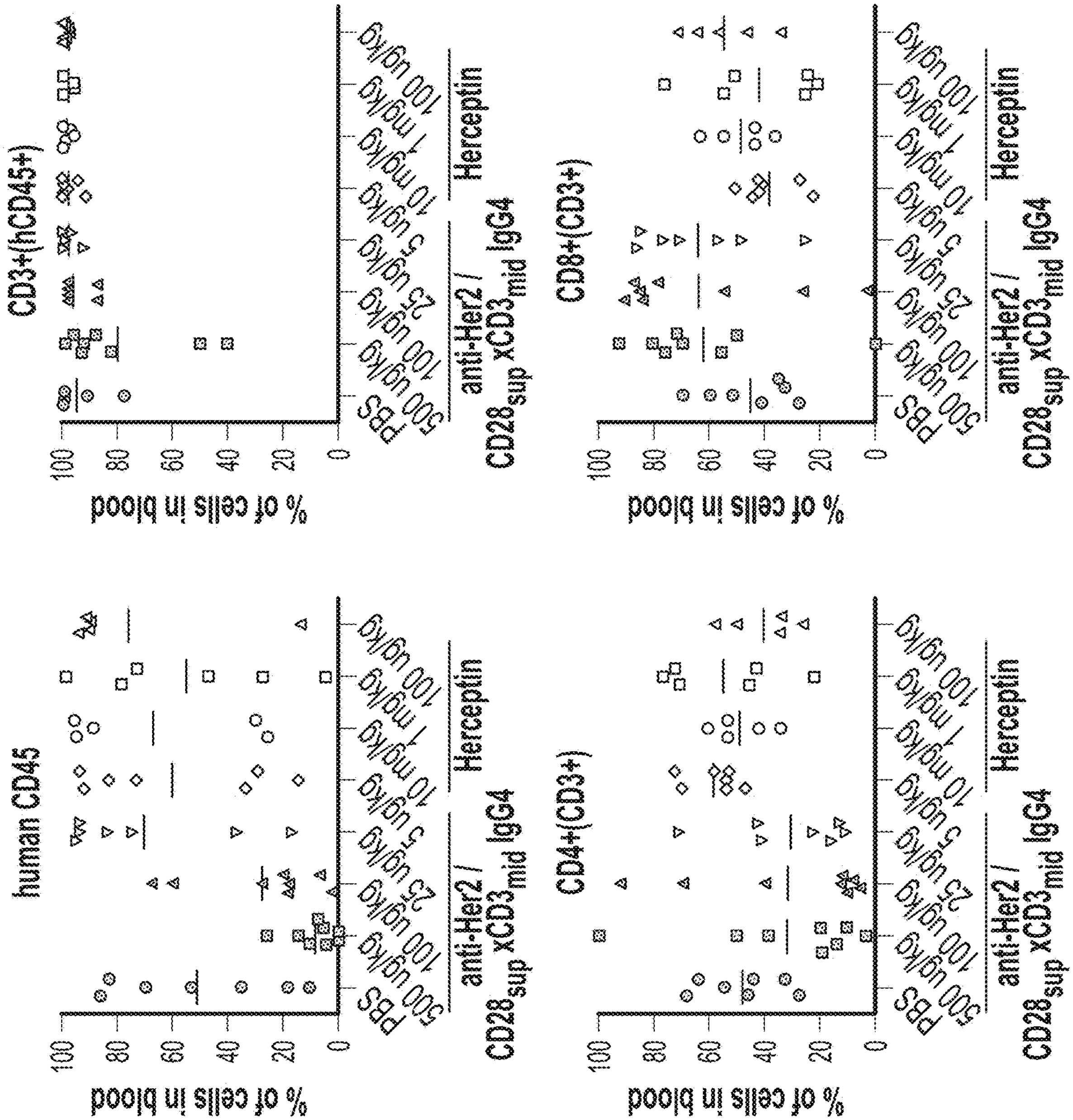
Figure 20H:
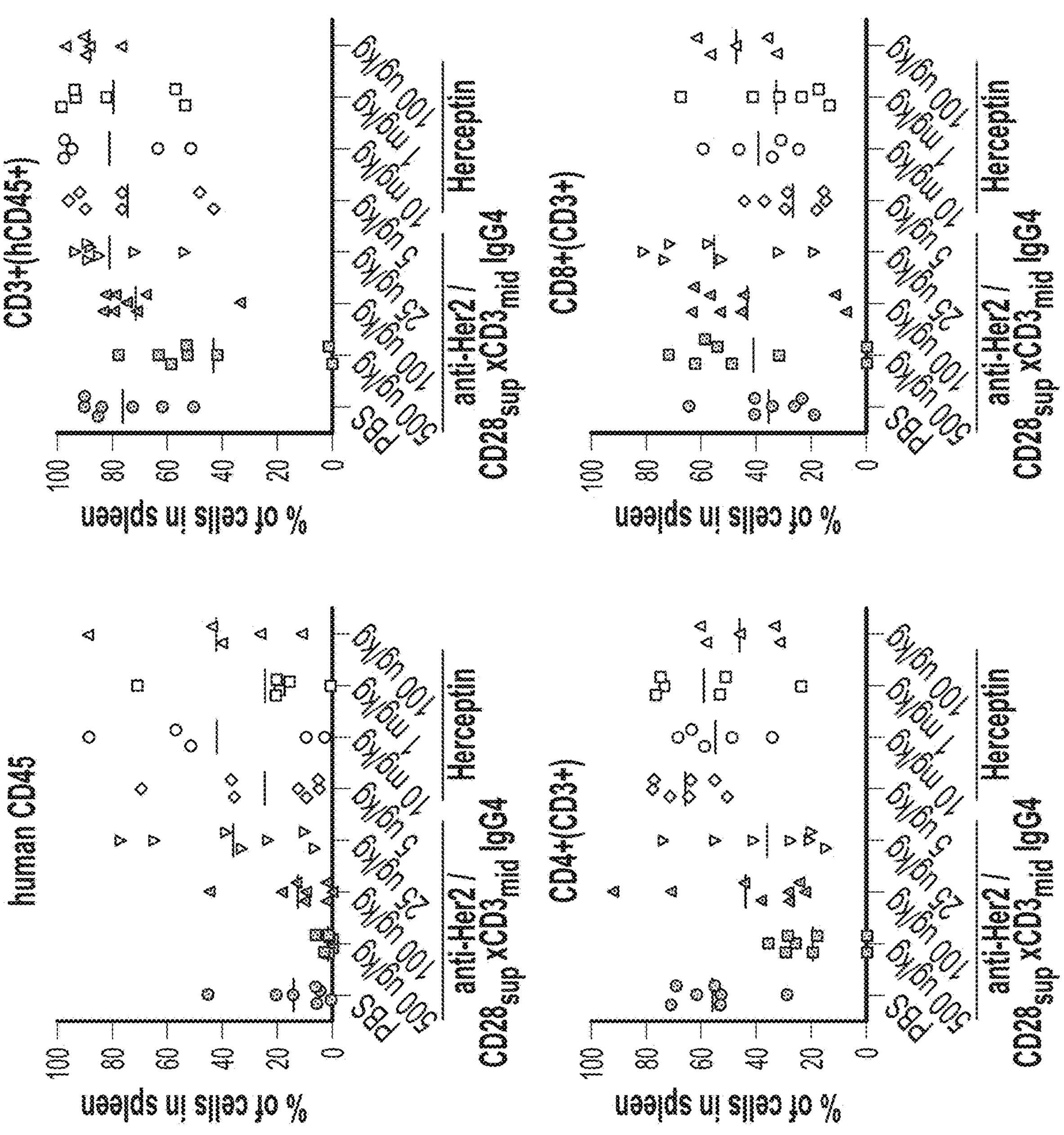

Next, the effect of the trispecific anti-Her2×CD28×CD3 Binding protein 1 antibody on tumor growth in humanized mouse models was examined as described in Example 1 (FIGS. 19A-20H). FIGS. 19A & 19B summarize the results obtained using the human CD34+ hematopoietic stem cell-engrafted NSG mice (hu-CD34) model inoculated with human HER2+ breast cancer line BT474. Significant anti-tumor activities were evident within all dose groups. The anti-tumor activity was dose dependent, which is statistically different compared to the control group at 25 mg/kg. No significant body weight loss in any treated groups observed.

A 2$^{nd}$ in vivo study using human PBMC reconstituted NSG mice model inoculated with human HER2+ breast cancer line BT474 was also done (FIGS. 20A-20H). Significant anti-tumor activities were observed within high dose groups (100 and 500 μg/kg). Tumor shrinkage was seen in 40% of the mice in 500 μg/kg group. The anti-tumor activity was dose dependent. The anti-tumor activity in groups treated with 100 and 500 μg/kg doses were significantly better than anti-HER2-treated groups (0.1 to 10 mg/kg), indicating superior anti-tumor activity from Binding protein 1. No significant body weight loss in any treated groups observed.

In Vivo Assays Using Trispecific Binding Proteins Comprising Anti-CD38

Figures 21A, 21B, 21C, 21D:
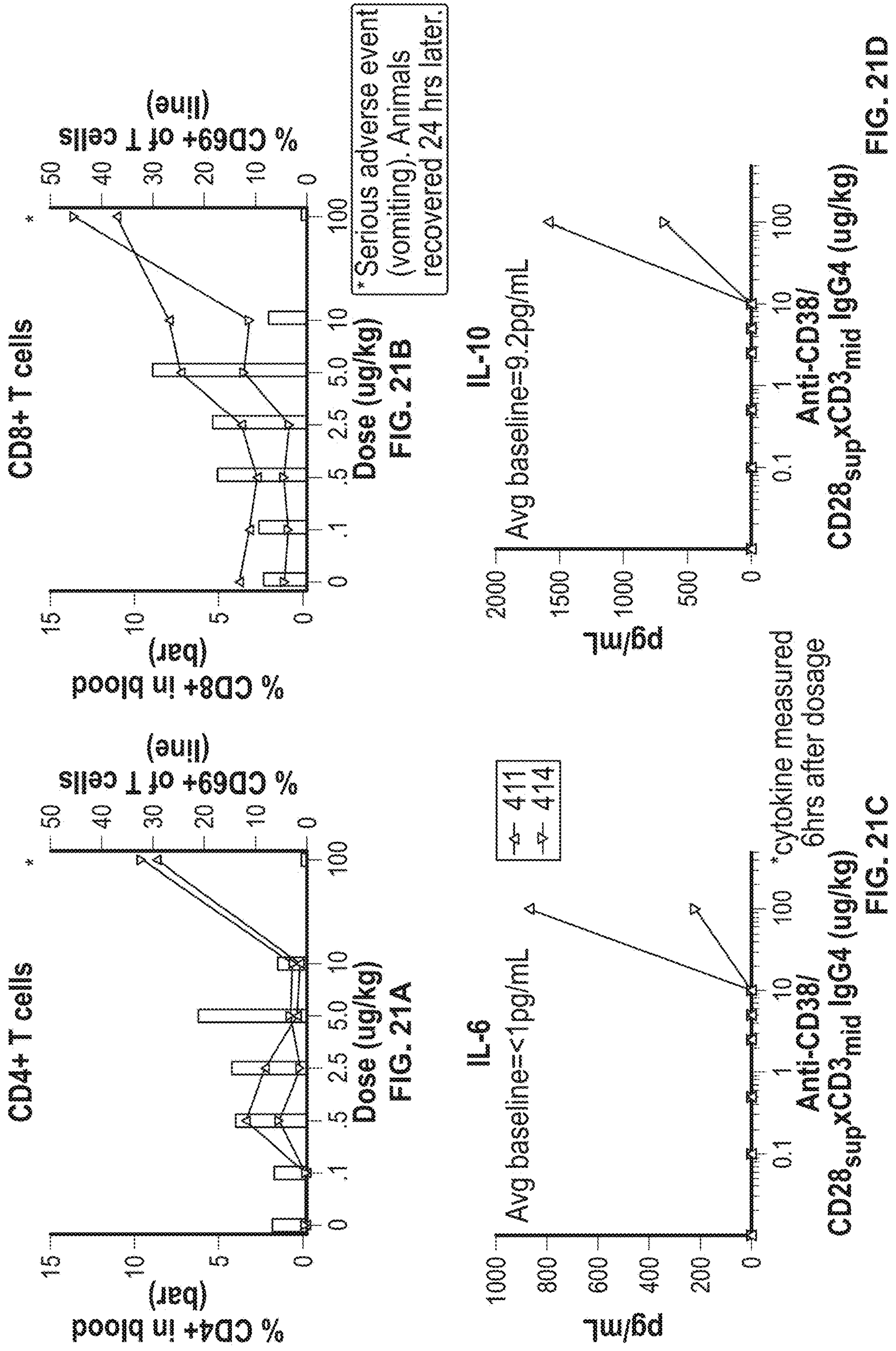
FIGS. 21A-F show the results of a dose escalation toxicity study using the anti-CD38×CD28×CD3 IgG4 trispecific antibody (Binding protein 5) in non-human primates (dose escalating from 0.1, 0.5, 2.5, 5, 10, to 100 μg/kg).
Figure 21E:
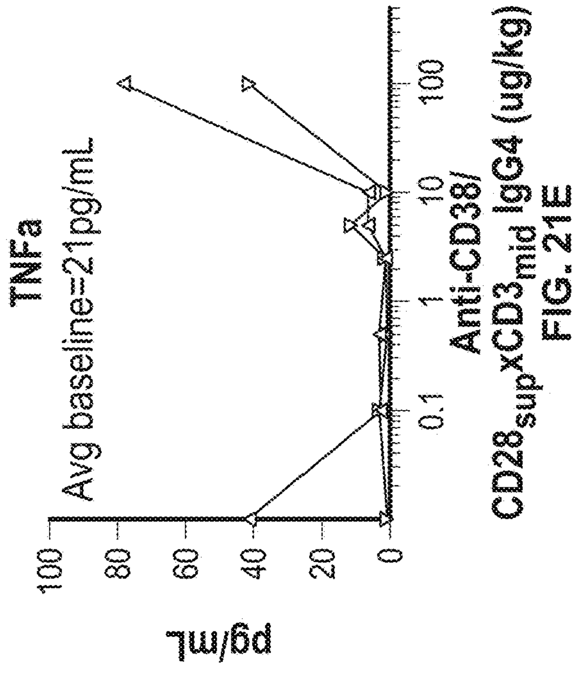
Figure 21F:
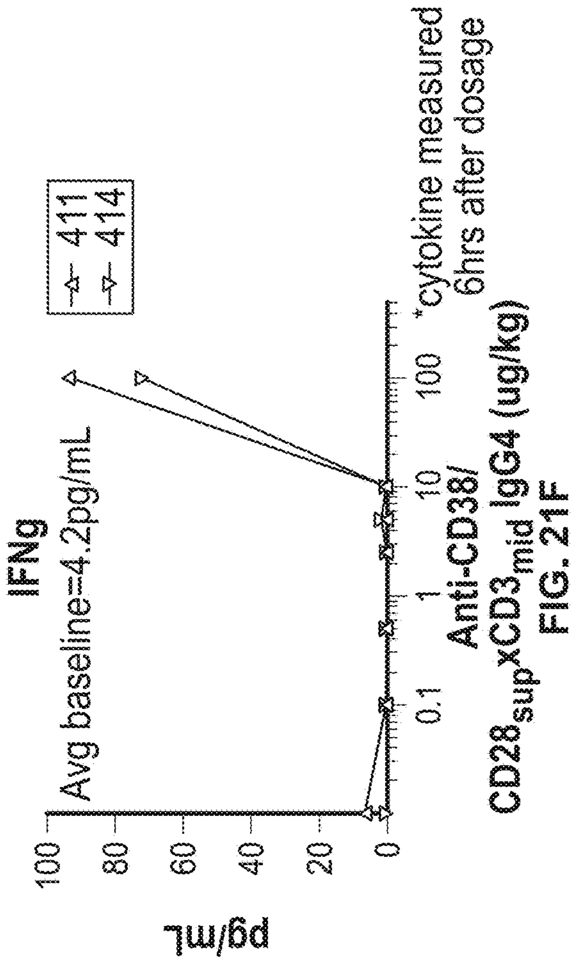

A dose escalation study was conducted in non-human primates using the trispecific anti-CD38×CD28×CD3 antibody (Binding protein 5) as described in Example 1 (FIGS. 21A-21F). Two of the three binding domains in Binding protein 5 are cross-reactive with monkey CD3 and CD28. A dose escalation toxicity study was devised to assess the potential toxicity profile of the molecule. Blood samples were collected for serum and PBMC isolations. Circulating T cell populations were investigated after each dosing (FIGS. 21A & 21B, bar graphs), along with T cell subpopulation activation (CD69+) (FIGS. 21A & 21B, line graphs). Percentage of CD4 and CD8 T-cells in circulation increased at low dose escalation, but eventually decreased at high dose escalation. Significant CD4 and CD8 T cell activation were only prominent at 100 μg/kg dose, suggesting rather a relative high tolerable dose. Serum level of several cytokines was also measured. Significant cytokine release was only observed at the highest dose (100 μg/kg; FIGS. 21C-21F).

Figure 22A:
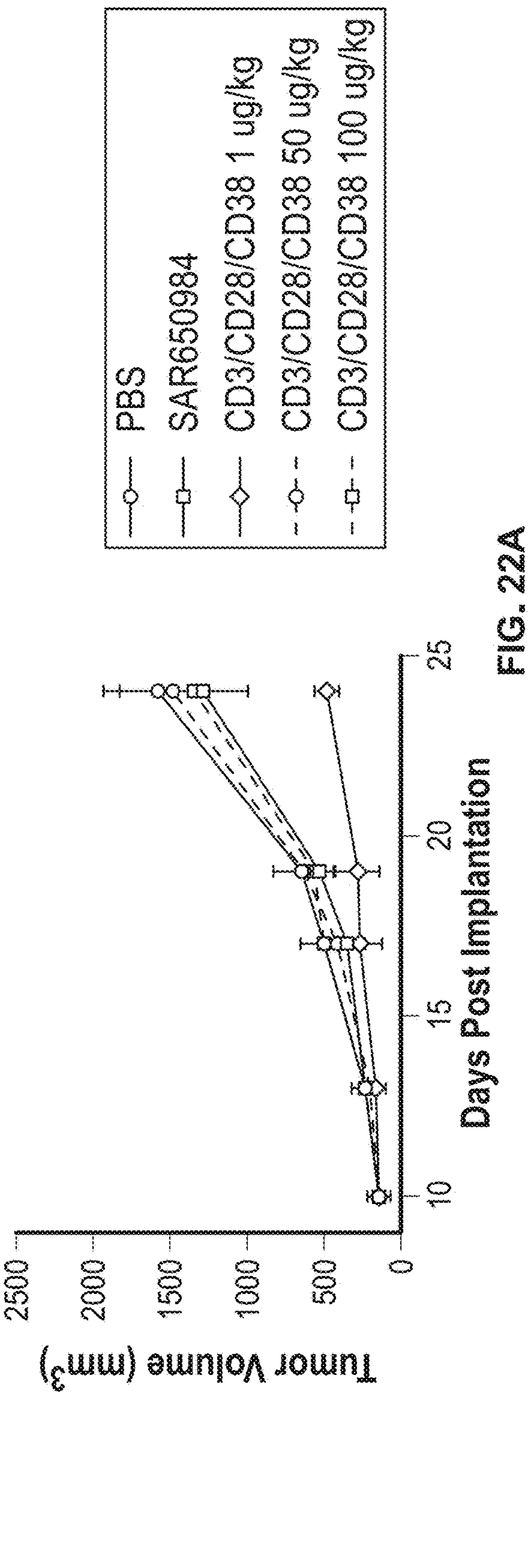
FIGS. 22A-22C show the in vivo anti-tumor activity of the anti-CD38×CD28×CD3 IgG4 trispecific antibody (Binding protein 5) in the CD34+ umbilical cord blood cells humanized NSG mouse model implanted with RPMI-8226 multiple myeloma cells transduced with CD38 and PD-L1. As a pilot study, this experiment determined the working dose range for the Binding protein 5.
Figure 22B:
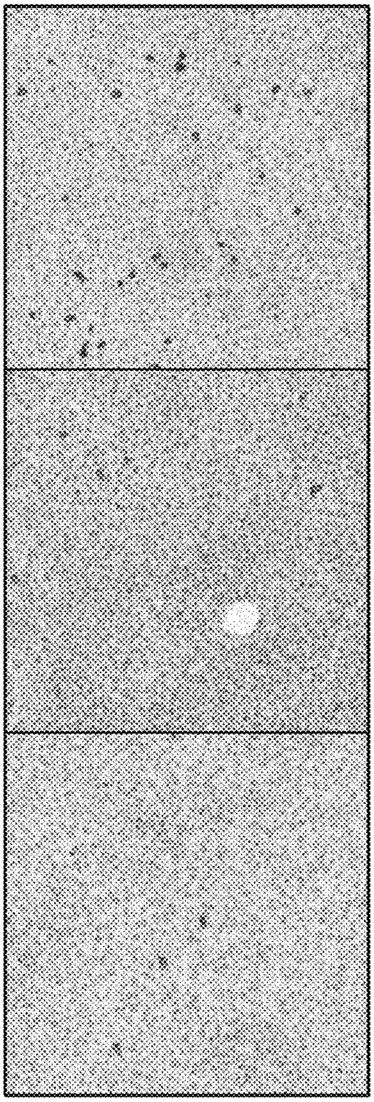
Figure 22C:

The in vivo activity of the anti-CD38×CD28×CD3 trispecific antibody was next tested in humanized mice (FIGS. 22A-23D) as described in Example 1. FIGS. 22A-22C summarized the result from a dose determining pilot study using the human CD34+ hematopoietic stem cell-engrafted NSG mice (hu-CD34) model implanted with human MM cell line RPMI-8226 transduced with CD38 and PD-L1, treated with Binding protein 5 at doses 5, 50 and 100 μg/kg. Significant anti-tumor activity was only evident in group treated with 5 μg/kg (FIG. 22A). CD8 T cell infiltration was observed in Binding protein 5 treated mice (5 μg/kg) (FIGS. 22B & 22C).

Figure 23A:
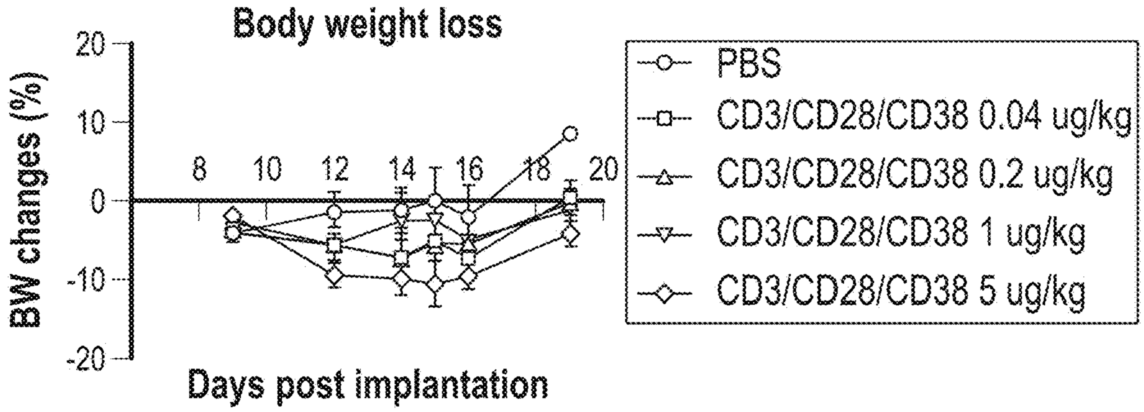
FIGS. 23A-23D show the in vivo activity of the anti-CD38×CD28×CD3 IgG4 trispecific antibody (Binding protein 5) in the CD34+ umbilical cord blood cells humanized NSG mouse model implanted with RPMI-8226 cells transduced with CD38 and PD-L1.
Figure 23B:
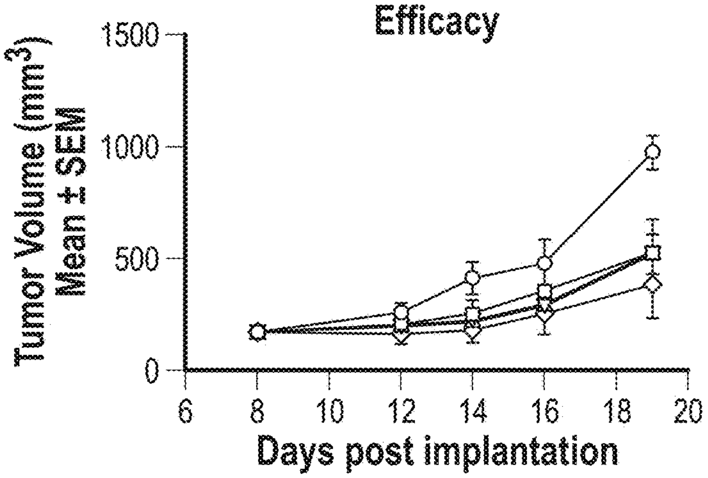
Figure 23C:
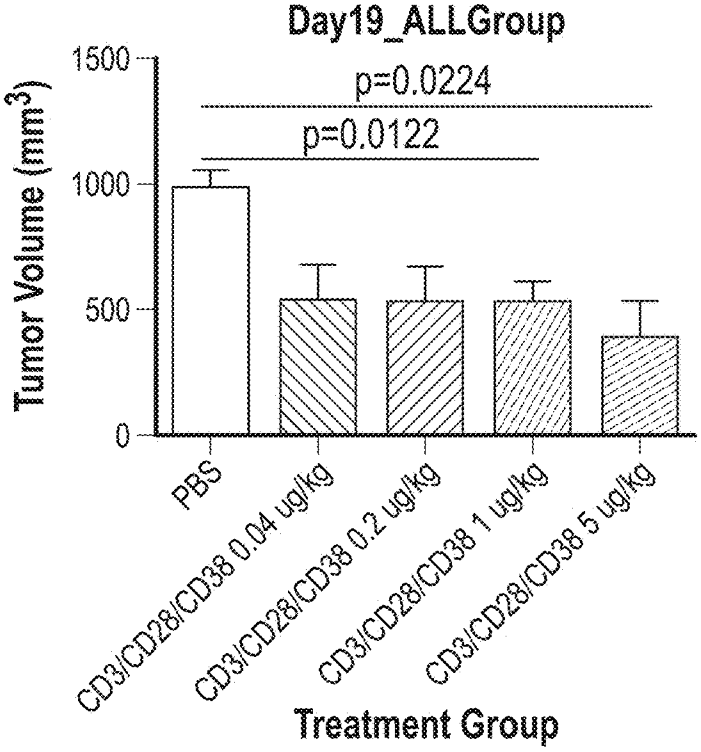
Figure 23D:
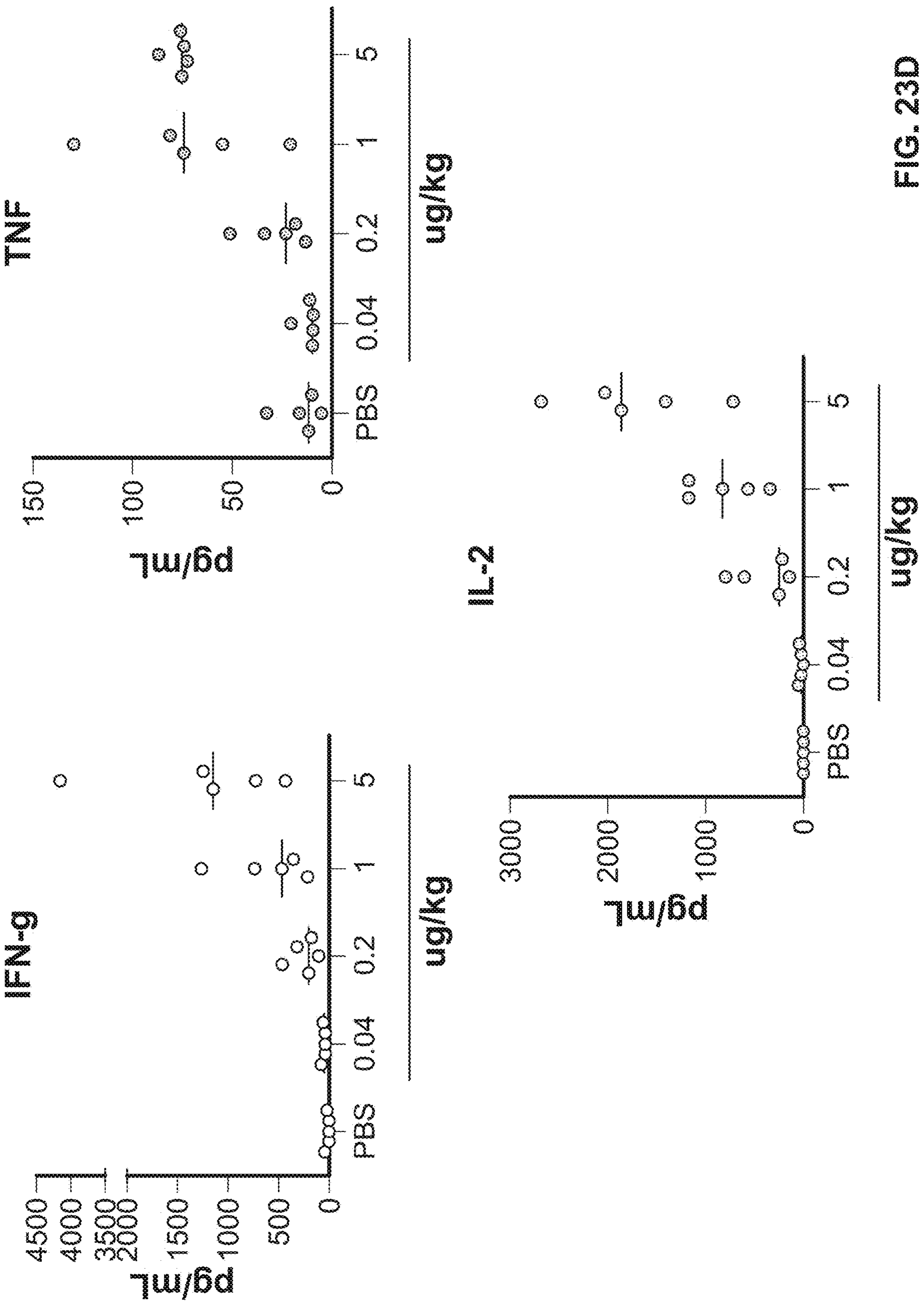

A follow up study in the same model was performed using Binding protein 5 at dosing from 0.04-5 μg/kg (FIGS. 23A-23D). Significant anti-tumor activity was shown in all group treated with Binding protein 5 (FIG. 23B), which were statistically different from the control at the end of study (FIG. 23C). No significant body weight loss was observed in any treated groups (FIG. 23A). Dose dependent induction of serum inflammatory cytokines IFN-γ, TNF-α and IL-2 four hours after the first dose was observed in mice treated with indicated concentrations of the Binding protein 5 or PBS control (FIG. 23D), indicating effective T cell activation by trispecific Binding protein 5 in vivo.

Humanized CD34+ NSG mice (n=3) were injected i.v. with 100 mcg/kg of Trispecific Ab (triangel), Bi-specific Ab (square), or single-specific Ab (circle). Activation of CD4+ or CD8+ T cells was measured at 0 (pre-injection), 1, 24, and 72 hours after Ab injection by determining mean increase in % of CD69, decrease % of CD62L and/or concentration of inflammatory cytokines in plasma at each time points by Luminex's xMAP multiplexing technology. The T cell activation results of various trispecific antibodies are shown in FIGS. 24-26C.

Figure 24:
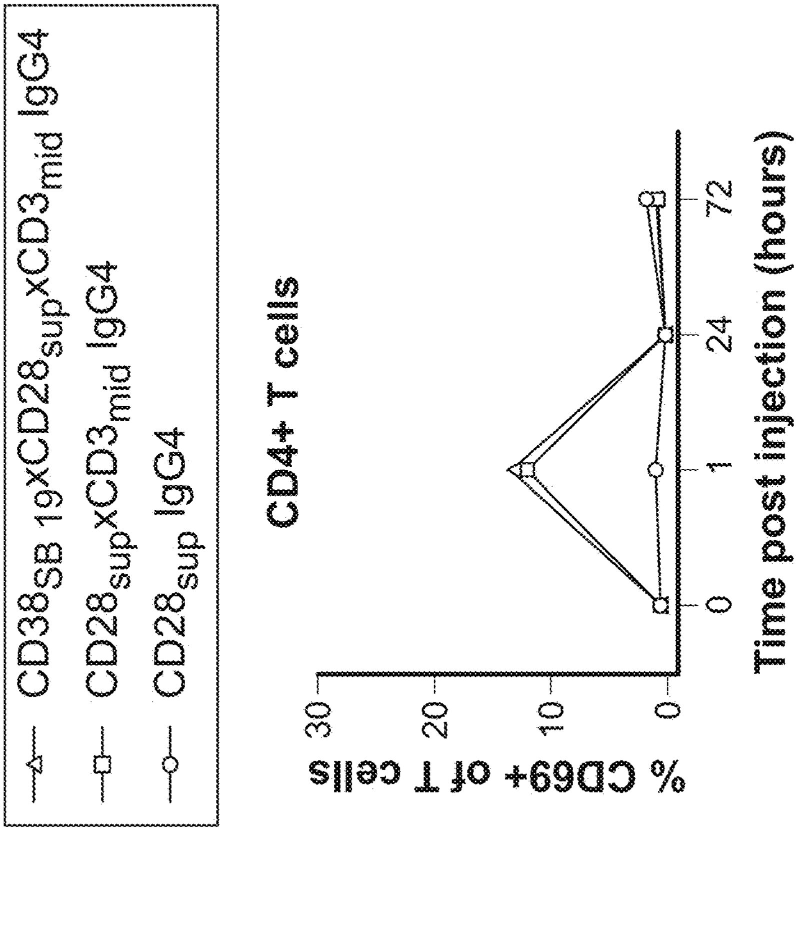
FIGS. 24 & 25 show the in vivo activation of T cells in the CD34+ umbilical cord blood cells humanized NSG mouse model by administering an anti-CD38×CD28×CD3 IgG4 trispecific antibody (Binding protein 5; triangles), an anti-CD28×CD3 IgG4 bispecific antibody (squares), or an anti-CD28 IgG4 antibody (circles) by determining the increase in the percentage of $CD69^+$ T cells.
Figure 25:
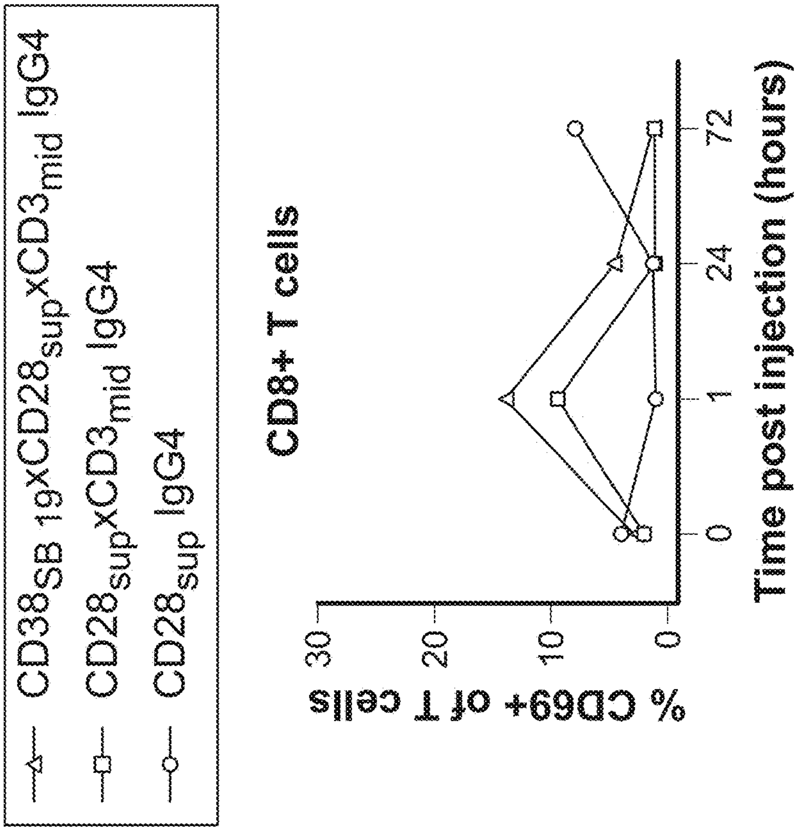
Figures 26A, 26B, 26C:
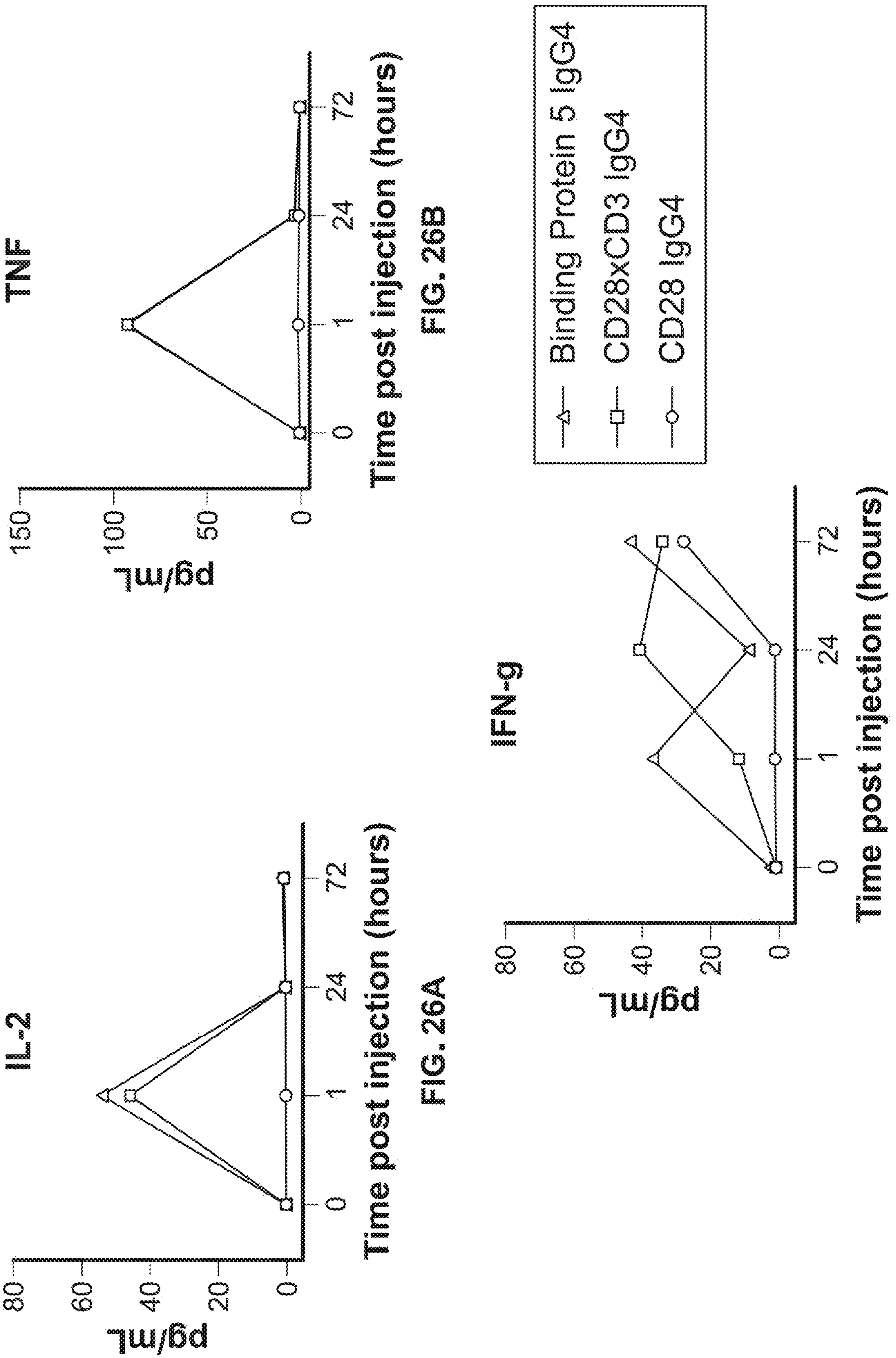
FIGS. 26A-26C show the in vivo activation of T cells in the CD34+ umbilical cord blood cells humanized NSG mouse model by administering an anti-CD38×CD28×CD3 IgG4 trispecific antibody (Binding protein 5; triangles), an anti-CD28×CD3 IgG4 bispecific antibody (squares), or an anti-CD28 IgG4 antibody (circles) by determining the serum levels of inflammatory cytokines.

Systemic in vivo T cell activation was studied in human CD34+ hematopoietic stem cell-engrafted NSG mice (hu-CD34) model after administration of Binding protein 5, anti-CD3/CD28_IgG4 bispecific antibody and anti-CD28 IgG4 antibody controls (FIG. 24). 100 μg/kg of the Binding protein 5 and control antibodies were administered into 3 mice/group. Blood samples were collected at pre, 1 hour, 24 hours and 72 hours post administration. Mouse sera and human T cells were isolated from blood, and preserved for T cell activation analysis and for measurement of serum cytokine level. FIGS. 24 & 25 show that both human CD4 and CD8 T cell were activated 1 hour post antibody infusion, which returned to baseline at 72 hours. FIGS. 26A-26C shows the elevation of serum IFN-γ, TNF-α and IL-2 release in the same mice, which was observed 1 hour post infusion, and returned to baseline 24 hours later. These results demonstrated both Binding protein 5 and anti-CD3/CD28 IgG4 bispecific antibody are effective in activating T cell in the given animal model, making it suitable for in vivo efficacy study.

Example 5: Characterization of Cytokine-Directed Trispecific and Bispecific-Trivalent Binding Proteins The follow example describes experiments characterizing the stability, binding properties, and activities of novel trispecific and bispecific-trivalent binding proteins that target human cytokines.

Trispecific binding proteins (e.g., that bind three different target proteins; Binding Proteins 9-15), as well as bispecific-trivalent binding proteins (e.g., that bind one antigen bivalently on one antigen monovalently; Binding Proteins 16-19), were designed (Table C). With the exception of Binding Protein 11 where a kappa constant domain was used on both the CODV-LC and the Fab-arm-LC, all other Binding Proteins (9-10 and 12-19) were produced with a kappa constant domain on the CODV-LC and a lambda constant domain on the Fab-arm-LC. As Fc-backbone the IgG1 sequence was used. Whereas the CODV-HC harbors the knob-RF mutations (S354C, T366W; H435R and Y436F) the Fab-arm-HC contains the hole mutations (Y349C, T366S, L368A, Y407V).

TABLE C summary of the trispecific/trivalent binding proteins directed to anti-IL-4/IL-13/TNFα

| Antibody | Specificity | Construct | Format |
|---|---|---|---|
| Binding Protein 9 | (anti-IL4 × anti-IL13) × anti-TNFα | (CODV-Fab) × Fab-IgG1 Fc | Trispecific |
| Binding Protein 10 | (anti-IL13 × anti-IL4) × anti-TNFα | (CODV-Fab) × Fab-IgG1 Fc | Trispecific |
| Binding Protein 11 | (anti-IL13 × anti-IL4) × anti-TNFα | (CODV-Fab) × Fab-IgG1 Fc | Trispecific |
| Binding Protein 12 | (anti-IL4 × anti-TNFα) × anti-IL13 | (CODV-Fab) × Fab-IgG1 Fc | Trispecific |
| Binding Protein 13 | (anti-TNFα × anti-IL4) × anti-IL13 | (CODV-Fab) × Fab-IgG1 Fc | Trispecific |
| Binding Protein 14 | (anti-IL13 × anti-TNFα) × anti-IL4 | (CODV-Fab) × Fab-IgG1 Fc | Trispecific |
| Binding Protein 15 | (anti-TNFα × anti-IL13) × anti-IL4 | (CODV-Fab) × Fab-IgG1 Fc | Trispecific |
| Binding Protein 16 | (anti-IL13 × anti-IL4) × anti-IL13 | (CODV-Fab) × Fab-IgG1 Fc | Bispecific Trivalent |
| Binding Protein 17 | (anti-IL13 × anti-IL4) × anti-IL4 | (CODV-Fab) × Fab-IgG1 Fc | Bispecific Trivalent |
| Binding Protein 18 | (anti-IL4 × anti-IL13) × anti-IL13 | (CODV-Fab) × Fab-IgG1 Fc | Bispecific Trivalent |
| Binding Protein 19 | (anti-IL4 × anti-IL13) × anti-IL4 | (CODV-Fab) × Fab-IgG1 Fc | Bispecific Trivalent |

Figure 27A:
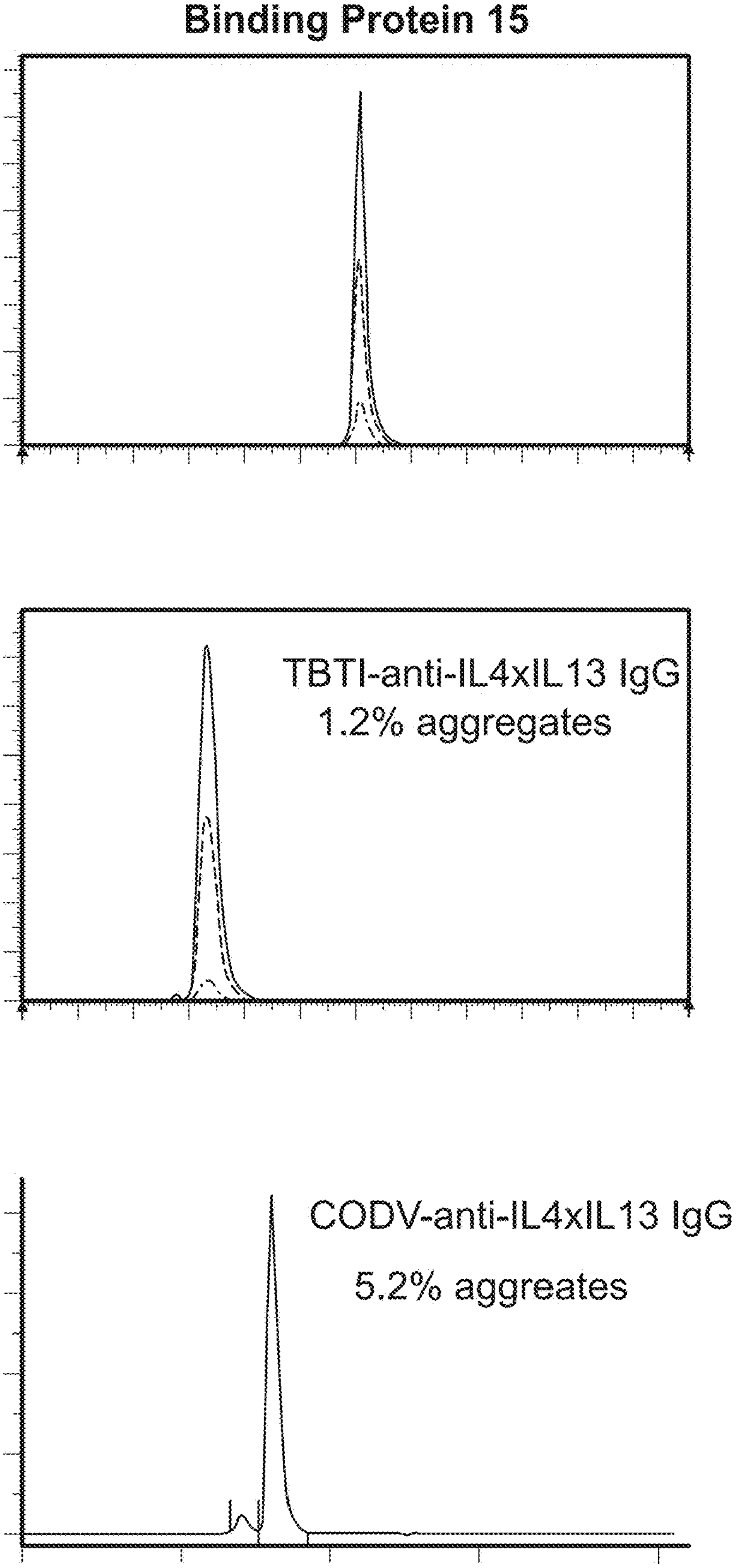
FIGS. 27A & 27B show the purification of the indicated proteins by size exclusion chromatography.
Figure 27B:
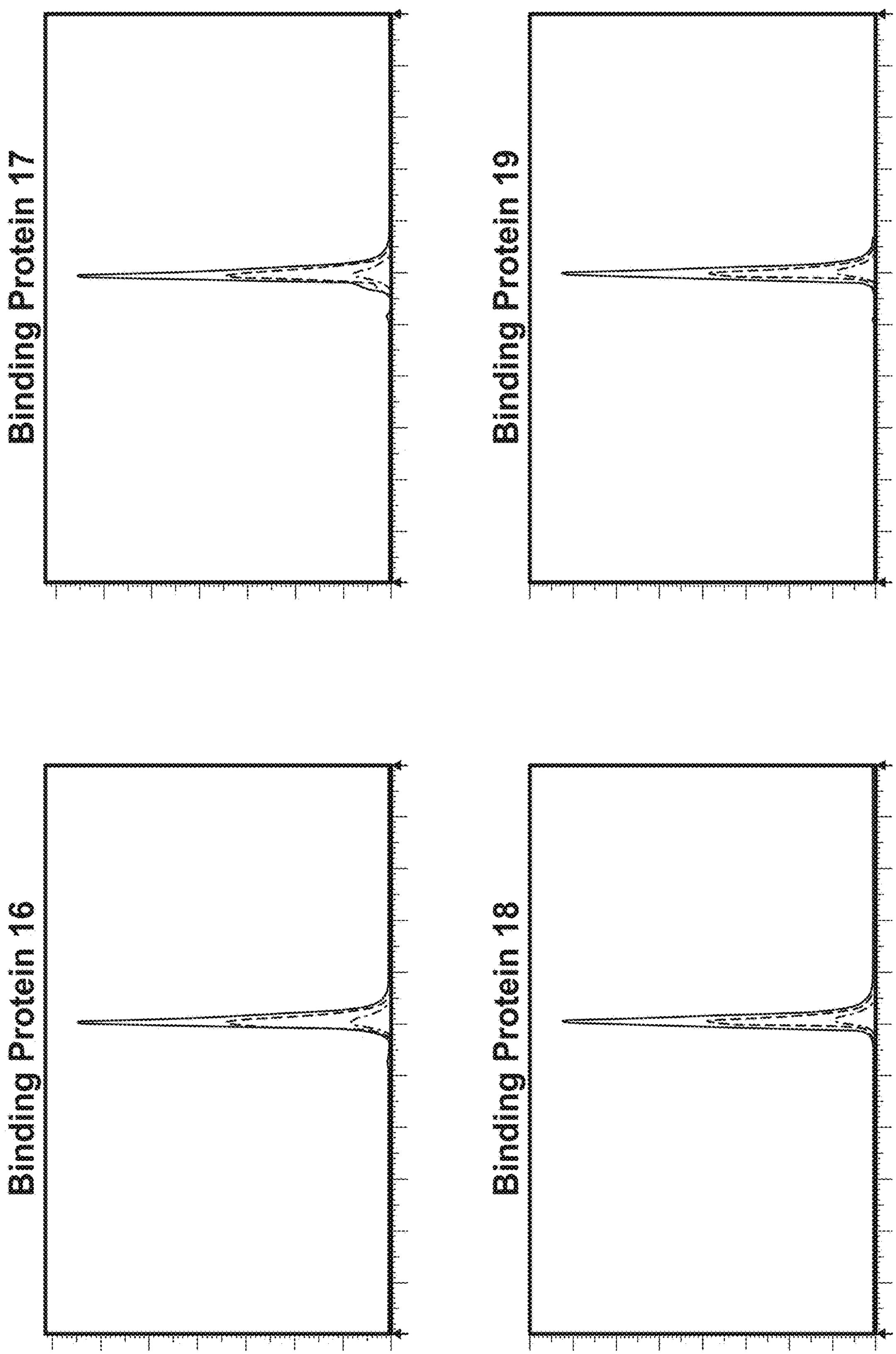

The trispecific and bispecific-trivalent binding proteins were produced and purified as described above (FIG. 27).

TABLE D

SEC purification of Binding Proteins 16-19

| Construct | Retention (mL) | Peak Height (mAU) | Area (mAU*mL) | Aggregation (%) | MW by SEC (kDa) | MW Calc. (kDa) |
|---|---|---|---|---|---|---|
| Binding Protein 16 | 3.02 | 64.8 | 8.1 | 1.5 | 211 | 11 |
| Binding Protein 17 | 2.99 | 65.9 | 8.9 | 2.1 | 225 | 172 |
| Binding Protein 18 | 3.01 | 72.9 | 8.8 | 0.0 | 214 | 171 |
| Binding Protein 19 | 2.98 | 73.2 | 8.8 | 0.9 | 228 | 171 |

In order to assess the stability of the trispecific binding proteins, their melting point was assessed by DSF and compared with the thermostability of the parental antibodies (Table E).

TABLE E summary of the thermostability by DSF and percent monomers from preparative size exclusion chromatography for various trispecific binding proteins

| Construct | Tm (° C.) | | Prep SEC Monomer (%) |
|---|---|---|---|
| IL4 | 70 | 81 | 100 |
| IL13 | 67 | 78 | 92.5 |
| TNFα | 70 | — | nd |
| Binding Protein 9 | 63 | — | 92.2 |
| Binding Protein 10 | 62 | — | 85.7 |
| Binding Protein 11 | 63 | 70 | 65.7 |
| Binding Protein 12 | 59 | 70 | 87.3 |
| Binding Protein 13 | 59 | 70 | 94.5 |
| Binding Protein 14 | 56 | 69 | 92.4 |
| Binding Protein 15 | 58 | 66 | 92.2 |
| IL13 × IL4 | 63 | 75 | 88.0 |
| IL4 × IL13 | 64 | — | nd |

nd = not determined

To assess the binding affinity of every single antibody binding domain within the trispecific format, SPR analysis for each single antigen was performed as described previously. The results were benchmarked against the affinities of the parental antibodies (Tables F, G, and H).

TABLE F summary of surface plasmon resonance results for IL-4 for various trispecific binding proteins

| Construct | $K_a$ [1/M*s] | $K_d$ [1/s] | $K_D$ [M] | Rmax | Chi^2 |
|---|---|---|---|---|---|
| IL4 | 8.70E+07 | 1.57E−04 | 1.81E−12 | 24 | 0.24 |
| IL13 | | | | | |
| TNFα | | | | | |
| Binding Protein 9 | 7.86E+07 | 3.80E−04 | 4.83E−12 | 26 | 0.309 |
| Binding Protein 10 | 1.88E+07 | 8.41E−05 | 4.47E−12 | 23 | 0.763 |
| Binding Protein 11 | 5.92E+07 | 2.39E−04 | 4.04E−12 | 20 | 0.198 |
| Binding Protein 12 | 6.02E+07 | 2.39E−04 | 3.97E−12 | 35 | 0.406 |
| Binding Protein 13 | 3.57E+07 | 1.81E−04 | 5.07E−12 | 30 | 0.257 |
| Binding Protein 14 | 8.96E+07 | 1.52E−04 | 1.69E−12 | 33 | 0.254 |
| Binding Protein 15 | 7.35E+07 | 1.23E−04 | 1.67E−12 | 31 | 0.547 |

TABLE G summary of surface plasmon resonance results for IL-13 for various trispecific binding proteins

| Construct | $K_a$ [1/M*s] | $K_d$ [1/s] | $K_D$ [M] | Rmax | Chi^2 |
|---|---|---|---|---|---|
| IL4 | | | | | |
| IL13 | 2.44E+05 | 2.50E−05 | 1.03E−10 | 33 | 0.938 |
| TNFα | | | | | |
| Binding Protein 9 | 6.25E+05 | 9.27E−06 | 1.48E−11 | 22 | 0.176 |
| Binding Protein 10 | 7.16E+05 | 3.76E−05 | 5.25E−11 | 25 | 0.145 |
| Binding Protein 11 | 2.95E+05 | 4.28E−05 | 1.45E−10 | 16 | 0.372 |
| Binding Protein 12 | 4.17E+05 | 5.06E−05 | 1.21E−10 | 28 | 0.338 |
| Binding Protein 13 | 6.15E+05 | 7.58E−05 | 1.23E−10 | 23 | 0.186 |
| Binding Protein 14 | 6.93E+05 | 1.19E−04 | 1.72E−10 | 22 | 0.232 |
| Binding Protein 15 | 2.50E+05 | 5.61E−05 | 2.24E−10 | 30 | 0.631 |

TABLE H summary of surface plasmon resonance results for TNFα for various trispecific binding proteins

| Construct | $K_a$ [1/M*s] | $K_d$ [1/s] | $K_D$ [M] | Rmax | Chi^2 |
|---|---|---|---|---|---|
| IL4 | | | | | |
| IL13 | | | | | |
| TNFα | 1.78E+05 | 1.64E−04 | 9.22E−10 | 33 | 0.745 |
| Binding Protein 9 | 1.32E+05 | 3.20E−04 | 2.42E−9 | 23 | 0.213 |
| Binding Protein 10 | 1.40E+05 | 2.90E−04 | 2.07E−9 | 27 | 0.241 |
| Binding Protein 11 | 3.36E+05 | 1.82E−04 | 5.41E−10 | 28 | 0.539 |
| Binding Protein 12 | 4.49E+05 | 1.80E−04 | 4.00E−10 | 28 | 0.647 |
| Binding Protein 13 | 5.84E+05 | 1.96E−04 | 3.35E−10 | 27 | 0.529 |
| Binding Protein 14 | 5.29E+05 | 1.86E−04 | 3.52E−10 | 25 | 0.485 |
| Binding Protein 15 | 5.59E+05 | 1.84E−04 | 3.28E−10 | 27 | 0.409 |

In order to assess the neutralization activity of the trispecific binding proteins, a cellular assay was performed using different HEK Blue kits (Invivogen). Cytokines were pre-incubated with different concentrations of anti-cytokine antibodies for 30 minutes at room temperatures in a 96 well plate. Controls included use of only the cytokine or only the antibody. 50,000 HEK Blue Cells (HEK Blue TNFa/IL113 cells (InvivoGen, Cat. #hkb-tnfil1; HEK Blue STAT-6 cells (InvivoGen, Cat. #Hkb.stat6) were added to the cytokine/antibody mixture and incubated for 23 hours at 37° C., 5% CO2 in an incubator. QuantiBlue Reagent was added to each culture well and incubated for 2 hours at 37° C. The OD was measured at 620 nm and the IC50 was calculated using BioStat Speed 2.0. The HEK Blue Reporter Cell Assay results of various trispecific antibodies are shown in Tables I and M.

Next, $IC_{50}$ values were calculated for Binding Proteins 9-15 and benchmarked against the single parental antibodies (Table I).

TABLE I

| summary of HEK Blue Reporter Assays ($IC_{50}$ Data) for various trispecific binding proteins | | | |
|---|---|---|---|
| Construct | IL4 $IC_{50}$ (ng/mL) | IL13 $IC_{50}$ (ng/mL) | TNFα $IC_{50}$ (ng/mL) |
| IL4 | 2.14E+00<br>1.85E+00<br>1.82E+01 | — | — |
| IL13 | — | 1.10E+02<br>8.83E+01<br>1.42E+01 | — |
| TNFα | — | — | 3.63E+00<br>5.78E+00<br>2.41E+00 |
| Binding Protein 9 | 4.51E+00 | 1.77E+02 | 3.95E+01 |
| Binding Protein 10 | 5.93E+00 | 4.68E+02 | 4.76E+01 |
| Binding Protein 11 | 6.96E+00 | 4.89E+02 | 2.65E+01 |
| Binding Protein 12 | 5.03E+00 | 1.83E+02 | 2.17E+01 |
| Binding Protein 13 | 1.38E+01 | 7.54E+01 | 2.26E+01 |
| Binding Protein 14 | 1.02E+01 | 1.20E+02 | 6.26E+00 |
| Binding Protein 15 | 1.30E+01 | 1.07E+02 | 2.38E+01 |

The thermostability of the bispecific-trivalent binding proteins was measured by differential scanning fluorimetry (DSF; Table J).

TABLE J

| summary of the thermostability by DSF for various trivalent binding proteins | | |
|---|---|---|
| Construct | Tm1 (° C.) | Tm2 (° C.) |
| IL4 | 70 | 81 |
| IL13 | 67 | 78 |
| Binding Protein 16 | 63 | — |
| Binding Protein 17 | 63 | — |
| Binding Protein 18 | 65 | — |
| Binding Protein 19 | 55 | — |

The binding affinity and number of target proteins bound by each of the bispecific-trivalent binding proteins was measured for human IL-4 (Table K) and IL-13 (Tables K and L).

TABLE K

| summary of surface plasmon resonance results for IL-4 for various trivalent binding proteins | | | | | | | | | |
|---|---|---|---|---|---|---|---|---|---|
| Construct | RU Capture | Analyte | Ka (1/Ms) | Kd (1/s) | Rmax (RU) | KD (M) | Chi2 | kDa Bound | No. of ILs Bound |
| IL4 | 116 | IL4 | 8.70E+07 | 1.57E−04 | 24 | 1.81E−12 | 0.240 | 15 | 1 |
| Binding Protein 16 | 218 | IL4 | 4.77E+07 | 2.80E−04 | 20 | 5.88E−12 | 0.172 | 17 | 1 |
| Binding Protein 17 | 218 | IL4 | 3.16E+08 | 7.60E−04 | 43 | 2.40E−12 | 0.278 | 35 | 2 |
| Binding Protein 18 | 215 | IL4 | 3.52E+07 | 3.59E−04 | 22 | 1.02E−12 | 0.408 | 18 | 1 |
| Binding Protein 19 | 226 | IL4 | 8.27E+07 | 3.85E−04 | 43 | 4.65E−12 | 0.486 | 34 | 2 |

TABLE L

| summary of surface plasmon resonance results for IL-13 for various trivalent binding proteins | | | | | | | | | |
|---|---|---|---|---|---|---|---|---|---|
| Construct | RU Capture | Analyte | Ka (1/Ms) | Kd (1/s) | Rmax (RU) | KD (M) | Chi2 | kDa Bound | No. of ILs Bound |
| IL13 | 201 | IL13 | 8.95E+05 | 5.47E−05 | 37 | 6.11E−11 | 0.211 | 14 | 1 |
| Binding Protein 16 | 226 | IL13 | 7.17E+05 | 4.54E−05 | 35 | 6.34E−11 | 0.132 | 26 | 2 |
| Binding Protein 17 | 235 | IL13 | 5.92E+05 | 5.70E−05 | 15 | 9.64E−11 | 0.128 | 11 | 1 |
| Binding Protein 18 | 231 | IL13 | 1.00E+06 | 3.54E−05 | 35 | 3.53E−11 | 0.166 | 28 | 2 |
| Binding Protein 19 | 282 | IL13 | 1.91E+06 | 3.81E−05 | 18 | 2.00E−11 | 0.265 | 14 | 1 |

Finally, $IC_{50}$ values were calculated for Binding Proteins 16-19 (Table M).

TABLE M summary of HEK Blue Reporter Assays ($IC_{50}$ Data) for various trivalent binding proteins

| Construct | IL4 $IC_{50}$ (ng/mL) | IL13 $IC_{50}$ (ng/mL) |
|---|---|---|
| IL4 | 6.07E+00 | — |
| IL13 | — | 1.12E+03 |
| Binding Protein 16 | 1.30E+01 | 1.24E+03 |
| Binding Protein 17 | 8.62E+00 | 9.30E+03 |
| Binding Protein 18 | 1.46E+01 | 1.10E+03 |
| Binding Protein 19 | 5.73E+00 | 6.93E+03 |

Example 6: Trispecific Binding Protein Format Optimization

A problem with many existing heterodimeric binding protein formats (e.g., bispecific antibodies and variants thereof) is that it can be difficult to purify only the desired heterodimeric species without also including either homodimeric species. Thus, a process for efficient purification of the desired, heterodimeric binding protein is of great interest, e.g., for industrial-scale production.

As described herein, binding proteins of the present disclosure can include several optional features, including without limitation knob and hole mutations (e.g., to promote proper heterodimer formation) and mutations to improve purification. In addition, these binding proteins include two light chains, leading to four potential configurations: two kappa light chains, two lambda light chains, a kappa light chain on the arm with dual variable domains (the "CODV arm") and a lambda light chain on the traditional antibody arm (the "Fab arm"), and a lambda light chain on the CODV arm and a kappa light chain on the Fab arm.

Therefore, experiments were undertaken to identify a process that allows for efficient purification of the desired binding protein of interest. Binding protein variants were also tested for their efficiency of purification.

FIG. 28A shows a diagram of an exemplary binding protein of the present disclosure, indicating variations that lead to unique configurations. These experiments tested the effect of the placement of: kappa and lambda light chains (e.g., two kappa, two lambda, kappa on CODV arm and lambda on Fab arm, and lambda on CODV arm and kappa on Fab arm), knob and hole mutations (e.g., knob mutations on CODV arm and hole mutations on Fab arm, or hole mutations on CODV arm and knob mutations on Fab arm), and H435R/Y436F mutations ("RF mutations," e.g., RF mutations on CODV or Fab arm, or no RF mutations). A total of 18 different variants were tested, as shown in FIG. 28B. For these experiments, the CODV arm had antigen binding sites specific for TNFa (i.e., VH and VL sequences of SEQ ID NOs:168 and 169, respectively) and IL4 (i.e., VH and VL sequences of SEQ ID NOs:170 and 171, respectively), whereas the Fab arm had an antigen binding site specific for IL13 (i.e., VH and VL sequences of SEQ ID NOs:172 and 173, respectively). S354C and T366W were used for the knob mutations, and Y349C, T366S, L368A, and Y407V were used for the hole mutations.

Figure 29:
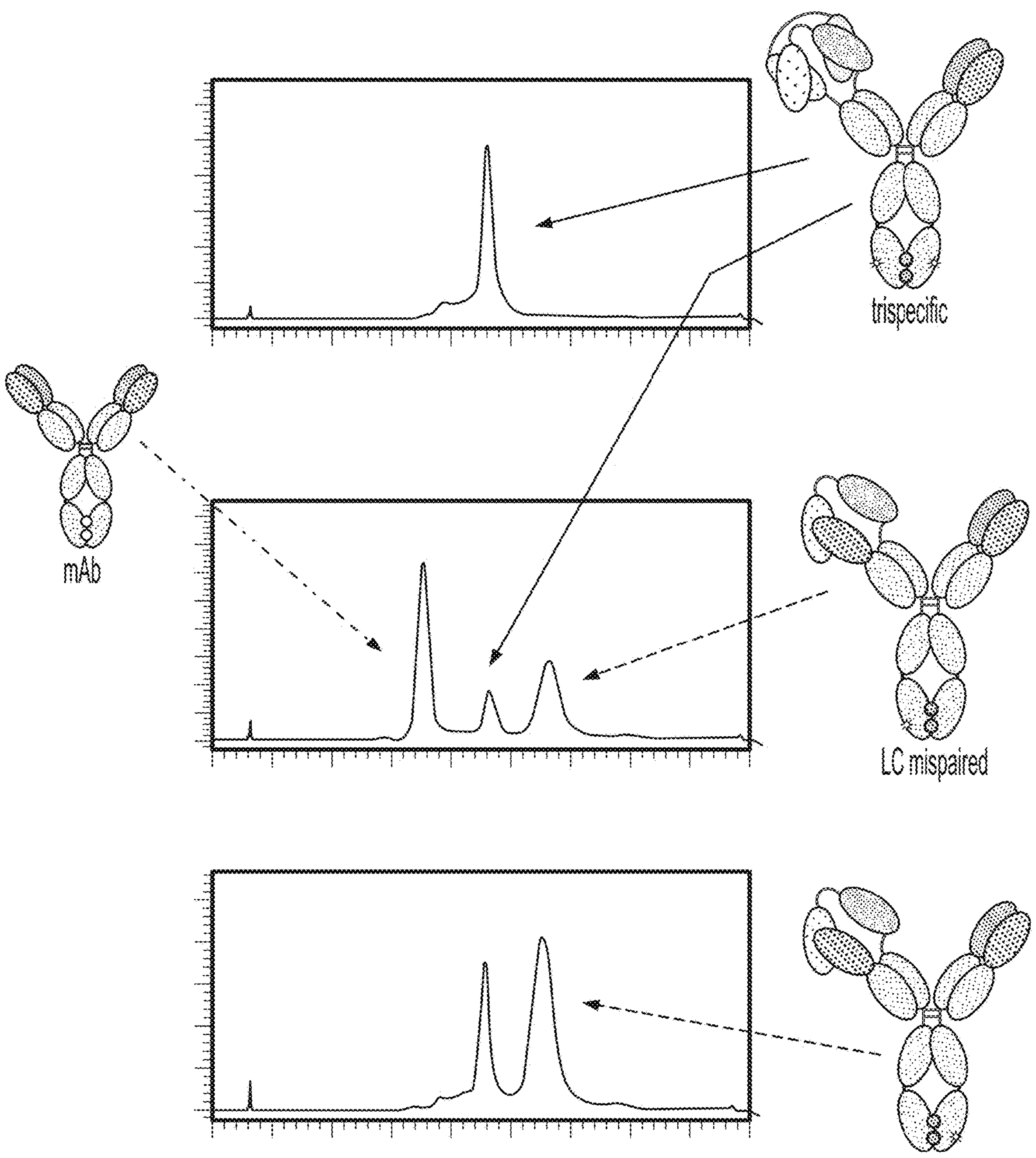
FIG. 29 shows representative chromatograms from analytical hydrophobic interaction chromatography (HIC), demonstrating that trispecific binding proteins were distinguishable from mispaired species.

Various processing steps were tested for the ability to monitor correct pairing of CODV and Fab arms (e.g., as opposed to CODV or Fab homodimers), as well as correct heavy chain-light chain pairing (e.g., as opposed to pairing between Fab arm light chain and CODV arm heavy chain, or between Fab arm heavy chain and CODV arm light chain). Analytical size exclusion chromatography (SEC) was found to be ineffective at distinguishing correct heavy chain and light chain pairing; binding proteins with Fab arm light chain mispaired with CODV heavy chain and homodimeric binding proteins with two Fab arms were found to co-elute with the desired trispecific binding proteins. However, analytical hydrophobic interaction chromatography (HIC) was found to resolve the desired trispecific binding proteins from binding proteins with Fab arm light chain mispaired with CODV heavy chain and homodimeric binding proteins with two Fab arms (FIG. 29).

Figure 30A:
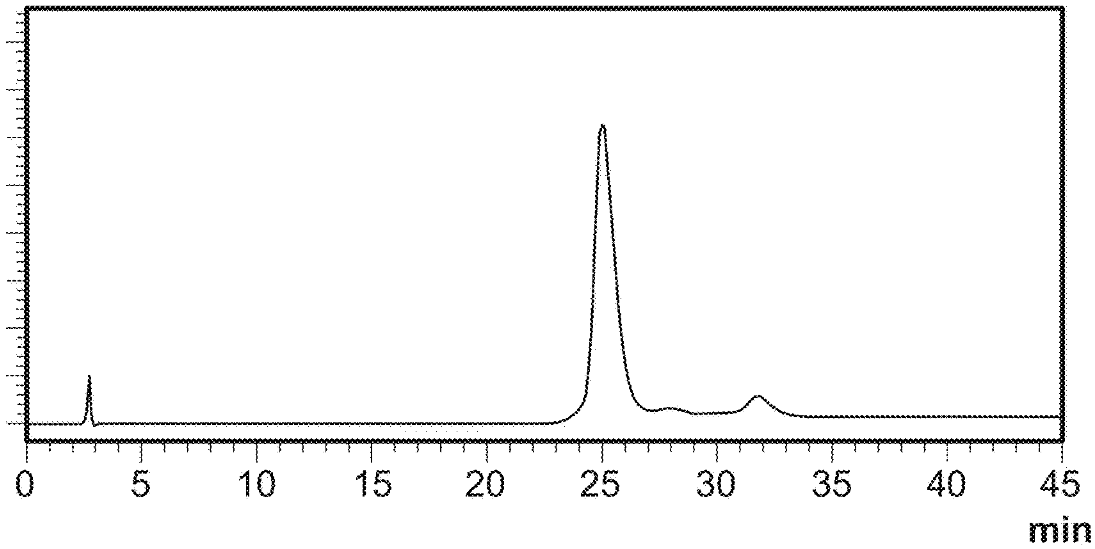
FIGS. 30A & 30B show the successful purification of a binding protein with lambda light chain for CODV arm, kappa light chain for Fab arm, knob mutations on CODV arm, hole mutations on Fab arm, and RF mutations on Fab arm by Protein A followed by KappaSelect (GE Healthcare) purification steps. Successful purification of binding protein from mispaired species was demonstrated by hydrophobic interaction chromatography (HIC.
Figure 30B:
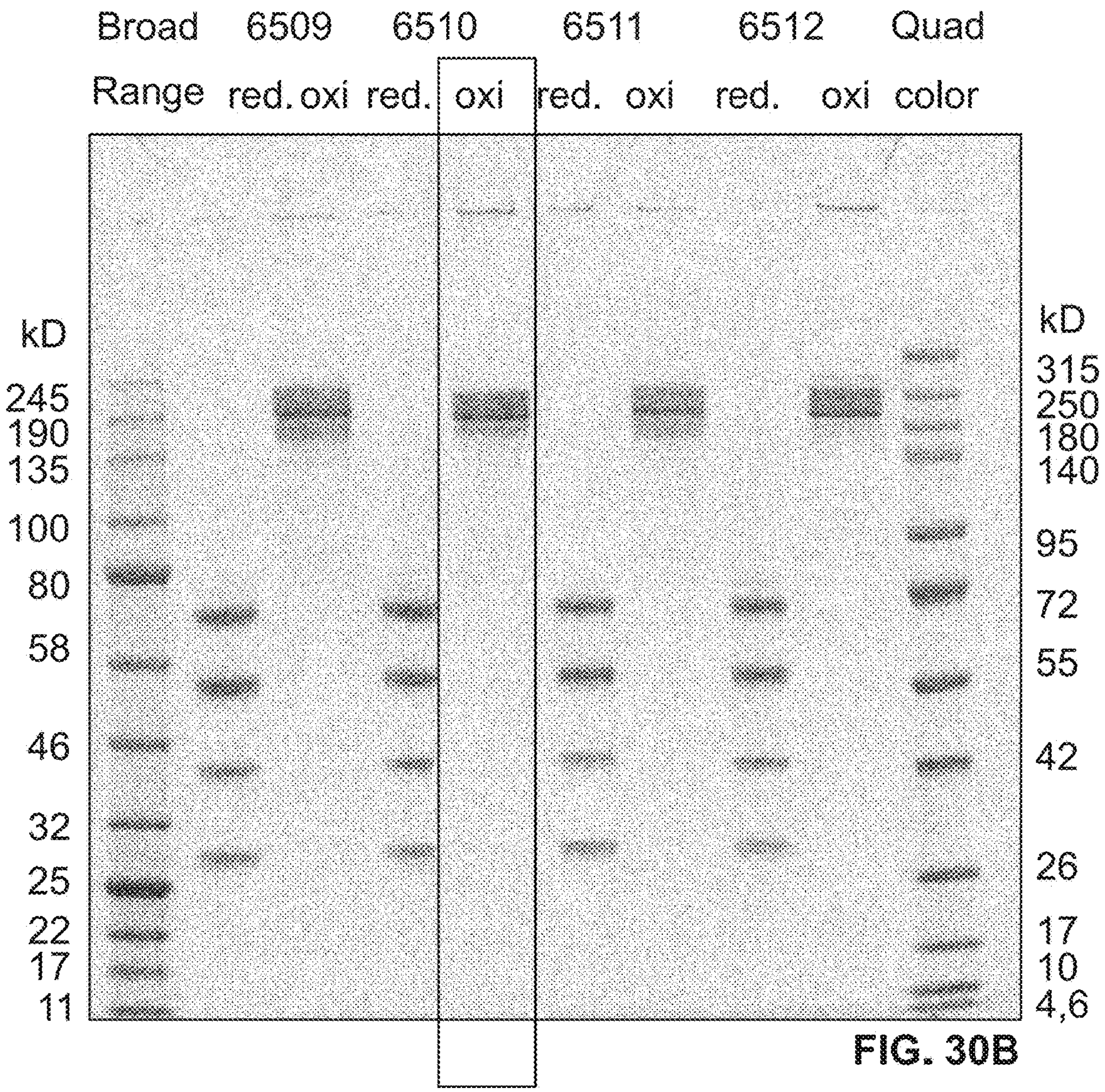

The 18 binding protein configurations shown in FIG. 28B were purified by Protein A affinity chromatography, then KappaSelect (GE Healthcare) purification. Species were monitored by HIC chromatography. One binding protein configuration was purified efficiently without inclusion of mispaired species: lambda light chain for CODV arm, kappa light chain for Fab arm, knob mutations on CODV arm, hole mutations on Fab arm, and RF mutations on Fab arm. HIC chromatography (FIG. 30A), SDS-PAGE (FIG. 30B), and intact mass analysis demonstrated that a single species corresponding to the desired trispecific binding protein was purified.

These results identify a binding protein configuration that allows for more efficient purification of binding proteins of interest away from mispaired species. Moreover, the purification process of Protein A followed by KappaSelect purification steps was shown to provide effective separation of binding proteins of interest away from mispaired species.

While the disclosure includes various embodiments, it is understood that variations and modifications will occur to those skilled in the art. Therefore, it is intended that the appended claims cover all such equivalent variations that come within the scope of the disclosure. In addition, the section headings used herein are for organizational purposes only and are not to be construed as limiting the subject matter described.

Each embodiment herein described may be combined with any other embodiment or embodiments unless clearly indicated to the contrary. In particular, any feature or embodiment indicated as being preferred or advantageous may be combined with any other feature or features or embodiment or embodiments indicated as being preferred or advantageous, unless clearly indicated to the contrary.

All references cited in this application are expressly incorporated by reference herein.

SEQUENCES

TABLE 1

Heavy and light chain SEQ ID NOs for binding proteins 1-21 and the target antigens to which the binding proteins are directed.

| Binding Protein # | SEQ ID NOs Included | Directed to: |
|---|---|---|
| 1 | 1, 2, 3, 4 | Her2 × (CD28 × CD3) |
| 2 | 1, 2, 9, 10 | Her2 × (CD28 × CD3) |
| 3 | 13, 14, 3, 4 | CD19 × (CD28 × CD3) |
| 4 | 13, 14, 9, 10 | CD19 × (CD28 × CD3) |
| 5 | 17, 18, 3, 4 | CD38 × (CD28 × CD3) |

TABLE 1-continued

Heavy and light chain SEQ ID NOs for binding proteins 1-21 and the target antigens to which the binding proteins are directed.

| Binding Protein # | SEQ ID NOs Included | Directed to: |
|---|---|---|
| 6 | 17, 18, 9, 10 | CD38 × (CD28 × CD3) |
| 7 | 21, 22, 3, 4 | LAMP1 × (CD28 × CD3) |
| 8 | 21, 22, 9, 10 | LAMP1 × (CD28 × CD3) |
| 9 | 60, 61, 62, 63 | TNFa × (IL4 × IL13) |
| 10 | 60, 61, 68, 69 | TNFa × (IL13 × IL4) |
| 11 | 60, 71, 68, 69 | TNFa × (IL13 × IL4) |
| 12 | 73, 74, 75, 76 | IL13 × (IL4 × TNFa) |
| 13 | 73, 74, 81, 82 | IL13 × (TNFa × IL4) |
| 14 | 85, 86, 87, 88 | IL4 × (IL13 × TNFa) |
| 15 | 85, 86, 93, 94 | IL4 × (TNFa × IL13) |
| 16 | 73, 74, 68, 69 | IL13 × (IL13 × IL4) |
| 17 | 85, 86, 68, 69 | IL4 × (IL13 × IL4) |
| 18 | 73, 74, 62, 63 | IL13 × (IL4 × IL13) |
| 19 | 85, 86, 62, 63 | IL4 × (IL4 × IL13) |
| 20 | 114, 115, 3, 4 | CD20 × (CD28 × CD3) |
| 21 | 114, 115, 9, 10 | CD20 × (CD28 × CD3) |

TABLE 2

Heavy and light chain sequences of binding proteins specifically directed to Her2, CD3, CD28, CD19 and/or CD20. CDR sequences are bolded and italicized.

| | | |
|---|---|---|
| | Binding Protein 1 Amino Acid Sequences | |
| Heavy chain A (Anti-Her2-H_knob) | Anti-Her2-H_Knob:<br>Evqlvesggglvqpggslrlscaas***gfnikdty***ihwvrqapgkglewvar***iyptngyt***r<br>yadsvkgrftisadtskntaylqmnstraedtavyyc***srwggdgfyamdy***wgqgtlvt<br>vssastkgpsvfplapcsrstsestaalgclvkdyfpepvtvswnsgaltsgvhtfpavlqs<br>sglyslssvvtvpssslgtktytcnvdhkpsntkvdkrveskygppcppcpapeflggps<br>vflfppkpkdtlmisrtpevtcvvvdvsqedpevqfnwyvdgvevhnaktkpreeqfn<br>styrvvsvltvlhqdwlngkeykckvsnkglpssiektiskakgqprepqvytlppcqe<br>emtknqvslwclvkgfypsdiavewesngqpennykttppvldsdgsfflyskltvdk<br>srwqegnvfscsvmhealhnhytqkslslslgk | SEQ ID NO: 1 |
| Light chain A (Anti-Her2-L) | Anti-Her2-L:<br>Diqmtqspsslsasvgdrvtitcras***qdvnta***vawyqqkpgkapklliy***sas***flysgvp<br>srfsgsrsgtdftltisslqpedfatyyc***qqhyttppt***fgqgtkveikrtvaapsvfifppsde<br>qlksgtasvvcllnnfypreakvqwkvdnalqsgnsqesvteqdskdstyslsstltlska<br>dyekhkvyacevthqglsspvtksfnrgec | SEQ ID NO: 2 |
| Heavy chain B (Anti-CD28 × Anti-CD3-H_Hole) | Anti-CD28 × Anti-CD3-H_Hole:<br>Qvqlvqsgaevvkpgasvkvsckas***gytftsyy***ihwvrqapgqglewigs***iyp***<br>***gnvnt***nyaqkfqgratltvdtsistaymelsrlrsddtavyyc***trshygldwnfdv***<br>wgkgttvtvsssqvqlvesgggvvqpgrslrlscaas***gftftkaw***mhwvrqap<br>gkqlewvaq***ikdksns***yatyyadsvkgrftisrddskntlylqmnslraedtav<br>yyc***rgvyyalspfdy***wgqgtlvtvssrtastkgpsvfplapcsrstsestaalgclv<br>kdyfpepvtvswnsgaltsgvhtfpavlqssglyslssvvtvpssslgtktytcnv<br>dhkpsntkvdkrveskygppcppcpapeflggpsvflfppkpkdtlmisrtpe<br>vtcvvvdvsqedpevqfnwyvdgvevhnaktkpreeqfnstyrvvsvltvlhq<br>dwlngkeykckvsnkglpssiektiskakgqprepqvctlppsqeemtknqvs<br>lscavkgfypsdiavewesngqpennykttppvldsdgsfflvskltvdksrwq<br>egnvfscsvmhealhnhytqkslslslgk | SEQ ID NO: 3 |
| Light chain B (Anti-CD3 × Anti-CD28-L) | Anti-CD3 × Anti-CD28-L:<br>Divmtqtplslsvtpgqpasisckss***qslvhnnanty***lswylqkpgqspqsliy***kvs***nrf<br>sgvpdrfsgsgsgtdftlkisrveaedvgvyyc***gqgtqyp***ftfgsgtkveikgqpkaapd<br>iqmtqspsslsasvgdrvtitcqas***qniyvw***lnwyqqkpgkapklliy***kas***nlhtgvpsr<br>fsgsgsgtdftltisslqpediatyyc***qqgqtypyt***fgqgtkleiktkgpsrtvaapsvfifpp<br>sdeqlksgtasvvcllnnfypreakvqwkvdnalqsgnsqesvteqdskdstyslsstltl<br>skadyekhkvyacevthqglsspvtksfnrgec | SEQ ID NO: 4 |
| | Binding Protein 1 Nucleotide Sequences | |
| Heavy chain A (Anti-Her2-H_Knob:) | Anti-Her2-H_Knob:<br>gaagtgcagctggtggaatctggcggcggactggtgcagcctggcggatctctgagactg<br>agctgtgccgccagcggcttcaacatcaaggacacctacatccactgggtgcgccaggcc<br>cctggcaagggactggaatgggtggccagaatctaccccaccaacggctacaccagatac<br>gccgacagcgtgaagggccggttcaccatcagcgccgacaccagcaagaacaccgccta<br>cctgcagatgaacagcctgcgggccgaggacaccgccgtgtactactgtagtagatgggg<br>aggcgacggcttctacgccatggactattggggccagggcaccctcgtgaccgtgtctagt<br>gcgtcgaccaagggcccatcggtgttccctctggccccttgcagcagaagcaccagcgaa<br>tctacagccgccctgggctgcctcgtgaaggactactttcccgagcccgtgaccgtgtcctg<br>gaactctggcgctctgacaagcggcgtgcacacctttccagccgtgctccagagcagcgg<br>cctgtactctctgagcagcgtcgtgacagtgcccagcagcagcctgggcaccaagaccta<br>cacctgtaacgtggaccacaagcccagcaacaccaaggtggacaagcgggtggaatcta<br>agtacggccctccctgccctccttgcccagcccctgaatttctgggcggaccctccgtgttcc<br>tgttccccccaaagcccaaggacaccctgatgatcagccggacccccgaagtgacctgcg<br>tggtggtggatgtgtcccaggaagatcccgaggtgcagttcaattggtacgtggacggcgt<br>ggaagtgcacaacgccaagaccaagcccagagaggaacagttcaacagcacctaccgg<br>gtggtgtccgtgctgaccgtgctgcaccaggactggctgaacggcaaagagtacaagtgc | SEQ ID NO: 5 |

TABLE 2-continued

Heavy and light chain sequences of binding proteins specifically directed to Her2, CD3, CD28, CD19 and/or CD20. CDR sequences are bolded and italicized.

| | | |
|---|---|---|
| | aaggtgtccaacaagggcctgcccagctccatcgagaaaaccatcagcaaggccaaggg<br>ccagccccgcgagcctcaagtgtataccctgccccccttgccaggaagagatgaccaagaa<br>ccaggtgtccctgtggtgtctcgtgaaaggcttctaccccagcgacattgccgtggaatggg<br>agagcaacggccagcccgagaacaactacaagaccaccccccctgtgctggacagcga<br>cggctcattcttcctgtactccaagctgaccgtggacaagagccggtggcaggaaggcaac<br>gtgttcagctgctccgtgatgcacgaggccctgcacaaccactacacccagaagtccctgt<br>ctctgtccctgggcaag | |
| Light chain A (Anti-Her2-L:) | Anti-Her2-L:<br>gacatccagatgacccagagccccagcagcctgtctgccagcgtgggcgacagagtgac<br>catcacctgtagagccagccaggacgtgaacaccgccgtggcctggtatcagcagaagcc<br>tggcaaggcccccaagctgctgatctacagcgccagcttcctgtacagcggcgtgcccag<br>cagattcagcggaagcagaagcggcaccgacttcaccctgaccatcagctccctgcagcc<br>cgaggacttcgccacctactactgccagcagcactacaccaccccccccacatttggccag<br>ggcaccaaggtggaaatcaagcgtacggtggccgctcccagcgtgttcatcttcccaccta<br>gcgacgagcagctgaagtccggcacagcctctgtcgtgtgcctgctgaacaacttctaccc<br>ccgcgaggccaaagtgcagtggaaggtggacaacgccctgcagagcggcaacagccag<br>gaaagcgtgaccgagcaggacagcaaggactccacctacagcctgagcagcaccctgac<br>actgagcaaggccgactacgagaagcacaaggtgtacgcctgcgaagtgacccaccagg<br>gcctgtctagccccgtgaccaagagcttcaaccggggcgagtgt | SEQ ID NO: 6 |
| Heavy chain B (Anti-CD28 × Anti-CD3-H_Hole:) | Anti-CD28 × Anti-CD3-H_Hole:<br>caggtgcagctggtgcagtctggcgccgaggtcgtgaaacctggcgcctctgtgaaggtgt<br>cctgcaaggccagcggctacacctttaccagctactacatccactgggtgcgccaggcccc<br>tggacagggactggaatggatcggcagcatctaccccggcaacgtgaacaccaactacgc<br>ccagaagttccagggcagagccaccctgaccgtggacaccagcatcagcaccgcctacat<br>ggaactgagccggctgagaagcgacgacaccgccgtgtactactgcacccggtcccacta<br>cggcctggattggaacttcgacgtgtggggcaagggcaccaccgtgacagtgtctagcag<br>ccaggtgcagctggtggaatctggcggcggagtggtgcagcctggcagaagcctgagac<br>tgagctgtgccgccagcggcttcaccttcaccaaggcctggatgcactgggtgcgccagg<br>cccctggaaagcagctggaatgggtggcccagatcaaggacaagagcaacagctacgcc<br>acctactacgccgacagcgtgaagggccggttcaccatcagccgggacgacagcaagaa<br>caccctgtacctgcagatgaacagcctgcgggccgaggacaccgccgtgtactactgtcg<br>gggcgtgtactatgccctgagccccttcgattactggggccagggaaccctcgtgaccgtg<br>tctagtcggaccgccagcacaaagggcccatcggtgttccctctggccccttgcagcagaa<br>gcaccagcgaatctacagccgccctgggctgcctcgtgaaggactactttcccgagcccgt<br>gaccgtgtcctggaactctggcgctctgacaagcggcgtgcacacctttccagccgtgctc<br>cagagcagcggcctgtactctctgagcagcgtcgtgacagtgcccagcagcagcctgggc<br>accaagacctacacctgtaacgtggaccacaagcccagcaacaccaaggtggacaagcg<br>ggtggaatctaagtacggccctccctgccctccttgcccagcccctgaatttctgggcggac<br>cctccgtgttcctgttcccccccaaagcccaaggacaccctgatgatcagccggacccccga<br>agtgacctgcgtggtggtggatgtgtcccaggaagatcccgaggtgcagttcaattggtac<br>gtggacggcgtggaagtgcacaacgccaagaccaagcccagagaggaacagttcaaca<br>gcacctaccgggtggtgtccgtgctgaccgtgctgcaccaggactggctgaacggcaaag<br>agtacaagtgcaaggtgtccaacaagggcctgcccagctccatcgagaaaaccatcagca<br>aggccaagggccagccccgcgagcctcaagtgtgtaccctgcccccctagccaggaagag<br>atgaccaagaaccaggtgtccctgagctgtgccgtgaaaggcttctaccccagcgacattg<br>ccgtggaatgggagagcaacggccagcccgagaacaactacaagaccaccccccctgtg<br>ctggacagcgacggctcattcttcctggtgtccaagctgaccgtggacaagagccggtggc<br>aggaaggcaacgtgttcagctgctccgtgatgcacgaggccctgcacaaccactacaccc<br>agaagtccctgtctctgtccctgggcaag | SEQ ID NO: 7 |
| Light chain B (Anti-CD3 × Anti-CD28-L:) | Anti-CD3 × Anti-CD28-L:<br>gacatcgtgatgacccagacccccctgagcctgagcgtgacacctggacagcctgccagc<br>atcagctgcaagagcagccagagcctggtgcacaacaacgccaacacctacctgagctg<br>gtatctgcagaagcccggccagagccccagtccctgatctacaaggtgtccaacagattc<br>agcggcgtgcccgacagattctccggcagcggctctggcaccgacttcaccctgaagatc<br>agccgggtggaagccgaggacgtgggcgtgtactattgtggccagggcacccagtaccc<br>cttcacctttggcagcggcaccaaggtggaaatcaagggccagcccaaggccgcccccg<br>acatccagatgacccagagccccagcagcctgtctgccagcgtgggcgacagagtgacc<br>atcacctgtcaggccagccagaacatctacgtgtggctgaactggtatcagcagaagcccg<br>gcaaggcccccaagctgctgatctacaaggccagcaacctgcacaccggcgtgcccagc<br>agattttctggcagcggctccggcaccgacttcaccctgacaatcagctccctgcagcccg<br>aggacattgccacctactactgccagcagggccagacctacccctacacctttggccaggg<br>caccaagctggaaatcaagaccaagggccccagccgtacggtggccgctcccagcgtgtt<br>catcttcccacctagcgacgagcagctgaagtccggcacagcctctgtcgtgtgcctgctga<br>acaacttctacccccgcgaggccaaagtgcagtggaaggtggacaacgccctgcagagc<br>ggcaacagccaggaaagcgtgaccgagcaggacagcaaggactccacctacagcctga<br>gcagcaccctgacactgagcaaggccgactacgagaagcacaaggtgtacgcctgcgaa<br>gtgacccaccagggcctgtctagccccgtgaccaagagcttcaaccggggcgagtgt | SEQ ID NO: 8 |

TABLE 2-continued

Heavy and light chain sequences of binding proteins specifically directed to Her2, CD3, CD28, CD19 and/or CD20. CDR sequences are bolded and italicized.

| Binding Protein 2 Amino Acid Sequences | | |
|---|---|---|
| Heavy chain A (Anti-Her2-H_knob) | Anti-Her2-H_Knob:<br>Evqlvesggglvqpggslrlscaas***gfnikdty***ihwvrqapgkglewvar***iyptngyt***r<br>yadsvkgrftisadtskntaylqmnslraedtavyyc***srwggdgfyamdy***wgqgtlvt<br>vssastkgpsvfplapcsrstsestaalgclvkdyfpepvtvswnsgaltsgvhtfpavlqs<br>sglyslssvvtvpssslgtktytcnvdhkpsntkvdkrveskygppcppcpapeflggps<br>vflfppkpkdtlmisrtpevtcvvvdvsqedpevqfnwyvdgvevhnaktkpreeqfn<br>styrvvsvltvlhqdwlngkeykckvsnkglpssiektiskakgqprepqvytlppcqe<br>emtknqvslwclvkgfypsdiavewesngqpennykttppvldsdgsfflyskltvdk<br>srwqegnvfscsvmhealhnhytqkslslslgk | SEQ ID NO: 1 |
| Light chain A (Anti-Her2-L) | Anti-Her2-L:<br>Diqmtqspsslsasvgdrvtitcras***qdvnta***vawyqqkpgkapklliy***sas***flysgvp<br>srfsgsrsgtdftltisslqpedfatyyc***qqhyttppt***fgqgtkveikrtvaapsvfifppsde<br>qlksgtasvvcllnnfypreakvqwkvdnalqsgnsqesvteqdskdstyslsstltlska<br>dyekhkvyacevthqglsspvtksfnrgec | SEQ ID NO: 2 |
| Heavy chain B (Anti-CD28 × Anti-CD3-H_Hole) | Anti-CD28 × Anti-CD3-H_Hole:<br>Qvqlqesgpglvkpsqtlsltctvsgfslsdygvhwvrqppgkglewlgviwa<br>gggtnynpslksrktiskdtsknqvslklssvtaadtavyycardkgysyyysm<br>dywgqgttvtvsssqvqlvesgggvvqpgrslrlscaasgftftkawmhwvrq<br>apgkqlewvaqikdksnsyatyyadsvkgrftisrddskntlylqmnslraedta<br>vyycrgvyyalspfdywgqgtlvtvssrtastkgpsvfplapcsrstsestaalgcl<br>vkdyfpepvtvswnsgaltsgvhtfpavlqssglyslssvvtvpssslgtktytcn<br>vdhkpsntkvdkrveskygppcppcpapeflggpsvflfppkpkdtlmisrtpe<br>vtcvvvdvsqedpevqfnwyvdgvevhnaktkpreeqfnstyrvvsvltvlhq<br>dwlngkeykckvsnkglpssiektiskakgqprepqvctlppsqeemtknqvs<br>lscavkgfypsdiavewesngqpennykttppvldsdgsfflvskltvdksrwq<br>egnvfscsvmhealhnhytqkslslslgk | SEQ ID NO: 9 |
| Light chain B (Anti-CD3 × Anti-CD28-L) | Anti-CD3 × Anti-CD28-L:<br>Divmtqtplslsvtpgqpasisckssqslvhnnantylswylqkpgqspqsliykvsnrf<br>sgvpdrfsgsgsgtdftlkisrveaedvgvyycgqgtqypftfgsgtkveikgqpkaapd<br>ivltqspaslayspgqratitcrasesveyyvtslmqwyqqkpgqppkllifaasnvesg<br>vparfsgsgsgtdftltinpveandvanyycqqsrkvpytfgqgtkleiktkgpsrtvaap<br>svfifppsdeqlksgtasvvcllnnfypreakvqwkvdnalqsgnsqesvteqdskdst<br>yslsstltlskadyekhkvyacevthqglsspvtksfnrgec | SEQ ID NO: 10 |

| Binding Protein 2 Nucleotide Sequences | | |
|---|---|---|
| Heavy chain A (Anti-Her2-H_Knob:) | Anti-Her2-H_Knob:<br>gaagtgcagctggtggaatctggcggcggactggtgcagcctggcggatctctgagactg<br>agctgtgccgccagcggcttcaacatcaaggacacctacatccactgggtgcgccaggcc<br>cctggcaagggactggaatgggtggccagaatctaccccaccaacggctacaccagatac<br>gccgacagcgtgaagggccggttcaccatcagcgccgacaccagcaagaacaccgccta<br>cctgcagatgaacagcctgcgggccgaggacaccgccgtgtactactgtagtagatgggg<br>aggcgacggcttctacgccatggactattggggccagggcaccctcgtgaccgtgtctagt<br>gcgtcgaccaagggcccatcggtgttccctctggccccttgcagcagaagcaccagcgaat<br>ctacagccgccctgggctgcctcgtgaaggactactttcccgagcccgtgaccgtgtcctgg<br>aactctggcgctctgacaagcggcgtgcacacctttccagccgtgctccagagcagcggcc<br>tgtactctctgagcagcgtcgtgacagtgcccagcagcagcctgggcaccaagacctacac<br>ctgtaacgtggaccacaagcccagcaacaccaaggtggacaagcgggtggaatctaagta<br>cggccctccctgccctccttgcccagcccctgaatttctgggcggaccctccgtgttcctgttc<br>cccccaaagcccaaggacaccctgatgatcagccggacccccgaagtgacctgcgtggtg<br>gtggatgtgtcccaggaagatcccgaggtgcagttcaattggtacgtggacggcgtggaag<br>tgcacaacgccaagaccaagcccagagaggaacagttcaacagcacctaccgggtggtgt<br>ccgtgctgaccgtgctgcaccaggactggctgaacggcaaagagtacaagtgcaaggtgt<br>ccaacaagggcctgcccagctccatcgagaaaaccatcagcaaggccaagggccagccc<br>cgcgagcctcaagtgtataccctgcccccttgccaggaagagatgaccaagaaccaggtgt<br>ccctgtggtgtctcgtgaaaggcttctaccccagcgacattgccgtggaatgggagagcaa<br>cggccagcccgagaacaactacaagaccaccccccctgtgctggacagcgacggctcatt<br>cttcctgtactccaagctgaccgtggacaagagccggtggcaggaaggcaacgtgttcagc<br>tgctccgtgatgcacgaggccctgcacaaccactacacccagaagtccctgtctctgtccct<br>gggcaag | SEQ ID NO: 5 |
| Light chain A (Anti-Her2-L:) | Anti-Her2-L:<br>gacatccagatgacccagagccccagcagcctgtctgccagcgtgggcgacagagtgac<br>catcacctgtagagccagccaggacgtgaacaccgccgtggcctggtatcagcagaagcc<br>tggcaaggcccccaagctgctgatctacagcgccagcttcctgtacagcggcgtgcccagc<br>agattcagcggaagcagaagcggcaccgacttcaccctgaccatcagctccctgcagccc<br>gaggacttcgccacctactactgccagcagcactacaccacccccccacatttggccagg<br>gcaccaaggtggaaatcaagcgtacggtggccgctcccagcgtgttcatcttcccacctag<br>cgacgagcagctgaagtccggcacagcctctgtcgtgtgcctgctgaacaacttctacccc<br>gcgaggccaaagtgcagtggaaggtggacaacgccctgcagagcggcaacagccagga<br>aagcgtgaccgagcaggacagcaaggactccacctacagcctgagcagcaccctgacac | SEQ ID NO: 6 |

TABLE 2-continued

Heavy and light chain sequences of binding proteins specifically directed to Her2, CD3, CD28, CD19 and/or CD20. CDR sequences are bolded and italicized.

| | | |
|---|---|---|
| | tgagcaaggccgactacgagaagcacaaggtgtacgcctgcgaagtgacccaccagggc<br>ctgtctagccccgtgaccaagagcttcaaccggggcgagtgt | |
| Heavy chain B (Anti-CD28 × Anti-CD3-H_Hole:) | Anti-CD28 × Anti-CD3_Hole:<br>caggtgcagctgcaggaatctggccctggcctcgtgaagcctagccagaccctgagcctg<br>acctgtaccgtgtccggcttcagcctgagcgactacggcgtgcactgggtgcgccagccac<br>ctggaaaaggcctggaatggctgggcgtgatctgggctggcggaggcaccaactacaacc<br>ccagcctgaagtccagaaagaccatcagcaaggacaccagcaagaaccaggtgtccctg<br>aagctgagcagcgtgacagccgccgataccgccgtgtactactgcgccagagacaaggg<br>ctacagctactactacagcatggactactggggccagggcaccaccgtgaccgtgtcatcct<br>ctcaggtgcagctggtggaatctggcggcggagtggtgcagcctggcagaagcctgagac<br>tgagctgtgccgccagcggcttcaccttcaccaaggcctggatgcactgggtgcgccaggc<br>ccctggaaagcagctggaatgggtggcccagatcaaggacaagagcaacagctacgcca<br>cctactacgccgacagcgtgaagggccggttcaccatcagccgggacgacagcaagaac<br>accctgtacctgcagatgaacagcctgcgggccgaggacaccgccgtgtactactgtcgg<br>ggcgtgtactatgccctgagccccttcgattactggggccagggaaccctcgtgaccgtgtc<br>tagtcggaccgcttcgaccaagggcccatcggtgttccctctggccccttgcagcagaagc<br>accagcgaatctacagccgccctgggctgcctcgtgaaggactactttcccgagcccgtga<br>ccgtgtcctggaactctggcgctctgacaagcggcgtgcacacctttccagccgtgctccag<br>agcagcggcctgtactctctgagcagcgtcgtgacagtgcccagcagcagcctgggcacc<br>aagacctacacctgtaacgtggaccacaagcccagcaacaccaaggtggacaagcgggt<br>ggaatctaagtacggccctccctgccctccttgcccagcccctgaatttctgggcggaccct<br>ccgtgttcctgttcccccaaagcccaaggacaccctgatgatcagccggacccccgaagt<br>gacctgcgtggtggtggatgtgtcccaggaagatcccgaggtgcagttcaattggtacgtgg<br>acggcgtggaagtgcacaacgccaagaccaagcccagagaggaacagttcaacagcac<br>ctaccgggtggtgtccgtgctgaccgtgctgcaccaggactggctgaacggcaaagagta<br>caagtgcaaggtgtccaacaagggcctgcccagctccatcgagaaaaccatcagcaaggc<br>caagggccagccccgcgagcctcaagtgtgtaccctgcccccctagccaggaagagatga<br>ccaagaaccaggtgtccctgagctgtgccgtgaaaggcttctaccccagcgacattgccgt<br>ggaatgggagagcaacggccagcccgagaacaactacaagaccacccccccctgtgctgg<br>acagcgacggctcattcttcctggtgtccaagctgaccgtggacaagagccggtggcagga<br>aggcaacgtgttcagctgctccgtgatgcacgaggccctgcacaaccactacacccagaa<br>gtccctgtctctgtccctgggcaag | SEQ ID NO: 11 |
| Light chain B (Anti-CD3 × Anti-CD28-L:) | Anti-CD3 × Anti-CD28-L:<br>gacatcgtgatgacccagacccccctgagcctgagcgtgacacctggacagcctgccagc<br>atcagctgcaagagcagccagagcctggtgcacaacaacgccaacacctacctgagctgg<br>tatctgcagaagcccggccagagcccccagtccctgatctacaaggtgtccaacagattca<br>gcggcgtgcccgacagattctccggcagcggctctggcaccgacttcaccctgaagatca<br>gccgggtggaagccgaggacgtgggcgtgtactattgtggccagggcacccagtacccct<br>tcacctttggcagcggcaccaaggtggaaatcaagggccagcccaaggccgcccccgac<br>atcgtgctgacacagagccctgctagcctggccgtgtctcctggacagagggccaccatca<br>cctgtagagccagcgagagcgtggaatattacgtgaccagcctgatgcagtggtatcagca<br>gaagcccggccagccccccaagctgctgattttcgccgccagcaacgtggaaagcggcgt<br>gccagccagattttccggcagcggctctggcaccgacttcaccctgaccatcaaccccgtg<br>gaagccaacgacgtggccaactactactgccagcagagccggaaggtgccctacaccttt<br>ggccagggcaccaagctggaaatcaagaccaagggccccagccgtacggtggccgctc<br>ccagcgtgttcatcttcccacctagcgacgagcagctgaagtccggcacagcctctgtcgtg<br>tgcctgctgaacaacttctacccccgcgaggccaaagtgcagtggaaggtggacaacgcc<br>ctgcagagcggcaacagccaggaaagcgtgaccgagcaggacagcaaggactccacct<br>acagcctgagcagcaccctgacactgagcaaggccgactacgagaagcacaaggtgtac<br>gcctgcgaagtgacccaccagggcctgtctagccccgtgaccaagagcttcaaccggggc<br>gagtgt | SEQ ID NO: 12 |

Binding Protein 3 Amino Acid Sequences

| | | |
|---|---|---|
| Heavy chain A (Anti-CD19(B34)-H_knob) | Anti-CD19(B34)-H_Knob:<br>Qvqlvqsgaevkkpgssvkvsckasgyafssywmnwvrqapgqglewigqiwpg<br>dgdtnynqkfkgratltadeststaymelsslrsedtavyycarretttvgryyyamdyw<br>gqgttvtvssastkgpsvfplapcsrstsestaalgclvkdyfpepvtvswnsgaltsgvht<br>fpavlqssglyslssvvtvpssslgtktytcnvdhkpsntkvdkrveskygppcppcpap<br>eflggpsvflfppkpkdtlmisrtpevtcvvvdvsqedpevqfnwyvdgvevhnaktk<br>preeqfnstyrvvsvltvlhqdwlngkeykckvsnkglpssiektiskakgqprepqvyt<br>lppcqeemtknqvslwclvkgfypsdiavewesngqpennykttppvldsdgsfflys<br>kltvdksrwqegnvfscsvmhealhnhytqkslslslgk | SEQ ID NO: 13 |
| Light chain A (Anti-CD19(B34)-L) | Anti-CD19(B34)-L:<br>Dlvltqspaslavspgqratitckasqsvdydgdsylnwyqqkpgqppklliydasnlvs<br>gvparfsgsgsgtdftltinpveandtanyycqqstedpwtfgqgtkleikrtvaapsvfif<br>ppsdeqlksgtasvvcllnnfypreakvqwkvdnalqsgnsqesvteqdskdstyslsst<br>ltlskadyekhkvyacevthqglsspvtksfnrgec | SEQ ID NO: 14 |

TABLE 2-continued

| Heavy and light chain sequences of binding proteins specifically directed to Her2, CD3, CD28, CD19 and/or CD20. CDR sequences are bolded and italicized. | | |
|---|---|---|
| Heavy chain B (Anti-CD28 × Anti-CD3-H_Hole) | Anti-CD28 × Anti-CD3-H_Hole:<br>Qvqlvqsgaevvkpgasvkvsckas***gytftsyy***ihwvrqapgqglewigs***iyp***<br>***gnvnt***nyaqkfqgratltvdtsistaymelsrlrsddtavyyc***trshygldwnfdv***<br>wgkgttvtvsssqvqlvesgggvvqpgrslrlscaas***gftftkaw***mhwvrqap<br>gkqlewvaq***ikdksns***yatyyadsvkgrftisrddskntlylqmnslraedtavy<br>yc***rgvyyalspfdy***wgqgtlvtvssrtastkgpsvfplapcsrstsestaalgclvk<br>dyfpepvtvswnsgaltsgvhtfpavlqssglyslssvvtvpssslgtktytcnvd<br>hkpsntkvdkrveskygppcppcpapeflggpsvflfppkpkdtlmisrtpevt<br>cvvvdvsqedpevqfnwyvdgvevhnaktkpreeqfnstyrvvsvltvlhqd<br>wlngkeykckvsnkglpssiektiskakgqprepqvctlppsqeemtknqvsls<br>cavkgfypsdiavewesngqpennykttppvldsdgsfflvskltvdksrwqeg<br>nvfscsvmhealhnhytqkslslslgk | SEQ ID NO: 3 |
| Light chain B (Anti-CD3 × Anti-CD28-L) | Anti-CD3 × Anti-CD28-L:<br>Divmtqtplslsvtpgqpasiscks***sqslvhnnanty***lswylqkpgqspqsliy***kvs***nrf<br>sgvpdrfsgsgsgtdftlkisrveaedvgvyyc***gqgtqyp***ftfgsgtkveikgqpkaapdi<br>qmtqspsslsasvgdrvtitcqas***qniyvw***lnwyqqkpgkapkiliy***kas***nlhtgvpsrf<br>sgsgsgtdftltisslqpediatyyc***qqgqtypyt***fgqgtkleiktkgpsrtvaapsvfifpps<br>deqlksgtasvvcllnnfypreakvqwkvdnalqsgnsqesvteqdskdstyslsstltls<br>kadyekhkvyacevthqglsspvtksfnrgec | SEQ ID NO: 4 |
| Binding Protein 3 Nucleotide Sequence | | |
| Heavy chain A (Anti-CD19(B34)-H_Knob) | Anti-CD19(B34)-H_Knob:<br>caggtgcagctggtgcagagcggcgccgaagtgaagaagcctggcagcagcgtgaagg<br>tgagctgcaaggccagcggctatgccttcagcagctactggatgaactgggtgaggcagg<br>cacctggccagggcctggagtggataggccaaatatggcctggcgatggcgacaccaact<br>acaaccagaagttcaagggcagagcgaccttgaccgccgacgagagcaccagcaccgc<br>gtacatggagctgagcagcctgaggagcgaggacaccgccgtgtactattgcgccagaag<br>ggagaccaccaccgtgggcaggtactactacgccatggactactggggccagggaacca<br>ccgtgaccgtgagcagcgcctcgaccaagggcccatcggtgttccctctggccccttgcag<br>cagaagcaccagcgaatctacagccgccctgggctgcctcgtgaaggactactttcccgag<br>cccgtgaccgtgtcctggaactctggcgctctgacaagcggcgtgcacacctttccagccgt<br>gctccagagcagcggcctgtactctctgagcagcgtcgtgacagtgcccagcagcagcct<br>gggcaccaagacctacacctgtaacgtggaccacaagcccagcaacaccaaggtggaca<br>agcgggtggaatctaagtacggccctccctgccctccttgcccagcccctgaatttctgggc<br>ggaccctccgtgttcctgttccccccaaagcccaaggacaccctgatgatcagccggaccc<br>ccgaagtgacctgcgtggtggtggatgtgtcccaggaagatcccgaggtgcagttcaattg<br>gtacgtggacggcgtggaagtgcacaacgccaagaccaagcccagagaggaacagttca<br>acagcacctaccgggtggtgtccgtgctgaccgtgctgcaccaggactggctgaacggca<br>aagagtacaagtgcaaggtgtccaacaagggcctgcccagctccatcgagaaaaccatca<br>gcaaggccaagggccagccccgcgagcctcaagtgtataccctgcccccttgccaggaa<br>gagatgaccaagaaccaggtgtccctgtggtgtctcgtgaaaggcttctaccccagcgacat<br>tgccgtggaatgggagagcaacggccagcccgagaacaactacaagaccaccccccctg<br>tgctggacagcgacggctcattcttcctgtactccaagctgaccgtggacaagagccggtg<br>gcaggaaggcaacgtgttcagctgctccgtgatgcacgaggccctgcacaaccactacac<br>ccagaagtccctgtctctgtccctgggcaag | SEQ ID NO: 15 |
| Light chain A (Anti-CD19(B34)-L) | Anti-CD19(B34)-L:<br>gacctcgtgctgacccagagccctgcgagcctggctgtgagccctggccagagagccacc<br>atcacctgcaaagccagccagagcgtggactacgacggcgacagctacctcaactggtac<br>cagcagaagcctggccagcccccaagctgctgatttacgatgccagcaacctggtgagc<br>ggcgtgcctgctagattcagcggctccggcagcggcaccgacttcaccctgaccatcaacc<br>ccgtggaggccaacgacaccgccaactactactgccagcagagcacggaggacccctgg<br>accttcggccagggcacaaagctggagatcaagcgtacggtggccgctcccagcgtgttc<br>atcttcccacctagcgacgagcagctgaagtccggcacagcctctgtcgtgtgcctgctgaa<br>caacttctaccccgcgaggccaaagtgcagtggaaggtggacaacgccctgcagagcg<br>gcaacagccaggaaagcgtgaccgagcaggacagcaaggactccacctacagcctgag<br>cagcaccctgacactgagcaaggccgactacgagaagcacaaggtgtacgcctgcgaag<br>tgacccaccagggcctgtctagccccgtgaccaagagcttcaaccggggcgagtgt | SEQ ID NO: 16 |
| Heavy chain B (Anti-CD28 × Anti-CD3-H_Hole) | Anti-CD28 × Anti-CD3-H_Hole:<br>caggtgcagctggtgcagtctggcgccgaggtcgtgaaacctggcgcctctgtgaaggtgt<br>cctgcaaggccagcggctacacctttaccagctactacatccactgggtgcgccaggcccc<br>tggacagggactggaatggatcggcagcatctaccccggcaacgtgaacaccaactacgc<br>ccagaagttccagggcagagccaccctgaccgtggacaccagcatcagcaccgcctacat<br>ggaactgagccggctgagaagcgacgacaccgccgtgtactactgcacccggtcccacta<br>cggcctggattggaacttcgacgtgtggggcaagggcaccaccgtgacagtgtctagcag<br>ccaggtgcagctggtggaatctggcggcggagtggtgcagcctggcagaagcctgagact<br>gagctgtgccgccagcggcttcaccttcaccaaggcctggatgcactgggtgcgccaggc<br>ccctggaaagcagctggaatgggtggcccagatcaaggacaagagcaacagctacgcca<br>cctactacgccgacagcgtgaagggccggttcaccatcagccgggacgacagcaagaac<br>accctgtacctgcagatgaacagcctgcgggccgaggacaccgccgtgtactactgtcgg<br>ggcgtgtactatgccctgagccccttcgattactggggccagggaaccctcgtgaccgtgtc<br>tagtcggaccgccagcacaaagggcccatcggtgttccctctggccccttgcagcagaagc<br>accagcgaatctacagccgccctgggctgcctcgtgaaggactactttcccgagcccgtga | SEQ ID NO: 7 |

TABLE 2-continued

| Heavy and light chain sequences of binding proteins specifically directed to Her2, CD3, CD28, CD19 and/or CD20. CDR sequences are bolded and italicized. | | |
|---|---|---|
| | ccgtgtcctggaactctggcgctctgacaagcggcgtgcacacctttccagccgtgctccag<br>agcagcggcctgtactctctgagcagcgtcgtgacagtgcccagcagcagcctgggcacc<br>aagacctacacctgtaacgtggaccacaagcccagcaacaccaaggtggacaagcgggt<br>ggaatctaagtacggccctccctgccctccttgcccagcccctgaatttctgggcggaccct<br>ccgtgttcctgttcccccaaagcccaaggacaccctgatgatcagccggacccccgaagt<br>gacctgcgtggtggtggatgtgtcccaggaagatcccgaggtgcagttcaattggtacgtgg<br>acggcgtggaagtgcacaacgccaagaccaagcccagagaggaacagttcaacagcac<br>ctaccgggtggtgtccgtgctgaccgtgctgcaccaggactggctgaacggcaaagagta<br>caagtgcaaggtgtccaacaagggcctgcccagctccatcgagaaaaccatcagcaaggc<br>caagggccagccccgcgagcctcaagtgtgtaccctgcccccctagccaggaagagatga<br>ccaagaaccaggtgtccctgagctgtgccgtgaaaggcttctaccccagcgacattgccgt<br>ggaatgggagagcaacggccagcccgagaacaactacaagaccacccccccctgtgctgg<br>acagcgacggctcattcttcctggtgtccaagctgaccgtggacaagagccggtggcagga<br>aggcaacgtgttcagctgctccgtgatgcacgaggccctgcacaaccactacacccagaa<br>gtccctgtctctgtccctgggcaag | |
| Light chain B (Anti-CD3 × Anti-CD28-L:) | Anti-CD3 × Anti-CD28-L:<br>gacatcgtgatgacccagacccccctgagcctgagcgtgacacctggacagcctgccagc<br>atcagctgcaagagcagccagagcctggtgcacaacaacgccaacacctacctgagctgg<br>tatctgcagaagcccggccagagcccccagtccctgatctacaaggtgtccaacagattca<br>gcggcgtgcccgacagattctccggcagcggctctggcaccgacttcaccctgaagatca<br>gccgggtggaagccgaggacgtgggcgtgtactattgtggccagggcacccagtacccct<br>tcacctttggcagcggcaccaaggtggaaatcaagggccagcccaaggccgcccccgac<br>atccagatgacccagagccccagcagcctgtctgccagcgtgggcgacagagtgaccatc<br>acctgtcaggccagccagaacatctacgtgtggctgaactggtatcagcagaagcccggca<br>aggcccccaagctgctgatctacaaggccagcaacctgcacaccggcgtgcccagcagat<br>tttctggcagcggctccggcaccgacttcaccctgacaatcagctccctgcagcccgagga<br>cattgccacctactactgccagcagggccagacctacccctacacctttggccagggcacc<br>aagctggaaatcaagaccaagggccccagccgtacggtggccgctcccagcgtgttcatct<br>tcccacctagcgacgagcagctgaagtccggcacagcctctgtcgtgtgcctgctgaacaa<br>cttctacccccgcgaggccaaagtgcagtggaaggtggacaacgccctgcagagcggca<br>acagccaggaaagcgtgaccgagcaggacagcaaggactccacctacagcctgagcag<br>caccctgacactgagcaaggccgactacgagaagcacaaggtgtacgcctgcgaagtga<br>cccaccagggcctgtctagccccgtgaccaagagcttcaaccggggcgagtgt | SEQ ID NO: 8 |
| | Binding Protein 4 Amino Acid Sequences | |
| Heavy chain A (Anti-CD19(B34)-H_knob) | Anti-CD19(B34)-H_Knob:<br>Qvqlvqsgaevkkpgssvkvsckasgyafssywmnwvrqapgqglewigqiwpg<br>dgdtnynqkfkgratltadeststaymelsslrsedtavyycarretttvgryyyamdyw<br>gqgttvtvssastkgpsvfplapcsrstsestaalgclvkdyfpepvtvswnsgaltsgvht<br>fpavlqssglyslssvvtvpssslgtktytcnvdhkpsntkvdkrveskygppcppcpap<br>eflggpsvflfppkpkdtlmisrtpevtcvvvdvsqedpevqfnwyvdgvevhnaktk<br>preeqfnstyrvvsvltvlhqdwlngkeykckvsnkglpssiektiskakgqprepqvyt<br>lppcqeemtknqvslwclvkgfypsdiavewesngqpennykttppvldsdgsfflys<br>kltvdksrwqegnvfscsvmhealhnhytqkslslslgk | SEQ ID NO: 13 |
| Light chain A (Anti-CD19(B34)-L) | Anti-CD19(B34)-L:<br>Dlvltqspaslavspgqratitckasqsvdydgdsylnwyqqkpgqppklliydasnlvs<br>gvparfsgsgsgtdftltinpveandtanyycqqstedpwtfgqgtkleikrtvaapsvfif<br>ppsdeqlksgtasvvcllnnfypreakvqwkvdnalqsgnsqesvteqdskdstyslsst<br>ltlskadyekhkvyacevthqglsspvtksfnrgec | SEQ ID NO: 14 |
| Heavy chain B (Anti-CD28 × Anti-CD3-H_Hole) | Anti-CD28 × Anti-CD3-H_Hole:<br>Qvqlqesgpglvkpsqtlsltctvsgfslsdygvhwvrqppgkglewlgviwa<br>gggtnynpslksrktiskdtsknqvslklssvtaadtavyycardkgysyyysmd<br>ywgqgttvtvsssqvqlvesgggvvqpgrslrlscaasgftftkawmhwvrqa<br>pgkqlewvaqikdksnsyatyyadsvkgrftisrddskntlylqmnslraedtav<br>yycrgvyyalspfdywgqgtivtvssrtastkgpsvfplapcsrstsestaalgclv<br>kdyfpepvtvswnsgaltsgvhtfpavlqssglyslssvvtvpssslgtktytcnv<br>dhkpsntkvdkrveskygppcppcpapeflggpsvflfppkpkdtlmisrtpev<br>tcvvvdvsqedpevqfnwyvdgvevhnaktkpreeqfnstyrvvsvltvlhqd<br>wlngkeykckvsnkglpssiektiskakgqprepqvctlppsqeemtknqvsls<br>cavkgfypsdiavewesngqpennykttppvldsdgsfflvskltvdksrwqeg<br>nvfscsvmhealhnhytqkslslslgk | SEQ ID NO: 9 |
| Light chain B (Anti-CD3 × Anti-CD28-L) | Anti-CD3 × Anti-CD28-L:<br>Divmtqtplslsvtpgqpasisckssqslvhnnantylswylqkpgqspqsliykvsnrf<br>sgvpdrfsgsgsgtdftlkisrveaedvgvyycgqgtqypftfgsgtkveikgqpkaapd<br>ivltqspaslavspgqratitcrasesveyyvtslmqwyqqkpgqppkllifaasnvesgv<br>parfsgsgsgtdftltinpveandvanyycqqsrkvpytfgqgtkleiktkgpsrtvaaps<br>vfifppsdeqlksgtasvvcllnnfypreakvqwkvdnalqsgnsqesvteqdskdstys<br>lsstltlskadyekhkvyacevthqglsspvtksfnrgec | SEQ ID NO: 10 |

TABLE 2-continued

Heavy and light chain sequences of binding proteins specifically directed to Her2, CD3, CD28, CD19 and/or CD20. CDR sequences are bolded and italicized.

Binding Protein 4 Nucleotide Sequences

| | | |
|---|---|---|
| Heavy chain A (Anti-CD19(B34)-H_Knob) | Anti-CD19(B34)-H_Knob:<br>caggtgcagctggtgcagagcggcgccgaagtgaagaagcctggcagcagcgtgaagg<br>tgagctgcaaggccagcggctatgccttcagcagctactggatgaactgggtgaggcagg<br>cacctggccagggcctggagtggataggccaaatatggcctggcgatggcgacaccaact<br>acaaccagaagttcaagggcagagcgaccttgaccgccgacgagagcaccagcaccgc<br>gtacatggagctgagcagcctgaggagcgaggacaccgccgtgtactattgcgccagaag<br>ggagaccaccaccgtgggcaggtactactacgccatggactactggggccagggaacca<br>ccgtgaccgtgagcagcgcctcgaccaagggcccatcggtgttccctctggccccttgcag<br>cagaagcaccagcgaatctacagccgccctgggctgcctcgtgaaggactactttcccgag<br>cccgtgaccgtgtcctggaactctggcgctctgacaagcggcgtgcacacctttccagccgt<br>gctccagagcagcggcctgtactctctgagcagcgtcgtgacagtgcccagcagcagcct<br>gggcaccaagacctacacctgtaacgtggaccacaagcccagcaacaccaaggtggaca<br>agcgggtggaatctaagtacggccctccctgccctccttgcccagcccctgaatttctgggc<br>ggaccctccgtgttcctgttccccccaaagcccaaggacaccctgatgatcagccggaccc<br>ccgaagtgacctgcgtggtggtggatgtgtcccaggaagatcccgaggtgcagttcaattg<br>gtacgtggacggcgtggaagtgcacaacgccaagaccaagcccagagaggaacagttca<br>acagcacctaccgggtggtgtccgtgctgaccgtgctgcaccaggactggctgaacggca<br>aagagtacaagtgcaaggtgtccaacaagggcctgcccagctccatcgagaaaaccatca<br>gcaaggccaagggccagccccgcgagcctcaagtgtataccctgcccccttgccaggaa<br>gagatgaccaagaaccaggtgtccctgtggtgtctcgtgaaaggcttctaccccagcgacat<br>tgccgtggaatgggagagcaacggccagcccgagaacaactacaagaccaccccccctg<br>tgctggacagcgacggctcattcttcctgtactccaagctgaccgtggacaagagccggtg<br>gcaggaaggcaacgtgttcagctgctccgtgatgcacgaggccctgcacaaccactacac<br>ccagaagtccctgtctctgtccctgggcaag | SEQ ID NO: 15 |
| Light chain A (Anti-CD19(B34)-L) | Anti-CD19(B34)-L:<br>gacctcgtgctgacccagagccctgcgagcctggctgtgagccctggccagagagccacc<br>atcacctgcaaagccagccagagcgtggactacgacggcgacagctacctcaactggtac<br>cagcagaagcctggccagcccccaagctgctgatttacgatgccagcaacctggtgagc<br>ggcgtgcctgctagattcagcggctccggcagcggcaccgacttcaccctgaccatcaacc<br>ccgtggaggccaacgacaccgccaactactactgccagcagagcacggaggacccctgg<br>accttcggccagggcacaaagctggagatcaagcgtacggtggccgctcccagcgtgttc<br>atcttcccacctagcgacgagcagctgaagtccggcacagcctctgtcgtgtgcctgctgaa<br>caacttctacccccgcgaggccaaagtgcagtggaaggtggacaacgccctgcagagcg<br>gcaacagccaggaaagcgtgaccgagcaggacagcaaggactccacctacagcctgag<br>cagcaccctgacactgagcaaggccgactacgagaagcacaaggtgtacgcctgcgaag<br>tgacccaccagggcctgtctagccccgtgaccaagagcttcaaccggggcgagtgt | SEQ ID NO: 16 |
| Heavy chain B (Anti-CD28 × Anti-CD3-H_Hole:) | Anti-CD28 × Anti-CD3-H_Hole:<br>caggtgcagctgcaggaatctggccctggcctcgtgaagcctagccagaccctgagcctg<br>acctgtaccgtgtccggcttcagcctgagcgactacggcgtgcactgggtgcgccagccac<br>ctggaaaaggcctggaatggctgggcgtgatctgggctggcggaggcaccaactacaacc<br>ccagcctgaagtccagaaagaccatcagcaaggacaccagcaagaaccaggtgtccctg<br>aagctgagcagcgtgacagccgccgataccgccgtgtactactgcgccagagacaaggg<br>ctacagctactactacagcatggactactggggccagggcaccaccgtgaccgtgtcatcct<br>ctcaggtgcagctggtggaatctggcggcggagtggtgcagcctggcagaagcctgagac<br>tgagctgtgccgccagcggcttcaccttcaccaaggcctggatgcactgggtgcgccaggc<br>ccctggaaagcagctggaatgggtggcccagatcaaggacaagagcaacagctacgcca<br>cctactacgccgacagcgtgaagggccggttcaccatcagccgggacgacagcaagaac<br>accctgtacctgcagatgaacagcctgcgggccgaggacaccgccgtgtactactgtcgg<br>ggcgtgtactatgccctgagccccttcgattactggggccagggaaccctcgtgaccgtgtc<br>tagtcggaccgcttcgaccaagggcccatcggtgttccctctggccccttgcagcagaagc<br>accagcgaatctacagccgccctgggctgcctcgtgaaggactactttcccgagcccgtga<br>ccgtgtcctggaactctggcgctctgacaagcggcgtgcacacctttccagccgtgctccag<br>agcagcggcctgtactctctgagcagcgtcgtgacagtgcccagcagcagcctgggcacc<br>aagacctacacctgtaacgtggaccacaagcccagcaacaccaaggtggacaagcgggt<br>ggaatctaagtacggccctccctgccctccttgcccagcccctgaatttctgggcggaccct<br>ccgtgttcctgttccccccaaagcccaaggacaccctgatgatcagccggacccccgaagt<br>gacctgcgtggtggtggatgtgtcccaggaagatcccgaggtgcagttcaattggtacgtgg<br>acggcgtggaagtgcacaacgccaagaccaagcccagagaggaacagttcaacagcac<br>ctaccgggtggtgtccgtgctgaccgtgctgcaccaggactggctgaacggcaaagagta<br>caagtgcaaggtgtccaacaagggcctgcccagctccatcgagaaaaccatcagcaaggc<br>caagggccagccccgcgagcctcaagtgtgtaccctgcccccctagccaggaagagatga<br>ccaagaaccaggtgtccctgagctgtgccgtgaaaggcttctaccccagcgacattgccgt<br>ggaatgggagagcaacggccagcccgagaacaactacaagaccaccccccctgtgctgg<br>acagcgacggctcattcttcctggtgtccaagctgaccgtggacaagagccggtggcagga<br>aggcaacgtgttcagctgctccgtgatgcacgaggccctgcacaaccactacacccagaa<br>gtccctgtctctgtccctgggcaag | SEQ ID NO: 11 |

TABLE 2-continued

Heavy and light chain sequences of binding proteins specifically directed to Her2, CD3, CD28, CD19 and/or CD20. CDR sequences are bolded and italicized.

| | | |
|---|---|---|
| Light chain B (Anti-CD3 × Anti-CD28-L:) | Anti-CD3 × Anti-CD28-L:<br>gacatcgtgatgacccagacccccctgagcctgagcgtgacacctggacagcctgccagc<br>atcagctgcaagagcagccagagcctggtgcacaacaacgccaacacctacctgagctgg<br>tatctgcagaagcccggccagagcccccagtccctgatctacaaggtgtccaacagattca<br>gcggcgtgcccgacagattctccggcagcggctctggcaccgacttcaccctgaagatca<br>gccgggtggaagccgaggacgtgggcgtgtactattgtggccagggcacccagtacccct<br>tcacctttggcagcggcaccaaggtggaaatcaagggccagcccaaggccgcccccgac<br>atcgtgctgacacagagccctgctagcctggccgtgtctcctggacagagggccaccatca<br>cctgtagagccagcgagagcgtggaatattacgtgaccagcctgatgcagtggtatcagca<br>gaagcccggccagcccccccaagctgctgattttcgccgccagcaacgtggaaagcggcgt<br>gccagccagattttccggcagcggctctggcaccgacttcaccctgaccatcaaccccgtg<br>gaagccaacgacgtggccaactactactgccagcagagccggaaggtgccctacaccttt<br>ggccagggcaccaagctggaaatcaagaccaagggccccagccgtacggtggccgctc<br>ccagcgtgttcatcttcccacctagcgacgagcagctgaagtccggcacagcctctgtcgtg<br>tgcctgctgaacaacttctacccccgcgaggccaaagtgcagtggaaggtggacaacgcc<br>ctgcagagcggcaacagccaggaaagcgtgaccgagcaggacagcaaggactccacct<br>acagcctgagcagcaccctgacactgagcaaggccgactacgagaagcacaaggtgtac<br>gcctgcgaagtgacccaccagggcctgtctagccccgtgaccaagagcttcaaccggggc<br>gagtgt | SEQ ID NO: 12 |

Binding Protein 5 Amino Acid Sequences

| | | |
|---|---|---|
| Heavy chain A (Anti-CD38-H_knob) | Anti-CD38-H_Knob:<br>Qvqlvqsgaevakpgtsvklsckasgytftdywmqwvkqrpgqglewigtiypgdg<br>dtgyaqkfqgkatltadkssktvymhlsslasedsavyycargdyygsnsldywgqgts<br>vtvssastkgpsvfplapcsrstsestaalgclvkdyfpepvtvswnsgaltsgvhtfpavl<br>qssglyslssvvtvpssslgtktytcnvdhkpsntkvdkrveskygppcppcpapeflgg<br>psvflfppkpkdtlmisrtpevtcvvvdvsqedpevqfnwyvdgvevhnaktkpreeq<br>fnstyrvvsvltvlhqdwlngkeykckvsnkglpssiektiskakgqprepqvytlppcq<br>eemtknqvslwclvkgfypsdiavewesngqpennykttppvldsdgsfflyskltvd<br>ksrwqegnvfscsvmhealhnhytqkslslslgk | SEQ ID NO: 17 |
| Light chain A (Anti-CD38-L) | Anti-CD38-L:<br>Divmtqshlsmstslgdpvsitckasqdvstvvawyqqkpgqsprrliysasyryigvp<br>drftgsgagtdftftissvqaedlavyycqqhysppytfgggtkleikrtvaapsvfifpps<br>deqlksgtasvvcllnnfypreakvqwkvdnalqsgnsqesvteqdskdstyslsstltls<br>kadyekhkvyacevthqglsspvtksfnrgec | SEQ ID NO: 18 |
| Heavy chain B (Anti-CD28 × Anti-CD3-H_Hole) | Anti-CD28 × Anti-CD3-H_Hole:<br>Qvqlvqsgaevvkpgasvkvsckas***gytftsyy***ihwvrqapgqglewigs***iyp***<br>***gnvnt***nyaqkfqgratltvdtsistaymelsrlrsddtavyyc***trshygldwnfdv***<br>wgkgttvtvsssqvqlvesgggvvqpgrslrlscaas***gftftkaw***mhwvrqap<br>gkqlewvaq***ikdksns***yatyyadsvkgrftisrddskntlylqmnslraedtavy<br>yc***rgvyyalspfdy***wgqgtlvtvssrtastkgpsvfplapcsrstsestaalgclvk<br>dyfpepvtvswnsgaltsgvhtfpavlqssglyslssvvtvpssslgtktytcnvd<br>hkpsntkvdkrveskygppcppcpapeflggpsvflfppkpkdtlmisrtpevt<br>cvvvdvsqedpevqfnwyvdgvevhnaktkpreeqfnstyrvvsvltvlhqd<br>wlngkeykckvsnkglpssiektiskakgqprepqvctlppsqeemtknqvsls<br>cavkgfypsdiavewesngqpennykttppvldsdgsfflvskltvdksrwqe<br>gnvfscsvmhealhnhytqkslslslgk | SEQ ID NO: 3 |
| Light chain B (Anti-CD3 × Anti-CD28-L) | Anti-CD3 × Anti-CD28-L:<br>Divmtqtplslsvtpgqpasisckss***qslvhnnanty***lswylqkpgqspqsliy***kvs***nrf<br>sgvpdrfsgsgsgtdftlkisrveaedvgvyyc***gqgtqyp***ftfgsgtkveikgqpkaapd<br>iqmtqspsslsasvgdrvtitcqas***qniyvw***lnwyqqkpgkapklliy***kas***nlhtgvpsr<br>fsgsgsgtdftltisslqpediatyyc***qqgqtypyt***fgqgtkleiktkgpsrtvaapsvfifpp<br>sdeqlksgtasvvcllnnfypreakvqwkvdnalqsgnsqesvteqdskdstyslsstltl<br>skadyekhkvyacevthqglsspvtksfnrgec | SEQ ID NO: 4 |

Binding Protein 5 Nucleotide Sequences

| | | |
|---|---|---|
| Heavy chain A (Anti-CD38-H_Knob) | Anti-CD38-H_Knob:<br>caggtgcagctggtgcagtctggcgccgaagtggccaagcctggcacaagcgtgaagct<br>gagctgcaaggccagcggctacaccttcaccgactactggatgcagtgggtcaagcagag<br>gccaggccagggcctggaatggatcggcacaatctatcccggcgacggcgataccggct<br>acgcccagaagtttcagggcaaggccaccctgaccgccgacaagagcagcaagaccgtg<br>tacatgcacctgagcagcctggccagcgaggacagcgccgtgtactattgcgccagaggc<br>gactactacggcagcaacagcctggactattggggccagggcaccagcgtgacagtgtct<br>agtgcgtcgaccaagggcccatcggtgttccctctggccccttgcagcagaagcaccagc<br>gaatctacagccgccctgggctgcctcgtgaaggactactttcccgagcccgtgaccgtgtc<br>ctggaactctggcgctctgacaagcggcgtgcacacctttccagccgtgctccagagcagc<br>ggcctgtactctctgagcagcgtcgtgacagtgcccagcagcagcctgggcaccaagacc<br>tacacctgtaacgtggaccacaagcccagcaacaccaaggtggacaagcgggtggaatct<br>aagtacggccctccctgccctccttgcccagcccctgaatttctgggcggaccctccgtgttc<br>ctgttcccccaaagcccaaggacaccctgatgatcagccggacccccgaagtgacctgc<br>gtggtggtggatgtgtcccaggaagatcccgaggtgcagttcaattggtacgtggacggcg | SEQ ID NO: 19 |

TABLE 2-continued

| Heavy and light chain sequences of binding proteins specifically directed to Her2, CD3, CD28, CD19 and/or CD20. CDR sequences are bolded and italicized. | | |
|---|---|---|
| | tggaagtgcacaacgccaagaccaagcccagagaggaacagttcaacagcacctaccgg<br>gtggtgtccgtgctgaccgtgctgcaccaggactggctgaacggcaaagagtacaagtgc<br>aaggtgtccaacaagggcctgcccagctccatcgagaaaaccatcagcaaggccaaggg<br>ccagccccgcgagcctcaagtgtataccctgccccccttgccaggaagagatgaccaagaa<br>ccaggtgtccctgtggtgtctcgtgaaaggcttctaccccagcgacattgccgtggaatggg<br>agagcaacggccagcccgagaacaactacaagaccaccccccctgtgctggacagcgac<br>ggctcattcttcctgtactccaagctgaccgtggacaagagccggtggcaggaaggcaacg<br>tgttcagctgctccgtgatgcacgaggccctgcacaaccactacacccagaagtccctgtct<br>ctgtccctgggcaag | |
| Light chain A (Anti-CD38-L) | Anti-CD38-L:<br>gacatcgtgatgacccagagccacctgagcatgagcaccagcctgggcgaccccgtgtcc<br>atcacctgtaaagccagccaggacgtgtccaccgtggtggcctggtatcagcagaagcctg<br>gccagagccccagacggctgatctacagcgccagctatcggtacatcggcgtgcccgaca<br>gattcaccggaagcggagccggcaccgacttcaccttcaccatcagctctgtgcaggccga<br>ggacctggccgtgtactactgccagcagcactacagcccccccctacacctttggcggaggc<br>accaagctggaaatcaagcgtacggtggccgctcccagcgtgttcatcttcccacctagcg<br>acgagcagctgaagtccggcacagcctctgtcgtgtgcctgctgaacaacttctacccccg<br>cgaggccaaagtgcagtggaaggtggacaacgccctgcagagcggcaacagccaggaa<br>agcgtgaccgagcaggacagcaaggactccacctacagcctgagcagcaccctgacact<br>gagcaaggccgactacgagaagcacaaggtgtacgcctgcgaagtgacccaccagggc<br>ctgtctagccccgtgaccaagagcttcaaccggggcgagtgt | SEQ ID NO: 20 |
| Heavy chain B (Anti-CD28 × Anti-CD3-H_Hole) | Anti-CD28 × Anti-CD3-H_Hole:<br>caggtgcagctggtgcagtctggcgccgaggtcgtgaaacctggcgcctctgtgaaggtgt<br>cctgcaaggccagcggctacacctttaccagctactacatccactgggtgcgccaggcccc<br>tggacagggactggaatggatcggcagcatctaccccggcaacgtgaacaccaactacgc<br>ccagaagttccagggcagagccaccctgaccgtggacaccagcatcagcaccgcctacat<br>ggaactgagccggctgagaagcgacgacaccgccgtgtactactgcacccggtcccacta<br>cggcctggattggaacttcgacgtgtggggcaagggcaccaccgtgacagtgtctagcag<br>ccaggtgcagctggtggaatctggcggcggagtggtgcagcctggcagaagcctgagac<br>tgagctgtgccgccagcggcttcaccttcaccaaggcctggatgcactgggtgcgccagg<br>cccctggaaagcagctggaatgggtggcccagatcaaggacaagagcaacagctacgcc<br>acctactacgccgacagcgtgaagggccggttcaccatcagccgggacgacagcaagaa<br>caccctgtacctgcagatgaacagcctgcgggccgaggacaccgccgtgtactactgtcg<br>gggcgtgtactatgccctgagccccttcgattactggggccagggaaccctcgtgaccgtgt<br>ctagtcggaccgccagcacaaagggcccatcggtgttccctctggccccttgcagcagaa<br>gcaccagcgaatctacagccgccctgggctgcctcgtgaaggactactttcccgagcccgt<br>gaccgtgtcctggaactctggcgctctgacaagcggcgtgcacacctttccagccgtgctcc<br>agagcagcggcctgtactctctgagcagcgtcgtgacagtgcccagcagcagcctgggca<br>ccaagacctacacctgtaacgtggaccacaagcccagcaacaccaaggtggacaagcgg<br>gtggaatctaagtacggccctccctgccctccttgcccagcccctgaatttctgggcggacc<br>ctccgtgttcctgttccccccaaagcccaaggacaccctgatgatcagccggacccccgaa<br>gtgacctgcgtggtggtggatgtgtcccaggaagatcccgaggtgcagttcaattggtacgt<br>ggacggcgtggaagtgcacaacgccaagaccaagcccagagaggaacagttcaacagc<br>acctaccgggtggtgtccgtgctgaccgtgctgcaccaggactggctgaacggcaaagag<br>tacaagtgcaaggtgtccaacaagggcctgcccagctccatcgagaaaaccatcagcaag<br>gccaagggccagccccgcgagcctcaagtgtgtaccctgcccccctagccaggaagagat<br>gaccaagaaccaggtgtccctgagctgtgccgtgaaaggcttctaccccagcgacattgcc<br>gtggaatgggagagcaacggccagcccgagaacaactacaagaccaccccccctgtgct<br>ggacagcgacggctcattcttcctggtgtccaagctgaccgtggacaagagccggtggca<br>ggaaggcaacgtgttcagctgctccgtgatgcacgaggccctgcacaaccactacaccca<br>gaagtccctgtctctgtccctgggcaag | SEQ ID NO: 7 |
| Light chain B (Anti-CD3 × Anti-CD28-L:) | Anti-CD3 × Anti-CD28-L:<br>gacatcgtgatgacccagacccccctgagcctgagcgtgacacctggacagcctgccagc<br>atcagctgcaagagcagccagagcctggtgcacaacaacgccaacacctacctgagctgg<br>tatctgcagaagcccggccagagccccccagtccctgatctacaaggtgtccaacagattca<br>gcggcgtgcccgacagattctccggcagcggctctggcaccgacttcaccctgaagatca<br>gccgggtggaagccgaggacgtgggcgtgtactattgtggccagggcacccagtacccct<br>tcacctttggcagcggcaccaaggtggaaatcaagggccagcccaaggccgcccccgac<br>atccagatgacccagagccccagcagcctgtctgccagcgtgggcgacagagtgaccatc<br>acctgtcaggccagccagaacatctacgtgtggctgaactggtatcagcagaagcccggc<br>aaggcccccaagctgctgatctacaaggccagcaacctgcacaccggcgtgcccagcag<br>attttctggcagcggctccggcaccgacttcaccctgacaatcagctccctgcagcccgag<br>gacattgccacctactactgccagcagggccagacctacccctacacctttggccagggca<br>ccaagctggaaatcaagaccaagggccccagccgtacggtggccgctcccagcgtgttca<br>tcttcccacctagcgacgagcagctgaagtccggcacagcctctgtcgtgtgcctgctgaac<br>aacttctacccccgcgaggccaaagtgcagtggaaggtggacaacgccctgcagagcgg<br>caacagccaggaaagcgtgaccgagcaggacagcaaggactccacctacagcctgagc<br>agcaccctgacactgagcaaggccgactacgagaagcacaaggtgtacgcctgcgaagt<br>gacccaccagggcctgtctagccccgtgaccaagagcttcaaccggggcgagtgt | SEQ ID NO: 8 |

TABLE 2-continued

Heavy and light chain sequences of binding proteins specifically directed to Her2, CD3, CD28, CD19 and/or CD20. CDR sequences are bolded and italicized.

Binding Protein 6 Amino Acid Sequences

| | | |
|---|---|---|
| Heavy chain A (Anti-CD38-H_knob) | Anti-CD38-H_Knob:<br>qvqlvqsgaevakpgtsvklsckasgytftdywmqwvkqrpgqglewigtiypgdgd<br>tgyaqkfqgkatltadkssktvymhlsslasedsavyycargdyygsnsldywgqgtsv<br>tvssastkgpsvfplapcsrstsestaalgclvkdyfpepvtvswnsgaltsgvhtfpavlq<br>ssglyslssvvtvpssslgtktytcnvdhkpsntkvdkrveskygppcppcpapeflggp<br>svflfppkpkdtlmisrtpevtcvvvdvsqedpevqfnwyvdgvevhnaktkpreeqf<br>nstyrvvsvltvlhqdwlngkeykckvsnkglpssiektiskakgqprepqvytlppcq<br>eemtknqvslwclvkgfypsdiavewesngqpennykttppvldsdgsfflyskltvd<br>ksrwqegnvfscsvmhealhnhytqkslslslgk | SEQ ID NO: 17 |
| Light chain A (Anti-CD38-L) | Anti-CD38-L:<br>Divmtqshlsmstslgdpvsitckasqdvstvvawyqqkpgqsprrliysasyryigvp<br>drftgsgagtdftftissvqaedlavyycqqhysppytfgggtkleikrtvaapsvfifpps<br>deqlksgtasvvcllnnfypreakvqwkvdnalqsgnsqesvteqdskdstyslsstltls<br>kadyekhkvyacevthqglsspvtksfnrgec | SEQ ID NO: 18 |
| Heavy chain B (Anti-CD28 × Anti-CD3-H_Hole) | Anti-CD28 × Anti-CD3-H_Hole:<br>Qvqlqesgpglvkpsqtlsltctvsgfslsdygvhwvrqppgkglewlgviwa<br>gggtnynpslksrktiskdtsknqvslklssvtaadtavyycardkgysyyysm<br>dywgqgttvtvsssqvqlvesgggvvqpgrslrlscaasgftftkawmhwvrq<br>apgkqlewvaqikdksnsyatyyadsvkgrftisrddskntlylqmnslraedta<br>vyycrgvyyalspfdywgqgtivtvssrtastkgpsvfplapcsrstsestaalgcl<br>vkdyfpepvtvswnsgaltsgvhtfpavlqssglyslssvvtvpssslgtktytcn<br>vdhkpsntkvdkrveskygppcppcpapeflggpsvflfppkpkdtlmisrtpe<br>vtcvvvdvsqedpevqfnwyvdgvevhnaktkpreeqfnstyrvvsvltvlhq<br>dwlngkeykckvsnkglpssiektiskakgqprepqvctlppsqeemtknqvs<br>lscavkgfypsdiavewesngqpennykttppvldsdgsfflvskltvdksrwq<br>egnvfscsvmhealhnhytqkslslslgk | SEQ ID NO: 9 |
| Light chain B (Anti-CD3 × Anti-CD28-L) | Anti-CD3 × Anti-CD28-L:<br>Divmtqtplslsvtpgqpasisckssqslvhnnantylswylqkpgqspqsliykvsnrf<br>sgvpdrfsgsgsgtdftlkisrveaedvgvyycgqgtqypftfgsgtkveikgqpkaapd<br>ivltqspaslayspgqratitcrasesveyyvtslmqwyqqkpgqppkllifaasnvesg<br>vparfsgsgsgtdftltinpveandvanyycqqsrkvpytfgqgtkleiktkgpsrtvaap<br>svfifppsdeqlksgtasvvcllnnfypreakvqwkvdnalqsgnsqesvteqdskdsty<br>slsstltlskadyekhkvyacevthqglsspvtksfnrgec | SEQ ID NO: 10 |

Binding Protein 6 Nucleotide Sequences

| | | |
|---|---|---|
| Heavy chain A (Anti-CD38-H_Knob) | Anti-CD38-H_Knob:<br>caggtgcagctggtgcagtctggcgccgaagtggccaagcctggcacaagcgtgaagct<br>gagctgcaaggccagcggctacaccttcaccgactactggatgcagtgggtcaagcagag<br>gccaggccagggcctggaatggatcggcacaatctatcccggcgacggcgataccggct<br>acgcccagaagtttcagggcaaggccaccctgaccgccgacaagagcagcaagaccgtg<br>tacatgcacctgagcagcctggccagcgaggacagcgccgtgtactattgcgccagaggc<br>gactactacggcagcaacagcctggactattggggccagggcaccagcgtgacagtgtct<br>agtgcgtcgaccaagggcccatcggtgttccctctggccccttgcagcagaagcaccagc<br>gaatctacagccgccctgggctgcctcgtgaaggactactttcccgagcccgtgaccgtgtc<br>ctggaactctggcgctctgacaagcggcgtgcacacctttccagccgtgctccagagcagc<br>ggcctgtactctctgagcagcgtcgtgacagtgcccagcagcagcctgggcaccaagacc<br>tacacctgtaacgtggaccacaagcccagcaacaccaaggtggacaagcgggtggaatct<br>aagtacggccctccctgccctccttgcccagcccctgaatttctgggcggaccctccgtgttc<br>ctgttccccccaaagcccaaggacaccctgatgatcagccggacccccgaagtgacctgc<br>gtggtggtggatgtgtcccaggaagatcccgaggtgcagttcaattggtacgtggacggcg<br>tggaagtgcacaacgccaagaccaagcccagagaggaacagttcaacagcacctaccgg<br>gtggtgtccgtgctgaccgtgctgcaccaggactggctgaacggcaaagagtacaagtgc<br>aaggtgtccaacaagggcctgcccagctccatcgagaaaaccatcagcaaggccaaggg<br>ccagccccgcgagcctcaagtgtataccctgcccccttgccaggaagagatgaccaagaa<br>ccaggtgtccctgtggtgtctcgtgaaaggcttctaccccagcgacattgccgtggaatggg<br>agagcaacggccagcccgagaacaactacaagaccaccccccctgtgctggacagcgac<br>ggctcattcttcctgtactccaagctgaccgtggacaagagccggtggcaggaaggcaacg<br>tgttcagctgctccgtgatgcacgaggccctgcacaaccactacacccagaagtccctgtct<br>ctgtccctgggcaag | SEQ ID NO: 19 |
| Light chain A (Anti-CD38-L) | Anti-CD38-L:<br>gacatcgtgatgacccagagccacctgagcatgagcaccagcctgggcgaccccgtgtcc<br>atcacctgtaaagccagccaggacgtgtccaccgtggtggcctggtatcagcagaagcctg<br>gccagagccccagacggctgatctacagcgccagctatcggtacatcggcgtgcccgaca<br>gattcaccggaagcggagccggcaccgacttcaccttcaccatcagctctgtgcaggccga<br>ggacctggccgtgtactactgccagcagcactacagcccccccctacacctttggcggaggc<br>accaagctggaaatcaagcgtacggtggccgctcccagcgtgttcatcttcccacctagcg<br>acgagcagctgaagtccggcacagcctctgtcgtgtgcctgctgaacaacttctacccccg<br>cgaggccaaagtgcagtggaaggtggacaacgccctgcagagcggcaacagccaggaa<br>agcgtgaccgagcaggacagcaaggactccacctacagcctgagcagcaccctgacact | SEQ ID NO: 20 |

TABLE 2-continued

| Heavy and light chain sequences of binding proteins specifically directed to Her2, CD3, CD28, CD19 and/or CD20. CDR sequences are bolded and italicized. | | |
|---|---|---|
| | gagcaaggccgactacgagaagcacaaggtgtacgcctgcgaagtgacccaccagggc<br>ctgtctagccccgtgaccaagagcttcaaccggggcgagtgt | |
| Heavy chain B (Anti-CD28 × Anti-CD3-H_Hole:) | Anti-CD28 × Anti-CD3_Hole:<br>caggtgcagctgcaggaatctggccctggcctcgtgaagcctagccagaccctgagcctg<br>acctgtaccgtgtccggcttcagcctgagcgactacggcgtgcactgggtgcgccagccac<br>ctggaaaaggcctggaatggctgggcgtgatctgggctggcggaggcaccaactacaac<br>cccagcctgaagtccagaaagaccatcagcaaggacaccagcaagaaccaggtgtccct<br>gaagctgagcagcgtgacagccgccgataccgccgtgtactactgcgccagagacaagg<br>gctacagctactactacagcatggactactggggccagggcaccaccgtgaccgtgtcatc<br>ctctcaggtgcagctggtggaatctggcggcggagtggtgcagcctggcagaagcctgag<br>actgagctgtgccgccagcggcttcaccttcaccaaggcctggatgcactgggtgcgccag<br>gcccctggaaagcagctggaatgggtggcccagatcaaggacaagagcaacagctacgc<br>cacctactacgccgacagcgtgaagggccggttcaccatcagccgggacgacagcaaga<br>acaccctgtacctgcagatgaacagcctgcgggccgaggacaccgccgtgtactactgtc<br>ggggcgtgtactatgccctgagccccttcgattactggggccagggaaccctcgtgaccgt<br>gtctagtcggaccgcttcgaccaagggcccatcggtgttccctctggccccttgcagcagaa<br>gcaccagcgaatctacagccgccctgggctgcctcgtgaaggactactttcccgagcccgt<br>gaccgtgtcctggaactctggcgctctgacaagcggcgtgcacacctttccagccgtgctcc<br>agagcagcggcctgtactctctgagcagcgtcgtgacagtgcccagcagcagcctgggca<br>ccaagacctacacctgtaacgtggaccacaagcccagcaacaccaaggtggacaagcgg<br>gtggaatctaagtacggccctccctgccctccttgcccagcccctgaatttctgggcggacc<br>ctccgtgttcctgttccccccaaagcccaaggacaccctgatgatcagccggacccccgaa<br>gtgacctgcgtggtggtggatgtgtcccaggaagatcccgaggtgcagttcaattggtacgt<br>ggacggcgtggaagtgcacaacgccaagaccaagcccagagaggaacagttcaacagc<br>acctaccgggtggtgtccgtgctgaccgtgctgcaccaggactggctgaacggcaaagag<br>tacaagtgcaaggtgtccaacaagggcctgcccagctccatcgagaaaaccatcagcaag<br>gccaagggccagccccgcgagcctcaagtgtgtaccctgcccccctagccaggaagagat<br>gaccaagaaccaggtgtccctgagctgtgccgtgaaaggcttctaccccagcgacattgcc<br>gtggaatgggagagcaacggccagcccgagaacaactacaagaccaccccccctgtgct<br>ggacagcgacggctcattcttcctggtgtccaagctgaccgtggacaagagccggtggca<br>ggaaggcaacgtgttcagctgctccgtgatgcacgaggccctgcacaaccactacaccca<br>gaagtccctgtctctgtccctgggcaag | SEQ ID NO: 11 |
| Light chain B (Anti-CD3 × Anti-CD28-L:) | Anti-CD3 × Anti-CD28-L:<br>gacatcgtgatgacccagacccccctgagcctgagcgtgacacctggacagcctgccagc<br>atcagctgcaagagcagccagagcctggtgcacaacaacgccaacacctacctgagctgg<br>tatctgcagaagcccggccagagcccccagtccctgatctacaaggtgtccaacagattca<br>gcggcgtgcccgacagattctccggcagcggctctggcaccgacttcaccctgaagatca<br>gccgggtggaagccgaggacgtgggcgtgtactattgtggccagggcacccagtacccct<br>tcacctttggcagcggcaccaaggtggaaatcaagggccagcccaaggccgcccccgac<br>atcgtgctgacacagagccctgctagcctggccgtgtctcctggacagagggccaccatca<br>cctgtagagccagcgagagcgtggaatattacgtgaccagcctgatgcagtggtatcagca<br>gaagcccggccagccccccaagctgctgattttcgccgccagcaacgtggaaagcggcgt<br>gccagccagatttccggcagcggctctggcaccgacttcaccctgaccatcaacccccgtg<br>gaagccaacgacgtggccaactactactgccagcagagccggaaggtgccctacacctttt<br>ggccagggcaccaagctggaaatcaagaccaagggccccagccgtacggtggccgctc<br>ccagcgtgttcatcttcccacctagcgacgagcagctgaagtccggcacagcctctgtcgtg<br>tgcctgctgaacaacttctacccccgcgaggccaaagtgcagtggaaggtggacaacgcc<br>ctgcagagcggcaacagccaggaaagcgtgaccgagcaggacagcaaggactccacct<br>acagcctgagcagcaccctgacactgagcaaggccgactacgagaagcacaaggtgtac<br>gcctgcgaagtgacccaccagggcctgtctagccccgtgaccaagagcttcaaccggggc<br>gagtgt | SEQ ID NO: 12 |
| | Binding Protein 7 Amino Acid Sequences: | |
| Heavy chain A (Anti-LAMP1-H_knob) | Anti-LAMP1-H_Knob:<br>qvqlvqsgaevkkpgssvkvsckas***gyiftnynih***wvkkspgqglewig***aiypgngd***<br>***ap***ysqkfqgkatltadtststtymelsslrsedtavyycvr***anwdvafay***wgqgtlvtvss<br>astkgpsvfplapcsrstsestaalgclvkdyfpepvtvswnsgaltsgvhtfpavlqssgl<br>yslssvvtvpssslgtktytcnvdhkpsntkvdkrveskygppcppcpapeflggpsvfl<br>fppkpkdtlmisrtpevtcvvvdvsqedpevqfnwyvdgvevhnaktkpreeqfnsty<br>rvvsvltvlhqdwlngkeykckvsnkglpssiektiskakgqprepqvytlppcqeemt<br>knqvslwclvkgfypsdiavewesngqpennykttppvldsdgsfflyskltvdksrw<br>qegnvfscsvmhealhnhytqkslslslgk | SEQ ID NO: 21 |
| Light chain A (Anti-LAMP1-L) | Anti-LAMP1-L:<br>Diqmtqspsslsasvgdrvtitc***kasqdidryma***wyqdkpgkaprllih***dtstlqs***gvp<br>srfsgsgsgrdytltisnlepedfatyyc***lqydnlwt***fgggtkveikrtvaapsvfifppsde<br>qlksgtasvvcllnnfypreakvqwkvdnalqsgnsqesvteqdskdstyslsstltlska<br>dyekhkvyacevthqglsspvtksfnrgec | SEQ ID NO: 22 |

TABLE 2-continued

Heavy and light chain sequences of binding proteins specifically directed to Her2, CD3, CD28, CD19 and/or CD20. CDR sequences are bolded and italicized.

| | | |
|---|---|---|
| Heavy chain B (Anti-CD28 × Anti-CD3-H_Hole) | Anti-CD28 × Anti-CD3-H_Hole:<br>Qvqlvqsgaevvkpgasvkvsckas***gytftsyy***ihwvrqapgqglewigs***iyp***<br>***gnvnt***nyaqkfqgratltvdtsistaymelsrlrsddtavyyc***trshygldwnfdv***<br>wgkgttvtvsssqvqlvesgggvvqpgrslrlscaas***gftftkaw***mhwvrqap<br>gkqlewvaq***ikdksns***yatyyadsvkgrftisrddskntlylqmnslraedtavy<br>yc***rgvyyalspfdy***wgqgtlvtvssrtastkgpsvfplapcsrstsestaalgclvk<br>dyfpepvtvswnsgaltsgvhtfpavlqssglyslssvvtvpssslgtktytcnvd<br>hkpsntkvdkrveskygppcppcpapeflggpsvflfppkpkdtlmisrtpevt<br>cvvvdvsqedpevqfnwyvdgvevhnaktkpreeqfnstyrvvsvltvlhqd<br>wlngkeykckvsnkglpssiektiskakgqprepqvctlppsqeemtknqvsls<br>cavkgfypsdiavewesngqpennykttppvldsdgsfflvskltvdksrwqeg<br>nvfscsvmhealhnhytqkslslslgk | SEQ ID NO: 3 |
| Light chain B (Anti-CD3 × Anti-CD28L) | Anti-CD3 × Anti-CD28-L:<br>Divmtqtplslsvtpgqpasisckss***qslvhnnanty***lswylqkpgqspqsliy***kvs***nrf<br>sgvpdrfsgsgsgtdftlkisrveaedvgvyyc***gqgtqyp***ftfgsgtkveikgqpkaapdi<br>qmtqspsslsasvgdrvtitcqas***qniyvw***lnwyqqkpgkapklliy***kas***nlhtgvpsrf<br>sgsgsgtdftltisslqpediatyyc***qqgqtypyt***fgqgtkleiktkgpsrtvaapsvfifpps<br>deqlksgtasvvcllnnfypreakvqwkvdnalqsgnsqesvteqdskdstyslsstltls<br>kadyekhkvyacevthqglsspvtksfnrgec | SEQ ID NO: 4 |

Binding Protein 7 Nucleotide Sequences

| | | |
|---|---|---|
| Heavy chain A (Anti-LAMP1-H_Knob) | Anti-LAMP1-H_Knob:<br>caggtgcagctggtgcagtctggcgccgaagtgaagaaacccggcagcagcgtgaaggt<br>gtcctgcaaggccagcggctacatcttcaccaactacaacatccactgggtcaagaagtccc<br>caggccagggcctggaatggatcggcgccatctatcccggaaacggcgacgccccttaca<br>gccagaagttccagggcaaggccaccctgaccgccgataccagcacctccaccacctaca<br>tggaactgagcagcctgcggagcgaggacaccgccgtgtactattgcgtgcgggccaact<br>gggatgtggccttcgcctattggggccagggcacactcgtgaccgtgtcctctgcgtcgacc<br>aagggcccatcggtgttccctctggccccttgcagcagaagcaccagcgaatctacagccg<br>ccctgggctgcctcgtgaaggactactttcccgagcccgtgaccgtgtcctggaactctggc<br>gctctgacaagcggcgtgcacacctttccagccgtgctccagagcagcggcctgtactctct<br>gagcagcgtcgtgacagtgcccagcagcagcctgggcaccaagacctacacctgtaacgt<br>ggaccacaagcccagcaacaccaaggtggacaagcgggtggaatctaagtacggccctc<br>cctgccctccttgcccagcccctgaatttctgggcggaccctccgtgttcctgttccccccaa<br>agcccaaggacaccctgatgatcagccggacccccgaagtgacctgcgtggtggtggatg<br>tgtcccaggaagatcccgaggtgcagttcaattggtacgtggacggcgtggaagtgcacaa<br>cgccaagaccaagcccagagaggaacagttcaacagcacctaccgggtggtgtccgtgct<br>gaccgtgctgcaccaggactggctgaacggcaaagagtacaagtgcaaggtgtccaacaa<br>gggcctgcccagctccatcgagaaaaccatcagcaaggccaagggccagccccgcgag<br>cctcaagtgtataccctgcccccttgccaggaagagatgaccaagaaccaggtgtccctgtg<br>gtgtctcgtgaaaggcttctaccccagcgacattgccgtggaatgggagagcaacggccag<br>cccgagaacaactacaagaccacccccctgtgctggacagcgacggctcattcttcctgta<br>ctccaagctgaccgtggacaagagccggtggcaggaaggcaacgtgttcagctgctccgt<br>gatgcacgaggccctgcacaaccactacacccagaagtccctgtctctgtccctgggcaag | SEQ ID NO: 23 |
| Light chain A (Anti-LAMP1-L) | Anti-LAMP1-L:<br>gacatccagatgacccagagccccagcagcctgtctgccagcgtgggcgacagagtgac<br>catcacatgcaaggccagccaggacatcgatcggtacatggcctggtatcaggacaagcc<br>cggcaaggcccccagactgctgatccacgataccagcacactgcagagcggcgtgccca<br>gcagattttccggctctggcagcggcagagactacaccctgaccatcagcaacctggaacc<br>cgaggacttcgccacctactactgcctgcagtacgacaacctgtggaccttcggcggaggc<br>accaaggtggaaatcaagcgtacggtggccgctcccagcgtgttcatcttcccacctagcg<br>acgagcagctgaagtccggcacagcctctgtcgtgtgcctgctgaacaacttctacccccgc<br>gaggccaaagtgcagtggaaggtggacaacgccctgcagagcggcaacagccaggaaa<br>gcgtgaccgagcaggacagcaaggactccacctacagcctgagcagcaccctgacactg<br>agcaaggccgactacgagaagcacaaggtgtacgcctgcgaagtgacccaccagggcct<br>gtctagccccgtgaccaagagcttcaaccggggcgagtgt | SEQ ID NO: 24 |
| Heavy chain B (Anti-CD28 × Anti-CD3-H_Hole) | Anti-CD28 × Anti-CD3-H_Hole:<br>caggtgcagctggtgcagtctggcgccgaggtcgtgaaacctggcgcctctgtgaaggtgt<br>cctgcaaggccagcggctacacctttaccagctactacatccactgggtgcgccaggcccc<br>tggacagggactggaatggatcggcagcatctaccccggcaacgtgaacaccaactacgc<br>ccagaagttccagggcagagccaccctgaccgtggacaccagcatcagcaccgcctacat<br>ggaactgagccggctgagaagcgacgacaccgccgtgtactactgcacccggtcccacta<br>cggcctggattggaacttcgacgtgtggggcaagggcaccaccgtgacagtgtctagcag<br>ccaggtgcagctggtggaatctggcggcggagtggtgcagcctggcagaagcctgagact<br>gagctgtgccgccagcggcttcaccttcaccaaggcctggatgcactgggtgcgccaggc<br>ccctggaaagcagctggaatgggtggcccagatcaaggacaagagcaacagctacgcca<br>cctactacgccgacagcgtgaagggccggttcaccatcagccgggacgacagcaagaac<br>accctgtacctgcagatgaacagcctgcgggccgaggacaccgccgtgtactactgtcgg<br>ggcgtgtactatgccctgagccccttcgattactggggccagggaaccctcgtgaccgtgtc<br>tagtcggaccgccagcacaaagggcccatcggtgttccctctggccccttgcagcagaagc<br>accagcgaatctacagccgccctgggctgcctcgtgaaggactactttcccgagcccgtga<br>ccgtgtcctggaactctggcgctctgacaagcggcgtgcacacctttccagccgtgctccag | SEQ ID NO: 7 |

TABLE 2-continued

Heavy and light chain sequences of binding proteins specifically directed to Her2, CD3, CD28, CD19 and/or CD20. CDR sequences are bolded and italicized.

| | | |
|---|---|---|
| | agcagcggcctgtactctctgagcagcgtcgtgacagtgcccagcagcagcctgggcacc<br>aagacctacacctgtaacgtggaccacaagcccagcaacaccaaggtggacaagcgggt<br>ggaatctaagtacggccctccctgccctccttgcccagcccctgaatttctgggcggaccct<br>ccgtgttcctgttcccccaaagcccaaggacaccctgatgatcagccggacccccgaagt<br>gacctgcgtggtggtggatgtgtcccaggaagatcccgaggtgcagttcaattggtacgtgg<br>acggcgtggaagtgcacaacgccaagaccaagcccagagaggaacagttcaacagcac<br>ctaccgggtggtgtccgtgctgaccgtgctgcaccaggactggctgaacggcaaagagta<br>caagtgcaaggtgtccaacaagggcctgcccagctccatcgagaaaaccatcagcaaggc<br>caagggccagccccgcgagcctcaagtgtgtaccctgcccccctagccaggaagagatga<br>ccaagaaccaggtgtccctgagctgtgccgtgaaaggcttctaccccagcgacattgccgt<br>ggaatgggagagcaacggccagcccgagaacaactacaagaccacccccccctgtgctgg<br>acagcgacggctcattcttcctggtgtccaagctgaccgtggacaagagccggtggcagga<br>aggcaacgtgttcagctgctccgtgatgcacgaggccctgcacaaccactacacccagaa<br>gtccctgtctctgtccctgggcaag | |
| Light chain B (Anti-CD3 × Anti-CD28-L:) | Anti-CD3 × Anti-CD28-L:<br>gacatcgtgatgacccagacccccctgagcctgagcgtgacacctggacagcctgccagc<br>atcagctgcaagagcagccagagcctggtgcacaacaacgccaacacctacctgagctgg<br>tatctgcagaagcccggccagagcccccagtccctgatctacaaggtgtccaacagattca<br>gcggcgtgcccgacagattctccggcagcggctctggcaccgacttcaccctgaagatca<br>gccgggtggaagccgaggacgtgggcgtgtactattgtggccagggcacccagtacccct<br>tcacctttggcagcggcaccaaggtggaaatcaagggccagcccaaggccgcccccgac<br>atccagatgacccagagccccagcagcctgtctgccagcgtgggcgacagagtgaccatc<br>acctgtcaggccagccagaacatctacgtgtggctgaactggtatcagcagaagcccggca<br>aggcccccaagctgctgatctacaaggccagcaacctgcacaccggcgtgcccagcagat<br>ttctggcagcggctccggcaccgacttcaccctgacaatcagctccctgcagcccgagga<br>cattgccacctactactgccagcagggccagacctacccctacacctttggccagggcacc<br>aagctggaaatcaagaccaagggccccagccgtacggtggccgctcccagcgtgttcatct<br>tcccacctagcgacgagcagctgaagtccggcacagcctctgtcgtgtgcctgctgaacaa<br>cttctacccccgcgaggccaaagtgcagtggaaggtggacaacgccctgcagagcggca<br>acagccaggaaagcgtgaccgagcaggacagcaaggactccacctacagcctgagcag<br>caccctgacactgagcaaggccgactacgagaagcacaaggtgtacgcctgcgaagtga<br>cccaccagggcctgtctagccccgtgaccaagagcttcaaccggggcgagtgt | SEQ ID NO: 8 |
| | Binding Protein 8 Amino Acid Sequences | |
| Heavy chain A (Anti-LAMP1-H_knob) | Anti-LAMP1-H_Knob:<br>qvqlvqsgaevkkpgssvkvsckas***gyiftnynih***wvkkspgqglewig***aiypgngd***<br>***ap***ysqkfqgkatltadtststtymelsslrsedtavyycvr***anwdvafay***wgqgtlvtvss<br>astkgpsvfplapcsrstsestaalgclvkdyfpepvtvswnsgaltsgvhtfpavlqssgl<br>yslssvvtvpssslgtktytcnvdhkpsntkvdkrveskygppcppcpapeflggpsvfl<br>fppkpkdtlmisrtpevtcvvvdvsqedpevqfnwyvdgvevhnaktkpreeqfnsty<br>rvvsvltvlhqdwlngkeykckvsnkglpssiektiskakgqprepqvytlppcqeemt<br>knqvslwclvkgfypsdiavewesngqpennykttppvldsdgsfflyskltvdksrw<br>qegnvfscsvmhealhnhytqkslslslgk | SEQ ID NO: 21 |
| Light chain A (Anti-LAMP1-L) | Anti-LAMP1-L:<br>Diqmtqspsslsasvgdrvtitc***kasqdidryma***wyqdkpgkaprllih***dtstlqs***gvp<br>srfsgsgsgrdytltisnlepedfatyyc***lqydnlwt***fgggtkveikrtvaapsvfifppsde<br>qlksgtasvvcllnnfypreakvqwkvdnalqsgnsqesvteqdskdstyslsstltlska<br>dyekhkvyacevthqglsspvtksfnrgec | SEQ ID NO: 22 |
| Heavy chain B (Anti-CD28 × Anti-CD3-H_Hole) | Anti-CD28 × Anti-CD3-H_Hole:<br>Qvqlqesgpglvkpsqtlsltctvsgfslsdygvhwvrqppgkglewlgviwa<br>gggtnynpslksrktiskdtsknqvslklssvtaadtavyycardkgysyyysmd<br>ywgqgttvtvsssqvqlvesgggvvqpgrslrlscaasgftftkawmhwvrqa<br>pgkqlewvaqikdksnsyatyyadsvkgrftisrddskntlylqmnslraedtav<br>yycrgvyyalspfdywgqgtlvtvssrtastkgpsvfplapcsrstsestaalgclv<br>kdyfpepvtvswnsgaltsgvhtfpavlqssglyslssvvtvpssslgtktytcnv<br>dhkpsntkvdkrveskygppcppcpapeflggpsvflfppkpkdtlmisrtpev<br>tcvvvdvsqedpevqfnwyvdgvevhnaktkpreeqfnstyrvvsvltvlhqd<br>wlngkeykckvsnkglpssiektiskakgqprepqvctlppsqeemtknqvsls<br>cavkgfypsdiavewesngqpennykttppvldsdgsfflvskltvdksrwqeg<br>nvfscsvmhealhnhytqkslslslgk | SEQ ID NO: 9 |
| Light chain B (Anti-CD3 × Anti-CD28-L) | Anti-CD3 × Anti-CD28-L:<br>Divmtqtplslsvtpgqpasisckssqslvhnnantylswylqkpgqspqsliykvsnrf<br>sgvpdrfsgsgsgtdftlkisrveaedvgvyycgqgtqypftfgsgtkveikgqpkaapd<br>ivltqspaslavspgqratitcrasesveyyvtslmqwyqqkpgqppkllifaasnvesgv<br>parfsgsgsgtdftltinpveandvanyycqqsrkvpytfgqgtkleiktkgpsrtvaaps<br>vfifppsdeqlksgtasvvcllnnfypreakvqwkvdnalqsgnsqesvteqdskdstys<br>lsstltlskadyekhkvyacevthqglsspvtksfnrgec | SEQ ID NO: 10 |

TABLE 2-continued

Heavy and light chain sequences of binding proteins specifically directed to Her2, CD3, CD28, CD19 and/or CD20. CDR sequences are bolded and italicized.

Binding Protein 8 Nucleotide Sequences

| | | |
|---|---|---|
| Heavy chain A (Anti-LAMP1-H_Knob) | Anti-LAMP1-H_Knob:<br>caggtgcagctggtgcagtctggcgccgaagtgaagaaacccggcagcagcgtgaaggt<br>gtcctgcaaggccagcggctacatcttcaccaactacaacatccactgggtcaagaagtccc<br>caggccagggcctggaatggatcggcgccatctatcccggaaacggcgacgccccttaca<br>gccagaagttccagggcaaggccaccctgaccgccgataccagcacctccaccacctaca<br>tggaactgagcagcctgcggagcgaggacaccgccgtgtactattgcgtgcgggccaact<br>gggatgtggccttcgcctattggggccagggcacactcgtgaccgtgtcctctgcgtcgacc<br>aagggcccatcggtgttccctctggccccttgcagcagaagcaccagcgaatctacagccg<br>ccctgggctgcctcgtgaaggactactttcccgagcccgtgaccgtgtcctggaactctggc<br>gctctgacaagcggcgtgcacacctttccagccgtgctccagagcagcggcctgtactctct<br>gagcagcgtcgtgacagtgcccagcagcagcctgggcaccaagacctacacctgtaacgt<br>ggaccacaagcccagcaacaccaaggtggacaagcgggtggaatctaagtacggccctc<br>cctgccctccttgcccagcccctgaatttctgggcggaccctccgtgttcctgttccccccaa<br>agcccaaggacaccctgatgatcagccggacccccgaagtgacctgcgtggtggtggatg<br>tgtcccaggaagatcccgaggtgcagttcaattggtacgtggacggcgtggaagtgcacaa<br>cgccaagaccaagcccagagaggaacagttcaacagcacctaccgggtggtgtccgtgct<br>gaccgtgctgcaccaggactggctgaacggcaaagagtacaagtgcaaggtgtccaacaa<br>gggcctgcccagctccatcgagaaaaccatcagcaaggccaagggccagccccgcgag<br>cctcaagtgtataccctgcccccttgccaggaagagatgaccaagaaccaggtgtccctgtg<br>gtgtctcgtgaaaggcttctaccccagcgacattgccgtggaatgggagagcaacggccag<br>cccgagaacaactacaagaccaccccccctgtgctggacagcgacggctcattcttcctgta<br>ctccaagctgaccgtggacaagagccggtggcaggaaggcaacgtgttcagctgctccgt<br>gatgcacgaggccctgcacaaccactacacccagaagtccctgtctctgtccctgggcaag | SEQ ID NO: 23 |
| Light chain A (Anti-LAMP1-L) | Anti-LAMP1-L:<br>gacatccagatgacccagagccccagcagcctgtctgccagcgtgggcgacagagtgac<br>catcacatgcaaggccagccaggacatcgatcggtacatggcctggtatcaggacaagcc<br>cggcaaggcccccagactgctgatccacgataccagcacactgcagagcggcgtgccca<br>gcagattttccggctctggcagcggcagagactacaccctgaccatcagcaacctggaacc<br>cgaggacttcgccacctactactgcctgcagtacgacaacctgtggaccttcggcggaggc<br>accaaggtggaaatcaagcgtacggtggccgctcccagcgtgttcatcttcccacctagcg<br>acgagcagctgaagtccggcacagcctctgtcgtgtgcctgctgaacaacttctaccccgc<br>gaggccaaagtgcagtggaaggtggacaacgccctgcagagcggcaacagccaggaaa<br>gcgtgaccgagcaggacagcaaggactccacctacagcctgagcagcaccctgacactg<br>agcaaggccgactacgagaagcacaaggtgtacgcctgcgaagtgacccaccagggcct<br>gtctagccccgtgaccaagagcttcaaccggggcgagtgt | SEQ ID NO: 24 |
| Heavy chain B (Anti-CD28 × Anti-CD3-H_Hole:) | Anti-CD28 × Anti-CD3-H_Hole:<br>caggtgcagctgcaggaatctggccctggcctcgtgaagcctagccagaccctgagcctg<br>acctgtaccgtgtccggcttcagcctgagcgactacggcgtgcactgggtgcgccagccac<br>ctggaaaaggcctggaatggctgggcgtgatctgggctggcggaggcaccaactacaacc<br>ccagcctgaagtccagaaagaccatcagcaaggacaccagcaagaaccaggtgtccctg<br>aagctgagcagcgtgacagccgccgataccgccgtgtactactgcgccagagacaaggg<br>ctacagctactactacagcatggactactggggccagggcaccaccgtgaccgtgtcatcct<br>ctcaggtgcagctggtggaatctggcggcggagtggtgcagcctggcagaagcctgagac<br>tgagctgtgccgccagcggcttcaccttcaccaaggcctggatgcactgggtgcgccaggc<br>ccctggaaagcagctggaatgggtggcccagatcaaggacaagagcaacagctacgcca<br>cctactacgccgacagcgtgaagggccggttcaccatcagccgggacgacagcaagaac<br>accctgtacctgcagatgaacagcctgcgggccgaggacaccgccgtgtactactgtcgg<br>ggcgtgtactatgccctgagccccttcgattactggggccagggaaccctcgtgaccgtgtc<br>tagtcggaccgcttcgaccaagggcccatcggtgttccctctggccccttgcagcagaagc<br>accagcgaatctacagccgccctgggctgcctcgtgaaggactactttcccgagcccgtga<br>ccgtgtcctggaactctggcgctctgacaagcggcgtgcacacctttccagccgtgctccag<br>agcagcggcctgtactctctgagcagcgtcgtgacagtgcccagcagcagcctgggcacc<br>aagacctacacctgtaacgtggaccacaagcccagcaacaccaaggtggacaagcgggt<br>ggaatctaagtacggccctccctgccctccttgcccagcccctgaatttctgggcggaccct<br>ccgtgttcctgttccccccaaagcccaaggacaccctgatgatcagccggacccccgaagt<br>gacctgcgtggtggtggatgtgtcccaggaagatcccgaggtgcagttcaattggtacgtgg<br>acggcgtggaagtgcacaacgccaagaccaagcccagagaggaacagttcaacagcac<br>ctaccgggtggtgtccgtgctgaccgtgctgcaccaggactggctgaacggcaaagagta<br>caagtgcaaggtgtccaacaagggcctgcccagctccatcgagaaaaccatcagcaaggc<br>caagggccagccccgcgagcctcaagtgtgtaccctgcccccctagccaggaagagatga<br>ccaagaaccaggtgtccctgagctgtgccgtgaaaggcttctaccccagcgacattgccgt<br>ggaatgggagagcaacggccagcccgagaacaactacaagaccaccccccctgtgctgg<br>acagcgacggctcattcttcctggtgtccaagctgaccgtggacaagagccggtggcagga<br>aggcaacgtgttcagctgctccgtgatgcacgaggccctgcacaaccactacacccagaa<br>gtccctgtctctgtccctgggcaag | SEQ ID NO: 11 |
| Light chain B (Anti-CD3 × Anti-CD28-L:) | Anti-CD3 × Anti-CD28-L:<br>gacatcgtgatgacccagacccccctgagcctgagcgtgacacctggacagcctgccagc<br>atcagctgcaagagcagccagagcctggtgcacaacaacgccaacacctacctgagctgg<br>tatctgcagaagcccggccagagcccccagtccctgatctacaaggtgtccaacagattca<br>gcggcgtgcccgacagattctccggcagcggctctggcaccgacttcaccctgaagatca<br>gccgggtggaagccgaggacgtgggcgtgtactattgtggccagggcacccagtacccct | SEQ ID NO: 12 |

TABLE 2-continued

Heavy and light chain sequences of binding proteins specifically directed to Her2, CD3, CD28, CD19 and/or CD20. CDR sequences are bolded and italicized.

| | | |
|---|---|---|
| | tcacctttggcagcggcaccaaggtggaaatcaagggccagcccaaggccgcccccgac<br>atcgtgctgacacagagccctgctagcctggccgtgtctcctggacagagggccaccatca<br>cctgtagagccagcgagagcgtggaatattacgtgaccagcctgatgcagtggtatcagca<br>gaagcccggccagcccccaagctgctgattttcgccgccagcaacgtggaaagcggcgt<br>gccagccagattttccggcagcggctctggcaccgacttcaccctgaccatcaaccccgtg<br>gaagccaacgacgtggccaactactactgccagcagagccggaaggtgccctacaccttt<br>ggccagggcaccaagctggaaatcaagaccaagggccccagccgtacggtggccgctc<br>ccagcgtgttcatcttcccacctagcgacgagcagctgaagtccggcacagcctctgtcgtg<br>tgcctgctgaacaacttctacccccgcgaggccaaagtgcagtggaaggtggacaacgcc<br>ctgcagagcggcaacagccaggaaagcgtgaccgagcaggacagcaaggactccacct<br>acagcctgagcagcaccctgacactgagcaaggccgactacgagaagcacaaggtgtac<br>gcctgcgaagtgacccaccagggcctgtctagccccgtgaccaagagcttcaaccggggc<br>gagtgt | |
| | Binding Protein 20 Amino Acid Sequences | |
| Heavy chain A (Anti-CD20-H_knob) | Anti-CD20-H_Knob:<br>Qvqlqqpgaelvkpgasvkmsckas***gytftsyn***mhwvkqtpgrglewiga***iypgng dt***synqkfkgkatltadkssstaymqlssltsedsavyyc***arstyyggdwyfn***vwgagtt<br>vtvsaastkgpsvfplapcsrstsestaalgclvkdyfpepvtvswnsgaltsgvhtfpavl<br>qssglyslssvvtvpssslgtktytcnvdhkpsntkvdkrveskygppcppcpapeflgg<br>psvflfppkpkdtlmisrtpevtcvvvdvsqedpevqfnwyvdgvevhnaktkpreeq<br>fnstyrvvsvltvlhqdwlngkeykckvsnkglpssiektiskakgqprepqvytlppcq<br>eemtknqvslwclvkgfypsdiavewesngqpennykttppvldsdgsfflyskltvd<br>ksrwqegnvfscsvmhealhnhytqkslslslgk | SEQ ID NO: 114 |
| Light chain A (Anti-CD20-L) | Anti-CD20-L:<br>Qivlsqspailsaspgekvtmtcrasssvsyihwfqqkpgsspkpwiy***ats***nlasgvpv<br>rfsgsgsgtsysltisrveaedaatyyc***qqwtsnp***ptfgggtkleikrtvaapsvfifppsde<br>qlksgtasvvcllnnfypreakvqwkvdnalqsgnsqesvteqdskdstyslsstltlska<br>dyekhkvyacevthqglsspvtksfnrgec | SEQ ID NO: 115 |
| Heavy chain B (CD28 × CD3-H_Hole) | CD28 × CD3-H_Hole:<br>Qvqlvqsgaevvkpgasvkvsckas***gytftsyy***ihwvrqapgqglewigs***iyp gnvnt***nyaqkfqgratltvdtsistaymelsrlrsddtavyyc***trshygldwnfdv***<br>wgkgttvtvsssqvqlvesgggvvqpgrslrlscaas***gftftkaw***mhwvrqap<br>gkqlewvaq***ikdksns***yatyyadsvkgrftisrddskntlylqmnslraedtavy<br>yc***rgvyyalspfdy***wgqgtlvtvssrtastkgpsvfplapcsrstsestaalgclvk<br>dyfpepvtvswnsgaltsgvhtfpavlqssglyslssvvtvpssslgtktytcnvd<br>hkpsntkvdkrveskygppcppcpapeflggpsvflfppkpkdtlmisrtpevt<br>cvvvdvsqedpevqfnwyvdgvevhnaktkpreeqfnstyrvvsvltvlhqd<br>wlngkeykckvsnkglpssiektiskakgqprepqvctlppsqeemtknqvsls<br>cavkgfypsdiavewesngqpennykttppvldsdgsfflvskltvdksrwqeg<br>nvfscsvmhealhnhytqkslslslgk | SEQ ID NO: 3 |
| Light chain B (CD3 × CD28-L) | CD3 × CD28-L:<br>Divmtqtplslsvtpgqpasisckss***qslvhnnanty***lswylqkpgqspqsliy***kvs***nrf<br>sgvpdrfsgsgsgtdftlkisrveaedvgvyyc***gqgtqyp***ftfgsgtkveikgqpkaapd<br>iqmtqspsslsasvgdrvtitcqas***qniyvw***lnwyqqkpgkapklliy***kas***nlhtgvpsr<br>fsgsgsgtdftltisslqpediatyyc***qqgqtypyt***fgqgtkleiktkgpsrtvaapsvfifpp<br>sdeqlksgtasvvcllnnfypreakvqwkvdnalqsgnsqesvteqdskdstyslsstltl<br>skadyekhkvyacevthqglsspvtksfnrgec | SEQ ID NO: 4 |
| | Binding Protein 20 Nucleotide Sequences | |
| Heavy chain A (Anti-CD20-H_Knob:) | Anti-CD20-H_Knob:<br>caggtgcagctgcagcagcctggcgccgaactcgtgaaacctggcgcctccgtgaagatg<br>agctgcaaggccagcggctacaccttcaccagctacaacatgcactgggtcaagcagacc<br>cccggcagaggcctggaatggatcggcgccatctaccccggcaacggcgacacctccta<br>caaccagaagttcaagggcaaggccaccctgaccgccgacaagagcagcagcacagcct<br>acatgcagctgtccagcctgaccagcgaggacagcgccgtgtactactgcgccagaagca<br>cctactacggcggcgactggtacttcaacgtgtggggagccggcaccaccgtgacagtgtc<br>tgctgcttcgaccaagggcccatcggtgttccctctggccccttgcagcagaagcaccagc<br>gaatctacagccgccctgggctgcctcgtgaaggactactttcccgagcccgtgaccgtgtc<br>ctggaactctggcgctctgacaagcggcgtgcacacctttccagccgtgctccagagcagc<br>ggcctgtactctctgagcagcgtcgtgacagtgcccagcagcagcctgggcaccaagacc<br>tacacctgtaacgtggaccacaagcccagcaacaccaaggtggacaagcgggtggaatct<br>aagtacggccctccctgccctccttgcccagcccctgaatttctgggcggaccctccgtgttc<br>ctgttcccccccaaagcccaaggacaccctgatgatcagccggacccccgaagtgacctgc<br>gtggtggtggatgtgtcccaggaagatcccgaggtgcagttcaattggtacgtggacggcg<br>tggaagtgcacaacgccaagaccaagcccagagaggaacagttcaacagcacctaccgg<br>gtggtgtccgtgctgaccgtgctgcaccaggactggctgaacggcaaagagtacaagtgc<br>aaggtgtccaacaagggcctgcccagctccatcgagaaaaccatcagcaaggccaaggg<br>ccagccccgcgagcctcaagtgtataccctgcccccttgccaggaagagatgaccaagaa<br>ccaggtgtccctgtggtgtctcgtgaaaggcttctaccccagcgacattgccgtggaatggg<br>agagcaacggccagcccgagaacaactacaagaccaccccccctgtgctggacagcgac<br>ggctcattcttcctgtactccaagctgaccgtggacaagagccggtggcaggaaggcaacg | SEQ ID NO: 116 |

TABLE 2-continued

Heavy and light chain sequences of binding proteins specifically directed to Her2, CD3, CD28, CD19 and/or CD20. CDR sequences are bolded and italicized.

| | | |
|---|---|---|
| | tgttcagctgctccgtgatgcacgaggccctgcacaaccactacacccagaagtccctgtct<br>ctgtccctgggcaag | |
| Light chain A (Anti-CD20-L) | Anti-CD20-L:<br>cagatcgtgctgagccagagccctgccatcctgagcgcttccccaggcgagaaagtgacc<br>atgacctgcagagccagcagcagcgtgtcctacatccactggttccagcagaagcccggc<br>agcagccccaagccttggatctacgccaccagcaatctggccagcggagtgcctgtgcgg<br>tttagcggctctggcagcggcacaagctacagcctgaccatcagccgggtggaagccgaa<br>gatgccgccacctactactgccagcagtggaccagcaacccccccacatttggcggaggc<br>accaagctggaaatcaagcgtacggtggccgctcccagcgtgttcatcttcccacctagcga<br>cgagcagctgaagtccggcacagcctctgtcgtgtgcctgctgaacaacttctacccccgc<br>gaggccaaagtgcagtggaaggtggacaacgccctgcagagcggcaacagccaggaaa<br>gcgtgaccgagcaggacagcaaggactccacctacagcctgagcagcaccctgacactg<br>agcaaggccgactacgagaagcacaaggtgtacgcctgcgaagtgacccaccagggcct<br>gtctagccccgtgaccaagagcttcaaccggggcgagtgt | SEQ ID NO: 117 |
| Heavy chain B (CD28 × CD3-H_ Hole:) | CD28 × CD3-H_Hole:<br>caggtgcagctggtgcagtctggcgccgaggtcgtgaaacctggcgcctctgtgaaggtgt<br>cctgcaaggccagcggctacacctttaccagctactacatccactgggtgcgccaggcccc<br>tggacagggactggaatggatcggcagcatctaccccggcaacgtgaacaccaactacgc<br>ccagaagttccagggcagagccaccctgaccgtggacaccagcatcagcaccgcctacat<br>ggaactgagccggctgagaagcgacgacaccgccgtgtactactgcacccggtcccacta<br>cggcctggattggaacttcgacgtgtggggcaagggcaccaccgtgacagtgtctagcag<br>ccaggtgcagctggtggaatctggcggcggagtggtgcagcctggcagaagcctgagact<br>gagctgtgccgccagcggcttcaccttcaccaaggcctggatgcactgggtgcgccaggc<br>ccctggaaagcagctggaatgggtggcccagatcaaggacaagagcaacagctacgcca<br>cctactacgccgacagcgtgaagggccggttcaccatcagccgggacgacagcaagaac<br>accctgtacctgcagatgaacagcctgcgggccgaggacaccgccgtgtactactgtcgg<br>ggcgtgtactatgccctgagccccttcgattactggggccagggaaccctcgtgaccgtgtc<br>tagtcggaccgccagcacaaagggcccatcggtgttccctctggccccttgcagcagaagc<br>accagcgaatctacagccgccctgggctgcctcgtgaaggactactttcccgagcccgtga<br>ccgtgtcctggaactctggcgctctgacaagcggcgtgcacacctttccagccgtgctccag<br>agcagcggcctgtactctctgagcagcgtcgtgacagtgcccagcagcagcctgggcacc<br>aagacctacacctgtaacgtggaccacaagcccagcaacaccaaggtggacaagcgggt<br>ggaatctaagtacggccctccctgccctccttgcccagcccctgaatttctgggcggaccct<br>ccgtgttcctgttccccccaaagcccaaggacaccctgatgatcagccggacccccgaagt<br>gacctgcgtggtggtggatgtgtcccaggaagatcccgaggtgcagttcaattggtacgtgg<br>acggcgtggaagtgcacaacgccaagaccaagcccagagaggaacagttcaacagcac<br>ctaccgggtggtgtccgtgctgaccgtgctgcaccaggactggctgaacggcaaagagta<br>caagtgcaaggtgtccaacaagggcctgcccagctccatcgagaaaaccatcagcaaggc<br>caagggccagccccgcgagcctcaagtgtgtaccctgccccctagccaggaagagatga<br>ccaagaaccaggtgtccctgagctgtgccgtgaaaggcttctaccccagcgacattgccgt<br>ggaatgggagagcaacggccagcccgagaacaactacaagaccaccccccctgtgctgg<br>acagcgacggctcattcttcctggtgtccaagctgaccgtggacaagagccggtggcagga<br>aggcaacgtgttcagctgctccgtgatgcacgaggccctgcacaaccactacacccagaa<br>gtccctgtctctgtccctgggcaag | SEQ ID NO: 7 |
| Light chain B (CD3 × CD28-L_ Hole:) | CD3 × CD28-L_Hole:<br>gacatcgtgatgacccagacccccctgagcctgagcgtgacacctggacagcctgccagc<br>atcagctgcaagagcagccagagcctggtgcacaacaacgccaacacctacctgagctgg<br>tatctgcagaagcccggccagagcccccagtccctgatctacaaggtgtccaacagattca<br>gcggcgtgcccgacagattctccggcagcggctctggcaccgacttcaccctgaagatca<br>gccgggtggaagccgaggacgtgggcgtgtactattgtggccagggcacccagtacccct<br>tcacctttggcagcggcaccaaggtggaaatcaagggccagcccaaggccgcccccgac<br>atccagatgacccagagccccagcagcctgtctgccagcgtgggcgacagagtgaccatc<br>acctgtcaggccagccagaacatctacgtgtggctgaactggtatcagcagaagcccggca<br>aggcccccaagctgctgatctacaaggccagcaacctgcacaccggcgtgcccagcagat<br>tttctggcagcggctccggcaccgacttcaccctgacaatcagctccctgcagcccgagga<br>cattgccacctactactgccagcagggccagacctacccctacacctttggccagggcacc<br>aagctggaaatcaagaccaagggccccagccgtacggtggccgctcccagcgtgttcatct<br>tcccacctagcgacgagcagctgaagtccggcacagcctctgtcgtgtgcctgctgaacaa<br>cttctacccccgcgaggccaaagtgcagtggaaggtggacaacgccctgcagagcggca<br>acagccaggaaagcgtgaccgagcaggacagcaaggactccacctacagcctgagcag<br>caccctgacactgagcaaggccgactacgagaagcacaaggtgtacgcctgcgaagtga<br>cccaccagggcctgtctagccccgtgaccaagagcttcaaccggggcgagtgt | SEQ ID NO: 8 |
| | Binding Protein 21 Amino Acid Sequences | |
| Heavy chain A (Anti-CD20-H_knob) | Anti-CD20-H_Knob:<br>qvqlqqpgaelvkpgasvkmsckas***gytftsyn***mhwvkqtpgrglewiga***iypgngdt***synqkfkg<br>katltadkssstaymqlssltsedsavyyc***arstyyggdwyfnv***wgagttvtvsaastkgpsvfplapcsr<br>stsestaalgclvkdyfpepvtvswnsgaltsgvhtfpavlqssglyslssvvtvpssslgtkytcnvdhkp<br>sntkvdkrveskygppcppcpapeflggpsvflfppkpkdtlmisrtpevtcvvvdvsqedpevqfnw<br>yvdgvevhnaktkpreeqfnstyrvvsyltvlhqdwlngkeykckvsnkglpssiektiskakgqprep<br>qvytlppcqeemtknqvslwclvkgfypsdiavewesngqpennykttppvldsdgsfflyskltvdks<br>rwqegnvfscsvmhealhnhytqkslslslgk | SEQ ID NO: 114 |

TABLE 2-continued

| Heavy and light chain sequences of binding proteins specifically directed to Her2, CD3, CD28, CD19 and/or CD20. CDR sequences are bolded and italicized. | | |
|---|---|---|
| Light chain A (Anti-CD20-L) | Anti-CD20-L:<br>qivlsqspailsaspgekvtmtcrasssvsyihwfqqkpgsspkpwiy***ats***nlasgvpvrfsgsgsgtsys<br>ltisrveaedaatyyc***qqwtsnp***ptfgggtkleikrtvaapsvfifppsdeqlksgtasvvcllnnfypreak<br>vqwkvdnalqsgnsqesvteqdskdstyslsstltlskadyekhkvyacevthqglsspvtksfnrgec | SEQ ID NO: 115 |
| Heavy chain B (CD28 × CD3-H_Hole) | CD28 × CD3-H_Hole:<br>qvqlqesgpglvkpsqtlsltctvsgfslsdygvhwvrqppgkglewlgviwagggtnynpsl<br>ksrktiskdtsknqvslklssvtaadtavyycardkgysyyysmdywgqgttvtvsssqvqlve<br>sgggvvqpgrslrlscaasgftftkawmhwvrqapgkqlewvaqikdksnsyatyyadsvkg<br>rftisrddskntlylqmnslraedtavyycrgvyyalspfdywgqgtlvtvssrtastkgpsvfpla<br>pcsrstsestaalgclvkdyfpepvtvswnsgaltsgvhtfpavlqssglyslssvvtvpssslgtkt<br>ytcnvdhkpsntkvdkrveskygppcppcpapeflggpsvflfppkpkdtlmisrtpevtcvv<br>vdvsqedpevqfnwyvdgvevhnaktkpreeqfnstyrvvsvltvlhqdwlngkeykckvs<br>nkglpssiektiskakgqprepqvctlppsqeemtknqvslscavkgfypsdiavewesngqp<br>ennykttppvldsdgsfflvsklt vdksrwqegnvfscsvmhealhnhytqkslslslgk | SEQ ID NO: 9 |
| Light chain B (CD3 × CD28-L) | CD3 × CD28-L<br>divmtqtplslsvtpgqpasisckssqslvhnnantylswylqkpgqspqsliykvsnrfsgvpdrfsgsg<br>sgtdftlkisrveaedvgvyycgqgtqypftfgsgtkveikgqpkaapdivliqspaslavspgqratitcra<br>sesveyyvtslmqwyqqkpgqppkllifaasnvesgvparfsgsgsgtdftltinpveandvanyycqq<br>srkvpytfgqgtkleiktkgpsrtvaapsvfifppsdeqlksgtasvvcllnnfypreakvqwkvdnalqs<br>gnsqesvteqdskdstyslsstltlskadyekhkvyacevthqglsspvtksfnrgec | SEQ ID NO: 10 |
| Binding Protein 21 Nucleotide Sequences | | |
| Heavy chain A (Anti-CD20-H_Knob:) | Anti-CD20-H_Knob:<br>caggtgcagctgcagcagcctggcgccgaactcgtgaaacctggcgcctccgtgaagatgagctgcaag<br>gccagcggctacaccttcaccagctacaacatgcactgggtcaagcagacccccggcagaggcctggaa<br>tggatcggcgccatctaccccggcaacggcgacacctcctacaaccagaagttcaagggcaaggccacc<br>ctgaccgccgacaagagcagcagcacagcctacatgcagctgtccagcctgaccagcgaggacagcgc<br>cgtgtactactgcgccagaagcacctactacggcggcgactggtacttcaacgtgtggggagccggcacc<br>accgtgacagtgtctgctgcttcgaccaagggcccatcggtgttccctctggccccttgcagcagaagcac<br>cagcgaatctacagccgccctgggctgcctcgtgaaggactactttcccgagcccgtgaccgtgtcctgga<br>actctggcgctctgacaagcggcgtgcacacctttccagccgtgctccagagcagcggcctgtactctctg<br>agcagcgtcgtgacagtgcccagcagcagcctgggcaccaagacctacacctgtaacgtggaccacaag<br>cccagcaacaccaaggtggacaagcgggtggaatctaagtacggccctccctgccctccttgcccagccc<br>ctgaatttctgggcggaccctccgtgttcctgttcccccaaagcccaaggacaccctgatgatcagccgga<br>cccccgaagtgacctgcgtggtggtggatgtgtcccaggaagatcccgaggtgcagttcaattggtacgtg<br>gacggcgtggaagtgcacaacgccaagaccaagcccagagaggaacagttcaacagcacctaccgggt<br>ggtgtccgtgctgaccgtgctgcaccaggactggctgaacggcaaagagtacaagtgcaaggtgtccaac<br>aagggcctgcccagctccatcgagaaaaccatcagcaaggccaagggccagccccgcgagcctcaagt<br>gtataccctgcccccttgccaggaagagatgaccaagaaccaggtgtccctgtggtgtctcgtgaaaggctt<br>ctaccccagcgacattgccgtggaatgggagagcaacggccagcccgagaacaactacaagaccaccc<br>cccctgtgctggacagcgacggctcattcttcctgtactccaagctgaccgtggacaagagccggtggcag<br>gaaggcaacgtgttcagctgctccgtgatgcacgaggccctgcacaaccactacacccagaagtccctgtc<br>tctgtccctgggcaag | SEQ ID NO: 116 |
| Light chain A (Anti-CD20-L:) | Anti-CD20-L:<br>cagatcgtgctgagccagagccctgccatcctgagcgcttccccaggcgagaaagtgaccatgacctgca<br>gagccagcagcagcgtgtcctacatccactggttccagcagaagcccggcagcagccccaagccttggat<br>ctacgccaccagcaatctggccagcggagtgcctgtgcggtttagcggctctggcagcggcacaagctac<br>agcctgaccatcagccgggtggaagccgaagatgccgccacctactactgccagcagtggaccagcaac<br>ccccccacatttggcggaggcaccaagctggaaatcaagcgtacggtggccgctcccagcgtgttcatctt<br>cccacctagcgacgagcagctgaagtccggcacagcctctgtcgtgtgcctgctgaacaacttctacccc c<br>gcgaggccaaagtgcagtggaaggtggacaacgccctgcagagcggcaacagccaggaaagcgtgac<br>cgagcaggacagcaaggactccacctacagcctgagcagcaccctgacactgagcaaggccgactacg<br>agaagcacaaggtgtacgcctgcgaagtgacccaccagggcctgtctagccccgtgaccaagagcttcaa<br>ccggggcgagtgt | SEQ ID NO: 117 |
| Heavy chain B (CD28 × CD3-H_Hole: | CD28 × CD3-H_Hole:<br>caggtgcagctgcaggaatctggccctggcctcgtgaagcctagccagaccctgagcctgacctgtaccg<br>tgtccggcttcagcctgagcgactacggcgtgcactgggtgcgccagccacctggaaaaggcctggaatg<br>gctgggcgtgatctgggctggcggaggcaccaactacaaccccagcctgaagtccagaaagaccatcag<br>caaggacaccagcaagaaccaggtgtccctgaagctgagcagcgtgacagccgccgataccgccgtgta<br>ctactgcgccagagacaagggctacagctactactacagcatggactactggggccagggcaccaccgt<br>gaccgtgtcatcctctcaggtgcagctggtggaatctggcggcggagtggtgcagcctggcagaagcctg<br>agactgagctgtgccgccagcggcttcaccttcaccaaggcctggatgcactgggtgcgccaggcccctg<br>gaaagcagctggaatgggtggcccagatcaaggacaagagcaacagctacgccacctactacgccgac<br>agcgtgaagggccggttcaccatcagccgggacgacagcaagaacaccctgtacctgcagatgaacagc<br>ctgcgggccgaggacaccgccgtgtactactgtcggggcgtgtactatgccctgagccccttcgattactg<br>gggccagggaaccctcgtgaccgtgtctagtcggaccgcttcgaccaagggcccatcggtgttccctctgg<br>ccccttgcagcagaagcaccagcgaatctacagccgccctgggctgcctcgtgaaggactactttcccga<br>gcccgtgaccgtgtcctggaactctggcgctctgacaagcggcgtgcacacctttccagccgtgctccaga<br>gcagcggcctgtactctctgagcagcgtcgtgacagtgcccagcagcagcctgggcaccaagacctaca<br>cctgtaacgtggaccacaagcccagcaacaccaaggtggacaagcgggtggaatctaagtacggccctc<br>cctgccctccttgcccagcccctgaatttctgggcggaccctccgtgttcctgttcccccaaagcccaagg<br>acaccctgatgatcagccggacccccgaagtgacctgcgtggtggtggatgtgtcccaggaagatcccga | SEQ ID NO: 118 |

TABLE 2-continued

Heavy and light chain sequences of binding proteins specifically directed to Her2, CD3, CD28, CD19 and/or CD20. CDR sequences are bolded and italicized.

| | | |
|---|---|---|
| | ggtgcagttcaattggtacgtggacggcgtggaagtgcacaacgccaagaccaagcccagagaggaaca<br>gttcaacagcacctaccgggtggtgtccgtgctgaccgtgctgcaccaggactggctgaacggcaaagag<br>tacaagtgcaaggtgtccaacaagggcctgcccagctccatcgagaaaaccatcagcaaggccaagggc<br>cagccccgcgagcctcaagtgtgtaccctgcccccctagccaggaagagatgaccaagaaccaggtgtcc<br>ctgagctgtgccgtgaaaggcttctaccccagcgacattgccgtggaatgggagagcaacggccagccc<br>gagaacaactacaagaccacccccccctgtgctggacagcgacggctcattcttcctggtgtccaagctgac<br>cgtggacaagagccggtggcaggaaggcaacgtgttcagctgctccgtgatgcacgaggccctgcacaa<br>ccactacacccagaagtccctgtctctgtccctgggcaag | |
| Light chain B (CD3_CD28-L:) | (CD3_CD28-L::<br>gacatcgtgatgacccagacccccctgagcctgagcgtgacacctggacagcctgccagcatcagctgca<br>agagcagccagagcctggtgcacaacaacgccaacacctacctgagctggtatctgcagaagcccggcc<br>agagcccccagtccctgatctacaaggtgtccaacagattcagcggcgtgcccgacagattctccggcag<br>cggctctggcaccgacttcaccctgaagatcagccgggtggaagccgaggacgtgggcgtgtactattgt<br>ggccagggcacccagtaccccttcacctttggcagcggcaccaaggtggaaatcaagggccagcccaag<br>gccgcccccgacatcgtgctgacacagagccctgctagcctggccgtgtctcctggacagagggccacc<br>atcacctgtagagccagcgagagcgtggaatattacgtgaccagcctgatgcagtggtatcagcagaagc<br>ccggccagcccccaagctgctgattttcgccgccagcaacgtggaaagcggcgtgccagccagattttc<br>cggcagcggctctggcaccgacttcaccctgaccatcaaccccgtggaagccaacgacgtggccaacta<br>ctactgccagcagagccggaaggtgccctacacctttggccagggcaccaagctggaaatcaagaccaa<br>gggccccagccgtacggtggccgctcccagcgtgttcatcttcccacctagcgacgagcagctgaagtcc<br>ggcacagcctctgtcgtgtgcctgctgaacaacttctacccccgcgaggccaaagtgcagtggaaggtgg<br>acaacgccctgcagagcggcaacagccaggaaagcgtgaccgagcaggacagcaaggactccaccta<br>cagcctgagcagcaccctgacactgagcaaggccgactacgagaagcacaaggtgtacgcctgcgaagt<br>gacccaccagggcctgtctagccccgtgaccaagagcttcaaccggggcgagtgt | SEQ ID NO: 119 |

TABLE 3

Heavy and light chain sequences of binding proteins specifically directed to IL-4, IL-13 and/or TNFa.

Binding Protein 9 Amino Acid Sequences

| | | |
|---|---|---|
| Heavy chain A | HC:<br>EVQLVESGGGLVQPGRSLRLSCAAS***GFTFDDYAMH***WVRQAPGK<br>GLEWVS***AITWNSGHID***YADSVEGRFTISRDNAKNSLYLQMNSLR<br>AEDTAVYYCAK***VSYLSTASSLDY***WGQGTLVTVSSASTKGPSVFPL<br>APSSKSTSGGTAALGCLVKDYFPEPVTVSWNSGALTSGVHTFPA<br>VLQSSGLYSLSSVVTVPSSSLGTQTYICNVNHKPSNTKVDKKVEP<br>KSCDKTHTCPPCPAPELLGGPSVFLFPPKPKDTLMISRTPEVTCVV<br>VDVSHEDPEVKFNWYVDGVEVHNAKTKPREEQYNSTYRVVSVL<br>TVLHQDWLNGKEYKCKVSNKALPAPIEKTISKAKGQPREPQVCT<br>LPPSRDELTKNQVSLSCAVKGFYPSDIAVEWESNGQPENNYKTTP<br>PVLDSDGSFFLVSKLTVDKSRWQQGNVFSCSVMHEALHNHYTQ<br>KSLSLSPG | SEQ ID NO: 60 |
| Light chain A | LC:<br>DIQMTQSPSSLSASVGDRVTITC***RASQGIRNYLA***WYQQKPGKAPK<br>LLIY***AASTLQS***GVPSRFSGSGSGTDFTLTISSLQPEDVATYYC***QRY<br>NRAPYT***FGQGTKVEIKGQPKAAPSVTLFPPSSEELQANKATLVCLI<br>SDFYPGAVTVAWKADSSPVKAGVETTTPSKQSNNKYAASSYLSL<br>TPEQWKSHRSYSCQVTHEGSTVEKTVAPTECS | SEQ ID NO: 61 |
| Heavy chain B | HC:<br>QVQLQQSGPELVKPGASVKISCKAS***GYSFTSYWIH***WIKQRPGQGL<br>EWIG***MIDPSDGET***RLNQRFQGRATLTVDESTSTAYMQLRSPTSED<br>SAVYYCTR***LKEYGNYDSFYFDV***WGAGTLVTVSSEVQLKESGPGL<br>VAPGGSLSITCTVS***GFSLTDSSIN***WVRQPPGKGLEWLG***MIWGDG<br>RID***YADALKSRLSISKDSSKSQVFLEMTSLRTDDTATYYCAR***DGY<br>FPYAMDF***WGQGTSVTVSSASTKGPSVFPLAPSSKSTSGGTAALG<br>CLVKDYFPEPVTVSWNSGALTSGVHTFPAVLQSSGLYSLSSVVTV<br>PSSSLGTQTYICNVNHKPSNTKVDKKVEPKSCDKTHTCPPCPAPE<br>LLGGPSVFLFPPKPKDTLMISRTPEVTCVVVDVSHEDPEVKFNWY<br>VDGVEVHNAKTKPREEQYNSTYRVVSVLTVLHQDWLNGKEYK<br>CKVSNKALPAPIEKTISKAKGQPREPQVYTLPPCRDELTKNQVSL<br>WCLVKGFYPSDIAVEWESNGQPENNYKTTPPVLDSDGSFFLYSK<br>LTVDKSRWQQGNVFSCSVMHEALHNRFTQKSLSLSPG | SEQ ID NO: 62 |
| Light chain B | LC:<br>DIVLTQSPASLAVSLGQRATISC***RASESVDSYGQSYMH***WYQQKA<br>GQPPKLLIY***LASNLES***GVPARFSGSGSRTDFTLTIDPVQAEDAATY<br>YC***QQNAEDSRT***FGGGTKLEIKGGSGSSGSGGDIQMTQSPASLSVS<br>VGDTITLTC***HASQNIDVWLS***WFQQKPGNIPKLLIY***KASNLHT***GVP<br>SRFSGSGSGTGFTLTISSLQPEDIATYYC***QQAHSYPFT***FGGGTKLEI | SEQ ID NO: 63 |

TABLE 3-continued

| Heavy and light chain sequences of binding proteins specifically directed to IL-4, IL-13 and/or TNFa. | | |
|---|---|---|
| | KGGSGSSGSGGRTVAAPSVFIFPPSDEQLKSGTASVVCLLNNFYP<br>REAKVQWKVDNALQSGNSQESVTEQDSKDSTYSLSSTLTLSKAD<br>YEKHKVYACEVTHQGLSSPVTKSFNRGEC | |
| | Binding Protein 9 Nucleotide Sequences | |
| Heavy chain A | HC:<br>gaggtgcagctggtggaaagcggcggaggactggtgcagcccggcagaagcctgagactgagctg<br>cgccgccagcggcttcaccttcgacgactacgccatgcactgggtccgccaggcccctggcaagggc<br>ctggaatgggtgtccgccatcacctggaacagcggccacatcgactacgccgacagcgtggaaggcc<br>ggttcaccatcagccgggacaacgccaagaacagcctgtacctgcagatgaacagcctgcgggccga<br>ggacaccgccgtgtactactgcgccaaggtgtcctacctgagcaccgccagcagcctggactactgg<br>ggccagggcaccctggtgacagtgtccagcgcttccaccaagggccccagcgtgttccccctggccc<br>ctagcagcaagagcacatctggcggcacagccgccctgggctgcctggtcaaggactacttccccga<br>gcccgtgacagtgtcctggaactctggcgccctgaccagcggagtgcataccttccctgccgtgctgca<br>gtccagcggcctgtacagcctgagcagcgtggtcacagtgcccagcagcagcctgggcacccagac<br>ctacatctgcaacgtgaaccacaagcccagcaacaccaaggtggacaagaaggtggaacccaagag<br>ctgcgacaagacccacacctgtccccctgccctgcccctgaactgctgggcggaccctccgtgttcct<br>gttcccccaaagcccaaggacaccctgatgatcagccggacccccgaagtgacctgcgtggtggtg<br>gacgtgtcccacgaggaccctgaagtgaagttcaattggtacgtggacggcgtggaagtgcataacgc<br>caagaccaagcccagagaggaacagtacaacagcacctaccgggtggtgtccgtgctgaccgtgctg<br>caccaggactggctgaacggcaaagagtacaagtgcaaggtgtccaacaaggccctgcctgcccccca<br>tcgagaaaaccatcagcaaggccaagggccagcctagagagccccaagtctgcaccctgccccccca<br>gcagagatgagctgaccaagaaccaggtgtccctgagctgcgccgtgaagggcttctaccccagcga<br>tatcgccgtggaatgggagagcaacggccagcccgagaacaactacaagaccacccccccctgtgctg<br>gacagcgacggctcattcttcctggtgtccaagctgacagtggacaagagccggtggcagcagggca<br>acgtgttcagctgcagcgtgatgcacgaggccctgcacaaccattacacccagaagtccctgagcctg<br>agccccggc | SEQ ID NO: 64 |
| Light chain A | LC:<br>gacatccagatgacccagagccccagcagcctgagcgccagcgtgggcgacagagtgaccatcacc<br>tgtcgggccagccagggcatccggaactacctggcctggtatcagcagaagcccggcaaggccccc<br>aagctgctgatctacgccgccagcacactgcagagcggcgtgcccagcagattcagcggcagcggct<br>ccggcaccgacttcaccctgaccatcagcagcctgcagcccgaggacgtggccacctactactgcca<br>gcggtacaacagagccccctacaccttcggccagggcaccaaggtggaaatcaagggacagcccaa<br>ggctgccccctcggtcaccctgttcccccaagcagcgaggaactgcaggccaacaaggccaccctc<br>gtgtgcctgatcagcgacttctaccctggcgccgtgaccgtggcctggaaggccgatagctctcccgtg<br>aaggccggcgtggaaaccaccacccccagcaagcagagcaacaacaaatacgccgcctccagctac<br>ctgagcctgacccccgagcagtggaagtcccaccggtcctacagctgccaggtcacacacgagggca<br>gcaccgtggaaaagaccgtggcccccaccgagtgcagc | SEQ ID NO: 65 |
| Heavy chain B | HC:<br>caggtgcagctgcagcagagcggccctgagctggtcaagcctggcgccagcgtgaagatcagctgc<br>aaggccagcggctacagcttcaccagctactggatccactggatcaagcagcggcctggccagggcc<br>tggaatggatcggcatgatcgaccccagcgacggcgagacacggctgaaccagagattccagggca<br>gagccaccctgaccgtggacgagagcaccagcaccgcctacatgcagctgcggagccccaccagc<br>gaggacagcgccgtgtactactgcacccggctgaaagagtacggcaactacgacagcttctacttcga<br>cgtgtggggagccggcaccctggtcaccgtgtccagcgaagtgcagctgaaagaaagcggccctgg<br>cctggtggcccctggcggcagcctgagcatcacctgtaccgtgtccggcttcagcctgaccgacagca<br>gcatcaactgggtccgacagccccctggcaagggcctcgagtggctgggaatgatctggggcgacg<br>gccggatcgactacgccgacgccctgaagtcccggctgagcatcagcaaggacagcagcaagagcc<br>aggtgttcctggaaatgaccagcctgcggaccgacgacaccgccacctactactgcgccagggacgg<br>ctacttcccctacgccatggatttctggggccagggcaccagcgtgaccgtgtcctctgcttccaccaag<br>ggccccagcgtgttccctctggcccctagcagcaagagcacatctggcggaacagccgccctgggct<br>gcctggtcaaggactactttcccgagcccgtgaccgtgtcctggaactctggtgccctgacaagcgga<br>gtgcataccttccctgccgtgctgcagagcagcggcctgtactctctgagcagcgtggtcaccgtgcca<br>agcagcagcctgggcacccagacctacatctgcaacgtgaaccacaagccctccaacaccaaggtgg<br>acaagaaggtggaacccaagagctgcgacaagacccacacctgtcctccctgtcctgcccctgaactg<br>ctgggcggaccctccgtgttcctgttccctccaaagcccaaggataccctgatgatcagccggacccct<br>gaagtgacctgcgtggtggtggacgtgtcccacgaggatcccgaagtgaagttcaattggtacgtgga<br>cggcgtggaagtgcataacgccaagaccaagcccagagaggaacagtacaacagcacctaccgggt<br>ggtgtccgtgctgacagtgctgcaccaggactggctgaacggcaaagagtacaagtgcaaggtgtcc<br>aacaaggccctgccagcccctatcgagaaaaccatcagcaaggccaagggccagccccgcgagcct<br>caggtgtacacactgcctccatgccgggacgagctgaccaagaaccaggtgtccctgtggtgcctcgt<br>gaagggcttctacccctccgatatcgccgtggaatgggagagcaacggccagcccgagaacaactac<br>aagaccacccctcccgtgctggacagcgacggctcattcttcctgtacagcaagctgaccgtggacaa<br>gtcccggtggcagcagggcaacgtgttcagctgctctgtgatgcacgaggccctgcacaaccggttca<br>cccagaagtccctgagcctgagccctggc | SEQ ID NO: 66 |
| Light chain B | LC:<br>Gacatcgtgctgacccagagccctgccagcctggccgtgtctctgggccagagagccaccatcagct<br>gccgggccagcgagagcgtggacagctacggccagagctacatgcactggtatcagcagaaggcc<br>ggccagcccccccaagctgctgatctacctggccagcaacctggaaagcggcgtgcccgccagattca<br>gcggcagcggcagcagaaccgacttcaccctgaccatcgaccccgtgcaggccgaggacgccgcc<br>acctactactgccagcagaacgccgaggacagccggaccttcggcggaggcaccaagctggaaatc<br>aagggcggctccggcagcagcggctctggcggcgatatccagatgacccagtcccccgcctccctga<br>gcgtgtccgtgggcgacaccatcaccctgacatgccacgccagccagaacatcgacgtgtggctgag | SEQ ID NO: 67 |

TABLE 3-continued

Heavy and light chain sequences of binding proteins specifically directed to IL-4, IL-13 and/or TNFa.

| | | |
|---|---|---|
| | ctggttccagcagaagcctggcaacatccctaagctgctcatctataaggcctccaacctgcacaccgg | |
| | cgtgcccagcaggttttccggctctggcagcggcaccggctttaccctgacaatcagcagcctgcagc | |
| | ccgaggatatcgccacatattactgtcagcaggcccacagctaccccttcacctttggcggcggaacaa | |
| | agctcgagattaagggcggcagcggaagctccggctccggcggacgtacggtggccgctccttccgt | |
| | gttcatcttccctccctccgacgagcagctgaagtccggcaccgcctccgtggtgtgtctgctgaacaac | |
| | ttctaccctcgggaggccaaggtgcagtggaaggtggacaacgccctgcagtccggcaactcccagg | |
| | agtccgtcaccgagcaggactccaaggacagcacctactccctgtcctccaccctgaccctgtccaag | |
| | gccgactacgagaagcacaaggtgtacgcctgtgaggtgacccaccagggcctgtccagccctgtga | |
| | ccaagtccttcaaccggggcgagtgc | |
| | Binding Protein 10 _Amino Acid Sequences | |
| Heavy | HC: | SEQ ID |
| chain A | EVQLVESGGGLVQPGRSLRLSCAAS***GFTFDDYAMH***WVRQAPGK | NO: 60 |
| | GLEWVS***AITWNSGHID***YADSVEGRFTISRDNAKNSLYLQMNSLR | |
| | AEDTAVYYCAK***VSYLSTASSLDY***WGQGTLVTVSSASTKGPSVFPL | |
| | APSSKSTSGGTAALGCLVKDYFPEPVTVSWNSGALTSGVHTFPA | |
| | VLQSSGLYSLSSVVTVPSSSLGTQTYICNVNHKPSNTKVDKKVEP | |
| | KSCDKTHTCPPCPAPELLGGPSVFLFPPKPKDTLMISRTPEVTCVV | |
| | VDVSHEDPEVKFNWYVDGVEVHNAKTKPREEQYNSTYRVVSVL | |
| | TVLHQDWLNGKEYKCKVSNKALPAPIEKTISKAKGQPREPQVCT | |
| | LPPSRDELTKNQVSLSCAVKGFYPSDIAVEWESNGQPENNYKTTP | |
| | PVLDSDGSFFLVSKLTVDKSRWQQGNVFSCSVMHEALHNHYTQ | |
| | KSLSLSPG | |
| Light | LC: | SEQ ID |
| chain A | DIQMTQSPSSLSASVGDRVTITC***RASQGIRNYLA***WYQQKPGKAPK | NO: 61 |
| | LLIY***AASTLQS***GVPSRFSGSGSGTDFTLTISSLQPEDVATYYC***QRY*** | |
| | ***NRAPTY***FGQGTKVEIKGQPKAAPSVTLFPPSSEELQANKATLVCLI | |
| | SDFYPGAVTVAWKADSSPVKAGVETTTPSKQSNNKYAASSYLSL | |
| | TPEQWKSHRSYSCQVTHEGSTVEKTVAPTECS | |
| Heavy | HC: | SEQ ID |
| chain B | EVQLKESGPGLVAPGGSLSITCTVS***GFSLTDSSIN***WVRQPPGKGL | NO: 68 |
| | EWLG***MIWGDGRID***YADALKSRLSISKDSSKSQVFLEMTSLRTDD | |
| | TATYYCAR***DGYFPYAMDF***WGQGTSVTVSSQVQLQQSGPELVKP | |
| | GASVKISCKAS***GYSFTSYWIH***WIKQRPGQGLEWIG***MIDPSDGET***R | |
| | LNQRFQGRATLTVDESTSTAYMQLRSPTSEDSAVYYCTR***LKEYG*** | |
| | ***NYDSFYFD***VWGAGTLVTVSSASTKGPSVFPLAPSSKSTSGGTAAL | |
| | GCLVKDYFPEPVTVSWNSGALTSGVHTFPAVLQSSGLYSLSSVVT | |
| | VPSSSLGTQTYICNVNHKPSNTKVDKKVEPKSCDKTHTCPPCPAP | |
| | ELLGGPSVFLFPPKPKDTLMISRTPEVTCVVVDVSHEDPEVKFNW | |
| | YVDGVEVHNAKTKPREEQYNSTYRVVSVLTVLHQDWLNGKEY | |
| | KCKVSNKALPAPIEKTISKAKGQPREPQVYTLPPCRDELTKNQVS | |
| | LWCLVKGFYPSDIAVEWESNGQPENNYKTTPPVLDSDGSFFLYS | |
| | KLTVDKSRWQQGNVFSCSVMHEALHNRFTQKSLSLSPG | |
| Light | LC: | SEQ ID |
| chain B | DIQMTQSPASLSVSVGDTITLTC***HASQNIDVWLS***WFQQKPGNIPK | NO: 69 |
| | LLIY***KASNLHT***GVPSRFSGSGSGTGFTLTISSLQPEDIATYYC***QQA*** | |
| | ***HSYPFT***FGGGTKLEIKGGSGSSGSGGDIVLTQSPASLAVSLGQRA | |
| | TISC***RASESVDSYGQSYMH***WYQQKAGQPPKLLIY***LASNLES***GVPA | |
| | RFSGSGSRTDFTLTIDPVQAEDAATYYC***QQNAEDSRT***FGGGTKLE | |
| | IKGGSGSSGSGGRTVAAPSVFIFPPSDEQLKSGTASVVCLLNNFYP | |
| | REAKVQWKVDNALQSGNSQESVTEQDSKDSTYSLSSTLTLSKAD | |
| | YEKHKVYACEVTHQGLSSPVTKSFNRGEC | |
| | Binding Protein 10 Nucleotide Sequences | |
| Heavy | HC: | SEQ ID |
| chain A | gaggtgcagctggtggaaagcggcggaggactggtgcagcccggcagaagcctgagactgagctg | NO: 64 |
| | cgccgccagcggcttcaccttcgacgactacgccatgcactgggtccgccaggcccctggcaagggc | |
| | ctggaatgggtgtccgccatcacctggaacagcggccacatcgactacgccgacagcgtggaaggcc | |
| | ggttcaccatcagccgggacaacgccaagaacagcctgtacctgcagatgaacagcctgcgggccga | |
| | ggacaccgccgtgtactactgcgccaaggtgtcctacctgagcaccgccagcagcctggactactgg | |
| | ggccagggcaccctggtgacagtgtccagcgcttccaccaagggccccagcgtgttccccctggccc | |
| | ctagcagcaagagcacatctggcggcacagccgccctgggctgcctggtcaaggactacttccccga | |
| | gcccgtgacagtgtcctggaactctggcgccctgaccagcggagtgcataccttccctgccgtgctgca | |
| | gtccagcggcctgtacagcctgagcagcgtggtcacagtgcccagcagcagcctgggcacccagac | |
| | ctacatctgcaacgtgaaccacaagcccagcaacaccaaggtggacaagaaggtggaacccaagag | |
| | ctgcgacaagacccacacctgtccccctgccctgcccctgaactgctgggcggaccctccgtgttcct | |
| | gttcccccccaaagcccaaggacaccctgatgatcagccggacccccgaagtgacctgcgtggtggtg | |
| | gacgtgtcccacgaggaccctgaagtgaagttcaattggtacgtggacggcgtggaagtgcataacgc | |
| | caagaccaagcccagagaggaacagtacaacagcacctaccgggtggtgtccgtgctgaccgtgctg | |
| | caccaggactggctgaacggcaaagagtacaagtgcaaggtgtccaacaaggccctgcctgcccccca | |
| | tcgagaaaaccatcagcaaggccaagggccagcctagagagccccaagtctgcaccctgcccccca | |
| | gcagagatgagctgaccaagaaccaggtgtccctgagctgcgccgtgaagggcttctaccccagcga | |

TABLE 3-continued

| Heavy and light chain sequences of binding proteins specifically directed to IL-4, IL-13 and/or TNFa. | | |
|---|---|---|
| | tatcgccgtggaatgggagagcaacggccagcccgagaacaactacaagaccaccccccctgtgctg gacagcgacggctcattcttcctggtgtccaagctgacagtggacaagagccggtggcagcagggca acgtgttcagctgcagcgtgatgcacgaggccctgcacaaccattacacccagaagtccctgagcctg agccccggc | |
| Light chain A | LC: gacatccagatgacccagagccccagcagcctgagcgccagcgtgggcgacagagtgaccatcacc tgtcgggccagccagggcatccggaactacctggcctggtatcagcagaagcccggcaaggccccc aagctgctgatctacgccgccagcacactgcagagcggcgtgcccagcagattcagcggcagcggct ccggcaccgacttcaccctgaccatcagcagcctgcagcccgaggacgtggccacctactactgcca gcggtacaacagagcccccctacaccttcggccagggcaccaaggtggaaatcaagggacagcccaa ggctgcccccctcggtcaccctgttcccccaagcagcgaggaactgcaggccaacaaggccaccctc gtgtgcctgatcagcgacttctaccctggcgccgtgaccgtggcctggaaggccgatagctctcccgtg aaggccggcgtggaaaccaccaccccccagcaagcagagcaacaacaaatacgccgcctccagctac ctgagcctgacccccgagcagtggaagtcccaccggtcctacagctgccaggtcacacacgagggca gcaccgtggaaaagaccgtggcccccaccgagtgcagc | SEQ ID NO: 65 |
| Heavy chain B | HC: gaggtgcagctgaaagagtccggccctggactggtggcccctggcggcagcctgagcatcacctgta ccgtgtccggcttcagcctgaccgacagcagcatcaactgggtccgacagccccctggcaagggcct ggaatggctgggcatgatctggggcgacggccggatcgactacgccgacgccctgaagtcccggct gagcatcagcaaggacagcagcaagagccaggtgttcctggaaatgaccagcctgcggaccgacga caccgccacctactactgcgccagggacggctacttcccctacgccatggatttctggggccagggca ccagcgtgaccgtgtccagtcaggtccagctgcagcagagcggccctgagctggtcaagcctggcgc cagcgtgaagatcagctgcaaggccagcggctacagcttcaccagctactggatccactggatcaagc agcggcctggccagggcctcgagtggatcggaatgatcgaccccagcgacggcgagacacggctg aaccagagattccagggcagagccaccctgaccgtggacgagagcaccagcaccgcctacatgcag ctgcggagccccaccagcgaggacagcgccgtgtactactgcacccggctgaaagaatacggcaact acgacagcttctacttcgacgtgtggggagccggcaccctggtcaccgtgtctagcgcttccaccaagg gccccagcgtgttccctctggcccctagcagcaagagcacatctggcggaacagccgccctgggctg cctggtcaaggactactttcccgagcccgtgaccgtgtcctggaactctggtgccctgacaagcggagt gcataccttccctgccgtgctgcagagcagcggcctgtactctctgagcagcgtggtcaccgtgccaag cagcagcctgggcacccagacctacatctgcaacgtgaaccacaagccctccaacaccaaggtggac aagaaggtggaacccaagagctgcgacaagacccacacctgtcctccctgtcctgcccctgaactgct gggcggaccctccgtgttcctgttccctccaaagcccaaggataccctgatgatcagccggacccctga agtgacctgcgtggtggtggacgtgtcccacgaggatcccgaagtgaagttcaattggtacgtggacg gcgtggaagtgcataacgccaagaccaagcccagagaggaacagtacaacagcacctaccgggtgg tgtccgtgctgacagtgctgcaccaggactggctgaacggcaaagagtacaagtgcaaggtgtccaac aaggccctgccagcccctatcgagaaaaccatcagcaaggccaagggccagccccgcgagcctcag gtgtacacactgcctccatgccgggacgagctgaccaagaaccaggtgtccctgtggtgcctcgtgaa gggcttctaccccctccgatatcgccgtggaatgggagagcaacggccagcccgagaacaactacaag accacccctcccgtgctggacagcgacggctcattcttcctgtacagcaagctgaccgtggacaagtcc cggtggcagcagggcaacgtgttcagctgctctgtgatgcacgaggccctgcacaaccggttcaccca gaagtccctgagcctgagccctggc | SEQ ID NO: 97 |
| Light chain B | LC: gacatccagatgacccagagccccgccagcctgagcgtgtccgtgggcgataccatcaccctgacct gccacgccagccagaacatcgacgtgtggctgagctggttccagcagaagcccggcaacatccccaa gctgctgatctacaaggccagcaacctgcacaccggcgtgcccagcagattcagcggctctggcagc ggcaccggctttaccctgaccatcagcagcctgcagcccgaggatatcgccacctactactgccagca ggcccacagctaccccttcaccttcggcggaggcaccaagctggaaatcaagggcggcagcggcag ctccggctctggcggcgatatcgtgctgacccagtctcccgcctccctggccgtgtctctgggccagag agccaccatcagctgccgggccagcgagagcgtggacagctacggccagagctacatgcactggtat cagcagaaggccggacagccccctaaactgctcatctacctggcctccaacctggaaagcggcgtgc ccgccaggttttccggcagcggctccagaaccgacttcaccctgacaatcgaccccgtgcaggccga ggacgccgccacatattactgtcagcagaacgccgaggacagcagaacctttggcggcggaacaaa gctcgagattaagggcggctccggctccagcggatctggcggacgtacggtggccgctccttccgtgt tcatcttccctccctccgacgagcagctgaagtccggcaccgcctccgtggtgtgtctgctgaacaactt ctaccctcgggaggccaaggtgcagtggaaggtggacaacgccctgcagtccggcaactcccagga gtccgtcaccgagcaggactccaaggacagcacctactccctgtcctccaccctgaccctgtccaagg ccgactacgagaagcacaaggtgtacgcctgtgaggtgacccaccagggcctgtccagccctgtgac caagtccttcaaccggggcgagtgc | SEQ ID NO: 70 |

Binding Protein 11 Amino Acid Sequences

| | | |
|---|---|---|
| Heavy chain A | HC: EVQLVESGGGLVQPGRSLRLSCAAS***GFTFDDYAMH***WVRQAPGK GLEWVS***AITWNSGHID***YADSVEGRFTISRDNAKNSLYLQMNSLR AEDTAVYYCAK***VSYLSTASSLDY***WGQGTLVTVSSASTKGPSVFPL APSSKSTSGGTAALGCLVKDYFPEPVTVSWNSGALTSGVHTFPA VLQSSGLYSLSSVVTVPSSSLGTQTYICNVNHKPSNTKVDKKVEP KSCDKTHTCPPCPAPELLGGPSVFLFPPKPKDTLMISRTPEVTCVV VDVSHEDPEVKFNWYVDGVEVHNAKTKPREEQYNSTYRVVSVL TVLHQDWLNGKEYKCKVSNKALPAPIEKTISKAKGQPREPQVCT LPPSRDELTKNQVSLSCAVKGFYPSDIAVEWESNGQPENNYKTTP PVLDSDGSFFLVSKLTVDKSRWQQGNVFSCSVMHEALHNHYTQ KSLSLSPG | SEQ ID NO: 60 |

TABLE 3-continued

| Heavy and light chain sequences of binding proteins specifically directed to IL-4, IL-13 and/or TNFa. | | |
|---|---|---|
| Light chain A | LC:<br>DIQMTQSPSSLSASVGDRVTITC***RASQGIRNYLA***WYQQKPGKAPK<br>LLIY***AASTLQS***GVPSRFSGSGSGTDFTLTISSLQPEDVATYYC***QRY***<br>***NRAPYT***FGQGTKVEIKRTVAAPSVFIFPPSDEQLKSGTASVVCLLN<br>NFYPREAKVQWKVDNALQSGNSQESVTEQDSKDSTYSLSSTLTL<br>SKADYEKHKVYACEVTHQGLSSPVTKSFNRGEC | SEQ ID NO: 71 |
| Heavy chain B | HC:<br>EVQLKESGPGLVAPGGSLSITCTVS***GFSLTDSSIN***WVRQPPGKGL<br>EWLG***MIWGDGRID***YADALKSRLSISKDSSKSQVFLEMTSLRTDD<br>TATYYCAR***DGYFPYAMDF***WGQGTSVTVSSQVQLQQSGPELVKP<br>GASVKISCKAS***GYSFTSYWIH***WIKQRPGQGLEWIG***MIDPSDGET***R<br>LNQRFQGRATLTVDESTSTAYMQLRSPTSEDSAVYYCTR***LKEYG***<br>***NYDSFYFDV***WGAGTLVTVSSASTKGPSVFPLAPSSKSTSGGTAAL<br>GCLVKDYFPEPVTVSWNSGALTSGVHTFPAVLQSSGLYSLSSVVT<br>VPSSSLGTQTYICNVNHKPSNTKVDKKVEPKSCDKTHTCPPCPAP<br>ELLGGPSVFLFPPKPKDTLMISRTPEVTCVVVDVSHEDPEVKFNW<br>YVDGVEVHNAKTKPREEQYNSTYRVVSVLTVLHQDWLNGKEY<br>KCKVSNKALPAPIEKTISKAKGQPREPQVYTLPPCRDELTKNQVS<br>LWCLVKGFYPSDIAVEWESNGQPENNYKTTPPVLDSDGSFFLYS<br>KLTVDKSRWQQGNVFSCSVMHEALHNRFTQKSLSLSPG | SEQ ID NO: 68 |
| Light chain B | LC:<br>DIQMTQSPASLSVSVGDTITLTC***HASQNIDVWLS***WFQQKPGNIPK<br>LLIY***KASNLHT***GVPSRFSGSGSGTGFTLTISSLQPEDIATYYC***QQA***<br>***HSYPFT***FGGGTKLEIKGGSGSSGSGGDIVLTQSPASLAVSLGQRA<br>TISC***RASESVDSYGQSYMN***WYQQKAGQPPKLLIY***LASNLES***GVPA<br>RFSGSGSRTDFTLTIDPVQAEDAATYYC***QQNAEDSRT***FGGGTKLE<br>IKGGSGSSGSGGRTVAAPSVFIFPPSDEQLKSGTASVVCLLNNFYP<br>REAKVQWKVDNALQSGNSQESVTEQDSKDSTYSLSSTLTLSKAD<br>YEKHKVYACEVTHQGLSSPVTKSFNRGEC | SEQ ID NO: 69 |
| Binding Protein 11 _Nucleotide Sequences | | |
| Heavy chain A | HC:<br>gaggtgcagctggtggaaagcggcggaggactggtgcagcccggcagaagcctgagactgagctg<br>cgccgccagcggcttcaccttcgacgactacgccatgcactgggtccgccaggcccctggcaagggc<br>ctggaatgggtgtccgccatcacctggaacagcggccacatcgactacgccgacagcgtggaaggcc<br>ggttcaccatcagccgggacaacgccaagaacagcctgtacctgcagatgaacagcctgcgggccga<br>ggacaccgccgtgtactactgcgccaaggtgtcctacctgagcaccgccagcagcctggactactgg<br>ggccagggcaccctggtgacagtgtccagcgcttccaccaagggccccagcgtgttccccctggccc<br>ctagcagcaagagcacatctggcggcacagccgccctgggctgcctggtcaaggactacttccccga<br>gcccgtgacagtgtcctggaactctggcgccctgaccagcggagtgcataccttccctgccgtgctgca<br>gtccagcggcctgtacagcctgagcagcgtggtcacagtgcccagcagcagcctgggcacccagac<br>ctacatctgcaacgtgaaccacaagcccagcaacaccaaggtggacaagaaggtggaacccaagag<br>ctgcgacaagacccacacctgtccccctgccctgcccctgaactgctgggcggaccctccgtgttcct<br>gttcccccaaagcccaaggacaccctgatgatcagccggacccccgaagtgacctgcgtggtggtg<br>gacgtgtcccacgaggaccctgaagtgaagttcaattggtacgtggacggcgtggaagtgcataacgc<br>caagaccaagcccagagaggaacagtacaacagcacctaccgggtggtgtccgtgctgaccgtgctg<br>caccaggactggctgaacggcaaagagtacaagtgcaaggtgtccaacaaggccctgcctgcccca<br>tcgagaaaaccatcagcaaggccaagggccagcctagagagccccaagtctgcaccctgcccccca<br>gcagagatgagctgaccaagaaccaggtgtccctgagctgcgccgtgaagggcttctaccccagcga<br>tatcgccgtggaatgggagagcaacggccagcccgagaacaactacaagaccacccccctgtgctg<br>gacagcgacggctcattcttcctggtgtccaagctgacagtggacaagagccggtggcagcagggca<br>acgtgttcagctgcagcgtgatgcacgaggccctgcacaaccattacacccagaagtccctgagcctg<br>agccccggc | SEQ ID NO: 64 |
| Light chain A | LC:<br>gacatccagatgacccagagccccagcagcctgagcgccagcgtgggcgacagagtgaccatcacc<br>tgtcgggccagccagggcatccggaactacctggcctggtatcagcagaagcccggcaaggccccc<br>aagctgctgatctacgccgccagcacactgcagagcggcgtgcccagcagattcagcggcagcggct<br>ccggcaccgacttcaccctgaccatcagcagcctgcagcccgaggacgtggccacctactactgcca<br>gcggtacaacagagcccccctacaccttcggccagggcaccaaggtggaaatcaagcgtacggtggc<br>cgctccttccgtgttcatcttccctccctccgacgagcagctgaagtccggcaccgcctccgtggtgtgt<br>ctgctgaacaacttctaccctcgggaggccaaggtgcagtggaaggtggacaacgccctgcagtccg<br>gcaactcccaggagtccgtcaccgagcaggactccaaggacagcacctactccctgtcctccaccctg<br>accctgtccaaggccgactacgagaagcacaaggtgtacgcctgtgaggtgacccaccagggcctgt<br>ccagccctgtgaccaagtccttcaaccggggcgagtgc | SEQ ID NO: 72 |
| Heavy chain B | HC:<br>gaggtgcagctgaaagagtccggccctggactggtggcccctggcggcagcctgagcatcacctgta<br>ccgtgtccggcttcagcctgaccgacagcagcatcaactgggtccgacagccccctggcaagggcct<br>ggaatggctgggcatgatctggggcgacggccggatcgactacgccgacgccctgaagtcccggct<br>gagcatcagcaaggacagcagcaagagccaggtgttcctggaaatgaccagcctgcggaccgacga<br>caccgccacctactactgcgccagggacggctacttcccctacgccatggatttctggggccagggca<br>ccagcgtgaccgtgtccagtcaggtccagctgcagcagagcggccctgagctggtcaagcctggcgc | SEQ ID NO: 97 |

TABLE 3-continued

| Heavy and light chain sequences of binding proteins specifically directed to IL-4, IL-13 and/or TNFa. | | |
|---|---|---|
| | cagcgtgaagatcagctgcaaggccagcggctacagcttcaccagctactggatccactggatcaagc<br>agcggcctggccagggcctcgagtggatcggaatgatcgaccccagcgacggcgagacacggctg<br>aaccagagattccagggcagagccaccctgaccgtggacgagagcaccagcaccgcctacatgcag<br>ctgcggagccccaccagcgaggacagcgccgtgtactactgcacccggctgaaagaatacggcaact<br>acgacagcttctacttcgacgtgtggggagccggcaccctggtcaccgtgtctagcgcttccaccaagg<br>gccccagcgtgttccctctggcccctagcagcaagagcacatctggcggaacagccgccctgggctg<br>cctggtcaaggactactttcccgagcccgtgaccgtgtcctggaactctggtgccctgacaagcggagt<br>gcataccttccctgccgtgctgcagagcagcggcctgtactctctgagcagcgtggtcaccgtgccaag<br>cagcagcctgggcacccagacctacatctgcaacgtgaaccacaagccctccaacaccaaggtggac<br>aagaaggtggaacccaagagctgcgacaagacccacacctgtcctccctgtcctgcccctgaactgct<br>gggcggaccctccgtgttcctgttccctccaaagcccaaggataccctgatgatcagccggacccctga<br>agtgacctgcgtggtggtggacgtgtcccacgaggatcccgaagtgaagttcaattggtacgtggacg<br>gcgtggaagtgcataacgccaagaccaagcccagagaggaacagtacaacagcacctaccgggtgg<br>tgtccgtgctgacagtgctgcaccaggactggctgaacggcaaagagtacaagtgcaaggtgtccaac<br>aaggccctgccagcccctatcgagaaaaccatcagcaaggccaagggccagccccgcgagcctcag<br>gtgtacacactgcctccatgccgggacgagctgaccaagaaccaggtgtccctgtggtgcctcgtgaa<br>gggcttctaccccctccgatatcgccgtggaatgggagagcaacggccagcccgagaacaactacaag<br>accaccccctcccgtgctggacagcgacggctcattcttcctgtacagcaagctgaccgtggacaagtcc<br>cggtggcagcagggcaacgtgttcagctgctctgtgatgcacgaggccctgcacaaccggttcaccca<br>gaagtccctgagcctgagccctggc | |
| Light chain B | LC:<br>gacatccagatgacccagagccccgccagcctgagcgtgtccgtgggcgataccatcaccctgacct<br>gccacgccagccagaacatcgacgtgtggctgagctggttccagcagaagcccggcaacatccccaa<br>gctgctgatctacaaggccagcaacctgcacaccggcgtgcccagcagattcagcggctctggcagc<br>ggcaccggctttaccctgaccatcagcagcctgcagcccgaggatatcgccacctactactgccagca<br>ggcccacagctaccccttcaccttcggcggaggcaccaagctggaaatcaagggcggcagcggcag<br>ctccggctctggcggcgatatcgtgctgacccagtctcccgcctccctggccgtgtctctgggccagag<br>agccaccatcagctgccgggccagcgagagcgtggacagctacggccagagctacatgcactggtat<br>cagcagaaggccggacagccccctaaactgctcatctacctggcctccaacctggaaagcggcgtgc<br>ccgccaggttttccggcagcggctccagaaccgacttcaccctgacaatcgaccccgtgcaggccga<br>ggacgccgccacatattactgtcagcagaacgccgaggacagcagaacctttggcggcggaacaaa<br>gctcgagattaagggcggctccggctccagcggatctggcggacgtacggtggccgctccttccgtgt<br>tcatcttccctccctccgacgagcagctgaagtccggcaccgcctccgtggtgtgtctgctgaacaactt<br>ctaccctcgggaggccaaggtgcagtggaaggtggacaacgccctgcagtccggcaactcccagga<br>gtccgtcaccgagcaggactccaaggacagcacctactccctgtcctccaccctgaccctgtccaagg<br>ccgactacgagaagcacaaggtgtacgcctgtgaggtgacccaccagggcctgtccagccctgtgac<br>caagtccttcaaccggggcgagtgc | SEQ ID NO: 70 |

Binding Protein 12 Amino Acid Sequences

| | | |
|---|---|---|
| Heavy chain A | HC:<br>EVQLKESGPGLVAPGGSLSITCTVS***GFSLTDSSIN***WVRQPPGKGL<br>EWLG***MIWGDGRID***YADALKSRLSISKDSSKSQVFLEMTSLRTDD<br>TATYYCAR***DGYFPYAMDF***WGQGTSVTVSSASTKGPSVFPLAPSS<br>KSTSGGTAALGCLVKDYFPEPVTVSWNSGALTSGVHTFPAVLQS<br>SGLYSLSSVVTVPSSSLGTQTYICNVNHKPSNTKVDKKVEPKSCD<br>KTHTCPPCPAPELLGGPSVFLFPPKPKDTLMISRTPEVTCVVVDVS<br>HEDPEVKFNWYVDGVEVHNAKTKPREEQYNSTYRVVSVLTVLH<br>QDWLNGKEYKCKVSNKALPAPIEKTISKAKGQPREPQVCTLPPSR<br>DELTKNQVSLSCAVKGFYPSDIAVEWESNGQPENNYKTTPPVLD<br>SDGSFFLVSKLTVDKSRWQQGNVFSCSVMHEALHNHYTQKSLSL<br>SPG | SEQ ID NO: 73 |
| Light chain A | LC:<br>DIVLTQSPASLAVSLGQRATISC***RASESVDSYGQSYMH***WYQQKA<br>GQPPKLLIY***LASNLES***GVPARFSGSGSRTDFTLTIDPVQAEDAATY<br>YC***QQNAEDSRT***FGGGTKLEIKGQPKAAPSVTLFPPSSEELQANKA<br>TLVCLISDFYPGAVTVAWKADSSPVKAGVETTTPSKQSNNKYAA<br>SSYLSLTPEQWKSHRSYSCQVTHEGSTVEKTVAPTECS | SEQ ID NO: 74 |
| Heavy chain B | HC:<br>QVQLQQSGPELVKPGASVKISCKAS***GYSFTSYWIH***WIKQRPGQGL<br>EWIG***MIDPSDGET***RLNQRFQGRATLTVDESTSTAYMQLRSPTSED<br>SAVYYCTR***LKEYGNYDSFYFD***VWGAGTLVTVSSEVQLVESGGGL<br>VQPGRSLRLSCAAS***GFTFDDYAMH***WVRQAPGKGLEWVS***AITWN***<br>***SGHID***YADSVEGRFTISRDNAKNSLYLQMNSLRAEDTAVYYCAK<br>***VSYLSTASSLDY***WGQGTLVTVSSASTKGPSVFPLAPSSKSTSGGTA<br>ALGCLVKDYFPEPVTVSWNSGALTSGVHTFPAVLQSSGLYSLSSV<br>VTVPSSSLGTQTYICNVNHKPSNTKVDKKVEPKSCDKTHTCPPCP<br>APELLGGPSVFLFPPKPKDTLMISRTPEVTCVVVDVSHEDPEVKF<br>NWYVDGVEVHNAKTKPREEQYNSTYRVVSVLTVLHQDWLNGK<br>EYKCKVSNKALPAPIEKTISKAKGQPREPQVYTLPPCRDELTKNQ<br>VSLWCLVKGFYPSDIAVEWESNGQPENNYKTTPPVLDSDGSFFL<br>YSKLTVDKSRWQQGNVFSCSVMHEALHNRFTQKSLSLSPG | SEQ ID NO: 75 |

TABLE 3-continued

| Heavy and light chain sequences of binding proteins specifically directed to IL-4, IL-13 and/or TNFa. | | |
|---|---|---|
| Light chain B | LC:<br>DIQMTQSPSSLSASVGDRVTITC***RASQGIRNYLA***WYQQKPGKAPK<br>LLIY***AASTLQS***GVPSRFSGSGSGTDFTLTISSLQPEDVATYYC***QRY***<br>***NRAPYT***FGQGTKVEIKGGSGSSGSGGDIQMTQSPASLSVSVGDTIT<br>LTC***HASQNIDVWLS***WFQQKPGNIPKLLIY***KASNLHT***GVPSRFSGS<br>GSGTGFTLTISSLQPEDIATYYC***QQAHSYPFT***FGGGTKLEIKGGSG<br>SSGSGGRTVAAPSVFIFPPSDEQLKSGTASVVCLLNNFYPREAKV<br>QWKVDNALQSGNSQESVTEQDSKDSTYSLSSTLTLSKADYEKHK<br>VYACEVTHQGLSSPVTKSFNRGEC | SEQ ID NO: 76 |
| Binding Protein 12 Nucleotide Sequences | | |
| Heavy chain A | HC:<br>gaggtgcagctgaaggagagcggccccggcctggtggcccccggcggcagcctgagcatcacctg<br>caccgtgagcggcttcagcctgaccgacagcagcatcaactgggtgcgccagcccccggcaaggg<br>cctggagtggctgggcatgatctggggcgacggccgcatcgactacgccgacgccctgaagagccg<br>cctgagcatcagcaaggacagcagcaagagccaggtgttcctggagatgaccagcctgcgcaccga<br>cgacaccgccacctactactgcgcccgcgacggctacttcccctacgccatggacttctggggccagg<br>gcaccagcgtgaccgtgagcagcgccagcaccaagggccccagcgtgttccccctggcccctagca<br>gcaagagcacatctggcggcacagccgccctgggctgcctggtcaaggactacttccccgagcccgt<br>gacagtgtcctggaactctggcgccctgaccagcggagtgcataccttccctgccgtgctgcagtccag<br>cggcctgtacagcctgagcagcgtggtcacagtgcccagcagcagcctgggcacccagacctacatc<br>tgcaacgtgaaccacaagcccagcaacaccaaggtggacaagaaggtggaacccaagagctgcgac<br>aagacccacacctgtccccccctgccctgcccctgaactgctgggcggaccctccgtgttcctgttcccc<br>ccaaagcccaaggacaccctgatgatcagccggacccccgaagtgacctgcgtggtggtggacgtgt<br>cccacgaggaccctgaagtgaagttcaattggtacgtggacggcgtggaagtgcataacgccaagac<br>caagcccagagaggaacagtacaacagcacctaccgggtggtgtccgtgctgaccgtgctgcaccag<br>gactggctgaacggcaaagagtacaagtgcaaggtgtccaacaaggccctgcctgcccccatcgaga<br>aaaccatcagcaaggccaagggccagcctagagagccccaagtctgcaccctgcccccccagcagag<br>atgagctgaccaagaaccaggtgtccctgagctgcgccgtgaagggcttctaccccagcgatatcgcc<br>gtggaatgggagagcaacggccagcccgagaacaactacaagaccaccccccctgtgctggacagc<br>gacggctcattcttcctggtgtccaagctgacagtggacaagagccggtggcagcagggcaacgtgtt<br>cagctgcagcgtgatgcacgaggccctgcacaaccattacacccagaagtccctgagcctgagcccc<br>ggc | SEQ ID NO: 77 |
| Light chain A | LC:<br>gacatcgtgctgacccagagccctgccagcctggccgtgtctctgggccagagagccaccatcagct<br>gccgggccagcgagagcgtggacagctacggccagagctacatgcactggtatcagcagaaggcc<br>ggccagcccccaagctgctgatctacctggccagcaacctggaaagcggcgtgcccgccagattca<br>gcggcagcggcagcagaaccgacttcaccctgaccatcgaccccgtgcaggccgaggacgccgcc<br>acctactactgccagcagaacgccgaggacagccggaccttcggcggaggcaccaagctggaaatc<br>aagggacagcccaaggctgcccccctcggtcaccctgttcccccccaagcagcgaggaactgcaggcc<br>aacaaggccaccctcgtgtgcctgatcagcgacttctaccctggcgccgtgaccgtggcctggaaggc<br>cgatagctctcccgtgaaggccggcgtggaaaccaccaccccccagcaagcagagcaacaacaaata<br>cgccgccagcagctacctgagcctgacccccgagcagtggaagtcccaccggtcctacagctgccag<br>gtcacacacgagggcagcaccgtggaaaagaccgtggcccccaccgagtgcagc | SEQ ID NO: 78 |
| Heavy chain B | HC:<br>caggtgcagctgcagcagagcggccctgagctggtcaagcctggcgccagcgtgaagatcagctgc<br>aaggccagcggctacagcttcaccagctactggatccactggatcaagcagcggcctggccagggcc<br>tggaatggatcggcatgatcgaccccagcgacggcgagacacggctgaaccagagattccagggca<br>gagccaccctgaccgtggacgagagcaccagcaccgcctacatgcagctgcggagccccaccagc<br>gaggacagcgccgtgtactactgcacccggctgaaagagtacggcaactacgacagcttctacttcga<br>cgtgtggggagccggcaccctggtcaccgtgtccagcgaagtgcagctggtggaaagcggcggagg<br>cctggtgcagcccggcagaagcctgagactgagctgcgccgccagcggcttcaccttcgacgactac<br>gccatgcactgggtccgacaggcccctggcaaaggactggaatgggtgtccgccatcacctggaaca<br>gcggccacatcgactacgccgacagcgtggaaggccggttcaccatcagccgggacaacgccaaga<br>acagcctgtacctgcagatgaacagcctgcgggccgaggataccgccgtgtattattgcgccaaggtg<br>tcctacctgagcaccgccagcagcctggactactggggccagggcaccctcgtgacagtgtcctccgc<br>ttccaccaagggccccagcgtgttccctctggcccctagcagcaagagcacatctggcggaacagcc<br>gccctgggctgcctggtcaaggactactttcccgagcccgtgaccgtgtcctggaactctggtgccctg<br>acaagcggagtgcataccttccctgccgtgctgcagagcagcggcctgtactctctgagcagcgtggt<br>caccgtgccaagcagcagcctgggcacccagacctacatctgcaacgtgaaccacaagccctccaac<br>accaaggtggacaagaaggtggaacccaagagctgcgacaagacccacacctgtcctccctgtcctg<br>cccctgaactgctgggcggaccctccgtgttcctgttccctccaaagcccaaggataccctgatgatca<br>gccggacccctgaagtgacctgcgtggtggtggacgtgtcccacgaggatcccgaagtgaagttcaat<br>tggtacgtggacggcgtggaagtgcataacgccaagaccaagcccagagaggaacagtacaacagc<br>acctaccgggtggtgtccgtgctgacagtgctgcaccaggactggctgaacggcaaagagtacaagt<br>gcaaggtgtccaacaaggccctgccagcccctatcgagaaaaccatcagcaaggccaagggccagc<br>cccgcgagcctcaggtgtacacactgcctccatgccgggacgagctgaccaagaaccaggtgtccct<br>gtggtgcctcgtgaagggcttctaccccctccgatatcgccgtggaatgggagagcaacggccagccc<br>gagaacaactacaagaccacccctcccgtgctggacagcgacggctcattcttcctgtacagcaagctg<br>accgtggacaagtcccggtggcagcagggcaacgtgttcagctgctctgtgatgcacgaggccctgc<br>acaaccggttcacccagaagtccctgagcctgagccctggc | SEQ ID NO: 79 |

TABLE 3-continued

Heavy and light chain sequences of binding proteins specifically directed to IL-4, IL-13 and/or TNFa.

| | | |
|---|---|---|
| Light chain B | LC:<br>gacatccagatgacccagagccccagcagcctgagcgccagcgtgggcgacagagtgaccatcacc<br>tgtcgggccagccagggcatccggaactacctggcctggtatcagcagaagcccggcaaggccccc<br>aagctgctgatctacgccgccagcacactgcagagcggcgtgcccagcagattcagcggcagcggct<br>ccggcaccgacttcaccctgaccatcagcagcctgcagcccgaggacgtggccacctactactgcca<br>gcggtacaacagagcccccctacaccttcggccagggcaccaaggtggaaatcaagggcggctctgg<br>cagctccggcagcggcggagacattcagatgacacagtcccccgccagcctgtccgtgtccgtgggc<br>gataccatcaccctgacatgccacgccagccagaacatcgacgtgtggctgagctggttccagcagaa<br>acctggcaacatccctaagctgctcatctataaggccagcaacctgcacacaggcgtgccctccagatt<br>ctccggctctggctctggcaccggctttacactgacaatcagttctctgcagcctgaggatatcgccacat<br>attactgtcagcaggcccacagctaccctttcaccttcggaggcggcaccaagctcgagattaagggc<br>ggaagcggctcctccggctccggcggacgtacggtggccgctccttccgtgttcatcttccctccctcc<br>gacgagcagctgaagtccggcaccgcctccgtggtgtgtctgctgaacaacttctaccctcgggaggc<br>caaggtgcagtggaaggtggacaacgccctgcagtccggcaactcccaggagtccgtcaccgagca<br>ggactccaaggacagcacctactccctgtcctccaccctgaccctgtccaaggccgactacgagaagc<br>acaaggtgtacgcctgtgaggtgacccaccagggcctgtccagccctgtgaccaagtccttcaaccgg<br>ggcgagtgc | SEQ ID NO: 80 |

Binding Protein 13 Amino Acid Sequences

| | | |
|---|---|---|
| Heavy chain A | HC:<br>EVQLKESGPGLVAPGGSLSITCTVS***GFSLTDSSIN***WVRQPPGKGL<br>EWLG***MIWGDGRID***YADALKSRLSISKDSSKSQVFLEMTSLRTDD<br>TATYYCAR***DGYFPYAMDF***WGQGTSVTVSSASTKGPSVFPLAPSS<br>KSTSGGTAALGCLVKDYFPEPVTVSWNSGALTSGVHTFPAVLQS<br>SGLYSLSSVVTVPSSSLGTQTYICNVNHKPSNTKVDKKVEPKSCD<br>KTHTCPPCPAPELLGGPSVFLFPPKPKDTLMISRTPEVTCVVVDVS<br>HEDPEVKFNWYVDGVEVHNAKTKPREEQYNSTYRVVSVLTVLH<br>QDWLNGKEYKCKVSNKALPAPIEKTISKAKGQPREPQVCTLPPSR<br>DELTKNQVSLSCAVKGFYPSDIAVEWESNGQPENNYKTTPPVLD<br>SDGSFFLVSKLTVDKSRWQQGNVFSCSVMHEALHNHYTQKSLSL<br>SPG | SEQ ID NO: 73 |
| Light chain A | LC:<br>DIVLTQSPASLAVSLGQRATISC***RASESVDSYGQSYMH***WYQQKA<br>GQPPKLLIY***LASNLES***GVPARFSGSGSRTDFTLTIDPVQAEDAATY<br>YC***QQNAEDSRT***FGGGTKLEIKGQPKAAPSVTLFPPSSEELQANKA<br>TLVCLISDFYPGAVTVAWKADSSPVKAGVETTTPSKQSNNKYAA<br>SSYLSLTPEQWKSHRSYSCQVTHEGSTVEKTVAPTECS | SEQ ID NO: 74 |
| Heavy chain B | HC:<br>EVQLVESGGGLVQPGRSLRLSCAAS***GFTFDDYAMH***WVRQAPGK<br>GLEWVS***AITWNSGHID***YADSVEGRFTISRDNAKNSLYLQMNSLR<br>AEDTAVYYCAK***VSYLSTASSLDY***WGQGTLVTVSSQVQLQQSGPE<br>LVKPGASVKISCKAS***GYSFTSYWIH***WIKQRPGQGLEWIG***MIDPSD***<br>***GET***RLNQRFQGRATLTVDESTSTAYMQLRSPTSEDSAVYYCTR***L***<br>***KEYGNYDSFYFDV***WGAGTLVTVSSASTKGPSVFPLAPSSKSTSGG<br>TAALGCLVKDYFPEPVTVSWNSGALTSGVHTFPAVLQSSGLYSLS<br>SVVTVPSSSLGTQTYICNVNHKPSNTKVDKKVEPKSCDKTHTCPP<br>CPAPELLGGPSVFLFPPKPKDTLMISRTPEVTCVVVDVSHEDPEVK<br>FNWYVDGVEVHNAKTKPREEQYNSTYRVVSVLTVLHQDWLNG<br>KEYKCKVSNKALPAPIEKTISKAKGQPREPQVYTLPPCRDELTKN<br>QVSLWCLVKGFYPSDIAVEWESNGQPENNYKTTPPVLDSDGSFF<br>LYSKLTVDKSRWQQGNVFSCSVMHEALHNRFTQKSLSLSPG | SEQ ID NO: 81 |
| Light chain B | LC:<br>DIQMTQSPASLSVSVGDTITLTC***HASQNIDVWLS***WFQQKPGNIPK<br>LLIY***KASNLHT***GVPSRFSGSGSGTGFTLTISSLQPEDIATYYC***QQA***<br>***HSYPFT***FGGGTKLEIKGGSGSSGSGGDIQMTQSPSSLSASVGDRV<br>TITC***RASQGIRNYLA***WYQQKPGKAPKLLIY***AASTLQS***GVPSRFSGS<br>GSGTDFTLTISSLQPEDVATYYC***QRYNRAPYT***FGQGTKVEIKGGS<br>GSSGSGGRTVAAPSVFIFPPSDEQLKSGTASVVCLLNNFYPREAK<br>VQWKVDNALQSGNSQESVTEQDSKDSTYSLSSTLTLSKADYEKH<br>KVYACEVTHQGLSSPVTKSFNRGEC | SEQ ID NO: 82 |

Binding Protein 13 _Nucleotide Sequences

| | | |
|---|---|---|
| Heavy chain A | HC:<br>gaggtgcagctgaaggagagcggccccggcctggtggcccccggcggcagcctgagcatcacctg<br>caccgtgagcggcttcagcctgaccgacagcagcatcaactgggtgcgccagcccccggcaaggg<br>cctggagtggctgggcatgatctggggcgacggccgcatcgactacgccgacgccctgaagagccg<br>cctgagcatcagcaaggacagcagcaagagccaggtgttcctggagatgaccagcctgcgcaccga<br>cgacaccgccacctactactgcgcccgcgacggctacttcccctacgccatggacttctggggccagg<br>gcaccagcgtgaccgtgagcagcgccagcaccaagggccccagcgtgttccccctggcccctagca<br>gcaagagcacatctggcggcacagccgccctgggctgcctggtcaaggactacttccccgagcccgt<br>gacagtgtcctggaactctggcgccctgaccagcggagtgcataccttccctgccgtgctgcagtccag | SEQ ID NO: 77 |

TABLE 3-continued

| Heavy and light chain sequences of binding proteins specifically directed to IL-4, IL-13 and/or TNFa. | | |
|---|---|---|
| | cggcctgtacagcctgagcagcgtggtcacagtgcccagcagcagcctgggcacccagacctacatc<br>tgcaacgtgaaccacaagcccagcaacaccaaggtggacaagaaggtggaacccaagagctgcgac<br>aagacccacacctgtcccccctgccctgcccctgaactgctgggcggaccctccgtgttcctgttcccc<br>ccaaagcccaaggacaccctgatgatcagccggacccccgaagtgacctgcgtggtggtggacgtgt<br>cccacgaggaccctgaagtgaagttcaattggtacgtggacggcgtggaagtgcataacgccaagac<br>caagcccagagaggaacagtacaacagcacctaccgggtggtgtccgtgctgaccgtgctgcaccag<br>gactggctgaacggcaaagagtacaagtgcaaggtgtccaacaaggccctgcctgcccccatcgaga<br>aaaccatcagcaaggccaagggccagcctagagagccccaagtctgcaccctgcccccccagcagag<br>atgagctgaccaagaaccaggtgtccctgagctgcgccgtgaagggcttctaccccagcgatatcgcc<br>gtggaatgggagagcaacggccagcccgagaacaactacaagaccacccccccctgtgctggacagc<br>gacggctcattcttcctggtgtccaagctgacagtggacaagagccggtggcagcagggcaacgtgtt<br>cagctgcagcgtgatgcacgaggccctgcacaaccattacacccagaagtccctgagcctgagcccc<br>ggc | |
| Light chain A | LC:<br>gacatcgtgctgacccagagccctgccagcctggccgtgtctctgggccagagagccaccatcagct<br>gccgggccagcgagagcgtggacagctacggccagagctacatgcactggtatcagcagaaggcc<br>ggccagcccccaagctgctgatctacctggccagcaacctggaaagcggcgtgcccgccagattca<br>gcggcagcggcagcagaaccgacttcaccctgaccatcgaccccgtgcaggccgaggacgccgcc<br>acctactactgccagcagaacgccgaggacagccggaccttcggcggaggcaccaagctggaaatc<br>aagggacagcccaaggctgcccccctcggtcaccctgttcccccaagcagcgaggaactgcaggcc<br>aacaaggccaccctcgtgtgcctgatcagcgacttctaccctggcgccgtgaccgtggcctggaaggc<br>cgatagctctcccgtgaaggccggcgtggaaaccaccaccccccagcaagcagagcaacaacaaata<br>cgccgccagcagctacctgagcctgacccccgagcagtggaagtcccaccggtcctacagctgccag<br>gtcacacacgagggcagcaccgtggaaaagaccgtggcccccaccgagtgcagc | SEQ ID NO: 78 |
| Heavy chain B | HC:<br>gaggtgcagctggtggaaagcggcggaggactggtgcagcccggcagaagcctgagactgagctg<br>cgccgccagcggcttcaccttcgacgactacgccatgcactgggtccgacaggcccctggcaagggc<br>ctggaatgggtgtccgccatcacctggaacagcggccacatcgactacgccgacagcgtggaaggcc<br>ggttcaccatcagccgggacaacgccaagaacagcctgtacctgcagatgaacagcctgcgggccga<br>ggacaccgccgtgtactactgcgccaaggtgtcctacctgagcaccgccagcagcctggactactgg<br>ggccagggcaccctggtcaccgtgtccagtcaggtccagctgcagcagagcggccctgagctggtca<br>agcctggcgccagcgtgaagatcagctgcaaggccagcggctacagcttcaccagctactggatcca<br>ctggatcaagcagcggcctggccagggcctcgagtggatcggcatgatcgaccccagcgacggcga<br>gacacggctgaaccagagattccagggcagagccaccctgaccgtggacgagagcaccagcaccg<br>cctacatgcagctgcggagccccaccagcgaggatagcgccgtgtattattgcacccggctgaaaga<br>gtacggcaactacgacagcttctacttcgacgtgtggggagccggcaccctcgtgacagtgtcctccgc<br>ttccaccaagggccccagcgtgttccctctggcccctagcagcaagagcacatctggcggaacagcc<br>gccctgggctgcctggtcaaggactactttcccgagcccgtgaccgtgtcctggaactctggtgccctg<br>acaagcggagtgcataccttccctgccgtgctgcagagcagcggcctgtactctctgagcagcgtggt<br>caccgtgccaagcagcagcctgggcacccagacctacatctgcaacgtgaaccacaagccctccaac<br>accaaggtggacaagaaggtggaacccaagagctgcgacaagacccacacctgtcctccctgtcctg<br>cccctgaactgctgggcggaccctccgtgttcctgttccctccaaagcccaaggataccctgatgatca<br>gccggacccctgaagtgacctgcgtggtggtggacgtgtcccacgaggatcccgaagtgaagttcaat<br>tggtacgtggacggcgtggaagtgcataacgccaagaccaagcccagagaggaacagtacaacagc<br>acctaccgggtggtgtccgtgctgacagtgctgcaccaggactggctgaacggcaaagagtacaagt<br>gcaaggtgtccaacaaggccctgccagcccctatcgagaaaaccatcagcaaggccaagggccagc<br>cccgcgagcctcaggtgtacacactgcctccatgccgggacgagctgaccaagaaccaggtgtccct<br>gtggtgcctcgtgaagggcttctacccctccgatatcgccgtggaatgggagagcaacggccagccc<br>gagaacaactacaagaccacccctcccgtgctggacagcgacggctcattcttcctgtacagcaagctg<br>accgtggacaagtcccggtggcagcagggcaacgtgttcagctgctctgtgatgcacgaggccctgc<br>acaaccggttcacccagaagtccctgagcctgagccctggc | SEQ ID NO: 83 |
| Light chain B | LC:<br>gacatccagatgacccagagccccgccagcctgagcgtgtccgtgggcgataccatcaccctgacct<br>gccacgccagccagaacatcgacgtgtggctgagctggttccagcagaagcccggcaacatccccaa<br>gctgctgatctacaaggccagcaacctgcacaccggcgtgcccagcagattcagcggctctggcagc<br>ggcaccggctttaccctgaccatcagcagcctgcagcccgaggatatcgccacctactactgccagca<br>ggcccacagctaccccttcaccttcggcggaggcaccaagctggaaatcaagggcggcagcggcag<br>ctccggcagcggcggagacattcagatgacacagtcccccagcagcctgtccgccagcgtgggcga<br>cagagtgaccatcacctgtcgggccagccagggcatccggaactacctggcctggtatcagcagaaa<br>cctggcaaggcccctaaactgctcatctacgccgccagcacactgcagtctggcgtgccctccagattc<br>tccggaagcggctccggcaccgatttcaccctgacaatctcatctctgcagcctgaggacgtggccaca<br>tattactgccagagatacaacagagccccctacacctttggccagggcaccaaggtcgagattaaggg<br>cggatccggctccagcggcagcggaggacgtacggtggccgctccttccgtgttcatcttccctccctc<br>cgacgagcagctgaagtccggcaccgcctccgtggtgtgtctgctgaacaacttctaccctcgggagg<br>ccaaggtgcagtggaaggtggacaacgccctgcagtccggcaactcccaggagtccgtcaccgagc<br>aggactccaaggacagcacctactccctgtcctccaccctgaccctgtccaaggccgactacgagaag<br>cacaaggtgtacgcctgtgaggtgacccaccagggcctgtccagccctgtgaccaagtccttcaaccg<br>gggcgagtgc | SEQ ID NO: 84 |

TABLE 3-continued

Heavy and light chain sequences of binding proteins specifically directed to IL-4, IL-13 and/or TNFa.

| | | |
|---|---|---|
| | **Binding Protein 14 Amino Acid Sequences** | |
| Heavy chain A | HC:<br>QVQLQQSGPELVKPGASVKISCKAS***GYSFTSYWIH***WIKQRPGQGL<br>EWIG***MIDPSDGET***RLNQRFQGRATLTVDESTSTAYMQLRSPTSED<br>SAVYYCTR***LKEYGNYDSFYFDV***WGAGTLVTVSSASTKGPSVFPL<br>APSSKSTSGGTAALGCLVKDYFPEPVTVSWNSGALTSGVHTFPA<br>VLQSSGLYSLSSVVTVPSSSLGTQTYICNVNHKPSNTKVDKKVEP<br>KSCDKTHTCPPCPAPELLGGPSVFLFPPKPKDTLMISRTPEVTCVV<br>VDVSHEDPEVKFNWYVDGVEVHNAKTKPREEQYNSTYRVVSVL<br>TVLHQDWLNGKEYKCKVSNKALPAPIEKTISKAKGQPREPQVCT<br>LPPSRDELTKNQVSLSCAVKGFYPSDIAVEWESNGQPENNYKTTP<br>PVLDSDGSFFLVSKLTVDKSRWQQGNVFSCSVMHEALHNHYTQ<br>KSLSLSPG | SEQ ID NO: 85 |
| Light chain A | LC:<br>DIQMTQSPASLSVSVGDTITLTC***HASQNIDVWLS***WFQQKPGNIPK<br>LLIY***KASNLHT***GVPSRFSGSGSGTGFTLTISSLQPEDIATYYC***QQA***<br>***HSYPFT***FGGGTKLEIKGQPKAAPSVTLFPPSSEELQANKATLVCLI<br>SDFYPGAVTVAWKADSSPVKAGVETTTPSKQSNNKYAASSYLSL<br>TPEQWKSHRSYSCQVTHEGSTVEKTVAPTECS | SEQ ID NO: 86 |
| Heavy chain B | HC:<br>EVQLKESGPGLVAPGGSLSITCTVS***GFSLTDSSIN***WVRQPPGKGL<br>EWLG***MIWGDGRID***YADALKSRLSISKDSSKSQVFLEMTSLRTDD<br>TATYYCAR***DGYFPYAMDF***WGQGTSVTVSSEVQLVESGGGLVQP<br>GRSLRLSCAAS***GFTFDDYAMH***WVRQAPGKGLEWVS***AITWNSGH***<br>***ID***YADSVEGRFTISRDNAKNSLYLQMNSLRAEDTAVYYCAK***VSY***<br>***LSTASSLDY***WGQGTLVTVSSASTKGPSVFPLAPSSKSTSGGTAAL<br>GCLVKDYFPEPVTVSWNSGALTSGVHTFPAVLQSSGLYSLSSVVT<br>VPSSSLGTQTYICNVNHKPSNTKVDKKVEPKSCDKTHTCPPCPAP<br>ELLGGPSVFLFPPKPKDTLMISRTPEVTCVVVDVSHEDPEVKFNW<br>YVDGVEVHNAKTKPREEQYNSTYRVVSVLTVLHQDWLNGKEY<br>KCKVSNKALPAPIEKTISKAKGQPREPQVYTLPPCRDELTKNQVS<br>LWCLVKGFYPSDIAVEWESNGQPENNYKTTPPVLDSDGSFFLYS<br>KLTVDKSRWQQGNVFSCSVMHEALHNRFTQKSLSLSPG | SEQ ID NO: 87 |
| Light chain B | LC:<br>IQMTQSPSSLSASVGDRVTITC***RASQGIRNYLA***WYQQKPGKAPKL<br>LIY***AASTLQS***GVPSRFSGSGSGTDFTLTISSLQPEDVATYYC***QRYN***<br>***RAPYT***FGQGTKVEIKGGSGSSGSGGDIVLTQSPASLAVSLGQRATI<br>SC***RASESVDSYGOSYMH***WYQQKAGQPPKLLIY***LASNLES***GVPAR<br>FSGSGSRTDFTLTIDPVQAEDAATYYC***QQNAEDSRT***FGGGTKLEI<br>KGGSGSSGSGGRTVAAPSVFIFPPSDEQLKSGTASVVCLLNNFYP<br>REAKVQWKVDNALQSGNSQESVTEQDSKDSTYSLSSTLTLSKAD<br>YEKHKVYACEVTHQGLSSPVTKSFNRGEC | SEQ ID NO: 88 |
| | **Binding Protein 14 _Nucleotide Sequences** | |
| Heavy chain A | HC:<br>caggtgcagctgcagcagagcggccccgagctggtgaagcccggcgccagcgtgaagatcagctg<br>caaggccagcggctacagcttcaccagctactggattcactggatcaagcagcgccccggccagggc<br>ctggagtggatcggcatgatcgaccccagcgacggcgagacccgcctgaaccagcgcttccagggc<br>cgcgccaccctgaccgtggacgagagcaccagcaccgcctacatgcagctgcgcagccccaccagc<br>gaggacagcgccgtgtactactgcacccgcctgaaggagtacggcaactacgacagcttctacttcga<br>cgtgtggggcgccggcaccctggtgaccgtgagcagcgccagcaccaagggccccagcgtgttccc<br>cctggcccctagcagcaagagcacatctggcggcacagccgccctgggctgcctggtcaaggactac<br>ttccccgagcccgtgacagtgtcctggaactctggcgccctgaccagcggagtgcataccttccctgcc<br>gtgctgcagtccagcggcctgtacagcctgagcagcgtggtcacagtgcccagcagcagcctgggca<br>cccagacctacatctgcaacgtgaaccacaagcccagcaacaccaaggtggacaagaaggtggaac<br>ccaagagctgcgacaagacccacacctgtccccctgccctgcccctgaactgctgggcggaccctc<br>cgtgttcctgttccccccaaagcccaaggacaccctgatgatcagccggacccccgaagtgacctgcg<br>tggtggtggacgtgtcccacgaggaccctgaagtgaagttcaattggtacgtggacggcgtggaagtg<br>cataacgccaagaccaagcccagagaggaacagtacaacagcacctaccgggtggtgtccgtgctga<br>ccgtgctgcaccaggactggctgaacggcaaagagtacaagtgcaaggtgtccaacaaggccctgcc<br>tgcccccatcgagaaaaccatcagcaaggccaagggccagcctagagagccccaagtctgcaccctg<br>cccccccagcagagatgagctgaccaagaaccaggtgtccctgagctgcgccgtgaagggcttctacc<br>ccagcgatatcgccgtggaatgggagagcaacggccagcccgagaacaactacaagaccaccccccc<br>ctgtgctggacagcgacggctcattcttcctggtgtccaagctgacagtggacaagagccggtggcag<br>cagggcaacgtgttcagctgcagcgtgatgcacgaggccctgcacaaccattacacccagaagtccct<br>gagcctgagccccggc | SEQ ID NO: 89 |
| Light chain A | LC:<br>gacatccagatgacccagagccccgccagcctgagcgtgtccgtgggcgataccatcaccctgacct<br>gccacgccagccagaacatcgacgtgtggctgagctggttccagcagaagcccggcaacatccccaa<br>gctgctgatctacaaggccagcaacctgcacaccggcgtgcccagcagattcagcggctctggcagc | SEQ ID NO: 90 |

TABLE 3-continued

| Heavy and light chain sequences of binding proteins specifically directed to IL-4, IL-13 and/or TNFa. | | |
|---|---|---|
| | ggcaccggctttaccctgaccatcagcagcctgcagcccgaggatatcgccacctactactgccagca<br>ggcccacagctaccccttcaccttcggcggaggcaccaagctggaaatcaagggacagcccaaggct<br>gccccctcggtcaccctgttcccccccaagctctgaggaactgcaggccaacaaggccaccctcgtgtg<br>cctgatcagcgacttctaccctggcgccgtgaccgtggcctggaaggccgatagctctcccgtgaagg<br>ccggcgtggaaaccaccacccccagcaagcagagcaacaacaaatacgccgccagcagctacctga<br>gcctgacccccgagcagtggaagtcccaccggtcctacagctgccaggtcacacacgagggcagca<br>ccgtggaaaagaccgtggcccccaccgagtgcagc | |
| Heavy chain B | HC:<br>gaggtgcagctgaaagagtccggccctggactggtggcccctggcggcagcctgagcatcacctgta<br>ccgtgtccggcttcagcctgaccgacagcagcatcaactgggtccgacagccccctggcaagggcct<br>ggaatggctgggcatgatctggggcgacggccggatcgactacgccgacgccctgaagtcccggct<br>gagcatcagcaaggacagcagcaagagccaggtgttcctggaaatgaccagcctgcggaccgacga<br>caccgccacctactactgcgccagggacggctacttcccctacgccatggatttctggggccagggca<br>ccagcgtgaccgtgtcctccgaagtgcagctggtggaaagcggcggaggcctggtgcagcccggca<br>gaagcctgagactgagctgcgccgccagcggcttcaccttcgacgactacgccatgcactgggtccgc<br>caggctcccggaaagggactcgagtgggtgtccgccatcacctggaacagcggccacatcgattacg<br>ccgatagcgtggaaggccggttcaccatcagccgggacaacgccaagaacagcctgtacctgcagat<br>gaacagcctgagagccgaggataccgccgtgtactactgtgccaaggtgtcctacctgagcaccgcca<br>gcagcctggactactggggacagggaaccctggtcaccgtgtccagcgcttccaccaagggccccag<br>cgtgttccctctggcccctagcagcaagagcacatctggcggaacagccgccctgggctgcctggtca<br>aggactactttcccgagcccgtgaccgtgtcctggaactctggtgccctgacaagcggagtgcatacctt<br>ccctgccgtgctgcagagcagcggcctgtactctctgagcagcgtggtcaccgtgccaagcagcagc<br>ctgggcacccagacctacatctgcaacgtgaaccacaagccctccaacaccaaggtggacaagaagg<br>tggaacccaagagctgcgacaagacccacacctgtcctccctgtcctgcccctgaactgctgggcgga<br>ccctccgtgttcctgttccctccaaagcccaaggataccctgatgatcagccggacccctgaagtgacct<br>gcgtggtggtggacgtgtcccacgaggatcccgaagtgaagttcaattggtacgtggacggcgtggaa<br>gtgcataacgccaagaccaagcccagagaggaacagtacaacagcacctaccgggtggtgtccgtgc<br>tgacagtgctgcaccaggactggctgaacggcaaagagtacaagtgcaaggtgtccaacaaggccct<br>gccagcccctatcgagaaaaccatcagcaaggccaagggccagccccgcgagcctcaggtgtacac<br>actgcctccatgccgggacgagctgaccaagaaccaggtgtccctgtggtgcctcgtgaagggcttcta<br>cccctccgatatcgccgtggaatgggagagcaacggccagcccgagaacaactacaagaccacccct<br>cccgtgctggacagcgacggctcattcttcctgtacagcaagctgaccgtggacaagtcccggtggca<br>gcagggcaacgtgttcagctgctctgtgatgcacgaggccctgcacaaccggttcacccagaagtccc<br>tgagcctgagccctggc | SEQ ID NO: 91 |
| Light chain B | LC:<br>gacatccagatgacccagagccccagcagcctgagcgccagcgtgggcgacagagtgaccatcacc<br>tgtcgggccagccagggcatccggaactacctggcctggtatcagcagaagcccggcaaggccccc<br>aagctgctgatctacgccgccagcacactgcagagcggcgtgcccagcagattcagcggcagcggct<br>ccggcaccgacttcaccctgaccatcagcagcctgcagcccgaggacgtggccacctactactgcca<br>gcggtacaacagagccccctacaccttcggccagggcaccaaggtggaaatcaagggcggctctgg<br>cagctccggctctggcggcgatatcgtgctgacccagtctcccgccagcctggccgtgtctctgggcca<br>gagagccaccatcagctgcagagccagcgagagcgtggacagctacggccagagctacatgcattg<br>gtatcagcagaaagccggccagcctcctaaactgctcatctacctggccagcaacctggaatccggcg<br>tgcccgccaggttttccggcagcggcagcagaaccgatttcacactgacaatcgaccccgtgcaggcc<br>gaggatgccgccacatattactgtcagcagaacgccgaggacagccggaccttcggcggaggcacc<br>aagctcgagattaagggcggaagcggctccagcggcagtggcggacgtacggtggccgctccttcc<br>gtgttcatcttccctccctccgacgagcagctgaagtccggcaccgcctccgtggtgtgtctgctgaaca<br>acttctaccctcgggaggccaaggtgcagtggaaggtggacaacgccctgcagtccggcaactccca<br>ggagtccgtcaccgagcaggactccaaggacagcacctactccctgtcctccaccctgaccctgtcca<br>aggccgactacgagaagcacaaggtgtacgcctgtgaggtgacccaccagggcctgtccagccctgt<br>gaccaagtccttcaaccggggcgagtgc | SEQ ID NO: 92 |

Binding Protein 15 Amino Acid Sequences

| | | |
|---|---|---|
| Heavy chain A | HC:<br>QVQLQQSGPELVKPGASVKISCKAS***GYSFTSYWIH***WIKQRPGQGL<br>EWIG***MIDPSDGET***RLNQRFQGRATLTVDESTSTAYMQLRSPTSED<br>SAVYYCTR***LKEYGNYDSFYFDV***WGAGTLVTVSSASTKGPSVFPL<br>APSSKSTSGGTAALGCLVKDYFPEPVTVSWNSGALTSGVHTFPA<br>VLQSSGLYSLSSVVTVPSSSLGTQTYICNVNHKPSNTKVDKKVEP<br>KSCDKTHTCPPCPAPELLGGPSVFLFPPKPKDTLMISRTPEVTCVV<br>VDVSHEDPEVKFNWYVDGVEVHNAKTKPREEQYNSTYRVVSVL<br>TVLHQDWLNGKEYKCKVSNKALPAPIEKTISKAKGQPREPQVCT<br>LPPSRDELTKNQVSLSCAVKGFYPSDIAVEWESNGQPENNYKTTP<br>PVLDSDGSFFLVSKLTVDKSRWQQGNVFSCSVMHEALHNHYTQ<br>KSLSLSPG | SEQ ID NO: 85 |
| Light chain A | LC:<br>DIQMTQSPASLSVSVGDTITLTC***HASQNIDVWLS***WFQQKPGNIPK<br>LLIY***KASNLHT***GVPSRFSGSGSGTGFTLTISSLQPEDIATYYC***QQA<br>HSYPFT***FGGGTKLEIKGQPKAAPSVTLFPPSSEELQANKATLVCLI<br>SDFYPGAVTVAWKADSSPVKAGVETTTPSKQSNNKYAASSYLSL<br>TPEQWKSHRSYSCQVTHEGSTVEKTVAPTECS | SEQ ID NO: 86 |

TABLE 3-continued

Heavy and light chain sequences of binding proteins specifically directed to IL-4, IL-13 and/or TNFa.

| | | |
|---|---|---|
| Heavy chain B | HC:<br>EVQLVESGGGLVQPGRSLRLSCAAS***GFTFDDYAMH***WVRQAPGK<br>GLEWVS***AITWNSGHID***YADSVEGRFTISRDNAKNSLYLQMNSLR<br>AEDTAVYYCAK***VSYLSTASSLDY***WGQGTLVTVSSEVQLKESGPG<br>LVAPGGSLSITCTVS***GFSLTDSSIN***WVRQPPGKGLEWLG***MIWGD***<br>***GRID***YADALKSRLSISKDSSKSQVFLEMTSLRTDDTATYYCAR***DG***<br>***YFPYAMDF***WGQGTSVTVSSASTKGPSVFPLAPSSKSTSGGTAALG<br>CLVKDYFPEPVTVSWNSGALTSGVHTFPAVLQSSGLYSLSSVVTV<br>PSSSLGTQTYICNVNHKPSNTKVDKKVEPKSCDKTHTCPPCPAPE<br>LLGGPSVFLFPPKPKDTLMISRTPEVTCVVVDVSHEDPEVKFNWY<br>VDGVEVHNAKTKPREEQYNSTYRVVSVLTVLHQDWLNGKEYK<br>CKVSNKALPAPIEKTISKAKGQPREPQVYTLPPCRDELTKNQVSL<br>WCLVKGFYPSDIAVEWESNGQPENNYKTTPPVLDSDGSFFLYSK<br>LTVDKSRWQQGNVFSCSVMHEALHNRFTQKSLSLSPG | SEQ ID NO: 93 |
| Light chain B | LC:<br>DIVLTQSPASLAVSLGQRATISC***RASESVDSYGQSYMH***WYQQKA<br>GQPPKLLIY***LASNLES***GVPARFSGSGSRTDFTLTIDPVQAEDAATY<br>YC***OONAEDSRT***FGGGTKLEIKGGSGSSGSGGDIQMTQSPSSLSAS<br>VGDRVTITC***RASOGIRNYLA***WYQQKPGKAPKLLIY***AASTLQS***GVP<br>SRFSGSGSGTDFTLTISSLQPEDVATYYC***QRYNRAPYT***FGQGTKVE<br>IKGGSGSSGSGGRTVAAPSVFIFPPSDEQLKSGTASVVCLLNNFYP<br>REAKVQWKVDNALQSGNSQESVTEQDSKDSTYSLSSTLTLSKAD<br>YEKHKVYACEVTHQGLSSPVTKSFNRGEC | SEQ ID NO: 94 |

Binding Protein 15 Nucleotide Sequences

| | | |
|---|---|---|
| Heavy chain A | HC:<br>caggtgcagctgcagcagagcggccccgagctggtgaagcccggcgccagcgtgaagatcagctg<br>caaggccagcggctacagcttcaccagctactggattcactggatcaagcagcgccccggccagggc<br>ctggagtggatcggcatgatcgaccccagcgacggcgagacccgcctgaaccagcgcttccagggc<br>cgcgccaccctgaccgtggacgagagcaccagcaccgcctacatgcagctgcgcagccccaccagc<br>gaggacagcgccgtgtactactgcacccgcctgaaggagtacggcaactacgacagcttctacttcga<br>cgtgtggggcgccggcaccctggtgaccgtgagcagcgccagcaccaagggccccagcgtgttccc<br>cctggcccctagcagcaagagcacatctggcggcacagccgccctgggctgcctggtcaaggactac<br>ttccccgagcccgtgacagtgtcctggaactctggcgccctgaccagcggagtgcataccttccctgcc<br>gtgctgcagtccagcggcctgtacagcctgagcagcgtggtcacagtgcccagcagcagcctgggca<br>cccagacctacatctgcaacgtgaaccacaagcccagcaacaccaaggtggacaagaaggtggaac<br>ccaagagctgcgacaagacccacacctgtccccccctgccctgcccctgaactgctgggcggaccctc<br>cgtgttcctgttcccccccaaagcccaaggacaccctgatgatcagccggacccccgaagtgacctgcg<br>tggtggtggacgtgtcccacgaggaccctgaagtgaagttcaattggtacgtggacggcgtggaagtg<br>cataacgccaagaccaagcccagagaggaacagtacaacagcacctaccgggtggtgtccgtgctga<br>ccgtgctgcaccaggactggctgaacggcaaagagtacaagtgcaaggtgtccaacaaggccctgcc<br>tgcccccatcgagaaaaccatcagcaaggccaagggccagcctagagagccccaagtctgcaccctg<br>ccccccagcagagatgagctgaccaagaaccaggtgtccctgagctgcgccgtgaagggcttctacc<br>ccagcgatatcgccgtggaatgggagagcaacggccagcccgagaacaactacaagaccaccccccc<br>ctgtgctggacagcgacggctcattcttcctggtgtccaagctgacagtggacaagagccggtggcag<br>cagggcaacgtgttcagctgcagcgtgatgcacgaggccctgcacaaccattacacccagaagtccct<br>gagcctgagccccggc | SEQ ID NO: 89 |
| Light chain A | LC:<br>gacatccagatgacccagagccccgccagcctgagcgtgtccgtgggcgataccatcaccctgacct<br>gccacgccagccagaacatcgacgtgtggctgagctggttccagcagaagcccggcaacatccccaa<br>gctgctgatctacaaggccagcaacctgcacaccggcgtgcccagcagattcagcggctctggcagc<br>ggcaccggctttaccctgaccatcagcagcctgcagcccgaggatatcgccacctactactgccagca<br>ggcccacagctaccccttcaccttcggcggaggcaccaagctggaaatcaagggacagcccaaggct<br>gccccctcggtcaccctgttcccccccaagctctgaggaactgcaggccaacaaggccaccctcgtgtg<br>cctgatcagcgacttctaccctggcgccgtgaccgtggcctggaaggccgatagctctcccgtgaagg<br>ccggcgtggaaaccaccaccccccagcaagcagagcaacaacaaatacgccgccagcagctacctga<br>gcctgacccccgagcagtggaagtcccaccggtcctacagctgccaggtcacacacgagggcagca<br>ccgtggaaaagaccgtggcccccaccgagtgcagc | SEQ ID NO: 90 |
| Heavy chain B | HC:<br>gaggtgcagctggtggaaagcggcggaggactggtgcagcccggcagaagcctgagactgagctg<br>cgccgccagcggcttcaccttcgacgactacgccatgcactgggtccgacaggcccctggcaagggc<br>ctggaatgggtgtccgccatcacctggaacagcggccacatcgactacgccgacagcgtggaaggcc<br>ggttcaccatcagccgggacaacgccaagaacagcctgtacctgcagatgaacagcctgcgggccga<br>ggacaccgccgtgtactactgcgccaaggtgtcctacctgagcaccgccagcagcctggactactgg<br>ggccagggcaccctggtcaccgtgtcctccgaagtgcagctgaaagagtccggccctggcctggtgg<br>cccctggcggcagcctgagcatcacctgtaccgtgtccggcttcagcctgaccgacagcagcatcaac<br>tgggtccgccagcctcccggaaagggactcgagtggctgggcatgatctggggcgacggccggatc<br>gattacgccgatgccctgaagtcccggctgagcatcagcaaggacagcagcaagagccaggtgttcc<br>tggaaatgaccagcctgagaaccgacgacaccgccacctactactgtgcccgggacggctacttcccc<br>tacgccatggatttctggggacagggaaccagcgtgaccgtgtccagcgcttccaccaagggcccca<br>gcgtgttccctctggcccctagcagcaagagcacatctggcggaacagccgccctgggctgcctggtc<br>aaggactactttcccgagcccgtgaccgtgtcctggaactctggtgccctgacaagcggagtgcatacc | SEQ ID NO: 95 |

TABLE 3-continued

| Heavy and light chain sequences of binding proteins specifically directed to IL-4, IL-13 and/or TNFa. | | |
|---|---|---|
| | ttccctgccgtgctgcagagcagcggcctgtactctctgagcagcgtggtcaccgtgccaagcagcag<br>cctgggcacccagacctacatctgcaacgtgaaccacaagccctccaacaccaaggtggacaagaag<br>gtggaacccaagagctgcgacaagacccacacctgtcctccctgtcctgcccctgaactgctgggcgg<br>accctccgtgttcctgttccctccaaagcccaaggataccctgatgatcagccggacccctgaagtgac<br>ctgcgtggtggtggacgtgtcccacgaggatcccgaagtgaagttcaattggtacgtggacggcgtgg<br>aagtgcataacgccaagaccaagcccagagaggaacagtacaacagcacctaccgggtggtgtccgt<br>gctgacagtgctgcaccaggactggctgaacggcaaagagtacaagtgcaaggtgtccaacaaggcc<br>ctgccagcccctatcgagaaaaccatcagcaaggccaagggccagccccgcgagcctcaggtgtac<br>acactgcctccatgccgggacgagctgaccaagaaccaggtgtccctgtggtgcctcgtgaagggctt<br>ctacccctccgatatcgccgtggaatgggagagcaacggccagcccgagaacaactacaagaccacc<br>cctcccgtgctggacagcgacggctcattcttcctgtacagcaagctgaccgtggacaagtcccggtgg<br>cagcagggcaacgtgttcagctgctctgtgatgcacgaggccctgcacaaccggttcacccagaagtc<br>cctgagcctgagccctggc | |
| Light chain B | LC:<br>gacatcgtgctgacccagagccctgccagcctggccgtgtctctgggccagagagccaccatcagct<br>gccgggccagcgagagcgtggacagctacggccagagctacatgcactggtatcagcagaaggcc<br>ggccagcccccccaagctgctgatctacctggccagcaacctggaaagcggcgtgcccgccagattca<br>gcggcagcggcagcagaaccgacttcaccctgaccatcgaccccgtgcaggccgaggacgccgcc<br>acctactactgccagcagaacgccgaggacagccggaccttcggcggaggcaccaagctggaaatc<br>aagggcggctccggcagcagcggctctggcggcgatatccagatgacccagtcccccagcagcctg<br>agcgccagcgtgggcgacagagtgaccatcacctgtagagccagccagggcatccggaactacctg<br>gcttggtatcagcagaaacccggaaaggcccctaaactgctcatctacgccgccagcaccctgcagtc<br>cggcgtgccaagcagattctccggctctggcagcggcaccgatttcacactgacaatcagcagcctgc<br>agcccgaggatgtggccacctattattgccagagatacaacagagcccccctacaccttcggccagggc<br>accaaggtcgagattaagggcggaagcggcagctccggctccggcggacgtacggtggccgctcct<br>tccgtgttcatcttccctccctccgacgagcagctgaagtccggcaccgcctccgtggtgtgtctgctga<br>acaacttctaccctcgggaggccaaggtgcagtggaaggtggacaacgccctgcagtccggcaactc<br>ccaggagtccgtcaccgagcaggactccaaggacagcacctactccctgtcctccaccctgaccctgt<br>ccaaggccgactacgagaagcacaaggtgtacgcctgtgaggtgacccaccagggcctgtccagcc<br>ctgtgaccaagtccttcaaccggggcgagtgc | SEQ ID NO: 96 |
| Binding Protein 16 Amino Acid Sequences | | |
| Heavy chain A | HC:<br>EVQLKESGPGLVAPGGSLSITCTVS***GFSLTDSSIN***WVRQPPGKGL<br>EWLG***MIWGDGRID***YADALKSRLSISKDSSKSQVFLEMTSLRTDD<br>TATYYCAR***DGYFPYAMDF***WGQGTSVTVSSASTKGPSVFPLAPSS<br>KSTSGGTAALGCLVKDYFPEPVTVSWNSGALTSGVHTFPAVLQS<br>SGLYSLSSVVTVPSSSLGTQTYICNVNHKPSNTKVDKKVEPKSCD<br>KTHTCPPCPAPELLGGPSVFLFPPKPKDTLMISRTPEVTCVVVDVS<br>HEDPEVKFNWYVDGVEVHNAKTKPREEQYNSTYRVVSVLTVLH<br>QDWLNGKEYKCKVSNKALPAPIEKTISKAKGQPREPQVCTLPPSR<br>DELTKNQVSLSCAVKGFYPSDIAVEWESNGQPENNYKTTPPVLD<br>SDGSFFLVSKLTVDKSRWQQGNVFSCSVMHEALHNHYTQKSLSL<br>SPG | SEQ ID NO: 73 |
| Light chain A | LC:<br>DIVLTQSPASLAVSLGQRATISC***RASESVDSYGOSYMH***WYQQKA<br>GQPPKLLIY***LASNLES***GVPARFSGSGSRTDFTLTIDPVQAEDAATY<br>YC***QQNAEDSRT***FGGGTKLEIKGQPKAAPSVTLFPPSSEELQANKA<br>TLVCLISDFYPGAVTVAWKADSSPVKAGVETTTPSKQSNNKYAA<br>SSYLSLTPEQWKSHRSYSCQVTHEGSTVEKTVAPTECS | SEQ ID NO: 74 |
| Heavy chain B | HC:<br>EVQLKESGPGLVAPGGSLSITCTVS***GFSLTDSSIN***WVRQPPGKGL<br>EWLG***MIWGDGRID***YADALKSRLSISKDSSKSQVFLEMTSLRTDD<br>TATYYCAR***DGYFPYAMDF***WGQGTSVTVSSQVQLQQSGPELVKP<br>GASVKISCKAS***GYSFTSYWIH***WIKQRPGQGLEWIG***MIDPSDGET***R<br>LNQRFQGRATLTVDESTSTAYMQLRSPTSEDSAVYYCTR***LKEYG<br>NYDSFYFDV***WGAGTLVTVSSASTKGPSVFPLAPSSKSTSGGTAAL<br>GCLVKDYFPEPVTVSWNSGALTSGVHTFPAVLQSSGLYSLSSVVT<br>VPSSSLGTQTYICNVNHKPSNTKVDKKVEPKSCDKTHTCPPCPAP<br>ELLGGPSVFLFPPKPKDTLMISRTPEVTCVVVDVSHEDPEVKFNW<br>YVDGVEVHNAKTKPREEQYNSTYRVVSVLTVLHQDWLNGKEY<br>KCKVSNKALPAPIEKTISKAKGQPREPQVYTLPPCRDELTKNQVS<br>LWCLVKGFYPSDIAVEWESNGQPENNYKTTPPVLDSDGSFFLYS<br>KLTVDKSRWQQGNVFSCSVMHEALHNRFTQKSLSLSPG | SEQ ID NO: 68 |
| Light chain B | LC:<br>DIQMTQSPASLSVSVGDTITLTC***HASQNIDVWLS***WFQQKPGNIPK<br>LLIY***KASNLHT***GVPSRFSGSGSGTGFTLTISSLQPEDIATYYC***QQA<br>HSYPFT***FGGGTKLEIKGGSGSSGSGGDIVLTQSPASLAVSLGQRA<br>TISC***RASESVDSYGQSYMH***WYQQKAGQPPKLLIY***LASNLES***GVPA<br>RFSGSGSRTDFTLTIDPVQAEDAATYYC***QQNAEDSRT***FGGGTKLE<br>IKGGSGSSGSGGRTVAAPSVFIFPPSDEQLKSGTASVVCLLNNFYP<br>REAKVQWKVDNALQSGNSQESVTEQDSKDSTYSLSSTLTLSKAD | SEQ ID NO: 69 |

TABLE 3-continued

| Heavy and light chain sequences of binding proteins specifically directed to IL-4, IL-13 and/or TNFa. | | |
|---|---|---|
| | YEKHKVYACEVTHQGLSSPVTKSFNRGEC | |
| | Binding Protein 16 _Nucleotide Sequences | |
| Heavy chain A | HC: gaggtgcagctgaaggagagcggccccggcctggtggcccccggcggcagcctgagcatcacctg caccgtgagcggcttcagcctgaccgacagcagcatcaactgggtgcgccagcccccggcaaggg cctggagtggctgggcatgatctggggcgacggccgcatcgactacgccgacgccctgaagagccg cctgagcatcagcaaggacagcagcaagagccaggtgttcctggagatgaccagcctgcgcaccga cgacaccgccacctactactgcgcccgcgacggctacttcccctacgccatggacttctggggccagg gcaccagcgtgaccgtgagcagcgccagcaccaagggccccagcgtgttccccctggcccctagca gcaagagcacatctggcggcacagccgccctgggctgcctggtcaaggactacttccccgagcccgt gacagtgtcctggaactctggcgccctgaccagcggagtgcataccttccctgccgtgctgcagtccag cggcctgtacagcctgagcagcgtggtcacagtgcccagcagcagcctgggcacccagacctacatc tgcaacgtgaaccacaagcccagcaacaccaaggtggacaagaaggtggaacccaagagctgcgac aagacccacacctgtccccccctgccctgcccctgaactgctgggcggaccctccgtgttcctgttcccc ccaaagcccaaggacaccctgatgatcagccggacccccgaagtgacctgcgtggtggtggacgtgt cccacgaggaccctgaagtgaagttcaattggtacgtggacggcgtggaagtgcataacgccaagac caagcccagagaggaacagtacaacagcacctaccgggtggtgtccgtgctgaccgtgctgcaccag gactggctgaacggcaaagagtacaagtgcaaggtgtccaacaaggccctgcctgcccccatcgaga aaaccatcagcaaggccaagggccagcctagagagccccaagtctgcaccctgcccccagcagag atgagctgaccaagaaccaggtgtccctgagctgcgccgtgaagggcttctaccccagcgatatcgcc gtggaatgggagagcaacggccagcccgagaacaactacaagaccacccccctgtgctggacagc gacggctcattcttcctggtgtccaagctgacagtggacaagagccggtggcagcagggcaacgtgtt cagctgcagcgtgatgcacgaggccctgcacaaccattacacccagaagtccctgagcctgagcccc ggc | SEQ ID NO: 77 |
| Light chain A | LC: gacatcgtgctgacccagagccctgccagcctggccgtgtctctgggccagagagccaccatcagct gccgggccagcgagagcgtggacagctacggccagagctacatgcactggtatcagcagaaggcc ggccagccccccaagctgctgatctacctggccagcaacctggaaagcggcgtgcccgccagattca gcggcagcggcagcagaaccgacttcaccctgaccatcgaccccgtgcaggccgaggacgccgcc acctactactgccagcagaacgccgaggacagccggaccttcggcggaggcaccaagctggaaatc aagggacagcccaaggctgcccccctcggtcaccctgttccccccaagcagcgaggaactgcaggcc aacaaggccaccctcgtgtgcctgatcagcgacttctacccctggcgccgtgaccgtggcctggaaggc cgatagctctcccgtgaaggccggcgtggaaaccaccacccccagcaagcagagcaacaacaaata cgccgccagcagctacctgagcctgacccccgagcagtggaagtcccaccggtcctacagctgccag gtcacacacgagggcagcaccgtggaaaagaccgtggcccccaccgagtgcagc | SEQ ID NO: 78 |
| Heavy chain B | HC: gaggtgcagctgaaagagtccggccctggactggtggcccctggcggcagcctgagcatcacctgta ccgtgtccggcttcagcctgaccgacagcagcatcaactgggtccgacagcccccctggcaagggcct ggaatggctgggcatgatctggggcgacggccggatcgactacgccgacgccctgaagtcccggct gagcatcagcaaggacagcagcaagagccaggtgttcctggaaatgaccagcctgcggaccgacga caccgccacctactactgcgccagggacggctacttcccctacgccatggatttctggggccagggca ccagcgtgaccgtgtccagtcaggtccagctgcagcagagcggccctgagctggtcaagcctggcgc cagcgtgaagatcagctgcaaggccagcggctacagcttcaccagctactggatccactggatcaagc agcggcctggccagggcctcgagtggatcggaatgatcgaccccagcgacggcgagacacggctg aaccagagattccagggcagagccaccctgaccgtggacgagagcaccagcaccgcctacatgcag ctgcggagccccaccagcgaggacagcgccgtgtactactgcacccggctgaaagaatacggcaact acgacagcttctacttcgacgtgtggggagccggcaccctggtcaccgtgtctagcgcttccaccaagg gccccagcgtgttccctctggcccctagcagcaagagcacatctggcggaacagccgccctgggctg cctggtcaaggactactttcccgagcccgtgaccgtgtcctggaactctggtgccctgacaagcggagt gcataccttccctgccgtgctgcagagcagcggcctgtactctctgagcagcgtggtcaccgtgccaag cagcagcctgggcacccagacctacatctgcaacgtgaaccacaagccctccaacaccaaggtggac aagaaggtggaacccaagagctgcgacaagacccacacctgtcctccctgtcctgcccctgaactgct gggcggaccctccgtgttcctgttccctccaaagcccaaggataccctgatgatcagccggacccctga agtgacctgcgtggtggtggacgtgtcccacgaggatcccgaagtgaagttcaattggtacgtggacg gcgtggaagtgcataacgccaagaccaagcccagagaggaacagtacaacagcacctaccgggtgg tgtccgtgctgacagtgctgcaccaggactggctgaacggcaaagagtacaagtgcaaggtgtccaac aaggccctgccagcccctatcgagaaaaccatcagcaaggccaagggccagccccgcgagcctcag gtgtacacactgcctccatgccgggacgagctgaccaagaaccaggtgtccctgtggtgcctcgtgaa gggcttctacccctccgatatcgccgtggaatgggagagcaacggccagcccgagaacaactacaag accacccctcccgtgctggacagcgacggctcattcttcctgtacagcaagctgaccgtggacaagtcc cggtggcagcagggcaacgtgttcagctgctctgtgatgcacgaggccctgcacaaccggttcaccca gaagtccctgagcctgagccctggc | SEQ ID NO: 97 |
| Light chain B | LC: gacatccagatgacccagagccccgccagcctgagcgtgtccgtgggcgataccatcaccctgacct gccacgccagccagaacatcgacgtgtggctgagctggttccagcagaagcccggcaacatccccaa gctgctgatctacaaggccagcaacctgcacaccggcgtgcccagcagattcagcggctctggcagc ggcaccggctttaccctgaccatcagcagcctgcagcccgaggatatcgccacctactactgccagca ggcccacagctaccccttcaccttcggcggaggcaccaagctggaaatcaagggcggcagcggcag ctccggctctggcggcgatatcgtgctgacccagtctcccgcctccctggccgtgtctctgggccagag agccaccatcagctgccgggccagcgagagcgtggacagctacggccagagctacatgcactggtat cagcagaaggccggacagccccctaaactgctcatctacctggcctccaacctggaaagcggcgtgc ccgccaggttttccggcagcggctccagaaccgacttcaccctgacaatcgaccccgtgcaggccga | SEQ ID NO: 70 |

TABLE 3-continued

| Heavy and light chain sequences of binding proteins specifically directed to IL-4, IL-13 and/or TNFa. | | |
|---|---|---|
| | ggacgccgccacatattactgtcagcagaacgccgaggacagcagaacctttggcggcggaacaaa<br>gctcgagattaagggcggctccggctccagcggatctggcggacgtacggtggccgctccttccgtgt<br>tcatcttccctccctccgacgagcagctgaagtccggcaccgcctccgtggtgtgtctgctgaacaactt<br>ctaccctcgggaggccaaggtgcagtggaaggtggacaacgccctgcagtccggcaactcccagga<br>gtccgtcaccgagcaggactccaaggacagcacctactccctgtcctccaccctgaccctgtccaagg<br>ccgactacgagaagcacaaggtgtacgcctgtgaggtgacccaccagggcctgtccagccctgtgac<br>caagtccttcaaccggggcgagtgc | |
| Binding Protein 17 Amino Acid Sequences | | |
| Heavy chain A | HC:<br>QVQLQQSGPELVKPGASVKISCKAS***GYSFTSYWIH***WIKQRPGQGL<br>EWIG***MIDPSDGET***RLNQRFQGRATLTVDESTSTAYMQLRSPTSED<br>SAVYYCTR***LKEYGNYDSFYFDV***WGAGTLVTVSSASTKGPSVFPL<br>APSSKSTSGGTAALGCLVKDYFPEPVTVSWNSGALTSGVHTFPA<br>VLQSSGLYSLSSVVTVPSSSLGTQTYICNVNHKPSNTKVDKKVEP<br>KSCDKTHTCPPCPAPELLGGPSVFLFPPKPKDTLMISRTPEVTCVV<br>VDVSHEDPEVKFNWYVDGVEVHNAKTKPREEQYNSTYRVVSVL<br>TVLHQDWLNGKEYKCKVSNKALPAPIEKTISKAKGQPREPQVCT<br>LPPSRDELTKNQVSLSCAVKGFYPSDIAVEWESNGQPENNYKTTP<br>PVLDSDGSFFLVSKLTVDKSRWQQGNVFSCSVMHEALHNHYTQ<br>KSLSLSPG | SEQ ID NO: 85 |
| Light chain A | LC:<br>DIQMTQSPASLSVSVGDTITLTC***HASQNIDVWLS***WFQQKPGNIPK<br>LLIY***KASNLHT***GVPSRFSGSGSGTGFTLTISSLQPEDIATYYC***QQA<br>HSYPFT***FGGGTKLEIKGQPKAAPSVTLFPPSSEELQANKATLVCLI<br>SDFYPGAVTVAWKADSSPVKAGVETTTPSKQSNNKYAASSYLSL<br>TPEQWKSHRSYSCQVTHEGSTVEKTVAPTECS | SEQ ID NO: 86 |
| Heavy chain B | HC:<br>EVQLKESGPGLVAPGGSLSITCTVS***GFSLTDSSIN***WVRQPPGKGL<br>EWLG***MIWGDGRID***YADALKSRLSISKDSSKSQVFLEMTSLRTDD<br>TATYYCAR***DGYFPYAMDF***WGQGTSVTVSSQVQLQQSGPELVKP<br>GASVKISCKAS***GYSFTSYWIH***WIKQRPGQGLEWIG***MIDPSDGET***R<br>LNQRFQGRATLTVDESTSTAYMQLRSPTSEDSAVYYCTR***LKEYG<br>NYDSFYFDV***WGAGTLVTVSSASTKGPSVFPLAPSSKSTSGGTAAL<br>GCLVKDYFPEPVTVSWNSGALTSGVHTFPAVLQSSGLYSLSSVVT<br>VPSSSLGTQTYICNVNHKPSNTKVDKKVEPKSCDKTHTCPPCPAP<br>ELLGGPSVFLFPPKPKDTLMISRTPEVTCVVVDVSHEDPEVKFNW<br>YVDGVEVHNAKTKPREEQYNSTYRVVSVLTVLHQDWLNGKEY<br>KCKVSNKALPAPIEKTISKAKGQPREPQVYTLPPCRDELTKNQVS<br>LWCLVKGFYPSDIAVEWESNGQPENNYKTTPPVLDSDGSFFLYS<br>KLTVDKSRWQQGNVFSCSVMHEALHNRFTQKSLSLSPG | SEQ ID NO: 68 |
| Light chain B | LC:<br>DIQMTQSPASLSVSVGDTITLTC***HASQNIDVWLS***WFQQKPGNIPK<br>LLIY***KASNLHT***GVPSRFSGSGSGTGFTLTISSLQPEDIATYYC***QQA<br>HSYPFT***FGGGTKLEIKGGSGSSGSGGDIVLTQSPASLAVSLGQRA<br>TISC***RASESVDSYGQSYMH***WYQQKAGQPPKLLIY***LASNLES***GVPA<br>RFSGSGSRTDFTLTIDPVQAEDAATYYC***QQNAEDSRT***FGGGTKLE<br>IKGGSGSSGSGGRTVAAPSVFIFPPSDEQLKSGTASVVCLLNNFYP<br>REAKVQWKVDNALQSGNSQESVTEQDSKDSTYSLSSTLTLSKAD<br>YEKHKVYACEVTHQGLSSPVTKSFNRGEC | SEQ ID NO: 69 |
| Binding Protein 17 _Nucleotide Sequences | | |
| Heavy chain A | HC:<br>caggtgcagctgcagcagagcggccccgagctggtgaagcccggcgccagcgtgaagatcagctg<br>caaggccagcggctacagcttcaccagctactggattcactggatcaagcagcgccccggccagggc<br>ctggagtggatcggcatgatcgaccccagcgacggcgagacccgcctgaaccagcgcttccagggc<br>cgcgccaccctgaccgtggacgagagcaccagcaccgcctacatgcagctgcgcagccccaccagc<br>gaggacagcgccgtgtactactgcacccgcctgaaggagtacggcaactacgacagcttctacttcga<br>cgtgtggggcgccggcaccctggtgaccgtgagcagcgccagcaccaagggccccagcgtgttccc<br>cctggcccctagcagcaagagcacatctggcggcacagccgccctgggctgcctggtcaaggactac<br>ttccccgagcccgtgacagtgtcctggaactctggcgccctgaccagcggagtgcataccttccctgcc<br>gtgctgcagtccagcggcctgtacagcctgagcagcgtggtcacagtgcccagcagcagcctgggca<br>cccagacctacatctgcaacgtgaaccacaagcccagcaacaccaaggtggacaagaaggtggaac<br>ccaagagctgcgacaagacccacacctgtccccctgccctgcccctgaactgctgggcggaccctc<br>cgtgttcctgttcccccaaagcccaaggacaccctgatgatcagccggacccccgaagtgacctgcg<br>tggtggtggacgtgtcccacgaggaccctgaagtgaagttcaattggtacgtggacggcgtggaagtg<br>cataacgccaagaccaagcccagagaggaacagtacaacagcacctaccgggtggtgtccgtgctga<br>ccgtgctgcaccaggactggctgaacggcaaagagtacaagtgcaaggtgtccaacaaggccctgcc<br>tgcccccatcgagaaaaccatcagcaaggccaagggccagcctagagagccccaagtctgcaccctg<br>ccccccagcagagatgagctgaccaagaaccaggtgtccctgagctgcgccgtgaagggcttctacc<br>ccagcgatatcgccgtggaatgggagagcaacggccagcccgagaacaactacaagaccacccccc<br>ctgtgctggacagcgacggctcattcttcctggtgtccaagctgacagtggacaagagccggtggcag | SEQ ID NO: 89 |

TABLE 3-continued

Heavy and light chain sequences of binding proteins specifically directed to IL-4, IL-13 and/or TNFa.

| | | |
|---|---|---|
| | cagggcaacgtgttcagctgcagcgtgatgcacgaggccctgcacaaccattacacccagaagtccct<br>gagcctgagccccggc | |
| Light chain A | LC:<br>Gacatccagatgacccagagccccgccagcctgagcgtgtccgtgggcgataccatcaccctgacct<br>gccacgccagccagaacatcgacgtgtggctgagctggttccagcagaagcccggcaacatccccaa<br>gctgctgatctacaaggccagcaacctgcacaccggcgtgcccagcagattcagcggctctggcagc<br>ggcaccggctttaccctgaccatcagcagcctgcagcccgaggatatcgccacctactactgccagca<br>ggcccacagctaccccttcaccttcggcggaggcaccaagctggaaatcaagggacagcccaaggct<br>gccccctcggtcaccctgttcccccccaagctctgaggaactgcaggccaacaaggccaccctcgtgtg<br>cctgatcagcgacttctaccctggcgccgtgaccgtggcctggaaggccgatagctctcccgtgaagg<br>ccggcgtggaaaccaccacccccagcaagcagagcaacaacaaatacgccgccagcagctacctga<br>gcctgacccccgagcagtggaagtcccaccggtcctacagctgccaggtcacacacgagggcagca<br>ccgtggaaaagaccgtggcccccaccgagtgcagc | SEQ ID NO: 90 |
| Heavy chain B | HC:<br>gaggtgcagctgaaagagtccggccctggactggtggcccctggcggcagcctgagcatcacctgta<br>ccgtgtccggcttcagcctgaccgacagcagcatcaactgggtccgacagccccctggcaagggcct<br>ggaatggctgggcatgatctggggcgacggccggatcgactacgccgacgccctgaagtcccggct<br>gagcatcagcaaggacagcagcaagagccaggtgttcctggaaatgaccagcctgcggaccgacga<br>caccgccacctactactgcgccagggacggctacttcccctacgccatggatttctggggccagggca<br>ccagcgtgaccgtgtccagtcaggtccagctgcagcagagcggccctgagctggtcaagcctggcgc<br>cagcgtgaagatcagctgcaaggccagcggctacagcttcaccagctactggatccactggatcaagc<br>agcggcctggccagggcctcgagtggatcggaatgatcgaccccagcgacggcgagacacggctg<br>aaccagagattccagggcagagccaccctgaccgtggacgagagcaccagcaccgcctacatgcag<br>ctgcggagccccaccagcgaggacagcgccgtgtactactgcacccggctgaaagaatacggcaact<br>acgacagcttctacttcgacgtgtggggagccggcaccctggtcaccgtgtctagcgcttccaccaagg<br>gccccagcgtgttccctctggcccctagcagcaagagcacatctggcggaacagccgccctgggctg<br>cctggtcaaggactactttcccgagcccgtgaccgtgtcctggaactctggtgccctgacaagcggagt<br>gcataccttccctgccgtgctgcagagcagcggcctgtactctctgagcagcgtggtcaccgtgccaag<br>cagcagcctgggcacccagacctacatctgcaacgtgaaccacaagccctccaacaccaaggtggac<br>aagaaggtggaacccaagagctgcgacaagacccacacctgtcctccctgtcctgcccctgaactgct<br>gggcggaccctccgtgttcctgttccctccaaagcccaaggataccctgatgatcagccggacccctga<br>agtgacctgcgtggtggtggacgtgtcccacgaggatcccgaagtgaagttcaattggtacgtggacg<br>gcgtggaagtgcataacgccaagaccaagcccagagaggaacagtacaacagcacctaccgggtgg<br>tgtccgtgctgacagtgctgcaccaggactggctgaacggcaaagagtacaagtgcaaggtgtccaac<br>aaggccctgccagcccctatcgagaaaaccatcagcaaggccaagggccagccccgcgagcctcag<br>gtgtacacactgcctccatgccgggacgagctgaccaagaaccaggtgtccctgtggtgcctcgtgaa<br>gggcttctaccccctccgatatcgccgtggaatgggagagcaacggccagcccgagaacaactacaag<br>accacccctcccgtgctggacagcgacggctcattcttcctgtacagcaagctgaccgtggacaagtcc<br>cggtggcagcagggcaacgtgttcagctgctctgtgatgcacgaggccctgcacaaccggttcaccca<br>gaagtccctgagcctgagccctggc | SEQ ID NO: 97 |
| Light chain B | LC:<br>gacatccagatgacccagagccccgccagcctgagcgtgtccgtgggcgataccatcaccctgacct<br>gccacgccagccagaacatcgacgtgtggctgagctggttccagcagaagcccggcaacatccccaa<br>gctgctgatctacaaggccagcaacctgcacaccggcgtgcccagcagattcagcggctctggcagc<br>ggcaccggctttaccctgaccatcagcagcctgcagcccgaggatatcgccacctactactgccagca<br>ggcccacagctaccccttcaccttcggcggaggcaccaagctggaaatcaagggcggcagcggcag<br>ctccggctctggcggcgatatcgtgctgacccagtctcccgcctccctggccgtgtctctgggccagag<br>agccaccatcagctgccgggccagcgagagcgtggacagctacggccagagctacatgcactggtat<br>cagcagaaggccggacagccccctaaactgctcatctacctggcctccaacctggaaagcggcgtgc<br>ccgccaggttttccggcagcggctccagaaccgacttcaccctgacaatcgaccccgtgcaggccga<br>ggacgccgccacatattactgtcagcagaacgccgaggacagcagaacctttggcggcggaacaaa<br>gctcgagattaagggcggctccggctccagcggatctggcggacgtacggtggccgctccttccgtgt<br>tcatcttccctccctccgacgagcagctgaagtccggcaccgcctccgtggtgtgtctgctgaacaactt<br>ctaccctcgggaggccaaggtgcagtggaaggtggacaacgccctgcagtccggcaactcccagga<br>gtccgtcaccgagcaggactccaaggacagcacctactccctgtcctccaccctgaccctgtccaagg<br>ccgactacgagaagcacaaggtgtacgcctgtgaggtgacccaccagggcctgtccagccctgtgac<br>caagtccttcaaccggggcgagtgc | SEQ ID NO: 70 |

Binding Protein 18 Amino Acid Sequences

| | | |
|---|---|---|
| Heavy chain A | HC:<br>EVQLKESGPGLVAPGGSLSITCTVS***GFSLTDSSIN***WVRQPPGKGL<br>EWLG***MIWGDGRID***YADALKSRLSISKDSSKSQVFLEMTSLRTDD<br>TATYYCAR***DGYFPYAMDF***WGQGTSVTVSSASTKGPSVFPLAPSS<br>KSTSGGTAALGCLVKDYFPEPVTVSWNSGALTSGVHTFPAVLQS<br>SGLYSLSSVVTVPSSSLGTQTYICNVNHKPSNTKVDKKVEPKSCD<br>KTHTCPPCPAPELLGGPSVFLFPPKPKDTLMISRTPEVTCVVVDVS<br>HEDPEVKFNWYVDGVEVHNAKTKPREEQYNSTYRVVSVLTVLH<br>QDWLNGKEYKCKVSNKALPAPIEKTISKAKGQPREPQVCTLPPSR<br>DELTKNQVSLSCAVKGFYPSDIAVEWESNGQPENNYKTTPPVLD<br>SDGSFFLVSKLTVDKSRWQQGNVFSCSVMHEALHNHYTQKSLSL<br>SPG | SEQ ID NO: 73 |

TABLE 3-continued

Heavy and light chain sequences of binding proteins specifically directed to IL-4, IL-13 and/or TNFa.

| | | |
|---|---|---|
| Light chain A | LC:<br>DIVLTQSPASLAVSLGQRATISC***RASESVDSYGQSYMH***WYQQKA<br>GQPPKLLIY***LASNLES***GVPARFSGSGSRTDFTLTIDPVQAEDAATY<br>YC***QQNAEDSRT***FGGGTKLEIKGQPKAAPSVTLFPPSSEELQANKA<br>TLVCLISDFYPGAVTVAWKADSSPVKAGVETTTPSKQSNNKYAA<br>SSYLSLTPEQWKSHRSYSCQVTHEGSTVEKTVAPTECS | SEQ ID NO: 74 |
| Heavy chain B | HC:<br>QVQLQQSGPELVKPGASVKISCKAS***GYSFTSYWIH***WIKQRPGQGL<br>EWIG***MIDPSDGET***RLNQRFQGRATLTVDESTSTAYMQLRSPTSED<br>SAVYYCTR***LKEYGNYDSFYFDV***WGAGTLVTVSSEVQLKESGPGL<br>VAPGGSLSITCTVS***GFSLTDSSIN***WVRQPPGKGLEWLG***MIWGDG***<br>***RID***YADALKSRLSISKDSSKSQVFLEMTSLRTDDTATYYCAR***DGY***<br>***FPYAMDF***WGQGTSVTVSSASTKGPSVFPLAPSSKSTSGGTAALG<br>CLVKDYFPEPVTVSWNSGALTSGVHTFPAVLQSSGLYSLSSVVTV<br>PSSSLGTQTYICNVNHKPSNTKVDKKVEPKSCDKTHTCPPCPAPE<br>LLGGPSVFLFPPKPKDTLMISRTPEVTCVVVDVSHEDPEVKFNWY<br>VDGVEVHNAKTKPREEQYNSTYRVVSVLTVLHQDWLNGKEYK<br>CKVSNKALPAPIEKTISKAKGQPREPQVYTLPPCRDELTKNQVSL<br>WCLVKGFYPSDIAVEWESNGQPENNYKTTPPVLDSDGSFFLYSK<br>LTVDKSRWQQGNVFSCSVMHEALHNRFTQKSLSLSPG | SEQ ID NO: 62 |
| Light chain B | LC:<br>DIVLTQSPASLAVSLGQRATISC***RASESVDSYGQSYMH***WYQQKA<br>GQPPKLLIY***LASNLES***GVPARFSGSGSRTDFTLTIDPVQAEDAATY<br>YC***QQNAEDSRT***FGGGTKLEIKGGSGSSGSGGDIQMTQSPASLSVS<br>VGDTITLTC***HASQNIDVWLS***WFQQKPGNIPKLLIY***KASNLHT***GVP<br>SRFSGSGSGTGFTLTISSLQPEDIATYYC***QQAHSYPFT***FGGGTKLEI<br>KGGSGSSGSGGRTVAAPSVFIFPPSDEQLKSGTASVVCLLNNFYP<br>REAKVQWKVDNALQSGNSQESVTEQDSKDSTYSLSSTLTLSKAD<br>YEKHKVYACEVTHQGLSSPVTKSFNRGEC | SEQ ID NO: 63 |

Binding Protein 18 Nucleotide Sequences

| | | |
|---|---|---|
| Heavy chain A | HC:<br>gaggtgcagctgaaggagagcggccccggcctggtggcccccggcggcagcctgagcatcacctg<br>caccgtgagcggcttcagcctgaccgacagcagcatcaactgggtgcgccagcccccggcaaggg<br>cctggagtggctgggcatgatctggggcgacggccgcatcgactacgccgacgccctgaagagccg<br>cctgagcatcagcaaggacagcagcaagagccaggtgttcctggagatgaccagcctgcgcaccga<br>cgacaccgccacctactactgcgcccgcgacggctacttcccctacgccatggacttctggggccagg<br>gcaccagcgtgaccgtgagcagcgccagcaccaagggccccagcgtgttccccctggcccctagca<br>gcaagagcacatctggcggcacagccgccctgggctgcctggtcaaggactacttccccgagcccgt<br>gacagtgtcctggaactctggcgccctgaccagcggagtgcataccttccctgccgtgctgcagtccag<br>cggcctgtacagcctgagcagcgtggtcacagtgcccagcagcagcctgggcacccagacctacatc<br>tgcaacgtgaaccacaagcccagcaacaccaaggtggacaagaaggtggaacccaagagctgcgac<br>aagacccacacctgtcccccctgccctgcccctgaactgctgggcggaccctccgtgttcctgttcccc<br>ccaaagcccaaggacaccctgatgatcagccggacccccgaagtgacctgcgtggtggtggacgtgt<br>cccacgaggaccctgaagtgaagttcaattggtacgtggacggcgtggaagtgcataacgccaagac<br>caagcccagagaggaacagtacaacagcacctaccgggtggtgtccgtgctgaccgtgctgcaccag<br>gactggctgaacggcaaagagtacaagtgcaaggtgtccaacaaggccctgcctgcccccatcgaga<br>aaaccatcagcaaggccaagggccagcctagagagccccaagtctgcaccctgcccccagcagag<br>atgagctgaccaagaaccaggtgtccctgagctgcgccgtgaagggcttctaccccagcgatatcgcc<br>gtggaatgggagagcaacggccagcccgagaacaactacaagaccaccccccctgtgctggacagc<br>gacggctcattcttcctggtgtccaagctgacagtggacaagagccggtggcagcagggcaacgtgtt<br>cagctgcagcgtgatgcacgaggccctgcacaaccattacacccagaagtccctgagcctgagcccc<br>ggc | SEQ ID NO: 77 |
| Light chain A | LC:<br>gacatcgtgctgacccagagccctgccagcctggccgtgtctctgggccagagagccaccatcagct<br>gccgggccagcgagagcgtggacagctacggccagagctacatgcactggtatcagcagaaggcc<br>ggccagcccccaagctgctgatctacctggccagcaacctggaaagcggcgtgcccgccagattca<br>gcggcagcggcagcagaaccgacttcaccctgaccatcgaccccgtgcaggccgaggacgccgcc<br>acctactactgccagcagaacgccgaggacagccggaccttcggcggaggcaccaagctggaaatc<br>aagggacagcccaaggctgcccccctcggtcaccctgttcccccaagcagcgaggaactgcaggcc<br>aacaaggccaccctcgtgtgcctgatcagcgacttctaccctggcgccgtgaccgtggcctggaaggc<br>cgatagctctcccgtgaaggccggcgtggaaaccaccaccccccagcaagcagagcaacaacaaata<br>cgccgccagcagctacctgagcctgacccccgagcagtggaagtcccaccggtcctacagctgccag<br>gtcacacacgagggcagcaccgtggaaaagaccgtggcccccaccgagtgcagc | SEQ ID NO: 78 |
| Heavy chain B | HC:<br>caggtgcagctgcagcagagcggccctgagctggtcaagcctggcgccagcgtgaagatcagctgc<br>aaggccagcggctacagcttcaccagctactggatccactggatcaagcagcggcctggccagggcc<br>tggaatggatcggcatgatcgaccccagcgacggcgagacacggctgaaccagagattccagggca<br>gagccaccctgaccgtggacgagagcaccagcaccgcctacatgcagctgcggagccccaccagc<br>gaggacagcgccgtgtactactgcacccggctgaaagagtacggcaactacgacagcttctacttcga<br>cgtgtggggagccggcaccctggtcaccgtgtccagcgaagtgcagctgaaagaaagcggccctgg | SEQ ID NO: 66 |

TABLE 3-continued

| Heavy and light chain sequences of binding proteins specifically directed to IL-4, IL-13 and/or TNFa. | | |
|---|---|---|
| | cctggtggcccctggcggcagcctgagcatcacctgtaccgtgtccggcttcagcctgaccgacagca<br>gcatcaactgggtccgacagcccccctggcaagggcctcgagtggctgggaatgatctggggcgacg<br>gccggatcgactacgccgacgccctgaagtcccggctgagcatcagcaaggacagcagcaagagcc<br>aggtgttcctggaaatgaccagcctgcggaccgacgacaccgccacctactactgcgccagggacgg<br>ctacttcccctacgccatggatttctggggccagggcaccagcgtgaccgtgtcctctgcttccaccaag<br>ggccccagcgtgttccctctggcccctagcagcaagagcacatctggcggaacagccgccctgggct<br>gcctggtcaaggactactttcccgagcccgtgaccgtgtcctggaactctggtgccctgacaagcgga<br>gtgcataccttccctgccgtgctgcagagcagcggcctgtactctctgagcagcgtggtcaccgtgcca<br>agcagcagcctgggcacccagacctacatctgcaacgtgaaccacaagccctccaacaccaaggtgg<br>acaagaaggtggaacccaagagctgcgacaagacccacacctgtcctccctgtcctgcccctgaactg<br>ctgggcggaccctccgtgttcctgttccctccaaagcccaaggataccctgatgatcagccggacccct<br>gaagtgacctgcgtggtggtggacgtgtcccacgaggatcccgaagtgaagttcaattggtacgtgga<br>cggcgtggaagtgcataacgccaagaccaagcccagagaggaacagtacaacagcacctaccgggt<br>ggtgtccgtgctgacagtgctgcaccaggactggctgaacggcaaagagtacaagtgcaaggtgtcc<br>aacaaggccctgccagcccctatcgagaaaaccatcagcaaggccaagggccagccccgcgagcct<br>caggtgtacacactgcctccatgccgggacgagctgaccaagaaccaggtgtccctgtggtgcctcgt<br>gaagggcttctacccctccgatatcgccgtggaatgggagagcaacggccagcccgagaacaactac<br>aagaccacccctcccgtgctggacagcgacggctcattcttcctgtacagcaagctgaccgtggacaa<br>gtcccggtggcagcagggcaacgtgttcagctgctctgtgatgcacgaggccctgcacaaccggttca<br>cccagaagtccctgagcctgagccctggc | |
| Light chain B | LC:<br>Gacatcgtgctgacccagagccctgccagcctggccgtgtctctgggccagagagccaccatcagct<br>gccgggccagcgagagcgtggacagctacggccagagctacatgcactggtatcagcagaaggcc<br>ggccagcccccccaagctgctgatctacctggccagcaacctggaaagcggcgtgcccgccagattca<br>gcggcagcggcagcagaaccgacttcaccctgaccatcgaccccgtgcaggccgaggacgccgcc<br>acctactactgccagcagaacgccgaggacagccggaccttcggcggaggcaccaagctggaaatc<br>aagggcggctccggcagcagcggctctggcggcgatatccagatgacccagtcccccgcctccctga<br>gcgtgtccgtgggcgacaccatcaccctgacatgccacgccagccagaacatcgacgtgtggctgag<br>ctggttccagcagaagcctggcaacatccctaagctgctcatctataaggcctccaacctgcacaccgg<br>cgtgcccagcaggttttccggctctggcagcggcaccggctttaccctgacaatcagcagcctgcagc<br>ccgaggatatcgccacatattactgtcagcaggcccacagctaccccttcacctttggcggcggaacaa<br>agctcgagattaagggcggcagcggaagctccggctccggcggacgtacggtggccgctccttccgt<br>gttcatcttccctccctccgacgagcagctgaagtccggcaccgcctccgtggtgtgtctgctgaacaac<br>ttctaccctcgggaggccaaggtgcagtggaaggtggacaacgccctgcagtccggcaactcccagg<br>agtccgtcaccgagcaggactccaaggacagcacctactccctgtcctccaccctgaccctgtccaag<br>gccgactacgagaagcacaaggtgtacgcctgtgaggtgacccaccagggcctgtccagccctgtga<br>ccaagtccttcaaccggggcgagtgc | SEQ ID NO: 67 |
| Binding Protein 19 Amino Acid Sequences | | |
| Heavy chain A | HC:<br>QVQLQQSGPELVKPGASVKISCKAS***GYSFTSYWIH***WIKQRPGQGL<br>EWIG***MIDPSDGET***RLNQRFQGRATLTVDESTSTAYMQLRSPTSED<br>SAVYYCTR***LKEYGNYDSFYFDV***WGAGTLVTVSSASTKGPSVFPL<br>APSSKSTSGGTAALGCLVKDYFPEPVTVSWNSGALTSGVHTFPA<br>VLQSSGLYSLSSVVTVPSSSLGTQTYICNVNHKPSNTKVDKKVEP<br>KSCDKTHTCPPCPAPELLGGPSVFLFPPKPKDTLMISRTPEVTCVV<br>VDVSHEDPEVKFNWYVDGVEVHNAKTKPREEQYNSTYRVVSVL<br>TVLHQDWLNGKEYKCKVSNKALPAPIEKTISKAKGQPREPQVCT<br>LPPSRDELTKNQVSLSCAVKGFYPSDIAVEWESNGQPENNYKTTP<br>PVLDSDGSFFLVSKLTVDKSRWQQGNVFSCSVMHEALHNHYTQ<br>KSLSLSPG | SEQ ID NO: 85 |
| Light chain A | LC:<br>DIQMTQSPASLSVSVGDTITLTC***HASQNIDVWLS***WFQQKPGNIPK<br>LLIY***KASNLHT***GVPSRFSGSGSGTGFTLTISSLQPEDIATYYC***QQA***<br>***HSYPFT***FGGGTKLEIKGQPKAAPSVTLFPPSSEELQANKATLVCLI<br>SDFYPGAVTVAWKADSSPVKAGVETTTPSKQSNNKYAASSYLSL<br>TPEQWKSHRSYSCQVTHEGSTVEKTVAPTECS | SEQ ID NO: 86 |
| Heavy chain B | HC:<br>QVQLQQSGPELVKPGASVKISCKAS***GYSFTSYWIH***WIKQRPGQGL<br>EWIG***MIDPSDGET***RLNQRFQGRATLTVDESTSTAYMQLRSPTSED<br>SAVYYCTR***LKEYGNYDSFYFDV***WGAGTLVTVSSEVQLKESGPGL<br>VAPGGSLSITCTVS***GFSLTDSSIN***WVRQPPGKGLEWLG***MIWGDG***<br>***RID***YADALKSRLSISKDSSKSQVFLEMTSLRTDDTATYYCAR***DGY***<br>***FPYAMDF***WGQGTSVTVSSASTKGPSVFPLAPSSKSTSGGTAALG<br>CLVKDYFPEPVTVSWNSGALTSGVHTFPAVLQSSGLYSLSSVVTV<br>PSSSLGTQTYICNVNHKPSNTKVDKKVEPKSCDKTHTCPPCPAPE<br>LLGGPSVFLFPPKPKDTLMISRTPEVTCVVVDVSHEDPEVKFNWY<br>VDGVEVHNAKTKPREEQYNSTYRVVSVLTVLHQDWLNGKEYK<br>CKVSNKALPAPIEKTISKAKGQPREPQVYTLPPCRDELTKNQVSL<br>WCLVKGFYPSDIAVEWESNGQPENNYKTTPPVLDSDGSFFLYSK<br>LTVDKSRWQQGNVFSCSVMHEALHNRFTQKSLSLSPG | SEQ ID NO: 62 |

TABLE 3-continued

Heavy and light chain sequences of binding proteins specifically directed to IL-4, IL-13 and/or TNFa.

| | | |
|---|---|---|
| Light chain B | LC:<br>DIVLTQSPASLAVSLGQRATISC***RASESVDSYGQSYMH***WYQQKA<br>GQPPKLLIY***LASNLES***GVPARFSGSGSRTDFTLTIDPVQAEDAATY<br>YC***QQNAEDSRT***FGGGTKLEIKGGSGSSGSGGDIQMTQSPASLSVS<br>VGDTITLTC***HASQNIDVWLS***WFQQKPGNIPKLLIY***KASNLHT***GVP<br>SRFSGSGSGTGFTLTISSLQPEDIATYYC***QQAHSYPFT***FGGGTKLEI<br>KGGSGSSGSGGRTVAAPSVFIFPPSDEQLKSGTASVVCLLNNFYP<br>REAKVQWKVDNALQSGNSQESVTEQDSKDSTYSLSSTLTLSKAD<br>YEKHKVYACEVTHQGLSSPVTKSFNRGEC | SEQ ID NO: 63 |

Binding Protein 19 Nucleotide Sequences

| | | |
|---|---|---|
| Heavy chain A | HC:<br>caggtgcagctgcagcagagcggccccgagctggtgaagcccggcgccagcgtgaagatcagctg<br>caaggccagcggctacagcttcaccagctactggattcactggatcaagcagcgccccggccagggc<br>ctggagtggatcggcatgatcgaccccagcgacggcgagacccgcctgaaccagcgcttccagggc<br>cgcgccaccctgaccgtggacgagagcaccagcaccgcctacatgcagctgcgcagccccaccagc<br>gaggacagcgccgtgtactactgcacccgcctgaaggagtacggcaactacgacagcttctacttcga<br>cgtgtggggcgccggcaccctggtgaccgtgagcagcgccagcaccaagggccccagcgtgttccc<br>cctggcccctagcagcaagagcacatctggcggcacagccgccctgggctgcctggtcaaggactac<br>ttccccgagcccgtgacagtgtcctggaactctggcgccctgaccagcggagtgcataccttccctgcc<br>gtgctgcagtccagcggcctgtacagcctgagcagcgtggtcacagtgcccagcagcagcctgggca<br>cccagacctacatctgcaacgtgaaccacaagcccagcaacaccaaggtggacaagaaggtggaac<br>ccaagagctgcgacaagacccacacctgtccccccctgccctgcccctgaactgctgggcggaccctc<br>cgtgttcctgttcccccccaaagcccaaggacaccctgatgatcagccggacccccgaagtgacctgcg<br>tggtggtggacgtgtcccacgaggaccctgaagtgaagttcaattggtacgtggacggcgtggaagtg<br>cataacgccaagaccaagcccagagaggaacagtacaacagcacctaccgggtggtgtccgtgctga<br>ccgtgctgcaccaggactggctgaacggcaaagagtacaagtgcaaggtgtccaacaaggccctgcc<br>tgcccccatcgagaaaaccatcagcaaggccaagggccagcctagagagccccaagtctgcaccctg<br>cccccccagcagagatgagctgaccaagaaccaggtgtccctgagctgcgccgtgaagggcttctacc<br>ccagcgatatcgccgtggaatgggagagcaacggccagcccgagaacaactacaagaccaccccccc<br>ctgtgctggacagcgacggctcattcttcctggtgtccaagctgacagtggacaagagccggtggcag<br>cagggcaacgtgttcagctgcagcgtgatgcacgaggccctgcacaaccattacacccagaagtccct<br>gagcctgagccccggc | SEQ ID NO: 89 |
| Light chain A | LC:<br>gacatccagatgacccagagccccgccagcctgagcgtgtccgtgggcgataccatcaccctgacct<br>gccacgccagccagaacatcgacgtgtggctgagctggttccagcagaagcccggcaacatccccaa<br>gctgctgatctacaaggccagcaacctgcacaccggcgtgcccagcagattcagcggctctggcagc<br>ggcaccggctttaccctgaccatcagcagcctgcagcccgaggatatcgccacctactactgccagca<br>ggcccacagctaccccttcaccttcggcggaggcaccaagctggaaatcaagggacagcccaaggct<br>gcccccctcggtcaccctgttcccccccaagctctgaggaactgcaggccaacaaggccaccctcgtgtg<br>cctgatcagcgacttctaccctggcgccgtgaccgtggcctggaaggccgatagctctcccgtgaagg<br>ccggcgtggaaaccaccacccccagcaagcagagcaacaacaaatacgccgccagcagctacctga<br>gcctgacccccgagcagtggaagtcccaccggtcctacagctgccaggtcacacacgagggcagca<br>ccgtggaaaagaccgtggcccccaccgagtgcagc | SEQ ID NO: 90 |
| Heavy chain B | HC:<br>caggtgcagctgcagcagagcggccctgagctggtcaagcctggcgccagcgtgaagatcagctgc<br>aaggccagcggctacagcttcaccagctactggatccactggatcaagcagcggcctggccagggcc<br>tggaatggatcggcatgatcgaccccagcgacggcgagacacggctgaaccagagattccagggca<br>gagccaccctgaccgtggacgagagcaccagcaccgcctacatgcagctgcggagccccaccagc<br>gaggacagcgccgtgtactactgcacccggctgaaagagtacggcaactacgacagcttctacttcga<br>cgtgtggggagccggcaccctggtcaccgtgtccagcgaagtgcagctgaaagaaagcggccctgg<br>cctggtggcccctggcggcagcctgagcatcacctgtaccgtgtccggcttcagcctgaccgacagca<br>gcatcaactgggtccgacagccccctggcaagggcctcgagtggctgggaatgatctggggcgacg<br>gccggatcgactacgccgacgccctgaagtcccggctgagcatcagcaaggacagcagcaagagcc<br>aggtgttcctggaaatgaccagcctgcggaccgacgacaccgccacctactactgcgccagggacgg<br>ctacttcccctacgccatggatttctggggccagggcaccagcgtgaccgtgtcctctgcttccaccaag<br>ggccccagcgtgttccctctggcccctagcagcaagagcacatctggcggaacagccgccctgggct<br>gcctggtcaaggactactttcccgagcccgtgaccgtgtcctggaactctggtgccctgacaagcgga<br>gtgcataccttccctgccgtgctgcagagcagcggcctgtactctctgagcagcgtggtcaccgtgcca<br>agcagcagcctgggcacccagacctacatctgcaacgtgaaccacaagccctccaacaccaaggtgg<br>acaagaaggtggaacccaagagctgcgacaagacccacacctgtcctccctgtcctgcccctgaactg<br>ctgggcggaccctccgtgttcctgttccctccaaagcccaaggataccctgatgatcagccggacccct<br>gaagtgacctgcgtggtggtggacgtgtcccacgaggatcccgaagtgaagttcaattggtacgtgga<br>cggcgtggaagtgcataacgccaagaccaagcccagagaggaacagtacaacagcacctaccgggt<br>ggtgtccgtgctgacagtgctgcaccaggactggctgaacggcaaagagtacaagtgcaaggtgtcc<br>aacaaggccctgccagcccctatcgagaaaaccatcagcaaggccaagggccagccccgcgagcct<br>caggtgtacacactgcctccatgccgggacgagctgaccaagaaccaggtgtccctgtggtgcctcgt<br>gaagggcttctacccctccgatatcgccgtggaatgggagagcaacggccagcccgagaacaactac<br>aagaccacccctcccgtgctggacagcgacggctcattcttcctgtacagcaagctgaccgtggacaa<br>gtcccggtggcagcagggcaacgtgttcagctgctctgtgatgcacgaggccctgcacaaccggttca<br>cccagaagtccctgagcctgagccctggc | SEQ ID NO: 66 |

TABLE 3-continued

| Heavy and light chain sequences of binding proteins specifically directed to IL-4, IL-13 and/or TNFa. | | |
|---|---|---|
| Light chain B | LC:<br>gacatcgtgctgacccagagccctgccagcctggccgtgtctctgggccagagagccaccatcagct<br>gccgggccagcgagagcgtggacagctacggccagagctacatgcactggtatcagcagaaggcc<br>ggccagcccccccaagctgctgatctacctggccagcaacctggaaagcggcgtgcccgccagattca<br>gcggcagcggcagcagaaccgacttcaccctgaccatcgaccccgtgcaggccgaggacgccgcc<br>acctactactgccagcagaacgccgaggacagccggaccttcggcggaggcaccaagctggaaatc<br>aagggcggctccggcagcagcggctctggcggcgatatccagatgacccagtcccccgcctccctga<br>gcgtgtccgtgggcgacaccatcaccctgacatgccacgccagccagaacatcgacgtgtggctgag<br>ctggttccagcagaagcctggcaacatccctaagctgctcatctataaggcctccaacctgcacaccgg<br>cgtgcccagcaggttttccggctctggcagcggcaccggctttaccctgacaatcagcagcctgcagc<br>ccgaggatatcgccacatattactgtcagcaggcccacagctaccccttcacctttggcggcggaacaa<br>agctcgagattaagggcggcagcggaagctccggctccggcggacgtacggtggccgctccttccgt<br>gttcatcttccctccctccgacgagcagctgaagtccggcaccgcctccgtggtgtgtctgctgaacaac<br>ttctaccctcgggaggccaaggtgcagtggaaggtggacaacgccctgcagtccggcaactcccagg<br>agtccgtcaccgagcaggactccaaggacagcacctactccctgtcctccaccctgaccctgtccaag<br>gccgactacgagaagcacaaggtgtacgcctgtgaggtgacccaccagggcctgtccagccctgtga<br>ccaagtccttcaaccggggcgagtgc | SEQ ID NO: 67 |

TABLE 4

| CDR sequences of binding proteins | | | | | | |
|---|---|---|---|---|---|---|
| Ab | CDR_H1 | CDR_H2 | CDR_H3 | CDR_L1 | CDR_L2 | CDR_L3 |
| Anti-Her2 | GFNIKDTY (SEQ ID NO: 25) | IYPTNGYT (SEQ ID NO: 26) | SRWGGDGFYAMDY (SEQ ID NO: 27) | QDVNTA (SEQ ID NO: 43) | SAS (SEQ ID NO: 44) | QQHYTTPPT (SEQ ID NO: 45) |
| Anti-CD3 | GFTFTKAW (SEQ ID NO: 34) | IKDKSNS (SEQ ID NO: 35) | RGVYYALSPFDY (SEQ ID NO: 36) | QSLVHNNANTY (SEQ ID NO: 52) | KVS (SEQ ID NO: 53) | GQGTQYP (SEQ ID NO: 54) |
| Anti-CD3-2 | GFTFTKAW (SEQ ID NO: 34) | IKDKSNS (SEQ ID NO: 35) | RGVYYALSPFDY (SEQ ID NO: 36) | QSLVHNNGNTY (SEQ ID NO: 149) | KVS (SEQ ID NO: 53) | GQGTQYP (SEQ ID NO: 54) |
| Anti-CD19 | GYAFSSYW (SEQ ID NO: 37) | IWPGDGDT (SEQ ID NO: 38) | ARRETTTVGRYYYAMD (SEQ ID NO: 39) | QSVDYDGDSY (SEQ ID NO: 55) | DAS (SEQ ID NO: 56) | QQSTEDPWT (SEQ ID NO: 57) |
| Anti-CD20 | GYTFTSYN (SEQ ID NO: 120) | IYPGNGDT (SEQ ID NO: 121) | ARSTYYGGDWYFNV (SEQ ID NO: 122) | SSVSY (SEQ ID NO: 123) | ATS (SEQ ID NO: 124) | QQWTSNP (SEQ ID NO: 125) |
| Anti-CD28-1 | GYTFTSYY (SEQ ID NO: 28) | IYPGNVNT (SEQ ID NO: 29) | TRSHYGLDWNFDV (SEQ ID NO: 30) | QNIYVW (SEQ ID NO: 46) | KAS (SEQ ID NO: 47) | QQGQTYPYT (SEQ ID NO: 48) |
| Anti-CD28-2 | GFSLSDYG (SEQ ID NO: 31) | IWAGGGT (SEQ ID NO: 32) | ARDKGYSYYYSMD (SEQ ID NO: 33) | ESVEYYVTSL (SEQ ID NO: 49) | AAS (SEQ ID NO: 50) | QQSRKVPYT (SEQ ID NO: 51) |
| Anti-CD38 | GYTFTDYW (SEQ ID NO: 40) | IYPGDGDT (SEQ ID NO: 41) | ARGDYYGSNSLDY (SEQ ID NO: 42) | QDVSTV (SEQ ID NO: 58) | SAS (SEQ ID NO: 44) | QQHYSPPYT (SEQ ID NO: 59) |
| Anti-LAMP1 | GYIFTNYNIH (SEQ ID NO: 126) | AIYPGNGDAP (SEQ ID NO: 127) | ANWDVAFAY (SEQ ID NO: 128) | KASQDIDRYMA (SEQ ID NO: 138) | DTSTLQS (SEQ ID NO: 139) | LQYDNLWT (SEQ ID NO: 140) |
| Anti-TNFα | GFTFDDYAMH (SEQ ID NO: 129) | AITWNSGHID (SEQ ID NO: 130) | VSYLSTASSLDY (SEQ ID NO: 131) | RASQGIRNYLA (SEQ ID NO: 141) | AASTLQS (SEQ ID NO: 178) | QRYNRAPYT (SEQ ID NO: 142) |
| Anti-IL4 | GYSFTSYWIH (SEQ ID NO: 132) | MIDPSDGET (SEQ ID NO: 133) | LKEYGNYDSFYFDV (SEQ ID NO: 134) | HASQNIDVWLS (SEQ ID NO: 143) | KASNLHT (SEQ ID NO: 179) | QQAHSYPFT (SEQ ID NO: 144) |
| Anti-IL13 | GFSLTDSSIN (SEQ ID NO: 135) | MIWGDGRID (SEQ ID NO: 136) | DGYFPYAMDF (SEQ ID NO: 137) | RASESVDSYGQSYMH (SEQ ID NO: 145) | LASNLES (SEQ ID NO: 146) | QQNAEDSRT (SEQ ID NO: 147) |

TABLE 5

VH/VL sequences of binding proteins

| Ab | VH (protein) | VL (protein) |
|---|---|---|
| Anti-<br>Her2 | EVQLVESGGGLVQPGGSLRLSCAAS***GFNIKDTY***<br>IHWVRQAPGKGLEWVAR***IYPTNGYT***RYADSVK<br>GRFTISADTSKNTAYLQMNSLRAEDTAVYYC***SR***<br>***WGGDGFYAMDY***WGQGTLVTVSS<br>(SEQ ID NO: 150) | DIQMTQSPSSLSASVGDRVTITCRAS***QDV***<br>***NTA***VAWYQQKPGKAPKLLIY***SAS***FLYSG<br>VPSRFSGSRSGTDFTLTISSLQPEDFATYY<br>C***QQHYTTPPT***FGQGTKVEIK<br>(SEQ ID NO: 151) |
| Anti-<br>CD3 | QVQLVESGGGVVQPGRSLRLSCAAS***GFTFTKA***<br>***W***MHWVRQAPGKQLEWVAQ***IKDKSNS***YATYYA<br>DSVKGRFTISRDDSKNTLYLQMNSLRAEDTAVY<br>YC***RGVYYALSPFDY***WGQGTLVTVSS<br>(SEQ ID NO: 152) | DIVMTQTPLSLSVTPGQPASISCKSS***QSLV***<br>***HNNANTY***YLSWYLQKPGQSPQSLIY***KVS***N<br>RFSGVPDRFSGSGSGTDFTLKISRVEAED<br>VGVYYC***GQGTQYP***FTFGSGTKVEIK<br>(SEQ ID NO: 153) |
| Anti-<br>CD3-2 | QVQLVESGGGVVQPGRSLRLSCAAS***GFTFTKA***<br>***W***MHWVRQAPGKGLEWVAQ***IKDKSNS***YATYYA<br>DSVKGRFTISRDNSKNTLYLQMNSLRAEDTAVY<br>YC***RGVYYALSPFDY***WGQGTLVTVSS<br>(SEQ ID NO: 154) | DIVMTQTPLSLSVTPGQPASISCKSS***QSLV***<br>***HNNGNTY***LSWYLQKPGQSPQLLIY***KVS***N<br>RFSGVPDRFSGSGSGTDFTLKISRVEAED<br>VGVYYC***GQGTQYP***FTFGGGTKVEIK<br>(SEQ ID NO: 155) |
| Anti-<br>CD19 | QVQLVQSGAEVKKPGSSVKVSCKAS***GYAFSSY***<br>***W***MNWVRQAPGQGLEWIGQ***IWPGDGDT***NYNQ<br>KFKGRATLTADESTSTAYMELSSLRSEDTAVYY<br>CA***RRETTTVGRYYYAMD***YWGQGTTVTVSS<br>(SEQ ID NO: 156) | DLVLTQSPASLAVSPGQRATITCKAS***QSV***<br>***DYDGDSY***LNWYQQKPGQPPKLLIY***DAS***N<br>LVSGVPARFSGSGSGTDFTLTINPVEAND<br>TANYYC***QQSTEDPWT***FGQGTKLEIK<br>(SEQ ID NO: 157) |
| Anti-<br>CD20 | QVQLQQPGAELVKPGASVKMSCKAS***GYTFTSY***<br>***N***MHWVKQTPGRGLEWIGA***IYPGNGDT***SYNQKF<br>KGKATLTADKSSSTAYMQLSSLTSEDSAVYYCA<br>***RSTYYGGDWYFNV***WGAGTTVTVSA<br>(SEQ ID NO: 158) | QIVLSQSPAILSASPGEKVTMTCRAS***SSVS***<br>***Y***IHWFQQKPGSSPKPWIY***ATS***NLASGVP<br>VRFSGSGSGTSYSLTISRVEAEDAATYYC<br>***QQWTSNP***PTFGGGTKLEIK<br>(SEQ ID NO: 159) |
| Anti-<br>CD28-1 | QVQLVQSGAEVVKPGASVKVSCKAS***GYTFTSY***<br>YIHWVRQAPGQGLEWIGS***IYPGNVNT***NYAQKF<br>QGRATLTVDTSISTAYMELSRLRSDDTAVYYC***T***<br>***RSHYGLDWNFDV***WGKGTTVTVSS<br>(SEQ ID NO: 160) | DIQMTQSPSSLSASVGDRVTITCQAS***QNI***<br>***YVW***LNWYQQKPGKAPKLLIY***KAS***NLHT<br>GVPSRFSGSGSGTDFTLTISSLQPEDIATY<br>YC***QQGQTYPYT***FGQGTKLEIK<br>(SEQ ID NO: 161) |
| Anti-<br>CD28-2 | QVQLQESGPGLVKPSQTLSLTCTVS***GFSLSDYG***<br>VHWVRQPPGKGLEWLGV***IWAAGGGT***NYNPSLK<br>SRKTISKDTSKNQVSLKLSSVTAADTAVYYC***AR***<br>***DKGYSYYYSMD***YWGQGTTVTVSS<br>(SEQ ID NO: 162) | DIVLTQSPASLAVSPGQRATITCRAS***ESV***<br>***EYYVTSL***MQWYQQKPGQPPKLLIF***AAS***N<br>VESGVPARFSGSGSGTDFTLTINPVEAND<br>VANYYC***QQSRKVPYT***FGQGTKLEIK<br>(SEQ ID NO: 163) |
| Anti-<br>CD38 | QVQLVQSGAEVAKPGTSVKLSCKAS***GYTFTDY***<br>***W***MQWVKQRPGQGLEWIGT***IYPGDGDT***GYAQK<br>FQGKATLTADKSSKTVYMHLSSLASEDSAVYY<br>CA***RGDYYGSNSLDY***WGQGTSVTVSS<br>(SEQ ID NO: 164) | DIVMTQSHLSMSTSLGDPVSITCKAS***QDV***<br>***STV***VAWYQQKPGQSPRRLIY***SAS***YRYIG<br>VPDRFTGSGAGTDFTFTISSVQAEDLAVY<br>YC***QQHYSPPYT***FGGGTKLEIK<br>(SEQ ID NO: 165) |
| Anti-<br>LAMP1 | QVQLVQSGAEVKKPGSSVKVSCKAS***GYIFTNYN***<br>***IH***WVKKSPGQGLEWIGA***IYPGNGDAP***YSQKFQ<br>GKATLTADTSTSTTYMELSSLRSEDTAVYYCVR<br>***ANWDVAFAY***WGQGTLVTVSS<br>(SEQ ID NO: 167) | DIQMTQSPSSLSASVGDRVTITC***KASQDI***<br>***DRYMA***WYQDKPGKAPRLLIH***DTSTLQS***<br>GVPSRFSGSGSGRDYTLTISNLEPEDFAT<br>YYC***LQYDNLWT***FGGGTKVEIK<br>(SEQ ID NO: 166) |
| Anti-<br>TNFα | EVQLVESGGGLVQPGRSLRLSCAAS***GFTFDDYA***<br>***MH***WVRQAPGKGLEWVS***AITWNSGHID***YADSV<br>EGRFTISRDNAKNSLYLQMNSLRAEDTAVYYC<br>AK***VSYLSTASSLDY***WGQGTLVTVSS<br>(SEQ ID NO: 168) | DIQMTQSPSSLSASVGDRVTITC***RASQGI***<br>***RNYLA***WYQQKPGKAPKLLIY***AASTLQS***G<br>VPSRFSGSGSGTDFTLTISSLQPEDVATY<br>YC***QRYNRAPYT***FGQGTKVEIK<br>(SEQ ID NO: 169) |
| Anti-<br>IL4 | QVQLQQSGPELVKPGASVKISCKAS***GYSFTSYW***<br>***IH***WIKQRPGQGLEWIG***MIDPSDGET***RLNQRFQG<br>RATLTVDESTSTAYMQLRSPTSEDSAVYYCTR***L***<br>***KEYGNYDSFYFDV***WGAGTLVTVSS<br>(SEQ ID NO: 170) | DIQMTQSPASLSVSVGDTITLTC***HASQNI***<br>***DVWLS***WFQQKPGNIPKLLIY***KASNLHT***G<br>VPSRFSGSGSGTGFTLTISSLQPEDIATYY<br>C***QQAHSYPFT***FGGGTKLEIK<br>(SEQ ID NO: 171) |
| Anti-<br>IL13 | EVQLKESGPGLVAPGGSLSITCTVS***GFSLTDSSI***<br>***N***WVRQPPGKGLEWLG***MIWGDGRID***YADALKS<br>RLSISKDSSKSQVFLEMTSLRTDDTATYYCAR***D***<br>***GYFPYAMDF***WGQGTSVTVSS<br>(SEQ ID NO: 172) | DIVLTQSPASLAVSLGQRATISC***RASESV***<br>***DSYGQSYMH***WYQQKAGQPPKLLIY***LAS***<br>***NLES***GVPARFSGSGSRTDFTLTIDPVQAE<br>DAATYYC***QQNAEDSRT***FGGGTKLEIK<br>(SEQ ID NO: 173) |

Note:
CDR sequences are bolded and italicized in amino acid sequences above.

What is claimed is:

1. A trispecific binding protein comprising four polypeptide chains that form three antigen binding sites that specifically bind one or more target proteins, wherein a first polypeptide chain of the binding protein comprises a structure represented by the formula:

$$V_{L2}\text{-}L_1\text{-}V_{L1}\text{-}L_2\text{-}C_L \quad [I]$$

and a second polypeptide chain of the binding protein comprises a structure represented by the formula:

$$V_{H1}\text{-}L_3\text{-}V_{H2}\text{-}L_4\text{-}C_{H1}\text{-hinge-}C_{H2}\text{-}C_{H3} \quad [II]$$

and a third polypeptide chain of the binding protein comprises a structure represented by the formula:

$$V_{H3}\text{-}C_{H1}\text{-hinge-}C_{H2}\text{-}C_{H3} \quad [III]$$

and a fourth polypeptide chain of the binding protein comprises a structure represented by the formula:

$$V_{L3}\text{-}C_L \quad [IV]$$

wherein:

$V_{L1}$ is a first immunoglobulin light chain variable domain;

$V_{L2}$ is a second immunoglobulin light chain variable domain;

$V_{L3}$ is a third immunoglobulin light chain variable domain;

$V_{H1}$ is a first immunoglobulin heavy chain variable domain;

$V_{H2}$ is a second immunoglobulin heavy chain variable domain;

$V_{H3}$ is a third immunoglobulin heavy chain variable domain;

$C_L$ is an immunoglobulin light chain constant domain;

$C_{H1}$ is an immunoglobulin $C_{H1}$ heavy chain constant domain;

$C_{H2}$ is an immunoglobulin $C_{H2}$ heavy chain constant domain;

$C_{H3}$ is an immunoglobulin $C_{H3}$ heavy chain constant domain;

hinge is an immunoglobulin hinge region connecting the $C_{H1}$ and $C_{H2}$ domains; and $L_1$, $L_2$, $L_3$ and $L_4$ are each independently amino acid linkers or zero amino acids in length;

wherein the polypeptide of formula I and the polypeptide of formula II form a cross-over light chain-heavy chain pair of the binding protein; wherein $V_{H1}$ and $V_{L1}$ form a binding pair and a first antigen binding site, and $V_{H2}$ and $V_{L2}$ form a binding pair and a second antigen binding site; and wherein $V_{H3}$ and $V_{L3}$ form a binding pair and a third antigen binding site.

2. The binding protein of claim 1, wherein $L_1$, $L_2$, $L_3$ and $L_4$ each independently are the amino acid S or comprise a sequence selected from the group consisting of GGGGSGGGGS (SEQ ID NO:104), GGGGSGGGGSGGGGS (SEQ ID NO:105), RT, TKGPS (SEQ ID NO:106), GQPKAAP (SEQ ID NO: 175), and GGSGSSGSGG (SEQ ID NO:148).

3. The binding protein of claim 1, wherein (a) $L_1$ comprises the sequence GQPKAAP (SEQ ID NO: 175), $L_2$ comprises the sequence TKGPS (SEQ ID NO:106), $L_3$ comprises the amino acid S, and $L_4$ comprises the sequence RT;

(b) $L_1$ comprises the sequence GGGGSGGGGS (SEQ ID NO:104), $L_2$ comprises the sequence GGGGSGGGGS (SEQ ID NO:104), $L_3$ is 0 amino acids in length, and $L_4$ is 0 amino acids in length;

(c) $L_1$ comprises the sequence GGSGSSGSGG (SEQ ID NO:148), $L_2$ comprises the sequence GGSGSSGSGG (SEQ ID NO:148), $L_3$ is 0 amino acids in length, and $L_4$ is 0 amino acids in length; or (d) $L_1$ comprises the sequence GGGGSGGGGSGGGGS (SEQ ID NO:105), $L_2$ is 0 amino acids in length, $L_3$ comprises the sequence GGGGSGGGGSGGGGS (SEQ ID NO:105), and $L_4$ is 0 amino acids in length.

4. The binding protein of claim 1, wherein the binding protein is trispecific and capable of specifically binding three different antigen targets.

5. The binding protein of claim 1, wherein the binding protein specifically binds three target proteins that correspond to two target proteins on T cells and to one tumor target protein.

6. The binding protein of claim 5, wherein one of said target proteins on T cells is CD3.

7. The binding protein of claim 5, wherein one of said target proteins on T cells is CD28.

8. The binding protein of claim 5, wherein said tumor target protein is CD38.

9. The binding protein of claim 1, wherein the binding protein specifically binds three target proteins that correspond to two target proteins on T cells and to one target protein, each protein selected from the group consisting of A2AR, APRIL, ATPDase, BAFF, BAFFR, BCMA, BlyS, BTK, BTLA, B7DC, B7H1, B7H4, B7H5, B7H6, B7H7, B7RP1, B7-4, C3, C5, CCL2, CCL3, CCL4, CCL5, CCL7, CCL8, CCL11, CCL15, CCL17, CCL19, CCL20, CCL21, CCL24, CCL25, CCL26, CCR3, CCR4, CD3, CD19, CD20, CD23, CD24, CD27, CD28, CD38, CD39, CD40, CD70, CD80, CD86, CD122, CD137, CD137L, CD152, CD154, CD160, CD272, CD273, CD274, CD275, CD276, CD278, CD279, CDH1, chitinase, CLEC9, CLEC91, CRTH2, CSF-1, CSF-2, CSF-3, CX3CL1, CXCL12, CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb, IL18, IL22, IL23, IL25, IL27, IL33, IL35, ITGB4, ITK, KIR, LAG3, LAMP1, leptin, LPFS2, MEW class II, NCR3LG1, NKG2D, NTP-Dase-1, OX40, OX40L, PD-1H, platelet receptor, PROM1, S152, SISP1, SLC, SPG64, ST2, STEAP2, Syk kinase, TACI, TDO, T14, TIGIT, TIM3, TLR, TLR2, TLR4, TLR5, TLR9, TMEF1, TNFα, TNFRSF7, Tp55, TREM1, TSLP, TSLPR, TWEAK, VEGF, VISTA, Vstm3, WUCAM, and XCR1.

10. The binding protein of claim 1, wherein the binding protein is capable of inhibiting the function of one or more target proteins.

11. The binding protein of claim 10, wherein the one or more target proteins are selected from the group consisting of A2AR, APRIL, ATPDase, BAFF, BAFFR, BCMA, BlyS, BTK, BTLA, B7DC, B7H1, B7H4, B7H5, B7H6, B7H7, B7RP1, B7-4, C3, C5, CCL2, CCL3, CCL4, CCL5, CCL7, CCL8, CCL11, CCL15, CCL17, CCL19, CCL20, CCL21, CCL24, CCL25, CCL26, CCR3, CCR4, CD3, CD19, CD20, CD23, CD24, CD27, CD28, CD38, CD39, CD40, CD70, CD80, CD86, CD122, CD137, CD137L, CD152, CD154, CD160, CD272, CD273, CD274, CD275, CD276, CD278, CD279, CDH1, chitinase, CLEC9, CLEC91, CRTH2, CSF-1, CSF-2, CSF-3, CX3CL1, CXCL12, CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb, IL18, IL22, IL23, IL25, IL27, IL33, IL35, ITGB4, ITK, KIR, LAG3, LAMP1, leptin, LPFS2, MEW class II, NCR3LG1, NKG2D, NTP-Dase-1, OX40, OX40L, PD-1H, platelet receptor, PROM1, S152, SISP1, SLC, SPG64, ST2, STEAP2, Syk kinase, TACI, TDO, T14, TIGIT, TIM3, TLR, TLR2, TLR4, TLR5, TLR9, TMEF1, TNFα, TNFRSF7, Tp55, TREM1, TSLP, TSLPR, TWEAK, VEGF, VISTA, Vstm3, WUCAM, and XCR1.

12. The binding protein of claim 1, wherein:

(a) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO:47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and $V_{L3}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45;

(b) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:25, a CDR-H2 comprising the amino acid sequence of SEQ ID NO:26, and a CDR-H3 comprising the amino acid sequence of SEQ ID NO:27; and $V_{L3}$ comprises a CDR-L1 comprising the amino acid sequence of SEQ ID NO:43, a CDR-L2 comprising the amino acid sequence of SEQ ID NO:44, and a CDR-L3 comprising the amino acid sequence of SEQ ID NO:45;

(c) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO:47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:37, a CDR-H2 comprising the amino acid sequence of SEQ ID NO:38, and a CDR-H3 comprising the amino acid sequence of SEQ ID NO:39; and $V_{L3}$ comprises a CDR-L1 comprising the amino acid sequence of SEQ ID NO:55, a CDR-L2 comprising the amino acid sequence of SEQ ID NO:56, and a CDR-L3 comprising the amino acid sequence of SEQ ID NO:57;

(d) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:37, a CDR-H2 comprising the amino acid sequence of SEQ ID NO:38, and a CDR-H3 comprising the amino acid sequence of SEQ ID NO:39; and $V_{L3}$ comprises a CDR-L1 comprising the amino acid sequence of SEQ ID NO:55, a CDR-L2 comprising the amino acid sequence of SEQ ID NO:56, and a CDR-L3 comprising the amino acid sequence of SEQ ID NO:57;

(e) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:40, a CDR-H2 comprising the amino acid sequence of SEQ ID NO:41, and a CDR-H3 comprising the amino acid sequence of SEQ ID NO:42; and $V_{L3}$ comprises a CDR-L1 comprising the amino acid sequence of SEQ ID NO:58, a CDR-L2 comprising the amino acid sequence of SEQ ID NO:44, and a CDR-L3 comprising the amino acid sequence of SEQ ID NO:59;

(f) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:40, a CDR-H2 comprising the amino acid sequence of SEQ ID NO:41, and a CDR-H3 comprising the amino acid sequence of SEQ ID NO:42; and $V_{L3}$ comprises a CDR-L1 comprising the amino acid sequence of SEQ ID NO:58, a CDR-L2 comprising the amino acid sequence of SEQ ID NO:44, and a CDR-L3 comprising the amino acid sequence of SEQ ID NO:59;

(g) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:126, a CDR-H2 comprising the amino acid sequence of SEQ ID NO:127, and a CDR-H3 comprising the amino acid sequence of SEQ ID NO:128; and $V_{L3}$ comprises a CDR-L1 comprising the amino acid sequence of SEQ ID NO:138, a CDR-L2 comprising the amino acid sequence of SEQ ID NO:139, and a CDR-L3 comprising the amino acid sequence of SEQ ID NO:140;

(h) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:126, a CDR-H2 comprising the amino acid sequence of SEQ ID NO:127, and a CDR-H3 comprising the amino acid sequence of SEQ ID NO:128; and $V_{L3}$ comprises a CDR-L1 comprising the amino acid sequence of SEQ ID NO:138, a CDR-L2 comprising the amino acid sequence of SEQ ID NO:139, and a CDR-L3 comprising the amino acid sequence of SEQ ID NO:140;

(i) $V_{H1}$ comprises a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; $V_{L1}$ comprises a CDR-L1 comprising the amino acid sequence of SEQ ID NO:46, a CDR-L2 comprising the amino acid sequence of SEQ ID NO: 47, and a CDR-L3 comprising the amino acid sequence of SEQ ID NO:48; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:120, a CDR-H2 comprising the amino acid sequence of SEQ ID NO:121, and a CDR-H3 comprising the amino acid sequence of SEQ ID NO:122; and $V_{L3}$ comprises a CDR-L1 comprising the amino acid sequence of SEQ ID NO:123, a CDR-L2 comprising the amino acid sequence of SEQ ID NO:124, and a CDR-L3 comprising the amino acid sequence of SEQ ID NO:125; or (j) $V_{H1}$ comprises a CDR-H1 comprising the amino acid sequence of SEQ ID NO:31, a CDR-H2 comprising the amino acid sequence of SEQ ID NO:32, and a CDR-H3 comprising the amino acid sequence of SEQ ID NO:33; $V_{L1}$ comprises a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51; $V_{H2}$ comprises a CDR-H1 comprising the amino acid sequence of SEQ ID NO:34, a CDR-H2 comprising the amino acid sequence of SEQ ID NO:35, and a CDR-H3 comprising the amino acid sequence of SEQ ID NO:36; $V_{L2}$ comprises a CDR-L1 comprising the amino acid sequence of SEQ ID NO:52, a CDR-L2 comprising the amino acid sequence of SEQ ID NO:53, and a CDR-L3 comprising the amino acid sequence of SEQ ID NO:54; $V_{H3}$ comprises a CDR-H1 comprising the amino acid sequence of SEQ ID NO:120, a CDR-H2 comprising the amino acid sequence of SEQ ID NO:121, and a CDR-H3 comprising the amino acid sequence of SEQ ID NO:122; and $V_{L3}$ comprises a CDR-L1 comprising the amino acid sequence of SEQ ID NO:123, a CDR-L2 comprising the amino acid sequence of SEQ ID NO:124, and a CDR-L3 comprising the amino acid sequence of SEQ ID NO:125.

13. The binding protein of claim 1, wherein:

(a) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; and $V_{L3}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142;

(b) $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:47, and a CDR-L3 comprising the amino acid sequence of SEQ ID NO:144; $V_{H3}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; and $V_{L3}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142;

(c) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L2}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147;

(d) $V_{H1}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L1}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147;

(e) $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L2}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144;

(f) $V_{H1}$ comprises a CDR-H1 comprising the amino acid sequence of SEQ ID NO:129, a CDR-H2 comprising the amino acid sequence of SEQ ID NO:130, and a CDR-H3 comprising the amino acid sequence of SEQ ID NO:131; $V_{L1}$ comprises a CDR-L1 comprising the amino acid sequence of SEQ ID NO:141, a CDR-L2 comprising the amino acid sequence of SEQ ID NO:178, and a CDR-L3 comprising the amino acid sequence of SEQ ID NO:142; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144;

(g) $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147;

(h) $V_{H1}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L1}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H2}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L2}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144;

(i) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; and $V_{L3}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; or (j) $V_{H1}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; $V_{L1}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144; $V_{H2}$ comprises a CDR-H1 comprising the amino acid sequence of SEQ ID NO:135, a CDR-H2 comprising the amino acid sequence of SEQ ID NO:136, and a CDR-H3 comprising the amino acid sequence of SEQ ID NO:137; $V_{L2}$ comprises a CDR-L1 comprising the amino acid sequence of SEQ ID NO:145, a CDR-L2 comprising the amino acid sequence of SEQ ID NO:146, and a CDR-L3 comprising the amino acid sequence of SEQ ID NO:147; $V_{H3}$ comprises a CDR-H1 comprising the amino acid sequence of SEQ ID NO:132, a CDR-H2 comprising the amino acid sequence of SEQ ID NO:133, and a CDR-H3 comprising the amino acid sequence of SEQ ID NO:134; and $V_{L3}$ comprises a CDR-L1 comprising the amino acid sequence of SEQ ID NO:143, a CDR-L2 comprising the amino acid sequence of SEQ ID NO:179, and a CDR-L3 comprising the amino acid sequence of SEQ ID NO:144.

14. The binding protein of claim 1, wherein the $C_{H3}$ domain of the second polypeptide chain comprises amino acid substitutions at positions corresponding to positions 354 and 366 of human IgG1 or IgG4 according to EU Index, wherein the amino acid substitutions are S354C and T366W; and wherein the $C_{H3}$ domain of the third polypeptide chain comprises amino acid substitutions at positions corresponding to positions 349, 366, 368, and 407 of human IgG1 or IgG4 according to EU Index, wherein the amino acid substitutions are Y349C, T366S, $L_{368}$A, and Y407V.

15. The binding protein of claim 1, wherein the $C_{H3}$ domain of the second polypeptide chain comprises amino acid substitutions at positions corresponding to positions 349, 366, 368, and 407 of human IgG1 or IgG4 according to EU Index, wherein the amino acid substitutions are Y349C, T366S, L368A, and Y407V; and wherein the $C_{H3}$ domain of the third polypeptide chain comprises amino acid substitutions at positions corresponding to positions 354 and 366 of human IgG1 or IgG4 according to EU Index, wherein the amino acid substitutions are S354C and T366W.

16. The binding protein of claim 1, wherein the $C_{H3}$ domains of the second and the third polypeptide chains both comprise amino acid substitutions at positions corresponding to positions 428 and 434 of human IgG1 or IgG4 according to EU Index, wherein the amino acid substitutions are M428L and N434S.

17. The binding protein of claim 1, wherein the $C_{H3}$ domains of the second and the third polypeptide chains are human IgG1 or IgG4 $C_{H3}$ domains, and wherein only one of the $C_{H3}$ domains comprises amino acid substitutions at positions corresponding to positions 435 and 436 of human IgG1 or IgG4 according to EU Index, wherein the amino acid substitutions are H435R and Y436F.

18. The binding protein of claim 1, wherein the $C_{H3}$ domains of the second and the third polypeptide chains are human IgG4 $C_{H3}$ domains, and wherein the $C_{H3}$ domains each comprise amino acid substitutions at positions corresponding to positions 228 and 409 of human IgG4 according to EU Index, wherein the amino acid substitutions are S228P and R409K.

19. The binding protein of claim 1, wherein the $C_{H3}$ domains of the second and the third polypeptide chains are human IgG4 $C_{H3}$ domains, and wherein the $C_{H3}$ domains each comprise amino acid substitutions at positions corresponding to positions 234 and 235 of human IgG4 according to EU Index, wherein the amino acid substitutions are F234A and L235A.

20. The binding protein of claim 1, wherein the $C_{H3}$ domains of the second and the third polypeptide chains are human IgG1 $C_{H3}$ domains, and wherein the $C_{H3}$ domains each comprise amino acid substitutions at positions corresponding to positions 234 and 235 of human IgG1 according to EU Index, wherein the amino acid substitutions are L234A and L235A.

21. The binding protein of claim 1, wherein $V_{H1}$ and $V_{L1}$ form a first antigen binding site that specifically binds human CD3, wherein $V_{H2}$ and $V_{L2}$ form a second antigen binding site that specifically binds human CD28, and wherein $V_{H3}$ and $V_{L3}$ form a third antigen binding site that specifically binds a human tumor target protein.

22. The binding protein of claim 1, wherein $V_{H1}$ and $V_{L1}$ form a first antigen binding site that specifically binds human CD28, wherein $V_{H2}$ and $V_{L2}$ form a second antigen binding site that specifically binds human CD3, and wherein $V_{H3}$ and $V_{L3}$ form a third antigen binding site that specifically binds a human tumor target protein.

23. The binding protein of claim 22, wherein the third antigen binding site specifically binds a human tumor target protein selected from the group consisting of CD19, CD20, CD38, Her2, and LAMP1.

24. The binding protein of claim 22, wherein the antigen binding site that specifically binds CD3 comprises:

(a) a heavy chain variable domain comprising the amino acid sequence of SEQ ID NO: 152 and a light chain variable domain comprising the amino acid sequence of SEQ ID NO: 153; or (b) a heavy chain variable domain comprising the amino acid sequence of SEQ ID NO: 154 and a light chain variable domain comprising the amino acid sequence of SEQ ID NO: 155.

25. The binding protein of claim 22, wherein the antigen binding site that specifically binds CD28 comprises:

(a) a heavy chain variable domain comprising the amino acid sequence of SEQ ID NO: 160 and a light chain variable domain comprising the amino acid sequence of SEQ ID NO: 161; or (b) a heavy chain variable domain comprising the amino acid sequence of SEQ ID NO: 162 and a light chain variable domain comprising the amino acid sequence of SEQ ID NO: 163.

26. The binding protein of claim 22, wherein the antigen binding site that specifically binds a tumor target protein comprises:

(a) a heavy chain variable domain comprising the amino acid sequence of SEQ ID NO: 156 and a light chain variable domain comprising the amino acid sequence of SEQ ID NO: 157;

(b) a heavy chain variable domain comprising the amino acid sequence of SEQ ID NO: 158 and a light chain variable domain comprising the amino acid sequence of SEQ ID NO: 159;

(c) a heavy chain variable domain comprising the amino acid sequence of SEQ ID NO: 164 and a light chain variable domain comprising the amino acid sequence of SEQ ID NO: 165;

(d) a heavy chain variable domain comprising the amino acid sequence of SEQ ID NO: 150 and a light chain variable domain comprising the amino acid sequence of SEQ ID NO: 151; or (e) a heavy chain variable domain comprising the amino acid sequence of SEQ ID NO: 166 and a light chain variable domain comprising the amino acid sequence of SEQ ID NO: 167.

27. The binding protein of claim 1, wherein:

(a) $V_{H1}$ and $V_{L1}$ form a first antigen binding site that specifically binds human TNFα, $V_{H2}$ and $V_{L2}$ form a second antigen binding site that specifically binds human IL13, and $V_{H3}$ and $V_{L3}$ form a third antigen binding site that specifically binds human IL4;

(b) $V_{H1}$ and $V_{L1}$ form a first antigen binding site that specifically binds human TNFα, $V_{H2}$ and $V_{L2}$ form a second antigen binding site that specifically binds human IL4, and $V_{H3}$ and $V_{L3}$ form a third antigen binding site that specifically binds human IL13;

(c) $V_{H1}$ and $V_{L1}$ form a first antigen binding site that specifically binds human IL4, $V_{H2}$ and $V_{L2}$ form a second antigen binding site that specifically binds human TNFα, and $V_{H3}$ and $V_{L3}$ form a third antigen binding site that specifically binds human IL13;

(d) $V_{H1}$ and $V_{L1}$ form a first antigen binding site that specifically binds human IL4, $V_{H2}$ and $V_{L2}$ form a second antigen binding site that specifically binds human IL13, and $V_{H3}$ and $V_{L3}$ form a third antigen binding site that specifically binds human TNFα;

(e) $V_{H1}$ and $V_{L1}$ form a first antigen binding site that specifically binds human IL13, $V_{H2}$ and $V_{L2}$ form a second antigen binding site that specifically binds human IL4, and $V_{H3}$ and $V_{L3}$ form a third antigen binding site that specifically binds human TNFα; or (f) $V_{H1}$ and $V_{L1}$ form a first antigen binding site that specifically binds human IL13, $V_{H2}$ and $V_{L2}$ form a second antigen binding site that specifically binds human TNFα, and $V_{H3}$ and $V_{L3}$ form a third antigen binding site that specifically binds human IL4.

28. The binding protein of claim 27, wherein the antigen binding site that specifically binds human TNFα comprises a heavy chain variable domain comprising the amino acid sequence of SEQ ID NO:168 and a light chain variable domain comprising the amino acid sequence of SEQ ID NO:169.

29. The binding protein of claim 27, wherein the antigen binding site that specifically binds human IL4 comprises a heavy chain variable domain comprising the amino acid sequence of SEQ ID NO:170 and a light chain variable domain comprising the amino acid sequence of SEQ ID NO:171.

30. The binding protein of claim 27, wherein the antigen binding site that specifically binds human IL13 comprises a heavy chain variable domain comprising the amino acid sequence of SEQ ID NO:172 and a light chain variable domain comprising the amino acid sequence of SEQ ID NO:173.

31. The binding protein of claim 1, wherein:

(a) the $C_L$ domain of the first polypeptide chain is a human kappa $C_L$ domain, and the $C_L$ domain of the fourth polypeptide chain is a human lambda $C_L$ domain; or (b) the $C_L$ domain of the first polypeptide chain is a human lambda $C_L$ domain, and the $C_L$ domain of the fourth polypeptide chain is a human kappa $C_L$ domain.

32. The binding protein of claim 1, wherein the first polypeptide chain comprises a lambda $C_L$ domain; wherein the $C_{H3}$ domain of the second polypeptide chain comprises amino acid substitutions at positions corresponding to positions 354 and 366 of human IgG1 according to EU Index, wherein the amino acid substitutions are S354C and T366W; wherein the $C_{H3}$ domain of the third polypeptide chain comprises amino acid substitutions at positions corresponding to positions 349, 366, 368, 407, 435, and 436 of human IgG1 according to EU Index, wherein the amino acid substitutions are Y349C, T366S, L368A, Y407V, H435R, and Y436F; and wherein the fourth polypeptide chain comprises a kappa $C_L$ domain.

33. The binding protein of claim 1, wherein:

(a) the first polypeptide chain of the binding protein comprises the amino acid sequence of SEQ ID NO: 4; the second polypeptide chain of the binding protein comprises the amino acid sequence of SEQ ID NO: 3; the third polypeptide chain of the binding protein comprises the amino acid sequence of SEQ ID NO: 1; and the fourth polypeptide chain of the binding protein comprises the amino acid sequence of SEQ ID NO: 2;

(b) the first polypeptide chain of the binding protein comprises the amino acid sequence of SEQ ID NO: 10; the second polypeptide chain of the binding protein comprises the amino acid sequence of SEQ ID NO: 9; the third polypeptide chain of the binding protein comprises the amino acid sequence of SEQ ID NO: 1; and the fourth polypeptide chain of the binding protein comprises the amino acid sequence of SEQ ID NO: 2;

(c) the first polypeptide chain of the binding protein comprises the amino acid sequence of SEQ ID NO: 4; the second polypeptide chain of the binding protein comprises the amino acid sequence of SEQ ID NO: 3; the third polypeptide chain of the binding protein comprises the amino acid sequence of SEQ ID NO: 13; and the fourth polypeptide chain of the binding protein comprises the amino acid sequence of SEQ ID NO: 14;

(d) the first polypeptide chain of the binding protein comprises the amino acid sequence of SEQ ID NO: 10; the second polypeptide chain of the binding protein comprises the amino acid sequence of SEQ ID NO: 9; the third polypeptide chain of the binding protein comprises the amino acid sequence of SEQ ID NO: 13; and the fourth polypeptide chain of the binding protein comprises the amino acid sequence of SEQ ID NO: 14;

(e) the first polypeptide chain of the binding protein comprises the amino acid sequence of SEQ ID NO: 4; the second polypeptide chain of the binding protein comprises the amino acid sequence of SEQ ID NO: 3; the third polypeptide chain of the binding protein comprises the amino acid sequence of SEQ ID NO: 17; and the fourth polypeptide chain of the binding protein comprises the amino acid sequence of SEQ ID NO: 18;

(f) the first polypeptide chain of the binding protein comprises the amino acid sequence of SEQ ID NO: 10; the second polypeptide chain of the binding protein comprises the amino acid sequence of SEQ ID NO: 9; the third polypeptide chain of the binding protein comprises the amino acid sequence of SEQ ID NO: 17; and the fourth polypeptide chain of the binding protein comprises the amino acid sequence of SEQ ID NO: 18;

(g) the first polypeptide chain of the binding protein comprises the amino acid sequence of SEQ ID NO: 4; the second polypeptide chain of the binding protein comprises the amino acid sequence of SEQ ID NO: 3; the third polypeptide chain of the binding protein comprises the amino acid sequence of SEQ ID NO: 21; and the fourth polypeptide chain of the binding protein comprises the amino acid sequence of SEQ ID NO: 22;

(h) the first polypeptide chain of the binding protein comprises the amino acid sequence of SEQ ID NO: 10; the second polypeptide chain of the binding protein comprises the amino acid sequence of SEQ ID NO: 9; the third polypeptide chain of the binding protein comprises the amino acid sequence of SEQ ID NO: 21; and the fourth polypeptide chain of the binding protein comprises the amino acid sequence of SEQ ID NO: 22;

(i) the first polypeptide chain of the binding protein comprises the amino acid sequence of SEQ ID NO: 63; the second polypeptide chain of the binding protein comprises the amino acid sequence of SEQ ID NO: 62; the third polypeptide chain of the binding protein comprises the amino acid sequence of SEQ ID NO: 60; and the fourth polypeptide chain of the binding protein comprises the amino acid sequence of SEQ ID NO: 61;

(j) the first polypeptide chain of the binding protein comprises the amino acid sequence of SEQ ID NO: 69; the second polypeptide chain of the binding protein comprises the amino acid sequence of SEQ ID NO: 68; the third polypeptide chain of the binding protein comprises the amino acid sequence of SEQ ID NO: 60; and the fourth polypeptide chain of the binding protein comprises the amino acid sequence of SEQ ID NO: 61;

(k) the first polypeptide chain of the binding protein comprises the amino acid sequence of SEQ ID NO: 69; the second polypeptide chain of the binding protein comprises the amino acid sequence of SEQ ID NO: 68; the third polypeptide chain of the binding protein comprises the amino acid sequence of SEQ ID NO: 60; and the fourth polypeptide chain of the binding protein comprises the amino acid sequence of SEQ ID NO: 71;

(l) the first polypeptide chain of the binding protein comprises the amino acid sequence of SEQ ID NO: 76; the second polypeptide chain of the binding protein comprises the amino acid sequence of SEQ ID NO: 75; the third polypeptide chain of the binding protein comprises the amino acid sequence of SEQ ID NO: 73; and the fourth polypeptide chain of the binding protein comprises the amino acid sequence of SEQ ID NO: 74;

(m) the first polypeptide chain of the binding protein comprises the amino acid sequence of SEQ ID NO: 82; the second polypeptide chain of the binding protein comprises the amino acid sequence of SEQ ID NO: 81; the third polypeptide chain of the binding protein comprises the amino acid sequence of SEQ ID NO: 73; and the fourth polypeptide chain of the binding protein comprises the amino acid sequence of SEQ ID NO: 74;

(n) the first polypeptide chain of the binding protein comprises the amino acid sequence of SEQ ID NO: 88; the second polypeptide chain of the binding protein comprises the amino acid sequence of SEQ ID NO: 87; the third polypeptide chain of the binding protein comprises the amino acid sequence of SEQ ID NO: 85; and the fourth polypeptide chain of the binding protein comprises the amino acid sequence of SEQ ID NO: 86;

(o) the first polypeptide chain of the binding protein comprises the amino acid sequence of SEQ ID NO: 94; the second polypeptide chain of the binding protein comprises the amino acid sequence of SEQ ID NO: 93; the third polypeptide chain of the binding protein comprises the amino acid sequence of SEQ ID NO: 85; and the fourth polypeptide chain of the binding protein comprises the amino acid sequence of SEQ ID NO: 86;

(p) the first polypeptide chain of the binding protein comprises the amino acid sequence of SEQ ID NO: 69; the second polypeptide chain of the binding protein comprises the amino acid sequence of SEQ ID NO: 68; the third polypeptide chain of the binding protein comprises the amino acid sequence of SEQ ID NO: 73;

and the fourth polypeptide chain of the binding protein comprises the amino acid sequence of SEQ ID NO: 74;

(q) the first polypeptide chain of the binding protein comprises the amino acid sequence of SEQ ID NO: 69; the second polypeptide chain of the binding protein comprises the amino acid sequence of SEQ ID NO: 68; the third polypeptide chain of the binding protein comprises the amino acid sequence of SEQ ID NO: 85; and the fourth polypeptide chain of the binding protein comprises the amino acid sequence of SEQ ID NO: 86;

(r) the first polypeptide chain of the binding protein comprises the amino acid sequence of SEQ ID NO: 63; the second polypeptide chain of the binding protein comprises the amino acid sequence of SEQ ID NO: 62; the third polypeptide chain of the binding protein comprises the amino acid sequence of SEQ ID NO: 73; and the fourth polypeptide chain of the binding protein comprises the amino acid sequence of SEQ ID NO: 74;

(s) the first polypeptide chain of the binding protein comprises the amino acid sequence of SEQ ID NO: 63; the second polypeptide chain of the binding protein comprises the amino acid sequence of SEQ ID NO: 62; the third polypeptide chain of the binding protein comprises the amino acid sequence of SEQ ID NO: 85; and the fourth polypeptide chain of the binding protein comprises the amino acid sequence of SEQ ID NO: 86;

(t) the first polypeptide chain of the binding protein comprises the amino acid sequence of SEQ ID NO: 4; the second polypeptide chain of the binding protein comprises the amino acid sequence of SEQ ID NO: 3; the third polypeptide chain of the binding protein comprises the amino acid sequence of SEQ ID NO: 114; and the fourth polypeptide chain of the binding protein comprises the amino acid sequence of SEQ ID NO: 115; or (u) the first polypeptide chain of the binding protein comprises the amino acid sequence of SEQ ID NO: 10; the second polypeptide chain of the binding protein comprises the amino acid sequence of SEQ ID NO: 9; the third polypeptide chain of the binding protein comprises the amino acid sequence of SEQ ID NO: 114; and the fourth polypeptide chain of the binding protein comprises the amino acid sequence of SEQ ID NO: 115.

34. An isolated nucleic acid molecule comprising a nucleotide sequence encoding the binding protein of claim 1.

35. An expression vector comprising the nucleic acid molecule of claim 34.

36. An isolated host cell comprising the nucleic acid molecule of claim 34.

37. An isolated host cell comprising the expression vector of claim 35.

38. The isolated host cell of claim 37, wherein the host cell is a mammalian cell or an insect cell.

39. A pharmaceutical composition comprising the binding protein of claim 1 and a pharmaceutically acceptable carrier.

40. A method of preventing or treating cancer in a patient comprising administering to the patient a therapeutically effective amount of the pharmaceutical composition of claim 39, wherein the binding protein comprises one antigen binding site that specifically binds a T-cell surface protein and another antigen binding site that specifically binds a tumor target protein.

41. The method of claim 40, wherein the binding protein comprises a first antigen binding site that specifically binds CD3, a second antigen binding site that specifically binds CD28, and a third antigen binding site that specifically binds a tumor target protein selected from the group consisting of CD19, CD20, CD38, Her2, and LAMP1.

42. The method of claim 40, wherein the at least one binding protein is co-administered with a chemotherapeutic agent.

43. A method of preventing or treating an inflammatory disease or disorder in a patient comprising administering to the patient a therapeutically effective amount of the pharmaceutical composition of claim 39, wherein the binding protein comprises three antigen binding sites that each specifically bind a cytokine target protein.

44. The method of claim 43, wherein the cytokine target proteins are selected from the group consisting of IL-4, IL-13 and TNFα.

45. The method of claim 43, wherein the at least one binding protein is co-administered with an anti-inflammatory agent.

46. The method of claim 40, wherein the patient is a human.

47. The method of claim 40, wherein the binding protein is capable of inhibiting the function of one or more target proteins selected from the group consisting of A2AR, APRIL, ATPDase, BAFF, BAFFR, BCMA, BlyS, BTK, BTLA, B7DC, B7H1, B7H4, B7H5, B7H6, B7H7, B7RP1, B7-4, C3, C5, CCL2, CCL3, CCL4, CCL5, CCL7, CCL8, CCL11, CCL15, CCL17, CCL19, CCL20, CCL21, CCL24, CCL25, CCL26, CCR3, CCR4, CD3, CD19, CD20, CD23, CD24, CD27, CD28, CD38, CD39, CD40, CD70, CD80, CD86, CD122, CD137, CD137L, CD152, CD154, CD160, CD272, CD273, CD274, CD275, CD276, CD278, CD279, CDH1, chitinase, CLEC9, CLEC91, CRTH2, CSF-1, CSF-2, CSF-3, CX3CL1, CXCL12, CXCL13, CXCR3, DNGR-1, ectonucleoside triphosphate diphosphohydrolase 1, EGFR, ENTPD1, FCER1A, FCER1, FLAP, FOLH1, Gi24, GITR, GITRL, GM-CSF, Her2, HHLA2, HMGB1, HVEM, ICOSLG, IDO, IFNα, IgE, IGF1R, IL2Rbeta, IL1, IL1A, IL1B, IL1F10, IL2, IL4, IL4Ra, IL5, IL5R, IL6, IL7, IL7Ra, IL8, IL9, IL9R, IL10, rhIL10, IL12, IL13, IL13Ra1, IL13Ra2, IL15, IL17, IL17Rb, IL18, IL22, IL23, IL25, IL27, IL33, IL35, ITGB4, ITK, KIR, LAG3, LAMP1, leptin, LPFS2, MEW class II, NCR3LG1, NKG2D, NTPDase-1, OX40, OX40L, PD-1H, platelet receptor, PROM1, S152, SISP1, SLC, SPG64, ST2, STEAP2, Syk kinase, TACI, TDO, T14, TIGIT, TIM3, TLR, TLR2, TLR4, TLR5, TLR9, TMEF1, TNFα, TNFRSF7, Tp55, TREM1, TSLP, TSLPR, TWEAK, VEGF, VISTA, Vstm3, WUCAM, and XCR1.

* * * * *

SEQUENCE LISTING

<160> NUMBER OF SEQ ID NOS: 179

<210> SEQ ID NO 1
<211> LENGTH: 447
<212> TYPE: PRT
<213> ORGANISM: Artificial Sequence
<220> FEATURE:
<223> OTHER INFORMATION: Synthetic Construct

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Gln Glu Glu Met Thr Lys Asn Gln Val Ser Leu Trp Cys Leu
```

355 360 365

Val Lys Gly Phe Tyr Pro Ser Asp Ile Ala Val Glu Trp Glu Ser Asn
370 375 380

Gly Gln Pro Glu Asn Asn Tyr Lys Thr Thr Pro Pro Val Leu Asp Ser
385 390 395 400

Asp Gly Ser Phe Phe Leu Tyr Ser Lys Leu Thr Val Asp Lys Ser Arg
405 410 415

Trp Gln Glu Gly Asn Val Phe Ser Cys Ser Val Met His Glu Ala Leu
420 425 430

His Asn His Tyr Thr Gln Lys Ser Leu Ser Leu Ser Leu Gly Lys
435 440 445

<210> SEQ ID NO 2
<211> LENGTH: 214
<212> TYPE: PRT
<213> ORGANISM: Artificial Sequence
<220> FEATURE:
<223> OTHER INFORMATION: Synthetic Construct

<400> SEQUENCE: 2

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 3
<211> LENGTH: 571
<212> TYPE: PRT
<213> ORGANISM: Artificial Sequence
<220> FEATURE:
<223> OTHER INFORMATION: Synthetic Construct

<400> SEQUENCE: 3

-continued

```
Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Ser Ile Tyr Pro Gly Asn Val Asn Thr Asn Tyr Ala Gln Lys Phe
    50                  55                  60

Gln Gly Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser His Tyr Gly Leu Asp Trp Asn Phe Asp Val Trp Gly Lys
            100                 105                 110

Gly Thr Thr Val Thr Val Ser Ser Ser Gln Val Gln Leu Val Glu Ser
        115                 120                 125

Gly Gly Gly Val Val Gln Pro Gly Arg Ser Leu Arg Leu Ser Cys Ala
    130                 135                 140

Ala Ser Gly Phe Thr Phe Thr Lys Ala Trp Met His Trp Val Arg Gln
145                 150                 155                 160

Ala Pro Gly Lys Gln Leu Glu Trp Val Ala Gln Ile Lys Asp Lys Ser
                165                 170                 175

Asn Ser Tyr Ala Thr Tyr Tyr Ala Asp Ser Val Lys Gly Arg Phe Thr
            180                 185                 190

Ile Ser Arg Asp Asp Ser Lys Asn Thr Leu Tyr Leu Gln Met Asn Ser
        195                 200                 205

Leu Arg Ala Glu Asp Thr Ala Val Tyr Tyr Cys Arg Gly Val Tyr Tyr
    210                 215                 220

Ala Leu Ser Pro Phe Asp Tyr Trp Gly Gln Gly Thr Leu Val Thr Val
225                 230                 235                 240

Ser Ser Arg Thr Ala Ser Thr Lys Gly Pro Ser Val Phe Pro Leu Ala
                245                 250                 255

Pro Cys Ser Arg Ser Thr Ser Glu Ser Thr Ala Ala Leu Gly Cys Leu
            260                 265                 270

Val Lys Asp Tyr Phe Pro Glu Pro Val Thr Val Ser Trp Asn Ser Gly
        275                 280                 285

Ala Leu Thr Ser Gly Val His Thr Phe Pro Ala Val Leu Gln Ser Ser
    290                 295                 300

Gly Leu Tyr Ser Leu Ser Ser Val Val Thr Val Pro Ser Ser Ser Leu
305                 310                 315                 320

Gly Thr Lys Thr Tyr Thr Cys Asn Val Asp His Lys Pro Ser Asn Thr
                325                 330                 335

Lys Val Asp Lys Arg Val Glu Ser Lys Tyr Gly Pro Pro Cys Pro Pro
            340                 345                 350

Cys Pro Ala Pro Glu Phe Leu Gly Gly Pro Ser Val Phe Leu Phe Pro
        355                 360                 365

Pro Lys Pro Lys Asp Thr Leu Met Ile Ser Arg Thr Pro Glu Val Thr
    370                 375                 380

Cys Val Val Val Asp Val Ser Gln Glu Asp Pro Glu Val Gln Phe Asn
385                 390                 395                 400

Trp Tyr Val Asp Gly Val Glu Val His Asn Ala Lys Thr Lys Pro Arg
                405                 410                 415

Glu Glu Gln Phe Asn Ser Thr Tyr Arg Val Val Ser Val Leu Thr Val
```

```
            420                 425                 430

Leu His Gln Asp Trp Leu Asn Gly Lys Glu Tyr Lys Cys Lys Val Ser
        435                 440                 445

Asn Lys Gly Leu Pro Ser Ser Ile Glu Lys Thr Ile Ser Lys Ala Lys
    450                 455                 460

Gly Gln Pro Arg Glu Pro Gln Val Cys Thr Leu Pro Pro Ser Gln Glu
465                 470                 475                 480

Glu Met Thr Lys Asn Gln Val Ser Leu Ser Cys Ala Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Val Ser Lys Leu Thr Val Asp Lys Ser Arg Trp Gln Glu Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Leu Gly Lys
                565                 570


<210> SEQ ID NO 4
<211> LENGTH: 338
<212> TYPE: PRT
<213> ORGANISM: Artificial Sequence
<220> FEATURE:
<223> OTHER INFORMATION: Synthetic Construct

<400> SEQUENCE: 4

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Asn
            20                  25                  30

Asn Ala Asn Thr Tyr Leu Ser Trp Tyr Leu Gln Lys Pro Gly Gln Ser
        35                  40                  45

Pro Gln Ser Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Tyr Pro Phe Thr Phe Gly Ser Gly Thr Lys Val Glu Ile Lys
            100                 105                 110

Gly Gln Pro Lys Ala Ala Pro Asp Ile Gln Met Thr Gln Ser Pro Ser
        115                 120                 125

Ser Leu Ser Ala Ser Val Gly Asp Arg Val Thr Ile Thr Cys Gln Ala
    130                 135                 140

Ser Gln Asn Ile Tyr Val Trp Leu Asn Trp Tyr Gln Gln Lys Pro Gly
145                 150                 155                 160

Lys Ala Pro Lys Leu Leu Ile Tyr Lys Ala Ser Asn Leu His Thr Gly
                165                 170                 175

Val Pro Ser Arg Phe Ser Gly Ser Gly Ser Gly Thr Asp Phe Thr Leu
            180                 185                 190

Thr Ile Ser Ser Leu Gln Pro Glu Asp Ile Ala Thr Tyr Tyr Cys Gln
        195                 200                 205

Gln Gly Gln Thr Tyr Pro Tyr Thr Phe Gly Gln Gly Thr Lys Leu Glu
```

```
    210                 215                 220

Ile Lys Thr Lys Gly Pro Ser Arg Thr Val Ala Ala Pro Ser Val Phe
225                 230                 235                 240

Ile Phe Pro Pro Ser Asp Glu Gln Leu Lys Ser Gly Thr Ala Ser Val
                245                 250                 255

Val Cys Leu Leu Asn Asn Phe Tyr Pro Arg Glu Ala Lys Val Gln Trp
            260                 265                 270

Lys Val Asp Asn Ala Leu Gln Ser Gly Asn Ser Gln Glu Ser Val Thr
        275                 280                 285

Glu Gln Asp Ser Lys Asp Ser Thr Tyr Ser Leu Ser Ser Thr Leu Thr
    290                 295                 300

Leu Ser Lys Ala Asp Tyr Glu Lys His Lys Val Tyr Ala Cys Glu Val
305                 310                 315                 320

Thr His Gln Gly Leu Ser Ser Pro Val Thr Lys Ser Phe Asn Arg Gly
                325                 330                 335

Glu Cys


<210> SEQ ID NO 5
<211> LENGTH: 1341
<212> TYPE: DNA
<213> ORGANISM: Artificial Sequence
<220> FEATURE:
<223> OTHER INFORMATION: Synthetic Construct

<400> SEQUENCE: 5

gaagtgcagc tggtggaatc tggcggcgga ctggtgcagc ctggcggatc tctgagactg     60

agctgtgccg ccagcggctt caacatcaag gacacctaca tccactgggt gcgccaggcc    120

cctggcaagg gactggaatg ggtggccaga atctacccca ccaacggcta caccagatac    180

gccgacagcg tgaagggccg gttcaccatc agcgccgaca ccagcaagaa caccgcctac    240

ctgcagatga acagcctgcg ggccgaggac accgccgtgt actactgtag tagatgggga    300

ggcgacggct tctacgccat ggactattgg ggccagggca ccctcgtgac cgtgtctagt    360

gcgtcgacca agggcccatc ggtgttccct ctggcccctt gcagcagaag caccagcgaa    420

tctacagccg ccctgggctg cctcgtgaag gactactttc ccgagcccgt gaccgtgtcc    480

tggaactctg gcgctctgac aagcggcgtg cacacctttc cagccgtgct ccagagcagc    540

ggcctgtact ctctgagcag cgtcgtgaca gtgcccagca gcagcctggg caccaagacc    600

tacacctgta acgtggacca caagcccagc aacaccaagg tggacaagcg ggtggaatct    660

aagtacggcc ctccctgccc tccttgccca gcccctgaat ttctgggcgg accctccgtg    720

ttcctgttcc ccccaaagcc caaggacacc ctgatgatca gccggacccc cgaagtgacc    780

tgcgtggtgg tggatgtgtc ccaggaagat cccgaggtgc agttcaattg gtacgtggac    840

ggcgtggaag tgcacaacgc caagaccaag cccagagagg aacagttcaa cagcacctac    900

cgggtggtgt ccgtgctgac cgtgctgcac caggactggc tgaacggcaa agagtacaag    960

tgcaaggtgt ccaacaaggg cctgcccagc tccatcgaga aaaccatcag caaggccaag   1020

ggccagcccc gcgagcctca agtgtatacc ctgcccccct gccaggaaga gatgaccaag   1080

aaccaggtgt ccctgtggtg tctcgtgaaa ggcttctacc ccagcgacat tgccgtggaa   1140

tgggagagca acggccagcc cgagaacaac tacaagacca cccccccctgt gctggacagc  1200

gacggctcat tcttcctgta ctccaagctg accgtggaca agagccggtg gcaggaaggc   1260

aacgtgttca gctgctccgt gatgcacgag gccctgcaca accactacac ccagaagtcc   1320
```

```
ctgtctctgt ccctgggcaa g                                              1341

<210> SEQ ID NO 6
<211> LENGTH: 642
<212> TYPE: DNA
<213> ORGANISM: Artificial Sequence
<220> FEATURE:
<223> OTHER INFORMATION: Synthetic Construct

<400> SEQUENCE: 6

gacatccaga tgacccagag ccccagcagc ctgtctgcca gcgtgggcga cagagtgacc        60

atcacctgta gagccagcca ggacgtgaac accgccgtgg cctggtatca gcagaagcct       120

ggcaaggccc ccaagctgct gatctacagc gccagcttcc tgtacagcgg cgtgcccagc       180

agattcagcg gaagcagaag cggcaccgac ttcaccctga ccatcagctc cctgcagccc       240

gaggacttcg ccacctacta ctgccagcag cactacacca ccccccccac atttggccag       300

ggcaccaagg tggaaatcaa gcgtacggtg gccgctccca gcgtgttcat cttcccacct       360

agcgacgagc agctgaagtc cggcacagcc tctgtcgtgt gcctgctgaa caacttctac       420

ccccgcgagg ccaaagtgca gtggaaggtg gacaacgccc tgcagagcgg caacagccag       480

gaaagcgtga ccgagcagga cagcaaggac tccacctaca gcctgagcag caccctgaca       540

ctgagcaagg ccgactacga gaagcacaag gtgtacgcct gcgaagtgac ccaccagggc       600

ctgtctagcc ccgtgaccaa gagcttcaac cggggcgagt gt                         642

<210> SEQ ID NO 7
<211> LENGTH: 1713
<212> TYPE: DNA
<213> ORGANISM: Artificial Sequence
<220> FEATURE:
<223> OTHER INFORMATION: Synthetic Construct

<400> SEQUENCE: 7

caggtgcagc tggtgcagtc tggcgccgag gtcgtgaaac ctggcgcctc tgtgaaggtg        60

tcctgcaagg ccagcggcta cacctttacc agctactaca tccactgggt gcgccaggcc       120

cctggacagg gactggaatg gatcggcagc atctaccccg gcaacgtgaa caccaactac       180

gcccagaagt tccagggcag agccaccctg accgtggaca ccagcatcag caccgcctac       240

atggaactga gccggctgag aagcgacgac accgccgtgt actactgcac ccggtcccac       300

tacggcctgg attggaactt cgacgtgtgg ggcaagggca ccaccgtgac agtgtctagc       360

agccaggtgc agctggtgga atctggcggc ggagtggtgc agcctggcag aagcctgaga       420

ctgagctgtg ccgccagcgg cttcaccttc accaaggcct ggatgcactg ggtgcgccag       480

gcccctggaa agcagctgga atgggtggcc cagatcaagg acaagagcaa cagctacgcc       540

acctactacg ccgacagcgt gaagggccgg ttcaccatca gccgggacga cagcaagaac       600

accctgtacc tgcagatgaa cagcctgcgg gccgaggaca ccgccgtgta ctactgtcgg       660

ggcgtgtact atgccctgag ccccttcgat tactggggcc agggaaccct cgtgaccgtg       720

tctagtcgga ccgccagcac aaagggccca tcggtgttcc ctctggcccc ttgcagcaga       780

agcaccagcg aatctacagc cgccctgggc tgcctcgtga aggactactt tcccgagccc       840

gtgaccgtgt cctggaactc tggcgctctg acaagcggcg tgcacacctt ccagccgtg        900

ctccagagca gcggcctgta ctctctgagc agcgtcgtga cagtgcccag cagcagcctg       960

ggcaccaaga cctacacctg taacgtggac cacaagccca gcaacaccaa ggtggacaag      1020

cgggtggaat ctaagtacgg ccctccctgc cctccttgcc cagcccctga atttctgggc      1080
```

```
ggaccctccg tgttcctgtt ccccccaaag cccaaggaca ccctgatgat cagccggacc   1140

cccgaagtga cctgcgtggt ggtggatgtg tcccaggaag atcccgaggt gcagttcaat   1200

tggtacgtgg acggcgtgga agtgcacaac gccaagacca agcccagaga ggaacagttc   1260

aacagcacct accgggtggt gtccgtgctg accgtgctgc accaggactg gctgaacggc   1320

aaagagtaca agtgcaaggt gtccaacaag ggcctgccca gctccatcga gaaaaccatc   1380

agcaaggcca agggccagcc ccgcgagcct caagtgtgta ccctgccccc tagccaggaa   1440

gagatgacca agaaccaggt gtccctgagc tgtgccgtga aaggcttcta ccccagcgac   1500

attgccgtgg aatgggagag caacggccag cccgagaaca actacaagac cacccccccct   1560

gtgctggaca gcgacggctc attcttcctg gtgtccaagc tgaccgtgga caagagccgg   1620

tggcaggaag gcaacgtgtt cagctgctcc gtgatgcacg aggccctgca caaccactac   1680

acccagaagt ccctgtctct gtccctgggc aag                                1713
```

<210> SEQ ID NO 8
<211> LENGTH: 1014
<212> TYPE: DNA
<213> ORGANISM: Artificial Sequence
<220> FEATURE:
<223> OTHER INFORMATION: Synthetic Construct

<400> SEQUENCE: 8

```
gacatcgtga tgacccagac ccccctgagc ctgagcgtga cacctggaca gcctgccagc     60

atcagctgca agagcagcca gagcctggtg cacaacaacg ccaacaccta cctgagctgg    120

tatctgcaga agcccggcca gagcccccag tccctgatct acaaggtgtc caacagattc    180

agcggcgtgc ccgacagatt ctccggcagc ggctctggca ccgacttcac cctgaagatc    240

agccgggtgg aagccgagga cgtgggcgtg tactattgtg gccagggcac ccagtacccc    300

ttcacctttg gcagcggcac caaggtggaa atcaagggcc agcccaaggc cgcccccgac    360

atccagatga cccagagccc cagcagcctg tctgccagcg tgggcgacag agtgaccatc    420

acctgtcagg ccagccagaa catctacgtg tggctgaact ggtatcagca gaagcccggc    480

aaggccccca agctgctgat ctacaaggcc agcaacctgc acaccggcgt gcccagcaga    540

ttttctggca gcggctccgg caccgacttc accctgacaa tcagctccct gcagcccgag    600

gacattgcca cctactactg ccagcagggc cagacctacc cctacacctt tggccagggc    660

accaagctgg aaatcaagac caagggcccc agccgtacgg tggccgctcc cagcgtgttc    720

atcttcccac ctagcgacga gcagctgaag tccggcacag cctctgtcgt gtgcctgctg    780

aacaacttct acccccgcga ggccaaagtg cagtggaagg tggacaacgc cctgcagagc    840

ggcaacagcc aggaaagcgt gaccgagcag gacagcaagg actccaccta cagcctgagc    900

agcaccctga cactgagcaa ggccgactac gagaagcaca aggtgtacgc ctgcgaagtg    960

acccaccagg gcctgtctag ccccgtgacc aagagcttca accggggcga gtgt         1014
```

<210> SEQ ID NO 9
<211> LENGTH: 571
<212> TYPE: PRT
<213> ORGANISM: Artificial Sequence
<220> FEATURE:
<223> OTHER INFORMATION: Synthetic Construct

<400> SEQUENCE: 9

```
Gln Val Gln Leu Gln Glu Ser Gly Pro Gly Leu Val Lys Pro Ser Gln
1               5                   10                  15
```

-continued

```
Thr Leu Ser Leu Thr Cys Thr Val Ser Gly Phe Ser Leu Ser Asp Tyr
            20                  25                  30

Gly Val His Trp Val Arg Gln Pro Pro Gly Lys Gly Leu Glu Trp Leu
        35                  40                  45

Gly Val Ile Trp Ala Gly Gly Gly Thr Asn Tyr Asn Pro Ser Leu Lys
    50                  55                  60

Ser Arg Lys Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Lys Gly Tyr Ser Tyr Tyr Tyr Ser Met Asp Tyr Trp Gly Gln
            100                 105                 110

Gly Thr Thr Val Thr Val Ser Ser Ser Gln Val Gln Leu Val Glu Ser
        115                 120                 125

Gly Gly Gly Val Val Gln Pro Gly Arg Ser Leu Arg Leu Ser Cys Ala
    130                 135                 140

Ala Ser Gly Phe Thr Phe Thr Lys Ala Trp Met His Trp Val Arg Gln
145                 150                 155                 160

Ala Pro Gly Lys Gln Leu Glu Trp Val Ala Gln Ile Lys Asp Lys Ser
                165                 170                 175

Asn Ser Tyr Ala Thr Tyr Tyr Ala Asp Ser Val Lys Gly Arg Phe Thr
            180                 185                 190

Ile Ser Arg Asp Asp Ser Lys Asn Thr Leu Tyr Leu Gln Met Asn Ser
        195                 200                 205

Leu Arg Ala Glu Asp Thr Ala Val Tyr Tyr Cys Arg Gly Val Tyr Tyr
    210                 215                 220

Ala Leu Ser Pro Phe Asp Tyr Trp Gly Gln Gly Thr Leu Val Thr Val
225                 230                 235                 240

Ser Ser Arg Thr Ala Ser Thr Lys Gly Pro Ser Val Phe Pro Leu Ala
                245                 250                 255

Pro Cys Ser Arg Ser Thr Ser Glu Ser Thr Ala Ala Leu Gly Cys Leu
            260                 265                 270

Val Lys Asp Tyr Phe Pro Glu Pro Val Thr Val Ser Trp Asn Ser Gly
        275                 280                 285

Ala Leu Thr Ser Gly Val His Thr Phe Pro Ala Val Leu Gln Ser Ser
    290                 295                 300

Gly Leu Tyr Ser Leu Ser Ser Val Val Thr Val Pro Ser Ser Ser Leu
305                 310                 315                 320

Gly Thr Lys Thr Tyr Thr Cys Asn Val Asp His Lys Pro Ser Asn Thr
                325                 330                 335

Lys Val Asp Lys Arg Val Glu Ser Lys Tyr Gly Pro Pro Cys Pro Pro
            340                 345                 350

Cys Pro Ala Pro Glu Phe Leu Gly Gly Pro Ser Val Phe Leu Phe Pro
        355                 360                 365

Pro Lys Pro Lys Asp Thr Leu Met Ile Ser Arg Thr Pro Glu Val Thr
    370                 375                 380

Cys Val Val Val Asp Val Ser Gln Glu Asp Pro Glu Val Gln Phe Asn
385                 390                 395                 400

Trp Tyr Val Asp Gly Val Glu Val His Asn Ala Lys Thr Lys Pro Arg
                405                 410                 415

Glu Glu Gln Phe Asn Ser Thr Tyr Arg Val Val Ser Val Leu Thr Val
            420                 425                 430
```

```
Leu His Gln Asp Trp Leu Asn Gly Lys Glu Tyr Lys Cys Lys Val Ser
        435                 440                 445

Asn Lys Gly Leu Pro Ser Ser Ile Glu Lys Thr Ile Ser Lys Ala Lys
    450                 455                 460

Gly Gln Pro Arg Glu Pro Gln Val Cys Thr Leu Pro Pro Ser Gln Glu
465                 470                 475                 480

Glu Met Thr Lys Asn Gln Val Ser Leu Ser Cys Ala Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Val Ser Lys Leu Thr Val Asp Lys Ser Arg Trp Gln Glu Gly
    530                 535                 540

Asn Val Phe Ser Cys Ser Val Met His Glu Ala Leu His Asn His Tyr
545                 550                 555                 560

Thr Gln Lys Ser Leu Ser Leu Ser Leu Gly Lys
                565                 570


<210> SEQ ID NO 10
<211> LENGTH: 342
<212> TYPE: PRT
<213> ORGANISM: Artificial Sequence
<220> FEATURE:
<223> OTHER INFORMATION: Synthetic Construct

<400> SEQUENCE: 10

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Asn
            20                  25                  30

Asn Ala Asn Thr Tyr Leu Ser Trp Tyr Leu Gln Lys Pro Gly Gln Ser
        35                  40                  45

Pro Gln Ser Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Tyr Pro Phe Thr Phe Gly Ser Gly Thr Lys Val Glu Ile Lys
            100                 105                 110

Gly Gln Pro Lys Ala Ala Pro Asp Ile Val Leu Thr Gln Ser Pro Ala
        115                 120                 125

Ser Leu Ala Val Ser Pro Gly Gln Arg Ala Thr Ile Thr Cys Arg Ala
    130                 135                 140

Ser Glu Ser Val Glu Tyr Tyr Val Thr Ser Leu Met Gln Trp Tyr Gln
145                 150                 155                 160

Gln Lys Pro Gly Gln Pro Pro Lys Leu Leu Ile Phe Ala Ala Ser Asn
                165                 170                 175

Val Glu Ser Gly Val Pro Ala Arg Phe Ser Gly Ser Gly Ser Gly Thr
            180                 185                 190

Asp Phe Thr Leu Thr Ile Asn Pro Val Glu Ala Asn Asp Val Ala Asn
        195                 200                 205

Tyr Tyr Cys Gln Gln Ser Arg Lys Val Pro Tyr Thr Phe Gly Gln Gly
    210                 215                 220
```

```
Thr Lys Leu Glu Ile Lys Thr Lys Gly Pro Ser Arg Thr Val Ala Ala
225                 230                 235                 240

Pro Ser Val Phe Ile Phe Pro Pro Ser Asp Glu Gln Leu Lys Ser Gly
                245                 250                 255

Thr Ala Ser Val Val Cys Leu Leu Asn Asn Phe Tyr Pro Arg Glu Ala
            260                 265                 270

Lys Val Gln Trp Lys Val Asp Asn Ala Leu Gln Ser Gly Asn Ser Gln
        275                 280                 285

Glu Ser Val Thr Glu Gln Asp Ser Lys Asp Ser Thr Tyr Ser Leu Ser
    290                 295                 300

Ser Thr Leu Thr Leu Ser Lys Ala Asp Tyr Glu Lys His Lys Val Tyr
305                 310                 315                 320

Ala Cys Glu Val Thr His Gln Gly Leu Ser Ser Pro Val Thr Lys Ser
                325                 330                 335

Phe Asn Arg Gly Glu Cys
            340


<210> SEQ ID NO 11
<211> LENGTH: 1713
<212> TYPE: DNA
<213> ORGANISM: Artificial Sequence
<220> FEATURE:
<223> OTHER INFORMATION: Synthetic Construct

<400> SEQUENCE: 11

caggtgcagc tgcaggaatc tggccctggc ctcgtgaagc ctagccagac cctgagcctg      60

acctgtaccg tgtccggctt cagcctgagc gactacggcg tgcactgggt gcgccagcca     120

cctggaaaag gcctggaatg gctgggcgtg atctgggctg gcggaggcac caactacaac     180

cccagcctga agtccagaaa gaccatcagc aaggacacca gcaagaacca ggtgtccctg     240

aagctgagca gcgtgacagc cgccgatacc gccgtgtact actgcgccag agacaagggc     300

tacagctact actacagcat ggactactgg ggccagggca ccaccgtgac cgtgtcatcc     360

tctcaggtgc agctggtgga atctggcggc ggagtggtgc agcctggcag aagcctgaga     420

ctgagctgtg ccgccagcgg cttcaccttc accaaggcct ggatgcactg ggtgcgccag     480

gcccctggaa agcagctgga atgggtggcc cagatcaagg acaagagcaa cagctacgcc     540

acctactacg ccgacagcgt gaagggccgg ttcaccatca gccgggacga cagcaagaac     600

accctgtacc tgcagatgaa cagcctgcgg gccgaggaca ccgccgtgta ctactgtcgg     660

ggcgtgtact atgccctgag ccccttcgat tactggggcc agggaaccct cgtgaccgtg     720

tctagtcgga ccgcttcgac caagggccca tcggtgttcc ctctggcccc ttgcagcaga     780

agcaccagcg aatctacagc cgccctgggc tgcctcgtga aggactactt tcccgagccc     840

gtgaccgtgt cctggaactc tggcgctctg acaagcggcg tgcacacctt tccagccgtg     900

ctccagagca gcggcctgta ctctctgagc agcgtcgtga cagtgcccag cagcagcctg     960

ggcaccaaga cctacacctg taacgtggac cacaagccca gcaacaccaa ggtggacaag    1020

cgggtggaat ctaagtacgg ccctccctgc cctccttgcc cagcccctga atttctgggc    1080

ggaccctccg tgttcctgtt ccccccaaag cccaaggaca ccctgatgat cagccggacc    1140

cccgaagtga cctgcgtggt ggtggatgtg tcccaggaag atcccgaggt gcagttcaat    1200

tggtacgtgg acggcgtgga agtgcacaac gccaagacca agcccagaga ggaacagttc    1260

aacagcacct accgggtggt gtccgtgctg accgtgctgc accaggactg gctgaacggc    1320

aaagagtaca agtgcaaggt gtccaacaag ggcctgccca gctccatcga gaaaaccatc    1380
```

agcaaggcca agggccagcc ccgcgagcct caagtgtgta ccctgccccc tagccaggaa 1440
gagatgacca agaaccaggt gtccctgagc tgtgccgtga aaggcttcta ccccagcgac 1500
attgccgtgg aatgggagag caacggccag cccgagaaca actacaagac cacccccccct 1560 gtgctggaca gcgacggctc attcttcctg gtgtccaagc tgaccgtgga caagagccgg 1620
tggcaggaag gcaacgtgtt cagctgctcc gtgatgcacg aggccctgca caaccactac 1680
acccagaagt ccctgtctct gtccctgggc aag 1713

<210> SEQ ID NO 12
<211> LENGTH: 1026
<212> TYPE: DNA
<213> ORGANISM: Artificial Sequence
<220> FEATURE:
<223> OTHER INFORMATION: Synthetic Construct

<400> SEQUENCE: 12
gacatcgtga tgacccagac ccccctgagc ctgagcgtga cacctggaca gcctgccagc 60
atcagctgca agagcagcca gagcctggtg cacaacaacg ccaacaccta cctgagctgg 120
tatctgcaga agcccggcca gagcccccag tccctgatct acaaggtgtc caacagattc 180
agcggcgtgc ccgacagatt ctccggcagc ggctctggca ccgacttcac cctgaagatc 240
agccgggtgg aagccgagga cgtgggcgtg tactattgtg gccagggcac ccagtacccc 300
ttcacctttg gcagcggcac caaggtggaa atcaagggcc agcccaaggc cgcccccgac 360
atcgtgctga cacagagccc tgctagcctg gccgtgtctc ctggacagag ggccaccatc 420
acctgtagag ccagcgagag cgtggaatat tacgtgacca gcctgatgca gtggtatcag 480
cagaagcccg gccagccccc caagctgctg attttcgccg ccagcaacgt ggaaagcggc 540
gtgccagcca gattttccgg cagcggctct ggcaccgact tcaccctgac catcaacccc 600
gtggaagcca acgacgtggc caactactac tgccagcaga gccggaaggt gccctacacc 660
tttggccagg gcaccaagct ggaaatcaag accaagggcc ccagccgtac ggtggccgct 720
cccagcgtgt tcatcttccc acctagcgac gagcagctga agtccggcac agcctctgtc 780
gtgtgcctgc tgaacaactt ctacccccgc gaggccaaag tgcagtggaa ggtggacaac 840
gccctgcaga gcggcaacag ccaggaaagc gtgaccgagc aggacagcaa ggactccacc 900
tacagcctga gcagcaccct gacactgagc aaggccgact acgagaagca caaggtgtac 960
gcctgcgaag tgacccacca gggcctgtct agccccgtga ccaagagctt caaccggggc 1020
gagtgt 1026

<210> SEQ ID NO 13
<211> LENGTH: 451
<212> TYPE: PRT
<213> ORGANISM: Artificial Sequence
<220> FEATURE:
<223> OTHER INFORMATION: Synthetic Construct

<400> SEQUENCE: 13

Gln Val Gln Leu Val Gln Ser Gly Ala Glu Val Lys Lys Pro Gly Ser
1 5 10 15

Ser Val Lys Val Ser Cys Lys Ala Ser Gly Tyr Ala Phe Ser Ser Tyr
20 25 30

Trp Met Asn Trp Val Arg Gln Ala Pro Gly Gln Gly Leu Glu Trp Ile
35 40 45

Gly Gln Ile Trp Pro Gly Asp Gly Asp Thr Asn Tyr Asn Gln Lys Phe

-continued

```
    50                  55                  60

Lys Gly Arg Ala Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Cys Gln Glu Glu Met Thr Lys Asn Gln Val Ser
        355                 360                 365

Leu Trp Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Lys
    450
```

<210> SEQ ID NO 14

<211> LENGTH: 218
<212> TYPE: PRT
<213> ORGANISM: Artificial Sequence
<220> FEATURE:
<223> OTHER INFORMATION: Synthetic Construct

<400> SEQUENCE: 14

```
Asp Leu Val Leu Thr Gln Ser Pro Ala Ser Leu Ala Val Ser Pro Gly
1               5                   10                  15

Gln Arg Ala Thr Ile Thr Cys Lys Ala Ser Gln Ser Val Asp Tyr Asp
            20                  25                  30

Gly Asp Ser Tyr Leu Asn Trp Tyr Gln Gln Lys Pro Gly Gln Pro Pro
        35                  40                  45

Lys Leu Leu Ile Tyr Asp Ala Ser Asn Leu Val Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Ser Thr
                85                  90                  95

Glu Asp Pro Trp Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 15
<211> LENGTH: 1353
<212> TYPE: DNA
<213> ORGANISM: Artificial Sequence
<220> FEATURE:
<223> OTHER INFORMATION: Synthetic Construct

<400> SEQUENCE: 15

```
caggtgcagc tggtgcagag cggcgccgaa gtgaagaagc ctggcagcag cgtgaaggtg      60

agctgcaagg ccagcggcta tgccttcagc agctactgga tgaactgggt gaggcaggca     120

cctggccagg gcctggagtg gataggccaa atatggcctg gcgatggcga caccaactac     180

aaccagaagt tcaagggcag agcgaccttg accgccgacg agagcaccag caccgcgtac     240

atggagctga gcagcctgag gagcgaggac accgccgtgt actattgcgc cagaagggag     300

accaccaccg tgggcaggta ctactacgcc atggactact ggggccaggg aaccaccgtg     360

accgtgagca gcgcctcgac caagggccca tcggtgttcc ctctggcccc ttgcagcaga     420

agcaccagcg aatctacagc cgccctgggc tgcctcgtga aggactactt tcccgagccc     480

gtgaccgtgt cctggaactc tggcgctctg acaagcggcg tgcacacctt tccagccgtg     540

ctccagagca gcggcctgta ctctctgagc agcgtcgtga cagtgcccag cagcagcctg     600
```

ggcaccaaga cctacacctg taacgtggac cacaagccca gcaacaccaa ggtggacaag 660
cgggtggaat ctaagtacgg ccctccctgc cctccttgcc cagcccctga atttctgggc 720
ggaccctccg tgttcctgtt ccccccaaag cccaaggaca ccctgatgat cagccggacc 780
cccgaagtga cctgcgtggt ggtggatgtg tcccaggaag atcccgaggt gcagttcaat 840
tggtacgtgg acggcgtgga agtgcacaac gccaagacca agcccagaga ggaacagttc 900
aacagcacct accgggtggt gtccgtgctg accgtgctgc accaggactg gctgaacggc 960
aaagagtaca agtgcaaggt gtccaacaag ggcctgccca gctccatcga gaaaaccatc 1020
agcaaggcca agggccagcc ccgcgagcct caagtgtata ccctgccccc ttgccaggaa 1080
gagatgacca agaaccaggt gtccctgtgg tgtctcgtga aaggcttcta ccccagcgac 1140
attgccgtgg aatgggagag caacggccag cccgagaaca actacaagac caccccccct 1200
gtgctggaca gcgacggctc attcttcctg tactccaagc tgaccgtgga caagagccgg 1260
tggcaggaag gcaacgtgtt cagctgctcc gtgatgcacg aggccctgca caaccactac 1320
acccagaagt ccctgtctct gtccctgggc aag 1353

<210> SEQ ID NO 16
<211> LENGTH: 654
<212> TYPE: DNA
<213> ORGANISM: Artificial Sequence
<220> FEATURE:
<223> OTHER INFORMATION: Synthetic Construct

<400> SEQUENCE: 16
gacctcgtgc tgacccagag ccctgcgagc ctggctgtga gccctggcca gagagccacc 60
atcacctgca aagccagcca gagcgtggac tacgacggcg acagctacct caactggtac 120
cagcagaagc ctggccagcc ccccaagctg ctgatttacg atgccagcaa cctggtgagc 180
ggcgtgcctg ctagattcag cggctccggc agcggcaccg acttcaccct gaccatcaac 240
cccgtggagg ccaacgacac cgccaactac tactgccagc agagcacgga ggacccctgg 300
accttcggcc agggcacaaa gctggagatc aagcgtacgg tggccgctcc cagcgtgttc 360
atcttcccac ctagcgacga gcagctgaag tccggcacag cctctgtcgt gtgcctgctg 420
aacaacttct acccccgcga ggccaaagtg cagtggaagg tggacaacgc cctgcagagc 480
ggcaacagcc aggaaagcgt gaccgagcag gacagcaagg actccaccta cagcctgagc 540
agcaccctga cactgagcaa ggccgactac gagaagcaca aggtgtacgc ctgcgaagtg 600
acccaccagg gcctgtctag ccccgtgacc aagagcttca accggggcga gtgt 654

<210> SEQ ID NO 17
<211> LENGTH: 447
<212> TYPE: PRT
<213> ORGANISM: Artificial Sequence
<220> FEATURE:
<223> OTHER INFORMATION: Synthetic Construct

<400> SEQUENCE: 17

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Gly Tyr Ala Gln Lys Phe

```
    50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Cys Gln Glu Glu Met Thr Lys Asn Gln Val Ser Leu Trp Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 18
<211> LENGTH: 214
<212> TYPE: PRT
<213> ORGANISM: Artificial Sequence
```

<220> FEATURE:
<223> OTHER INFORMATION: Synthetic Construct

<400> SEQUENCE: 18

Asp Ile Val Met Thr Gln Ser His Leu Ser Met Ser Thr Ser Leu Gly
1 5 10 15

Asp Pro Val Ser Ile Thr Cys Lys Ala Ser Gln Asp Val Ser Thr Val
20 25 30

Val Ala Trp Tyr Gln Gln Lys Pro Gly Gln Ser Pro Arg Arg Leu Ile
35 40 45

Tyr Ser Ala Ser Tyr Arg Tyr Ile Gly Val Pro Asp Arg Phe Thr Gly
50 55 60

Ser Gly Ala Gly Thr Asp Phe Thr Phe Thr Ile Ser Ser Val Gln Ala
65 70 75 80

Glu Asp Leu Ala Val Tyr Tyr Cys Gln Gln His Tyr Ser Pro Pro Tyr
85 90 95

Thr Phe Gly Gly Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 19
<211> LENGTH: 1341
<212> TYPE: DNA
<213> ORGANISM: Artificial Sequence
<220> FEATURE:
<223> OTHER INFORMATION: Synthetic Construct

<400> SEQUENCE: 19
caggtgcagc tggtgcagtc tggcgccgaa gtggccaagc ctggcacaag cgtgaagctg 60
agctgcaagg ccagcggcta caccttcacc gactactgga tgcagtgggt caagcagagg 120
ccaggccagg gcctggaatg gatcggcaca atctatcccg gcgacggcga taccggctac 180
gcccagaagt ttcagggcaa ggccaccctg accgccgaca agagcagcaa gaccgtgtac 240
atgcacctga gcagcctggc cagcgaggac agcgccgtgt actattgcgc cagaggcgac 300
tactacggca gcaacagcct ggactattgg ggccagggca ccagcgtgac agtgtctagt 360
gcgtcgacca agggcccatc ggtgttccct ctggcccctt gcagcagaag caccagcgaa 420
tctacagccg ccctgggctg cctcgtgaag gactactttc ccgagcccgt gaccgtgtcc 480
tggaactctg gcgctctgac aagcggcgtg cacacctttc cagccgtgct ccagagcagc 540
ggcctgtact ctctgagcag cgtcgtgaca gtgcccagca gcagcctggg caccaagacc 600
tacacctgta acgtggacca caagcccagc aacaccaagg tggacaagcg ggtggaatct 660
aagtacggcc ctccctgccc tccttgccca gcccctgaat ttctgggcgg accctccgtg 720
ttcctgttcc ccccaaagcc caaggacacc ctgatgatca gccggacccc cgaagtgacc 780
tgcgtggtgg tggatgtgtc ccaggaagat cccgaggtgc agttcaattg gtacgtggac 840
ggcgtggaag tgcacaacgc caagaccaag cccagagagg aacagttcaa cagcacctac 900
cgggtggtgt ccgtgctgac cgtgctgcac caggactggc tgaacggcaa agagtacaag 960
tgcaaggtgt ccaacaaggg cctgcccagc tccatcgaga aaaccatcag caaggccaag 1020
ggccagcccc gcgagcctca agtgtatacc ctgcccccct gccaggaaga gatgaccaag 1080
aaccaggtgt ccctgtggtg tctcgtgaaa ggcttctacc ccagcgacat tgccgtggaa 1140
tgggagagca acggccagcc cgagaacaac tacaagacca ccccccctgt gctggacagc 1200
gacggctcat tcttcctgta ctccaagctg accgtggaca agagccggtg gcaggaaggc 1260
aacgtgttca gctgctccgt gatgcacgag gccctgcaca accactacac ccagaagtcc 1320
ctgtctctgt ccctgggcaa g 1341

<210> SEQ ID NO 20
<211> LENGTH: 642
<212> TYPE: DNA
<213> ORGANISM: Artificial Sequence
<220> FEATURE:
<223> OTHER INFORMATION: Synthetic Construct

<400> SEQUENCE: 20
gacatcgtga tgacccagag ccacctgagc atgagcacca gcctgggcga ccccgtgtcc 60
atcacctgta aagccagcca ggacgtgtcc accgtggtgg cctggtatca gcagaagcct 120
ggccagagcc ccagacggct gatctacagc gccagctatc ggtacatcgg cgtgcccgac 180
agattcaccg gaagcggagc cggcaccgac ttcaccttca ccatcagctc tgtgcaggcc 240
gaggacctgg ccgtgtacta ctgccagcag cactacagcc ccccctacac ctttggcgga 300
ggcaccaagc tggaaatcaa gcgtacggtg gccgctccca gcgtgttcat cttcccacct 360
agcgacgagc agctgaagtc cggcacagcc tctgtcgtgt gcctgctgaa caacttctac 420
ccccgcgagg ccaaagtgca gtggaaggtg gacaacgccc tgcagagcgg caacagccag 480
gaaagcgtga ccgagcagga cagcaaggac tccacctaca gcctgagcag caccctgaca 540
ctgagcaagg ccgactacga gaagcacaag gtgtacgcct gcgaagtgac ccaccagggc 600
ctgtctagcc ccgtgaccaa gagcttcaac cggggcgagt gt 642

<210> SEQ ID NO 21
<211> LENGTH: 445
<212> TYPE: PRT
<213> ORGANISM: Artificial Sequence
<220> FEATURE:
<223> OTHER INFORMATION: Synthetic Construct

<400> SEQUENCE: 21

Gln Val Gln Leu Val Gln Ser Gly Ala Glu Val Lys Lys Pro Gly Ser
1 5 10 15

Ser Val Lys Val Ser Cys Lys Ala Ser Gly Tyr Ile Phe Thr Asn Tyr
20 25 30

Asn Ile His Trp Val Lys Lys Ser Pro Gly Gln Gly Leu Glu Trp Ile
35 40 45

Gly Ala Ile Tyr Pro Gly Asn Gly Asp Ala Pro Tyr Ser Gln Lys Phe
50 55 60

Gln Gly Lys Ala Thr Leu Thr Ala Asp Thr Ser Thr Ser Thr Thr Tyr 65 70 75 80

Met Glu Leu Ser Ser Leu Arg Ser Glu Asp Thr Ala Val Tyr Tyr Cys
85 90 95

Val Arg Ala Asn Trp Asp Val Ala Phe Ala Tyr Trp Gly Gln Gly Thr
100 105 110

Leu Val Thr Val Ser Ser Ala Ser Thr Lys Gly Pro Ser Val Phe Pro
115 120 125

Leu Ala Pro Cys Ser Arg Ser Thr Ser Glu Ser Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Lys Thr Tyr Thr Cys Asn Val Asp His Lys Pro Ser
195 200 205

Asn Thr Lys Val Asp Lys Arg Val Glu Ser Lys Tyr Gly Pro Pro Cys
210 215 220

Pro Pro Cys Pro Ala Pro Glu Phe Leu Gly Gly Pro Ser Val Phe Leu
225 230 235 240

Phe Pro Pro Lys Pro Lys Asp Thr Leu Met Ile Ser Arg Thr Pro Glu
245 250 255

Val Thr Cys Val Val Val Asp Val Ser Gln Glu Asp Pro Glu Val Gln
260 265 270

Phe Asn Trp Tyr Val Asp Gly Val Glu Val His Asn Ala Lys Thr Lys
275 280 285

Pro Arg Glu Glu Gln Phe Asn Ser Thr Tyr Arg Val Val Ser Val Leu
290 295 300

Thr Val Leu His Gln Asp Trp Leu Asn Gly Lys Glu Tyr Lys Cys Lys
305 310 315 320

Val Ser Asn Lys Gly Leu Pro Ser Ser Ile Glu Lys Thr Ile Ser Lys
325 330 335

Ala Lys Gly Gln Pro Arg Glu Pro Gln Val Tyr Thr Leu Pro Pro Cys
340 345 350

Gln Glu Glu Met Thr Lys Asn Gln Val Ser Leu Trp Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Lys Leu Thr Val Asp Lys Ser Arg Trp Gln
405 410 415

Glu Gly Asn Val Phe Ser Cys Ser Val Met His Glu Ala Leu His Asn
420 425 430

His Tyr Thr Gln Lys Ser Leu Ser Leu Ser Leu Gly Lys
435 440 445

<210> SEQ ID NO 22
<211> LENGTH: 213
<212> TYPE: PRT
<213> ORGANISM: Artificial Sequence
<220> FEATURE:
<223> OTHER INFORMATION: Synthetic Construct

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asp Arg Tyr
            20                  25                  30

Met Ala Trp Tyr Gln Asp Lys Pro Gly Lys Ala Pro Arg Leu Leu Ile
        35                  40                  45

His Asp Thr Ser Thr Leu Gln Ser Gly Val Pro Ser Arg Phe Ser Gly
    50                  55                  60

Ser Gly Ser Gly Arg Asp Tyr Thr Leu Thr Ile Ser Asn Leu Glu Pro
65                  70                  75                  80

Glu Asp Phe Ala Thr Tyr Tyr Cys Leu Gln Tyr Asp Asn Leu Trp Thr
                85                  90                  95

Phe Gly Gly Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 23
<211> LENGTH: 1335
<212> TYPE: DNA
<213> ORGANISM: Artificial Sequence
<220> FEATURE:
<223> OTHER INFORMATION: Synthetic Construct

<400> SEQUENCE: 23
caggtgcagc tggtgcagtc tggcgccgaa gtgaagaaac ccggcagcag cgtgaaggtg 60
tcctgcaagg ccagcggcta catcttcacc aactacaaca tccactgggt caagaagtcc 120
ccaggccagg gcctggaatg gatcggcgcc atctatcccg gaaacggcga cgccccttac 180
agccagaagt tccagggcaa ggccaccctg accgccgata ccagcacctc caccacctac 240
atggaactga gcagcctgcg gagcgaggac accgccgtgt actattgcgt gcgggccaac 300
tgggatgtgg ccttcgccta ttggggccag ggcacactcg tgaccgtgtc ctctgcgtcg 360
accaagggcc catcggtgtt ccctctggcc ccttgcagca gaagcaccag cgaatctaca 420
gccgccctgg gctgcctcgt gaaggactac tttcccgagc ccgtgaccgt gtcctggaac 480
tctggcgctc tgacaagcgg cgtgcacacc tttccagccg tgctccagag cagcggcctg 540
tactctctga gcagcgtcgt gacagtgccc agcagcagcc tgggcaccaa gacctacacc 600
tgtaacgtgg accacaagcc cagcaacacc aaggtggaca agcgggtgga atctaagtac 660
ggccctccct gccctccttg cccagcccct gaatttctgg gcggaccctc cgtgttcctg 720
ttccccccaa agcccaagga caccctgatg atcagccgga cccccgaagt gacctgcgtg 780

```
gtggtggatg tgtcccagga agatcccgag gtgcagttca attggtacgt ggacggcgtg    840

gaagtgcaca acgccaagac caagcccaga gaggaacagt tcaacagcac ctaccgggtg    900

gtgtccgtgc tgaccgtgct gcaccaggac tggctgaacg gcaaagagta caagtgcaag    960

gtgtccaaca agggcctgcc cagctccatc gagaaaacca tcagcaaggc caagggccag   1020

ccccgcgagc ctcaagtgta taccctgccc ccttgccagg aagagatgac caagaaccag   1080

gtgtccctgt ggtgtctcgt gaaaggcttc taccccagcg acattgccgt ggaatgggag   1140

agcaacggcc agcccgagaa caactacaag accacccccc ctgtgctgga cagcgacggc   1200

tcattcttcc tgtactccaa gctgaccgtg gacaagagcc ggtggcagga aggcaacgtg   1260

ttcagctgct ccgtgatgca cgaggccctg cacaaccact acacccagaa gtccctgtct   1320

ctgtccctgg gcaag                                                    1335
```

<210> SEQ ID NO 24
<211> LENGTH: 639
<212> TYPE: DNA
<213> ORGANISM: Artificial Sequence
<220> FEATURE:
<223> OTHER INFORMATION: Synthetic Construct

<400> SEQUENCE: 24

```
gacatccaga tgacccagag ccccagcagc ctgtctgcca gcgtgggcga cagagtgacc     60

atcacatgca aggccagcca ggacatcgat cggtacatgg cctggtatca ggacaagccc    120

ggcaaggccc ccagactgct gatccacgat accagcacac tgcagagcgg cgtgcccagc    180

agattttccg gctctggcag cggcagagac tacaccctga ccatcagcaa cctggaaccc    240

gaggacttcg ccacctacta ctgcctgcag tacgacaacc tgtggacctt cggcggaggc    300

accaaggtgg aaatcaagcg tacggtggcc gctcccagcg tgttcatctt cccacctagc    360

gacgagcagc tgaagtccgg cacagcctct gtcgtgtgcc tgctgaacaa cttctacccc    420

cgcgaggcca aagtgcagtg gaaggtggac aacgccctgc agagcggcaa cagccaggaa    480

agcgtgaccg agcaggacag caaggactcc acctacagcc tgagcagcac cctgacactg    540

agcaaggccg actacgagaa gcacaaggtg tacgcctgcg aagtgaccca ccagggcctg    600

tctagccccg tgaccaagag cttcaaccgg ggcgagtgt                           639
```

<210> SEQ ID NO 25
<211> LENGTH: 8
<212> TYPE: PRT
<213> ORGANISM: Artificial Sequence
<220> FEATURE:
<223> OTHER INFORMATION: Synthetic Construct

<400> SEQUENCE: 25

```
Gly Phe Asn Ile Lys Asp Thr Tyr
1               5
```

<210> SEQ ID NO 26
<211> LENGTH: 8
<212> TYPE: PRT
<213> ORGANISM: Artificial Sequence
<220> FEATURE:
<223> OTHER INFORMATION: Synthetic Construct

<400> SEQUENCE: 26

```
Ile Tyr Pro Thr Asn Gly Tyr Thr
1               5
```

<210> SEQ ID NO 27
<211> LENGTH: 13
<212> TYPE: PRT
<213> ORGANISM: Artificial Sequence
<220> FEATURE:
<223> OTHER INFORMATION: Synthetic Construct

<400> SEQUENCE: 27

Ser Arg Trp Gly Gly Asp Gly Phe Tyr Ala Met Asp Tyr
1 5 10

<210> SEQ ID NO 28
<211> LENGTH: 8
<212> TYPE: PRT
<213> ORGANISM: Artificial Sequence
<220> FEATURE:
<223> OTHER INFORMATION: Synthetic Construct

<400> SEQUENCE: 28

Gly Tyr Thr Phe Thr Ser Tyr Tyr
1 5

<210> SEQ ID NO 29
<211> LENGTH: 8
<212> TYPE: PRT
<213> ORGANISM: Artificial Sequence
<220> FEATURE:
<223> OTHER INFORMATION: Synthetic Construct

<400> SEQUENCE: 29

Ile Tyr Pro Gly Asn Val Asn Thr
1 5

<210> SEQ ID NO 30
<211> LENGTH: 13
<212> TYPE: PRT
<213> ORGANISM: Artificial Sequence
<220> FEATURE:
<223> OTHER INFORMATION: Synthetic Construct

<400> SEQUENCE: 30

Thr Arg Ser His Tyr Gly Leu Asp Trp Asn Phe Asp Val
1 5 10

<210> SEQ ID NO 31
<211> LENGTH: 8
<212> TYPE: PRT
<213> ORGANISM: Artificial Sequence
<220> FEATURE:
<223> OTHER INFORMATION: Synthetic Construct

<400> SEQUENCE: 31

Gly Phe Ser Leu Ser Asp Tyr Gly
1 5

<210> SEQ ID NO 32
<211> LENGTH: 7
<212> TYPE: PRT
<213> ORGANISM: Artificial Sequence
<220> FEATURE:
<223> OTHER INFORMATION: Synthetic Construct

<400> SEQUENCE: 32

Ile Trp Ala Gly Gly Gly Thr
1 5

-continued

<210> SEQ ID NO 33
<211> LENGTH: 13
<212> TYPE: PRT
<213> ORGANISM: Artificial Sequence
<220> FEATURE:
<223> OTHER INFORMATION: Synthetic Construct

<400> SEQUENCE: 33

Ala Arg Asp Lys Gly Tyr Ser Tyr Tyr Tyr Ser Met Asp
1 5 10

<210> SEQ ID NO 34
<211> LENGTH: 8
<212> TYPE: PRT
<213> ORGANISM: Artificial Sequence
<220> FEATURE:
<223> OTHER INFORMATION: Synthetic Construct

<400> SEQUENCE: 34

Gly Phe Thr Phe Thr Lys Ala Trp
1 5

<210> SEQ ID NO 35
<211> LENGTH: 7
<212> TYPE: PRT
<213> ORGANISM: Artificial Sequence
<220> FEATURE:
<223> OTHER INFORMATION: Synthetic Construct

<400> SEQUENCE: 35

Ile Lys Asp Lys Ser Asn Ser
1 5

<210> SEQ ID NO 36
<211> LENGTH: 12
<212> TYPE: PRT
<213> ORGANISM: Artificial Sequence
<220> FEATURE:
<223> OTHER INFORMATION: Synthetic Construct

<400> SEQUENCE: 36

Arg Gly Val Tyr Tyr Ala Leu Ser Pro Phe Asp Tyr
1 5 10

<210> SEQ ID NO 37
<211> LENGTH: 8
<212> TYPE: PRT
<213> ORGANISM: Artificial Sequence
<220> FEATURE:
<223> OTHER INFORMATION: Synthetic Construct

<400> SEQUENCE: 37

Gly Tyr Ala Phe Ser Ser Tyr Trp
1 5

<210> SEQ ID NO 38
<211> LENGTH: 8
<212> TYPE: PRT
<213> ORGANISM: Artificial Sequence
<220> FEATURE:
<223> OTHER INFORMATION: Synthetic Construct

<400> SEQUENCE: 38

Ile Trp Pro Gly Asp Gly Asp Thr
1 5

<210> SEQ ID NO 39

-continued

<211> LENGTH: 16
<212> TYPE: PRT
<213> ORGANISM: Artificial Sequence
<220> FEATURE:
<223> OTHER INFORMATION: Synthetic Construct

<400> SEQUENCE: 39

Ala Arg Arg Glu Thr Thr Thr Val Gly Arg Tyr Tyr Tyr Ala Met Asp
1 5 10 15

<210> SEQ ID NO 40
<211> LENGTH: 8
<212> TYPE: PRT
<213> ORGANISM: Artificial Sequence
<220> FEATURE:
<223> OTHER INFORMATION: Synthetic Construct

<400> SEQUENCE: 40

Gly Tyr Thr Phe Thr Asp Tyr Trp
1 5

<210> SEQ ID NO 41
<211> LENGTH: 8
<212> TYPE: PRT
<213> ORGANISM: Artificial Sequence
<220> FEATURE:
<223> OTHER INFORMATION: Synthetic Construct

<400> SEQUENCE: 41

Ile Tyr Pro Gly Asp Gly Asp Thr
1 5

<210> SEQ ID NO 42
<211> LENGTH: 13
<212> TYPE: PRT
<213> ORGANISM: Artificial Sequence
<220> FEATURE:
<223> OTHER INFORMATION: Synthetic Construct

<400> SEQUENCE: 42

Ala Arg Gly Asp Tyr Tyr Gly Ser Asn Ser Leu Asp Tyr
1 5 10

<210> SEQ ID NO 43
<211> LENGTH: 6
<212> TYPE: PRT
<213> ORGANISM: Artificial Sequence
<220> FEATURE:
<223> OTHER INFORMATION: Synthetic Construct

<400> SEQUENCE: 43

Gln Asp Val Asn Thr Ala
1 5

<210> SEQ ID NO 44
<211> LENGTH: 3
<212> TYPE: PRT
<213> ORGANISM: Artificial Sequence
<220> FEATURE:
<223> OTHER INFORMATION: Synthetic Construct

<400> SEQUENCE: 44

Ser Ala Ser
1

<210> SEQ ID NO 45
<211> LENGTH: 9

<212> TYPE: PRT
<213> ORGANISM: Artificial Sequence
<220> FEATURE:
<223> OTHER INFORMATION: Synthetic Construct

<400> SEQUENCE: 45

Gln Gln His Tyr Thr Thr Pro Pro Thr
1               5

<210> SEQ ID NO 46
<211> LENGTH: 6
<212> TYPE: PRT
<213> ORGANISM: Artificial Sequence
<220> FEATURE:
<223> OTHER INFORMATION: Synthetic Construct

<400> SEQUENCE: 46

Gln Asn Ile Tyr Val Trp
1               5

<210> SEQ ID NO 47
<211> LENGTH: 3
<212> TYPE: PRT
<213> ORGANISM: Artificial Sequence
<220> FEATURE:
<223> OTHER INFORMATION: Synthetic Construct

<400> SEQUENCE: 47

Lys Ala Ser
1

<210> SEQ ID NO 48
<211> LENGTH: 9
<212> TYPE: PRT
<213> ORGANISM: Artificial Sequence
<220> FEATURE:
<223> OTHER INFORMATION: Synthetic Construct

<400> SEQUENCE: 48

Gln Gln Gly Gln Thr Tyr Pro Tyr Thr
1               5

<210> SEQ ID NO 49
<211> LENGTH: 10
<212> TYPE: PRT
<213> ORGANISM: Artificial Sequence
<220> FEATURE:
<223> OTHER INFORMATION: Synthetic Construct

<400> SEQUENCE: 49

Glu Ser Val Glu Tyr Tyr Val Thr Ser Leu
1               5                   10

<210> SEQ ID NO 50
<211> LENGTH: 3
<212> TYPE: PRT
<213> ORGANISM: Artificial Sequence
<220> FEATURE:
<223> OTHER INFORMATION: Synthetic Construct

<400> SEQUENCE: 50

Ala Ala Ser
1

<210> SEQ ID NO 51
<211> LENGTH: 9
<212> TYPE: PRT

<213> ORGANISM: Artificial Sequence
<220> FEATURE:
<223> OTHER INFORMATION: Synthetic Construct

<400> SEQUENCE: 51

Gln Gln Ser Arg Lys Val Pro Tyr Thr
1               5

<210> SEQ ID NO 52
<211> LENGTH: 11
<212> TYPE: PRT
<213> ORGANISM: Artificial Sequence
<220> FEATURE:
<223> OTHER INFORMATION: Synthetic Construct

<400> SEQUENCE: 52

Gln Ser Leu Val His Asn Asn Ala Asn Thr Tyr
1               5                   10

<210> SEQ ID NO 53
<211> LENGTH: 3
<212> TYPE: PRT
<213> ORGANISM: Artificial Sequence
<220> FEATURE:
<223> OTHER INFORMATION: Synthetic Construct

<400> SEQUENCE: 53

Lys Val Ser
1

<210> SEQ ID NO 54
<211> LENGTH: 7
<212> TYPE: PRT
<213> ORGANISM: Artificial Sequence
<220> FEATURE:
<223> OTHER INFORMATION: Synthetic Construct

<400> SEQUENCE: 54

Gly Gln Gly Thr Gln Tyr Pro
1               5

<210> SEQ ID NO 55
<211> LENGTH: 10
<212> TYPE: PRT
<213> ORGANISM: Artificial Sequence
<220> FEATURE:
<223> OTHER INFORMATION: Synthetic Construct

<400> SEQUENCE: 55

Gln Ser Val Asp Tyr Asp Gly Asp Ser Tyr
1               5                   10

<210> SEQ ID NO 56
<211> LENGTH: 3
<212> TYPE: PRT
<213> ORGANISM: Artificial Sequence
<220> FEATURE:
<223> OTHER INFORMATION: Synthetic Construct

<400> SEQUENCE: 56

Asp Ala Ser
1

<210> SEQ ID NO 57
<211> LENGTH: 9
<212> TYPE: PRT
<213> ORGANISM: Artificial Sequence
<220> FEATURE:
<223> OTHER INFORMATION: Synthetic Construct

<400> SEQUENCE: 57

Gln Gln Ser Thr Glu Asp Pro Trp Thr
1 5

<210> SEQ ID NO 58
<211> LENGTH: 6
<212> TYPE: PRT
<213> ORGANISM: Artificial Sequence
<220> FEATURE:
<223> OTHER INFORMATION: Synthetic Construct

<400> SEQUENCE: 58

Gln Asp Val Ser Thr Val
1 5

<210> SEQ ID NO 59
<211> LENGTH: 9
<212> TYPE: PRT
<213> ORGANISM: Artificial Sequence
<220> FEATURE:
<223> OTHER INFORMATION: Synthetic Construct

<400> SEQUENCE: 59

Gln Gln His Tyr Ser Pro Pro Tyr Thr
1 5

<210> SEQ ID NO 60
<211> LENGTH: 450
<212> TYPE: PRT
<213> ORGANISM: Artificial Sequence
<220> FEATURE:
<223> OTHER INFORMATION: Synthetic Construct

<400> SEQUENCE: 60

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Ala Ile Thr Trp Asn Ser Gly His Ile Asp Tyr Ala Asp Ser Val
50 55 60

Glu Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Lys Val Ser Tyr Leu Ser Thr Ala Ser Ser Leu Asp Tyr Trp Gly
100 105 110

Gln Gly Thr Leu Val Thr Val Ser Ser Ala Ser Thr Lys Gly Pro Ser
115 120 125

Val Phe Pro Leu Ala Pro Ser Ser Lys Ser Thr Ser Gly Gly Thr Ala
130 135 140

Ala Leu Gly Cys Leu Val Lys Asp Tyr Phe Pro Glu Pro Val Thr Val
145 150 155 160

Ser Trp Asn Ser Gly Ala Leu Thr Ser Gly Val His Thr Phe Pro Ala
165 170 175

Val Leu Gln Ser Ser Gly Leu Tyr Ser Leu Ser Ser Val Val Thr Val
180 185 190

```
Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Cys Thr Leu Pro Pro Ser Arg Asp Glu Leu Thr Lys Asn Gln Val Ser
        355                 360                 365

Leu Ser Cys Ala Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 61
<211> LENGTH: 213
<212> TYPE: PRT
<213> ORGANISM: Artificial Sequence
<220> FEATURE:
<223> OTHER INFORMATION: Synthetic Construct

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95
```

```
Thr Phe Gly Gln Gly Thr Lys Val Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210


<210> SEQ ID NO 62
<211> LENGTH: 570
<212> TYPE: PRT
<213> ORGANISM: Artificial Sequence
<220> FEATURE:
<223> OTHER INFORMATION: Synthetic Construct

<400> SEQUENCE: 62

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Pro Ser Asp Gly Glu Thr Arg Leu Asn Gln Arg Phe
    50                  55                  60

Gln Gly Arg Ala Thr Leu Thr Val Asp Glu Ser Thr Ser Thr Ala Tyr
65                  70                  75                  80

Met Gln Leu Arg Ser Pro Thr Ser Glu Asp Ser Ala Val Tyr Tyr Cys
                85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Glu Val Gln Leu Lys
        115                 120                 125

Glu Ser Gly Pro Gly Leu Val Ala Pro Gly Gly Ser Leu Ser Ile Thr
    130                 135                 140

Cys Thr Val Ser Gly Phe Ser Leu Thr Asp Ser Ser Ile Asn Trp Val
145                 150                 155                 160

Arg Gln Pro Pro Gly Lys Gly Leu Glu Trp Leu Gly Met Ile Trp Gly
                165                 170                 175

Asp Gly Arg Ile Asp Tyr Ala Asp Ala Leu Lys Ser Arg Leu Ser Ile
            180                 185                 190

Ser Lys Asp Ser Ser Lys Ser Gln Val Phe Leu Glu Met Thr Ser Leu
        195                 200                 205

Arg Thr Asp Asp Thr Ala Thr Tyr Tyr Cys Ala Arg Asp Gly Tyr Phe
    210                 215                 220

Pro Tyr Ala Met Asp Phe Trp Gly Gln Gly Thr Ser Val Thr Val Ser
225                 230                 235                 240
```

```
Ser Ala Ser Thr Lys Gly Pro Ser Val Phe Pro Leu Ala Pro Ser Ser
                245                 250                 255

Lys Ser Thr Ser Gly Gly Thr Ala Ala Leu Gly Cys Leu Val Lys Asp
            260                 265                 270

Tyr Phe Pro Glu Pro Val Thr Val Ser Trp Asn Ser Gly Ala Leu Thr
        275                 280                 285

Ser Gly Val His Thr Phe Pro Ala Val Leu Gln Ser Ser Gly Leu Tyr
    290                 295                 300

Ser Leu Ser Ser Val Val Thr Val Pro Ser Ser Ser Leu Gly Thr Gln
305                 310                 315                 320

Thr Tyr Ile Cys Asn Val Asn His Lys Pro Ser Asn Thr Lys Val Asp
                325                 330                 335

Lys Lys Val Glu Pro Lys Ser Cys Asp Lys Thr His Thr Cys Pro Pro
            340                 345                 350

Cys Pro Ala Pro Glu Leu Leu Gly Gly Pro Ser Val Phe Leu Phe Pro
        355                 360                 365

Pro Lys Pro Lys Asp Thr Leu Met Ile Ser Arg Thr Pro Glu Val Thr
    370                 375                 380

Cys Val Val Val Asp Val Ser His Glu Asp Pro Glu Val Lys Phe Asn
385                 390                 395                 400

Trp Tyr Val Asp Gly Val Glu Val His Asn Ala Lys Thr Lys Pro Arg
                405                 410                 415

Glu Glu Gln Tyr Asn Ser Thr Tyr Arg Val Val Ser Val Leu Thr Val
            420                 425                 430

Leu His Gln Asp Trp Leu Asn Gly Lys Glu Tyr Lys Cys Lys Val Ser
        435                 440                 445

Asn Lys Ala Leu Pro Ala Pro Ile Glu Lys Thr Ile Ser Lys Ala Lys
    450                 455                 460

Gly Gln Pro Arg Glu Pro Gln Val Tyr Thr Leu Pro Pro Cys Arg Asp
465                 470                 475                 480

Glu Leu Thr Lys Asn Gln Val Ser Leu Trp Cys Leu Val Lys Gly Phe
                485                 490                 495

Tyr Pro Ser Asp Ile Ala Val Glu Trp Glu Ser Asn Gly Gln Pro Glu
            500                 505                 510

Asn Asn Tyr Lys Thr Thr Pro Pro Val Leu Asp Ser Asp Gly Ser Phe
        515                 520                 525

Phe Leu Tyr Ser Lys Leu Thr Val Asp Lys Ser Arg Trp Gln Gln Gly
    530                 535                 540

Asn Val Phe Ser Cys Ser Val Met His Glu Ala Leu His Asn Arg Phe
545                 550                 555                 560

Thr Gln Lys Ser Leu Ser Leu Ser Pro Gly
                565                 570
```

<210> SEQ ID NO 63
<211> LENGTH: 345
<212> TYPE: PRT
<213> ORGANISM: Artificial Sequence
<220> FEATURE:
<223> OTHER INFORMATION: Synthetic Construct

<400> SEQUENCE: 63

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30
```

```
Gly Gln Ser Tyr Met His Trp Tyr Gln Gln Lys Ala Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Gln Ala Glu Asp Ala Ala Thr Tyr Tyr Cys Gln Gln Asn Ala
                85                  90                  95

Glu Asp Ser Arg Thr Phe Gly Gly Gly Thr Lys Leu Glu Ile Lys Gly
            100                 105                 110

Gly Ser Gly Ser Ser Gly Ser Gly Gly Asp Ile Gln Met Thr Gln Ser
        115                 120                 125

Pro Ala Ser Leu Ser Val Ser Val Gly Asp Thr Ile Thr Leu Thr Cys
    130                 135                 140

His Ala Ser Gln Asn Ile Asp Val Trp Leu Ser Trp Phe Gln Gln Lys
145                 150                 155                 160

Pro Gly Asn Ile Pro Lys Leu Leu Ile Tyr Lys Ala Ser Asn Leu His
                165                 170                 175

Thr Gly Val Pro Ser Arg Phe Ser Gly Ser Gly Ser Gly Thr Gly Phe
            180                 185                 190

Thr Leu Thr Ile Ser Ser Leu Gln Pro Glu Asp Ile Ala Thr Tyr Tyr
        195                 200                 205

Cys Gln Gln Ala His Ser Tyr Pro Phe Thr Phe Gly Gly Gly Thr Lys
    210                 215                 220

Leu Glu Ile Lys Gly Gly Ser Gly Ser Ser Gly Ser Gly Gly Arg Thr
225                 230                 235                 240

Val Ala Ala Pro Ser Val Phe Ile Phe Pro Pro Ser Asp Glu Gln Leu
                245                 250                 255

Lys Ser Gly Thr Ala Ser Val Val Cys Leu Leu Asn Asn Phe Tyr Pro
            260                 265                 270

Arg Glu Ala Lys Val Gln Trp Lys Val Asp Asn Ala Leu Gln Ser Gly
        275                 280                 285

Asn Ser Gln Glu Ser Val Thr Glu Gln Asp Ser Lys Asp Ser Thr Tyr
    290                 295                 300

Ser Leu Ser Ser Thr Leu Thr Leu Ser Lys Ala Asp Tyr Glu Lys His
305                 310                 315                 320

Lys Val Tyr Ala Cys Glu Val Thr His Gln Gly Leu Ser Ser Pro Val
                325                 330                 335

Thr Lys Ser Phe Asn Arg Gly Glu Cys
            340                 345
```

<210> SEQ ID NO 64
<211> LENGTH: 1350
<212> TYPE: DNA
<213> ORGANISM: Artificial Sequence
<220> FEATURE:
<223> OTHER INFORMATION: Synthetic Construct

<400> SEQUENCE: 64

```
gaggtgcagc tggtggaaag cggcggagga ctggtgcagc ccggcagaag cctgagactg      60

agctgcgccg ccagcggctt caccttcgac gactacgcca tgcactgggt ccgccaggcc     120

cctggcaagg gcctggaatg ggtgtccgcc atcacctgga acagcggcca catcgactac     180

gccgacagcg tggaaggccg gttcaccatc agccgggaca acgccaagaa cagcctgtac     240
```

ctgcagatga acagcctgcg ggccgaggac accgccgtgt actactgcgc caaggtgtcc 300
tacctgagca ccgccagcag cctggactac tggggccagg gcaccctggt gacagtgtcc 360
agcgcttcca ccaagggccc cagcgtgttc cccctggccc ctagcagcaa gagcacatct 420
ggcggcacag ccgccctggg ctgcctggtc aaggactact tccccgagcc cgtgacagtg 480
tcctggaact ctggcgccct gaccagcgga gtgcatacct tccctgccgt gctgcagtcc 540
agcggcctgt acagcctgag cagcgtggtc acagtgccca gcagcagcct gggcacccag 600
acctacatct gcaacgtgaa ccacaagccc agcaacacca aggtggacaa gaaggtggaa 660
cccaagagct gcgacaagac ccacacctgt ccccccctgcc ctgcccctga actgctgggc 720
ggaccctccg tgttcctgtt cccccccaaag cccaaggaca ccctgatgat cagccggacc 780
cccgaagtga cctgcgtggt ggtggacgtg tcccacgagg accctgaagt gaagttcaat 840
tggtacgtgg acggcgtgga agtgcataac gccaagacca agcccagaga ggaacagtac 900
aacagcacct accgggtggt gtccgtgctg accgtgctgc accaggactg gctgaacggc 960
aaagagtaca agtgcaaggt gtccaacaag gccctgcctg cccccatcga gaaaaccatc 1020
agcaaggcca agggccagcc tagagagccc caagtctgca ccctgccccc cagcagagat 1080
gagctgacca agaaccaggt gtccctgagc tgcgccgtga agggcttcta ccccagcgat 1140
atcgccgtgg aatgggagag caacggccag cccgagaaca actacaagac caccccccct 1200
gtgctggaca gcgacggctc attcttcctg gtgtccaagc tgacagtgga caagagccgg 1260
tggcagcagg gcaacgtgtt cagctgcagc gtgatgcacg aggccctgca caaccattac 1320
acccagaagt ccctgagcct gagccccggc 1350

<210> SEQ ID NO 65
<211> LENGTH: 639
<212> TYPE: DNA
<213> ORGANISM: Artificial Sequence
<220> FEATURE:
<223> OTHER INFORMATION: Synthetic Construct

<400> SEQUENCE: 65
gacatccaga tgacccagag ccccagcagc ctgagcgcca gcgtgggcga cagagtgacc 60
atcacctgtc gggccagcca gggcatccgg aactacctgg cctggtatca gcagaagccc 120
ggcaaggccc ccaagctgct gatctacgcc gccagcacac tgcagagcgg cgtgcccagc 180
agattcagcg gcagcggctc cggcaccgac ttcaccctga ccatcagcag cctgcagccc 240
gaggacgtgg ccacctacta ctgccagcgg tacaacagag cccccctacac cttcggccag 300 ggcaccaagg tggaaatcaa gggacagccc aaggctgccc cctcggtcac cctgttcccc 360
ccaagcagcg aggaactgca ggccaacaag gccaccctcg tgtgcctgat cagcgacttc 420
taccctggcg ccgtgaccgt ggcctggaag gccgatagct ctcccgtgaa ggccggcgtg 480
gaaaccacca cccccagcaa gcagagcaac aacaaatacg ccgcctccag ctacctgagc 540
ctgacccccg agcagtggaa gtcccaccgg tcctacagct gccaggtcac acacgagggc 600
agcaccgtgg aaaagaccgt ggcccccacc gagtgcagc 639

<210> SEQ ID NO 66
<211> LENGTH: 1710
<212> TYPE: DNA
<213> ORGANISM: Artificial Sequence
<220> FEATURE:
<223> OTHER INFORMATION: Synthetic Construct

<400> SEQUENCE: 66
caggtgcagc tgcagcagag cggccctgag ctggtcaagc ctggcgccag cgtgaagatc 60
agctgcaagg ccagcggcta cagcttcacc agctactgga tccactggat caagcagcgg 120
cctggccagg gcctggaatg gatcggcatg atcgacccca gcgacggcga gacacggctg 180
aaccagagat tccagggcag agccaccctg accgtggacg agagcaccag caccgcctac 240
atgcagctgc ggagccccac cagcgaggac agcgccgtgt actactgcac ccggctgaaa 300
gagtacggca actacgacag cttctacttc gacgtgtggg gagccggcac cctggtcacc 360
gtgtccagcg aagtgcagct gaaagaaagc ggccctggcc tggtggcccc tggcggcagc 420
ctgagcatca cctgtaccgt gtccggcttc agcctgaccg acagcagcat caactgggtc 480
cgacagcccc ctggcaaggg cctcgagtgg ctgggaatga tctggggcga cggccggatc 540
gactacgccg acgccctgaa gtcccggctg agcatcagca aggacagcag caagagccag 600
gtgttcctgg aaatgaccag cctgcggacc gacgacaccg ccacctacta ctgcgccagg 660
gacggctact tcccctacgc catggatttc tggggccagg gcaccagcgt gaccgtgtcc 720
tctgcttcca ccaagggccc cagcgtgttc cctctggccc ctagcagcaa gagcacatct 780
ggcggaacag ccgccctggg ctgcctggtc aaggactact tccccgagcc cgtgaccgtg 840
tcctggaact ctggtgccct gacaagcgga gtgcatacct tccctgccgt gctgcagagc 900
agcggcctgt actctctgag cagcgtggtc accgtgccaa gcagcagcct gggcacccag 960
acctacatct gcaacgtgaa ccacaagccc tccaacacca aggtggacaa gaaggtggaa 1020
cccaagagct gcgacaagac ccacacctgt cctccctgtc ctgcccctga actgctgggc 1080
ggaccctccg tgttcctgtt ccctccaaag cccaaggata ccctgatgat cagccggacc 1140
cctgaagtga cctgcgtggt ggtggacgtg tcccacgagg atcccgaagt gaagttcaat 1200
tggtacgtgg acggcgtgga agtgcataac gccaagacca agcccagaga ggaacagtac 1260
aacagcacct accgggtggt gtccgtgctg acagtgctgc accaggactg gctgaacggc 1320
aaagagtaca agtgcaaggt gtccaacaag gccctgccag cccctatcga gaaaaccatc 1380
agcaaggcca agggccagcc ccgcgagcct caggtgtaca cactgcctcc atgccgggac 1440
gagctgacca agaaccaggt gtccctgtgg tgcctcgtga agggcttcta cccctccgat 1500
atcgccgtgg aatgggagag caacggccag cccgagaaca actacaagac cacccctccc 1560
gtgctggaca gcgacggctc attcttcctg tacagcaagc tgaccgtgga caagtcccgg 1620
tggcagcagg gcaacgtgtt cagctgctct gtgatgcacg aggccctgca caaccggttc 1680
acccagaagt ccctgagcct gagccctggc 1710

<210> SEQ ID NO 67
<211> LENGTH: 1035
<212> TYPE: DNA
<213> ORGANISM: Artificial Sequence
<220> FEATURE:
<223> OTHER INFORMATION: Synthetic Construct

<400> SEQUENCE: 67
gacatcgtgc tgacccagag ccctgccagc ctggccgtgt ctctgggcca gagagccacc 60
atcagctgcc gggccagcga gagcgtggac agctacggcc agagctacat gcactggtat 120
cagcagaagg ccggccagcc ccccaagctg ctgatctacc tggccagcaa cctggaaagc 180
ggcgtgcccg ccagattcag cggcagcggc agcagaaccg acttcaccct gaccatcgac 240
cccgtgcagg ccgaggacgc cgccacctac tactgccagc agaacgccga ggacagccgg 300

```
accttcggcg gaggcaccaa gctggaaatc aagggcggct ccggcagcag cggctctggc    360

ggcgatatcc agatgaccca gtcccccgcc tccctgagcg tgtccgtggg cgacaccatc    420

accctgacat gccacgccag ccagaacatc gacgtgtggc tgagctggtt ccagcagaag    480

cctggcaaca tccctaagct gctcatctat aaggcctcca acctgcacac cggcgtgccc    540

agcaggtttt ccggctctgg cagcggcacc ggctttaccc tgacaatcag cagcctgcag    600

cccgaggata tcgccacata ttactgtcag caggcccaca gctacccctt cacctttggc    660

ggcggaacaa agctcgagat taagggcggc agcggaagct ccggctccgg cggacgtacg    720

gtggccgctc cttccgtgtt catcttccct ccctccgacg agcagctgaa gtccggcacc    780

gcctccgtgg tgtgtctgct gaacaacttc taccctcggg aggccaaggt gcagtggaag    840

gtggacaacg ccctgcagtc cggcaactcc caggagtccg tcaccgagca ggactccaag    900

gacagcacct actccctgtc ctccaccctg accctgtcca aggccgacta cgagaagcac    960

aaggtgtacg cctgtgaggt gacccaccag ggcctgtcca gccctgtgac caagtccttc   1020

aaccggggcg agtgc                                                    1035
```

```
<210> SEQ ID NO 68
<211> LENGTH: 570
<212> TYPE: PRT
<213> ORGANISM: Artificial Sequence
<220> FEATURE:
<223> OTHER INFORMATION: Synthetic Construct

<400> SEQUENCE: 68

Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Thr Asp Ser
            20                  25                  30

Ser Ile Asn Trp Val Arg Gln Pro Pro Gly Lys Gly Leu Glu Trp Leu
        35                  40                  45

Gly Met Ile Trp Gly Asp Gly Arg Ile Asp Tyr Ala Asp Ala Leu Lys
    50                  55                  60

Ser Arg Leu Ser Ile Ser Lys Asp Ser Ser Lys Ser Gln Val Phe Leu
65                  70                  75                  80

Glu Met Thr Ser Leu Arg Thr Asp Asp Thr Ala Thr Tyr Tyr Cys Ala
                85                  90                  95

Arg Asp Gly Tyr Phe Pro Tyr Ala Met Asp Phe Trp Gly Gln Gly Thr
            100                 105                 110

Ser Val Thr Val Ser Ser Gln Val Gln Leu Gln Gln Ser Gly Pro Glu
        115                 120                 125

Leu Val Lys Pro Gly Ala Ser Val Lys Ile Ser Cys Lys Ala Ser Gly
    130                 135                 140

Tyr Ser Phe Thr Ser Tyr Trp Ile His Trp Ile Lys Gln Arg Pro Gly
145                 150                 155                 160

Gln Gly Leu Glu Trp Ile Gly Met Ile Asp Pro Ser Asp Gly Glu Thr
                165                 170                 175

Arg Leu Asn Gln Arg Phe Gln Gly Arg Ala Thr Leu Thr Val Asp Glu
            180                 185                 190

Ser Thr Ser Thr Ala Tyr Met Gln Leu Arg Ser Pro Thr Ser Glu Asp
        195                 200                 205

Ser Ala Val Tyr Tyr Cys Thr Arg Leu Lys Glu Tyr Gly Asn Tyr Asp
    210                 215                 220

Ser Phe Tyr Phe Asp Val Trp Gly Ala Gly Thr Leu Val Thr Val Ser
```

225 230 235 240

Ser Ala Ser Thr Lys Gly Pro Ser Val Phe Pro Leu Ala Pro Ser Ser
245 250 255

Lys Ser Thr Ser Gly Gly Thr Ala Ala Leu Gly Cys Leu Val Lys Asp
260 265 270

Tyr Phe Pro Glu Pro Val Thr Val Ser Trp Asn Ser Gly Ala Leu Thr
275 280 285

Ser Gly Val His Thr Phe Pro Ala Val Leu Gln Ser Ser Gly Leu Tyr
290 295 300

Ser Leu Ser Ser Val Val Thr Val Pro Ser Ser Ser Leu Gly Thr Gln
305 310 315 320

Thr Tyr Ile Cys Asn Val Asn His Lys Pro Ser Asn Thr Lys Val Asp
325 330 335

Lys Lys Val Glu Pro Lys Ser Cys Asp Lys Thr His Thr Cys Pro Pro
340 345 350

Cys Pro Ala Pro Glu Leu Leu Gly Gly Pro Ser Val Phe Leu Phe Pro
355 360 365

Pro Lys Pro Lys Asp Thr Leu Met Ile Ser Arg Thr Pro Glu Val Thr
370 375 380

Cys Val Val Val Asp Val Ser His Glu Asp Pro Glu Val Lys Phe Asn
385 390 395 400

Trp Tyr Val Asp Gly Val Glu Val His Asn Ala Lys Thr Lys Pro Arg
405 410 415

Glu Glu Gln Tyr Asn Ser Thr Tyr Arg Val Val Ser Val Leu Thr Val
420 425 430

Leu His Gln Asp Trp Leu Asn Gly Lys Glu Tyr Lys Cys Lys Val Ser
435 440 445

Asn Lys Ala Leu Pro Ala Pro Ile Glu Lys Thr Ile Ser Lys Ala Lys
450 455 460

Gly Gln Pro Arg Glu Pro Gln Val Tyr Thr Leu Pro Pro Cys Arg Asp
465 470 475 480

Glu Leu Thr Lys Asn Gln Val Ser Leu Trp Cys Leu Val Lys Gly Phe
485 490 495

Tyr Pro Ser Asp Ile Ala Val Glu Trp Glu Ser Asn Gly Gln Pro Glu
500 505 510

Asn Asn Tyr Lys Thr Thr Pro Pro Val Leu Asp Ser Asp Gly Ser Phe
515 520 525

Phe Leu Tyr Ser Lys Leu Thr Val Asp Lys Ser Arg Trp Gln Gln Gly
530 535 540

Asn Val Phe Ser Cys Ser Val Met His Glu Ala Leu His Asn Arg Phe
545 550 555 560

Thr Gln Lys Ser Leu Ser Leu Ser Pro Gly
565 570

<210> SEQ ID NO 69
<211> LENGTH: 345
<212> TYPE: PRT
<213> ORGANISM: Artificial Sequence
<220> FEATURE:
<223> OTHER INFORMATION: Synthetic Construct

<400> SEQUENCE: 69

Asp Ile Gln Met Thr Gln Ser Pro Ala Ser Leu Ser Val Ser Val Gly
1 5 10 15

Asp Thr Ile Thr Leu Thr Cys His Ala Ser Gln Asn Ile Asp Val Trp

```
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Gly Gly Ser Gly Ser
            100                 105                 110

Ser Gly Ser Gly Gly Asp Ile Val Leu Thr Gln Ser Pro Ala Ser Leu
        115                 120                 125

Ala Val Ser Leu Gly Gln Arg Ala Thr Ile Ser Cys Arg Ala Ser Glu
    130                 135                 140

Ser Val Asp Ser Tyr Gly Gln Ser Tyr Met His Trp Tyr Gln Gln Lys
145                 150                 155                 160

Ala Gly Gln Pro Pro Lys Leu Leu Ile Tyr Leu Ala Ser Asn Leu Glu
                165                 170                 175

Ser Gly Val Pro Ala Arg Phe Ser Gly Ser Gly Ser Arg Thr Asp Phe
            180                 185                 190

Thr Leu Thr Ile Asp Pro Val Gln Ala Glu Asp Ala Ala Thr Tyr Tyr
        195                 200                 205

Cys Gln Gln Asn Ala Glu Asp Ser Arg Thr Phe Gly Gly Gly Thr Lys
    210                 215                 220

Leu Glu Ile Lys Gly Gly Ser Gly Ser Ser Gly Ser Gly Gly Arg Thr
225                 230                 235                 240

Val Ala Ala Pro Ser Val Phe Ile Phe Pro Pro Ser Asp Glu Gln Leu
                245                 250                 255

Lys Ser Gly Thr Ala Ser Val Val Cys Leu Leu Asn Asn Phe Tyr Pro
            260                 265                 270

Arg Glu Ala Lys Val Gln Trp Lys Val Asp Asn Ala Leu Gln Ser Gly
        275                 280                 285

Asn Ser Gln Glu Ser Val Thr Glu Gln Asp Ser Lys Asp Ser Thr Tyr
    290                 295                 300

Ser Leu Ser Ser Thr Leu Thr Leu Ser Lys Ala Asp Tyr Glu Lys His
305                 310                 315                 320

Lys Val Tyr Ala Cys Glu Val Thr His Gln Gly Leu Ser Ser Pro Val
                325                 330                 335

Thr Lys Ser Phe Asn Arg Gly Glu Cys
            340                 345


<210> SEQ ID NO 70
<211> LENGTH: 1035
<212> TYPE: DNA
<213> ORGANISM: Artificial Sequence
<220> FEATURE:
<223> OTHER INFORMATION: Synthetic Construct

<400> SEQUENCE: 70

gacatccaga tgacccagag ccccgccagc ctgagcgtgt ccgtgggcga taccatcacc      60

ctgacctgcc acgccagcca gaacatcgac gtgtggctga gctggttcca gcagaagccc     120

ggcaacatcc ccaagctgct gatctacaag gccagcaacc tgcacaccgg cgtgcccagc     180

agattcagcg gctctggcag cggcaccggc tttaccctga ccatcagcag cctgcagccc     240
```

```
gaggatatcg ccacctacta ctgccagcag gcccacagct accccttcac cttcggcgga    300

ggcaccaagc tggaaatcaa gggcggcagc ggcagctccg gctctggcgg cgatatcgtg    360

ctgacccagt ctcccgcctc cctggccgtg tctctgggcc agagagccac catcagctgc    420

cgggccagcg agagcgtgga cagctacggc cagagctaca tgcactggta tcagcagaag    480

gccggacagc cccctaaact gctcatctac ctggcctcca acctggaaag cggcgtgccc    540

gccaggtttt ccggcagcgg ctccagaacc gacttcaccc tgacaatcga ccccgtgcag    600

gccgaggacg ccgccacata ttactgtcag cagaacgccg aggacagcag aacctttggc    660

ggcggaacaa agctcgagat taagggcggc tccggctcca gcggatctgg cggacgtacg    720

gtggccgctc cttccgtgtt catcttccct ccctccgacg agcagctgaa gtccggcacc    780

gcctccgtgg tgtgtctgct gaacaacttc taccctcggg aggccaaggt gcagtggaag    840

gtggacaacg ccctgcagtc cggcaactcc caggagtccg tcaccgagca ggactccaag    900

gacagcacct actccctgtc ctccaccctg accctgtcca aggccgacta cgagaagcac    960

aaggtgtacg cctgtgaggt gacccaccag ggcctgtcca gccctgtgac caagtccttc   1020

aaccggggcg agtgc                                                    1035
```

```
<210> SEQ ID NO 71
<211> LENGTH: 214
<212> TYPE: PRT
<213> ORGANISM: Artificial Sequence
<220> FEATURE:
<223> OTHER INFORMATION: Synthetic Construct

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

210

<210> SEQ ID NO 72
<211> LENGTH: 642
<212> TYPE: DNA
<213> ORGANISM: Artificial Sequence
<220> FEATURE:
<223> OTHER INFORMATION: Synthetic Construct

<400> SEQUENCE: 72
gacatccaga tgacccagag ccccagcagc ctgagcgcca gcgtgggcga cagagtgacc 60
atcacctgtc gggccagcca gggcatccgg aactacctgg cctggtatca gcagaagccc 120
ggcaaggccc ccaagctgct gatctacgcc gccagcacac tgcagagcgg cgtgcccagc 180
agattcagcg gcagcggctc cggcaccgac ttcaccctga ccatcagcag cctgcagccc 240
gaggacgtgg ccacctacta ctgccagcgg tacaacagag ccccctacac cttcggccag 300
ggcaccaagg tggaaatcaa gcgtacggtg gccgctcctt ccgtgttcat cttccctccc 360
tccgacgagc agctgaagtc cggcaccgcc tccgtggtgt gtctgctgaa caacttctac 420
cctcgggagg ccaaggtgca gtggaaggtg gacaacgccc tgcagtccgg caactcccag 480
gagtccgtca ccgagcagga ctccaaggac agcacctact ccctgtcctc caccctgacc 540
ctgtccaagg ccgactacga gaagcacaag gtgtacgcct gtgaggtgac ccaccagggc 600
ctgtccagcc ctgtgaccaa gtccttcaac cggggcgagt gc 642

<210> SEQ ID NO 73
<211> LENGTH: 447
<212> TYPE: PRT
<213> ORGANISM: Artificial Sequence
<220> FEATURE:
<223> OTHER INFORMATION: Synthetic Construct

<400> SEQUENCE: 73

Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Thr Asp Ser
            20                  25                  30

Ser Ile Asn Trp Val Arg Gln Pro Pro Gly Lys Gly Leu Glu Trp Leu
        35                  40                  45

Gly Met Ile Trp Gly Asp Gly Arg Ile Asp Tyr Ala Asp Ala Leu Lys
    50                  55                  60

Ser Arg Leu Ser Ile Ser Lys Asp Ser Ser Lys Ser Gln Val Phe Leu
65                  70                  75                  80

Glu Met Thr Ser Leu Arg Thr Asp Asp Thr Ala Thr Tyr Tyr Cys Ala
                85                  90                  95

Arg Asp Gly Tyr Phe Pro Tyr Ala Met Asp Phe Trp Gly Gln Gly Thr
            100                 105                 110

Ser Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Cys Thr Leu
            340                 345                 350

Pro Pro Ser Arg Asp Glu Leu Thr Lys Asn Gln Val Ser Leu Ser Cys
        355                 360                 365

Ala Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Val Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445

<210> SEQ ID NO 74
<211> LENGTH: 217
<212> TYPE: PRT
<213> ORGANISM: Artificial Sequence
<220> FEATURE:
<223> OTHER INFORMATION: Synthetic Construct

<400> SEQUENCE: 74

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Gln Ser Tyr Met His Trp Tyr Gln Gln Lys Ala Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Gln Ala Glu Asp Ala Ala Thr Tyr Tyr Cys Gln Gln Asn Ala
                85                  90                  95

Glu Asp Ser Arg Thr Phe Gly Gly Gly Thr Lys Leu Glu Ile Lys Gly
            100                 105                 110

```
Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215


<210> SEQ ID NO 75
<211> LENGTH: 573
<212> TYPE: PRT
<213> ORGANISM: Artificial Sequence
<220> FEATURE:
<223> OTHER INFORMATION: Synthetic Construct

<400> SEQUENCE: 75

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Pro Ser Asp Gly Glu Thr Arg Leu Asn Gln Arg Phe
    50                  55                  60

Gln Gly Arg Ala Thr Leu Thr Val Asp Glu Ser Thr Ser Thr Ala Tyr
65                  70                  75                  80

Met Gln Leu Arg Ser Pro Thr Ser Glu Asp Ser Ala Val Tyr Tyr Cys
                85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Glu Val Gln Leu Val
        115                 120                 125

Glu Ser Gly Gly Gly Leu Val Gln Pro Gly Arg Ser Leu Arg Leu Ser
    130                 135                 140

Cys Ala Ala Ser Gly Phe Thr Phe Asp Asp Tyr Ala Met His Trp Val
145                 150                 155                 160

Arg Gln Ala Pro Gly Lys Gly Leu Glu Trp Val Ser Ala Ile Thr Trp
                165                 170                 175

Asn Ser Gly His Ile Asp Tyr Ala Asp Ser Val Glu Gly Arg Phe Thr
            180                 185                 190

Ile Ser Arg Asp Asn Ala Lys Asn Ser Leu Tyr Leu Gln Met Asn Ser
        195                 200                 205

Leu Arg Ala Glu Asp Thr Ala Val Tyr Tyr Cys Ala Lys Val Ser Tyr
    210                 215                 220

Leu Ser Thr Ala Ser Ser Leu Asp Tyr Trp Gly Gln Gly Thr Leu Val
225                 230                 235                 240

Thr Val Ser Ser Ala Ser Thr Lys Gly Pro Ser Val Phe Pro Leu Ala
                245                 250                 255
```

Pro Ser Ser Lys Ser Thr Ser Gly Gly Thr Ala Ala Leu Gly Cys Leu
260 265 270

Val Lys Asp Tyr Phe Pro Glu Pro Val Thr Val Ser Trp Asn Ser Gly
275 280 285

Ala Leu Thr Ser Gly Val His Thr Phe Pro Ala Val Leu Gln Ser Ser
290 295 300

Gly Leu Tyr Ser Leu Ser Ser Val Val Thr Val Pro Ser Ser Ser Leu
305 310 315 320

Gly Thr Gln Thr Tyr Ile Cys Asn Val Asn His Lys Pro Ser Asn Thr
325 330 335

Lys Val Asp Lys Lys Val Glu Pro Lys Ser Cys Asp Lys Thr His Thr
340 345 350

Cys Pro Pro Cys Pro Ala Pro Glu Leu Leu Gly Gly Pro Ser Val Phe
355 360 365

Leu Phe Pro Pro Lys Pro Lys Asp Thr Leu Met Ile Ser Arg Thr Pro
370 375 380

Glu Val Thr Cys Val Val Val Asp Val Ser His Glu Asp Pro Glu Val
385 390 395 400

Lys Phe Asn Trp Tyr Val Asp Gly Val Glu Val His Asn Ala Lys Thr
405 410 415

Lys Pro Arg Glu Glu Gln Tyr Asn Ser Thr Tyr Arg Val Val Ser Val
420 425 430

Leu Thr Val Leu His Gln Asp Trp Leu Asn Gly Lys Glu Tyr Lys Cys
435 440 445

Lys Val Ser Asn Lys Ala Leu Pro Ala Pro Ile Glu Lys Thr Ile Ser
450 455 460

Lys Ala Lys Gly Gln Pro Arg Glu Pro Gln Val Tyr Thr Leu Pro Pro
465 470 475 480

Cys Arg Asp Glu Leu Thr Lys Asn Gln Val Ser Leu Trp Cys Leu Val
485 490 495

Lys Gly Phe Tyr Pro Ser Asp Ile Ala Val Glu Trp Glu Ser Asn Gly
500 505 510

Gln Pro Glu Asn Asn Tyr Lys Thr Thr Pro Pro Val Leu Asp Ser Asp
515 520 525

Gly Ser Phe Phe Leu Tyr Ser Lys Leu Thr Val Asp Lys Ser Arg Trp
530 535 540

Gln Gln Gly Asn Val Phe Ser Cys Ser Val Met His Glu Ala Leu His
545 550 555 560

Asn Arg Phe Thr Gln Lys Ser Leu Ser Leu Ser Pro Gly
565 570

<210> SEQ ID NO 76
<211> LENGTH: 341
<212> TYPE: PRT
<213> ORGANISM: Artificial Sequence
<220> FEATURE:
<223> OTHER INFORMATION: Synthetic Construct

<400> SEQUENCE: 76

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Arg Asn Tyr
20 25 30

Leu Ala Trp Tyr Gln Gln Lys Pro Gly Lys Ala Pro Lys Leu Leu Ile
35 40 45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Gly Gly Ser Gly Ser
            100                 105                 110

Ser Gly Ser Gly Gly Asp Ile Gln Met Thr Gln Ser Pro Ala Ser Leu
        115                 120                 125

Ser Val Ser Val Gly Asp Thr Ile Thr Leu Thr Cys His Ala Ser Gln
    130                 135                 140

Asn Ile Asp Val Trp Leu Ser Trp Phe Gln Gln Lys Pro Gly Asn Ile
145                 150                 155                 160

Pro Lys Leu Leu Ile Tyr Lys Ala Ser Asn Leu His Thr Gly Val Pro
                165                 170                 175

Ser Arg Phe Ser Gly Ser Gly Ser Gly Thr Gly Phe Thr Leu Thr Ile
            180                 185                 190

Ser Ser Leu Gln Pro Glu Asp Ile Ala Thr Tyr Tyr Cys Gln Gln Ala
        195                 200                 205

His Ser Tyr Pro Phe Thr Phe Gly Gly Gly Thr Lys Leu Glu Ile Lys
    210                 215                 220

Gly Gly Ser Gly Ser Ser Gly Ser Gly Gly Arg Thr Val Ala Ala Pro
225                 230                 235                 240

Ser Val Phe Ile Phe Pro Pro Ser Asp Glu Gln Leu Lys Ser Gly Thr
                245                 250                 255

Ala Ser Val Val Cys Leu Leu Asn Asn Phe Tyr Pro Arg Glu Ala Lys
            260                 265                 270

Val Gln Trp Lys Val Asp Asn Ala Leu Gln Ser Gly Asn Ser Gln Glu
        275                 280                 285

Ser Val Thr Glu Gln Asp Ser Lys Asp Ser Thr Tyr Ser Leu Ser Ser
    290                 295                 300

Thr Leu Thr Leu Ser Lys Ala Asp Tyr Glu Lys His Lys Val Tyr Ala
305                 310                 315                 320

Cys Glu Val Thr His Gln Gly Leu Ser Ser Pro Val Thr Lys Ser Phe
                325                 330                 335

Asn Arg Gly Glu Cys
            340

<210> SEQ ID NO 77
<211> LENGTH: 1341
<212> TYPE: DNA
<213> ORGANISM: Artificial Sequence
<220> FEATURE:
<223> OTHER INFORMATION: Synthetic Construct

<400> SEQUENCE: 77
gaggtgcagc tgaaggagag cggccccggc ctggtggccc ccggcggcag cctgagcatc 60
acctgcaccg tgagcggctt cagcctgacc gacagcagca tcaactgggt gcgccagccc 120
cccggcaagg gcctggagtg gctgggcatg atctggggcg acggccgcat cgactacgcc 180
gacgccctga agagccgcct gagcatcagc aaggacagca gcaagagcca ggtgttcctg 240
gagatgacca gcctgcgcac cgacgacacc gccacctact actgcgcccg cgacggctac 300
ttcccctacg ccatggactt ctggggccag ggcaccagcg tgaccgtgag cagcgccagc 360
accaagggcc ccagcgtgtt ccccctggcc cctagcagca agagcacatc tggcggcaca 420
gccgccctgg gctgcctggt caaggactac ttccccgagc ccgtgacagt gtcctggaac 480
tctggcgccc tgaccagcgg agtgcatacc ttccctgccg tgctgcagtc cagcggcctg 540
tacagcctga gcagcgtggt cacagtgccc agcagcagcc tgggcaccca gacctacatc 600
tgcaacgtga accacaagcc cagcaacacc aaggtggaca agaaggtgga acccaagagc 660
tgcgacaaga cccacacctg tccccctgc cctgcccctg aactgctggg cggaccctcc 720
gtgttcctgt tcccccaaa gcccaaggac accctgatga tcagccggac ccccgaagtg 780
acctgcgtgg tggtggacgt gtcccacgag gaccctgaag tgaagttcaa ttggtacgtg 840
gacggcgtgg aagtgcataa cgccaagacc aagcccagag aggaacagta caacagcacc 900
taccgggtgg tgtccgtgct gaccgtgctg caccaggact ggctgaacgg caaagagtac 960
aagtgcaagg tgtccaacaa ggccctgcct gcccccatcg agaaaaccat cagcaaggcc 1020
aagggccagc ctagagagcc ccaagtctgc accctgcccc ccagcagaga tgagctgacc 1080
aagaaccagg tgtccctgag ctgcgccgtg aagggcttct accccagcga tatcgccgtg 1140
gaatgggaga gcaacggcca gcccgagaac aactacaaga ccaccccccc tgtgctggac 1200
agcgacggct cattcttcct ggtgtccaag ctgacagtgg acaagagccg gtggcagcag 1260
ggcaacgtgt tcagctgcag cgtgatgcac gaggccctgc acaaccatta cacccagaag 1320
tccctgagcc tgagccccgg c 1341

<210> SEQ ID NO 78
<211> LENGTH: 651
<212> TYPE: DNA
<213> ORGANISM: Artificial Sequence
<220> FEATURE:
<223> OTHER INFORMATION: Synthetic Construct

<400> SEQUENCE: 78
gacatcgtgc tgacccagag ccctgccagc ctggccgtgt ctctgggcca gagagccacc 60
atcagctgcc gggccagcga gagcgtggac agctacggcc agagctacat gcactggtat 120
cagcagaagg ccggccagcc ccccaagctg ctgatctacc tggccagcaa cctggaaagc 180
ggcgtgcccg ccagattcag cggcagcggc agcagaaccg acttcaccct gaccatcgac 240
cccgtgcagg ccgaggacgc cgccacctac tactgccagc agaacgccga ggacagccgg 300
accttcggcg gaggcaccaa gctggaaatc aagggacagc ccaaggctgc cccctcggtc 360
accctgttcc ccccaagcag cgaggaactg caggccaaca aggccaccct cgtgtgcctg 420
atcagcgact tctaccctgg cgccgtgacc gtggcctgga aggccgatag ctctcccgtg 480
aaggccggcg tggaaaccac cacccccagc aagcagagca acaacaaata cgccgccagc 540
agctacctga gcctgacccc cgagcagtgg aagtcccacc ggtcctacag ctgccaggtc 600
acacacgagg gcagcaccgt ggaaaagacc gtggccccca ccgagtgcag c 651

<210> SEQ ID NO 79
<211> LENGTH: 1719
<212> TYPE: DNA
<213> ORGANISM: Artificial Sequence
<220> FEATURE:
<223> OTHER INFORMATION: Synthetic Construct

<400> SEQUENCE: 79
caggtgcagc tgcagcagag cggccctgag ctggtcaagc ctggcgccag cgtgaagatc 60
agctgcaagg ccagcggcta cagcttcacc agctactgga tccactggat caagcagcgg 120
cctggccagg gcctggaatg gatcggcatg atcgacccca gcgacggcga gacacggctg 180
aaccagagat tccagggcag agccaccctg accgtggacg agagcaccag caccgcctac 240
atgcagctgc ggagccccac cagcgaggac agcgccgtgt actactgcac ccggctgaaa 300
gagtacggca actacgacag cttctacttc gacgtgtggg gagccggcac cctggtcacc 360
gtgtccagcg aagtgcagct ggtggaaagc ggcggaggcc tggtgcagcc cggcagaagc 420
ctgagactga gctgcgccgc cagcggcttc accttcgacg actacgccat gcactgggtc 480
cgacaggccc ctggcaaagg actggaatgg gtgtccgcca tcacctggaa cagcggccac 540
atcgactacg ccgacagcgt ggaaggccgg ttcaccatca gccgggacaa cgccaagaac 600
agcctgtacc tgcagatgaa cagcctgcgg gccgaggata ccgccgtgta ttattgcgcc 660
aaggtgtcct acctgagcac cgccagcagc ctggactact ggggccaggg caccctcgtg 720
acagtgtcct ccgcttccac caagggcccc agcgtgttcc ctctggcccc tagcagcaag 780
agcacatctg gcggaacagc cgccctgggc tgcctggtca aggactactt tcccgagccc 840
gtgaccgtgt cctggaactc tggtgccctg acaagcggag tgcatacctt ccctgccgtg 900
ctgcagagca gcggcctgta ctctctgagc agcgtggtca ccgtgccaag cagcagcctg 960
ggcacccaga cctacatctg caacgtgaac cacaagccct ccaacaccaa ggtggacaag 1020
aaggtggaac ccaagagctg cgacaagacc cacacctgtc ctccctgtcc tgcccctgaa 1080
ctgctgggcg gaccctccgt gttcctgttc cctccaaagc ccaaggatac cctgatgatc 1140
agccggaccc ctgaagtgac ctgcgtggtg gtggacgtgt cccacgagga tcccgaagtg 1200
aagttcaatt ggtacgtgga cggcgtggaa gtgcataacg ccaagaccaa gcccagagag 1260
gaacagtaca acagcaccta ccgggtggtg tccgtgctga cagtgctgca ccaggactgg 1320
ctgaacggca aagagtacaa gtgcaaggtg tccaacaagg ccctgccagc ccctatcgag 1380
aaaaccatca gcaaggccaa gggccagccc cgcgagcctc aggtgtacac actgcctcca 1440
tgccgggacg agctgaccaa gaaccaggtg tccctgtggt gcctcgtgaa gggcttctac 1500
ccctccgata tcgccgtgga atgggagagc aacggccagc ccgagaacaa ctacaagacc 1560
acccctcccg tgctggacag cgacggctca ttcttcctgt acagcaagct gaccgtggac 1620
aagtcccggt ggcagcaggg caacgtgttc agctgctctg tgatgcacga ggccctgcac 1680
aaccggttca cccagaagtc cctgagcctg agccctggc 1719

<210> SEQ ID NO 80
<211> LENGTH: 1023
<212> TYPE: DNA
<213> ORGANISM: Artificial Sequence
<220> FEATURE:
<223> OTHER INFORMATION: Synthetic Construct

<400> SEQUENCE: 80
gacatccaga tgacccagag ccccagcagc ctgagcgcca gcgtgggcga cagagtgacc 60
atcacctgtc gggccagcca gggcatccgg aactacctgg cctggtatca gcagaagccc 120
ggcaaggccc ccaagctgct gatctacgcc gccagcacac tgcagagcgg cgtgcccagc 180
agattcagcg gcagcggctc cggcaccgac ttcaccctga ccatcagcag cctgcagccc 240
gaggacgtgg ccacctacta ctgccagcgg tacaacagag ccccctacac cttcggccag 300
ggcaccaagg tggaaatcaa gggcggctct ggcagctccg gcagcggcgg agacattcag 360
atgacacagt cccccgccag cctgtccgtg tccgtgggcg ataccatcac cctgacatgc 420
cacgccagcc agaacatcga cgtgtggctg agctggttcc agcagaaacc tggcaacatc 480
cctaagctgc tcatctataa ggccagcaac ctgcacacag gcgtgccctc cagattctcc 540
ggctctggct ctggcaccgg ctttacactg acaatcagtt ctctgcagcc tgaggatatc 600
gccacatatt actgtcagca ggcccacagc taccctttca ccttcggagg cggcaccaag 660
ctcgagatta agggcggaag cggctcctcc ggctccggcg gacgtacggt ggccgctcct 720
tccgtgttca tcttccctcc ctccgacgag cagctgaagt ccggcaccgc ctccgtggtg 780
tgtctgctga acaacttcta ccctcgggag gccaaggtgc agtggaaggt ggacaacgcc 840
ctgcagtccg gcaactccca ggagtccgtc accgagcagg actccaagga cagcacctac 900
tccctgtcct ccaccctgac cctgtccaag gccgactacg agaagcacaa ggtgtacgcc 960
tgtgaggtga cccaccaggg cctgtccagc cctgtgacca agtccttcaa ccggggcgag 1020
tgc 1023

<210> SEQ ID NO 81
<211> LENGTH: 573
<212> TYPE: PRT
<213> ORGANISM: Artificial Sequence
<220> FEATURE:
<223> OTHER INFORMATION: Synthetic Construct

<400> SEQUENCE: 81

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Gln Val Gln Leu Gln Gln Ser
        115                 120                 125

Gly Pro Glu Leu Val Lys Pro Gly Ala Ser Val Lys Ile Ser Cys Lys
    130                 135                 140

Ala Ser Gly Tyr Ser Phe Thr Ser Tyr Trp Ile His Trp Ile Lys Gln
145                 150                 155                 160

Arg Pro Gly Gln Gly Leu Glu Trp Ile Gly Met Ile Asp Pro Ser Asp
                165                 170                 175

Gly Glu Thr Arg Leu Asn Gln Arg Phe Gln Gly Arg Ala Thr Leu Thr
            180                 185                 190

Val Asp Glu Ser Thr Ser Thr Ala Tyr Met Gln Leu Arg Ser Pro Thr
        195                 200                 205

Ser Glu Asp Ser Ala Val Tyr Tyr Cys Thr Arg Leu Lys Glu Tyr Gly
    210                 215                 220

Asn Tyr Asp Ser Phe Tyr Phe Asp Val Trp Gly Ala Gly Thr Leu Val
225                 230                 235                 240

Thr Val Ser Ser Ala Ser Thr Lys Gly Pro Ser Val Phe Pro Leu Ala

```
                245                 250                 255

Pro Ser Ser Lys Ser Thr Ser Gly Gly Thr Ala Ala Leu Gly Cys Leu
            260                 265                 270

Val Lys Asp Tyr Phe Pro Glu Pro Val Thr Val Ser Trp Asn Ser Gly
        275                 280                 285

Ala Leu Thr Ser Gly Val His Thr Phe Pro Ala Val Leu Gln Ser Ser
    290                 295                 300

Gly Leu Tyr Ser Leu Ser Ser Val Val Thr Val Pro Ser Ser Ser Leu
305                 310                 315                 320

Gly Thr Gln Thr Tyr Ile Cys Asn Val Asn His Lys Pro Ser Asn Thr
                325                 330                 335

Lys Val Asp Lys Lys Val Glu Pro Lys Ser Cys Asp Lys Thr His Thr
            340                 345                 350

Cys Pro Pro Cys Pro Ala Pro Glu Leu Leu Gly Gly Pro Ser Val Phe
        355                 360                 365

Leu Phe Pro Pro Lys Pro Lys Asp Thr Leu Met Ile Ser Arg Thr Pro
    370                 375                 380

Glu Val Thr Cys Val Val Val Asp Val Ser His Glu Asp Pro Glu Val
385                 390                 395                 400

Lys Phe Asn Trp Tyr Val Asp Gly Val Glu Val His Asn Ala Lys Thr
                405                 410                 415

Lys Pro Arg Glu Glu Gln Tyr Asn Ser Thr Tyr Arg Val Val Ser Val
            420                 425                 430

Leu Thr Val Leu His Gln Asp Trp Leu Asn Gly Lys Glu Tyr Lys Cys
        435                 440                 445

Lys Val Ser Asn Lys Ala Leu Pro Ala Pro Ile Glu Lys Thr Ile Ser
    450                 455                 460

Lys Ala Lys Gly Gln Pro Arg Glu Pro Gln Val Tyr Thr Leu Pro Pro
465                 470                 475                 480

Cys Arg Asp Glu Leu Thr Lys Asn Gln Val Ser Leu Trp Cys Leu Val
                485                 490                 495

Lys Gly Phe Tyr Pro Ser Asp Ile Ala Val Glu Trp Glu Ser Asn Gly
            500                 505                 510

Gln Pro Glu Asn Asn Tyr Lys Thr Thr Pro Pro Val Leu Asp Ser Asp
        515                 520                 525

Gly Ser Phe Phe Leu Tyr Ser Lys Leu Thr Val Asp Lys Ser Arg Trp
    530                 535                 540

Gln Gln Gly Asn Val Phe Ser Cys Ser Val Met His Glu Ala Leu His
545                 550                 555                 560

Asn Arg Phe Thr Gln Lys Ser Leu Ser Leu Ser Pro Gly
                565                 570


<210> SEQ ID NO 82
<211> LENGTH: 341
<212> TYPE: PRT
<213> ORGANISM: Artificial Sequence
<220> FEATURE:
<223> OTHER INFORMATION: Synthetic Construct

<400> SEQUENCE: 82

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
```

```
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Gly Gly Ser Gly Ser
            100                 105                 110

Ser Gly Ser Gly Gly Asp Ile Gln Met Thr Gln Ser Pro Ser Ser Leu
        115                 120                 125

Ser Ala Ser Val Gly Asp Arg Val Thr Ile Thr Cys Arg Ala Ser Gln
    130                 135                 140

Gly Ile Arg Asn Tyr Leu Ala Trp Tyr Gln Gln Lys Pro Gly Lys Ala
145                 150                 155                 160

Pro Lys Leu Leu Ile Tyr Ala Ala Ser Thr Leu Gln Ser Gly Val Pro
                165                 170                 175

Ser Arg Phe Ser Gly Ser Gly Ser Gly Thr Asp Phe Thr Leu Thr Ile
            180                 185                 190

Ser Ser Leu Gln Pro Glu Asp Val Ala Thr Tyr Tyr Cys Gln Arg Tyr
        195                 200                 205

Asn Arg Ala Pro Tyr Thr Phe Gly Gln Gly Thr Lys Val Glu Ile Lys
    210                 215                 220

Gly Gly Ser Gly Ser Ser Gly Ser Gly Gly Arg Thr Val Ala Ala Pro
225                 230                 235                 240

Ser Val Phe Ile Phe Pro Pro Ser Asp Glu Gln Leu Lys Ser Gly Thr
                245                 250                 255

Ala Ser Val Val Cys Leu Leu Asn Asn Phe Tyr Pro Arg Glu Ala Lys
            260                 265                 270

Val Gln Trp Lys Val Asp Asn Ala Leu Gln Ser Gly Asn Ser Gln Glu
        275                 280                 285

Ser Val Thr Glu Gln Asp Ser Lys Asp Ser Thr Tyr Ser Leu Ser Ser
    290                 295                 300

Thr Leu Thr Leu Ser Lys Ala Asp Tyr Glu Lys His Lys Val Tyr Ala
305                 310                 315                 320

Cys Glu Val Thr His Gln Gly Leu Ser Ser Pro Val Thr Lys Ser Phe
                325                 330                 335

Asn Arg Gly Glu Cys
            340
```

```
<210> SEQ ID NO 83
<211> LENGTH: 1719
<212> TYPE: DNA
<213> ORGANISM: Artificial Sequence
<220> FEATURE:
<223> OTHER INFORMATION: Synthetic Construct

<400> SEQUENCE: 83

gaggtgcagc tggtggaaag cggcggagga ctggtgcagc ccggcagaag cctgagactg      60

agctgcgccg ccagcggctt caccttcgac gactacgcca tgcactgggt ccgacaggcc     120

cctggcaagg gcctggaatg ggtgtccgcc atcacctgga acagcggcca catcgactac     180

gccgacagcg tggaaggccg gttcaccatc agccgggaca acgccaagaa cagcctgtac     240

ctgcagatga acagcctgcg ggccgaggac accgccgtgt actactgcgc caaggtgtcc     300
```

tacctgagca ccgccagcag cctggactac tggggccagg gcaccctggt caccgtgtcc 360
agtcaggtcc agctgcagca gagcggccct gagctggtca agcctggcgc cagcgtgaag 420
atcagctgca aggccagcgg ctacagcttc accagctact ggatccactg gatcaagcag 480
cggcctggcc agggcctcga gtggatcggc atgatcgacc ccagcgacgg cgagacacgg 540
ctgaaccaga gattccaggg cagagccacc ctgaccgtgg acgagagcac cagcaccgcc 600
tacatgcagc tgcggagccc caccagcgag gatagcgccg tgtattattg cacccggctg 660
aaagagtacg gcaactacga cagcttctac ttcgacgtgt ggggagccgg caccctcgtg 720
acagtgtcct ccgcttccac caagggcccc agcgtgttcc ctctggcccc tagcagcaag 780
agcacatctg gcggaacagc cgccctgggc tgcctggtca aggactactt tcccgagccc 840
gtgaccgtgt cctggaactc tggtgccctg acaagcggag tgcatacctt ccctgccgtg 900
ctgcagagca gcggcctgta ctctctgagc agcgtggtca ccgtgccaag cagcagcctg 960
ggcacccaga cctacatctg caacgtgaac cacaagccct ccaacaccaa ggtggacaag 1020
aaggtggaac ccaagagctg cgacaagacc cacacctgtc ctccctgtcc tgcccctgaa 1080
ctgctgggcg gaccctccgt gttcctgttc cctccaaagc ccaaggatac cctgatgatc 1140
agccggaccc ctgaagtgac ctgcgtggtg gtggacgtgt cccacgagga tcccgaagtg 1200
aagttcaatt ggtacgtgga cggcgtggaa gtgcataacg ccaagaccaa gcccagagag 1260
gaacagtaca acagcaccta ccgggtggtg tccgtgctga cagtgctgca ccaggactgg 1320
ctgaacggca aagagtacaa gtgcaaggtg tccaacaagg ccctgccagc ccctatcgag 1380
aaaaccatca gcaaggccaa gggccagccc cgcgagcctc aggtgtacac actgcctcca 1440
tgccgggacg agctgaccaa gaaccaggtg tccctgtggt gcctcgtgaa gggcttctac 1500
ccctccgata tcgccgtgga atgggagagc aacggccagc ccgagaacaa ctacaagacc 1560
acccctcccg tgctggacag cgacggctca ttcttcctgt acagcaagct gaccgtggac 1620
aagtcccggt ggcagcaggg caacgtgttc agctgctctg tgatgcacga ggccctgcac 1680
aaccggttca cccagaagtc cctgagcctg agccctggc 1719

<210> SEQ ID NO 84
<211> LENGTH: 1023
<212> TYPE: DNA
<213> ORGANISM: Artificial Sequence
<220> FEATURE:
<223> OTHER INFORMATION: Synthetic Construct

<400> SEQUENCE: 84
gacatccaga tgacccagag ccccgccagc ctgagcgtgt ccgtgggcga taccatcacc 60
ctgacctgcc acgccagcca gaacatcgac gtgtggctga gctggttcca gcagaagccc 120
ggcaacatcc ccaagctgct gatctacaag gccagcaacc tgcacaccgg cgtgcccagc 180
agattcagcg gctctggcag cggcaccggc tttaccctga ccatcagcag cctgcagccc 240
gaggatatcg ccacctacta ctgccagcag gcccacagct acccccttcac cttcggcgga 300 ggcaccaagc tggaaatcaa gggcggcagc ggcagctccg gcagcggcgg agacattcag 360
atgacacagt cccccagcag cctgtccgcc agcgtgggcg acagagtgac catcacctgt 420
cgggccagcc agggcatccg gaactacctg gcctggtatc agcagaaacc tggcaaggcc 480
cctaaactgc tcatctacgc cgccagcaca ctgcagtctg gcgtgccctc cagattctcc 540
ggaagcggct ccggcaccga tttcaccctg acaatctcat ctctgcagcc tgaggacgtg 600
gccacatatt actgccagag atacaacaga gccccctaca cctttggcca gggcaccaag 660

```
gtcgagatta agggcggatc cggctccagc ggcagcggag gacgtacggt ggccgctcct    720

tccgtgttca tcttccctcc ctccgacgag cagctgaagt ccggcaccgc ctccgtggtg    780

tgtctgctga acaacttcta ccctcgggag gccaaggtgc agtggaaggt ggacaacgcc    840

ctgcagtccg gcaactccca ggagtccgtc accgagcagg actccaagga cagcacctac    900

tccctgtcct ccaccctgac cctgtccaag gccgactacg agaagcacaa ggtgtacgcc    960

tgtgaggtga cccaccaggg cctgtccagc cctgtgacca agtccttcaa ccggggcgag   1020

tgc                                                                 1023
```

```
<210> SEQ ID NO 85
<211> LENGTH: 452
<212> TYPE: PRT
<213> ORGANISM: Artificial Sequence
<220> FEATURE:
<223> OTHER INFORMATION: Synthetic Construct

<400> SEQUENCE: 85

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Pro Ser Asp Gly Glu Thr Arg Leu Asn Gln Arg Phe
    50                  55                  60

Gln Gly Arg Ala Thr Leu Thr Val Asp Glu Ser Thr Ser Thr Ala Tyr
65                  70                  75                  80

Met Gln Leu Arg Ser Pro Thr Ser Glu Asp Ser Ala Val Tyr Tyr Cys
                85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285
```

```
Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Cys Thr Leu Pro Pro Ser Arg Asp Glu Leu Thr Lys Asn Gln
        355                 360                 365

Val Ser Leu Ser Cys Ala Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Val Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450


<210> SEQ ID NO 86
<211> LENGTH: 213
<212> TYPE: PRT
<213> ORGANISM: Artificial Sequence
<220> FEATURE:
<223> OTHER INFORMATION: Synthetic Construct

<400> SEQUENCE: 86

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190
```

Ser Cys Gln Val Thr His Glu Gly Ser Thr Val Glu Lys Thr Val Ala
195 200 205

Pro Thr Glu Cys Ser
210

<210> SEQ ID NO 87
<211> LENGTH: 568
<212> TYPE: PRT
<213> ORGANISM: Artificial Sequence
<220> FEATURE:
<223> OTHER INFORMATION: Synthetic Construct

<400> SEQUENCE: 87

Glu Val Gln Leu Lys Glu Ser Gly Pro Gly Leu Val Ala Pro Gly Gly
1 5 10 15

Ser Leu Ser Ile Thr Cys Thr Val Ser Gly Phe Ser Leu Thr Asp Ser
20 25 30

Ser Ile Asn Trp Val Arg Gln Pro Pro Gly Lys Gly Leu Glu Trp Leu
35 40 45

Gly Met Ile Trp Gly Asp Gly Arg Ile Asp Tyr Ala Asp Ala Leu Lys
50 55 60

Ser Arg Leu Ser Ile Ser Lys Asp Ser Ser Lys Ser Gln Val Phe Leu
65 70 75 80

Glu Met Thr Ser Leu Arg Thr Asp Asp Thr Ala Thr Tyr Tyr Cys Ala
85 90 95

Arg Asp Gly Tyr Phe Pro Tyr Ala Met Asp Phe Trp Gly Gln Gly Thr
100 105 110

Ser Val Thr Val Ser Ser Glu Val Gln Leu Val Glu Ser Gly Gly Gly
115 120 125

Leu Val Gln Pro Gly Arg Ser Leu Arg Leu Ser Cys Ala Ala Ser Gly
130 135 140

Phe Thr Phe Asp Asp Tyr Ala Met His Trp Val Arg Gln Ala Pro Gly
145 150 155 160

Lys Gly Leu Glu Trp Val Ser Ala Ile Thr Trp Asn Ser Gly His Ile
165 170 175

Asp Tyr Ala Asp Ser Val Glu Gly Arg Phe Thr Ile Ser Arg Asp Asn
180 185 190

Ala Lys Asn Ser Leu Tyr Leu Gln Met Asn Ser Leu Arg Ala Glu Asp
195 200 205

Thr Ala Val Tyr Tyr Cys Ala Lys Val Ser Tyr Leu Ser Thr Ala Ser
210 215 220

Ser Leu Asp Tyr Trp Gly Gln Gly Thr Leu Val Thr Val Ser Ser Ala
225 230 235 240

Ser Thr Lys Gly Pro Ser Val Phe Pro Leu Ala Pro Ser Ser Lys Ser
245 250 255

Thr Ser Gly Gly Thr Ala Ala Leu Gly Cys Leu Val Lys Asp Tyr Phe
260 265 270

Pro Glu Pro Val Thr Val Ser Trp Asn Ser Gly Ala Leu Thr Ser Gly
275 280 285

Val His Thr Phe Pro Ala Val Leu Gln Ser Ser Gly Leu Tyr Ser Leu
290 295 300

Ser Ser Val Val Thr Val Pro Ser Ser Ser Leu Gly Thr Gln Thr Tyr
305 310 315 320

Ile Cys Asn Val Asn His Lys Pro Ser Asn Thr Lys Val Asp Lys Lys
325 330 335

```
Val Glu Pro Lys Ser Cys Asp Lys Thr His Thr Cys Pro Pro Cys Pro
            340                 345                 350

Ala Pro Glu Leu Leu Gly Gly Pro Ser Val Phe Leu Phe Pro Pro Lys
        355                 360                 365

Pro Lys Asp Thr Leu Met Ile Ser Arg Thr Pro Glu Val Thr Cys Val
    370                 375                 380

Val Val Asp Val Ser His Glu Asp Pro Glu Val Lys Phe Asn Trp Tyr
385                 390                 395                 400

Val Asp Gly Val Glu Val His Asn Ala Lys Thr Lys Pro Arg Glu Glu
                405                 410                 415

Gln Tyr Asn Ser Thr Tyr Arg Val Val Ser Val Leu Thr Val Leu His
            420                 425                 430

Gln Asp Trp Leu Asn Gly Lys Glu Tyr Lys Cys Lys Val Ser Asn Lys
        435                 440                 445

Ala Leu Pro Ala Pro Ile Glu Lys Thr Ile Ser Lys Ala Lys Gly Gln
    450                 455                 460

Pro Arg Glu Pro Gln Val Tyr Thr Leu Pro Pro Cys Arg Asp Glu Leu
465                 470                 475                 480

Thr Lys Asn Gln Val Ser Leu Trp Cys Leu Val Lys Gly Phe Tyr Pro
                485                 490                 495

Ser Asp Ile Ala Val Glu Trp Glu Ser Asn Gly Gln Pro Glu Asn Asn
            500                 505                 510

Tyr Lys Thr Thr Pro Pro Val Leu Asp Ser Asp Gly Ser Phe Phe Leu
        515                 520                 525

Tyr Ser Lys Leu Thr Val Asp Lys Ser Arg Trp Gln Gln Gly Asn Val
    530                 535                 540

Phe Ser Cys Ser Val Met His Glu Ala Leu His Asn Arg Phe Thr Gln
545                 550                 555                 560

Lys Ser Leu Ser Leu Ser Pro Gly
                565


<210> SEQ ID NO 88
<211> LENGTH: 344
<212> TYPE: PRT
<213> ORGANISM: Artificial Sequence
<220> FEATURE:
<223> OTHER INFORMATION: Synthetic Construct

<400> SEQUENCE: 88

Ile Gln Met Thr Gln Ser Pro Ser Ser Leu Ser Ala Ser Val Gly Asp
1               5                   10                  15

Arg Val Thr Ile Thr Cys Arg Ala Ser Gln Gly Ile Arg Asn Tyr Leu
            20                  25                  30

Ala Trp Tyr Gln Gln Lys Pro Gly Lys Ala Pro Lys Leu Leu Ile Tyr
        35                  40                  45

Ala Ala Ser Thr Leu Gln Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Val Ala Thr Tyr Tyr Cys Gln Arg Tyr Asn Arg Ala Pro Tyr Thr
                85                  90                  95

Phe Gly Gln Gly Thr Lys Val Glu Ile Lys Gly Gly Ser Gly Ser Ser
            100                 105                 110

Gly Ser Gly Gly Asp Ile Val Leu Thr Gln Ser Pro Ala Ser Leu Ala
        115                 120                 125
```

-continued

```
Val Ser Leu Gly Gln Arg Ala Thr Ile Ser Cys Arg Ala Ser Glu Ser
    130                 135                 140

Val Asp Ser Tyr Gly Gln Ser Tyr Met His Trp Tyr Gln Gln Lys Ala
145                 150                 155                 160

Gly Gln Pro Pro Lys Leu Leu Ile Tyr Leu Ala Ser Asn Leu Glu Ser
                165                 170                 175

Gly Val Pro Ala Arg Phe Ser Gly Ser Gly Ser Arg Thr Asp Phe Thr
            180                 185                 190

Leu Thr Ile Asp Pro Val Gln Ala Glu Asp Ala Ala Thr Tyr Tyr Cys
        195                 200                 205

Gln Gln Asn Ala Glu Asp Ser Arg Thr Phe Gly Gly Gly Thr Lys Leu
    210                 215                 220

Glu Ile Lys Gly Gly Ser Gly Ser Ser Gly Ser Gly Gly Arg Thr Val
225                 230                 235                 240

Ala Ala Pro Ser Val Phe Ile Phe Pro Pro Ser Asp Glu Gln Leu Lys
                245                 250                 255

Ser Gly Thr Ala Ser Val Val Cys Leu Leu Asn Asn Phe Tyr Pro Arg
            260                 265                 270

Glu Ala Lys Val Gln Trp Lys Val Asp Asn Ala Leu Gln Ser Gly Asn
        275                 280                 285

Ser Gln Glu Ser Val Thr Glu Gln Asp Ser Lys Asp Ser Thr Tyr Ser
    290                 295                 300

Leu Ser Ser Thr Leu Thr Leu Ser Lys Ala Asp Tyr Glu Lys His Lys
305                 310                 315                 320

Val Tyr Ala Cys Glu Val Thr His Gln Gly Leu Ser Ser Pro Val Thr
                325                 330                 335

Lys Ser Phe Asn Arg Gly Glu Cys
            340
```

<210> SEQ ID NO 89
<211> LENGTH: 1356
<212> TYPE: DNA
<213> ORGANISM: Artificial Sequence
<220> FEATURE:
<223> OTHER INFORMATION: Synthetic Construct

<400> SEQUENCE: 89

```
caggtgcagc tgcagcagag cggccccgag ctggtgaagc ccggcgccag cgtgaagatc     60

agctgcaagg ccagcggcta cagcttcacc agctactgga ttcactggat caagcagcgc    120

cccggccagg gcctggagtg gatcggcatg atcgacccca gcgacggcga gacccgcctg    180

aaccagcgct tccagggccg cgccaccctg accgtggacg agagcaccag caccgcctac    240

atgcagctgc gcagccccac cagcgaggac agcgccgtgt actactgcac ccgcctgaag    300

gagtacggca actacgacag cttctacttc gacgtgtggg gcgccggcac cctggtgacc    360

gtgagcagcg ccagcaccaa gggccccagc gtgttccccc tggcccctag cagcaagagc    420

acatctggcg gcacagccgc cctgggctgc ctggtcaagg actacttccc cgagcccgtg    480

acagtgtcct ggaactctgg cgccctgacc agcggagtgc ataccttccc tgccgtgctg    540

cagtccagcg gcctgtacag cctgagcagc gtggtcacag tgcccagcag cagcctgggc    600

acccagacct acatctgcaa cgtgaaccac aagcccagca acaccaaggt ggacaagaag    660

gtggaaccca agagctgcga caagacccac acctgtcccc cctgccctgc ccctgaactg    720

ctgggcggac cctccgtgtt cctgttcccc ccaaagccca aggacaccct gatgatcagc    780

cggacccccg aagtgacctg cgtggtggtg gacgtgtccc acgaggaccc tgaagtgaag    840
```

-continued

```
ttcaattggt acgtggacgg cgtggaagtg cataacgcca agaccaagcc cagagaggaa    900

cagtacaaca gcacctaccg ggtggtgtcc gtgctgaccg tgctgcacca ggactggctg    960

aacggcaaag agtacaagtg caaggtgtcc aacaaggccc tgcctgcccc catcgagaaa   1020

accatcagca aggccaaggg ccagcctaga gagccccaag tctgcaccct gcccccccagc   1080

agagatgagc tgaccaagaa ccaggtgtcc ctgagctgcg ccgtgaaggg cttctacccc   1140

agcgatatcg ccgtggaatg ggagagcaac ggccagcccg agaacaacta caagaccacc   1200

ccccctgtgc tggacagcga cggctcattc ttcctggtgt ccaagctgac agtggacaag   1260

agccggtggc agcagggcaa cgtgttcagc tgcagcgtga tgcacgaggc cctgcacaac   1320

cattacaccc agaagtccct gagcctgagc cccggc                             1356
```

<210> SEQ ID NO 90
<211> LENGTH: 639
<212> TYPE: DNA
<213> ORGANISM: Artificial Sequence
<220> FEATURE:
<223> OTHER INFORMATION: Synthetic Construct

<400> SEQUENCE: 90

```
gacatccaga tgacccagag ccccgccagc ctgagcgtgt ccgtgggcga taccatcacc     60

ctgacctgcc acgccagcca gaacatcgac gtgtggctga gctggttcca gcagaagccc    120

ggcaacatcc ccaagctgct gatctacaag gccagcaacc tgcacaccgg cgtgcccagc    180

agattcagcg gctctggcag cggcaccggc tttaccctga ccatcagcag cctgcagccc    240

gaggatatcg ccacctacta ctgccagcag gcccacagct accccttcac cttcggcgga    300

ggcaccaagc tggaaatcaa gggacagccc aaggctgccc cctcggtcac cctgttcccc    360

ccaagctctg aggaactgca ggccaacaag gccaccctcg tgtgcctgat cagcgacttc    420

taccctggcg ccgtgaccgt ggcctggaag gccgatagct ctcccgtgaa ggccggcgtg    480

gaaaccacca cccccagcaa gcagagcaac aacaaatacg ccgccagcag ctacctgagc    540

ctgacccccg agcagtggaa gtcccaccgg tcctacagct gccaggtcac acacgagggc    600

agcaccgtgg aaaagaccgt ggcccccacc gagtgcagc                          639
```

<210> SEQ ID NO 91
<211> LENGTH: 1704
<212> TYPE: DNA
<213> ORGANISM: Artificial Sequence
<220> FEATURE:
<223> OTHER INFORMATION: Synthetic Construct

<400> SEQUENCE: 91

```
gaggtgcagc tgaaagagtc cggccctgga ctggtggccc ctggcggcag cctgagcatc     60

acctgtaccg tgtccggctt cagcctgacc gacagcagca tcaactgggt ccgacagccc    120

cctggcaagg gcctggaatg gctgggcatg atctggggcg acggccggat cgactacgcc    180

gacgccctga agtcccggct gagcatcagc aaggacagca gcaagagcca ggtgttcctg    240

gaaatgacca gcctgcggac cgacgacacc gccacctact actgcgccag ggacggctac    300

ttcccctacg ccatggattt ctggggccag ggcaccagcg tgaccgtgtc ctccgaagtg    360

cagctggtgg aaagcggcgg aggcctggtg cagcccggca gaagcctgag actgagctgc    420

gccgccagcg gcttcacctt cgacgactac gccatgcact gggtccgcca ggctcccgga    480

aagggactcg agtgggtgtc cgccatcacc tggaacagcg gccacatcga ttacgccgat    540
```

-continued agcgtggaag gccggttcac catcagccgg gacaacgcca agaacagcct gtacctgcag 600
atgaacagcc tgagagccga ggataccgcc gtgtactact gtgccaaggt gtcctacctg 660
agcaccgcca gcagcctgga ctactgggga cagggaaccc tggtcaccgt gtccagcgct 720
tccaccaagg gccccagcgt gttccctctg gcccctagca gcaagagcac atctggcgga 780
acagccgccc tgggctgcct ggtcaaggac tactttcccg agcccgtgac cgtgtcctgg 840
aactctggtg ccctgacaag cggagtgcat accttccctg ccgtgctgca gagcagcggc 900
ctgtactctc tgagcagcgt ggtcaccgtg ccaagcagca gcctgggcac ccagacctac 960
atctgcaacg tgaaccacaa gccctccaac accaaggtgg acaagaaggt ggaacccaag 1020
agctgcgaca agacccacac ctgtcctccc tgtcctgccc ctgaactgct gggcggaccc 1080
tccgtgttcc tgttccctcc aaagcccaag gataccctga tgatcagccg gacccctgaa 1140
gtgacctgcg tggtggtgga cgtgtcccac gaggatcccg aagtgaagtt caattggtac 1200
gtggacggcg tggaagtgca taacgccaag accaagccca gagaggaaca gtacaacagc 1260
acctaccggg tggtgtccgt gctgacagtg ctgcaccagg actggctgaa cggcaaagag 1320
tacaagtgca aggtgtccaa caaggccctg ccagccccta tcgagaaaac catcagcaag 1380
gccaagggcc agccccgcga gcctcaggtg tacacactgc ctccatgccg ggacgagctg 1440
accaagaacc aggtgtccct gtggtgcctc gtgaagggct tctacccctc cgatatcgcc 1500
gtggaatggg agagcaacgg ccagcccgag aacaactaca agaccacccc tcccgtgctg 1560
gacagcgacg gctcattctt cctgtacagc aagctgaccg tggacaagtc ccggtggcag 1620
cagggcaacg tgttcagctg ctctgtgatg cacgaggccc tgcacaaccg gttcacccag 1680
aagtccctga gcctgagccc tggc 1704

<210> SEQ ID NO 92
<211> LENGTH: 1035
<212> TYPE: DNA
<213> ORGANISM: Artificial Sequence
<220> FEATURE:
<223> OTHER INFORMATION: Synthetic Construct

<400> SEQUENCE: 92
gacatccaga tgacccagag ccccagcagc ctgagcgcca gcgtgggcga cagagtgacc 60
atcacctgtc gggccagcca gggcatccgg aactacctgg cctggtatca gcagaagccc 120
ggcaaggccc ccaagctgct gatctacgcc gccagcacac tgcagagcgg cgtgcccagc 180
agattcagcg gcagcggctc cggcaccgac ttcaccctga ccatcagcag cctgcagccc 240
gaggacgtgg ccacctacta ctgccagcgg tacaacagag ccccctacac cttcggccag 300
ggcaccaagg tggaaatcaa gggcggctct ggcagctccg gctctggcgg cgatatcgtg 360
ctgacccagt ctcccgccag cctggccgtg tctctgggcc agagagccac catcagctgc 420
agagccagcg agagcgtgga cagctacggc cagagctaca tgcattggta tcagcagaaa 480
gccggccagc ctcctaaact gctcatctac ctggccagca acctggaatc cggcgtgccc 540
gccaggtttt ccggcagcgg cagcagaacc gatttcacac tgacaatcga ccccgtgcag 600
gccgaggatg ccgccacata ttactgtcag cagaacgccg aggacagccg gaccttcggc 660
ggaggcacca agctcgagat taagggcgga agcggctcca gcggcagtgg cggacgtacg 720
gtggccgctc cttccgtgtt catcttccct ccctccgacg agcagctgaa gtccggcacc 780
gcctccgtgg tgtgtctgct gaacaacttc taccctcggg aggccaaggt gcagtggaag 840
gtggacaacg ccctgcagtc cggcaactcc caggagtccg tcaccgagca ggactccaag 900

```
gacagcacct actccctgtc ctccaccctg accctgtcca aggccgacta cgagaagcac    960

aaggtgtacg cctgtgaggt gacccaccag ggcctgtcca gccctgtgac caagtccttc   1020

aaccggggcg agtgc                                                    1035
```

<210> SEQ ID NO 93
<211> LENGTH: 568
<212> TYPE: PRT
<213> ORGANISM: Artificial Sequence
<220> FEATURE:
<223> OTHER INFORMATION: Synthetic Construct

<400> SEQUENCE: 93

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Glu Val Gln Leu Lys Glu Ser
        115                 120                 125

Gly Pro Gly Leu Val Ala Pro Gly Gly Ser Leu Ser Ile Thr Cys Thr
    130                 135                 140

Val Ser Gly Phe Ser Leu Thr Asp Ser Ser Ile Asn Trp Val Arg Gln
145                 150                 155                 160

Pro Pro Gly Lys Gly Leu Glu Trp Leu Gly Met Ile Trp Gly Asp Gly
                165                 170                 175

Arg Ile Asp Tyr Ala Asp Ala Leu Lys Ser Arg Leu Ser Ile Ser Lys
            180                 185                 190

Asp Ser Ser Lys Ser Gln Val Phe Leu Glu Met Thr Ser Leu Arg Thr
        195                 200                 205

Asp Asp Thr Ala Thr Tyr Tyr Cys Ala Arg Asp Gly Tyr Phe Pro Tyr
    210                 215                 220

Ala Met Asp Phe Trp Gly Gln Gly Thr Ser Val Thr Val Ser Ser Ala
225                 230                 235                 240

Ser Thr Lys Gly Pro Ser Val Phe Pro Leu Ala Pro Ser Ser Lys Ser
                245                 250                 255

Thr Ser Gly Gly Thr Ala Ala Leu Gly Cys Leu Val Lys Asp Tyr Phe
            260                 265                 270

Pro Glu Pro Val Thr Val Ser Trp Asn Ser Gly Ala Leu Thr Ser Gly
        275                 280                 285

Val His Thr Phe Pro Ala Val Leu Gln Ser Ser Gly Leu Tyr Ser Leu
    290                 295                 300

Ser Ser Val Val Thr Val Pro Ser Ser Ser Leu Gly Thr Gln Thr Tyr
305                 310                 315                 320

Ile Cys Asn Val Asn His Lys Pro Ser Asn Thr Lys Val Asp Lys Lys
                325                 330                 335
```

Val Glu Pro Lys Ser Cys Asp Lys Thr His Thr Cys Pro Pro Cys Pro
340 345 350

Ala Pro Glu Leu Leu Gly Gly Pro Ser Val Phe Leu Phe Pro Pro Lys
355 360 365

Pro Lys Asp Thr Leu Met Ile Ser Arg Thr Pro Glu Val Thr Cys Val
370 375 380

Val Val Asp Val Ser His Glu Asp Pro Glu Val Lys Phe Asn Trp Tyr
385 390 395 400

Val Asp Gly Val Glu Val His Asn Ala Lys Thr Lys Pro Arg Glu Glu
405 410 415

Gln Tyr Asn Ser Thr Tyr Arg Val Val Ser Val Leu Thr Val Leu His
420 425 430

Gln Asp Trp Leu Asn Gly Lys Glu Tyr Lys Cys Lys Val Ser Asn Lys
435 440 445

Ala Leu Pro Ala Pro Ile Glu Lys Thr Ile Ser Lys Ala Lys Gly Gln
450 455 460

Pro Arg Glu Pro Gln Val Tyr Thr Leu Pro Pro Cys Arg Asp Glu Leu
465 470 475 480

Thr Lys Asn Gln Val Ser Leu Trp Cys Leu Val Lys Gly Phe Tyr Pro
485 490 495

Ser Asp Ile Ala Val Glu Trp Glu Ser Asn Gly Gln Pro Glu Asn Asn
500 505 510

Tyr Lys Thr Thr Pro Pro Val Leu Asp Ser Asp Gly Ser Phe Phe Leu
515 520 525

Tyr Ser Lys Leu Thr Val Asp Lys Ser Arg Trp Gln Gln Gly Asn Val
530 535 540

Phe Ser Cys Ser Val Met His Glu Ala Leu His Asn Arg Phe Thr Gln
545 550 555 560

Lys Ser Leu Ser Leu Ser Pro Gly
565

<210> SEQ ID NO 94
<211> LENGTH: 345
<212> TYPE: PRT
<213> ORGANISM: Artificial Sequence
<220> FEATURE:
<223> OTHER INFORMATION: Synthetic Construct

<400> SEQUENCE: 94

Asp Ile Val Leu Thr Gln Ser Pro Ala Ser Leu Ala Val Ser Leu Gly
1 5 10 15

Gln Arg Ala Thr Ile Ser Cys Arg Ala Ser Glu Ser Val Asp Ser Tyr
20 25 30

Gly Gln Ser Tyr Met His Trp Tyr Gln Gln Lys Ala Gly Gln Pro Pro
35 40 45

Lys Leu Leu Ile Tyr Leu Ala Ser Asn Leu Glu Ser Gly Val Pro Ala
50 55 60

Arg Phe Ser Gly Ser Gly Ser Arg Thr Asp Phe Thr Leu Thr Ile Asp
65 70 75 80

Pro Val Gln Ala Glu Asp Ala Ala Thr Tyr Tyr Cys Gln Gln Asn Ala
85 90 95

Glu Asp Ser Arg Thr Phe Gly Gly Gly Thr Lys Leu Glu Ile Lys Gly
100 105 110

Gly Ser Gly Ser Ser Gly Ser Gly Gly Asp Ile Gln Met Thr Gln Ser
115 120 125

```
Pro Ser Ser Leu Ser Ala Ser Val Gly Asp Arg Val Thr Ile Thr Cys
    130                 135                 140

Arg Ala Ser Gln Gly Ile Arg Asn Tyr Leu Ala Trp Tyr Gln Gln Lys
145                 150                 155                 160

Pro Gly Lys Ala Pro Lys Leu Leu Ile Tyr Ala Ala Ser Thr Leu Gln
                165                 170                 175

Ser Gly Val Pro Ser Arg Phe Ser Gly Ser Gly Ser Gly Thr Asp Phe
            180                 185                 190

Thr Leu Thr Ile Ser Ser Leu Gln Pro Glu Asp Val Ala Thr Tyr Tyr
        195                 200                 205

Cys Gln Arg Tyr Asn Arg Ala Pro Tyr Thr Phe Gly Gln Gly Thr Lys
    210                 215                 220

Val Glu Ile Lys Gly Gly Ser Gly Ser Ser Gly Ser Gly Gly Arg Thr
225                 230                 235                 240

Val Ala Ala Pro Ser Val Phe Ile Phe Pro Pro Ser Asp Glu Gln Leu
                245                 250                 255

Lys Ser Gly Thr Ala Ser Val Val Cys Leu Leu Asn Asn Phe Tyr Pro
            260                 265                 270

Arg Glu Ala Lys Val Gln Trp Lys Val Asp Asn Ala Leu Gln Ser Gly
        275                 280                 285

Asn Ser Gln Glu Ser Val Thr Glu Gln Asp Ser Lys Asp Ser Thr Tyr
    290                 295                 300

Ser Leu Ser Ser Thr Leu Thr Leu Ser Lys Ala Asp Tyr Glu Lys His
305                 310                 315                 320

Lys Val Tyr Ala Cys Glu Val Thr His Gln Gly Leu Ser Ser Pro Val
                325                 330                 335

Thr Lys Ser Phe Asn Arg Gly Glu Cys
            340                 345
```

```
<210> SEQ ID NO 95
<211> LENGTH: 1704
<212> TYPE: DNA
<213> ORGANISM: Artificial Sequence
<220> FEATURE:
<223> OTHER INFORMATION: Synthetic Construct

<400> SEQUENCE: 95

gaggtgcagc tggtggaaag cggcggagga ctggtgcagc ccggcagaag cctgagactg      60

agctgcgccg ccagcggctt caccttcgac gactacgcca tgcactgggt ccgacaggcc     120

cctggcaagg gcctggaatg ggtgtccgcc atcacctgga acagcggcca catcgactac     180

gccgacagcg tggaaggccg gttcaccatc agccgggaca acgccaagaa cagcctgtac     240

ctgcagatga acagcctgcg ggccgaggac accgccgtgt actactgcgc caaggtgtcc     300

tacctgagca ccgccagcag cctggactac tggggccagg gcaccctggt caccgtgtcc     360

tccgaagtgc agctgaaaga gtccggccct ggcctggtgg cccctggcgg cagcctgagc     420

atcacctgta ccgtgtccgg cttcagcctg accgacagca gcatcaactg ggtccgccag     480

cctcccggaa agggactcga gtggctgggc atgatctggg gcgacggccg gatcgattac     540

gccgatgccc tgaagtcccg gctgagcatc agcaaggaca gcagcaagag ccaggtgttc     600

ctggaaatga ccagcctgag aaccgacgac accgccacct actactgtgc ccgggacggc     660

tacttcccct acgccatgga tttctgggga cagggaacca gcgtgaccgt gtccagcgct     720

tccaccaagg gccccagcgt gttccctctg gcccctagca gcaagagcac atctggcgga     780
```

-continued

```
acagccgccc tgggctgcct ggtcaaggac tactttcccg agcccgtgac cgtgtcctgg     840

aactctggtg ccctgacaag cggagtgcat accttccctg ccgtgctgca gagcagcggc     900

ctgtactctc tgagcagcgt ggtcaccgtg ccaagcagca gcctgggcac ccagacctac     960

atctgcaacg tgaaccacaa gccctccaac accaaggtgg acaagaaggt ggaacccaag    1020

agctgcgaca agacccacac ctgtcctccc tgtcctgccc ctgaactgct gggcggaccc    1080

tccgtgttcc tgttccctcc aaagcccaag gataccctga tgatcagccg gacccctgaa    1140

gtgacctgcg tggtggtgga cgtgtcccac gaggatcccg aagtgaagtt caattggtac    1200

gtggacggcg tggaagtgca taacgccaag accaagccca gagaggaaca gtacaacagc    1260

acctaccggg tggtgtccgt gctgacagtg ctgcaccagg actggctgaa cggcaaagag    1320

tacaagtgca aggtgtccaa caaggccctg ccagccccta tcgagaaaac catcagcaag    1380

gccaagggcc agccccgcga gcctcaggtg tacacactgc ctccatgccg ggacgagctg    1440

accaagaacc aggtgtccct gtggtgcctc gtgaagggct tctacccctc cgatatcgcc    1500

gtggaatggg agagcaacgg ccagcccgag aacaactaca agaccacccc tcccgtgctg    1560

gacagcgacg gctcattctt cctgtacagc aagctgaccg tggacaagtc ccggtggcag    1620

cagggcaacg tgttcagctg ctctgtgatg cacgaggccc tgcacaaccg gttcacccag    1680

aagtccctga gcctgagccc tggc                                           1704


<210> SEQ ID NO 96
<211> LENGTH: 1035
<212> TYPE: DNA
<213> ORGANISM: Artificial Sequence
<220> FEATURE:
<223> OTHER INFORMATION: Synthetic Construct

<400> SEQUENCE: 96

gacatcgtgc tgacccagag ccctgccagc ctggccgtgt ctctgggcca gagagccacc      60

atcagctgcc gggccagcga gagcgtggac agctacggcc agagctacat gcactggtat     120

cagcagaagg ccggccagcc ccccaagctg ctgatctacc tggccagcaa cctggaaagc     180

ggcgtgcccg ccagattcag cggcagcggc agcagaaccg acttcaccct gaccatcgac     240

cccgtgcagg ccgaggacgc cgccacctac tactgccagc agaacgccga ggacagccgg     300

accttcggcg gaggcaccaa gctggaaatc aagggcggct ccggcagcag cggctctggc     360

ggcgatatcc agatgaccca gtcccccagc agcctgagcg ccagcgtggg cgacagagtg     420

accatcacct gtagagccag ccagggcatc cggaactacc tggcttggta tcagcagaaa     480

cccggaaagg cccctaaact gctcatctac gccgccagca ccctgcagtc cggcgtgcca     540

agcagattct ccggctctgg cagcggcacc gatttcacac tgacaatcag cagcctgcag     600

cccgaggatg tggccaccta ttattgccag agatacaaca gagcccccta caccttcggc     660

cagggcacca aggtcgagat taagggcgga agcggcagct ccggctccgg cggacgtacg     720

gtggccgctc cttccgtgtt catcttccct ccctccgacg agcagctgaa gtccggcacc     780

gcctccgtgg tgtgtctgct gaacaacttc taccctcggg aggccaaggt gcagtggaag     840

gtggacaacg ccctgcagtc cggcaactcc caggagtccg tcaccgagca ggactccaag     900

gacagcacct actccctgtc ctccaccctg accctgtcca aggccgacta cgagaagcac     960

aaggtgtacg cctgtgaggt gacccaccag ggcctgtcca gccctgtgac caagtccttc    1020

aaccggggcg agtgc                                                     1035
```

<210> SEQ ID NO 97
<211> LENGTH: 1710
<212> TYPE: DNA
<213> ORGANISM: Artificial Sequence
<220> FEATURE:
<223> OTHER INFORMATION: Synthetic Construct

<400> SEQUENCE: 97
gaggtgcagc tgaaagagtc cggccctgga ctggtggccc ctggcggcag cctgagcatc 60
acctgtaccg tgtccggctt cagcctgacc gacagcagca tcaactgggt ccgacagccc 120
cctggcaagg gcctggaatg gctgggcatg atctggggcg acggccggat cgactacgcc 180
gacgccctga agtcccggct gagcatcagc aaggacagca gcaagagcca ggtgttcctg 240
gaaatgacca gcctgcggac cgacgacacc gccacctact actgcgccag ggacggctac 300
ttcccctacg ccatggattt ctggggccag ggcaccagcg tgaccgtgtc cagtcaggtc 360
cagctgcagc agagcggccc tgagctggtc aagcctggcg ccagcgtgaa gatcagctgc 420
aaggccagcg gctacagctt caccagctac tggatccact ggatcaagca gcggcctggc 480
cagggcctcg agtggatcgg aatgatcgac cccagcgacg gcgagacacg gctgaaccag 540
agattccagg gcagagccac cctgaccgtg gacgagagca ccagcaccgc ctacatgcag 600
ctgcggagcc ccaccagcga ggacagcgcc gtgtactact gcacccggct gaaagaatac 660
ggcaactacg acagcttcta cttcgacgtg tggggagccg gcaccctggt caccgtgtct 720
agcgcttcca ccaagggccc cagcgtgttc cctctggccc ctagcagcaa gagcacatct 780
ggcggaacag ccgccctggg ctgcctggtc aaggactact ttcccgagcc cgtgaccgtg 840
tcctggaact ctggtgccct gacaagcgga gtgcatacct tccctgccgt gctgcagagc 900
agcggcctgt actctctgag cagcgtggtc accgtgccaa gcagcagcct gggcacccag 960
acctacatct gcaacgtgaa ccacaagccc tccaacacca aggtggacaa gaaggtggaa 1020
cccaagagct gcgacaagac ccacacctgt cctccctgtc ctgcccctga actgctgggc 1080
ggaccctccg tgttcctgtt ccctccaaag cccaaggata ccctgatgat cagccggacc 1140
cctgaagtga cctgcgtggt ggtggacgtg tcccacgagg atcccgaagt gaagttcaat 1200
tggtacgtgg acggcgtgga agtgcataac gccaagacca agcccagaga ggaacagtac 1260
aacagcacct accgggtggt gtccgtgctg acagtgctgc accaggactg gctgaacggc 1320
aaagagtaca agtgcaaggt gtccaacaag gccctgccag cccctatcga gaaaaccatc 1380
agcaaggcca agggccagcc ccgcgagcct caggtgtaca cactgcctcc atgccgggac 1440
gagctgacca agaaccaggt gtccctgtgg tgcctcgtga agggcttcta cccctccgat 1500
atcgccgtgg aatgggagag caacggccag cccgagaaca actacaagac cacccctccc 1560
gtgctggaca gcgacggctc attcttcctg tacagcaagc tgaccgtgga caagtcccgg 1620
tggcagcagg gcaacgtgtt cagctgctct gtgatgcacg aggccctgca caaccggttc 1680
acccagaagt ccctgagcct gagccctggc 1710

<210> SEQ ID NO 98
<211> LENGTH: 4
<212> TYPE: PRT
<213> ORGANISM: Artificial Sequence
<220> FEATURE:
<223> OTHER INFORMATION: Synthetic Construct

<400> SEQUENCE: 98

Gly Gly Gly Gly
1

<210> SEQ ID NO 99
<211> LENGTH: 5
<212> TYPE: PRT
<213> ORGANISM: Artificial Sequence
<220> FEATURE:
<223> OTHER INFORMATION: Synthetic Construct

<400> SEQUENCE: 99

Gly Gly Gly Gly Gly
1               5

<210> SEQ ID NO 100
<211> LENGTH: 6
<212> TYPE: PRT
<213> ORGANISM: Artificial Sequence
<220> FEATURE:
<223> OTHER INFORMATION: Synthetic Construct

<400> SEQUENCE: 100

Gly Gly Gly Gly Gly Gly
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic Construct

<400> SEQUENCE: 101

Gly Gly Gly Gly Gly Gly Gly
1               5

<210> SEQ ID NO 102
<211> LENGTH: 8
<212> TYPE: PRT
<213> ORGANISM: Artificial Sequence
<220> FEATURE:
<223> OTHER INFORMATION: Synthetic Construct

<400> SEQUENCE: 102

Gly Gly Gly Gly Gly Gly Gly Gly
1               5

<210> SEQ ID NO 103
<211> LENGTH: 5
<212> TYPE: PRT
<213> ORGANISM: Artificial Sequence
<220> FEATURE:
<223> OTHER INFORMATION: Synthetic Construct

<400> SEQUENCE: 103

Gly Gly Gly Gly Ser
1               5

<210> SEQ ID NO 104
<211> LENGTH: 10
<212> TYPE: PRT
<213> ORGANISM: Artificial Sequence
<220> FEATURE:
<223> OTHER INFORMATION: Synthetic Construct

<400> SEQUENCE: 104

Gly Gly Gly Gly Ser Gly Gly Gly Gly Ser
1               5                   10

<210> SEQ ID NO 105
<211> LENGTH: 15
<212> TYPE: PRT
<213> ORGANISM: Artificial Sequence
<220> FEATURE:
<223> OTHER INFORMATION: Synthetic Construct

<400> SEQUENCE: 105

Gly Gly Gly Gly Ser Gly Gly Gly Gly Ser Gly Gly Gly Gly Ser
1               5                   10                  15

<210> SEQ ID NO 106
<211> LENGTH: 5
<212> TYPE: PRT
<213> ORGANISM: Artificial Sequence
<220> FEATURE:
<223> OTHER INFORMATION: Synthetic Construct

<400> SEQUENCE: 106

Thr Lys Gly Pro Ser
1               5

<210> SEQ ID NO 107
<211> LENGTH: 5
<212> TYPE: PRT
<213> ORGANISM: Artificial Sequence
<220> FEATURE:
<223> OTHER INFORMATION: Synthetic Construct

<400> SEQUENCE: 107

Thr Val Ala Ala Pro
1               5

<210> SEQ ID NO 108
<211> LENGTH: 5
<212> TYPE: PRT
<213> ORGANISM: Artificial Sequence
<220> FEATURE:
<223> OTHER INFORMATION: Synthetic Construct

<400> SEQUENCE: 108

Gln Pro Lys Ala Ala
1               5

<210> SEQ ID NO 109
<211> LENGTH: 5
<212> TYPE: PRT
<213> ORGANISM: Artificial Sequence
<220> FEATURE:
<223> OTHER INFORMATION: Synthetic Construct

<400> SEQUENCE: 109

Gln Arg Ile Glu Gly
1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic Construct

<400> SEQUENCE: 110

Ala Ser Thr Lys Gly Pro Ser
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic Construct

<400> SEQUENCE: 111

Arg Thr Val Ala Ala Pro Ser
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic Construct

<400> SEQUENCE: 112

Gly Gln Pro Lys Ala Ala Pro
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic Construct

<400> SEQUENCE: 113

His Ile Asp Ser Pro Asn Lys
1               5

<210> SEQ ID NO 114
<211> LENGTH: 448
<212> TYPE: PRT
<213> ORGANISM: Artificial Sequence
<220> FEATURE:
<223> OTHER INFORMATION: Synthetic Construct

<400> SEQUENCE: 114

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala

```
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Cys Gln Glu Glu Met Thr Lys Asn Gln Val Ser Leu Trp Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445


<210> SEQ ID NO 115
<211> LENGTH: 213
<212> TYPE: PRT
<213> ORGANISM: Artificial Sequence
<220> FEATURE:
<223> OTHER INFORMATION: Synthetic Construct

<400> SEQUENCE: 115

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
```

```
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 116
<211> LENGTH: 1344
<212> TYPE: DNA
<213> ORGANISM: Artificial Sequence
<220> FEATURE:
<223> OTHER INFORMATION: Synthetic Construct

<400> SEQUENCE: 116

caggtgcagc tgcagcagcc tggcgccgaa ctcgtgaaac ctggcgcctc cgtgaagatg     60

agctgcaagg ccagcggcta caccttcacc agctacaaca tgcactgggt caagcagacc    120

cccggcagag gcctggaatg gatcggcgcc atctaccccg gcaacggcga cacctcctac    180

aaccagaagt tcaagggcaa ggccaccctg accgccgaca agagcagcag cacagcctac    240

atgcagctgt ccagcctgac cagcgaggac agcgccgtgt actactgcgc cagaagcacc    300

tactacggcg gcgactggta cttcaacgtg tggggagccg gcaccaccgt gacagtgtct    360

gctgcttcga ccaagggccc atcggtgttc cctctggccc cttgcagcag aagcaccagc    420

gaatctacag ccgccctggg ctgcctcgtg aaggactact ttcccgagcc cgtgaccgtg    480

tcctggaact ctggcgctct gacaagcggc gtgcacacct ttccagccgt gctccagagc    540

agcggcctgt actctctgag cagcgtcgtg acagtgccca gcagcagcct gggcaccaag    600

acctacacct gtaacgtgga ccacaagccc agcaacacca aggtggacaa gcgggtggaa    660

tctaagtacg gccctccctg ccctccttgc ccagcccctg aatttctggg cggaccctcc    720

gtgttcctgt tcccccaaa gcccaaggac accctgatga tcagccggac ccccgaagtg    780

acctgcgtgg tggtggatgt gtcccaggaa gatcccgagg tgcagttcaa ttggtacgtg    840

gacggcgtgg aagtgcacaa cgccaagacc aagcccagag aggaacagtt caacagcacc    900

taccgggtgg tgtccgtgct gaccgtgctg caccaggact ggctgaacgg caaagagtac    960

aagtgcaagg tgtccaacaa gggcctgccc agctccatcg agaaaaccat cagcaaggcc   1020

aagggccagc cccgcgagcc tcaagtgtat accctgcccc cttgccagga agagatgacc   1080

aagaaccagg tgtccctgtg gtgtctcgtg aaaggcttct accccagcga cattgccgtg   1140

gaatgggaga gcaacggcca gcccgagaac aactacaaga ccaccccccc tgtgctggac   1200

agcgacggct cattcttcct gtactccaag ctgaccgtgg acaagagccg gtggcaggaa   1260

ggcaacgtgt tcagctgctc cgtgatgcac gaggccctgc acaaccacta cacccagaag   1320
```

tccctgtctc tgtccctggg caag 1344

<210> SEQ ID NO 117
<211> LENGTH: 639
<212> TYPE: DNA
<213> ORGANISM: Artificial Sequence
<220> FEATURE:
<223> OTHER INFORMATION: Synthetic Construct

<400> SEQUENCE: 117
cagatcgtgc tgagccagag ccctgccatc ctgagcgctt ccccaggcga gaaagtgacc 60
atgacctgca gagccagcag cagcgtgtcc tacatccact ggttccagca gaagcccggc 120
agcagcccca agccttggat ctacgccacc agcaatctgg ccagcggagt gcctgtgcgg 180
tttagcggct ctggcagcgg cacaagctac agcctgacca tcagccgggt ggaagccgaa 240
gatgccgcca cctactactg ccagcagtgg accagcaacc cccccacatt tggcggaggc 300
accaagctgg aaatcaagcg tacggtggcc gctcccagcg tgttcatctt cccacctagc 360
gacgagcagc tgaagtccgg cacagcctct gtcgtgtgcc tgctgaacaa cttctacccc 420
cgcgaggcca aagtgcagtg gaaggtggac aacgccctgc agagcggcaa cagccaggaa 480
agcgtgaccg agcaggacag caaggactcc acctacagcc tgagcagcac cctgacactg 540
agcaaggccg actacgagaa gcacaaggtg tacgcctgcg aagtgaccca ccagggcctg 600
tctagccccg tgaccaagag cttcaaccgg ggcgagtgt 639

<210> SEQ ID NO 118
<211> LENGTH: 1713
<212> TYPE: DNA
<213> ORGANISM: Artificial Sequence
<220> FEATURE:
<223> OTHER INFORMATION: Synthetic Construct

<400> SEQUENCE: 118
caggtgcagc tgcaggaatc tggccctggc ctcgtgaagc ctagccagac cctgagcctg 60
acctgtaccg tgtccggctt cagcctgagc gactacggcg tgcactgggt gcgccagcca 120
cctggaaaag gcctggaatg gctgggcgtg atctgggctg gcggaggcac caactacaac 180
cccagcctga agtccagaaa gaccatcagc aaggacacca gcaagaacca ggtgtccctg 240
aagctgagca gcgtgacagc cgccgatacc gccgtgtact actgcgccag agacaagggc 300
tacagctact actacagcat ggactactgg ggccagggca ccaccgtgac cgtgtcatcc 360
tctcaggtgc agctggtgga atctggcggc ggagtggtgc agcctggcag aagcctgaga 420
ctgagctgtg ccgccagcgg cttcaccttc accaaggcct ggatgcactg ggtgcgccag 480
gcccctggaa agcagctgga atgggtggcc cagatcaagg acaagagcaa cagctacgcc 540
acctactacg ccgacagcgt gaagggccgg ttcaccatca gccgggacga cagcaagaac 600
accctgtacc tgcagatgaa cagcctgcgg gccgaggaca ccgccgtgta ctactgtcgg 660
ggcgtgtact atgccctgag ccccttcgat tactggggcc agggaaccct cgtgaccgtg 720
tctagtcgga ccgcttcgac caagggccca tcggtgttcc ctctggcccc ttgcagcaga 780
agcaccagcg aatctacagc cgccctgggc tgcctcgtga aggactactt tcccgagccc 840
gtgaccgtgt cctggaactc tggcgctctg acaagcggcg tgcacacctt tccagccgtg 900
ctccagagca gcggcctgta ctctctgagc agcgtcgtga cagtgcccag cagcagcctg 960
ggcaccaaga cctacacctg taacgtggac cacaagccca gcaacaccaa ggtggacaag 1020

```
cgggtggaat ctaagtacgg ccctccctgc cctccttgcc cagcccctga atttctgggc   1080

ggaccctccg tgttcctgtt ccccccaaag cccaaggaca ccctgatgat cagccggacc   1140

cccgaagtga cctgcgtggt ggtggatgtg tcccaggaag atcccgaggt gcagttcaat   1200

tggtacgtgg acggcgtgga agtgcacaac gccaagacca agcccagaga ggaacagttc   1260

aacagcacct accgggtggt gtccgtgctg accgtgctgc accaggactg gctgaacggc   1320

aaagagtaca agtgcaaggt gtccaacaag ggcctgccca gctccatcga gaaaaccatc   1380

agcaaggcca agggccagcc ccgcgagcct caagtgtgta ccctgccccc tagccaggaa   1440

gagatgacca agaaccaggt gtccctgagc tgtgccgtga aaggcttcta ccccagcgac   1500

attgccgtgg aatgggagag caacggccag cccgagaaca actacaagac caccccccct   1560

gtgctggaca gcgacggctc attcttcctg gtgtccaagc tgaccgtgga caagagccgg   1620

tggcaggaag gcaacgtgtt cagctgctcc gtgatgcacg aggccctgca caaccactac   1680

acccagaagt ccctgtctct gtccctgggc aag                                1713
```

<210> SEQ ID NO 119
<211> LENGTH: 1026
<212> TYPE: DNA
<213> ORGANISM: Artificial Sequence
<220> FEATURE:
<223> OTHER INFORMATION: Synthetic Construct

<400> SEQUENCE: 119

```
gacatcgtga tgacccagac ccccctgagc ctgagcgtga cacctggaca gcctgccagc     60

atcagctgca agagcagcca gagcctggtg cacaacaacg ccaacaccta cctgagctgg    120

tatctgcaga agcccggcca gagcccccag tccctgatct acaaggtgtc caacagattc    180

agcggcgtgc ccgacagatt ctccggcagc ggctctggca ccgacttcac cctgaagatc    240

agccgggtgg aagccgagga cgtgggcgtg tactattgtg gccagggcac ccagtacccc    300

ttcacctttg gcagcggcac caaggtggaa atcaagggcc agcccaaggc cgcccccgac    360

atcgtgctga cacagagccc tgctagcctg gccgtgtctc ctggacagag ggccaccatc    420

acctgtagag ccagcgagag cgtggaatat tacgtgacca gcctgatgca gtggtatcag    480

cagaagcccg gccagccccc caagctgctg attttcgccg ccagcaacgt ggaaagcggc    540

gtgccagcca gattttccgg cagcggctct ggcaccgact tcaccctgac catcaacccc    600

gtggaagcca acgacgtggc caactactac tgccagcaga gccggaaggt gccctacacc    660

tttggccagg gcaccaagct ggaaatcaag accaagggcc ccagccgtac ggtggccgct    720

cccagcgtgt tcatcttccc acctagcgac gagcagctga agtccggcac agcctctgtc    780

gtgtgcctgc tgaacaactt ctacccccgc gaggccaaag tgcagtggaa ggtggacaac    840

gccctgcaga gcggcaacag ccaggaaagc gtgaccgagc aggacagcaa ggactccacc    900

tacagcctga gcagcaccct gacactgagc aaggccgact acgagaagca caaggtgtac    960

gcctgcgaag tgacccacca gggcctgtct agccccgtga ccaagagctt caaccggggc   1020

gagtgt                                                              1026
```

<210> SEQ ID NO 120
<211> LENGTH: 8
<212> TYPE: PRT
<213> ORGANISM: Artificial Sequence
<220> FEATURE:
<223> OTHER INFORMATION: Synthetic Construct

<400> SEQUENCE: 120

Gly Tyr Thr Phe Thr Ser Tyr Asn
1 5

<210> SEQ ID NO 121
<211> LENGTH: 8
<212> TYPE: PRT
<213> ORGANISM: Artificial Sequence
<220> FEATURE:
<223> OTHER INFORMATION: Synthetic Construct

<400> SEQUENCE: 121

Ile Tyr Pro Gly Asn Gly Asp Thr
1 5

<210> SEQ ID NO 122
<211> LENGTH: 14
<212> TYPE: PRT
<213> ORGANISM: Artificial Sequence
<220> FEATURE:
<223> OTHER INFORMATION: Synthetic Construct

<400> SEQUENCE: 122

Ala Arg Ser Thr Tyr Tyr Gly Gly Asp Trp Tyr Phe Asn Val
1 5 10

<210> SEQ ID NO 123
<211> LENGTH: 5
<212> TYPE: PRT
<213> ORGANISM: Artificial Sequence
<220> FEATURE:
<223> OTHER INFORMATION: Synthetic Construct

<400> SEQUENCE: 123

Ser Ser Val Ser Tyr
1 5

<210> SEQ ID NO 124
<211> LENGTH: 3
<212> TYPE: PRT
<213> ORGANISM: Artificial Sequence
<220> FEATURE:
<223> OTHER INFORMATION: Synthetic Construct

<400> SEQUENCE: 124

Ala Thr Ser
1

<210> SEQ ID NO 125
<211> LENGTH: 7
<212> TYPE: PRT
<213> ORGANISM: Artificial Sequence
<220> FEATURE:
<223> OTHER INFORMATION: Synthetic Construct

<400> SEQUENCE: 125

Gln Gln Trp Thr Ser Asn Pro
1 5

<210> SEQ ID NO 126
<211> LENGTH: 10
<212> TYPE: PRT
<213> ORGANISM: Artificial Sequence
<220> FEATURE:
<223> OTHER INFORMATION: Synthetic Construct

<400> SEQUENCE: 126

Gly Tyr Ile Phe Thr Asn Tyr Asn Ile His
1 5 10

<210> SEQ ID NO 127
<211> LENGTH: 10
<212> TYPE: PRT
<213> ORGANISM: Artificial Sequence
<220> FEATURE:
<223> OTHER INFORMATION: Synthetic Construct

<400> SEQUENCE: 127

Ala Ile Tyr Pro Gly Asn Gly Asp Ala Pro
1 5 10

<210> SEQ ID NO 128
<211> LENGTH: 9
<212> TYPE: PRT
<213> ORGANISM: Artificial Sequence
<220> FEATURE:
<223> OTHER INFORMATION: Synthetic Construct

<400> SEQUENCE: 128

Ala Asn Trp Asp Val Ala Phe Ala Tyr
1 5

<210> SEQ ID NO 129
<211> LENGTH: 10
<212> TYPE: PRT
<213> ORGANISM: Artificial Sequence
<220> FEATURE:
<223> OTHER INFORMATION: Synthetic Construct

<400> SEQUENCE: 129

Gly Phe Thr Phe Asp Asp Tyr Ala Met His
1 5 10

<210> SEQ ID NO 130
<211> LENGTH: 10
<212> TYPE: PRT
<213> ORGANISM: Artificial Sequence
<220> FEATURE:
<223> OTHER INFORMATION: Synthetic Construct

<400> SEQUENCE: 130

Ala Ile Thr Trp Asn Ser Gly His Ile Asp
1 5 10

<210> SEQ ID NO 131
<211> LENGTH: 12
<212> TYPE: PRT
<213> ORGANISM: Artificial Sequence
<220> FEATURE:
<223> OTHER INFORMATION: Synthetic Construct

<400> SEQUENCE: 131

Val Ser Tyr Leu Ser Thr Ala Ser Ser Leu Asp Tyr
1 5 10

<210> SEQ ID NO 132
<211> LENGTH: 10
<212> TYPE: PRT
<213> ORGANISM: Artificial Sequence
<220> FEATURE:
<223> OTHER INFORMATION: Synthetic Construct

<400> SEQUENCE: 132

Gly Tyr Ser Phe Thr Ser Tyr Trp Ile His 1 5 10

<210> SEQ ID NO 133
<211> LENGTH: 9
<212> TYPE: PRT
<213> ORGANISM: Artificial Sequence
<220> FEATURE:
<223> OTHER INFORMATION: Synthetic Construct

<400> SEQUENCE: 133

Met Ile Asp Pro Ser Asp Gly Glu Thr
1 5

<210> SEQ ID NO 134
<211> LENGTH: 14
<212> TYPE: PRT
<213> ORGANISM: Artificial Sequence
<220> FEATURE:
<223> OTHER INFORMATION: Synthetic Construct

<400> SEQUENCE: 134

Leu Lys Glu Tyr Gly Asn Tyr Asp Ser Phe Tyr Phe Asp Val
1 5 10

<210> SEQ ID NO 135
<211> LENGTH: 10
<212> TYPE: PRT
<213> ORGANISM: Artificial Sequence
<220> FEATURE:
<223> OTHER INFORMATION: Synthetic Construct

<400> SEQUENCE: 135

Gly Phe Ser Leu Thr Asp Ser Ser Ile Asn
1 5 10

<210> SEQ ID NO 136
<211> LENGTH: 9
<212> TYPE: PRT
<213> ORGANISM: Artificial Sequence
<220> FEATURE:
<223> OTHER INFORMATION: Synthetic Construct

<400> SEQUENCE: 136

Met Ile Trp Gly Asp Gly Arg Ile Asp
1 5

<210> SEQ ID NO 137
<211> LENGTH: 10
<212> TYPE: PRT
<213> ORGANISM: Artificial Sequence
<220> FEATURE:
<223> OTHER INFORMATION: Synthetic Construct

<400> SEQUENCE: 137

Asp Gly Tyr Phe Pro Tyr Ala Met Asp Phe
1 5 10

<210> SEQ ID NO 138
<211> LENGTH: 11
<212> TYPE: PRT
<213> ORGANISM: Artificial Sequence
<220> FEATURE:
<223> OTHER INFORMATION: Synthetic Construct

<400> SEQUENCE: 138

Lys Ala Ser Gln Asp Ile Asp Arg Tyr Met Ala
1 5 10

-continued

<210> SEQ ID NO 139
<211> LENGTH: 7
<212> TYPE: PRT
<213> ORGANISM: Artificial Sequence
<220> FEATURE:
<223> OTHER INFORMATION: Synthetic Construct

<400> SEQUENCE: 139

Asp Thr Ser Thr Leu Gln Ser
1 5

<210> SEQ ID NO 140
<211> LENGTH: 8
<212> TYPE: PRT
<213> ORGANISM: Artificial Sequence
<220> FEATURE:
<223> OTHER INFORMATION: Synthetic Construct

<400> SEQUENCE: 140

Leu Gln Tyr Asp Asn Leu Trp Thr
1 5

<210> SEQ ID NO 141
<211> LENGTH: 11
<212> TYPE: PRT
<213> ORGANISM: Artificial Sequence
<220> FEATURE:
<223> OTHER INFORMATION: Synthetic Construct

<400> SEQUENCE: 141

Arg Ala Ser Gln Gly Ile Arg Asn Tyr Leu Ala
1 5 10

<210> SEQ ID NO 142
<211> LENGTH: 9
<212> TYPE: PRT
<213> ORGANISM: Artificial Sequence
<220> FEATURE:
<223> OTHER INFORMATION: Synthetic Construct

<400> SEQUENCE: 142

Gln Arg Tyr Asn Arg Ala Pro Tyr Thr
1 5

<210> SEQ ID NO 143
<211> LENGTH: 11
<212> TYPE: PRT
<213> ORGANISM: Artificial Sequence
<220> FEATURE:
<223> OTHER INFORMATION: Synthetic Construct

<400> SEQUENCE: 143

His Ala Ser Gln Asn Ile Asp Val Trp Leu Ser
1 5 10

<210> SEQ ID NO 144
<211> LENGTH: 9
<212> TYPE: PRT
<213> ORGANISM: Artificial Sequence
<220> FEATURE:
<223> OTHER INFORMATION: Synthetic Construct

<400> SEQUENCE: 144

Gln Gln Ala His Ser Tyr Pro Phe Thr
1 5

<210> SEQ ID NO 145
<211> LENGTH: 15
<212> TYPE: PRT
<213> ORGANISM: Artificial Sequence
<220> FEATURE:
<223> OTHER INFORMATION: Synthetic Construct

<400> SEQUENCE: 145

Arg Ala Ser Glu Ser Val Asp Ser Tyr Gly Gln Ser Tyr Met His
1 5 10 15

<210> SEQ ID NO 146
<211> LENGTH: 7
<212> TYPE: PRT
<213> ORGANISM: Artificial Sequence
<220> FEATURE:
<223> OTHER INFORMATION: Synthetic Construct

<400> SEQUENCE: 146

Leu Ala Ser Asn Leu Glu Ser
1 5

<210> SEQ ID NO 147
<211> LENGTH: 9
<212> TYPE: PRT
<213> ORGANISM: Artificial Sequence
<220> FEATURE:
<223> OTHER INFORMATION: Synthetic Construct

<400> SEQUENCE: 147

Gln Gln Asn Ala Glu Asp Ser Arg Thr
1 5

<210> SEQ ID NO 148
<211> LENGTH: 10
<212> TYPE: PRT
<213> ORGANISM: Artificial Sequence
<220> FEATURE:
<223> OTHER INFORMATION: Synthetic Construct

<400> SEQUENCE: 148

Gly Gly Ser Gly Ser Ser Gly Ser Gly Gly
1 5 10

<210> SEQ ID NO 149
<211> LENGTH: 11
<212> TYPE: PRT
<213> ORGANISM: Artificial Sequence
<220> FEATURE:
<223> OTHER INFORMATION: Synthetic Construct

<400> SEQUENCE: 149

Gln Ser Leu Val His Asn Asn Gly Asn Thr Tyr
1 5 10

<210> SEQ ID NO 150
<211> LENGTH: 120
<212> TYPE: PRT
<213> ORGANISM: Artificial Sequence
<220> FEATURE:
<223> OTHER INFORMATION: Synthetic Construct

<400> SEQUENCE: 150

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr

```
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120


<210> SEQ ID NO 151
<211> LENGTH: 107
<212> TYPE: PRT
<213> ORGANISM: Artificial Sequence
<220> FEATURE:
<223> OTHER INFORMATION: Synthetic Construct

<400> SEQUENCE: 151

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105


<210> SEQ ID NO 152
<211> LENGTH: 121
<212> TYPE: PRT
<213> ORGANISM: Artificial Sequence
<220> FEATURE:
<223> OTHER INFORMATION: Synthetic Construct

<400> SEQUENCE: 152

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Lys Ala
            20                  25                  30

Trp Met His Trp Val Arg Gln Ala Pro Gly Lys Gln Leu Glu Trp Val
        35                  40                  45

Ala Gln Ile Lys Asp Lys Ser Asn Ser Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95
```

```
Tyr Cys Arg Gly Val Tyr Tyr Ala Leu Ser Pro Phe Asp Tyr Trp Gly
            100                 105                 110

Gln Gly Thr Leu Val Thr Val Ser Ser
        115                 120


<210> SEQ ID NO 153
<211> LENGTH: 112
<212> TYPE: PRT
<213> ORGANISM: Artificial Sequence
<220> FEATURE:
<223> OTHER INFORMATION: Synthetic Construct

<400> SEQUENCE: 153

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Asn
            20                  25                  30

Asn Ala Asn Thr Tyr Leu Ser Trp Tyr Leu Gln Lys Pro Gly Gln Ser
        35                  40                  45

Pro Gln Ser Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Tyr Pro Phe Thr Phe Gly Ser Gly Thr Lys Val Glu Ile Lys
            100                 105                 110


<210> SEQ ID NO 154
<211> LENGTH: 121
<212> TYPE: PRT
<213> ORGANISM: Artificial Sequence
<220> FEATURE:
<223> OTHER INFORMATION: Synthetic Construct

<400> SEQUENCE: 154

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Thr Lys Ala
            20                  25                  30

Trp Met His Trp Val Arg Gln Ala Pro Gly Lys Gly Leu Glu Trp Val
        35                  40                  45

Ala Gln Ile Lys Asp Lys Ser Asn Ser Tyr Ala Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Arg Gly Val Tyr Tyr Ala Leu Ser Pro Phe Asp Tyr Trp Gly
            100                 105                 110

Gln Gly Thr Leu Val Thr Val Ser Ser
        115                 120


<210> SEQ ID NO 155
<211> LENGTH: 112
<212> TYPE: PRT
<213> ORGANISM: Artificial Sequence
<220> FEATURE:
<223> OTHER INFORMATION: Synthetic Construct
```

<400> SEQUENCE: 155

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Asn
            20                  25                  30

Asn Gly Asn Thr Tyr Leu Ser Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Gly Gln Gly
                85                  90                  95

Thr Gln Tyr Pro Phe Thr Phe Gly Gly Gly Thr Lys Val Glu Ile Lys
            100                 105                 110

<210> SEQ ID NO 156
<211> LENGTH: 124
<212> TYPE: PRT
<213> ORGANISM: Artificial Sequence
<220> FEATURE:
<223> OTHER INFORMATION: Synthetic Construct

<400> SEQUENCE: 156

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Ser Tyr
            20                  25                  30

Trp Met Asn Trp Val Arg Gln Ala Pro Gly Gln Gly Leu Glu Trp Ile
        35                  40                  45

Gly Gln Ile Trp Pro Gly Asp Gly Asp Thr Asn Tyr Asn Gln Lys Phe
    50                  55                  60

Lys Gly Arg Ala Thr Leu Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120

<210> SEQ ID NO 157
<211> LENGTH: 111
<212> TYPE: PRT
<213> ORGANISM: Artificial Sequence
<220> FEATURE:
<223> OTHER INFORMATION: Synthetic Construct

<400> SEQUENCE: 157

Asp Leu Val Leu Thr Gln Ser Pro Ala Ser Leu Ala Val Ser Pro Gly
1               5                   10                  15

Gln Arg Ala Thr Ile Thr Cys Lys Ala Ser Gln Ser Val Asp Tyr Asp
            20                  25                  30

Gly Asp Ser Tyr Leu Asn Trp Tyr Gln Gln Lys Pro Gly Gln Pro Pro
        35                  40                  45

Lys Leu Leu Ile Tyr Asp Ala Ser Asn Leu Val Ser Gly Val Pro Ala
    50                  55                  60

```
Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln Gln Ser Thr
                85                  90                  95

Glu Asp Pro Trp Thr Phe Gly Gln Gly Thr Lys Leu Glu Ile Lys
            100                 105                 110


<210> SEQ ID NO 158
<211> LENGTH: 121
<212> TYPE: PRT
<213> ORGANISM: Artificial Sequence
<220> FEATURE:
<223> OTHER INFORMATION: Synthetic Construct

<400> SEQUENCE: 158

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120


<210> SEQ ID NO 159
<211> LENGTH: 106
<212> TYPE: PRT
<213> ORGANISM: Artificial Sequence
<220> FEATURE:
<223> OTHER INFORMATION: Synthetic Construct

<400> SEQUENCE: 159

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105


<210> SEQ ID NO 160
<211> LENGTH: 120
<212> TYPE: PRT
<213> ORGANISM: Artificial Sequence
```

<220> FEATURE:
<223> OTHER INFORMATION: Synthetic Construct

<400> SEQUENCE: 160

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Ser Tyr
            20                  25                  30

Tyr Ile His Trp Val Arg Gln Ala Pro Gly Gln Gly Leu Glu Trp Ile
        35                  40                  45

Gly Ser Ile Tyr Pro Gly Asn Val Asn Thr Asn Tyr Ala Gln Lys Phe
    50                  55                  60

Gln Gly Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser His Tyr Gly Leu Asp Trp Asn Phe Asp Val Trp Gly Lys
            100                 105                 110

Gly Thr Thr Val Thr Val Ser Ser
        115                 120

<210> SEQ ID NO 161
<211> LENGTH: 107
<212> TYPE: PRT
<213> ORGANISM: Artificial Sequence
<220> FEATURE:
<223> OTHER INFORMATION: Synthetic Construct

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asn Ile Tyr Val Trp
            20                  25                  30

Leu Asn Trp Tyr Gln Gln Lys Pro Gly Lys Ala Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Gly Gln Thr Tyr Pro Tyr
                85                  90                  95

Thr Phe Gly Gln Gly Thr Lys Leu Glu Ile Lys
            100                 105

<210> SEQ ID NO 162
<211> LENGTH: 120
<212> TYPE: PRT
<213> ORGANISM: Artificial Sequence
<220> FEATURE:
<223> OTHER INFORMATION: Synthetic Construct

<400> SEQUENCE: 162

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Ser Asp Tyr
            20                  25                  30

Gly Val His Trp Val Arg Gln Pro Pro Gly Lys Gly Leu Glu Trp Leu
        35                  40                  45

Gly Val Ile Trp Ala Gly Gly Gly Thr Asn Tyr Asn Pro Ser Leu Lys
    50                  55                  60

Ser Arg Lys Thr Ile Ser Lys Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Lys Gly Tyr Ser Tyr Tyr Tyr Ser Met Asp Tyr Trp Gly Gln
            100                 105                 110

Gly Thr Thr Val Thr Val Ser Ser
        115                 120

<210> SEQ ID NO 163
<211> LENGTH: 111
<212> TYPE: PRT
<213> ORGANISM: Artificial Sequence
<220> FEATURE:
<223> OTHER INFORMATION: Synthetic Construct

<400> SEQUENCE: 163

Asp Ile Val Leu Thr Gln Ser Pro Ala Ser Leu Ala Val Ser Pro Gly
1               5                   10                  15

Gln Arg Ala Thr Ile Thr Cys Arg Ala Ser Glu Ser Val Glu Tyr Tyr
            20                  25                  30

Val Thr Ser Leu Met Gln Trp Tyr Gln Gln Lys Pro Gly Gln Pro Pro
        35                  40                  45

Lys Leu Leu Ile Phe Ala Ala Ser Asn Val Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Val Ala Asn Tyr Tyr Cys Gln Gln Ser Arg
                85                  90                  95

Lys Val Pro Tyr Thr Phe Gly Gln Gly Thr Lys Leu Glu Ile Lys
            100                 105                 110

<210> SEQ ID NO 164
<211> LENGTH: 120
<212> TYPE: PRT
<213> ORGANISM: Artificial Sequence
<220> FEATURE:
<223> OTHER INFORMATION: Synthetic Construct

<400> SEQUENCE: 164

Gln Val Gln Leu Val Gln Ser Gly Ala Glu Val Ala Lys Pro Gly Thr
1               5                   10                  15

Ser Val Lys Leu Ser Cys Lys Ala Ser Gly Tyr Thr Phe Thr Asp Tyr
            20                  25                  30

Trp Met Gln Trp Val Lys Gln Arg Pro Gly Gln Gly Leu Glu Trp Ile
        35                  40                  45

Gly Thr Ile Tyr Pro Gly Asp Gly Asp Thr Gly Tyr Ala Gln Lys Phe
    50                  55                  60

Gln Gly Lys Ala Thr Leu Thr Ala Asp Lys Ser Ser Lys Thr Val Tyr
65                  70                  75                  80

Met His Leu Ser Ser Leu Ala Ser Glu Asp Ser Ala Val Tyr Tyr Cys
                85                  90                  95

Ala Arg Gly Asp Tyr Tyr Gly Ser Asn Ser Leu Asp Tyr Trp Gly Gln
            100                 105                 110

Gly Thr Ser Val Thr Val Ser Ser
        115                 120

<210> SEQ ID NO 165
<211> LENGTH: 107
<212> TYPE: PRT
<213> ORGANISM: Artificial Sequence
<220> FEATURE:
<223> OTHER INFORMATION: Synthetic Construct

<400> SEQUENCE: 165

Asp Ile Val Met Thr Gln Ser His Leu Ser Met Ser Thr Ser Leu Gly
1 5 10 15

Asp Pro Val Ser Ile Thr Cys Lys Ala Ser Gln Asp Val Ser Thr Val
20 25 30

Val Ala Trp Tyr Gln Gln Lys Pro Gly Gln Ser Pro Arg Arg Leu Ile
35 40 45

Tyr Ser Ala Ser Tyr Arg Tyr Ile Gly Val Pro Asp Arg Phe Thr Gly
50 55 60

Ser Gly Ala Gly Thr Asp Phe Thr Phe Thr Ile Ser Ser Val Gln Ala
65 70 75 80

Glu Asp Leu Ala Val Tyr Tyr Cys Gln Gln His Tyr Ser Pro Pro Tyr
85 90 95

Thr Phe Gly Gly Gly Thr Lys Leu Glu Ile Lys
100 105

<210> SEQ ID NO 166
<211> LENGTH: 118
<212> TYPE: PRT
<213> ORGANISM: Artificial Sequence
<220> FEATURE:
<223> OTHER INFORMATION: Synthetic Construct

<400> SEQUENCE: 166

Gln Val Gln Leu Val Gln Ser Gly Ala Glu Val Lys Lys Pro Gly Ser
1 5 10 15

Ser Val Lys Val Ser Cys Lys Ala Ser Gly Tyr Ile Phe Thr Asn Tyr
20 25 30

Asn Ile His Trp Val Lys Lys Ser Pro Gly Gln Gly Leu Glu Trp Ile
35 40 45

Gly Ala Ile Tyr Pro Gly Asn Gly Asp Ala Pro Tyr Ser Gln Lys Phe
50 55 60

Gln Gly Lys Ala Thr Leu Thr Ala Asp Thr Ser Thr Ser Thr Thr Tyr
65 70 75 80

Met Glu Leu Ser Ser Leu Arg Ser Glu Asp Thr Ala Val Tyr Tyr Cys
85 90 95

Val Arg Ala Asn Trp Asp Val Ala Phe Ala Tyr Trp Gly Gln Gly Thr
100 105 110

Leu Val Thr Val Ser Ser
115

<210> SEQ ID NO 167
<211> LENGTH: 106
<212> TYPE: PRT
<213> ORGANISM: Artificial Sequence
<220> FEATURE:
<223> OTHER INFORMATION: Synthetic Construct

<400> SEQUENCE: 167

Asp Ile Gln Met Thr Gln Ser Pro Ser Ser Leu Ser Ala Ser Val Gly
1 5 10 15

```
Asp Arg Val Thr Ile Thr Cys Lys Ala Ser Gln Asp Ile Asp Arg Tyr
            20                  25                  30

Met Ala Trp Tyr Gln Asp Lys Pro Gly Lys Ala Pro Arg Leu Leu Ile
        35                  40                  45

His Asp Thr Ser Thr Leu Gln Ser Gly Val Pro Ser Arg Phe Ser Gly
    50                  55                  60

Ser Gly Ser Gly Arg Asp Tyr Thr Leu Thr Ile Ser Asn Leu Glu Pro
65                  70                  75                  80

Glu Asp Phe Ala Thr Tyr Tyr Cys Leu Gln Tyr Asp Asn Leu Trp Thr
                85                  90                  95

Phe Gly Gly Gly Thr Lys Val Glu Ile Lys
            100                 105


<210> SEQ ID NO 168
<211> LENGTH: 121
<212> TYPE: PRT
<213> ORGANISM: Artificial Sequence
<220> FEATURE:
<223> OTHER INFORMATION: Synthetic Construct

<400> SEQUENCE: 168

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120


<210> SEQ ID NO 169
<211> LENGTH: 107
<212> TYPE: PRT
<213> ORGANISM: Artificial Sequence
<220> FEATURE:
<223> OTHER INFORMATION: Synthetic Construct

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95
```

```
Thr Phe Gly Gln Gly Thr Lys Val Glu Ile Lys
            100                 105


<210> SEQ ID NO 170
<211> LENGTH: 123
<212> TYPE: PRT
<213> ORGANISM: Artificial Sequence
<220> FEATURE:
<223> OTHER INFORMATION: Synthetic Construct

<400> SEQUENCE: 170

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Trp Ile His Trp Ile Lys Gln Arg Pro Gly Gln Gly Leu Glu Trp Ile
        35                  40                  45

Gly Met Ile Asp Pro Ser Asp Gly Glu Thr Arg Leu Asn Gln Arg Phe
    50                  55                  60

Gln Gly Arg Ala Thr Leu Thr Val Asp Glu Ser Thr Ser Thr Ala Tyr
65                  70                  75                  80

Met Gln Leu Arg Ser Pro Thr Ser Glu Asp Ser Ala Val Tyr Tyr Cys
                85                  90                  95

Thr Arg Leu Lys Glu Tyr Gly Asn Tyr Asp Ser Phe Tyr Phe Asp Val
            100                 105                 110

Trp Gly Ala Gly Thr Leu Val Thr Val Ser Ser
        115                 120


<210> SEQ ID NO 171
<211> LENGTH: 107
<212> TYPE: PRT
<213> ORGANISM: Artificial Sequence
<220> FEATURE:
<223> OTHER INFORMATION: Synthetic Construct

<400> SEQUENCE: 171

Asp Ile Gln Met Thr Gln Ser Pro Ala Ser Leu Ser Val Ser Val Gly
1               5                   10                  15

Asp Thr Ile Thr Leu Thr Cys His Ala Ser Gln Asn Ile Asp Val Trp
            20                  25                  30

Leu Ser Trp Phe Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln Ala His Ser Tyr Pro Phe
                85                  90                  95

Thr Phe Gly Gly Gly Thr Lys Leu Glu Ile Lys
            100                 105


<210> SEQ ID NO 172
<211> LENGTH: 118
<212> TYPE: PRT
<213> ORGANISM: Artificial Sequence
<220> FEATURE:
<223> OTHER INFORMATION: Synthetic Construct

<400> SEQUENCE: 172
```

Glu Val Gln Leu Lys Glu Ser Gly Pro Gly Leu Val Ala Pro Gly Gly
1               5                   10                  15

Ser Leu Ser Ile Thr Cys Thr Val Ser Gly Phe Ser Leu Thr Asp Ser
            20                  25                  30

Ser Ile Asn Trp Val Arg Gln Pro Pro Gly Lys Gly Leu Glu Trp Leu
        35                  40                  45

Gly Met Ile Trp Gly Asp Gly Arg Ile Asp Tyr Ala Asp Ala Leu Lys
    50                  55                  60

Ser Arg Leu Ser Ile Ser Lys Asp Ser Ser Lys Ser Gln Val Phe Leu
65                  70                  75                  80

Glu Met Thr Ser Leu Arg Thr Asp Asp Thr Ala Thr Tyr Tyr Cys Ala
                85                  90                  95

Arg Asp Gly Tyr Phe Pro Tyr Ala Met Asp Phe Trp Gly Gln Gly Thr
            100                 105                 110

Ser Val Thr Val Ser Ser
        115

<210> SEQ ID NO 173
<211> LENGTH: 111
<212> TYPE: PRT
<213> ORGANISM: Artificial Sequence
<220> FEATURE:
<223> OTHER INFORMATION: Synthetic Construct

<400> SEQUENCE: 173

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Gln Ser Tyr Met His Trp Tyr Gln Gln Lys Ala Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Gln Ala Glu Asp Ala Ala Thr Tyr Tyr Cys Gln Gln Asn Ala
                85                  90                  95

Glu Asp Ser Arg Thr Phe Gly Gly Gly Thr Lys Leu Glu Ile Lys
            100                 105                 110

<210> SEQ ID NO 174
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)...(5)
<223> OTHER INFORMATION: Can be absent or present, or present in repeats
of up to 5 times

<400> SEQUENCE: 174

Gly Gly Gly Gly Ser
1               5

<210> SEQ ID NO 175
<211> LENGTH: 7
<212> TYPE: PRT
<213> ORGANISM: Artificial Sequence
<220> FEATURE:

-continued

<223> OTHER INFORMATION: Synthetic Construct

<400> SEQUENCE: 175

Gly Gln Pro Lys Ala Ala Pro
1 5

<210> SEQ ID NO 176
<211> LENGTH: 5
<212> TYPE: PRT
<213> ORGANISM: Artificial Sequence
<220> FEATURE:
<223> OTHER INFORMATION: Synthetic Construct

<400> SEQUENCE: 176

Asp Lys Thr His Thr
1 5

<210> SEQ ID NO 177
<211> LENGTH: 6
<212> TYPE: PRT
<213> ORGANISM: Artificial Sequence
<220> FEATURE:
<223> OTHER INFORMATION: Synthetic Construct

<400> SEQUENCE: 177

Thr Lys Gly Pro Ser Arg
1 5

<210> SEQ ID NO 178
<211> LENGTH: 7
<212> TYPE: PRT
<213> ORGANISM: Artificial Sequence
<220> FEATURE:
<223> OTHER INFORMATION: Synthetic Construct

<400> SEQUENCE: 178

Ala Ala Ser Thr Leu Gln Ser
1 5

<210> SEQ ID NO 179
<211> LENGTH: 7
<212> TYPE: PRT
<213> ORGANISM: Artificial Sequence
<220> FEATURE:
<223> OTHER INFORMATION: Synthetic Construct

<400> SEQUENCE: 179

Lys Ala Ser Asn Leu His Thr
1 5

UNITED STATES PATENT AND TRADEMARK OFFICE
CERTIFICATE OF CORRECTION

PATENT NO. : 10,882,922 B2
APPLICATION NO. : 15/487243
DATED : January 5, 2021
INVENTOR(S) : Zhi-Yong Yang Page 1 of 1

It is certified that error appears in the above-identified patent and that said Letters Patent is hereby corrected as shown below:

In the Claims
- In Claim 9, Column 384, Line 11: please replace "MEW class II" with --MHC class II--;
- In Claim 11, Column 384, Line 41: please replace "MEW class II" with --MHC class II--;
- In Claim 14, Column 392, Line 34: please replace "$L_{368}A$" with --L368A--; and
- In Claim 47, Column 398, Line 51: please replace "MEW class II" with --MHC class II--.

Signed and Sealed this
Thirteenth Day of April, 2021

Drew Hirshfeld
*Performing the Functions and Duties of the
Under Secretary of Commerce for Intellectual Property and
Director of the United States Patent and Trademark Office*